United States Patent [19]
Jennings-White et al.

[11] Patent Number: 6,117,860
[45] Date of Patent: *Sep. 12, 2000

[54] STEROIDS AS NEUROCHEMICAL STIMULATORS OF THE VNO TO TREAT PAROXISTIC TACHYCARDIA

[75] Inventors: Clive L. Jennings-White, Salt Lake City, Utah; David L. Berliner, Atherton, Calif.; Nathan W. Adams, West Jordan; Luis Monti-Bloch, Salt Lake City, both of Utah

[73] Assignee: Pherin Pharmaceuticals, Inc., Menlo Park, Calif.

[ * ] Notice: This patent is subject to a terminal disclaimer.

[21] Appl. No.: 08/899,094

[22] Filed: Jul. 23, 1997

Related U.S. Application Data

[63] Continuation-in-part of application No. 08/725,862, Oct. 4, 1996, which is a continuation-in-part of application No. 08/686,092, Jul. 23, 1996, which is a continuation-in-part of application No. 08/625,268, Mar. 29, 1996, which is a continuation-in-part of application No. 08/286,073, Aug. 4, 1994, Pat. No. 5,563,131.

[51] Int. Cl.[7] .................................................. A61K 31/56
[52] U.S. Cl. .......................... 514/177; 514/178; 514/179; 514/181; 514/182
[58] Field of Search .................................. 514/177, 178, 514/179, 181, 182

[56] References Cited

U.S. PATENT DOCUMENTS

| | | | |
|---|---|---|---|
| 2,840,582 | 6/1958 | Colton | 552/595 |
| 3,413,321 | 11/1968 | Boswell | 552/502 |
| 3,492,318 | 1/1970 | Crabbe | 552/514 |
| 3,681,410 | 8/1972 | Crabbe et al. | 552/511 |
| 3,682,983 | 8/1972 | Prezewowsky et al. | 552/502 |
| 5,208,227 | 5/1993 | Gee et al. | 514/172 |
| 5,272,134 | 12/1993 | Berliner | 512/3 |
| 5,563,131 | 10/1996 | Berliner et al. | 514/177 |

FOREIGN PATENT DOCUMENTS

| | | |
|---|---|---|
| 1363191 | 3/1963 | France . |
| 1536034 | 9/1967 | France . |
| 854 517 | 2/1952 | Germany . |
| 12 97 603 | 6/1969 | Germany . |
| 24 28 679 | 6/1974 | Germany . |
| 26 31 915 | 7/1976 | Germany . |
| 927515 | 5/1963 | Mexico . |
| WO 96/04296 | 2/1996 | WIPO . |
| WO 96/10032 | 4/1996 | WIPO . |
| WO 96/40727 | 12/1996 | WIPO . |

OTHER PUBLICATIONS

Adams, W.J., et al. (1956) "4:4–Dimethylsteroids. Part II. Some Androstane and Pregnane Derivatives" *J. Chem. Soc.* 4490–4495.

Andersch et al., (1986) "Premenstrual Complaints. I. Prevalence of Premenstrual Symptoms in a Swedish Urban Population," *J. Psychomsom. Obstet. Gynecol.* 5: 39–49.

Appenzeller, O. (1990) *The Autonomic Nervous System. An Introduction of Basic and Clinical Concepts.*

Barton, D.H.R., et al. (1983) "An Improved Preparation of Vinyl Iodides" *Tetrahedron Letters* 24(15):1605–1608.

Barton, D.H.R., et al. (1986) "Functionalisation of Saturated Hydrocarbons. Part 7. On the Mechanism of the Degradation of the Cholesterol Side–chain to 20–Ketone by Oxidation with the Gif System" *J. Chem. Soc.* Perkin Trans. I, p. 1805–1808.

Beauchamp, G.K., et al. (1976) "The Pheromone Concept in Mammalian Chemical Communication: A Critique" In: *Mammalian Olfaction. Reproductive Processes and Behavior*, Doty, R.L., Ed., Academic Press.

Beltramino, C., et al., 1983, "Release of LH in the Female Rat by Olfactory Stimuli," *Neuroendocrinol.* 36(1): 53–58.

Bergmann, W., and Dusza, J.P. (1958) "Contributions to the Study of Marine Products. XLVII 22–Dehydrocholesterol" *J. Org. Chem.* 23:1245–1247.

Bertin, D., and Nedelac, L. (1964) "Sur les hydroxymethyl–17 Testosterones" *Memoires Presentes a la Societe Chimique* 345:2140–2144.

Blackburn, G.M., et al. (1986) "Synthesis of Isomeric 16,17–epoxy [17–$^3$H]–Derivatives of 3–Hydroxy and 3–Methoxy–Oestra–1,3,5(10)–Trienes" *J. Labelled Compounds and Radiopharmaceuticals*, vol. XXIII, No. 2, p. 197–206.

Bose, A.K., and Steinberg, N.G. (1970) *Synthesis*, p. 595.

Boswell, G.A. (1969) "17–Fluoro $\Delta^{16}$–steroids" *Patent Chem. Abstr.* 70:58140g.

Boucsein, W. (1992) *Electrodermal Activity* (Plenum Press).

Breslow, R., and Maresca, L.M. (1977) "The Template–Directed Remote Epoxidation of Olefins" *Tetrahedron Letters* 7:623–626.

Brooksbank et al. (1950) "The Nature of Pregnanediol–like Glucuronide" *Biochem. J.* 47:36–43.

Brooksbank et al. (1972) "Fate of Androsta–4, 16–Dien–3–One and the Origin of 3α–Hydroxy–5α–Androst–16–Ene in Man" *J. Endocr.* 52:239–251.

Brown, F., and Djerassi, C. (1980) "Elucidation of the Course of the Electron Impact Induced Fragmentation of α,β–unsaturated 3–keto Steroids$^{1,2}$" *J. Amer. Chem. Soc.* 807–817.

Bull, J.R., and Floor, J. (1977) "Hydroxylation of $\Delta^4$–Steroids by Osmium Tetraoxide; Stereochemistry and Substituent Effects" *J. Chem. Soc.* Perkin I, 7: 724–730.

Burger, A., et al. (1988) "Acetlyenic Cholesteryl Derivatives as Irreversible Inhibitors of Ecdysone Biosynthesis" *Tetrahedron* 44(4):1141–1152.

(List continued on next page.)

Primary Examiner—Kimberly Jordan
Attorney, Agent, or Firm—Heller Ehrman White & McAuliffe LLP

[57] ABSTRACT

The invention relates to a method of alleviating the symptoms of PMS and anxiety. The method comprises nasally administering a steroid which is a human vomeropherin, such that the vomeropherin binds to a specific neuroepithelial receptor. The steroid or steroids is/are preferably administered in the form of a pharmaceutical composition containing one or more pharmaceutically acceptable carriers.

70 Claims, 148 Drawing Sheets

OTHER PUBLICATIONS

Burger, A., et al., (1989) "Allenic Cholesteryl Derivatives as Inhibitors of Ecdysone Biosynthesis" *Tetrahedron* 45(1):155–164.

Cabanac, M. (1975) "Temperature Regulation" *Annual Review of Physiology* 1137:415–439.

Cairns, J., et al. (1976) "Alkyated Steroids. Part 1. 16α–Substituted 17 α–Methylpregnanes" *J.C.S.* Perkins I, pp. 1558–1564.

Cherkasov, A.N., et al. (1971) *Zhurnal Organiskeskoi Khimii* 7(5):940–947.

Claus, et al. (1976) "Occurrence of 5α–Androst–16–En–3–One, A Boar Pheromone, In Man and Its Relationship to Testosterone" *J. Endocr.* 68:483–484.

Claus, et al. (1979) "The Boar–Pheromone Steriod Indentified in Vegetables" *Experimentia* 35:1674–1675.

Colton, F.B., et al. (1957) "17–Alkyl–19–nortestosterones" *J. Am. Chem. Soc.* 79:1123–1127.

Coquelin, A., et al., (1984), "Pheromonally Induced Release of Luteinizing Hormone in Male MiCe: Involvement of the Vomeronasal System," *J. Neurosci.* 4 (9): 2230–2236.

Deghenghi, R., and Gaudry, R. (1961) "Sterically Controlled Grignard Reactions. A New Simple Route to 17–α Methylated Steroid Analogs" *J. Amer. Chem. Soc.* 83:4668.

Deghenghi, R., and Gaudry, R. (1962) "A Direct Angular Alkylation in the Pregnane Series" *Tetrahedron Letters* 11:489–491.

Djerassi, C. et al., 1951, "Steroids. XII. Aromatization Experiments in the Progesterone Series," *J. Amer. Chem. Soc.* 73: 1523–1527.

Dory, I., et al. (1959) "Ozonolyse Von Ergosterinderivaten in Einem Mit Kontinuierlichem Betrieb" *Acta. Chim. Hung.* 20:67–72.

Drefahl, G., et al., (1965) *Berichte* 98:604.

Dusza, J.P., and Bergmann, W. (1960) "20–Methylpregnane and Derivatives" *J. Org. Chem.* 25:79–83.

Dvolaitzky, M., et al. (1963) "Extension Aromatisante du Noyau D Steroide. 1. Cas des Ethynylcarbinols–17" *Bull. Soc. Chim. France* 62–71.

Fedorova, O.I., et al. (1976) *Khim. Prir. Soedin.* 2:180.

Fishman, A.P., et al. editors (1986) "Section 3: Respiratory System. vol. II. Control of Breathing," *Handbook of Physiology,* Bethesda MD, American Physiological Society.

Garcia–Velasco, et al. (1991) "The Incidence of the Vomeronasal Organ in 1000 Human Subjects and Its Possible Clinical Significance" *J. Steroid Biochem. Molec. Biol.* 39(4B):561–563.

Gower, et al. (1988) "The Significance of Odorous Steroids in Axillary Odour" In *Perfumery,* pp. 57–60, 68–73, Van Toller and Dodds, Eds., Chapman and Hall.

Green, M.B., and Zeelen, F.J. (1982) "Biometric Total Synthesis of 14α–Methyl–19–Norsteroids Stereoselective Epoxidations with $Mo(CO)_6$/t–BuOOH" *Tetrahedron Letters* 23(35):3611–3614.

Habermehl, G., et al. (1980) "Synthese des 19–Oxo–3–aza–A–homo–5 β–androstans" *J. Naturforsch.* 256:191–195.

Hardy, J.D. (1980) "Body Temperature Regulation" In: *Medical Physiology.* vol. II, Chapter 59, pp. 1417–1456. Ed.: VB Mountcastle.

Hartman, J.A., et al. (1956), "The Partial Degradation and Reconstitution of the "A" Ring of Estradiol," *J. Am. Chem. Soc.* 78: 5662–5666.

Hazra, B.G., et al. (1993) *J. Chem. Soc.,* Perkin Trans I, 15:1819–22.

Hershberg, E.B. et al., (1951) Selective Reduction and Hydrogenation of Unsaturated Steroids, *J. Amer. Chem. Soc.* 73, 5073–5076.

Hirano, Y., et al. (1983) "Configuration at the C–23 Position of 23–Hydroxy– and 23,25–Dihydroxycholesterols" *Chem. Pharm. Bull.* 31(2):394–400.

Jiang, B., and Xu, Y. (1992) "Palladium–Catalyzed Cross––Coupling of Trifluoroisopropenylzinc Reagent with Vinyl Halides. A Novel Stereospecific Synthesis of Trifluoromethylated 1,3–Dienes" *Tetrahedron Letters* 33:511–514.

Johns, W.F. (1961) "Retropinacol Rearrangement of Estradiol 3–Methyl Ether" *J. Org. Chem.* 26:4583–4591.

Johnson, A., et al. (1985) "Clinical and Histological Evidence for the Presence of the Vomeronasal (Jacobson's) Organ in Adult Humans" *J. Otolaryngology* 14:71–79.

Jones, J.B., and Gordon, K.J. (1972) "Steroids and Steroidases. XVI. An Evaluation of Synthetic Routes to Variously C–17–Substituted ▲$^5$–3–Ketosteroids" *Can. J. Chem.* 50:2712–2718.

Julia, S., et al. (1962) "Nouveaux Derives du Dimethyl–7,7 Androstane et du Dimethyl 1–7,7 Pregnane" *Bull. Soc. Chim.* France, 7:1495–1496.

Julian, P.L., et al., (1948) "$\Delta^{20}$–Pregnenes from bisnor––Steroid Acids" *J. Am. Chem. Soc.* 70(3):887–892.

Kabore, I.Z., et al. (1978) "Reaction de $N_3H/BF_3$–$OEt_2$ Sur les Alcools Allyiques Steroidques. Synthese 'Stereocontrolee' D'Azides et D'Amines Allyiques" *Tetrahedron* 34:2807–2814.

Kaspar, P., and Witzel, H. (1985) "Steroid Binding to the Cytosolic Estrogen Receptor from Rat Uterus. Influence of the Orientation of Substituents in the 17–Position of the 8B– and 8α–Series" *J. Steroid Biochem.* 23(3):259–265.

Kaufmann, H., et al. (1973) "Elektrocyclischer Ringschluss als Nebenreaktion bei einer Wolff–Kishner–Reduktion" *Helv. Chim. Acta.,* 55(2):381–387.

Kirk, D.N., et al., "Synthesis of 18,21–Dihydroxypregn–4–ene–3,20–dione ('18–Hydroxy–Deoxycorticosterone')" *J. Chem. Soc.* (1974) 145–146.

Kirk–Smith, D.A., et al. (1978) "Human Social Attitudes Affected by Androstenol," *Res. Comm. Psychol. Psychiat. Behav.* 3(4):379–384.

Knobil, E. (1980) "The Neuroendocrine Control of the Menstrual Cycle" *Recent Prog. Horm. Res.* 36:53–88.

Kohli, J.M., et al., (1971) "Alkaloid C of *Sarcococca Pruniformis*" *Phytochemistry* 10:442–445.

Korner, P.I. (1979) Central Nervous Control of Autonomic Cardiovascular Function, In *Handbook of Physiology: Section 2; Cardiovascular System—The Heart,* vol. I, Washington DC, American Physiological Society.

Krubiner, A.M., et al. (1969) "The Synthesis of 17–Deoxy–17–α and –17β 20–pregnynes and –20–pregnenes" *J. Org. Chem.* 34(11):3502–3505.

Kwan, T.K., et al. (1987) "16–Androstenes, Putative Pheromones in Human Semen" *Med. Sci. Res.* 15:1443–1444.

Langer, R.S., and Peppas, N.A. (1981) "Present and Future Applications of Biomaterials in Controlled Drug Delivery Systems" *Biomaterials* 2:201–214.

Loughhead, D.G. (1985) "Preparation and Acid–Catalyzed Rearrangement of a C–17 Isopropylidene and a C–17 Isopropenyl Sterol" *J. Org. Chem.* 50(20):3931–3934.

Lupon, P., et al. (1988) "Photochemical Behavior of a $\Delta^4$–3–Oxo, $\Delta^1$–3–Oxo Steroids in Concentrated Acid Solution" *J. Org. Chem.* 53:2193–2198.

Macdonald, B.S., et al. (1971) "The Identification of a 17α–Hydroxy–17–Methyl–1,4–Androstadien–3–One As a Metabolite of the Anabolic Steroid Drug 17β–Hydroxy–17–Methyl–1, 4–Androstadien–3–One in Man" *Steroids* 18:753–766.

Matsui, M., and Fukushima, D.K. (1970) "Studies on the Heterolytic Fragmentation of Pregnane–16,20–diol Derivatives to Androst–16–enes" *J. Org. Chem.* 35(3):561–564.

Mauney, M., and Rigaudy, J. (1976) *Bull. Soo. Chien.* No. 11–12, 2012.

Mel'nikova, V.I., and Pivnitskii, K.K. (1974) "Reduction of Steroid Dienones with Lithium–Ammonia Complex" *Zhurnal Organickeskoi Khimii* 10(5):1014–1019.

Mel'nikova, V.I., and Pivnitskii, K.K. (1972) "Dianionic Mechanism for the Reductive Aromatization of 1,4–Cyclohexadienones Reduction of Unsaturated 3–Ketosteroids Through the Enolates by Alkali Metals in Ethers" *Zhurnal Organickeskoi Khimii* 8(1):68–74.

Melrose, D.R., et al. (1971) "Androgen Steroids Associated with Boar Odour as an Aid to the Detection of Oestrus in Pig Artificial Insemination" *Br. Vet. J.* 127:497–502.

Michael, R.P., et al. (1968) "Pheromones in the Communication of Sexual Status in Primates" *Nature* 218:746–749.

Monti–Bloch, L., and Grosser, B.l. (1991) "Effect of Putative Pheromones on the Electrical Activity of the Human Vomeronasal Organ and Olfactory Epithelium" *J. Steroid Biochem. Molec. Biol.* 39:573–582.

Monti–Bloch, L., et al., (1994), "The Human Vomeronasal System," *Psycho neuroendocrinology* 19: 673–686.

Morisaki, M., et al. (1980) "Studies on Steroids. LXIII. Synthesis of Cholesterol Analogs with a Modified Side Chain" *Chem. Pharm. Bull.* 28(2):606–611.

Muller–Schwarze & Silverstein (1980) *Chemical Signals (Vertebrates and Aquatic Invertebrates)*, Plenum Press, New York.

Nicholas, H.J. (1958) "Synthesis of Some 17–Methyl Phenolic Steroids" *J. Org. Chem.* 23:1747–1749.

Ohloff, G., et al. (1983) "Structural and Configurational Dependence of the Sensory Process in Steroid" *Helv. Chim. Acta* 66:192–217.

Parrott, R.F. (1976) "Homotypical Sexual Behavior in Gonadectomized Female and Male Rats Treated with 5α–19–Hydroxytestosterone: Comparison with Related Androgens" *Hormones and Behavior* 7:207–215.

Peters, R.H., et al. (1989) "17–Desoxy Estrogen Analogues" *J. Med. Chem.* 32:1642–1652.

Petrow, V., et al. (1983) "Prostatic Cancer II. Inhibitors of Rat Prostatic 4–ene–3–Ketosteroid 5α–Reductase Derived from 6–Methylene–4–Androsten–3–Ones" *Steroid Biochem.* 19:1491–1502.

Phoenix, C.H. (1976) "Sexual Behavior of Castrated Male Rhesus Monkeys Treated with 19–Hydroxytestosterone" *Physiol. and Behavior* 16:305–310.

Phoenix, C.H. (1977) "Induction of Sexual Behavior in Ovariectomized Rhesus Females with 19–Hydroxytestosterone" *Hormones and Behavior* 8:356–362.

Potter, G.A., et al., 1995, " Novel Steriodal Inhibitors of Human Cytochrome $P450_{17\alpha}$ (17α–Hydroxylase–$C_{17,20}$–lyase): Potential Agents for the Treatment of Prostatic Cancer," *Med. Chem.* 38(13):2463–2471.

von Prelog, V. et al., 1945, "Steriode and Sexualhormone," (III. Mitteilung) Uber ein neues Stereoisomeres des Oestriols, *Helv. Chem. Acta.* 28: 250–256.

*Remington's Pharmaceutical Sciences* (1975) 15th Ed., Mack Publishing Co., Easton, PA.

Rivera–Tovar, A. et al, (1990), "Late Luteal Phase Dysphoric Disorder in Young Women," *Am. J. Psychia* 147: 1634–1636.

Romer, J., et al. (1988) "Androsta–4,16–Diene–3,6–Dione: An Unknown Member Among the Smelling Androst–16–Enes" *Steroids* 51(5–6):577–581.

Ruelas, J. Perez, et al. (1958), "Steroids. XCVIII. Synthesis of Some 10β–Hydroxy–19–norsteroids," *J. Org. Chem.* 23: 1744–1747.

Sax, K.J., et al. (1964), "Microbiological 16–oxidation of Estr–4–en–3–one," *J. Org. Chem.* 29: 2351–2354.

Schmit, J.P., et al. (1975) "Application of Wittin Reaction to the Synthesis of Steroidal Side Chains. Possibility of 3β–Phenoxy Formation as a Secondary Reaction" *J. Org. Chem.* 40(11):1586–1588.

Schow, S.R., and McMorris, T.C. (1977) "Synthesis of 5α–Pregna–1,20–Dien–3–One" *Steroids* 30(3):389–392.

Sciaky, R., and Consonni, A. (1962) "Sintesi del $\Delta^4$–androsten–3,6–dione e del $\Delta^4$–pregnen–3,6–dione" *Gazz. Chim. Ital.* 92:730–737.

Shapiro, E., et al. (1962) "16–Alkylated Progesterones" *J. Med. Pharm. Chem.* 5:975–988.

Shapiro, R.H., and Djerassi, C. (1964) "Mass Spectrometry in Structural and Stereochemical Problems. L. Fragmentation and Hydrogen Migration Reactions of αβ–Unsaturated 3–Keto Steoids" *J. Am. Chem. Soc.* 86:2825–2832.

Sheikh, Y.M., and Djerassi, C. (1975) "Synthesis of Sterols with Modified Side Chains" *Steroids* 26(1):129–136.

Shoppee, C.W., et al. (1964) "Aza–Steroids. Part VII. 3–Aza–A–homopregn–4a–ene and Related Compounds" *J. Chem. Soc.,* pp. 3388–3392.

Sohdheimer, F., et al. (1995) "LXVII. The Decarboxylation of Unsaturated Steroidal Acids. Synthesis of 17–Epitestosterone and of 17–Methylepitestosterone" *J. Am. Chem. Soc.* 77:4145–4149.

Stensaas, L.J., et al. (1991) "Ultrastructure of the Human Vomeronasal Organ," *J. Steroid Biochem. and Molec. Biol.* 39:553–560.

Stephan, E. et al., 1995, "Improved synthesis of a protected 11–oxoestrone," *Steroids* 60: 809–811.

Takagi, H., et al. (1991) "Synthesis and Mechanism of Hydrolysis of Estroger 6–Sulfates: Model Compounds for Demonstrating the Cacinogenesis of Estogen" *Steroids* 56:173–179.

Trost, B.M., et al. (1993) "Ruthenium Catalyzed Reconstitutive Condensation. Application to Functionalized Steroid Side Chains" *Tetrahedron Letters* 34(4):587–590.

Turner, A.B. (1979) "Synthesis of 23–oxocholanes from Bisnorcholanes" *Chemistry and Industry*, p. 385.

Van Dijck, L.A., et al. (1971) "On the Formation of Allenes in the Steroid Series II. Synthesis and Structure of Several 19–Nor–17,20–Pregnadienes" *Recl. Trav. Chim. Pays–Bas Belg.* 90:801–818.-

Van Keep, P.A., et al. (1980) "The Premenstrual Syndrome—An Epdemiologic and Statisical Exercise," Pavan Keep and W.H. Utian (eds) Proc. 6th Int. Cong. of Psychosomatic obstet. and Gyne., Berlin, *The Premenstrual Syndrome,* MTP Press LTD, Lancaster, England, 31–34.

van Lier, J.E., and Smith, L.L. (1970) "Autoxidation of Cholesterol via Hydroperoxide Intermediates" *J. Org. Chem.* 36(8):2631.

Veldhuis et al. (1987) "Preferential Release of Bioactive Luteinizing Hormone in Response to Endogenous and Loe Dose Exogenous Gonadotropin–Releasing Hormone Pulses in Man" *J. Clin. Endocr. Metab.* 64:1275–1282.

Villotti, R. et al., (1960) "Optical Rotatory Dispersion Studies. XXXVII. Steroids. CXLVI On the Mechanism and Stereochemical Course of the Bromination of 3–Keto Steroids and Mechanism and and Stereochemical Course of the Bromination of 3–Keto Steroids and their Enol Acetates," *J. Am. Chem. Soc.* 82: 5693–5700.

Woods, N.F. et al., (1982) "Prevalence of Perimenstrual Symptoms," *Am J. Pub. Health,* 72: 1257–64.-

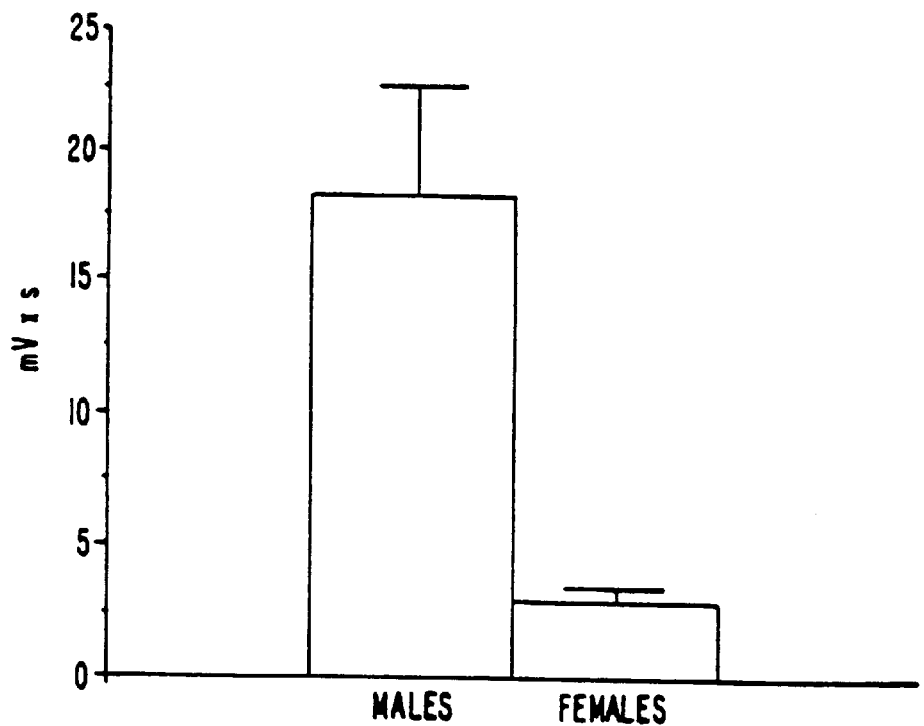
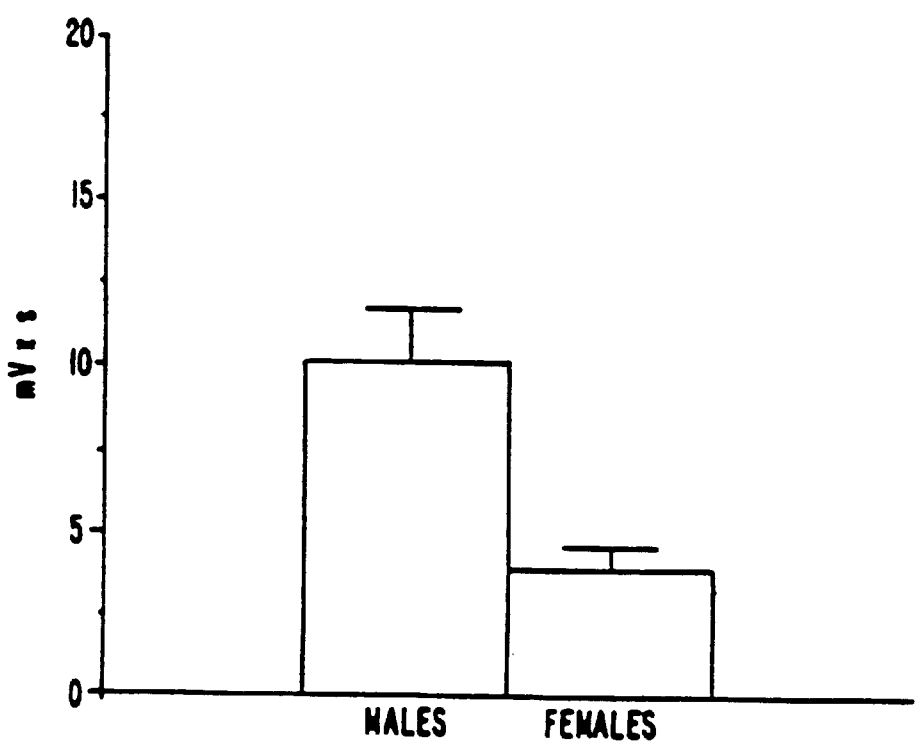
FIG. 144B.

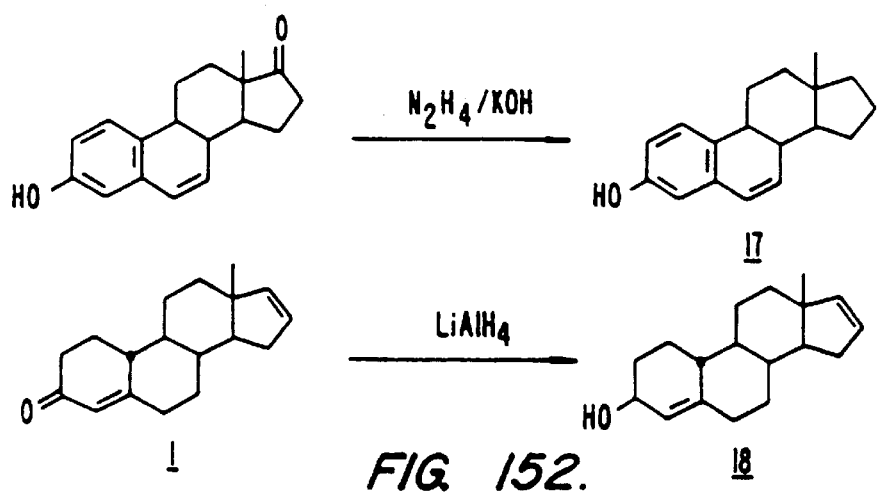
FIG. 152.
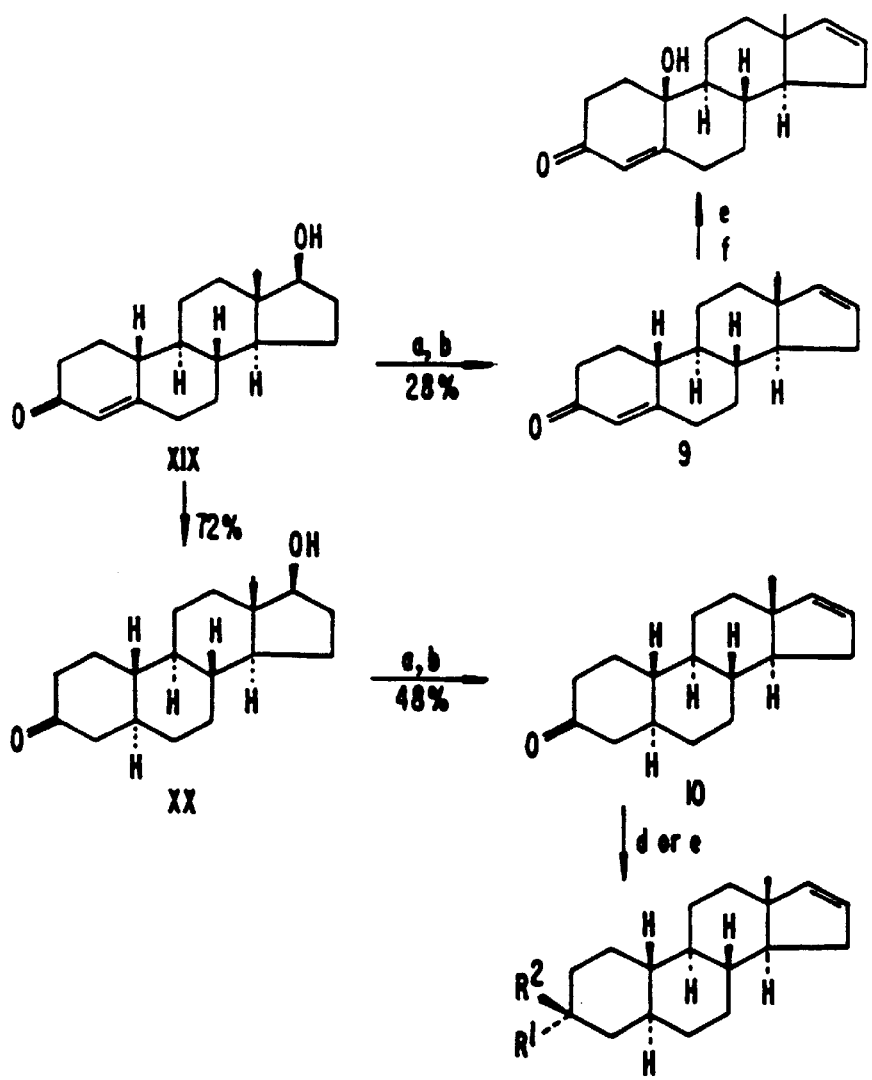
FIG. 153.  11 R¹ = OH; R² = H (87%)
12 R¹ = H; R² = OH (87%)

| Compound | EVG | RF | CF | EMG | EDA | BT | EEG-V | EEG-T |
|---|---|---|---|---|---|---|---|---|
| 16A,17A-EPOXYANDROST-4-EN-3-ONE | ++ | | | | | | | − |
| 17A,20A,EPOXY-19-NORPREGNA-1, 3, 5 (10)-TRIEN-3-OL | + | + | − | | | | | − |
| 16A,17A-EPOXY-10B-HYDROXY-19, 21-BISNORCHOL-4-EN-3^ONE | + | | | | | | | |
| 16A, 17A-EPOXYPREGN-4-EN-3-ONE | ++ | | | + | | | | |
| 10B,17A-DIMETHYL-13B,17B-EPOXYGON-4-EN-3-ONE | ++ | | | | | | | − |
| 17B, 21-EXPOXY-3-METHOXY-19-NOR-17A-PREGNA-1, 3, 5 (10)-TRIENE | ++ | | − | | | | | |
| 16A, 17A-EPOXYESTRA-1, 3, 5 (10)-TRIEN-3-OL | +++ | | + | | | | | |
| 16A,17A-EPOXY-10-HYDROXYESTR-4-EN-3-ONE | +++ | | + | ++ | | | | |

*FIG. 221A.*

| | EVG | RF | CF | EMG | EDA | BT | EEG-V | EEG-T |
|---|---|---|---|---|---|---|---|---|
| 16A,17A-EPOXYANDROST-4-EN-3-ONE | ++ | | | | | | | |
| 17A,20A,EPOXY-19-NORPREGNA-1, 3, 5 (10)-TRIEN-3-OL | +++ | + | − − | ++ | | | | − − |
| 16A,17A-EPOXY-10B-HYDROXY-19, 21-BISNORCHOL-4-EN-3-ONE | ++ | ++ | | − − | | | + | |
| 16A,17A-EPOXYPREGN-4-EN-3-ONE | ++ | | ++ | | | | + | |
| 10B,17A-DIMETHYL-13B,17B-EPOXYGON-4-EN-3-ONE | +++ | +++ | | − − | − − | | | |
| 17B, 21-EXPOXY-3-METHOXY-19-NOR-17A-PREGNA-1, 3, 5 (10)-TRIENE | +++ | ++ | | +++ | − − | | + | ++ |
| 16A,17A-EPOXYESTRA-1, 3, 5 (10)-TRIEN-3-OL | ++ | + | − − | | − − | | | |
| 16A,17A-EPOXY-10-HYDROXYESTR-4-EN-3-ONE | +++ | | | + | | | | |

*FIG. 221B.*

STEROIDS AS NEUROCHEMICAL STIMULATORS OF THE VNO TO TREAT PAROXISTIC TACHYCARDIA

CROSS REFERENCE TO RELATED APPLICATIONS

This is a continuation-in-part of U.S. Ser. No. 08/725,862, filed Oct. 4, 1996, which is a continuation-in-part of U.S. Ser. No. 08/686,092, filed Jul. 23, 1996 which is a continuation-in-part of U.S. Ser. No. 08/625,268, filed Mar. 29, 1996 which is a continuation-in-part of U.S. Ser. No. 08/286,073, filed Aug. 4, 1994, now U.S. Pat. No. 5,563,131.

This application is related to U.S. application Ser. No. 08/127,908, filed Sep. 28, 1993, now abandoned, which is a continuation-in-part of U.S. application Ser. No. 07/903,604, filed Jun. 24, 1992, now abandoned, which in turn is a continuation-in-part of U.S. application Ser. No. 07/708,936, filed May 31, 1991, now abandoned, which in turn is a continuation-in-part of U.S. application Ser. No. 07/638,185, filed Jan. 7, 1991, now abandoned.

The application also relates to U.S. application Ser. No. 08/127,980 filed Sep. 28, 1993, now U.S. Pat. No. 5,783,571, which is another continuation-in-part of U.S. patent application Ser. No. 07/903,604, now abandoned, U.S. patent application Ser. No. 08/077,359, filed Jun. 15, 1993, now abandoned, and to commonly assigned, U.S. patent application Ser. No. 07/903,525, filed Jun. 24, 1992, now abandoned, (a continuation-in-part of U.S. application Ser. No. 07/707,862, filed May 31, 1991, now abandoned, which in turn is a continuation-in-part of U.S. application Ser. No. 07/638,743, filed Jan. 7, 1991, now abandoned) entitled "Estrene Steroids as Neurochemical Initiators of Change in Human Hypothalamic Function and Related Pharmaceutical Compositions and Methods"; and to the commonly assigned, continuation-in-part of Ser. No. 07/903,525, now abandoned, U.S. patent application Ser. No. 08/077,140, now abandoned. The aforementioned U.S. patent applications are each incorporated herein by reference.

Finally, this application may relate to U.S. Pat. No. 5,278,141, issued Jan. 11, 1994 entitled "Fragrance Compositions Containing Human Pheromones", and U.S. Pat. No. 5,272,134, issued Dec. 21, 1993, entitled "Fragrance Compositions and Other Compositions which Contains Human Pheromones."

TECHNICAL FIELD

This invention relates generally to methods for treating paroxistic tachycardia.

DESCRIPTION OF THE RELATED ART

The present invention relates to certain steroids, and methods of using these steroids as human vomeropherins in order to alter hypothalamic function, thereby affecting certain consequent behavior and physiology, e.g., the reduction of anxiety. Ohloff, G. et al. (*Helv. Chim. Acta* (1983) 66:192–217), which is incorporated herein by reference, have shown that several steroids (androstenes) have an odor which varies with different isomeric, diastereomeric, and enantiomeric forms. Some members of this group have been reported to act as a pheromone in some mammalian species—for instance, 5α-androst-16-en-3-one and 5α-androst-16-en-3α-ol in pigs (Melrose, D. R., et al., *Br. vet. J.* (1971) 127:497–502). These 16-androstenes produced by the boar induce mating behavior in estrus sows (Claus, et al., *Experimentia* (1979) 35:1674–1675).

Some studies have noted that, in some species, various characteristics of certain 16-androstenes (including 5α-Androst-16-en-3α-ol and 5α-Androst-16-en-3-one), such as concentration, metabolism, and localization, are sexually dimorphic (Brooksbank et al., *J. Endocr.* (1972) 52: 239–251; Claus, et al., *J. Endocr.* (1976) 68:483–484; Kwan, et al., *Med. Sci. Res.* (1987) 15:1443–1444). For instance, 5α-Androst-16-en-3α-ol and 5α-Androst-16-en-3-one, as well as Androsta-4,16-dien-3-one, have been found at different concentrations in the peripheral blood, saliva and axillary secretions of men and of women (Kwan, T. K., et al., *Med. Sci. Res.* (1987) 15:1443–1444), and their function as a human pheromone, to the extent of affecting choice and judgment, has been suggested (Id.; see also Gower, et al., "The Significance of Odorous Steroids in Axillary Odour", In, *Perfumery*, pp. 68–72, Van Toller and Dodds, Eds., Chapman and Hall, 1988); Kirk-Smith, D. A., et al., *Res. Comm. Psychol. Psychiat. Behav.* (1978) 3:379). Androstenol (5α-androst-16-en-3α-ol) has been claimed to exhibit a pheromone-like activity in a commercial men's cologne and women's perfume (Andron™ for men and Andron™ for women by Jōvan). Japanese Kokai No. 2295916, refers to perfume compositions containing androstenol and/or its analogues. Androstadien-3β-ol (and perhaps the 3α-ol) has also been identified in human axillary secretion (Gower, et al., supra, at 57–60). On the other hand, there is little agreement in the literature as to whether or not any putative pheromone actually plays any role in the sexual or reproductive behavior of mammals, particularly of humans. See: Beauchamp, G. K., et al., "The Pheromone Concept in Mammalian Chemical Communication: A Critique", In: *Mammalian Olfaction, Reproductive Processes and Behavior,* Doty, R. L., Ed., Academic Press, 1976). See also: Gower, et al., supra at 68–73.

The pheromone properties of some estrene steroids for some mammalian species has been described. Michael, R. P. et al., *Nature* (1968) 218:746 refers to Estrogens (particularly Estradiol) as a pheromonal attractant of male rhesus monkeys. Parrot, R. F., *Hormones and Behavior* (1976) 7:207–215, reports Estradiol benzoate injection induces mating behavior in ovariectomized rats; and the role of the blood level of Estradiol in make sexual response (Phoenix, C. H., *Physiol. and Behavior* (1976) 16305–310) and female sexual response (Phoenix, C. H., *Hormones and Behavior* (1977) 8:356–362) in Rhesus monkeys has been described. On the other hand, there is little agreement in the literature as to whether or not pheromones as such play any role in the reproductive behavior and interpersonal communication of mammals (Beuchamp, G. K., et al., The Pheromone Concept in Mammalian Chemical Communication: A Critique', In: *Mammalian Olfaction, Reproductive Processes, and Behavior,* Doty R. L., Ed., Academic Press, 1976).

The subject invention concerns the non-systemic administration to the vomeronasal organ (VNO) of certain steroids to alleviate symptoms of PMS and anxiety, as well as for treatment of elevated body temperature and paroxistic tachycardia (high pulse rate). Administration provides for contacting neurochemical receptors in the VNO (also known as "Jacobson's organ"), with one or more steroid(s) or with compositions containing the steroid(s). This organ is accessed through the nostrils of most higher animals—from snakes to humans, and has been associated, inter alia, with pheromone reception in certain species (see generally Muller-Schwarze & Silverstein, *Chemical Signals,* Plenum Press, New York (1980)). The axons of the neuroepithelia of the vomeronasal organ, located supra palatinal, form the vomeronasal nerve and have direct synaptic connection to the accessory olfactory bulb and indirect input from there to the cortico-medial amygdaloid basal forebrain and hypothalamic nuclei of the brain. The distal axons of terminalis nerve neurons may also serve as neurochemical receptors in the VNO. Stensaas, L. J., et al., *J. Steroid Biochem. and Molec. Biol.* (1991) 39:553. This nerve has direct synaptic connection with the hypothalamus.

Johnson, A. et al. (*J. Otolaryngology* (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., supra; and by Moran, D. T., et al., Garcia-Velasco, J. and M. Mondragon; Monti-Bloch, L. and B. Grosser all in *J. Steroid Biochem. and Molec. Biol.* (1991) 39.

This invention relates to the unexpected discovery that, when administered into the VNO of human subjects, certain neurochemical ligands, particularly steroids, and related compounds, specifically bind to chemoreceptors of certain nasal neuroepithelial cells and this binding generates a series of neurophysiological responses resulting in alleviating symptoms of PMS and anxiety. An effect via the VNO on the hypothalamus can affect the function of the autonomic nervous system and a variety of behavioral-or physiological phenomena which include, but are not limited to the following: anxiety, premenstrual stress, fear, aggression, hunger, blood pressure, and other behavioral and physiological functions normally regulated by the hypothalamus. See Otto Appenzeller, *The Autonomic Nervous System. An Introduction of basic and clinical concepts* (1990); Korner, P. I. *Central nervous control of autonomic cardiovascular function*, and Levy, N. M. and Martin, P. J. *Neural control of the heart*, both in *Handbook of Physiology; Section 2; Cardiovascular System—the heart*, Vol. I, Washington D.C., 1979, American Physiological Society; Fishman, A. P., et al. editors, *Handbook of Physiology, Section 3: Respiratory System. Vol. II. Control of breathing*, Bethesda Md., 1986. American Physiological Society.

Patients diagnosed with premenstrual dysphoric disorder (PMDD, commonly referred as premenstrual syndrome or PMS), show negative changes in mood together with physical symptoms, during the luteal phase of the menstrual cycle (see Table I). The symptoms are severe enough to cause physical or emotional distress, and they remit shortly after the onset of menstruation. However, they are not unique or diagnostic for this disease. Several surveys show that 30% of women have classical premenstrual dysphoric disorder symptoms, 2% to 10% being severely affected (Woods et al., *Am. J. Pub. Health*, 72:1257–62, 1982; Van Keep et al., "The Premenstrual Syndrome—An Epidemiologic and Statistical Exercise", Van Keep, P. A. and Utian, W. H., Eds., *The Premenstrual Syndrome, MTP Press Ltd.*, Lancaster, England, 1981; and Andersch et al., J. Psychomsom. Obstet. Gyn. 5:39–46, 1986). It is also reported that PMDD is not a disease of just older women since teenagers and young women have symptomatology as frequently as older women (Rivera-Tovar et al., Am. J. Psychiatry, 147:1634–43, 1990).

Many patients that seek treatment for PMDD may be found to suffer from a generalized psychiatric disorder. However, the main feature distinguishing PMDD from chronic psychiatric disorders is the presence of at least one asymptomatic week in the follicular phase of every menstrual cycle. A list of the common symptoms of this syndrome is presented in Table I. Most women report a variety of emotional, physical and behavioral changes associated with the luteal phase of the menstrual cycle. But only those women that report cyclic luteal phase symptoms that remit during menstruation, and that significantly affect their level of psychological or occupational functioning have PMDD.

TABLE I

| Common PMDD symptoms | | |
|---|---|---|
| Emotional | Physical | Behavioral |
| Anxiety | Headache | Food cravings |
| Irritability | Migraines | Increased appetite |
| Labile moods | Breast tenderness | Increased alcohol intake |
| Depression | Swelling of extremities | Decreased motivation |
| Anger | Bloatedness | Decreased efficiency |
| Sadness | Fatigue | Avoid activities |
| Crying easily | Aodominal cramps | Staying at home |
| Nervous tension | Aches and pain | Sleep changes |
| Overly sensitive | Weight gain | Changes in libido |
| | Skin problems | Reduced cognitive function |
| | Hot flashes | Social isolation |
| | Gastrointestinal | Poor concentration |
| | Dizziness | Forgetfulness |
| | Palpitation | |

In recent studies it was found that picogram quantities of some vomeropherins locally delivered in vapor form to the VNO of normal women (20 to 60 years old), produce significant behavioral and autonomic changes. Monti-Bloch et al., *J. Ster. Biochem. Molec. Biol.*, 39 (4B):573–582 (1991); Monti-Bloch et al., *Psychoneuroendocrinology*, 19:673–686 (1994). Subjects show mood changes characterized by decreased negativity. There is a clear decrease in negative aspect and negative character, and the patients feel relaxed. These changes correlate with increased parasympathetic tone in all individuals (mild bradypnea and bradycardia, small but significant increased body temperature [0.7° C.+0.5], change in skin conductance, and also increased alpha-cortical activity). Also, noticeable is the latency of these effects that correlates well with the latency of polysynaptic reflexes. The conclusion is that those vomeropherins stimulated receptors in the vomeronasal organ that in turn influenced the hypothalamus via the vomeronasal-terminalis system.

The present invention also provides attenuation of symptoms of general anxiety, which are characterized by the Hamilton-A standard.

SUMMARY OF THE INVENTION

The method of the invention has the following advantages: 1) administration directly to the chemoreceptors in the nasal passage and the vomeronasal organ, without pills or needles—i.e., non-invasively; 2) a mode of drug action through the invention system and not through the circulatory system—thus brain function can be affected without consideration of the bloodbrain barrier; 3) a direct means of affecting the hypothalamus—there is only one synaptic junction between pheromone receptors and the hypothalamus; and, 4) providing a highly specific drug effect, thereby greatly reducing the potential for undesirable side-effects—this because sensory nerves are addressed to a specific location in the brain.

Additional objects, advantages and novel features of the invention will be set forth in part in the description which follows, and in part will become apparent to those skilled in the art upon examination of the following, or may be learned by practice of the invention.

Among the compositions, a preferred class contains a pharmaceutically acceptable carrier and a pregnane steroid with the formula:

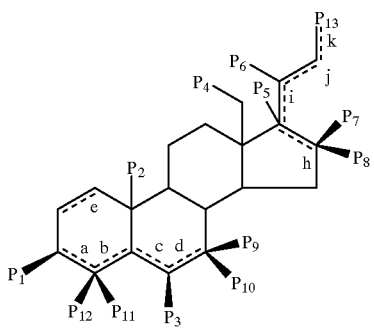

wherein $P_1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, oxo, halo, hydroxy, alkoxy, and acyloxy; $P_4$ through $P_{12}$ may each be, independently, hydrogen, halo, methyl, or halo-, dihalo-, or perhalomethyl and when $P_2$ is methyl and $P_3$ is β-hydroxy, $P_2$ and $P_3$ may be jointed to form a cylic ether; $P_{13}$ is hydrogen, methyl, methylene, halo-substituted methyl, halo-substituted methylene, ethyl, ethylenyl, acetylenyl, methyl-methylenyl, methyl-methinyl; and "a", "b", "c", "d", "e", "h", "i", and "j" are alternative sites for optional double bonds, and "j" or "k" may also be triple bonds. Halo substituents include fluoro, bromo, chloro and iodo atoms.

One class of preferred steroids has "b" as a double bond, particularly wherein "d" or "e" is also a double bond. Another preferred class has "a" and "c" as double bonds, or only "c" as a double bond. Yet another preferred class contains "h" as a double bond, with i and j being absent (i.e., single bonds), j being a double bond, or j being a triple bond. In another class, "h" is absent, and j or i is a double bond, or i and j are absent, or j and i are double bonds, or j is a triple bond.

The term lower alkyl, lower alkoxy, etc., is meant to encompass carbon chains of 1 to 6 carbon atoms, preferably 1 to 4 carbon atoms.

A second class of compositions contains a pharmaceutically acceptable carrier and a pregnane steroid with the formula:

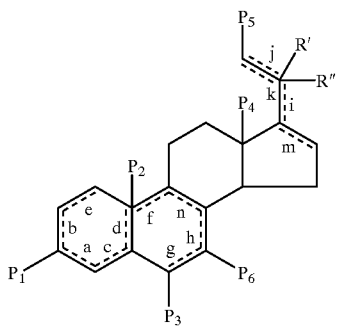

wherein $P_1$ is oxo, α- or β-hydroxy, α- or β-acetoxy, α- or β-propionoxy, α- or β-lower acetoxy, α- or β-acyloxy, or α- or β-benzyloxy;

"a", "b", "c", "d", "e", "f", "g", "h", "i", "j", "m" and "n" are alternative sites for optional double bonds, and "k" may be absent or present with "j" to form a triple bond;

$P_2$ is hydroxy, hydrogen, lower alkoxy of 1 to 6 carbon atoms, or $P_2$ is absent;

$P_3$ is oxo, hydrogen, hydroxy, lower alkoxy of 1–6 carbon atoms or halo;

$P_4$ is methyl or ethyl;

$P_5$ is hydrogen, methyl or halo;

$P_6$ is hydrogen or methyl.

One subset of the second preferred class of steroid compositions contains steroids wherein "d" is a double bond, and optionally "b" is present as a double bond. Another preferred class has "a", "d" and "e" present, and g or h are optionally present. If "g" is present in this case, then "n" is optionally present. Another preferred class has "c" present, with "f" optionally present.

A third class of compositions contain steroids with the formula:

wherein $R_1$ is selected from the group consisting essentially of one or two hydrogen atoms, methyl, methylene, and one or two halo atoms; $R_2$ is absent or is selected from the group consisting essentially of hydrogen and methyl; $R_3$ is selected from the group consisting essentially of oxo, hydroxy, lower alkoxy, lower acyloxy, benzoyl, cypionyl, glucuronide and sulfonyl; $R_4$ is selected from the group consisting essentially of hydrogen, hydroxy, lower alkoxy, lower acyloxy, oxo and halo; $R_5$ is absent or is selected from the group consisting essentially of hydrogen, hydroxy, lower alkoxy and lower acyloxy; $R_6$ is a hydrogen or a halo; and "all represents optional aromatic unsaturation of ring A of said steroid, or "b", "c", and "d" are each optional double bonds; "e", "f", "g", "h", "i" and "j" are each optional double bonds; and "e" may also form an expoxy ring with $C_{16}$ and $C_{17}$. In this embodiment, the steroid is preferably administered in the form of a pharmaceutical composition containing one or more pharmaceutically acceptable carriers.

A preferred subset of the third class of steroids are those in which "a" is present and "g", "h" or "i" are optional double bonds. Another preferred class contains "b", "c" or "j" as a double bond. Yet another class contains "c" and "d" as double bonds. Still another class contains $R_2$ as methyl and "e" as a double bond.

The term lower alkyl, lower alkoxy, etc., encompasses carbon chains of 1 to 6 carbon atoms, preferably 1 to 4 carbon atoms. Halo includes I, Br, F and Cl.

A fourth class of preferred compositions contains a pharmaceutically acceptable carrier and an androstane steroid with the formula:

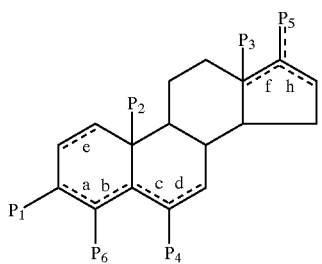

wherein $P_1$ is selected from the group consisting of oxo, α-(β-) hydroxy, α-(β-) acetoxy, α-(β-) propionoxy, α-(β-) methoxy, α-(β-)lower acyloxy, α-(β-) lower alkyloxy, and α-(β-) benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is absent or is selected from the group consisting of methyl, hydroxymethyl, acyloxymethyl, alkoxymethyl, lower alkyl, hydroxyalkyl, acyloxyalkyl, and alkoxylalkyl; $P_4$ is selected from the group consisting of hydrogen, oxo, halo, hydroxy, alkoxy, and acyloxy; $P_5$ represents one or 2 substituents, wherein $P_5$ comprises one or two hydrogen atoms, methyl, methylene, or one or two halo atoms; $P_6$ is hydrogen or halo; and "a", "b", "c", "lid", "e", "f", and "h" are alternative sites for optional double bonds.

One subset of the fourth preferred class of steroids as "b" as a double bond, particularly wherein "c" or "d" is also a double bond. Another subset has "a" and "c" as double bonds. Yet another subset contains $P_3$ as a methyl group, "h" as an optional double bond, and $P_3$ as methylene or one or two hydrogen atoms. A subset of steroids wherein "a" or "b" is a double bond is also preferred.

By halo, it is meant, F, Cl, Br, or I. The term lower alkyl, lower alkoxy, etc., is meant to encompass carbon chains of 1 to 6 carbon atoms, preferably 1 to 4 carbon atoms.

A fifth class of compositions comprise a pharmaceutical carrier and a 19-nor cholane of the formula:

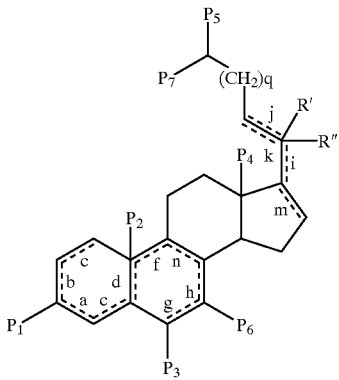

wherein $P_1$ is oxo, α- or β-hydroxy, α- or β-acetoxy, α- or β-propionoxy, α- or β-lower acetoxy, α- or #-lower acyloxy, or α- or β-benzyloxy;

"a", "b", "c", "d", "e", "f", "g", "h", "i", "j", "m", "s" and "n" are alternative sites for optional double bonds, and "k" may be absent or present with "j" to form a triple bond;

$P_2$ is hydroxy, hydrogen, lower alkoxy of 1 to 6 carbon atoms, or $P_2$ is absent;

$P_3$ is oxo, hydrogen, hydroxy, lower alkoxy of 1–6 carbon atoms or halo;

$P_4$ is methyl or ethyl;

each $P_5$ and $P_7$ independently is hydrogen, methyl or halo;

$P_6$ is hydrogen or methyl;

R' and R" are independently hydrogen or halo, are absent, or together form $=CH_2$; q is an integer from D to 2. Preferably, q=1.

One class of preferred 19-nor cholane steroid compositions contain steroids wherein "d" is a double bond, and optionally "b" is present as a double bond. Another preferred class has "a", "d" and "e" present, and g or h are optionally present. If "g" is present in this case, then "n" is optionally present. Other preferred classes have "c" or "s" present.

The novel class of 19-nor-cholanes are those of the above formula, excluding the compounds in the instances where $P_3$, $P_6$, $P_5$, $P_7$, R' and R" are hydrogen; $P_4$ is methyl, e, a, d are present; b, c, f, g, h, i, j, k, n, and s are absent, q=o, $P_1$ is hydroxy and m is present or absent.

The term lower alkyl, lower alkoxy, etc., is meant to encompass carbon chains of 1 to 6 carbon atoms, preferably 1 to 4 carbon atoms.

A class of novel steroids is also provided which have oxygen atoms attached to the D-ring. Such steroids have the formula:

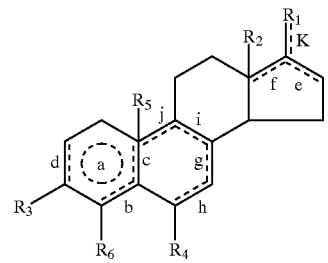

wherein $R_1$ is selected from the group consisting essentially of one or two hydrogen atoms, alkyl of 1 to 10 carbon atoms; $R_2$ is absent or is selected from the group consisting essentially of hydrogen, methyl and oxygen to form an epoxy ring with $C_{17}$; $R_3$ is selected from the group consisting essentially of oxo, hydroxy, lower alkoxy, lower acyloxy, benzoyl, cypionyl, glucuronide and sulfonyl; $R_4$ is selected from the group consisting essentially of hydrogen, hydroxy, lower alkoxy, lower acyloxy and halo; R, is absent or is selected from the group consisting essentially of hydrogen, hydroxy, lower alkoxy and lower acyloxy; $R_6$ is a hydrogen or a halo; and "a" represents optional aromatic unsaturation of ring A of said steroid, or "b", "c", and "d" are each optional double bonds; "g", "h", "i" and "j" are each optional double bonds; and "e" may form an epoxy ring with $C_{16}$ and $C_{17}$; "f" may form an epoxy ring with $C_{13}$ and $C_{17}$; and "k" may form an epoxy ring with $C_{17}$ and $C_{20}$.

Other objects of this invention are achieved by providing a method of altering hypothalamic function and/or autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence, whether or not the modified steroids are explicitly disclosed.

BRIEF DESCRIPTION OF THE DRAWINGS

FIGS. 85 and 86 show the data of measurements in men and women, respectively, of compound A8/C1.

FIGS. 87 and 88 show the data of measurements in men and women, respectively, of compound A2/C1.

FIGS. 89 and 90 show the data of measurements in men and women, respectively, of the acetate of compound A2/C1.

FIGS. 91 and 92 show the data of measurements in men and women, respectively, of compound A1/C1.

FIGS. 93 and 94 show the data of measurements in men and women, respectively, of compound A3/C1.

FIGS. 95 and 96 show the data of measurements in men and women, respectively, of compound A13/C1.

FIGS. 144A, 144B and 144C are graphic representations of the electrophysiological effect on receptor potential of the localized administration of particular steroids to the vomeronasal organ of male subjects (FIG. 144A) and to the olfactory epithelium (FIG. 144C). FIG. 144B is a graphic comparison of the effect of an Estrene on the VNO receptor potential of male and female subjects.

FIGS. 148A and 148B: EVG responses were measured as 15 described in male (A) and female (B) subjects.

FIGS. 148C and 148D: Electrodermal activity was measured as described. Changes (measured in xg) in response due to delivery of vomeropherins to the VNO of each subject are shown in male (C) and female (D) subjects.

FIGS. 148E and 148F: Alpha-cortical activity was measured as described. Changes in response due to delivery of vomeropherins to the VNO of male (E) and female (F) subjects.

FIGS. 148G and 148H: Skin temperature (ST) was measured as described. Changes in response due to delivery of vomeropherins to the VNO of each subject are shown in male (G) and female (H) subjects.

A=1,3,5(10),16-Estratetraen-3-yl acetate
B=Androsta-4,16-dien-3-one
C=1,3,5(10),16-Estratetraen-3-ol
D=3-Methoxy-Estra-1,3,5(10),16-tetraene
E=Androsta-4,16-dien-3α-ol
F=Androsta-4,16-dien-3β-ol

G=Androst-4-en-3-one
H=Androsta-4,16-dien-3,6-dione
J=10,17-Dimethylgona-4,13(17)-dien-3-one
K=1,3,5(10),16-Estratetraen-3-ol-methyl ether
L=1,3,5(10),16-Estratetraen-3-yl-propionate
EVG=Electro-vomeronasogram
GSR=Galvanic Skin Response
  =Electrodermal Activity (EDA)
ST=Skin Temperature

M=1,3,5(10)-Estratrien-3-ol

FIG. 152 depicts the synthesis of Estra-1,3,5(10),6-tetraen-3-ol and Estra-4,16-dien-3-ol.

FIG. 153 depicts the synthesis of compounds described in Examples 63 through 66.

Figure 154:
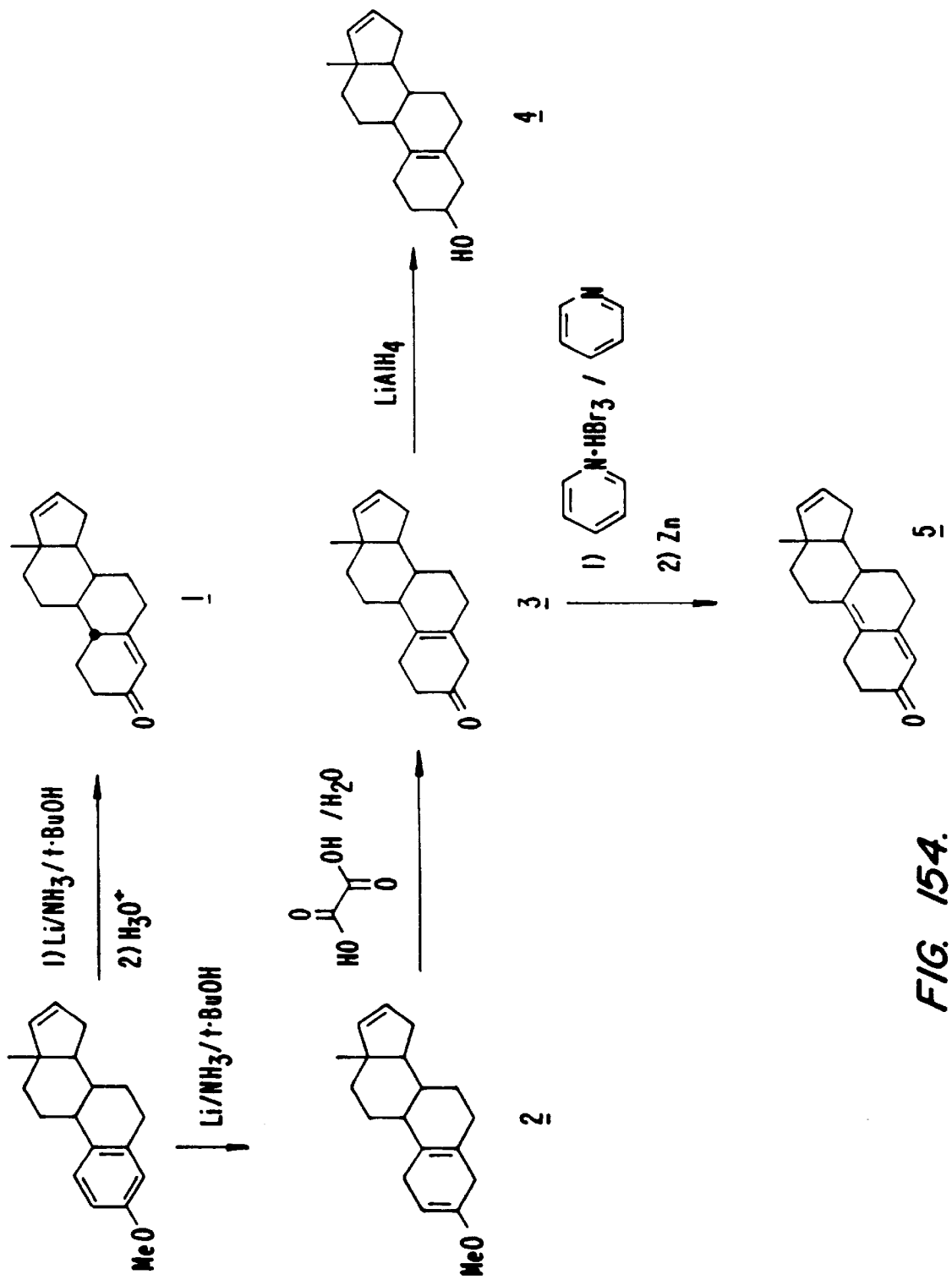

FIG. 154 illustrates the steps of synthesis described in Examples 67 through 71.

Figure 155:
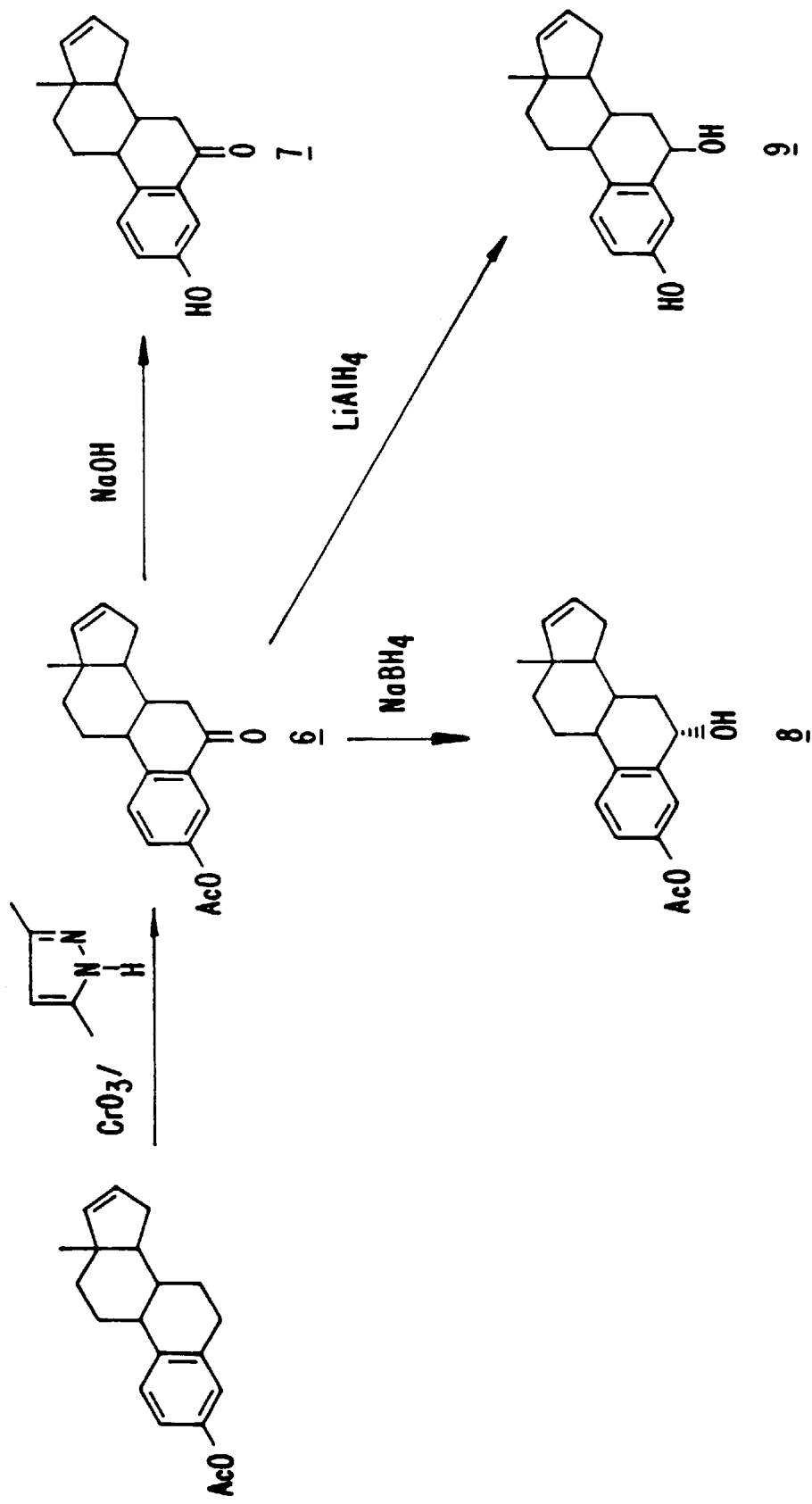

FIG. 155 illustrates the steps of synthesis described in Examples 72 through 75.

Figure 156:
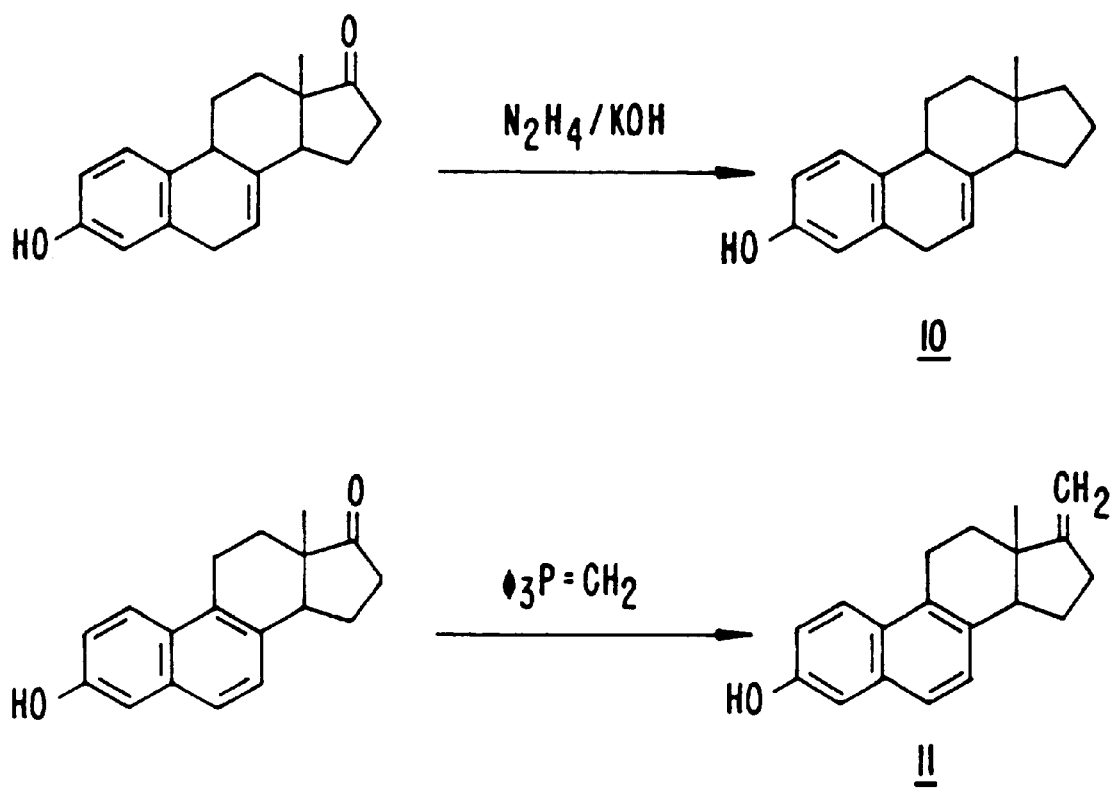

FIG. 156 illustrates the steps of synthesis described in Examples 76 through 77.

Figure 157:
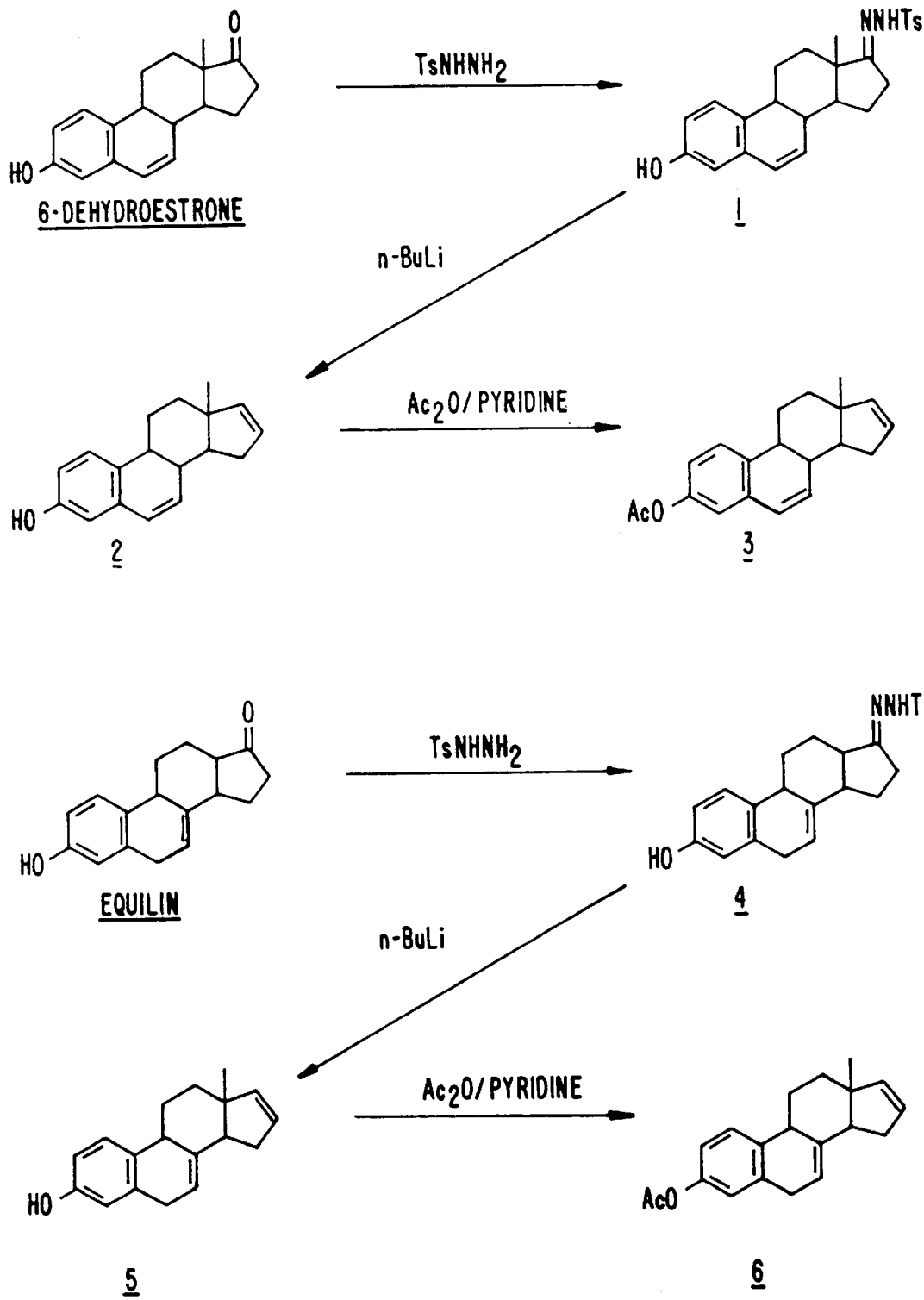

FIG. 157 illustrates the steps of synthesis described in Examples 78 through 83.

Figure 158:
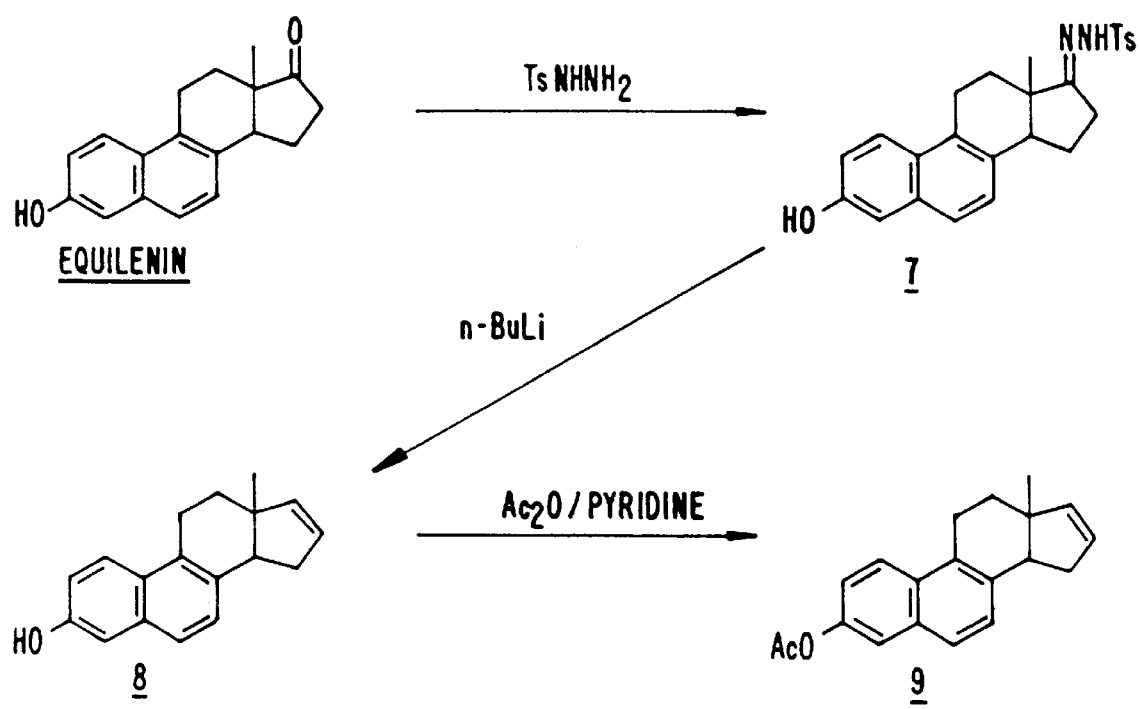

FIG. 158 illustrates the steps of synthesis described in Examples 84 through 86.

Figure 159:
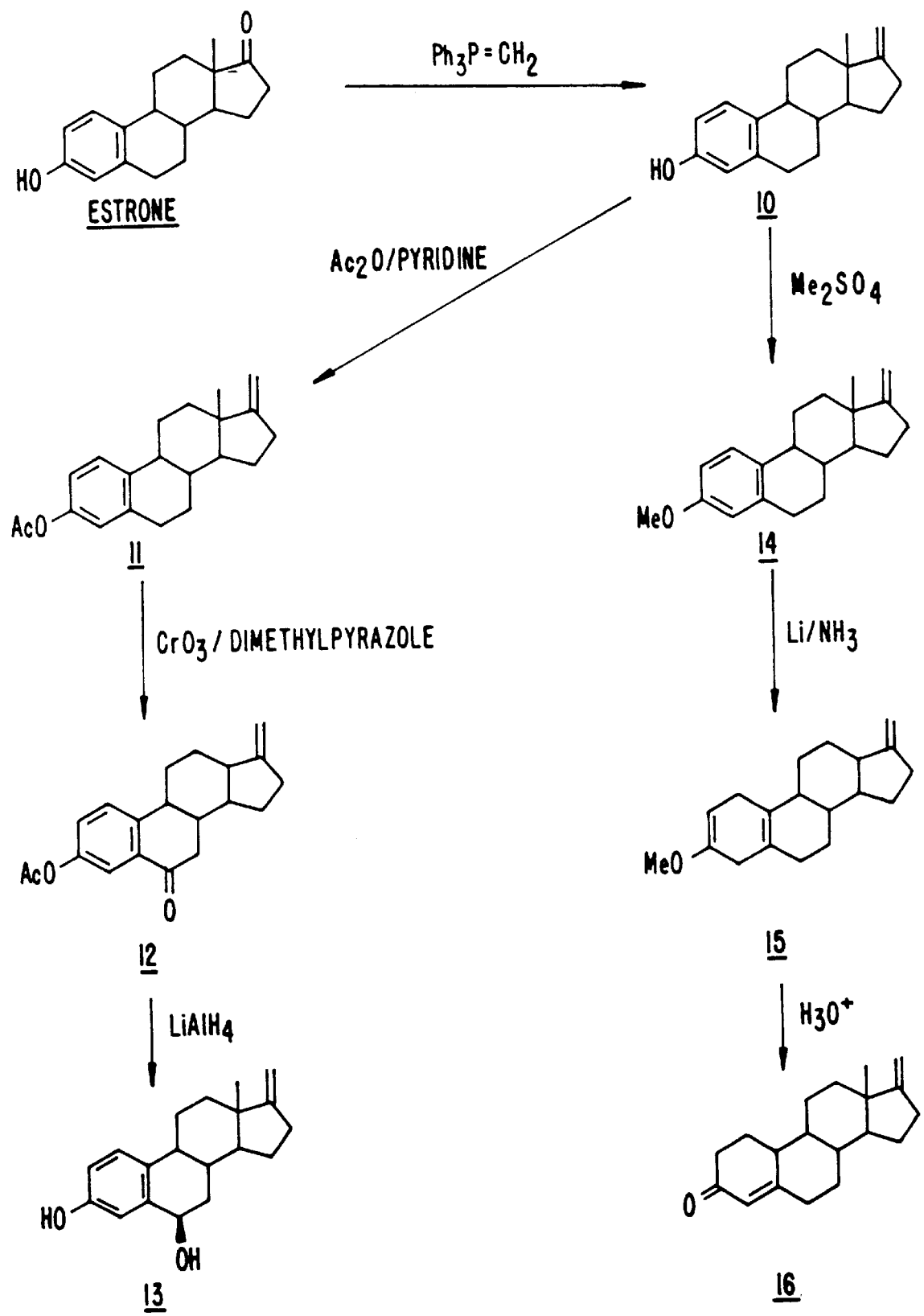
Figure 16O:
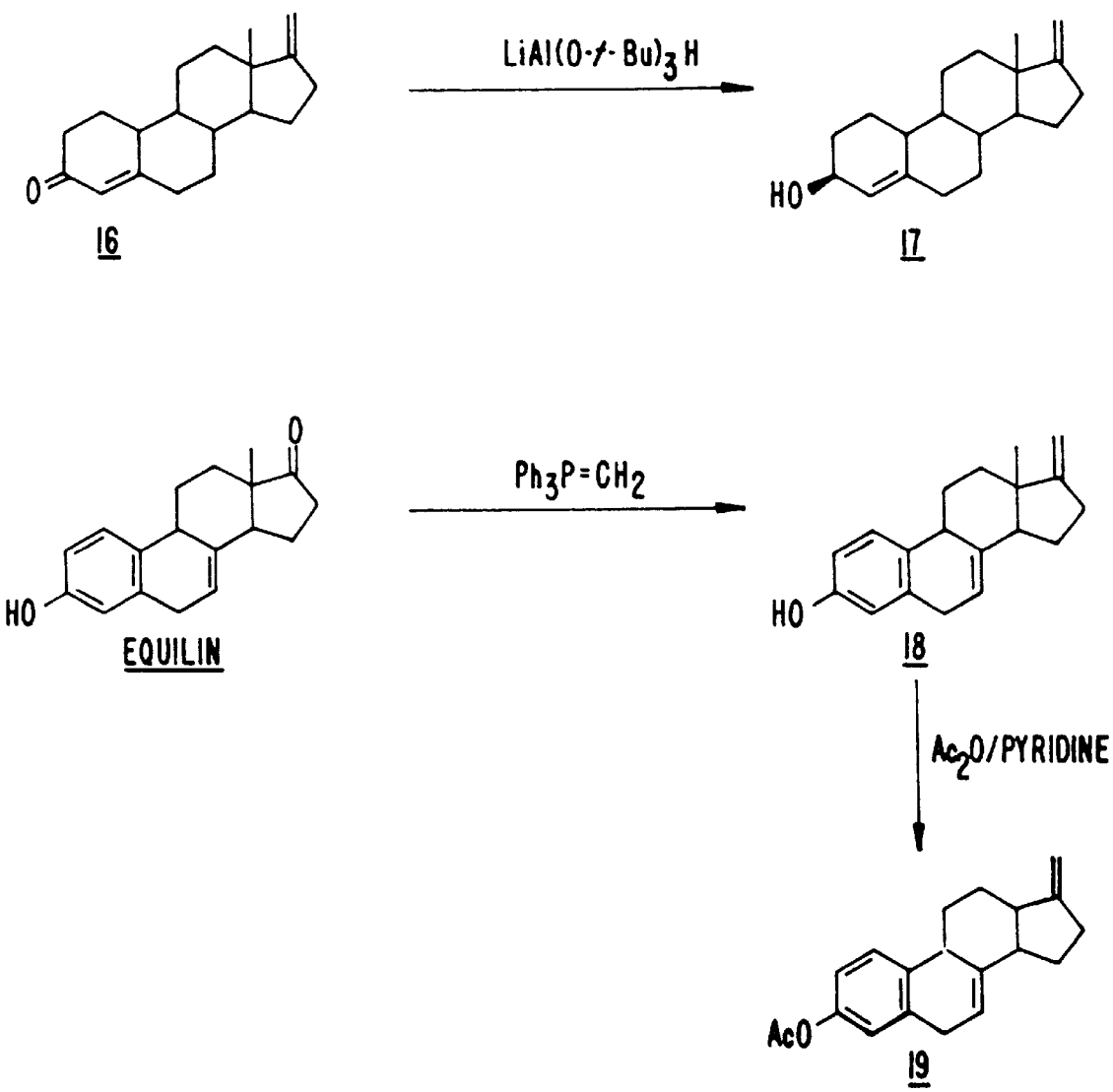

FIG. 159 illustrates the steps of synthesis described in Examples 87 through 93.

FIG. 160 illustrates the steps of synthesis described in Examples 94 through 96.

Figure 161:
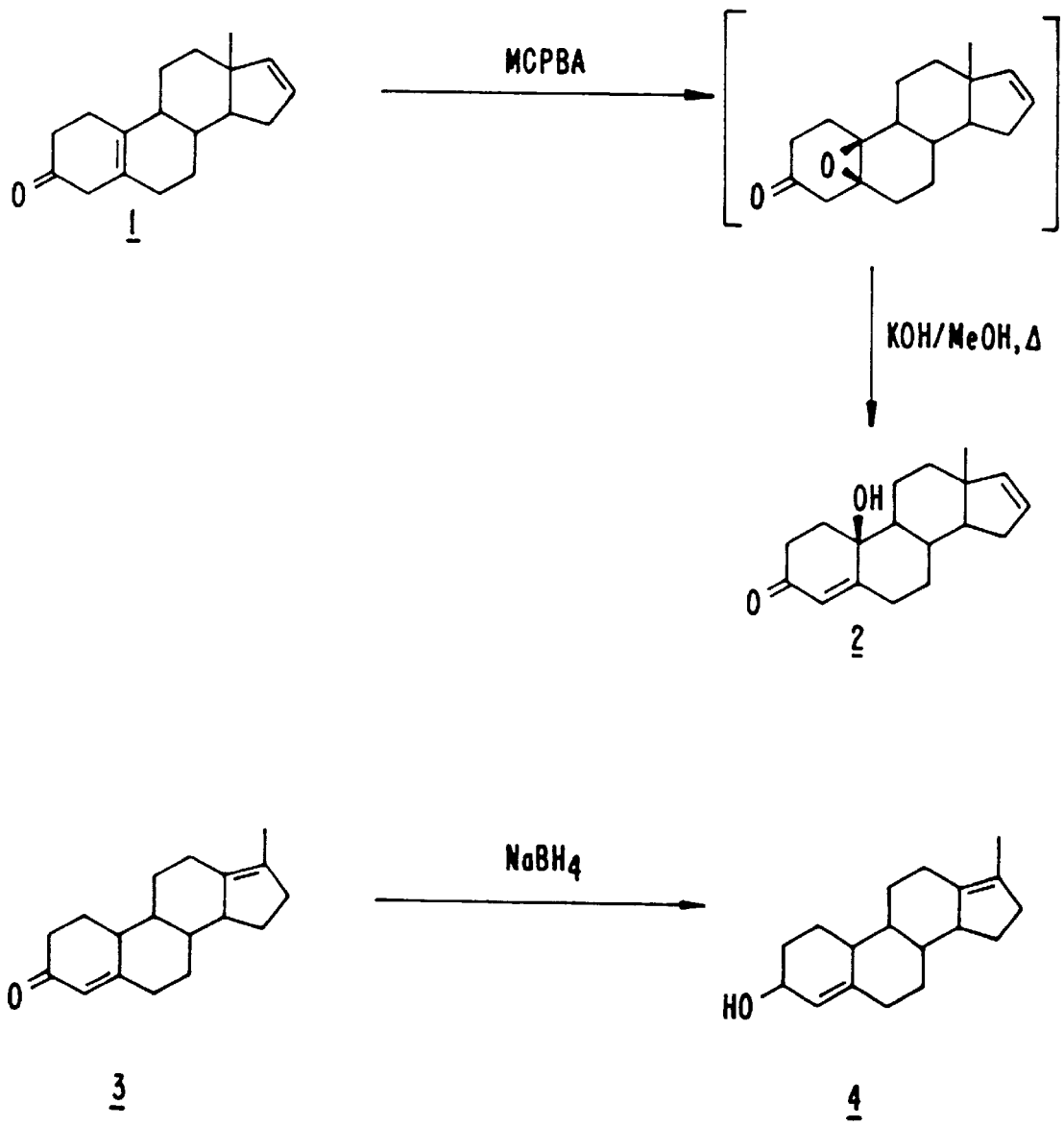

FIG. 161 illustrates the steps of synthesis described in Examples 97 through 98.

Figure 162A:
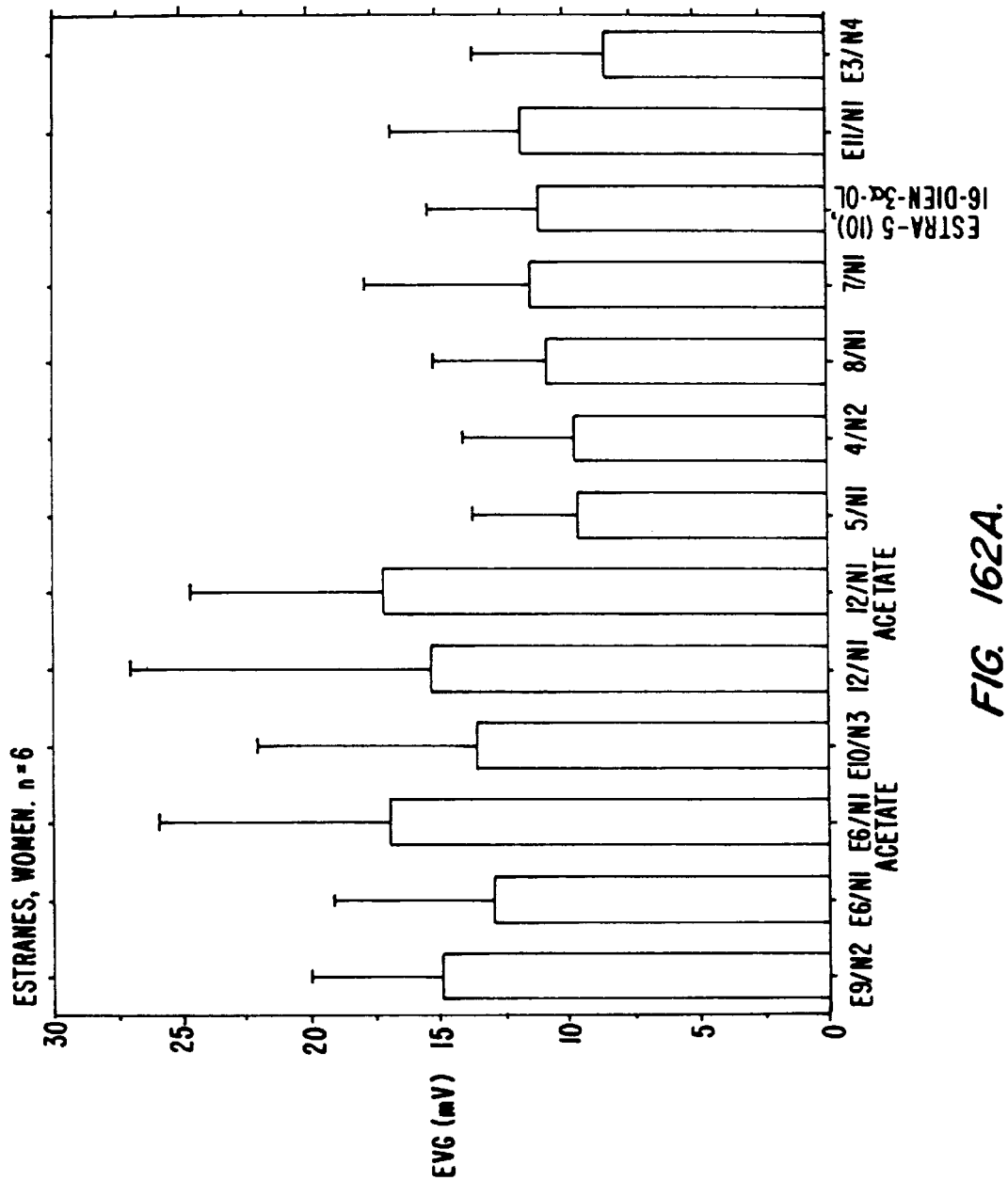
Figure 162B:
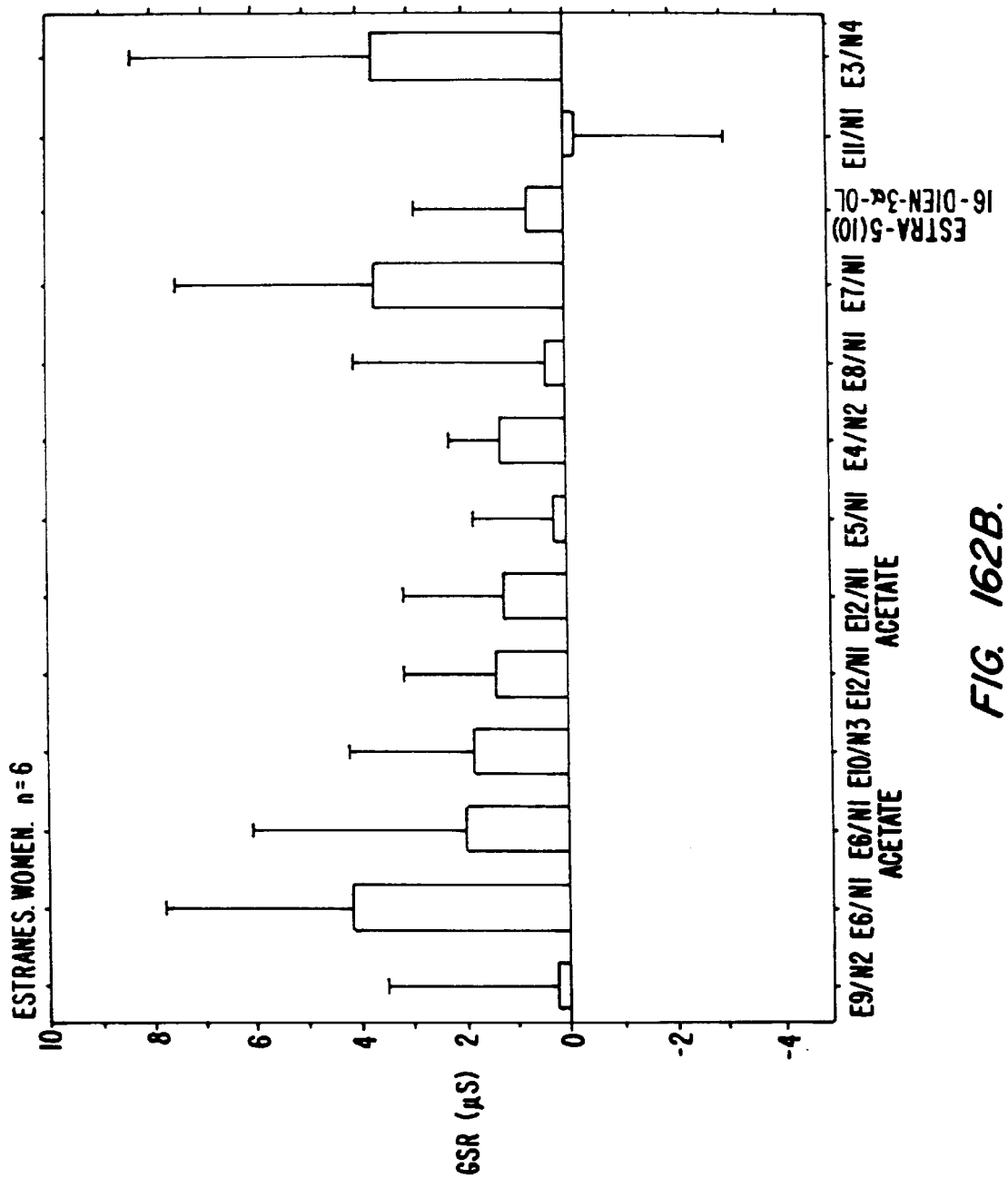
Figure 162C:
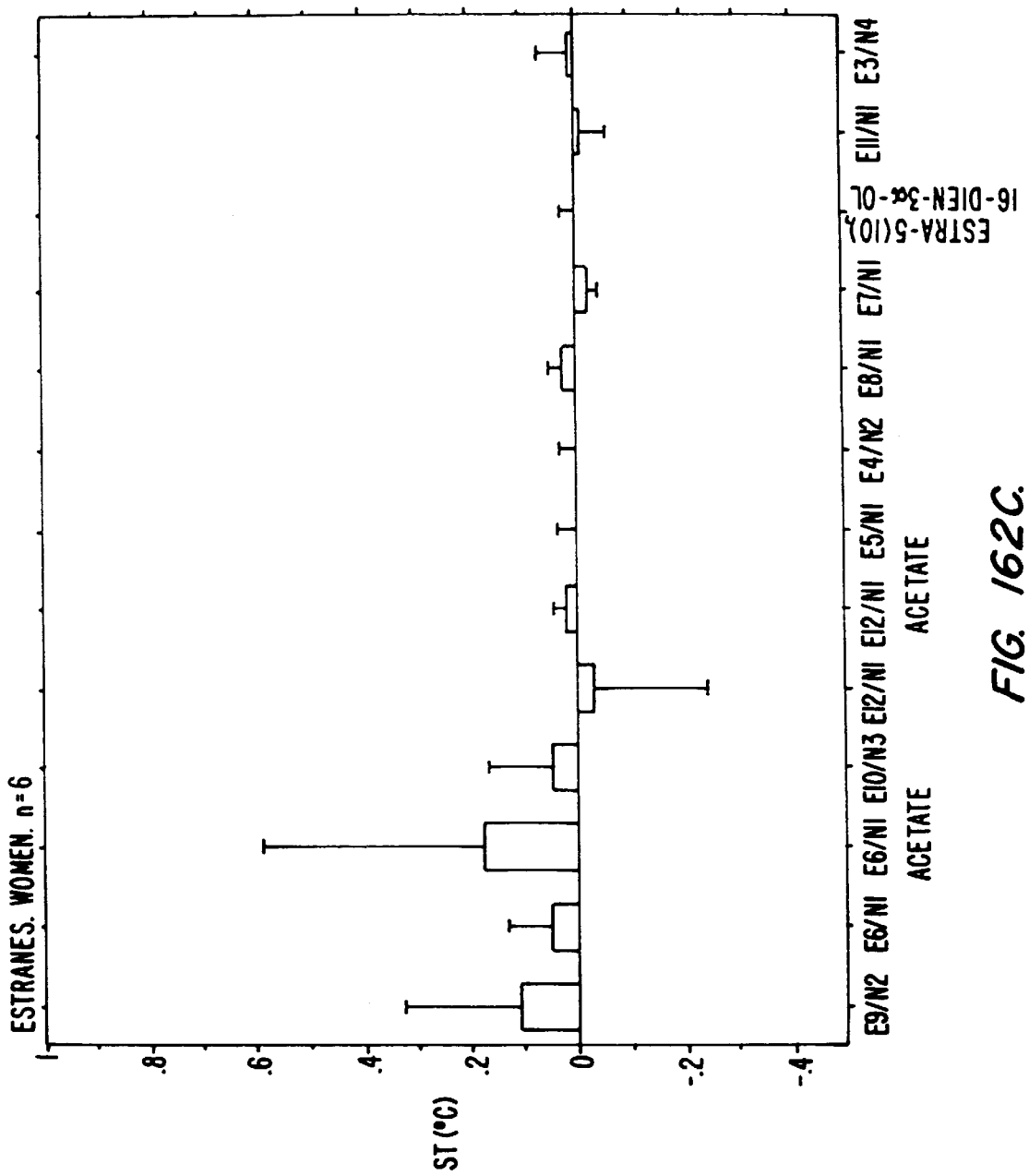

FIGS. 162A, 162B and 162C illustrate the EVG, GSR and ST data on women, respectively, for 13 estranes on Chart 1.

Figure 163A:
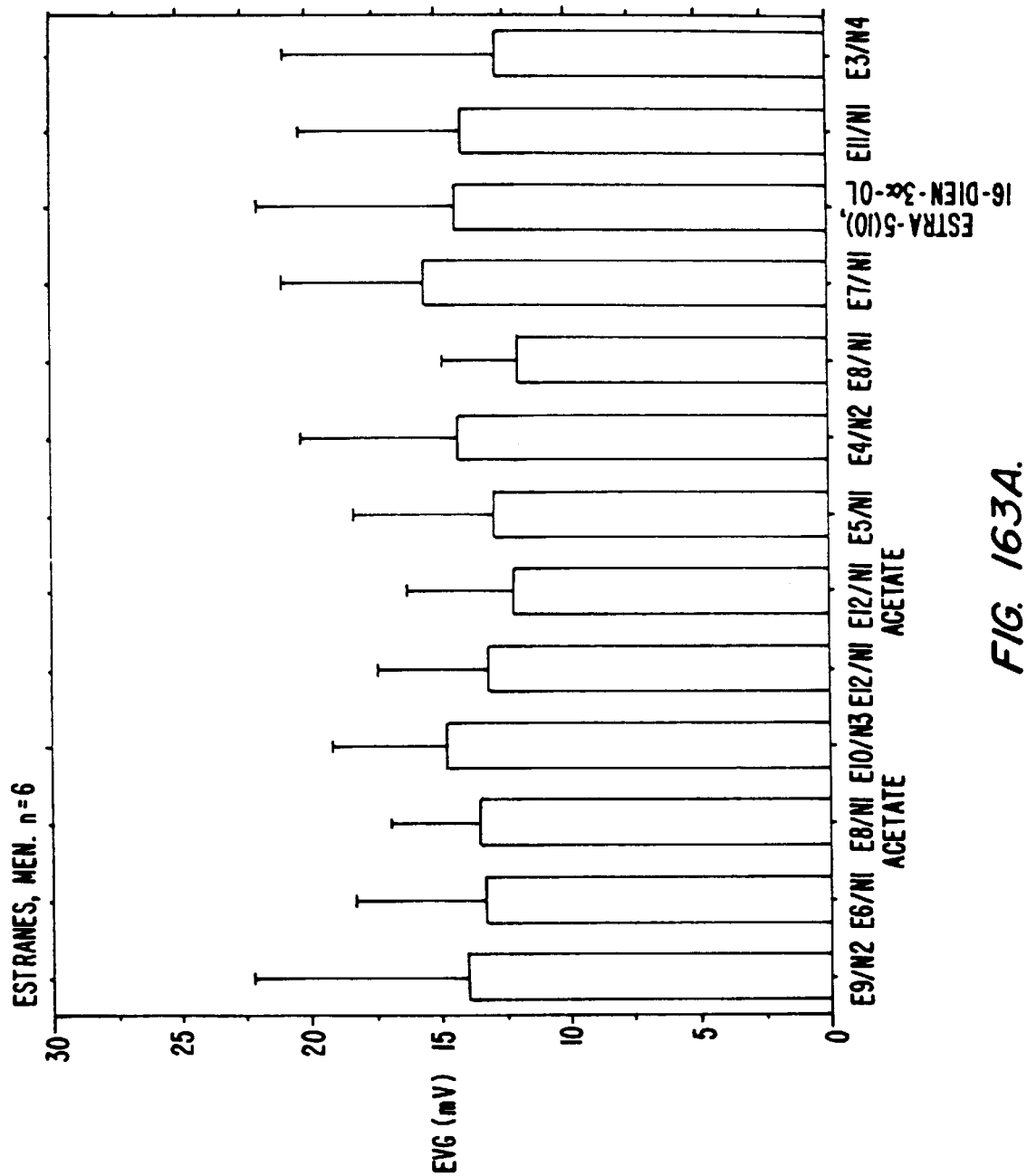
Figure 163B:
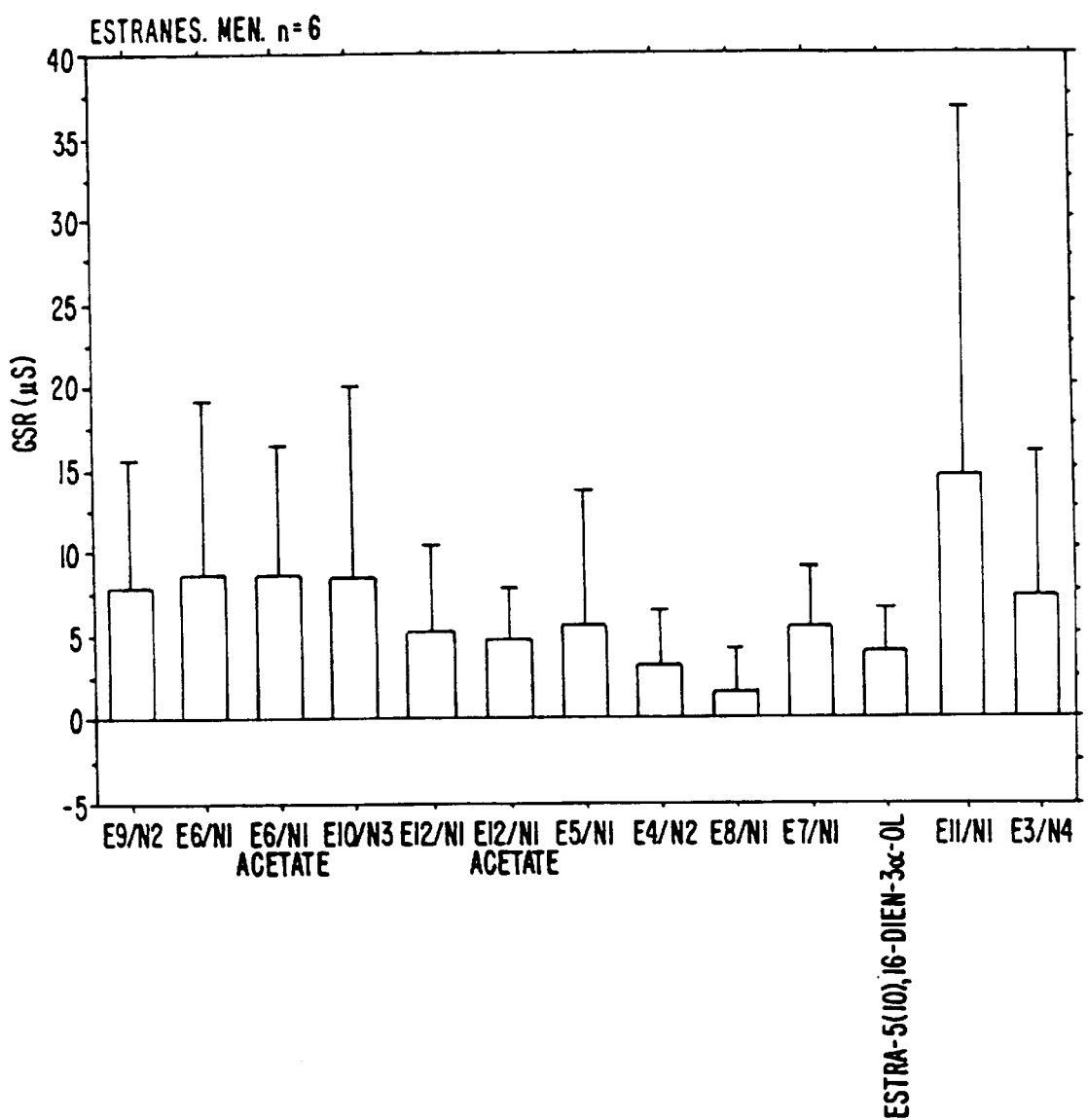
Figure 163C:
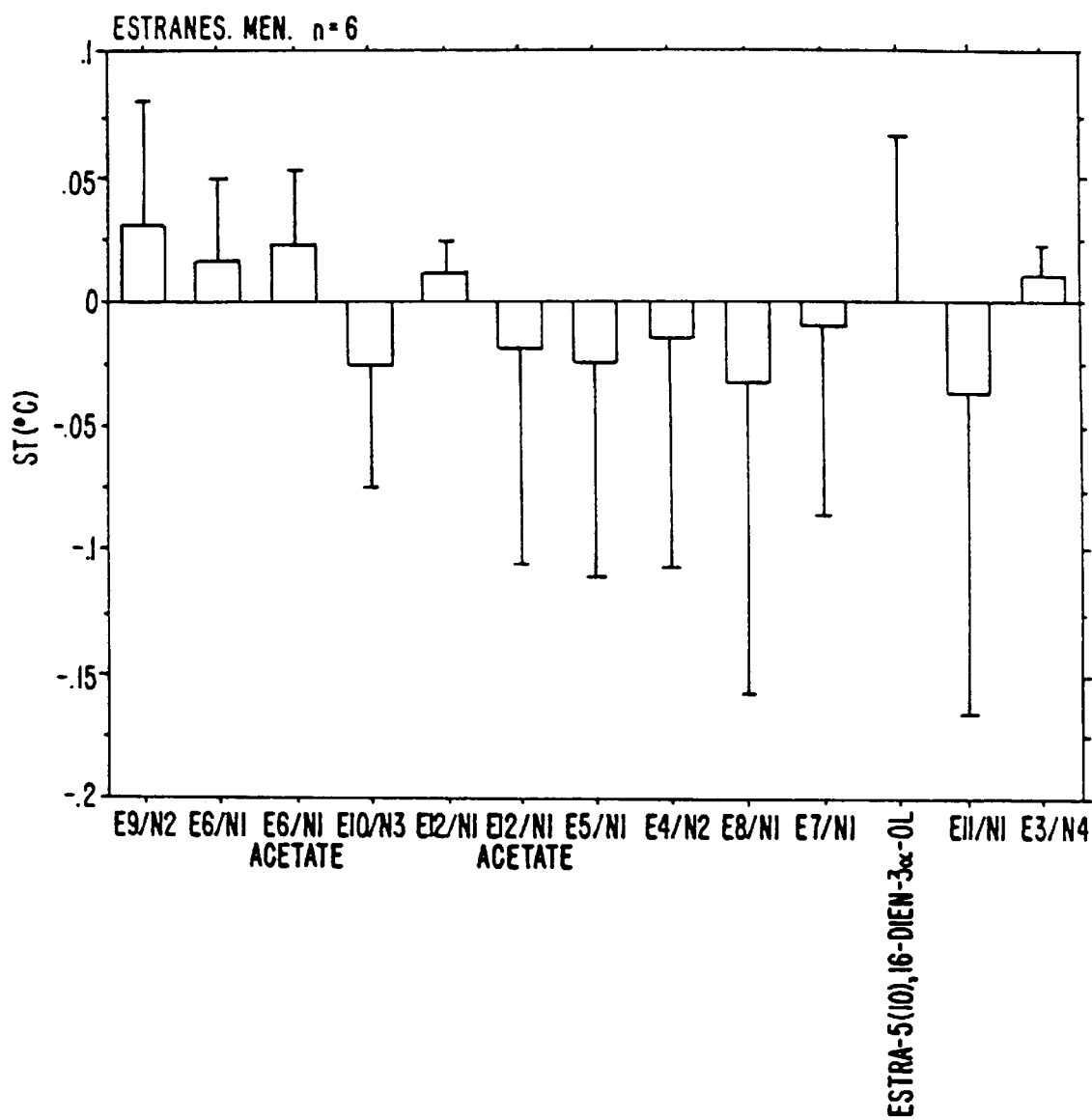
Figure 164A:
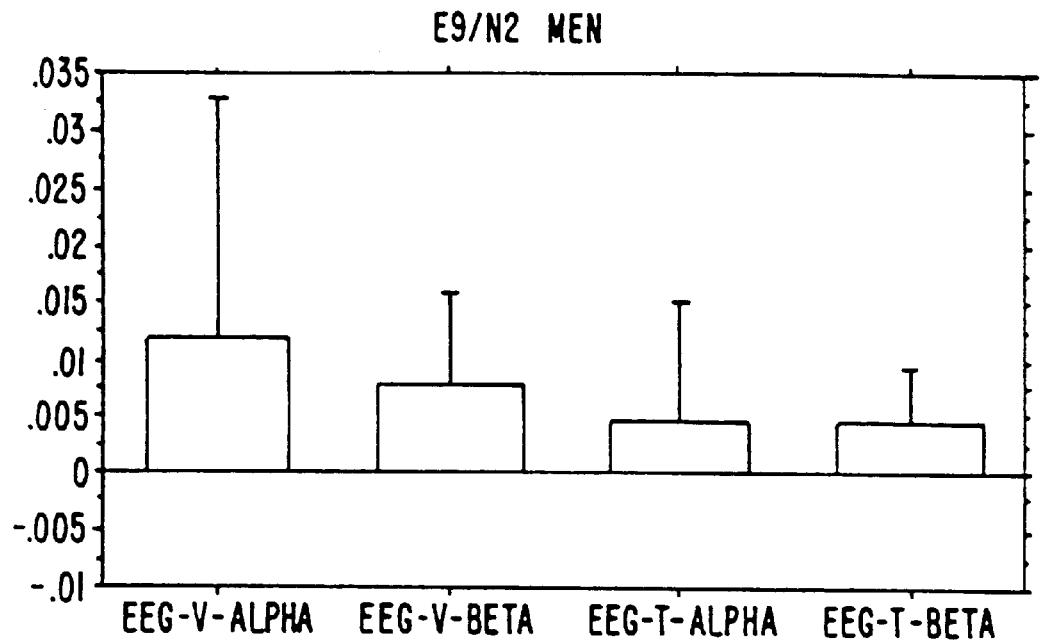
Figure 164B:
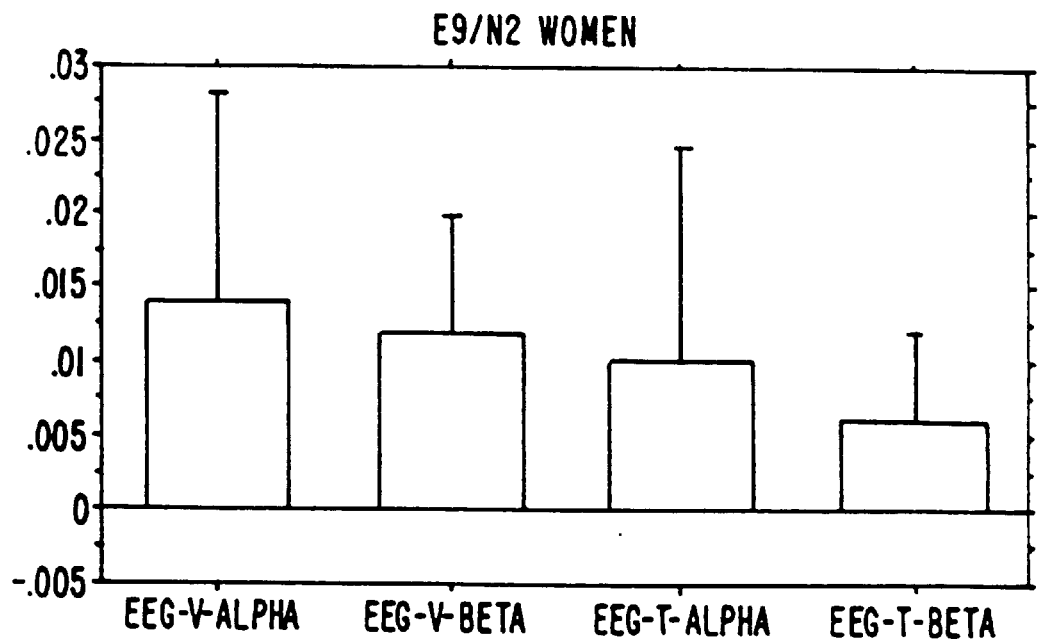
Figure 165A:
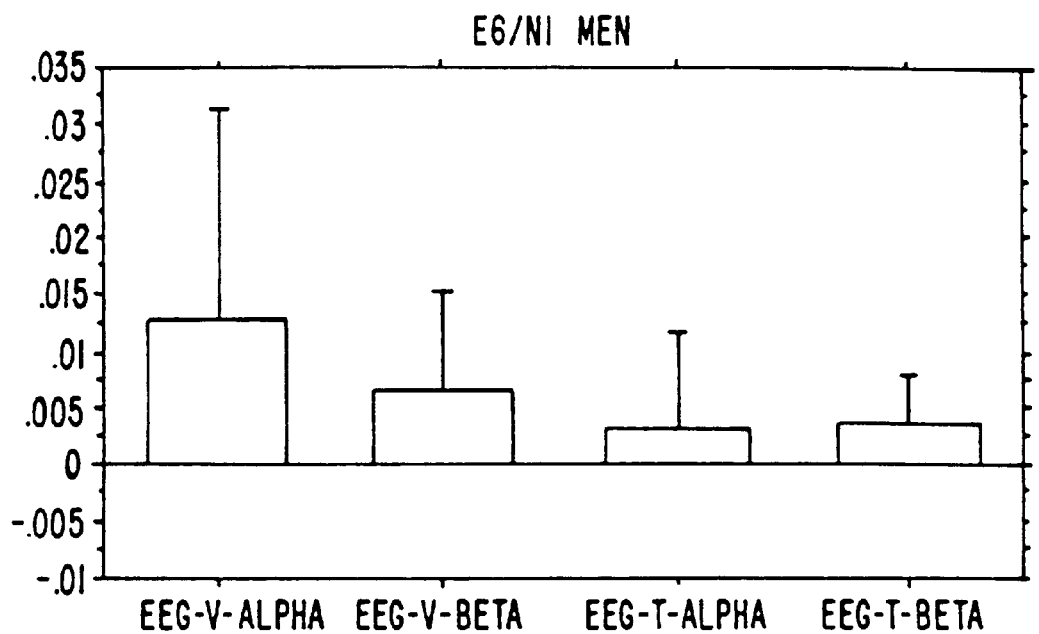
Figure 165B:
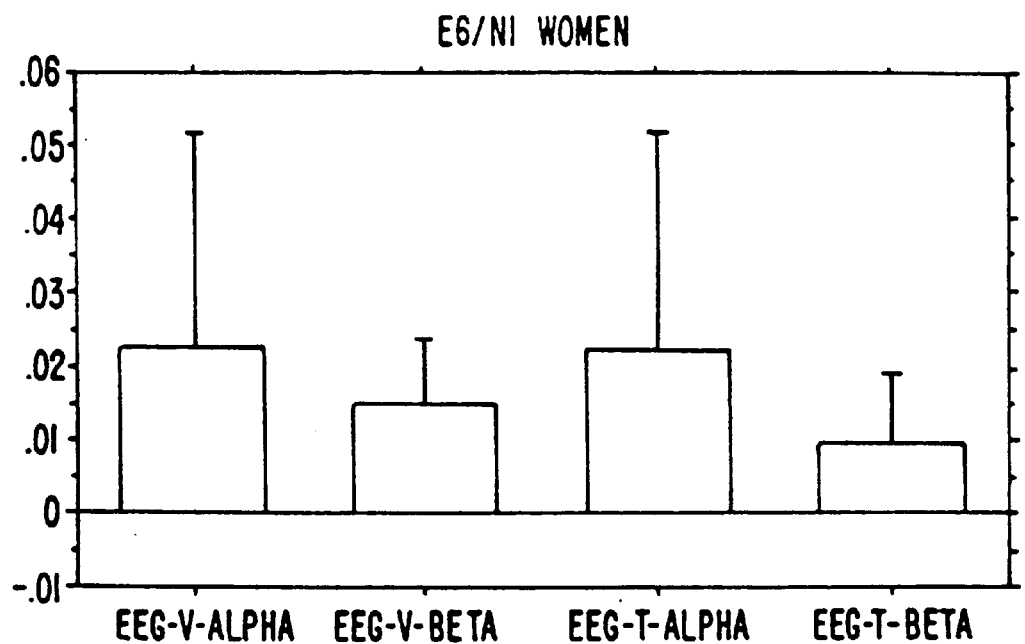
Figure 166A:
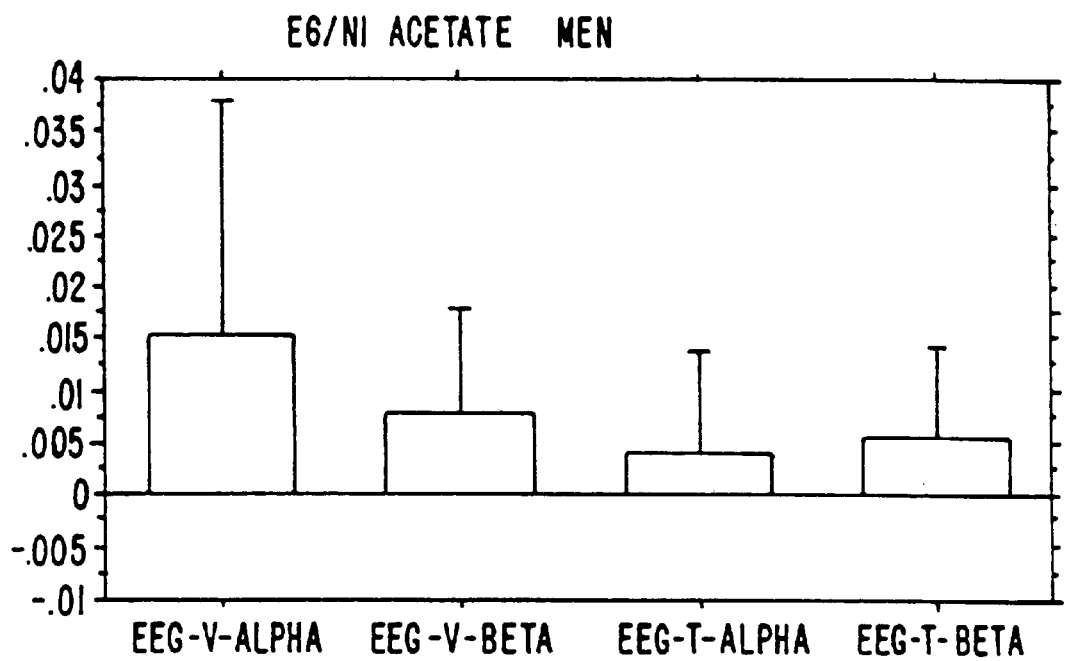
Figure 166B:
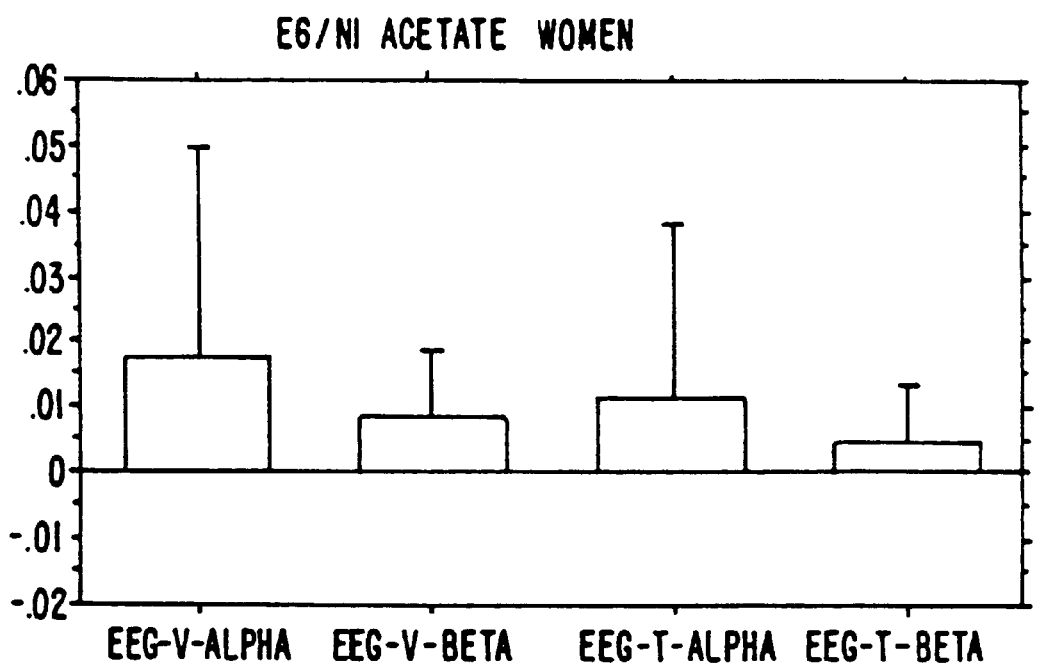
Figure 167A:
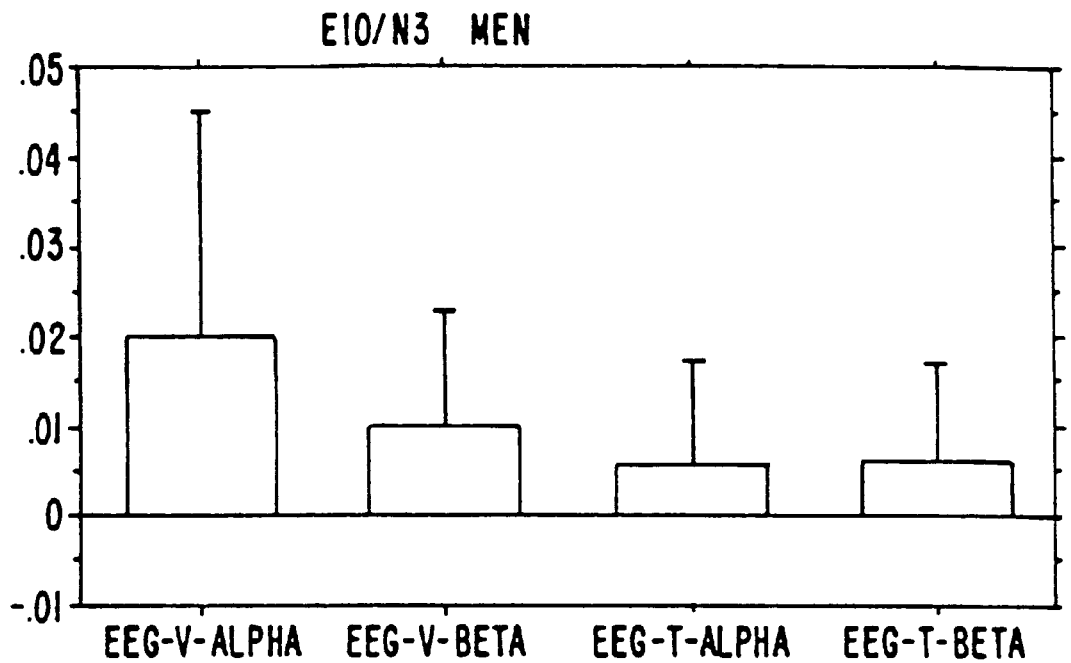
Figure 167B:
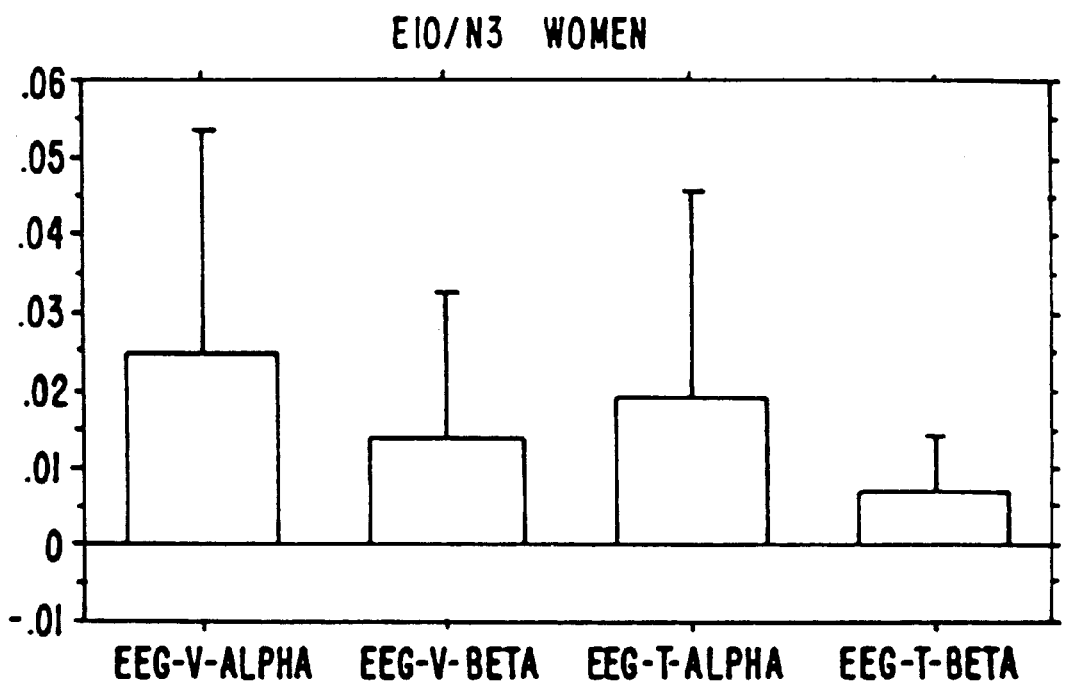
Figure 168A:
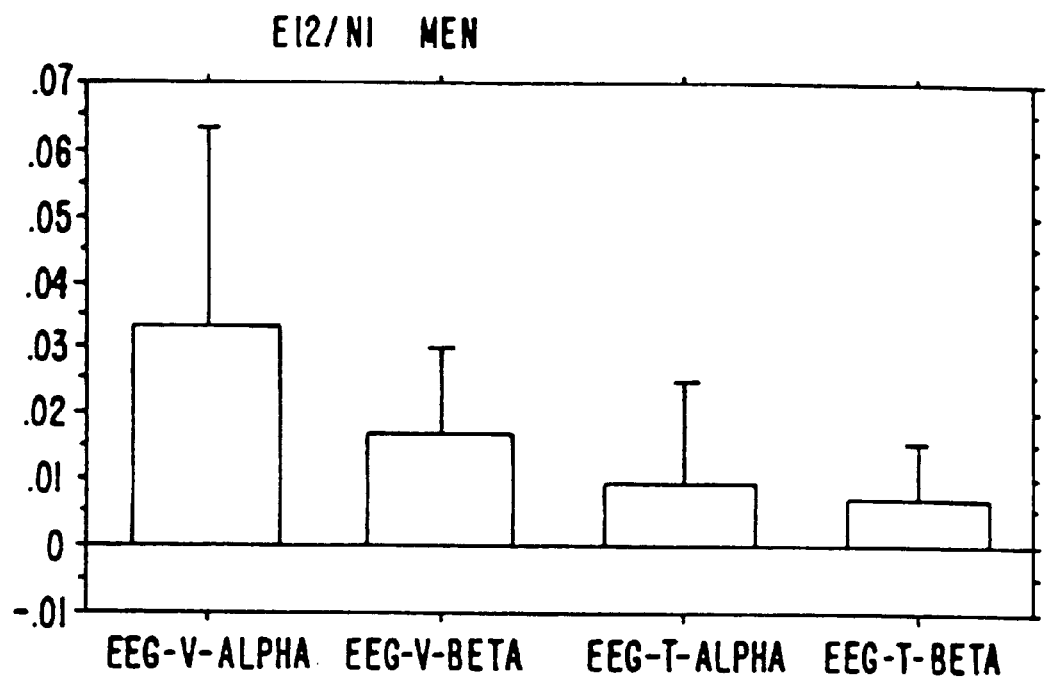
Figure 168B:
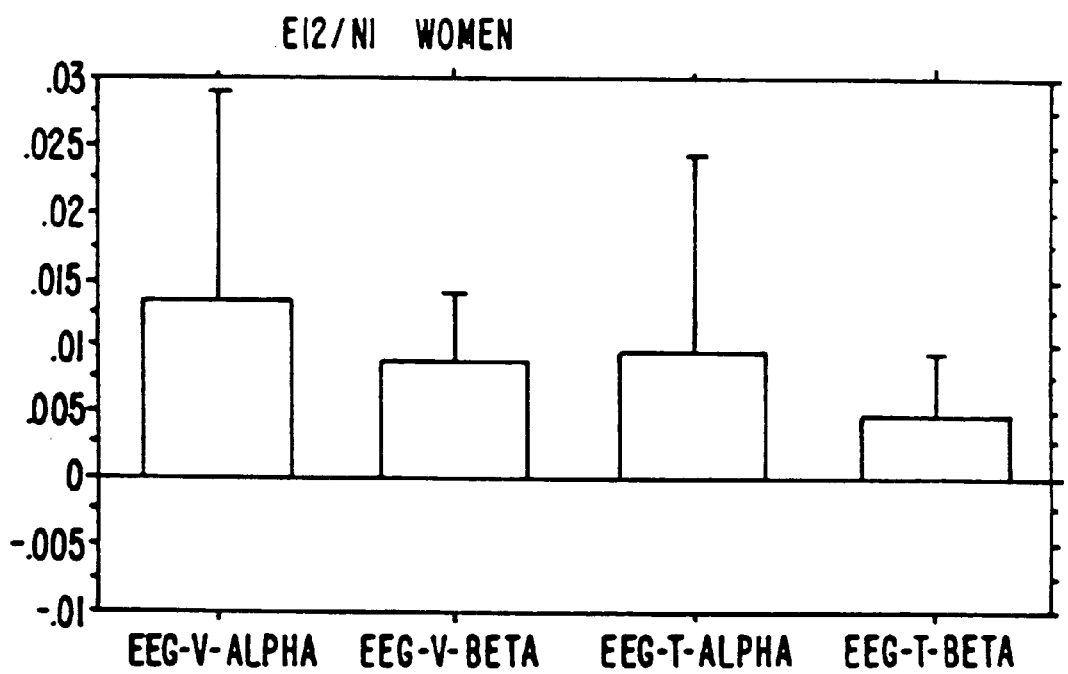
Figure 169A:
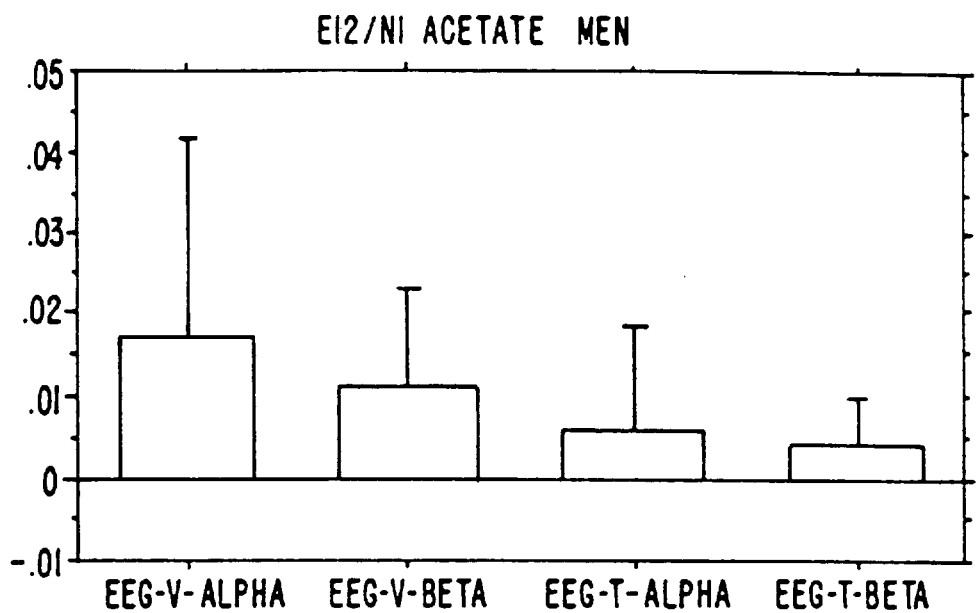
Figure 169B:
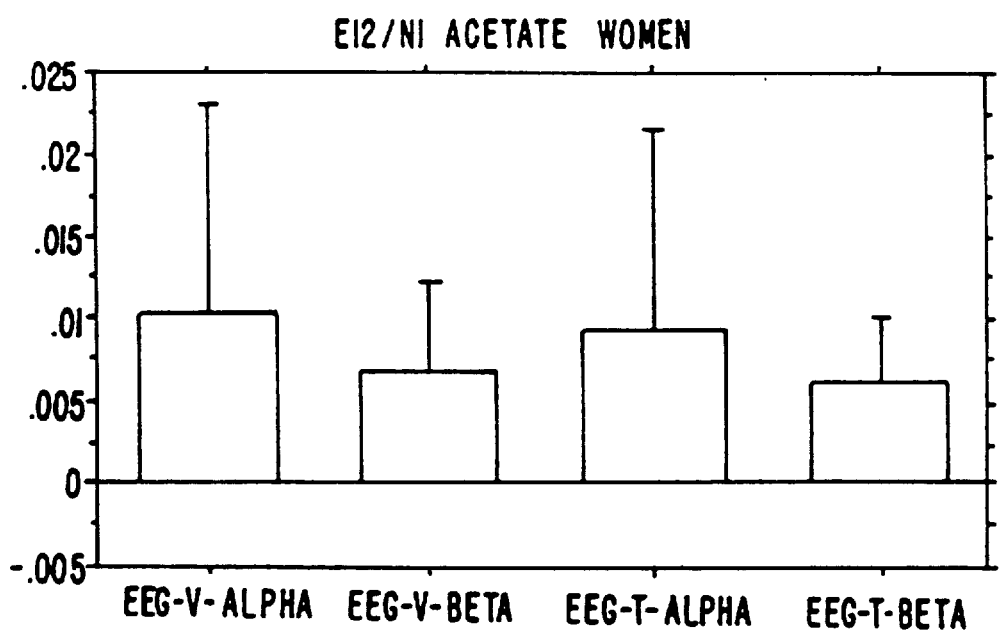
Figure 170A:
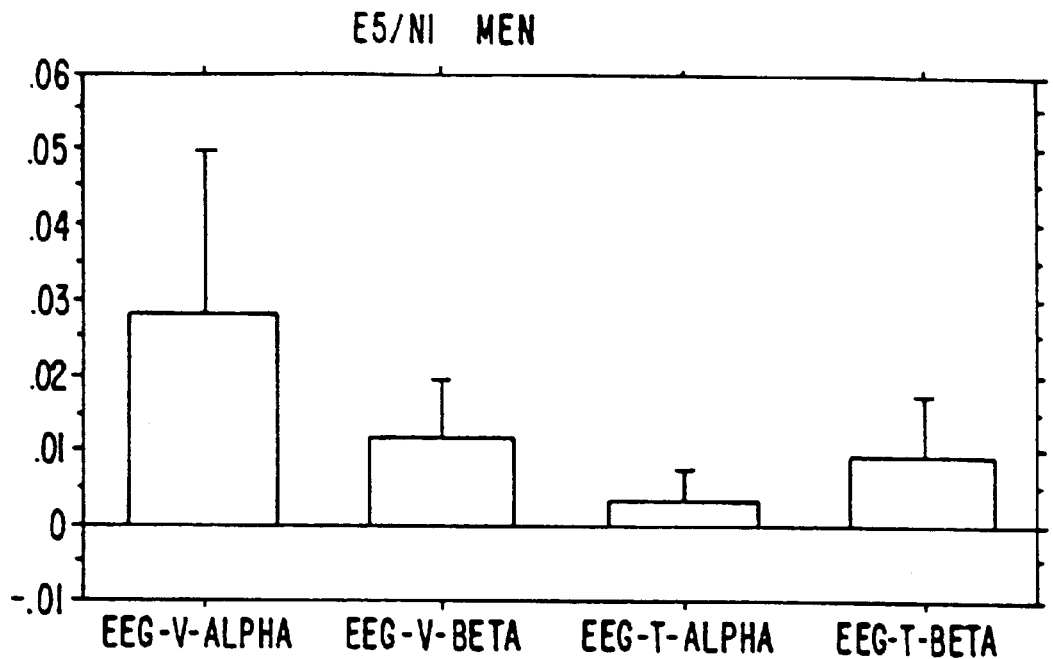
Figure 170B:
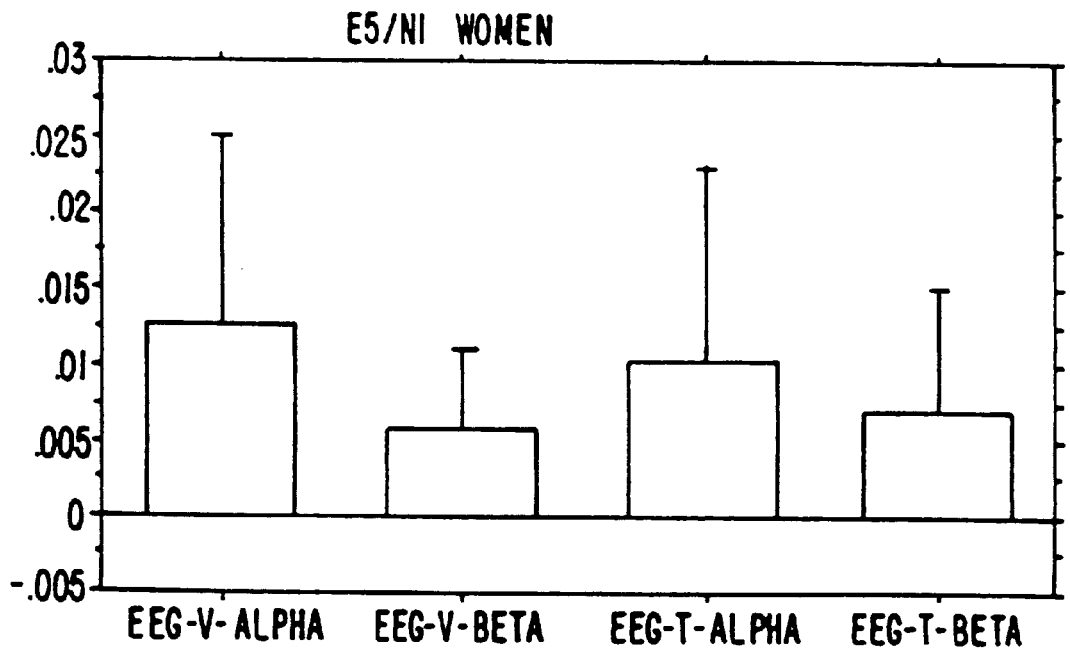
Figure 171A:
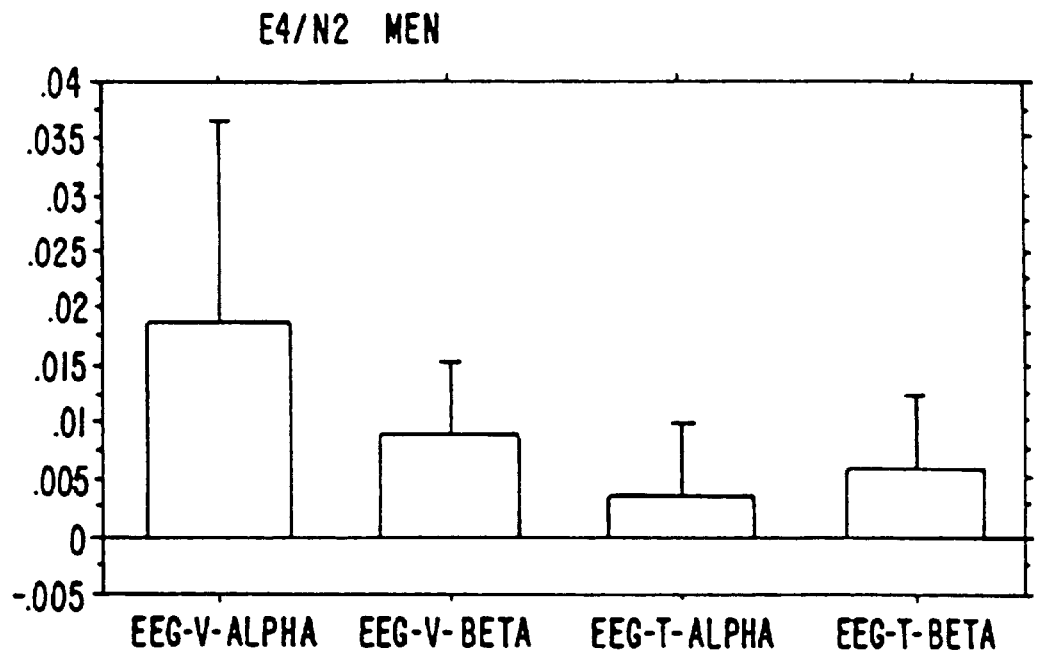
Figure 171B:
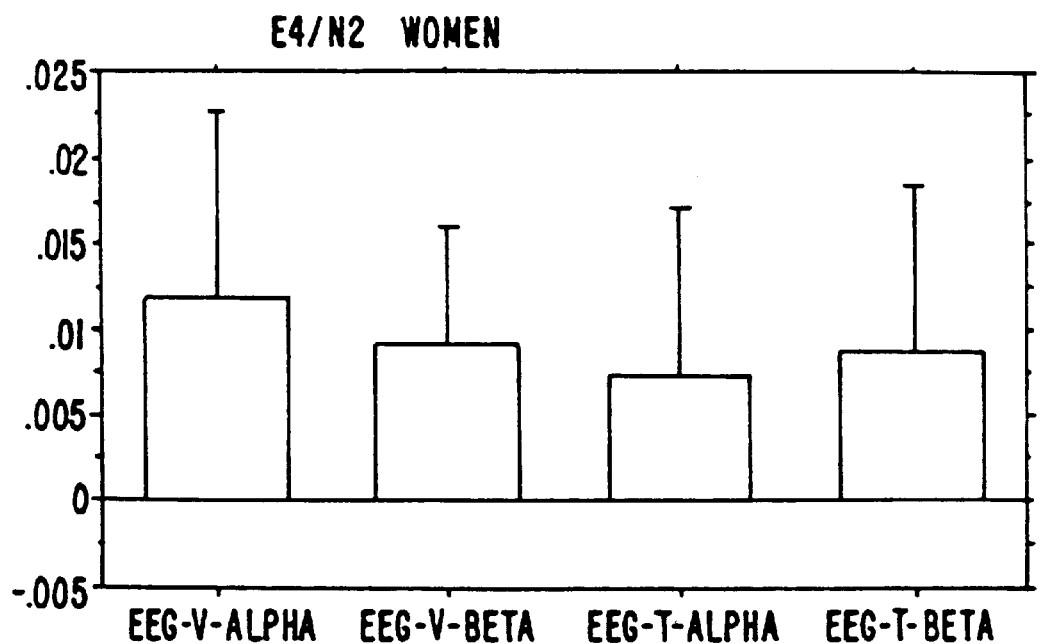
Figure 172A:
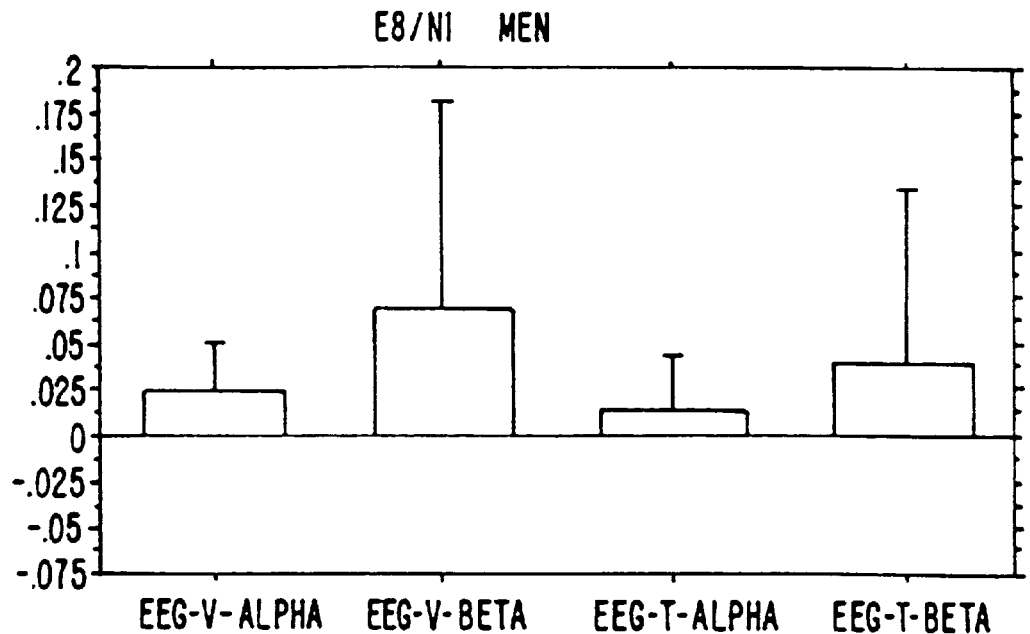
Figure 172B:
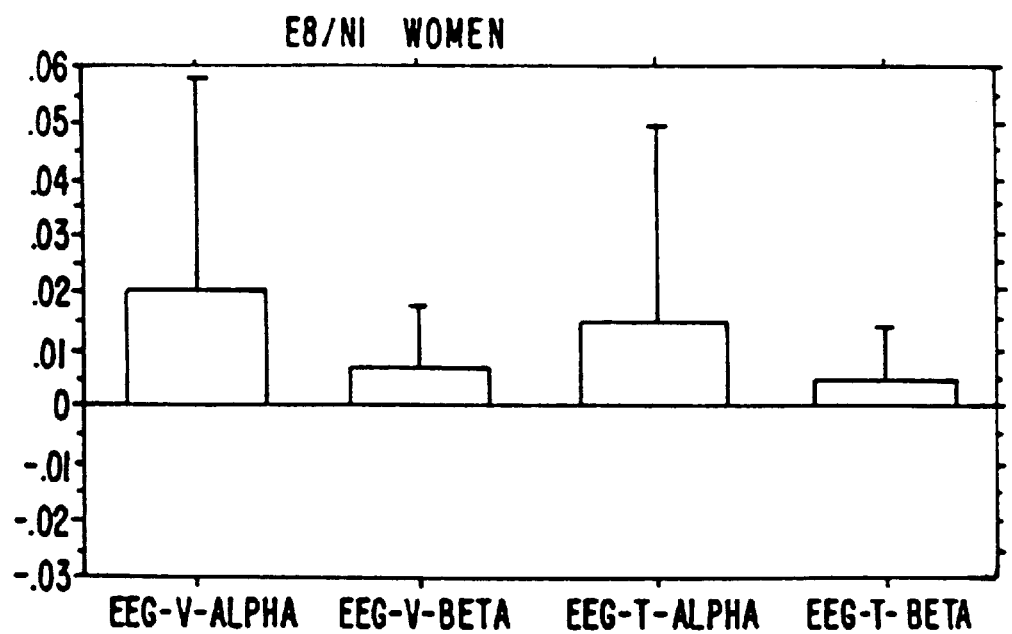
Figure 173A:
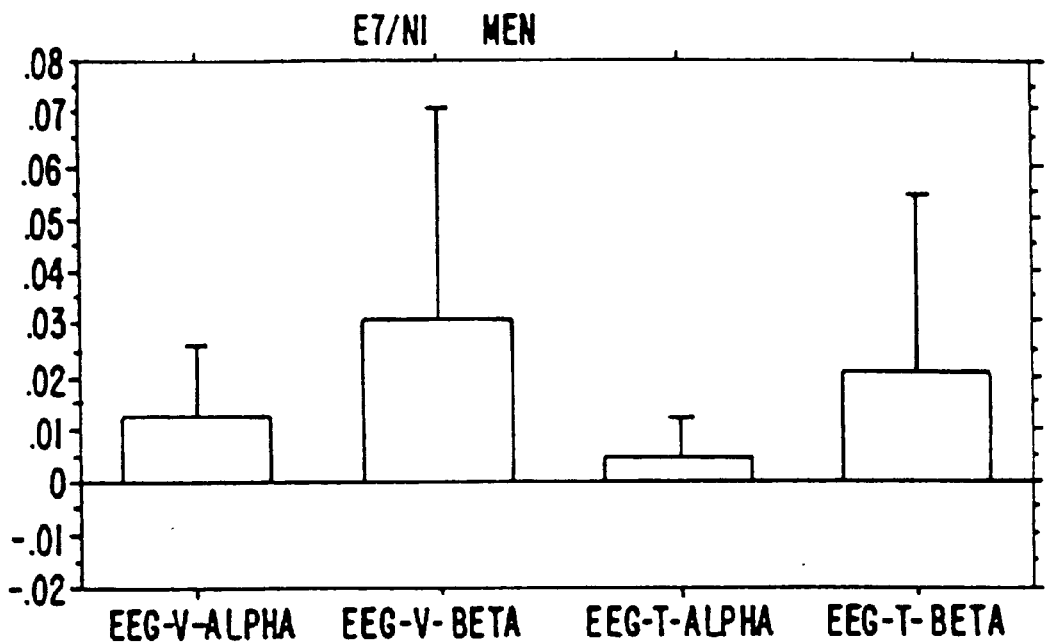
Figure 173B:
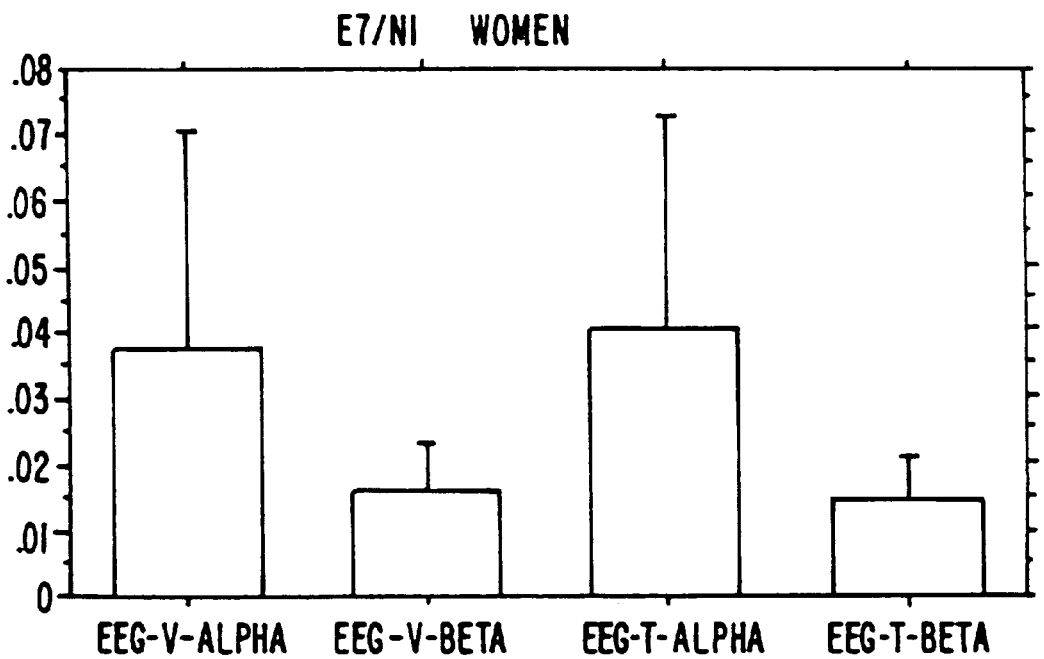
Figure 174A:
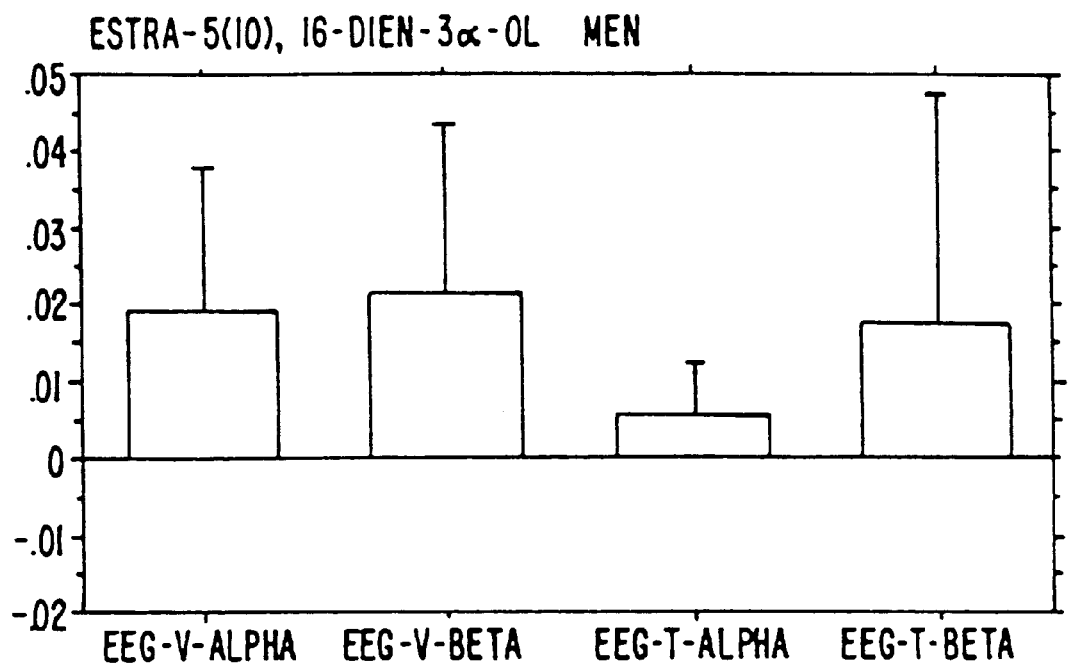
Figure 174B:
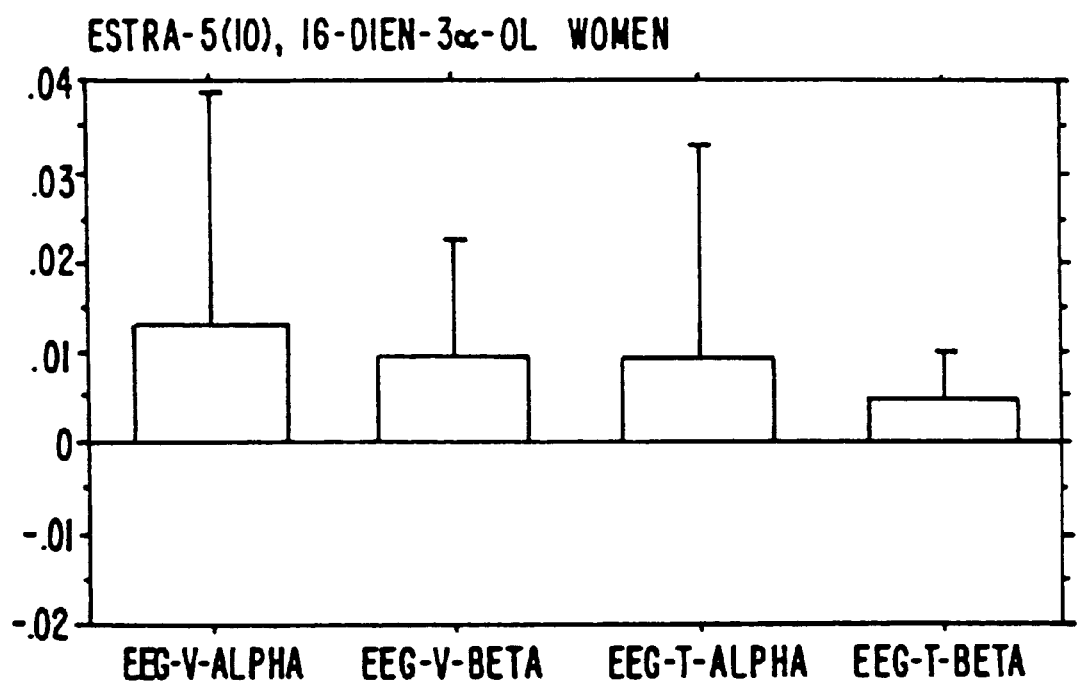
Figure 175A:
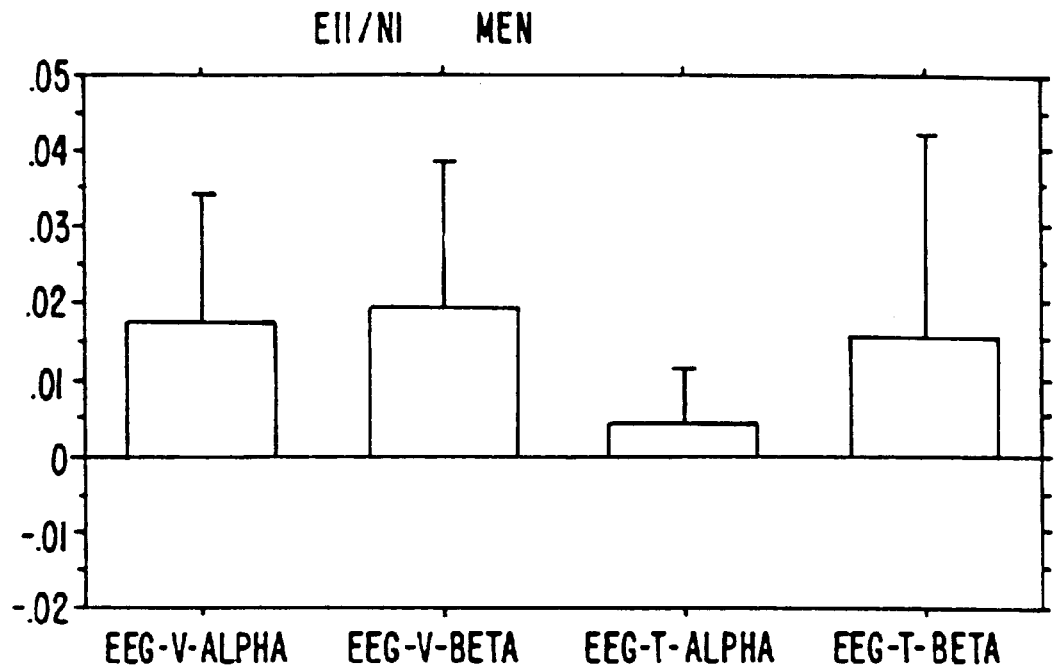
Figure 175B:
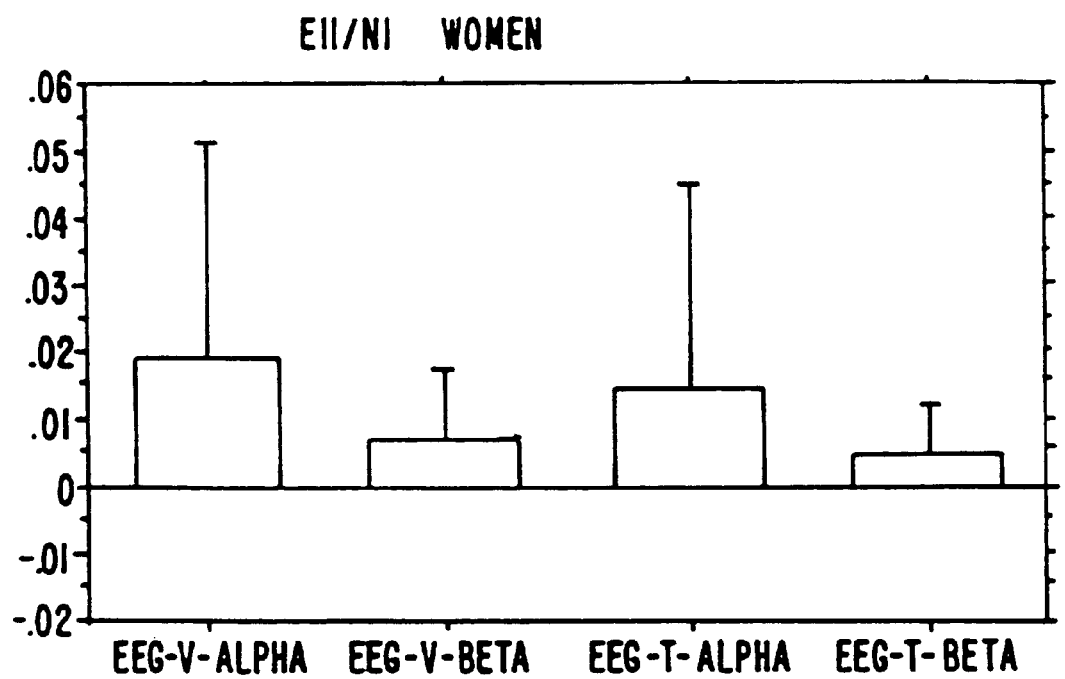
Figure 176A:
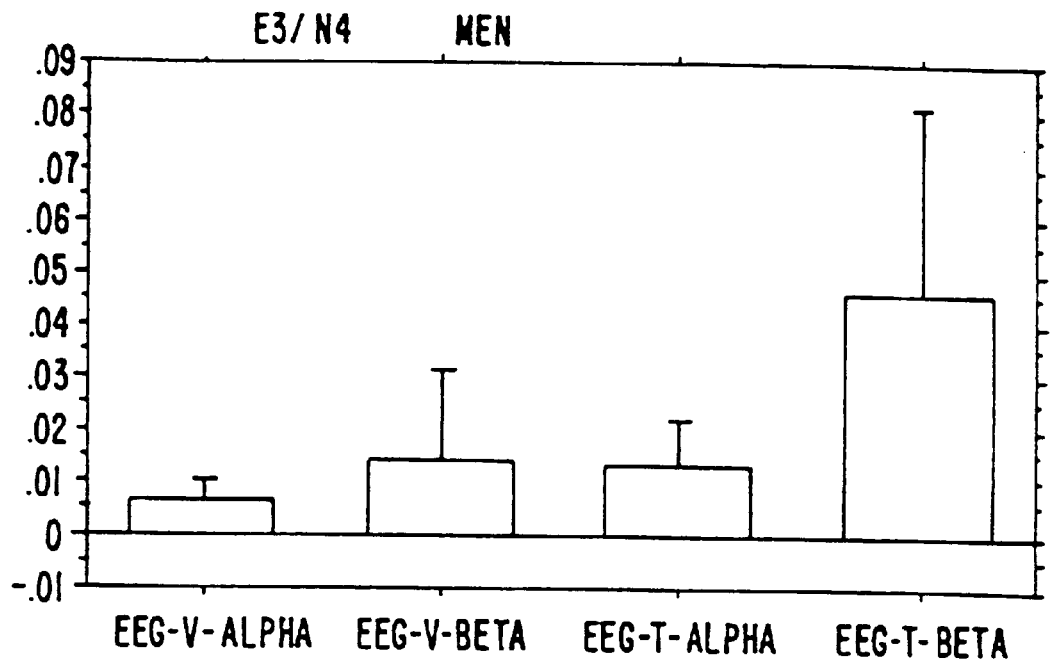
Figure 176B:
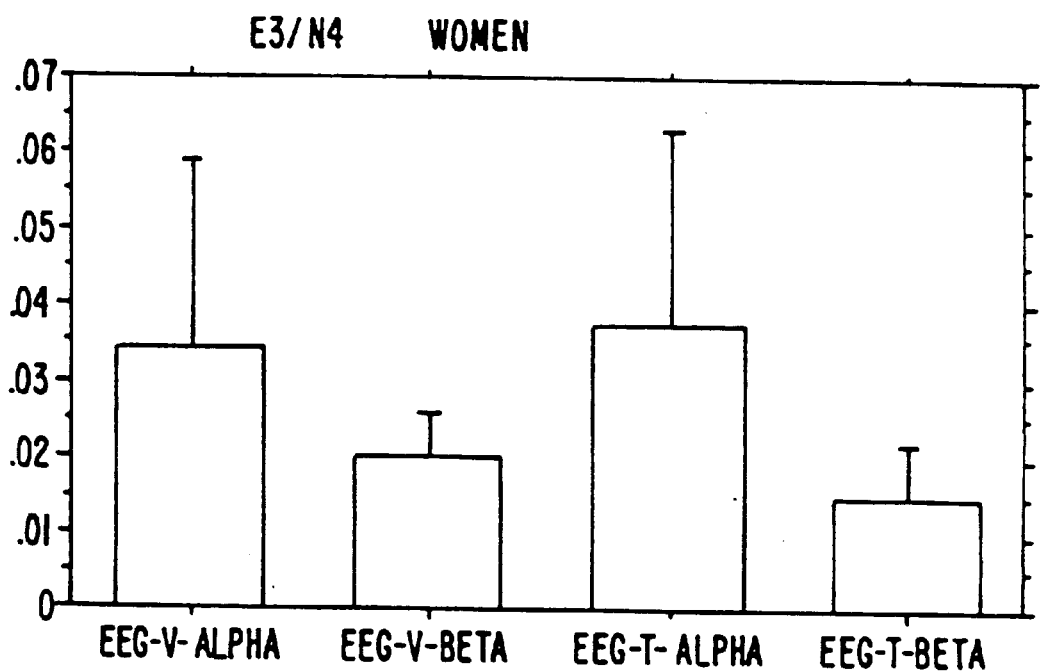

FIGS. 163A, 163B and 163C illustrate the EVG, GSR and ST data on men, respectively, for 13 estranes on Chart 1.

FIGS. 164A and 164B through 176A and 176B illustrate the EEG data on men (A) and women (B) for the 13 estranes, respectively, identified in FIGS. 163A–163C.

Figure 177:
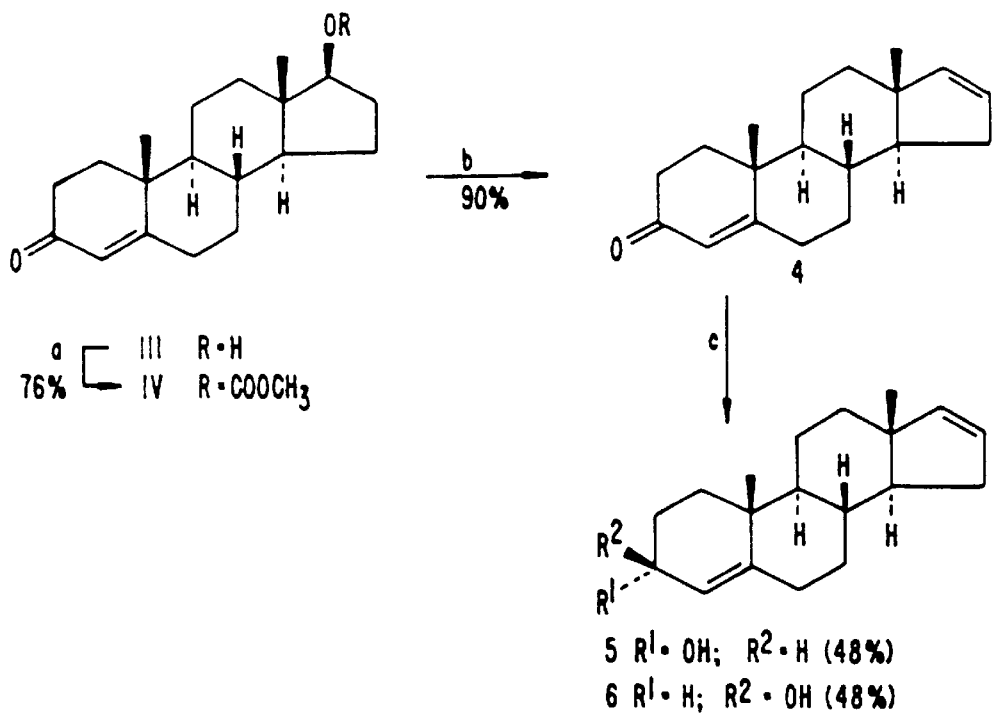

FIG. 177 illustrates the synthesis of Androsta-4,16-dien-3-one, Androsta-4,16-dien-3α-ol, and Androsta-4,16-dien-3β-ol.

Figure 178:
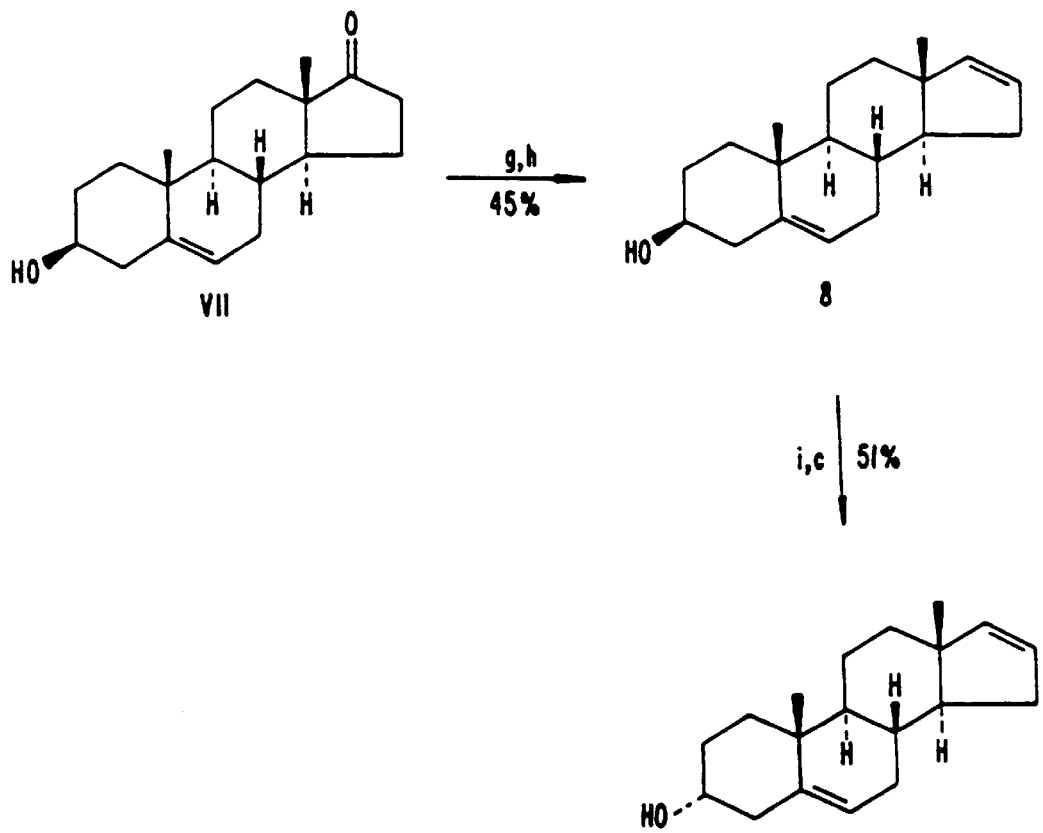

FIG. 178 illustrates the synthesis of Androsta-5,16-dien-3α-ol and Androsta-5,16-dien-3β-ol.

Figure 179:
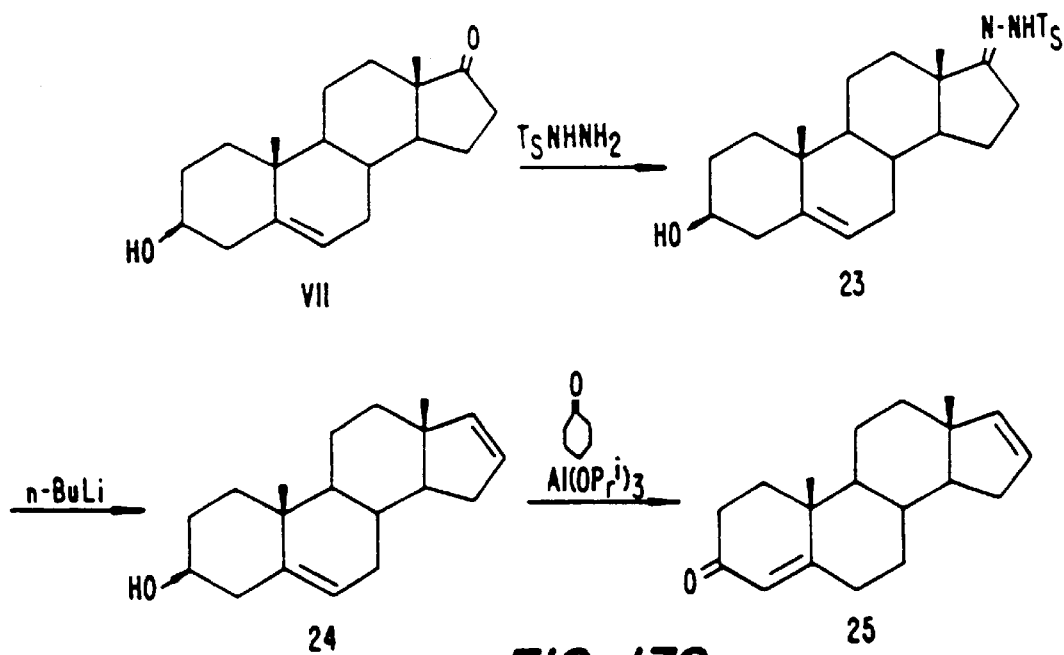

FIG. 179 illustrates an alternate synthesis of Androsta-4,16-dien-3-one.

Figure 180A:
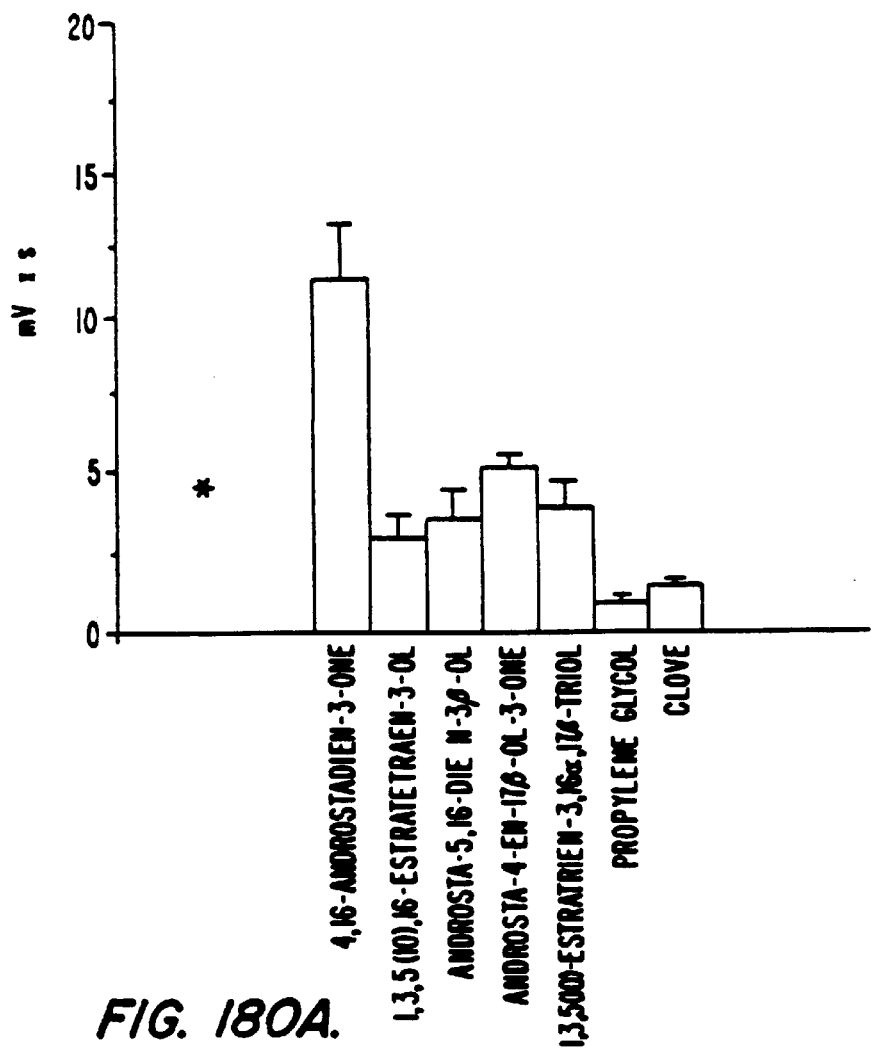
Figure 180B:
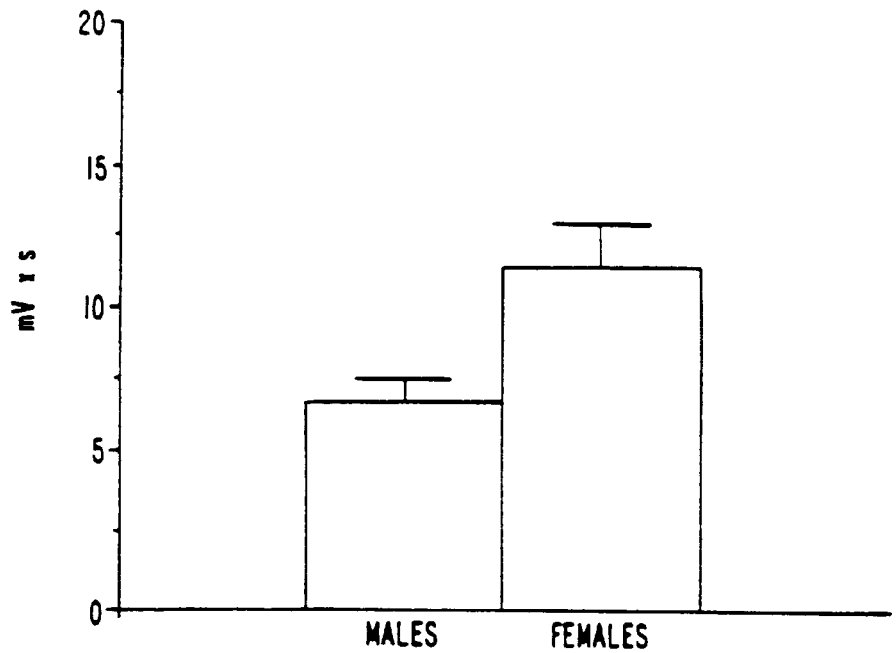

FIG. 180 is a graphic representation of the electrophysiological effect on receptor potential of the localized administration of particular steroids to the vomeronasal organ of female subjects (180A) and to the olfactory epithelium (180C). FIG. 180B is a graphic comparison of the effect of an Androstane on the VNO receptor potential of male and female subjects.

FIG. 181 is a graphic representation of the electrophysiological effect of the localized administration of particular steroids to the vomeronasal organ of male (182A) and female (182B) subjects.

FIGS. 182A through 182F depicts various autonomic responses of female subjects to an Androstane. A=receptor potential of the vomeronasal neuroepithelium; B=change in cortical alpha activity of an electroencephalogram (i); C=change in galvanic skin response (K-ohms); D=change in peripheral arterial pulse (counts/min.); E=change in skin temperature (degrees C.); and, F=change in respiratory frequency (counts/min.).

Figure 183:
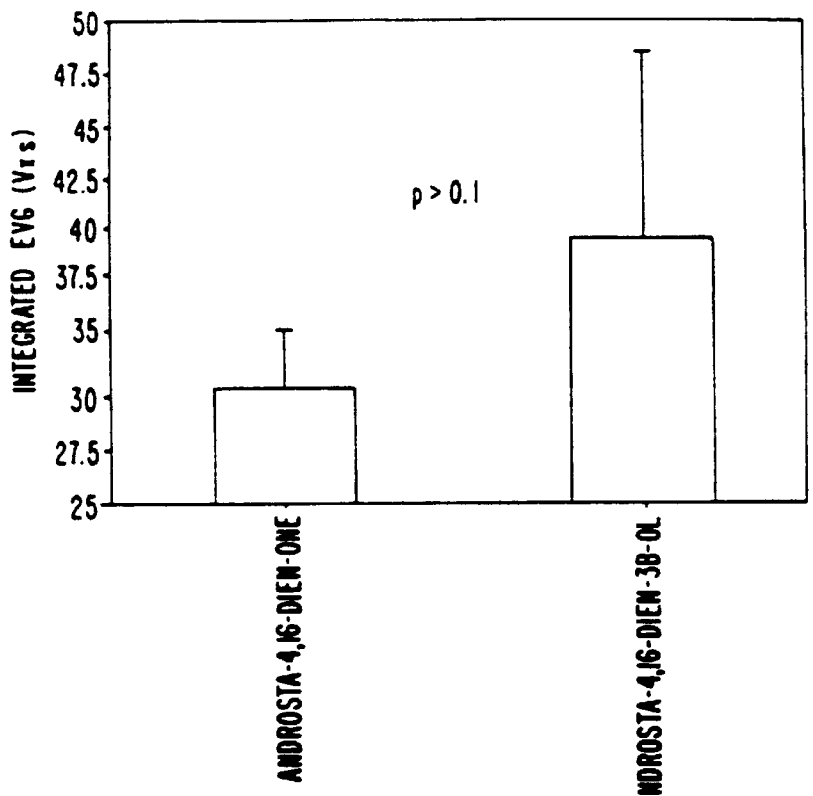

FIG. 183 depicts changes in receptor potential of the VNO after exposure of 5 females to two different Androstanes.

FIG. 184 depicts sexual dimorphism in local and autonomic responses to the stimulation of the VNO with vomeropherins. Various vomeropherins (200 fmoles) and the diluent control were administered to 30 male and 30 female subjects (ages 20 to 45) as described. Bars indicate the mean response of the population.

Figure 184A:
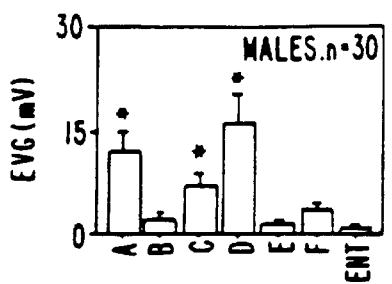
Figure 184B:

FIGS. 184A and 184B: EVG responses were measured as described in male (A) and female (B) subjects.

Figure 184C:
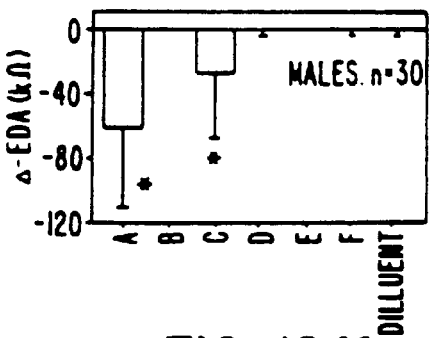
Figure 184D:
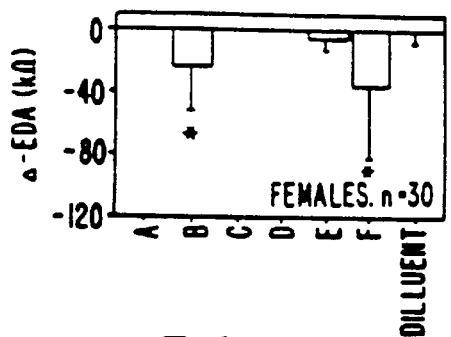

FIGS. 184C and 184D: Electrodermal activity was measured as described. Changes (measured in xΩ) in response due to delivery of vomeropherins to the VNO of each subject are shown in male (C) and female (D) subjects.

Figure 184E:
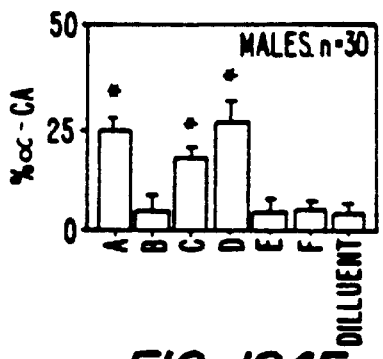
Figure 184F:
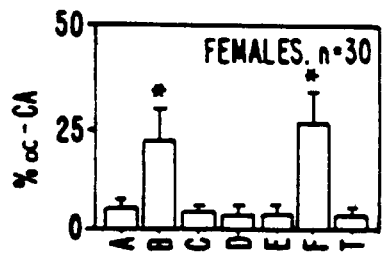

FIGS. 184E and 184F: Alpha-cortical activity was measured as described. Changes in response due to delivery of vomeropherins to the VNO of male (E) and female (F) subjects.

Figure 184G:
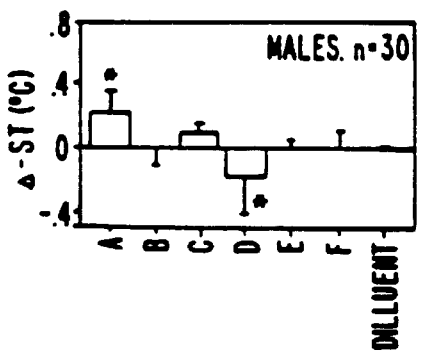
Figure 184H:
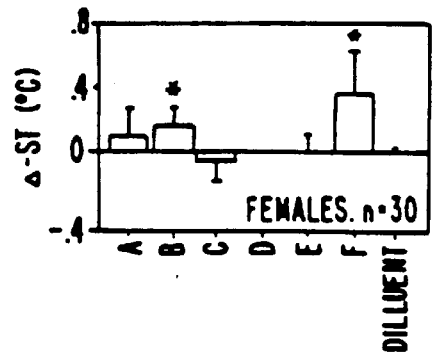

FIGS. 184G and 184H: Skin temperature (ST) was measured as described. Changes in response due to delivery of vomeropherins to the VNO of each subject are shown in male (G) and female (H) subjects.

Figure 185A:
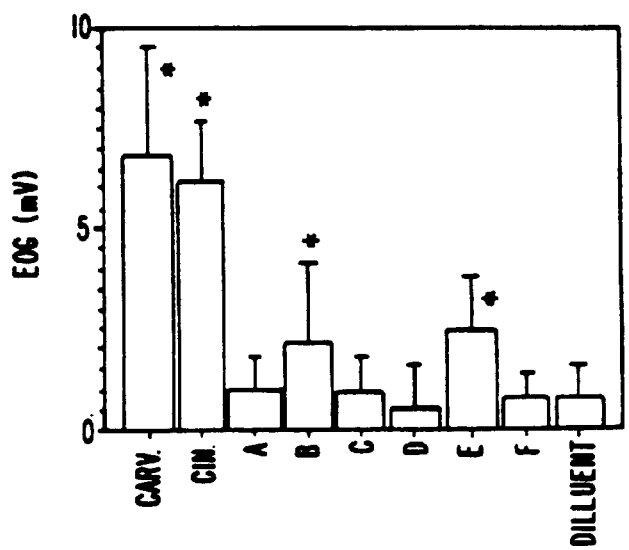
Figure 185B:
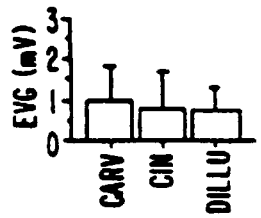

The compounds in the graphs are:
A=1,3,5(10),16-Estratetraen-3-yl acetate
B=Androsta-4,16-dien-3-one
C=1,3,5(10),16-Estratetraen-3-ol
D=3-Methoxy-Estra-1,3,5(10),16-tetraene
E=Androsta-4,16-dien-3α-ol
F=Androsta-4,16-dien-3β-ol FIG. 185 depicts electro-olfactograms of male and female subjects induced by stimulation of the OE with olfactants and vomeropherins. FIG. 185A: 400 fmoles of the olfactants 1-carvone and cineole as well as 200 fmoles of the vomeropherins A, B, C, D and F; and the stereoisomer E were applied separately as one second pulses to the OE of 20 subjects (both male and female) and each EOG response was recorded as described. The olfactants as well as E and B produced significant (p<0.01) local response. FIG. 185B: 400 fmoles of the olfactants 1-carvone and cineole do not induce a significant EVG response when delivered to the VNO of male and female subjects.

Figure 186A:
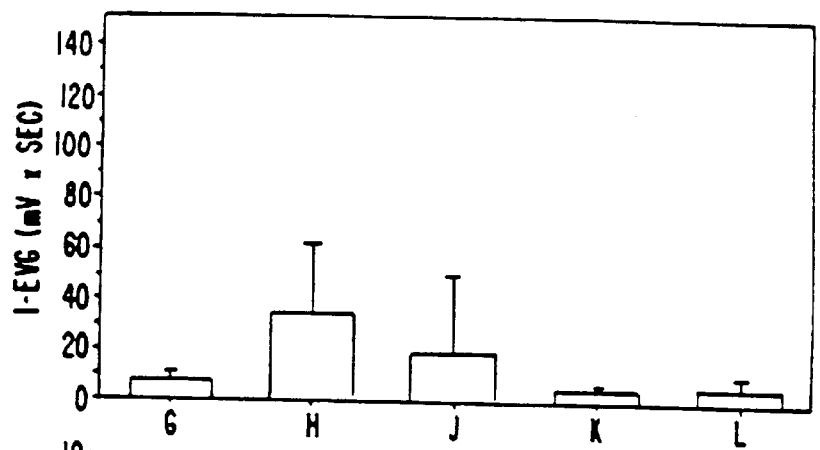
Figure 186B:
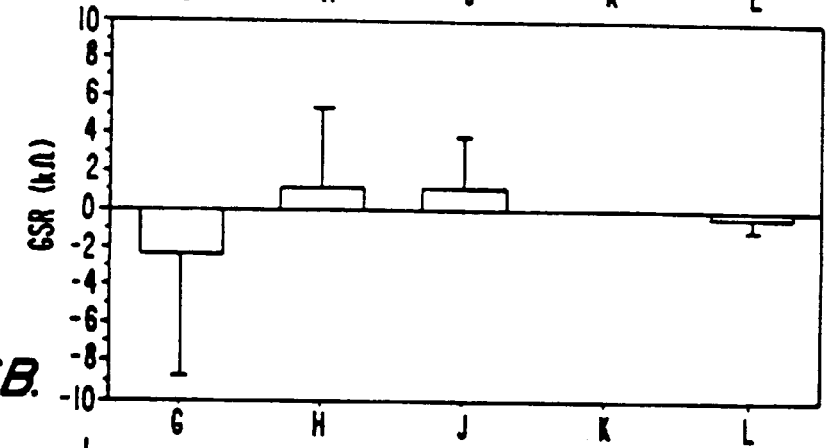
Figure 186C:
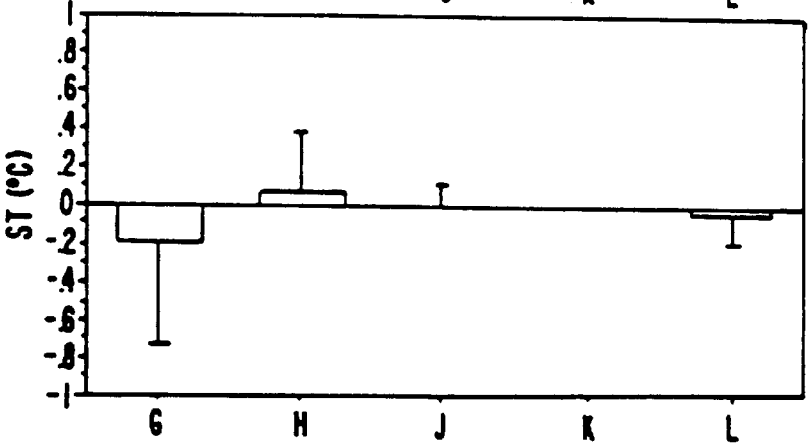
Figure 187A:
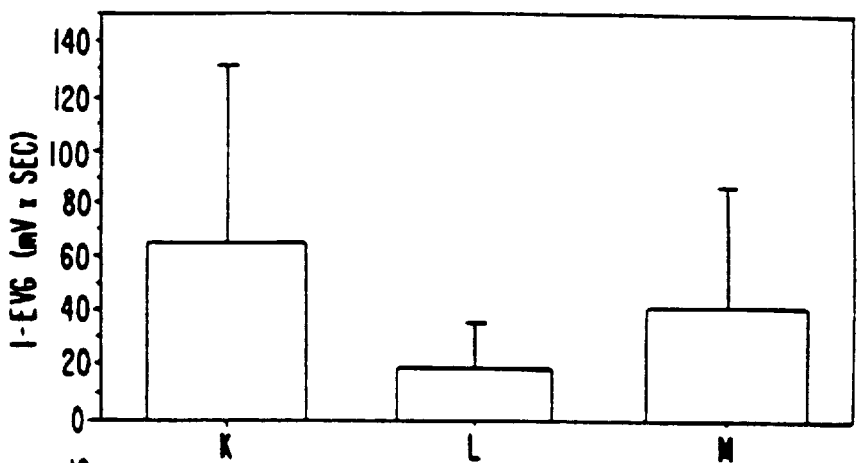
Figure 187B:
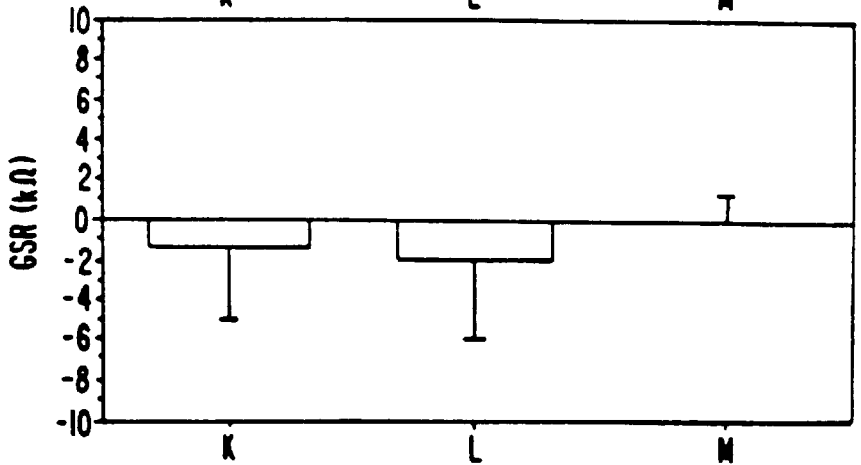
Figure 187C:
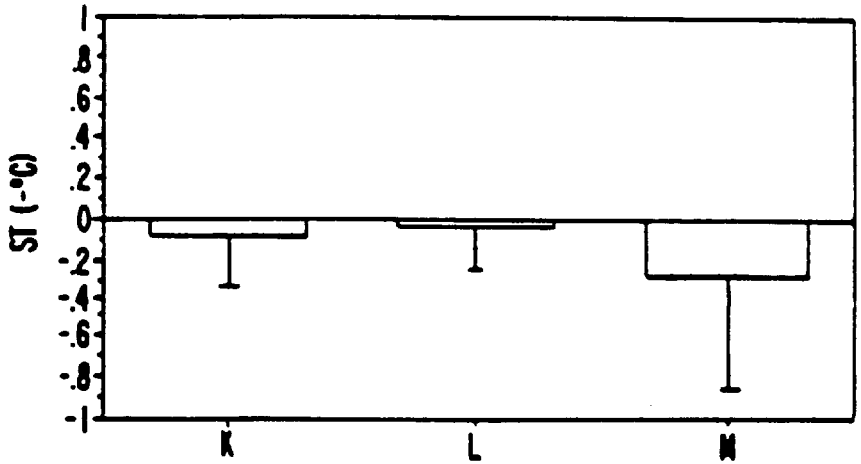
Figure 188:
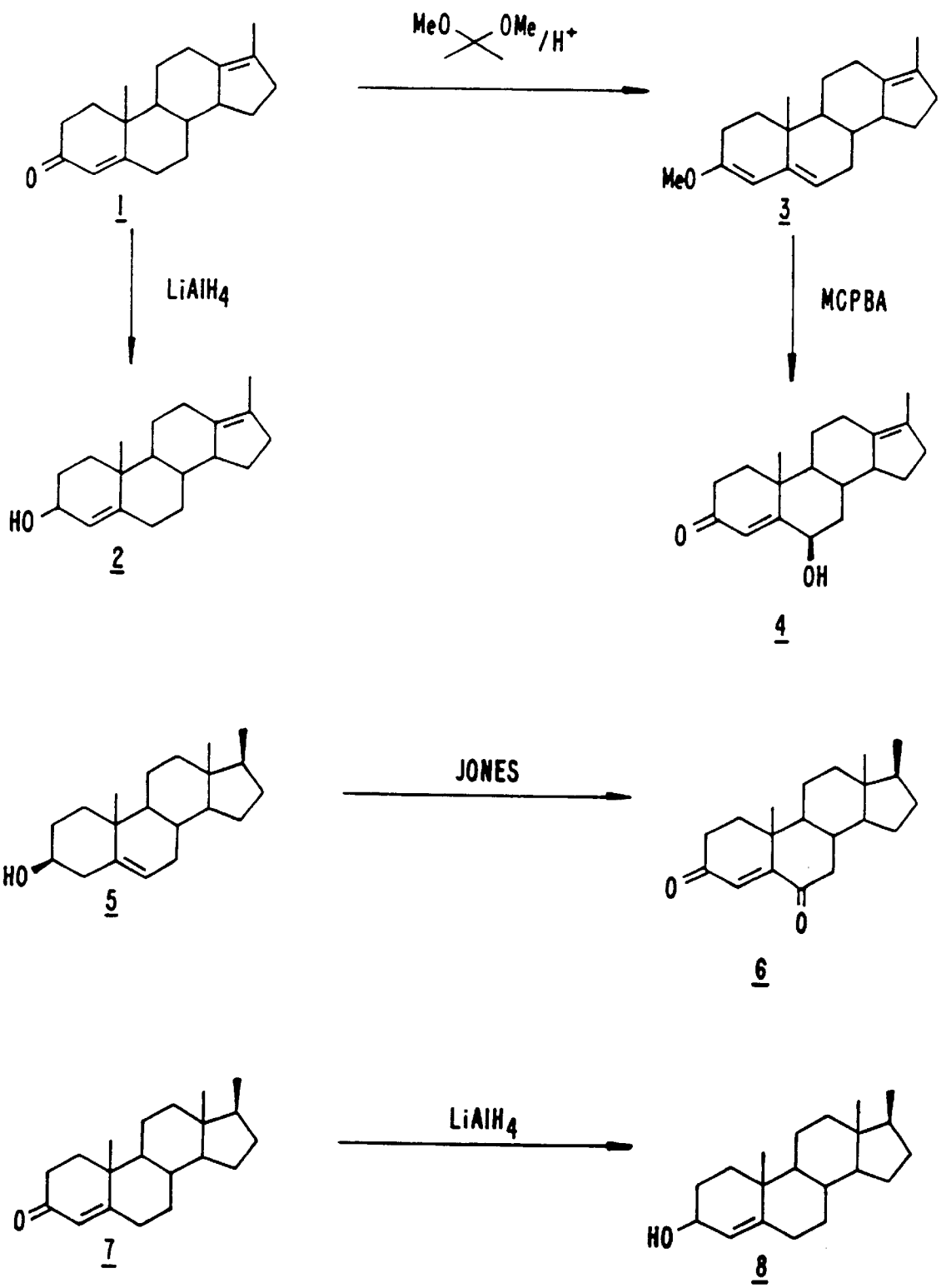

FIG. 186 depicts the electrophysiological effect of the following vomeropherins on the vomeronasal organ of 20 female subjects:
G=Androst-4-en-3-one
H=Androsta-4,16-diene-3,6-dione
J=10,17-Dimethylgona-4,13(17)-dien-3-one
K=1,3,5(10),16-Estratetraen-3-ol-methyl ether
L=1,3,5(10),16-Estratetraen-3-yl-propionate
EVG=Electro-vomeronasogram
GSR=Galvanic Skin Response
 =Electrodermal Activity, EDA
ST=Skin Temperature FIG. 187 depicts the electrophysiological effect of vomeropherins on the vomeronasal organ of 20 male subjects.
M=1,3,5(10)-Estratrien-3-ol FIG. 188 depicts the steps of synthesis for Examples 108 through 112.

Figure 189:
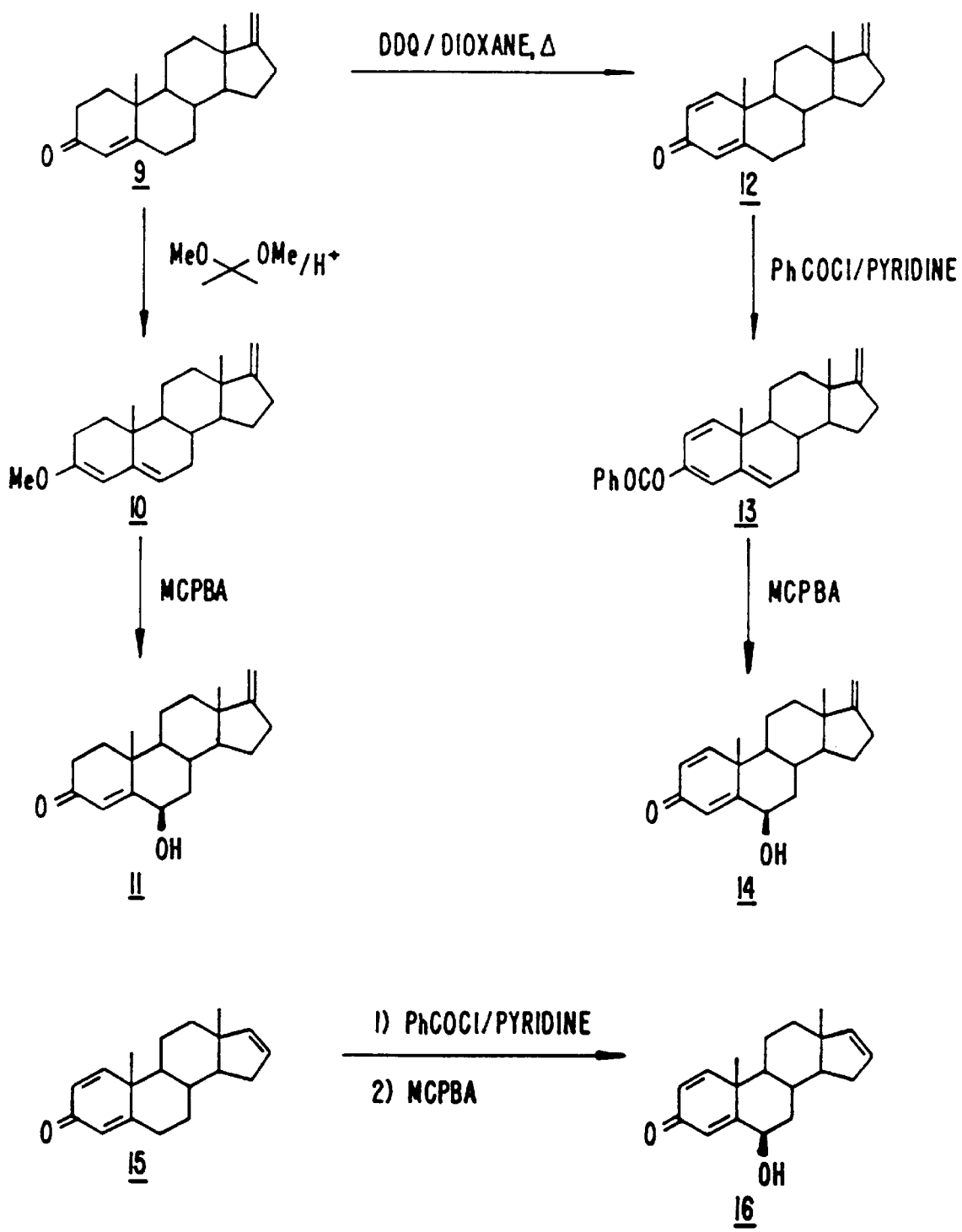

FIG. 189 illustrates the steps of synthesis for Examples 113 through 118.

Figure 190:
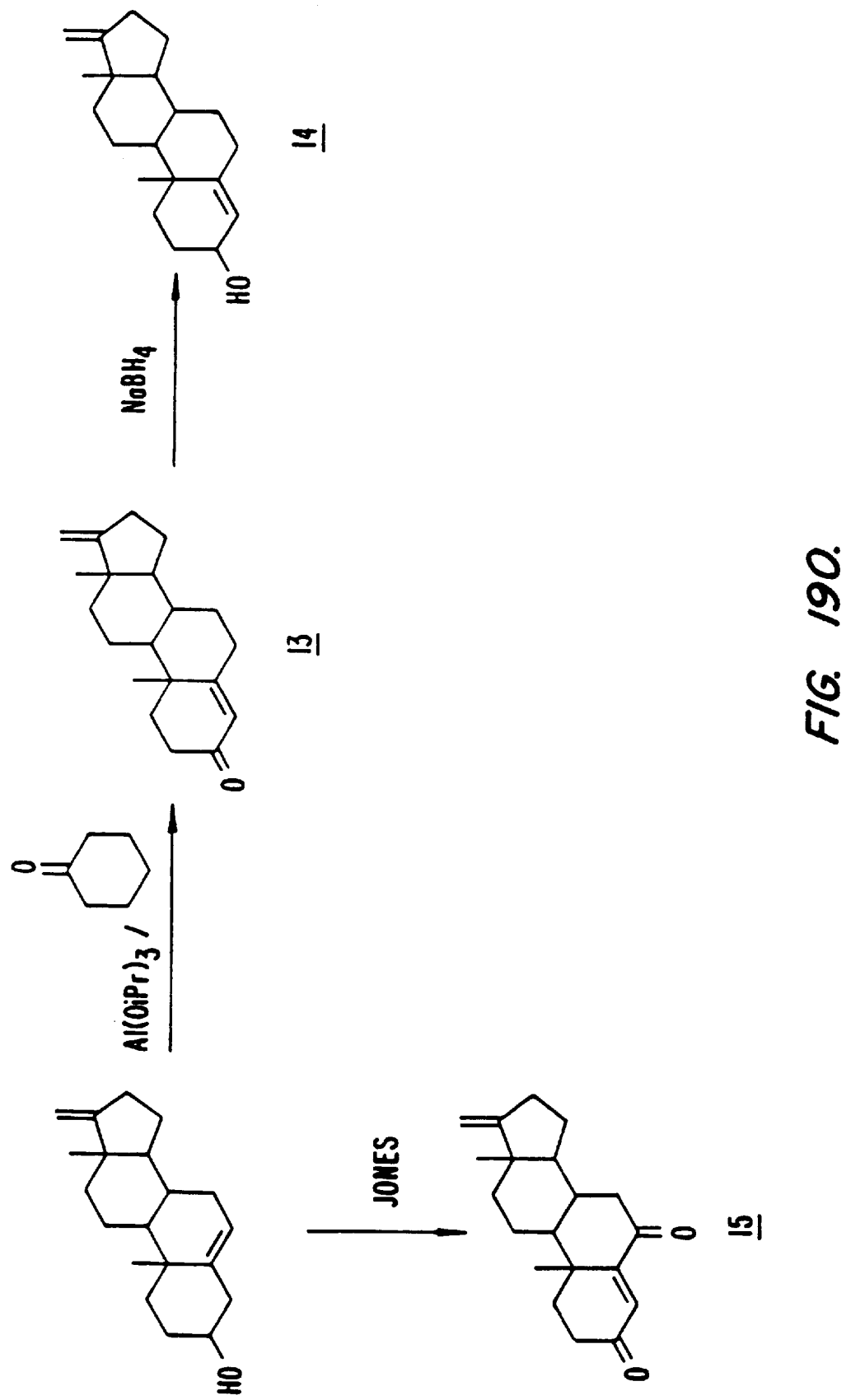

FIG. 190 illustrates the steps of synthesis for Examples 120 through 121.

Figure 191:
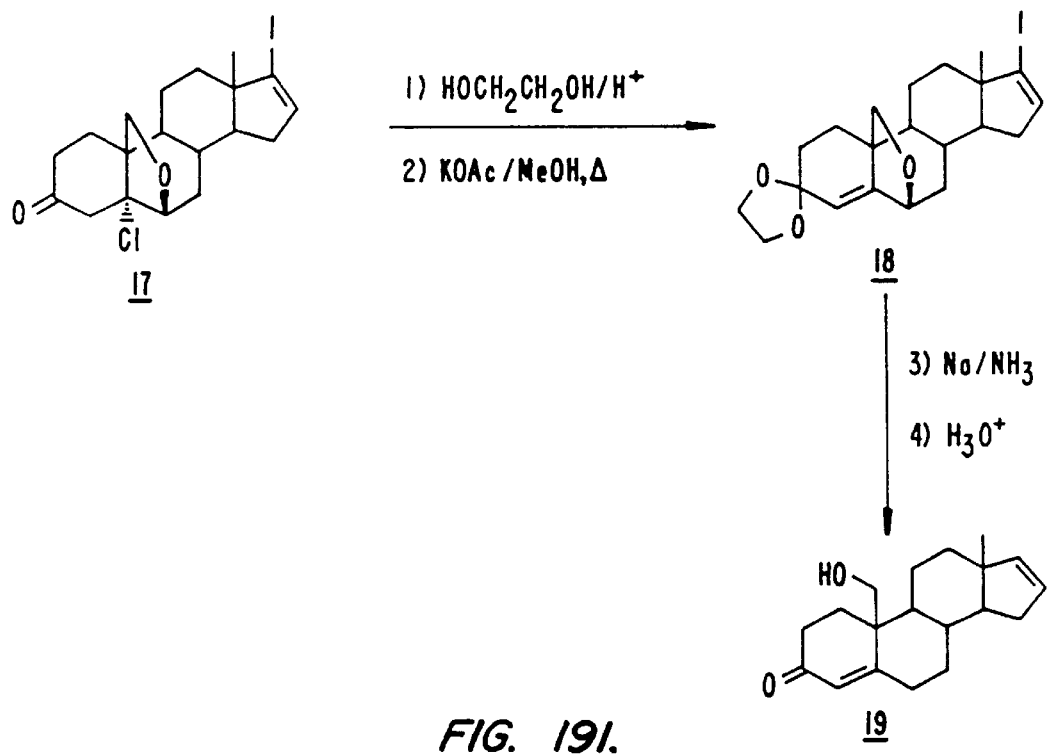

FIG. 191 illustrates the steps of synthesis described in Examples 123 through 124.

Figure 192:
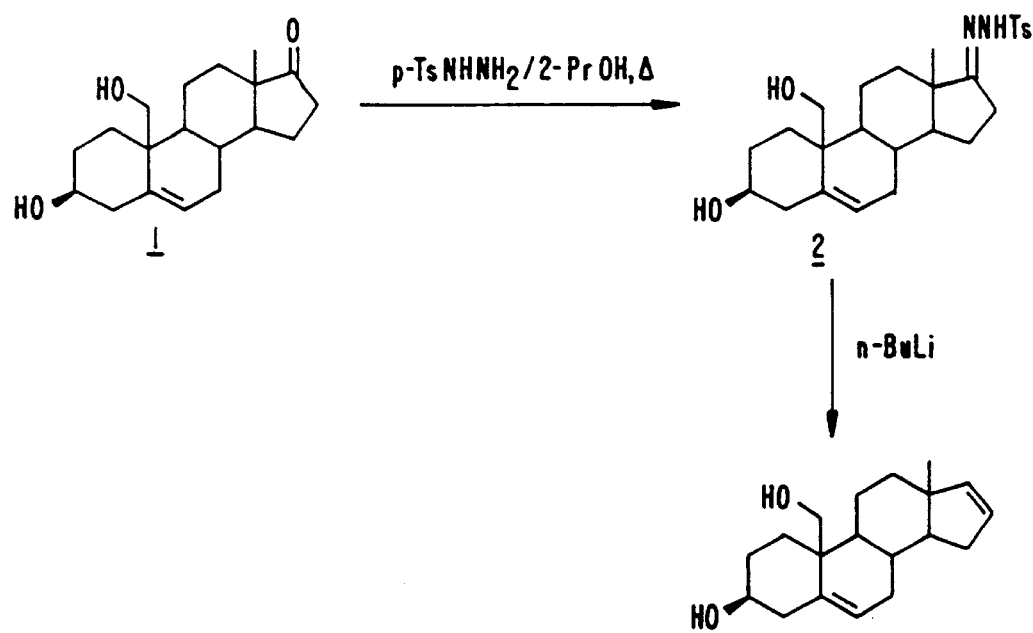

FIG. 192 illustrates the steps of synthesis for Examples 125 through 126.

Figure 193A:
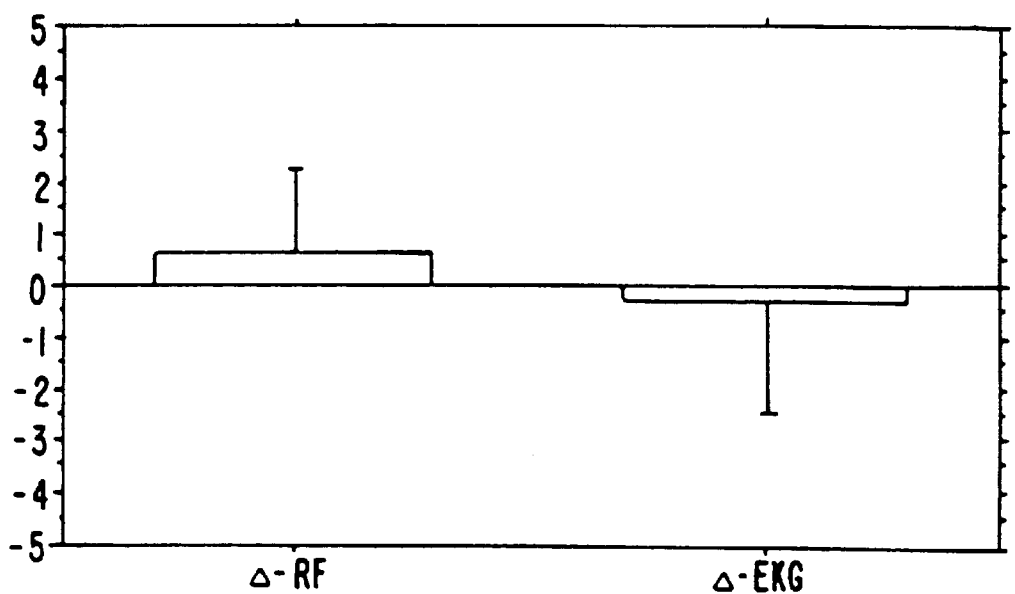

FIG. 193A shows the respiratory frequency and EKG data in females for tests of androsta-5,16-diene-3β,19-diol in the VNO.

Figure 193B:
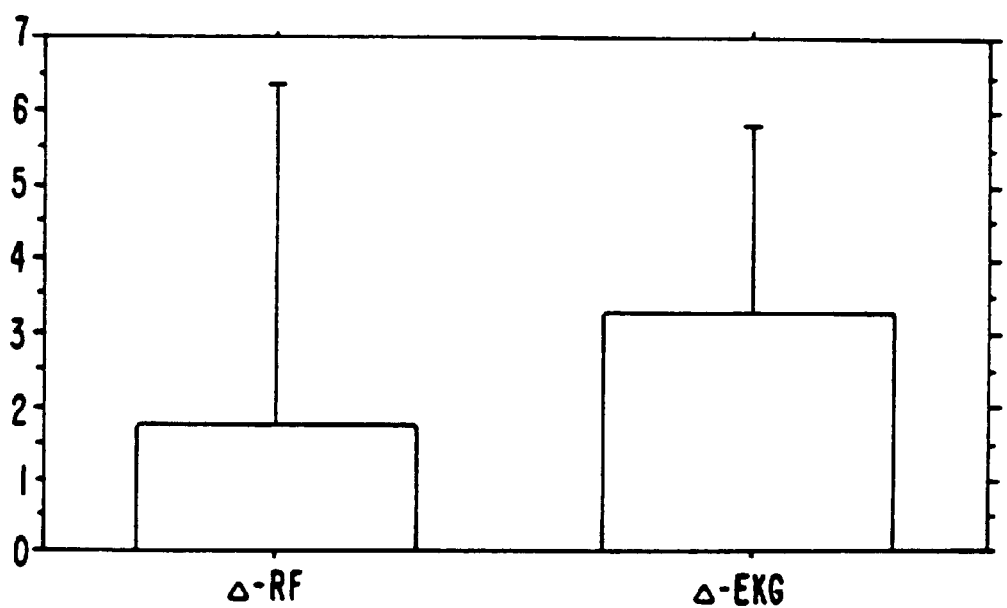

FIG. 193B shows the respiratory frequency and EKG data in females for tests of androsta-5,16-diene-3β,19-diol in the VNO.

Figure 194A:
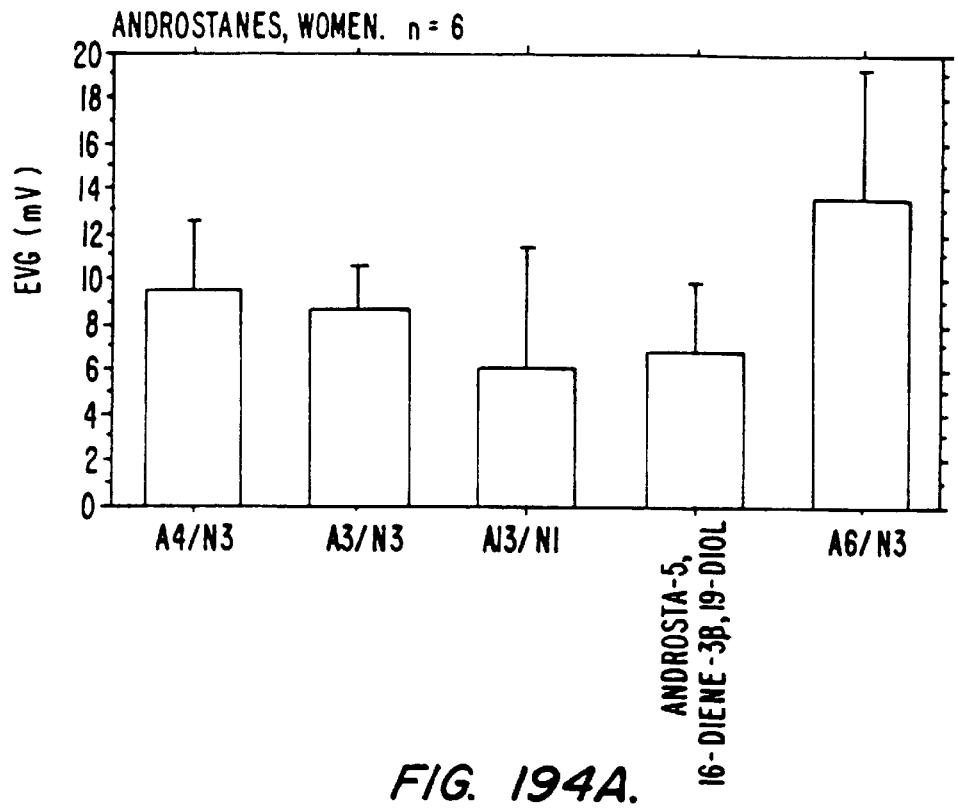
Figure 194B:
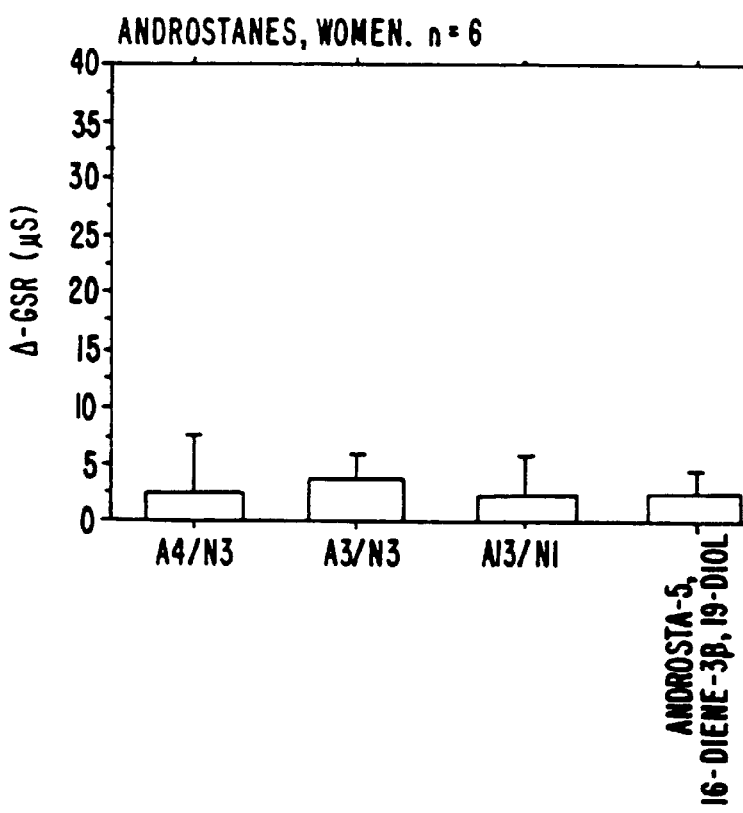
Figure 194C:
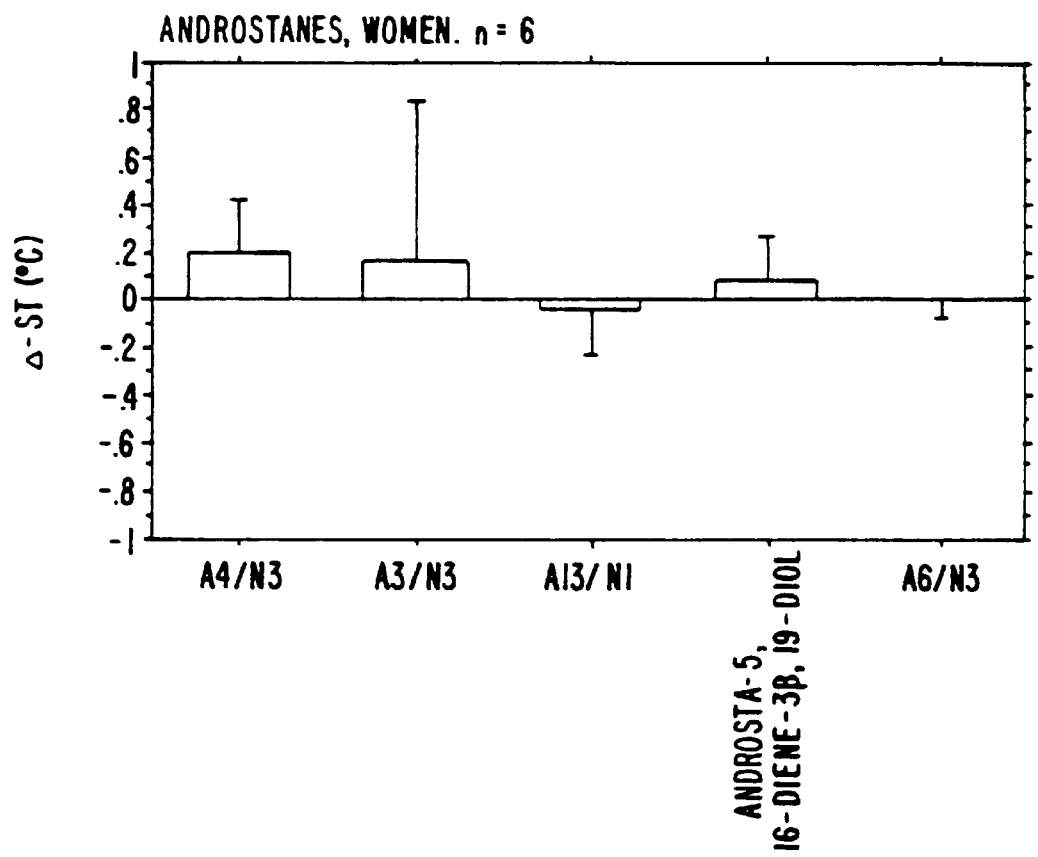

FIG. 194A, 194B and 194C show the EVG, GSR, and ST data in women for four androstanes on the chart and androsta-5,16-diene-3β,19-diol.

Figure 195A:
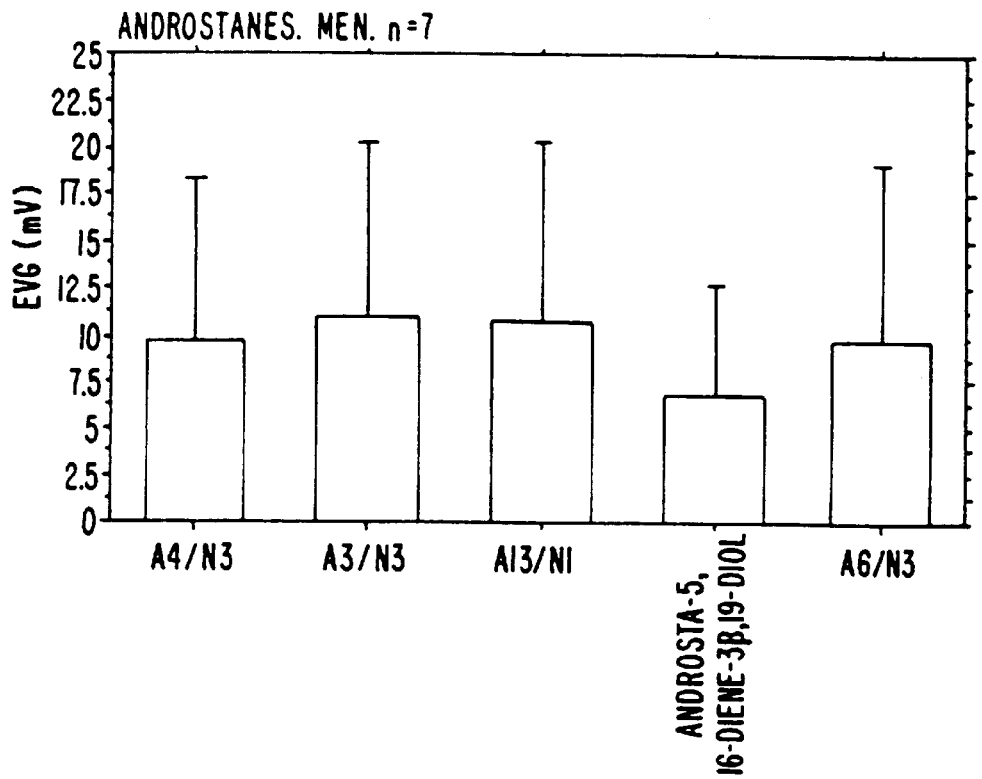
Figure 195B:
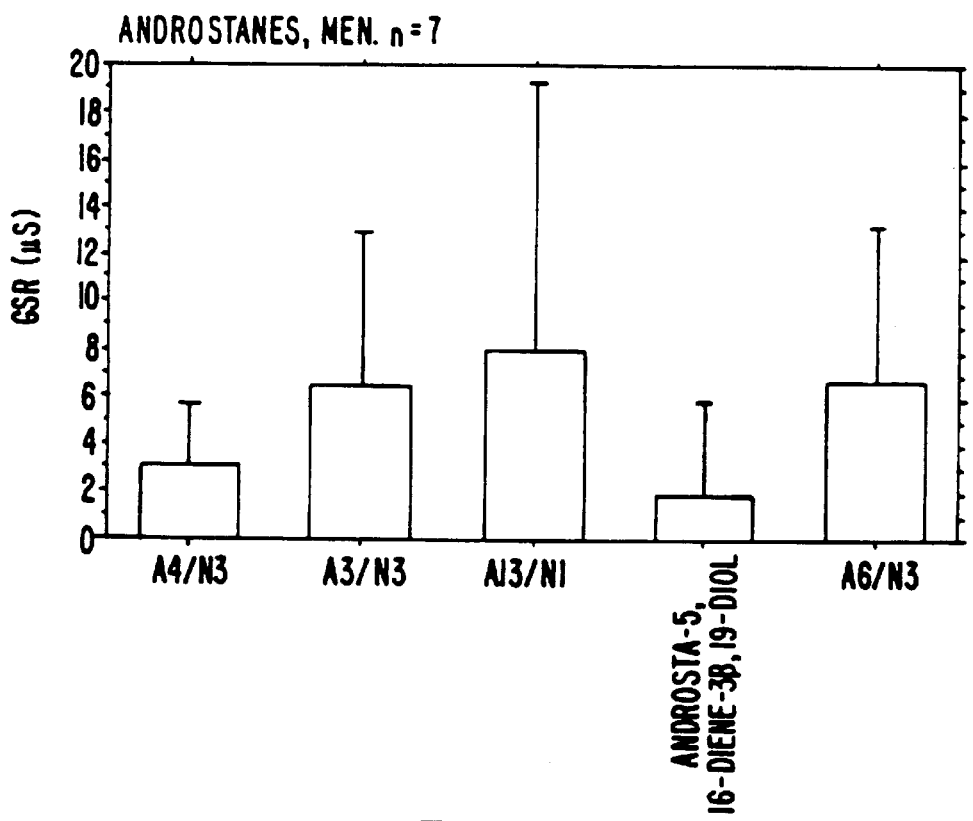
Figure 195C:
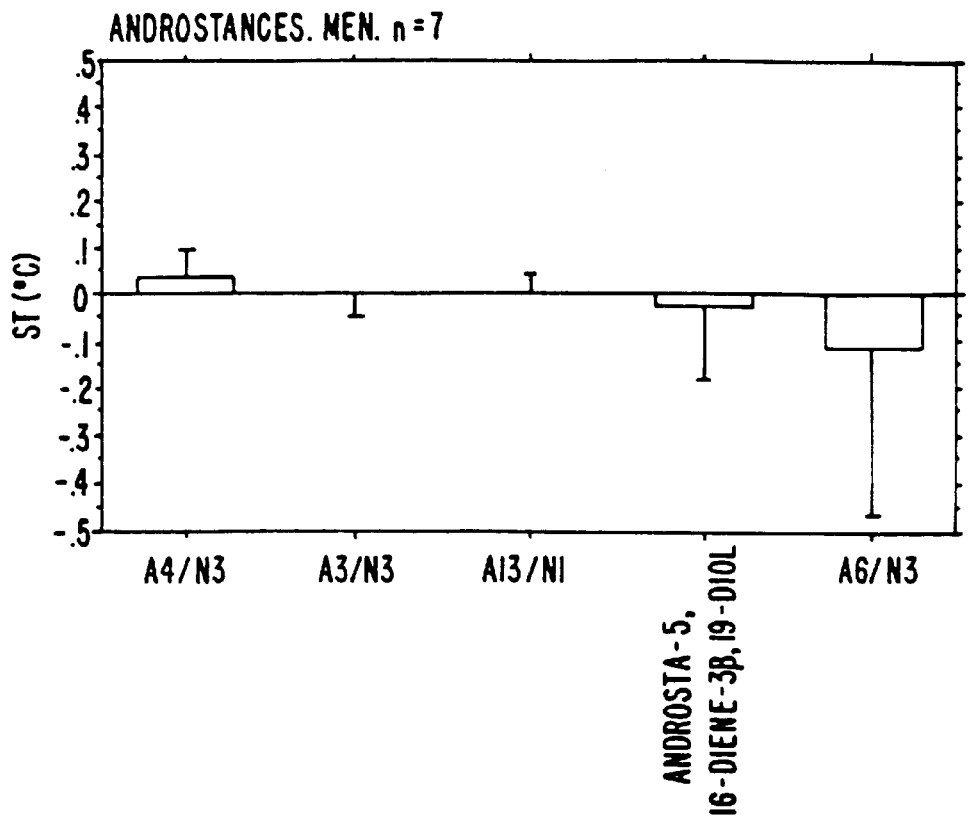

FIG. 195A, 195B and 195C show the EVG, GSR and ST data in men for the five androstanes identified in FIG. 194.

Figure 196A:
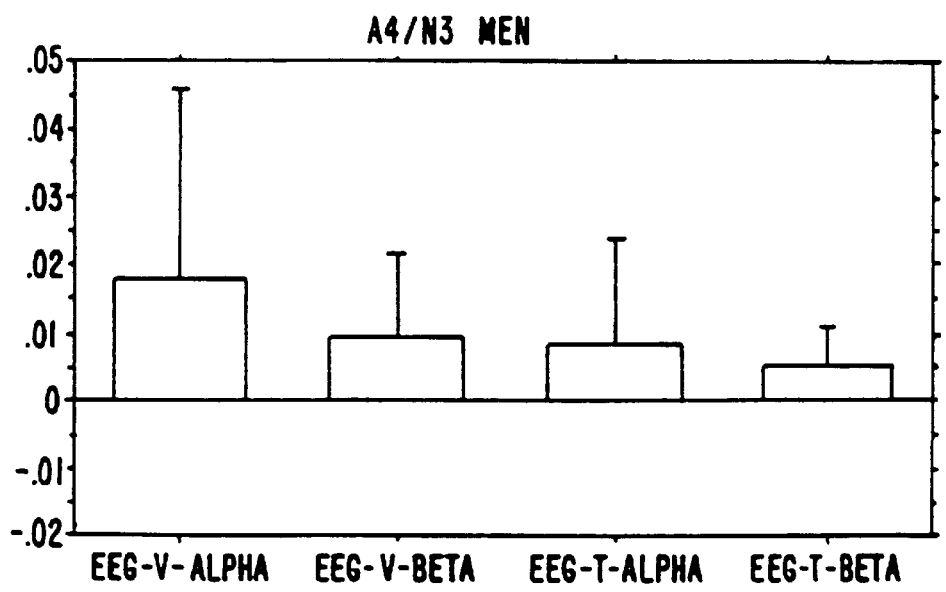
Figure 196B:
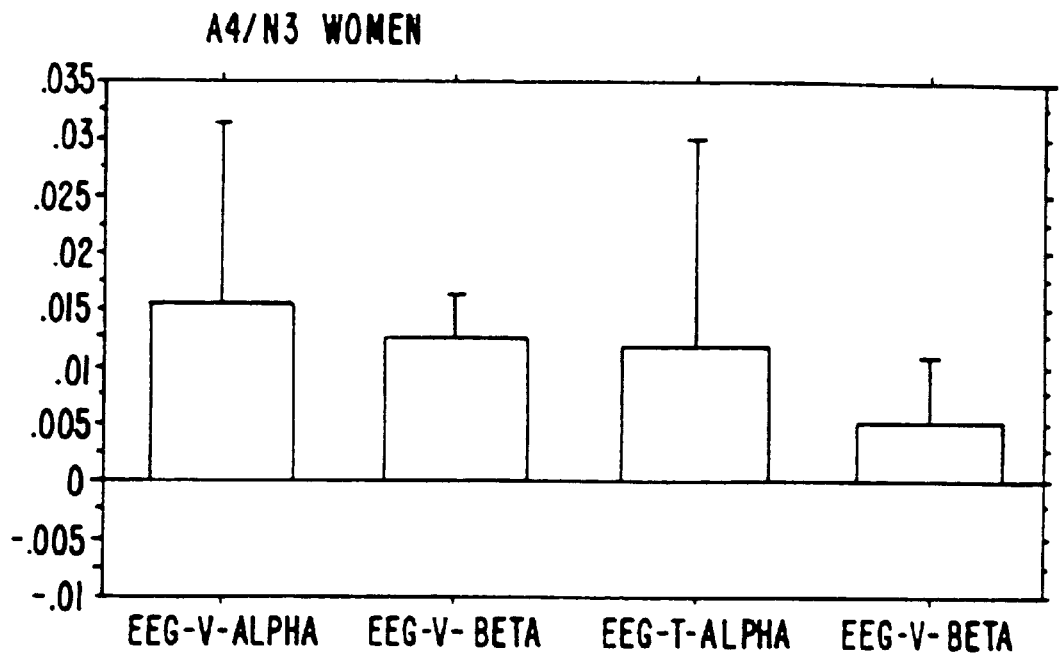

FIG. 196A and 196B show the EEG data in men and women for androstane A4/N3.

Figure 197A:
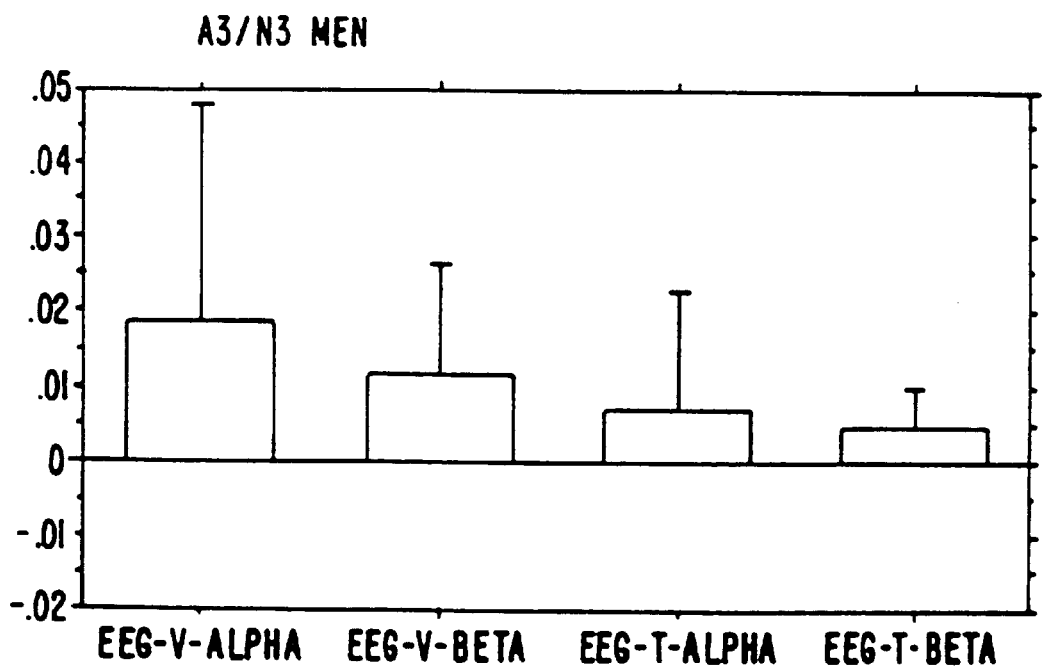
Figure 197B:
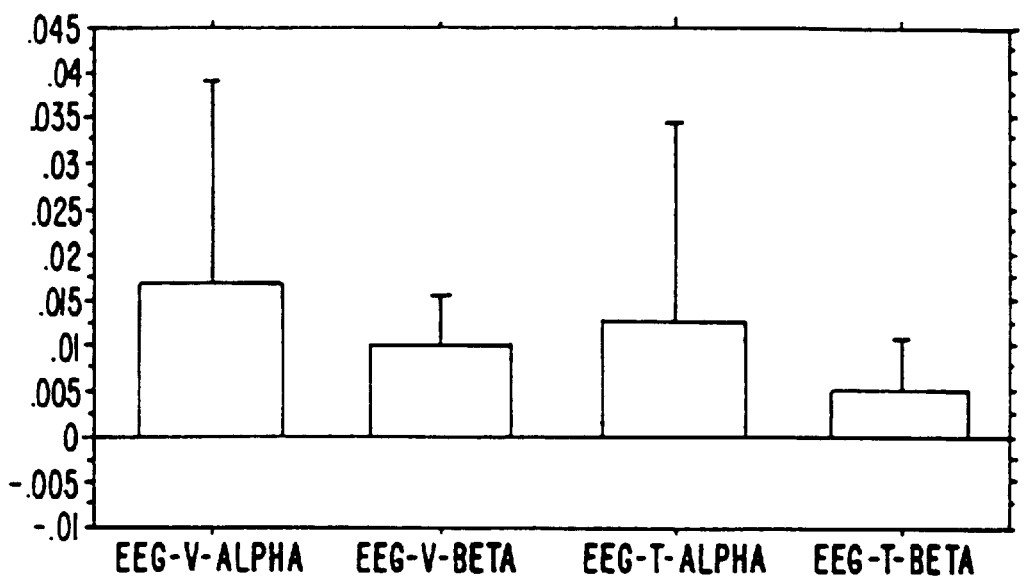

FIGS. 197A and 197B show the EEG data in men and women for androstane A3/N3.

Figure 198A:
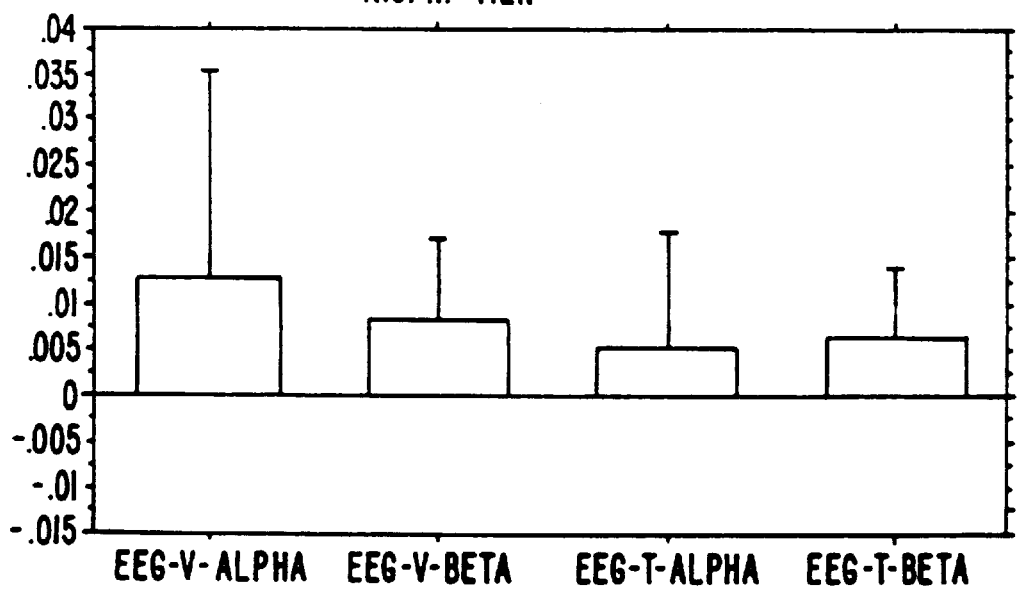
Figure 198B:
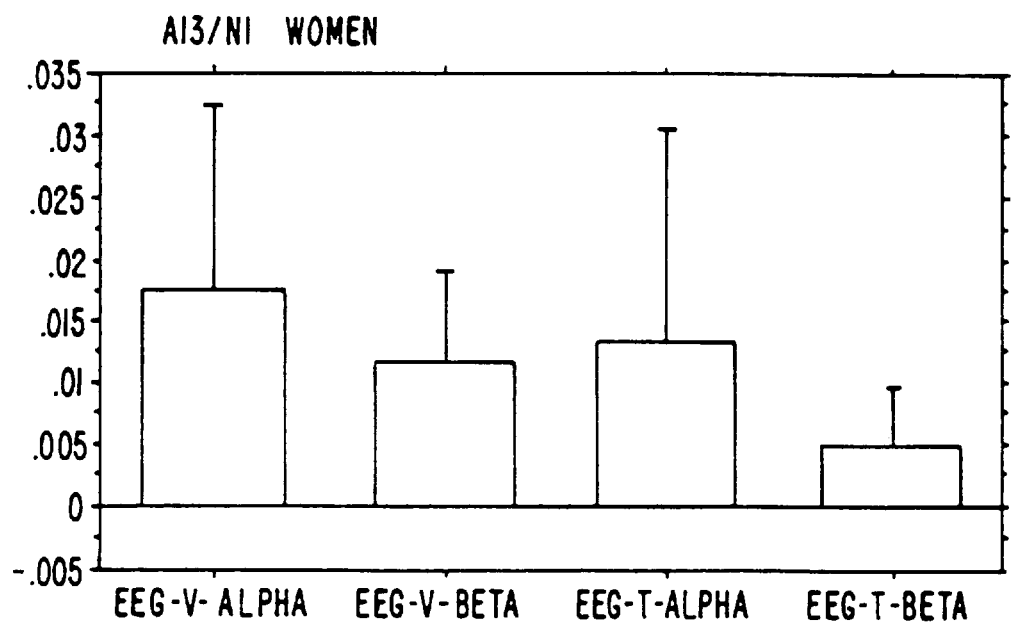

FIGS. 198A and 198B show the EEG data in men and women for androstane A13/N1.

Figure 199A:
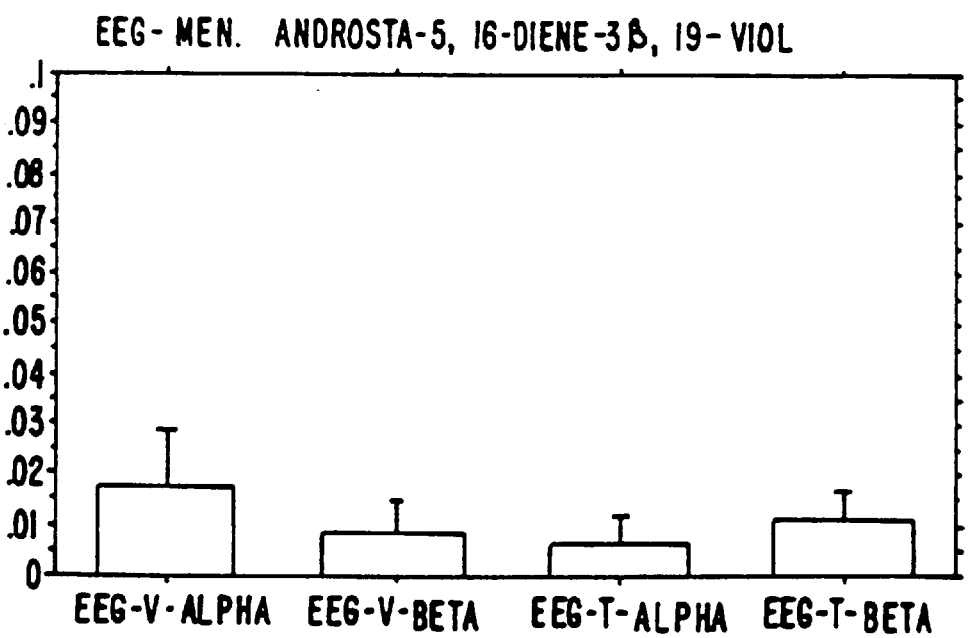
Figure 199B:
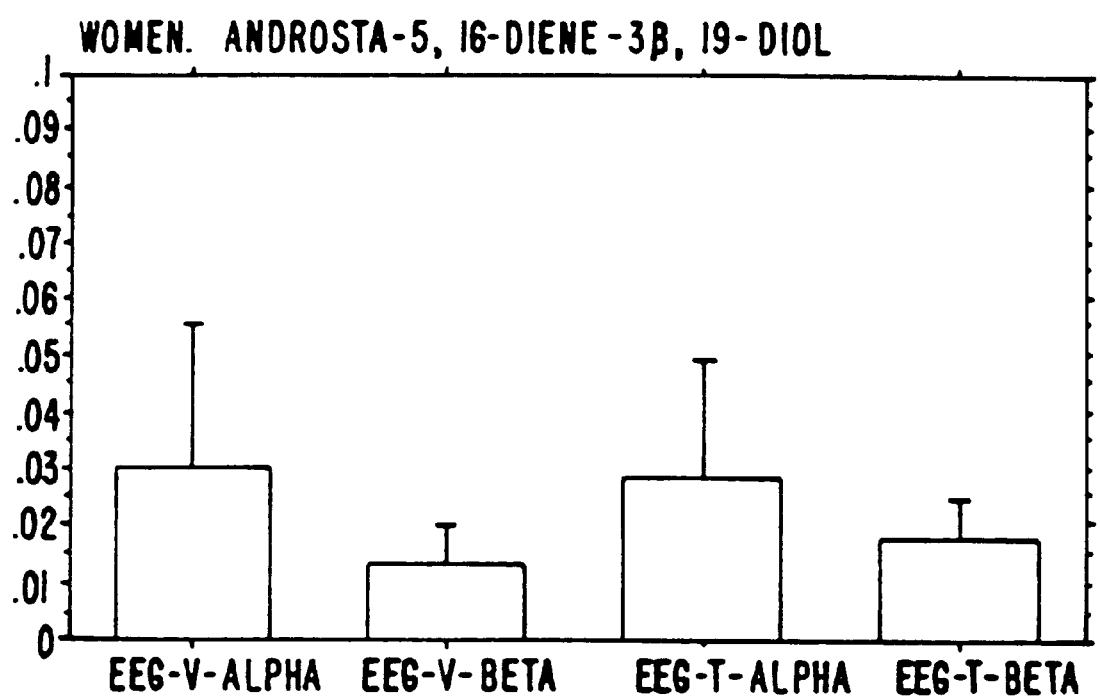

FIGS. 199A and 199B show the EEG data in men and women for androst-5,16-dien-3β,19-diol.

Figure 200A:
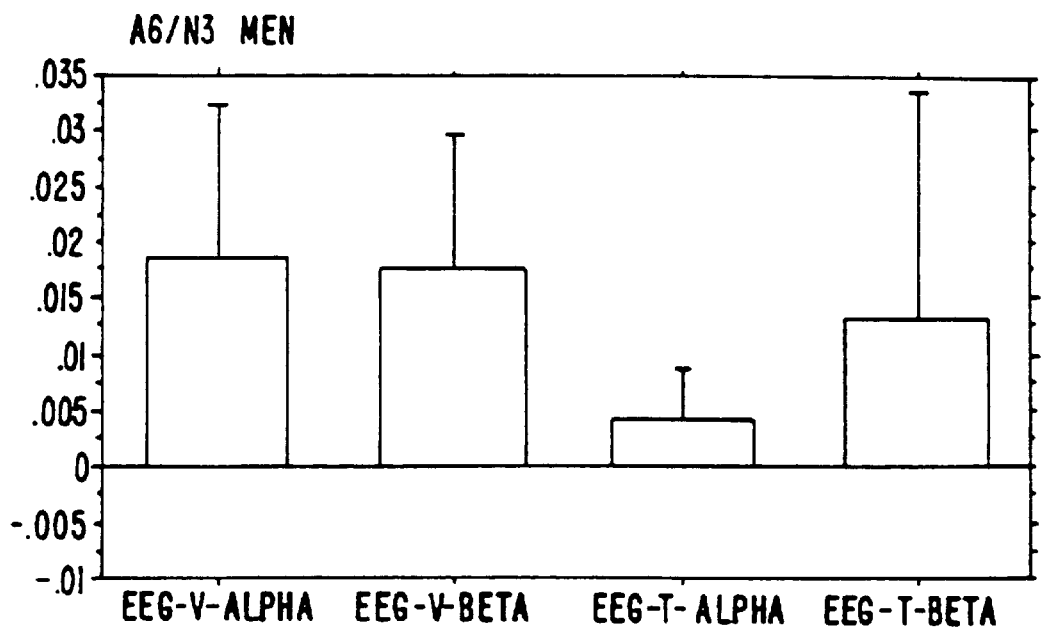
Figure 200B:
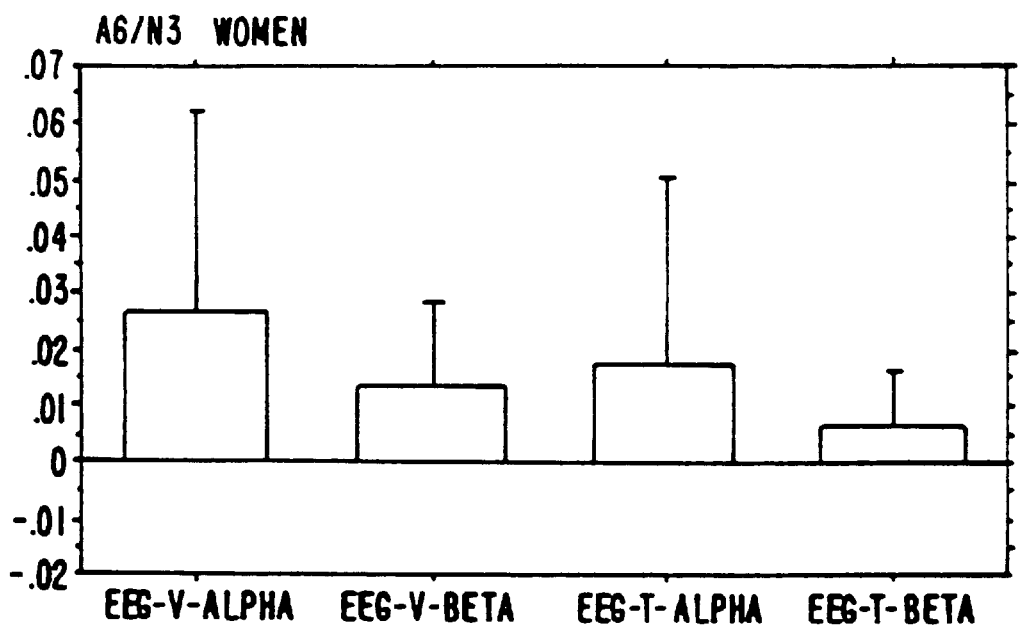

FIGS. 200A and 200B show the EEG data in men and women for androstane A6/N3.

Figure 201A:
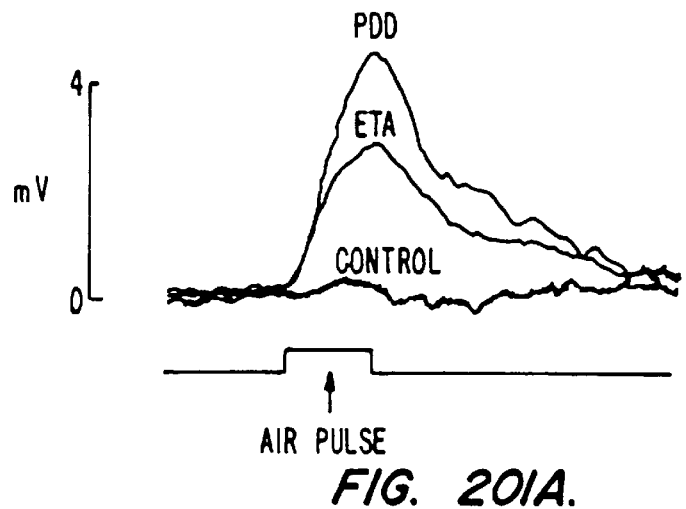
Figure 201B:
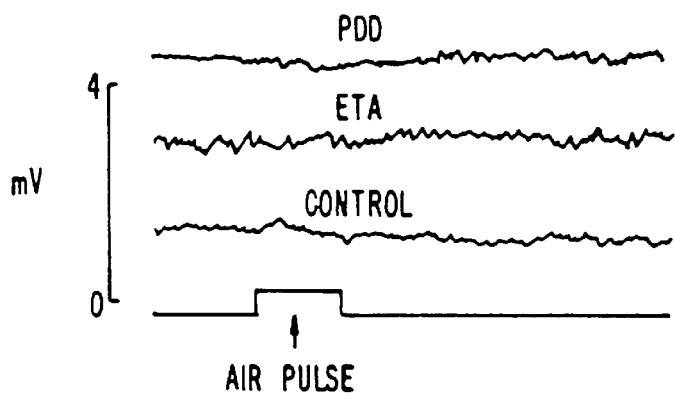

FIGS. 201A and 201B are traces of EVGs in the VNO of a male subject, tested with two vomeropherins (FIG. 201A), and electrograms from the nasal respiratory mucosa (FIG. 201B) using the same vomeropherins.

Figure 202:
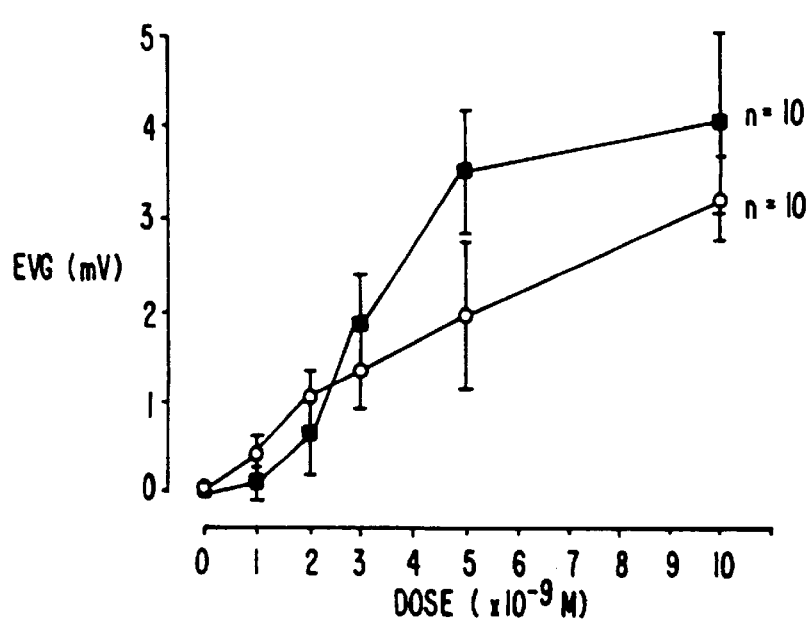

FIG. 202 shows the dose dependent effect of two vomeropherins in male subjects.

Figure 203:
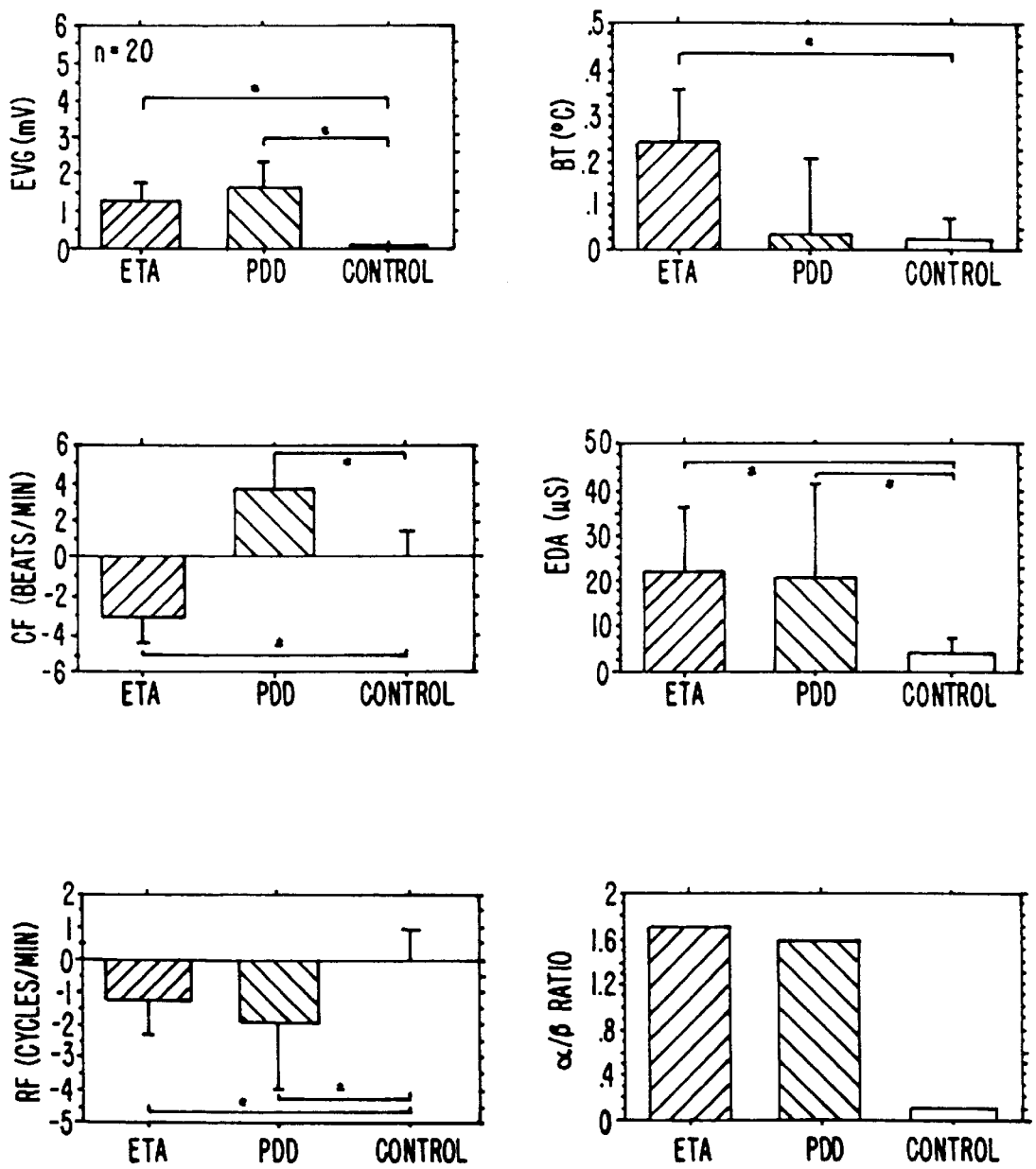

FIG. 203 shows the central nervous system reflex response of two vomeropherins.

Figure 204:
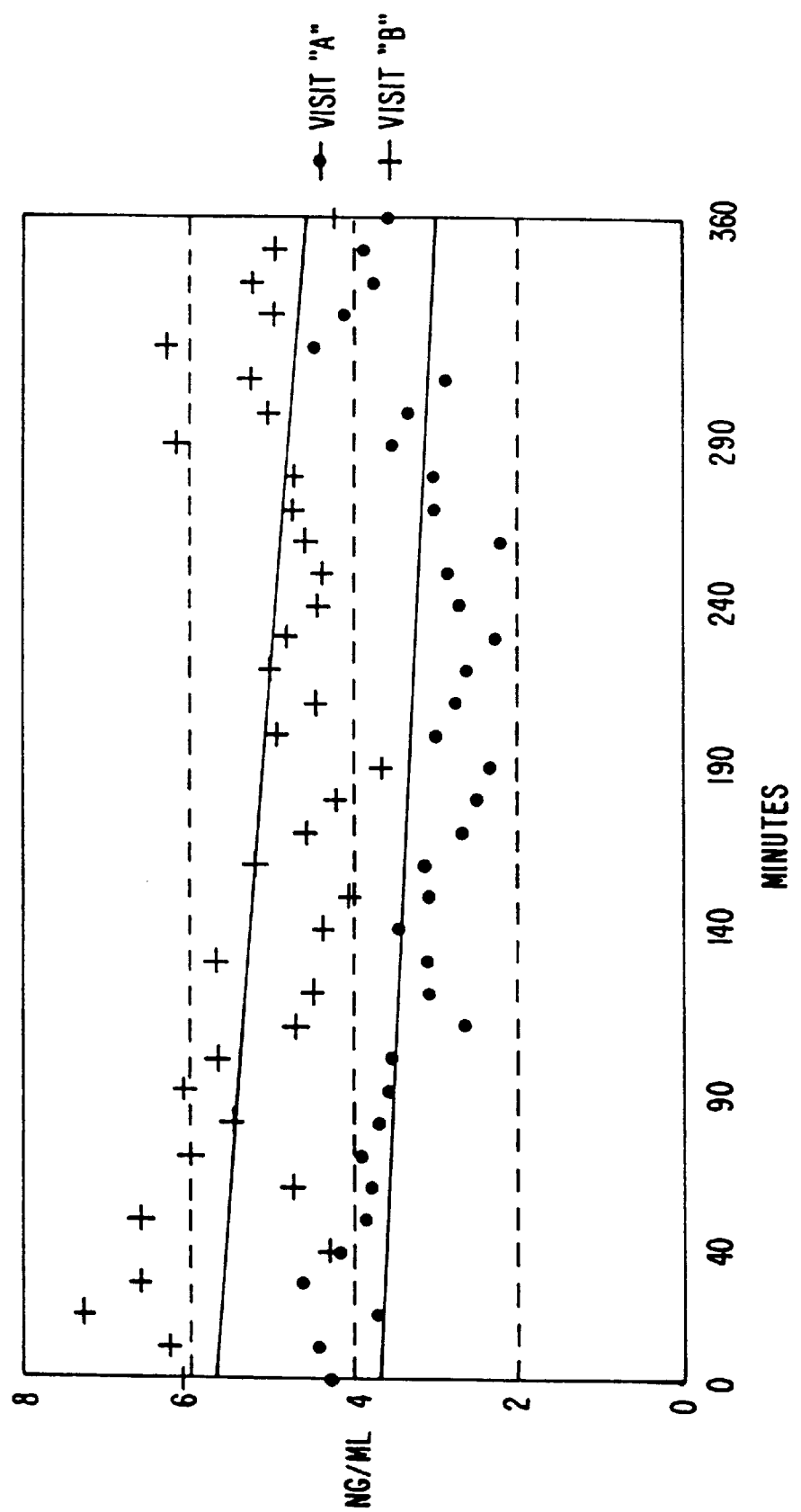

FIG. 204 shows the difference in testosterone levels in a subject administered in one visit a placebo (B curve) to the VNO, and on a second visit (A curve), the compound pregna-4,20 dien-3,6-dione.

Figure 205:
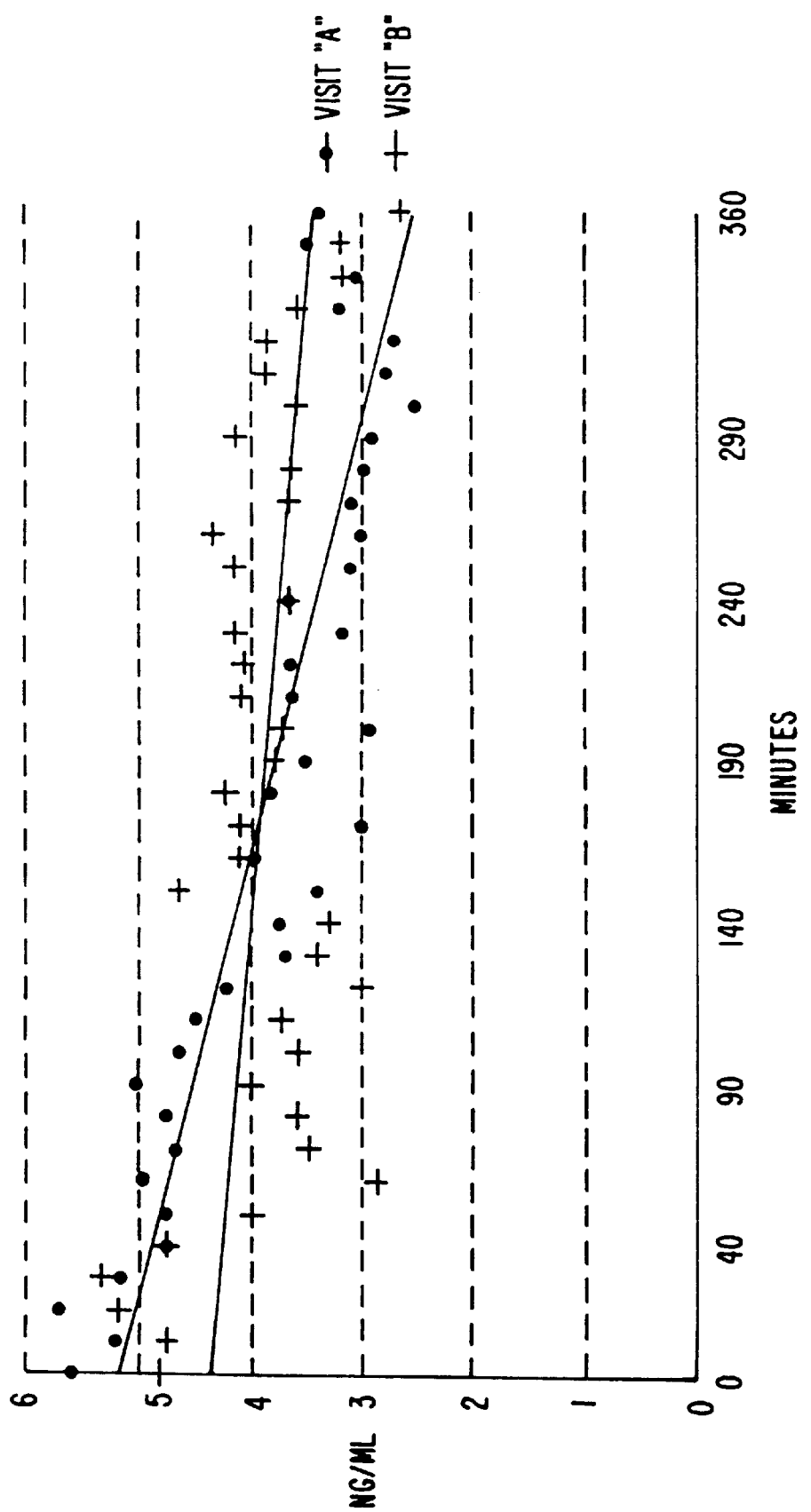
Figure 206:
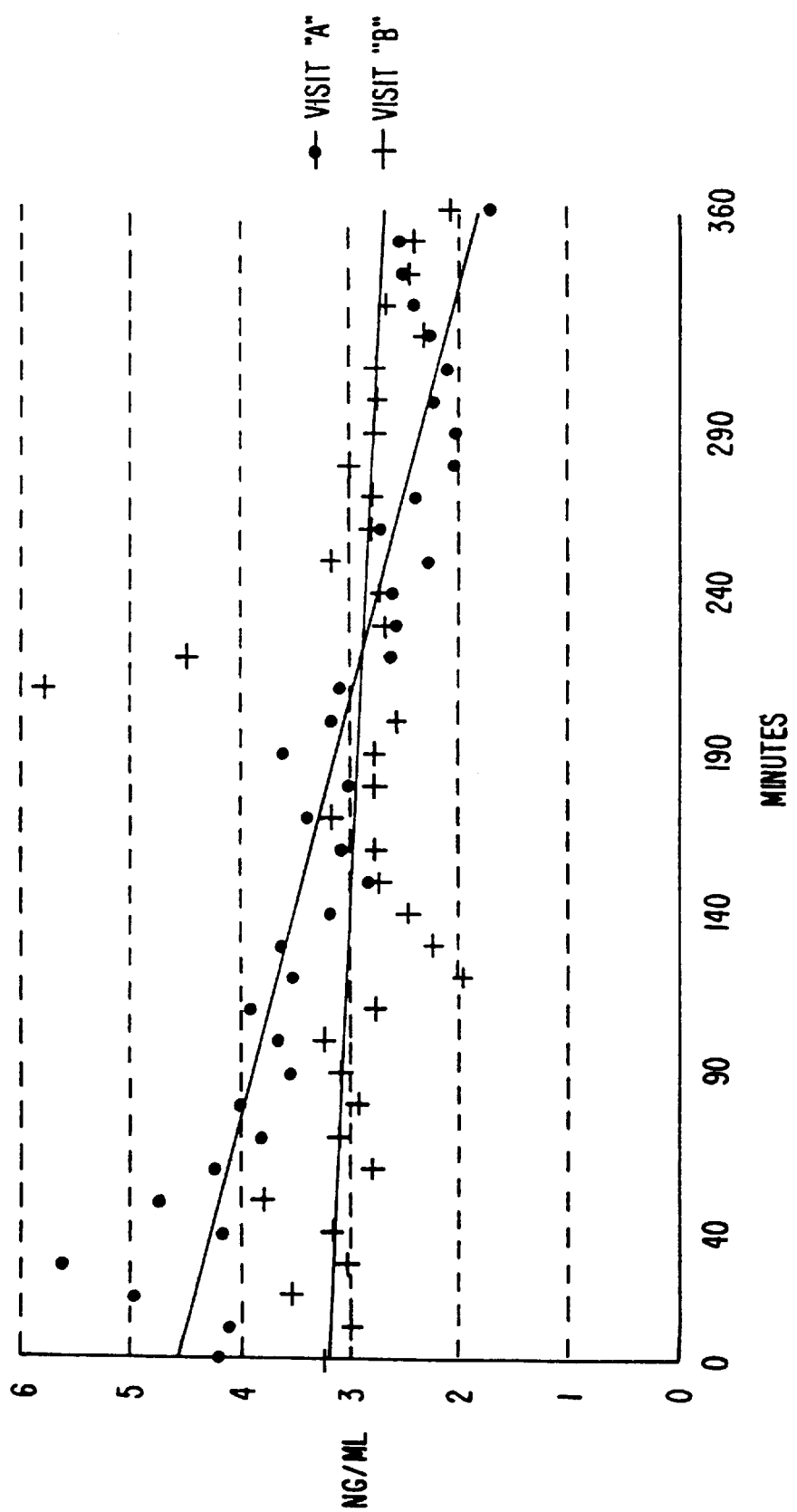
Figure 207:
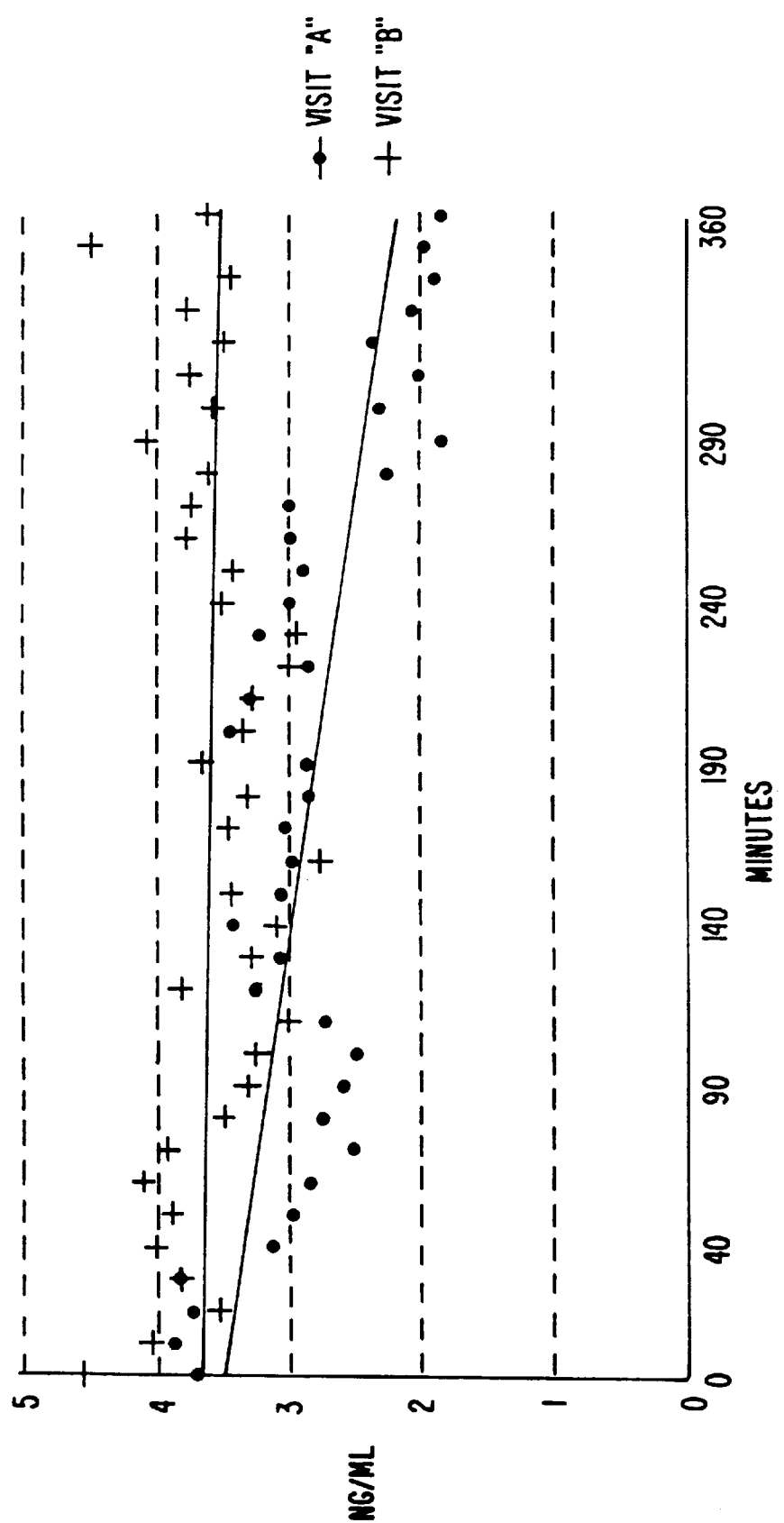

FIGS. 205, 206 and 207 show the data for the testosterone tests on three additional subjects given a placebo, in case B, and pregna-4,20-dien-3,6-dione in case A.

Figure 208:
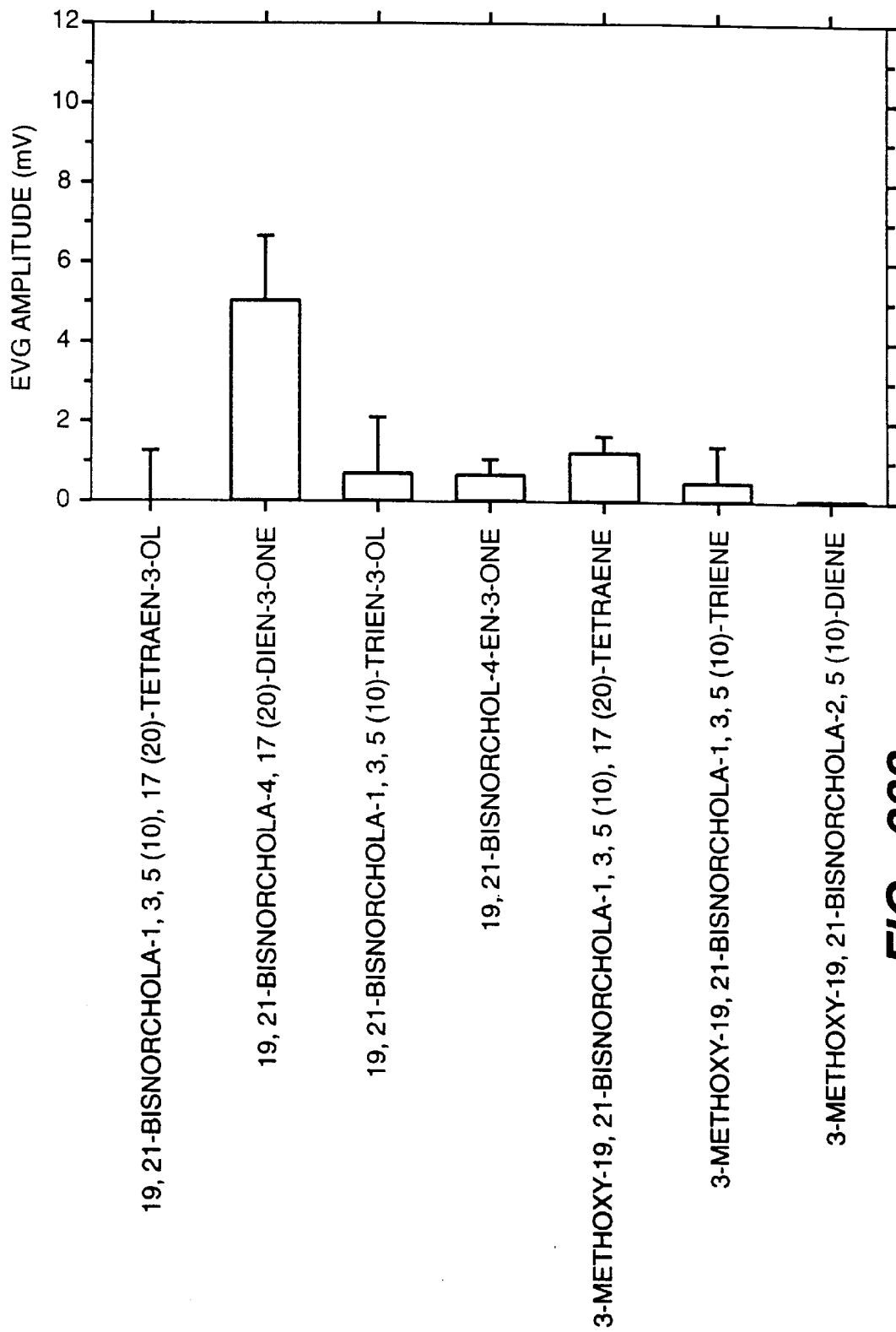
Figure 209:
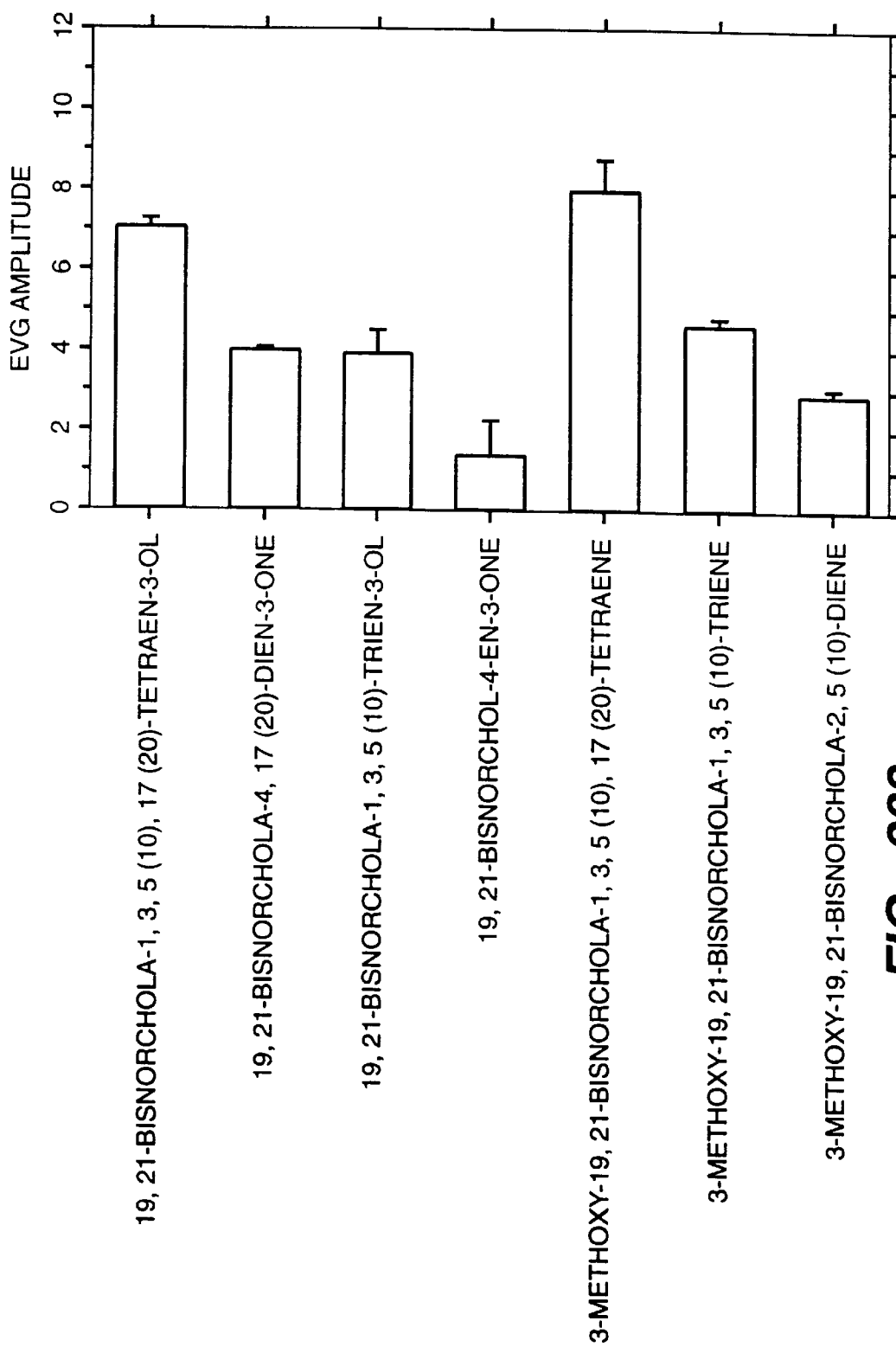
Figure 210A:
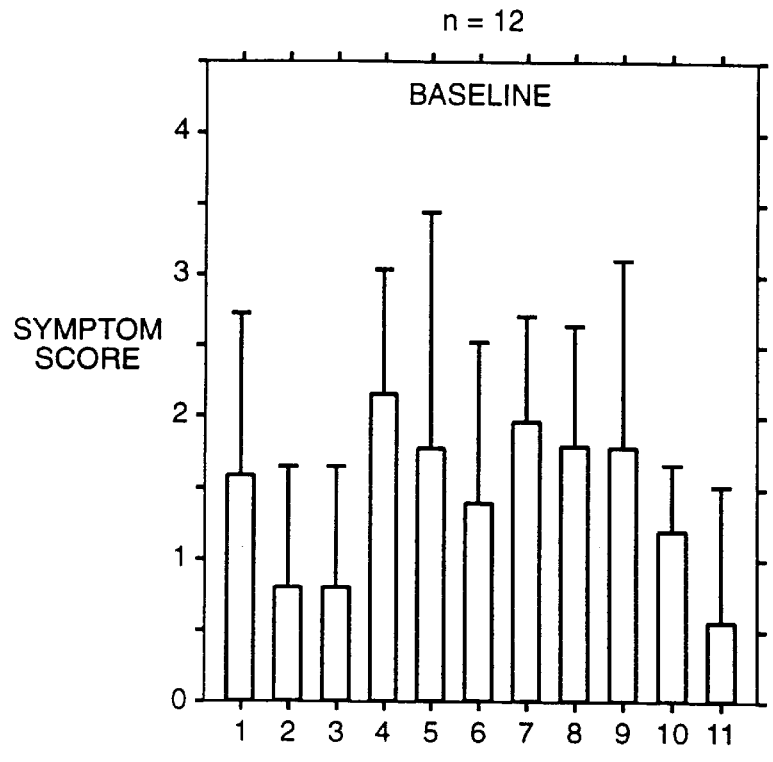
Figure 210B:
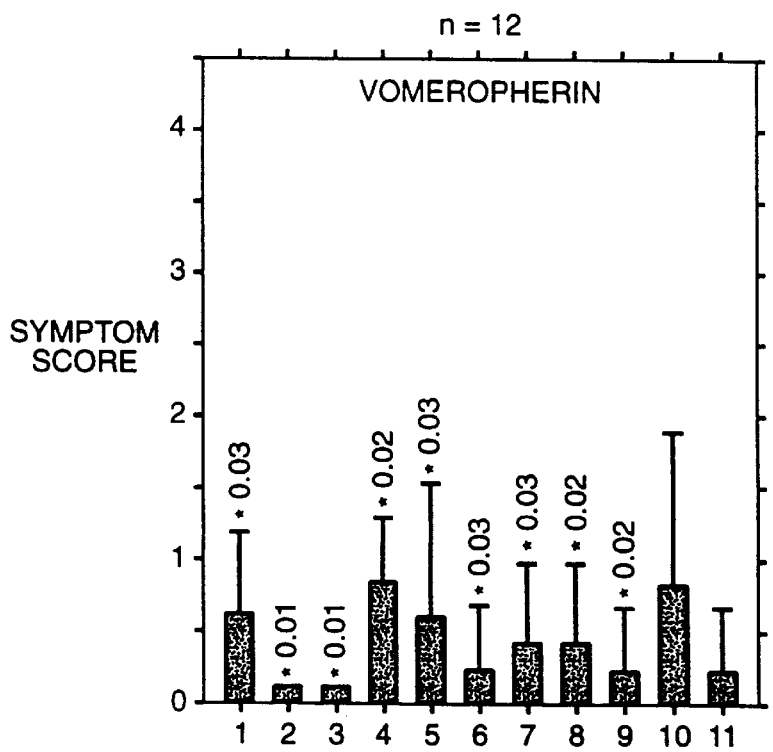
Figure 210C:
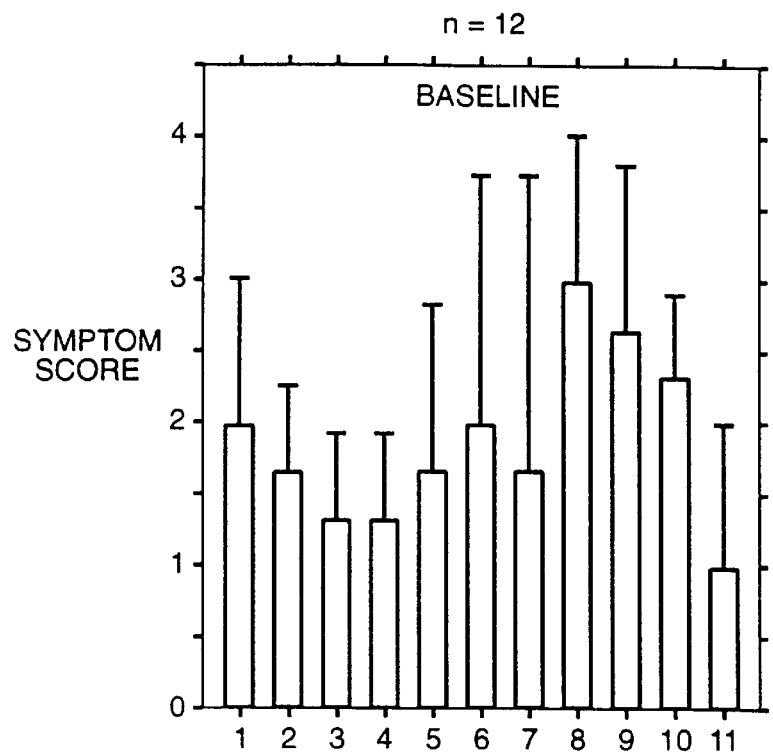
Figure 210D:
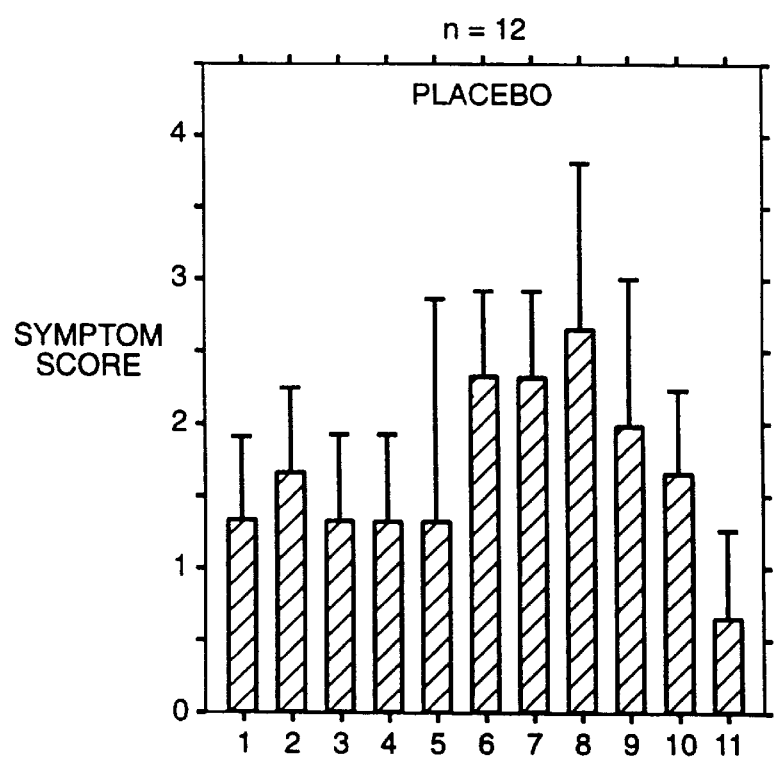

FIG. 208 and FIG. 209 show the amplitudes of steroids E2/NC2, E1/NC2, E2/NC3, E1/NC3, methylated E2/NC2, methylated E2/NC3 and E8/NC3 in Chart VI, in human male and female VNO's, respectively.

FIG. 210 shows the results on eleven PMDD symptoms in women administered a placebo or estra-4,16-dien-10β-ol-3-one.

Figure 211A:
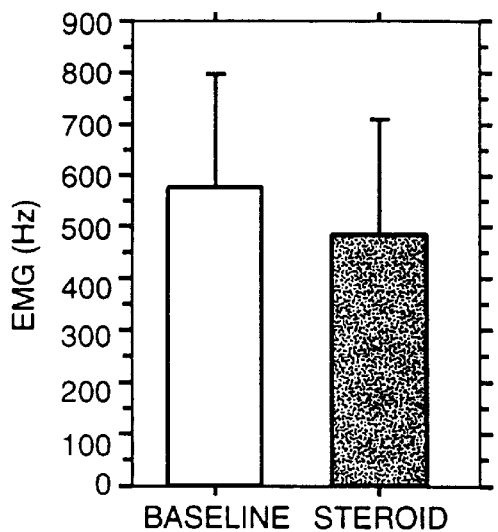
Figure 211B:
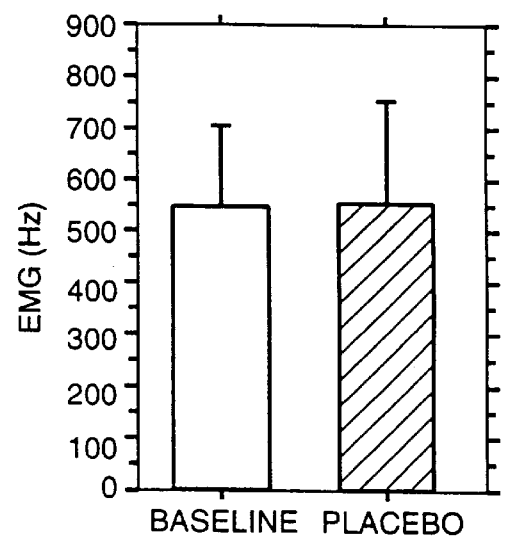

FIG. 211 shows the electromyogram results in women administered a placebo or estra-4,16-dien-10β-ol-3-one.

Figure 212A:
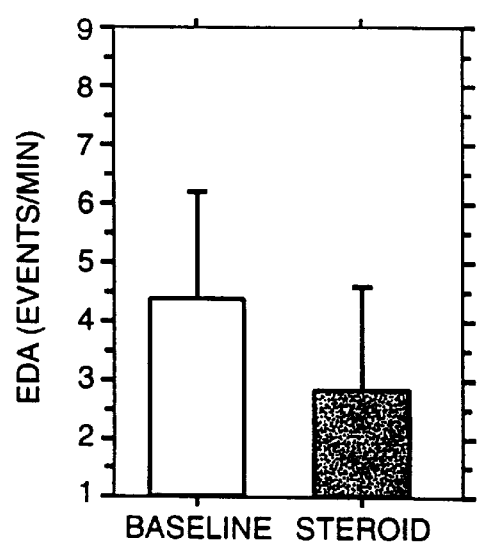
Figure 212B:
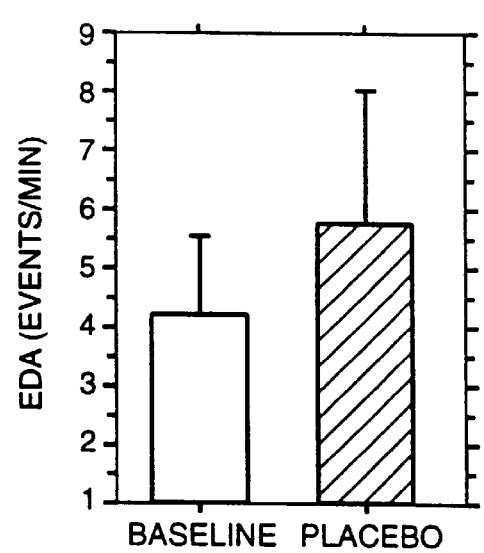

FIG. 212 shows the frequency of electrodermal activity events in women administered on placebo or estra-4,16-dien-10β-ol-3-one.

Figure 213:
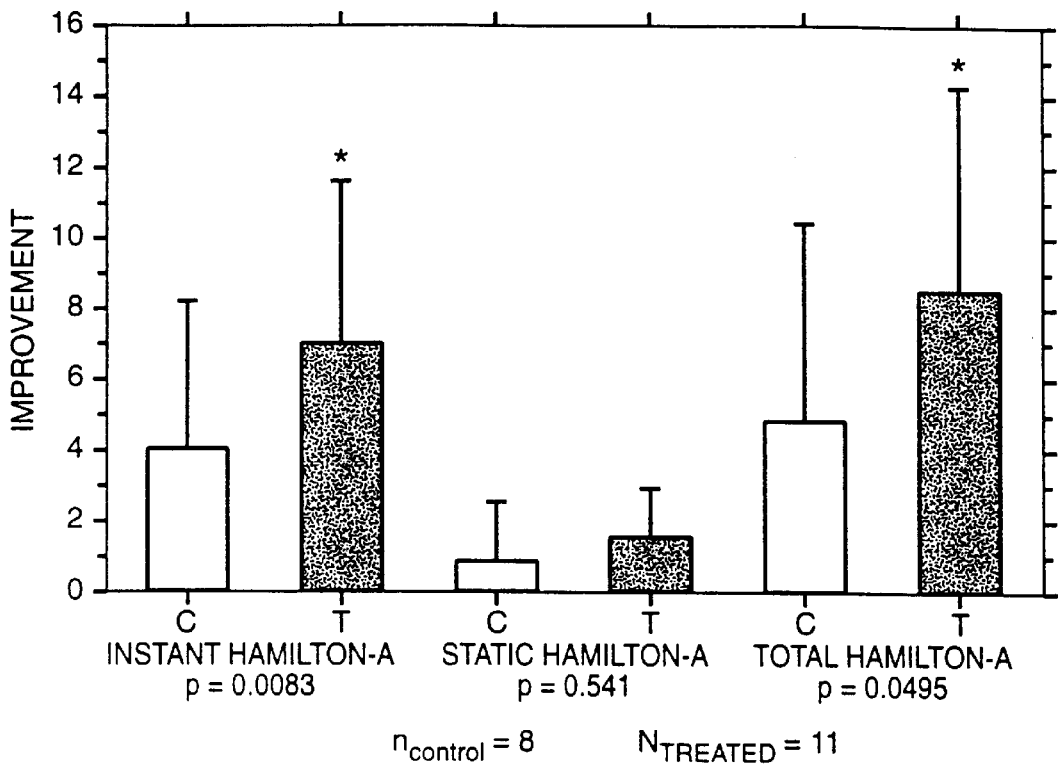
Figure 214:
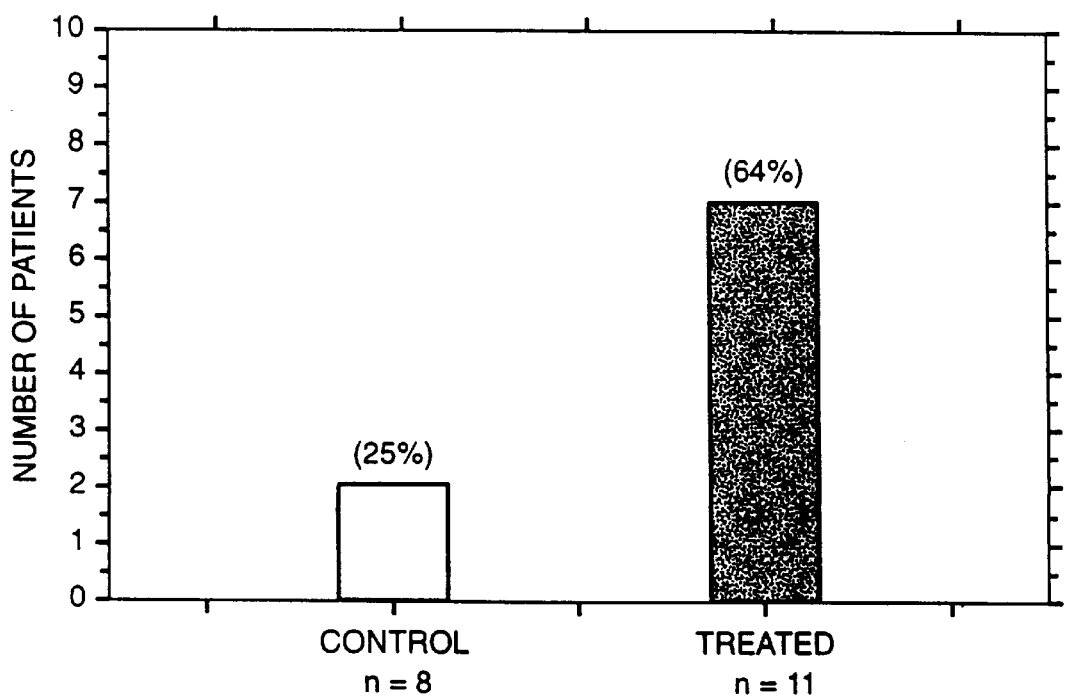

FIGS. 213 and 214 show the results of Hamilton-A anxiety tests for treatment to the VNO of anxious patients with androsta-4,16-dien-3β-ol.

Figure 215:
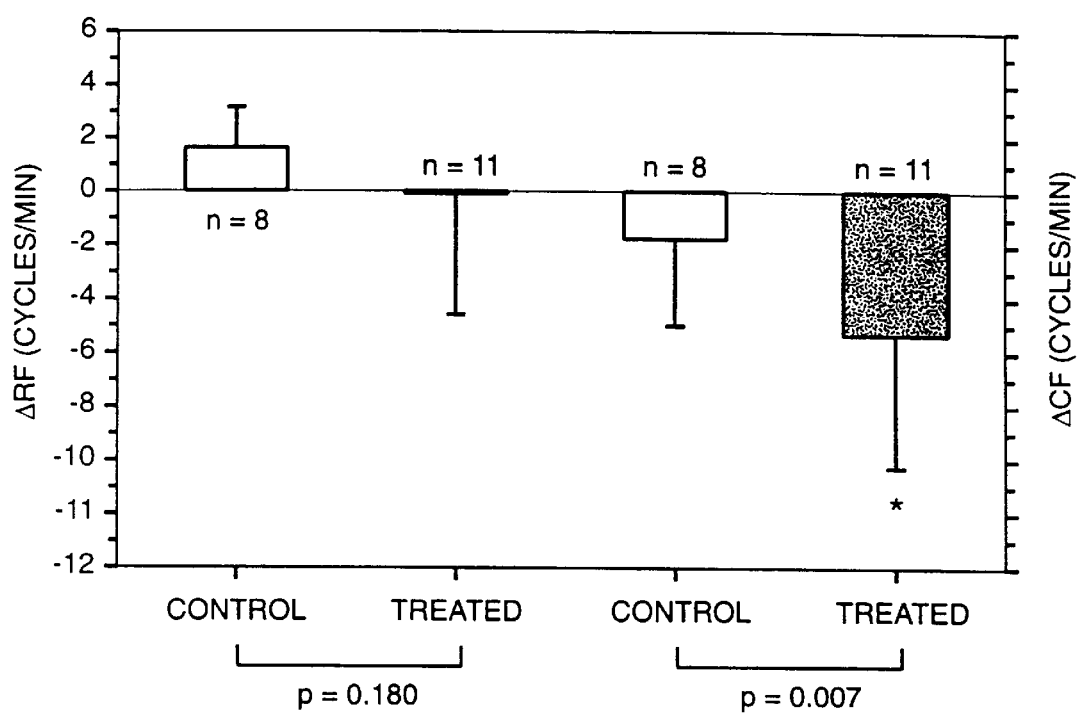

FIG. 215 shows the results on effect on respiratory frequency and cardiac frequency for treatment to the VNO of anxious patients with androsta-4,16-dien-3β-ol.

Figure 216:
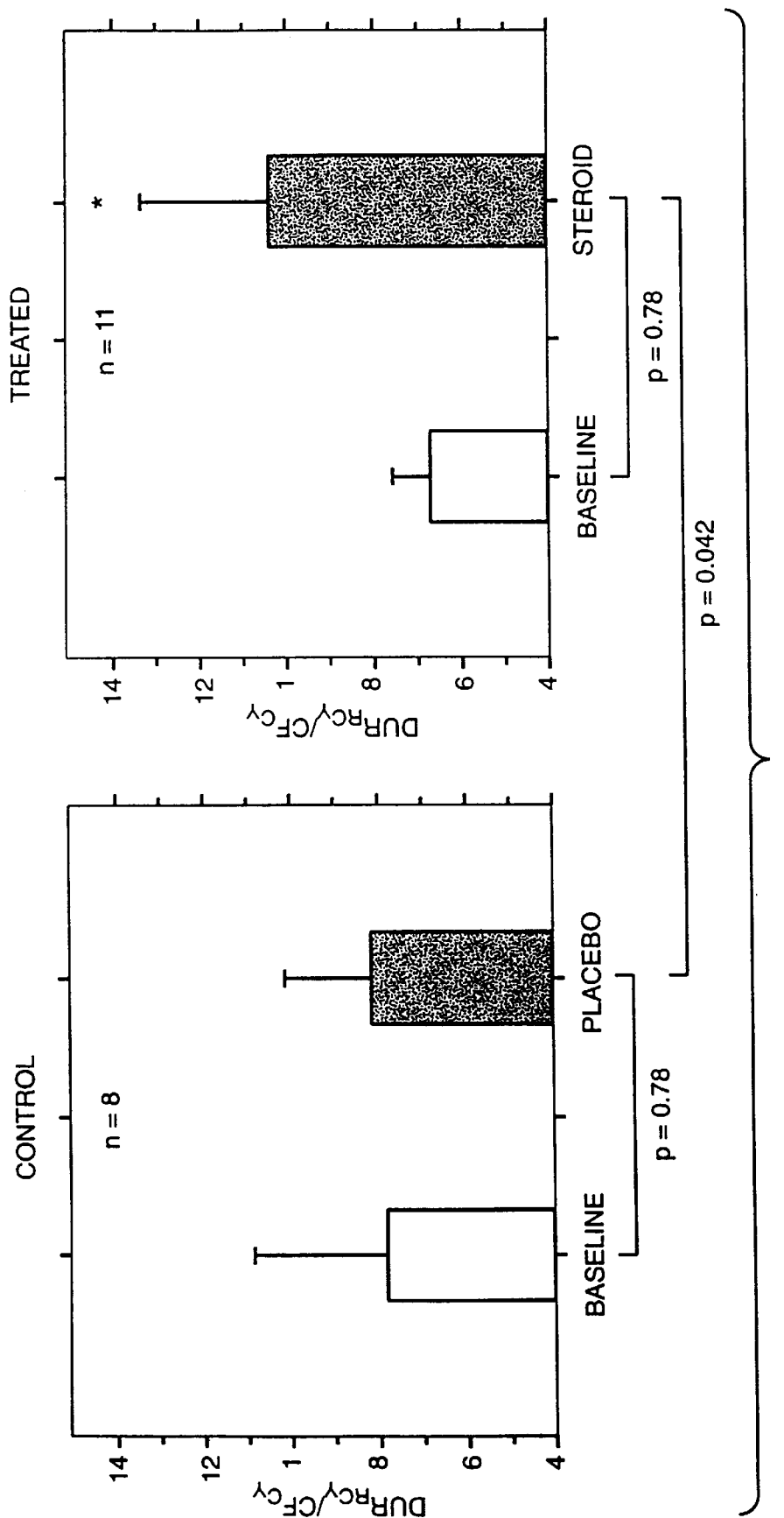

FIG. 216 shows the results on parasympathetic tone for treatment to the VNO of anxious patients with androsta-4,16-dien-3β-ol.

Figure 217:
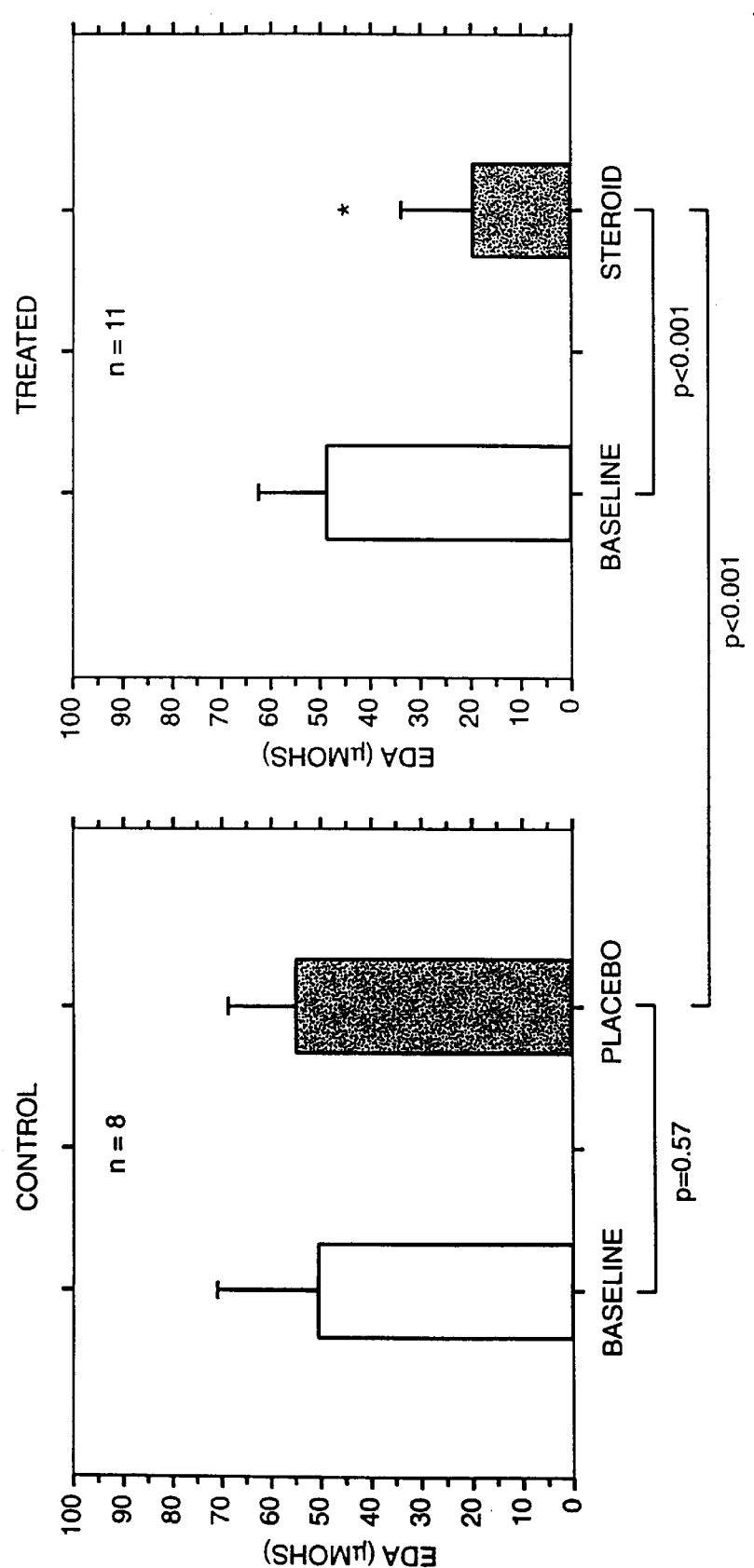

FIG. 217 shows the results on electrodermal activity for treatment to the VNO of anxious patients with androsta-4,16-dien-3β-ol.

Figure 218:
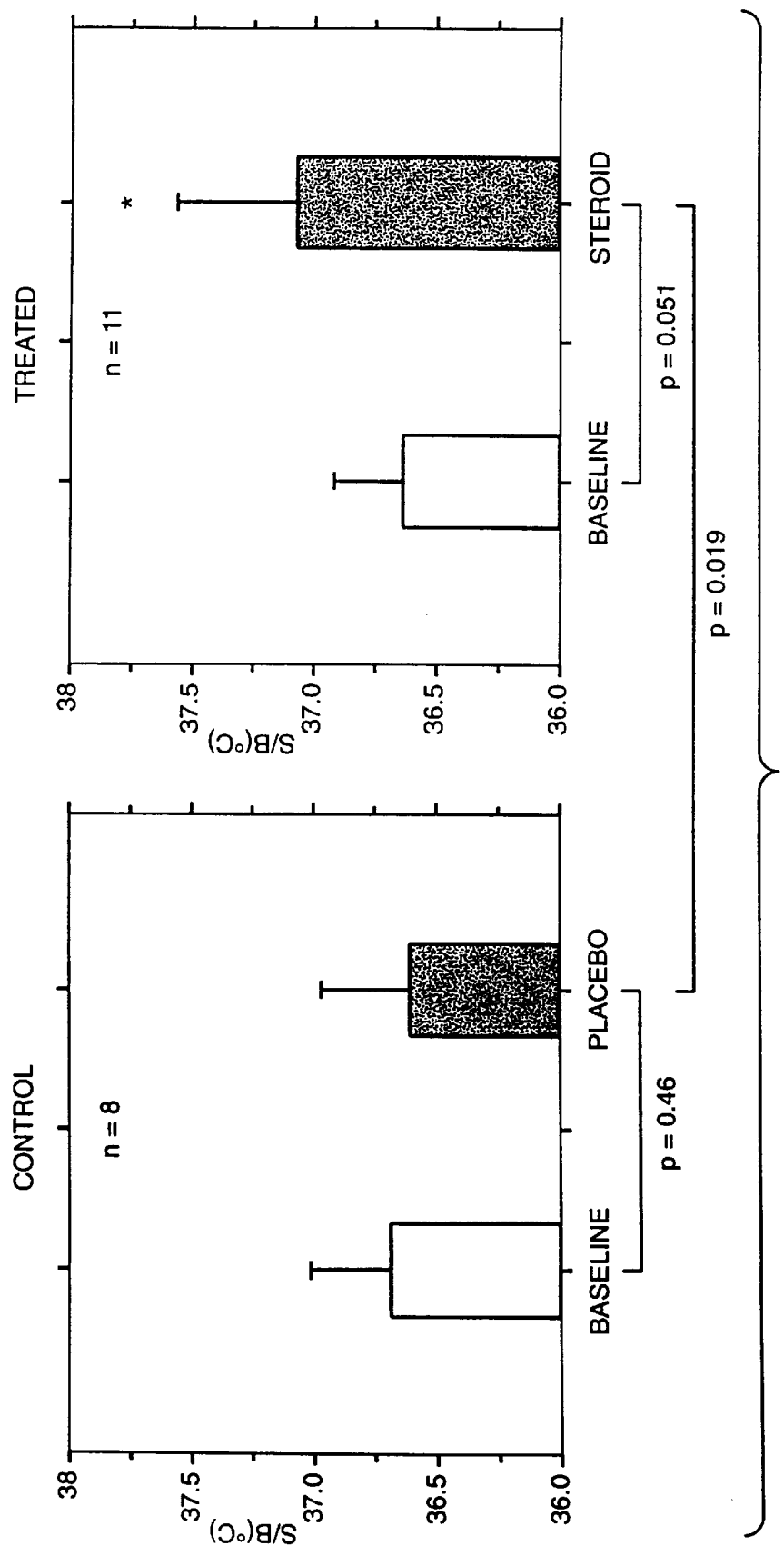

FIG. 218 shows the results on change in body temperature for treatment to the VNO of anxious patients with androsta-4,16-dien-3β-ol.

Figure 219:
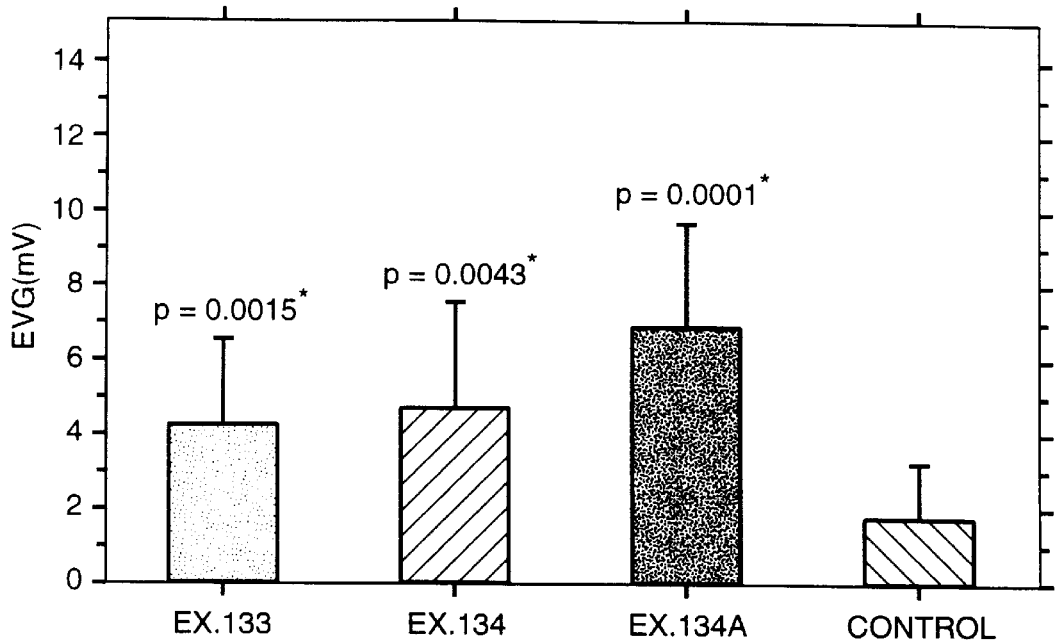

FIG. 219 shows the results of EVG tests on women administered the compounds of Examples 133, 134 and 134A.

Figure 220:
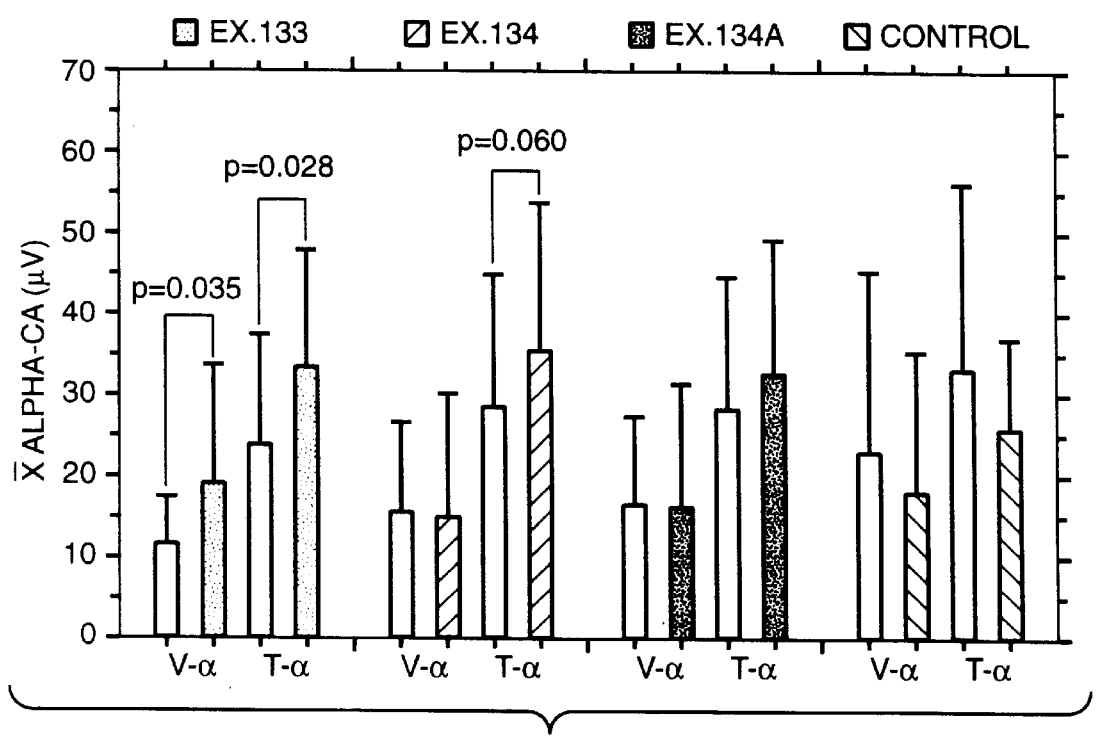

FIG. 220 shows the results of alpha brainwave testing on women administered the compounds of Examples 133, 134 and 134A.

FIG. 221A is a summary of electrophysical effects due to stimulation of the VNO in male subjects by eight steroids having epoxy groups on ring D.

FIG. 221B is a summary of electrophysical effects due to stimulation of the VNO in female subjects by eight steroids having epoxy groups on ring D.

DETAILED DESCRIPTION OF THE INVENTION

I. Definitions

An "affect" is a transient feeling state. Typical negative affects are feelings of nervousness, tenseness, shame, anxiousness, irritability, anger, rage and the like. "Moods" are longer lasting feeling states such as guilt, sadness, hopelessness, worthlessness, remorsefulness, misery, unhappiness and the like. "Character traits" are more permanent aspects of an individual's personality. Typical negative character traits are sensitivity, regretfulness, blameworthiness, stubbornness, resentfulness, bitterness, timidness, laziness and the like.

The vomeropherins according to the present invention may have use for stimulating, through contact with the VNO, of one or more of the hormonal, behavioral and autonomic functions of the hypothalamus. Due to the predominant role played by the hypothalamus in a wide variety of internal body functions and the neural connection between the VNO and the hypothalamus, the vomeropherins according to the present invention are in a position to stimulate such functions as endocrine output control, for example, the control of the pituitary output of vasopressin and oxytocin as well as a number of other peptides. Vasopressin is an anti-diuretic hormone because of its action within the kidney to enhance water uptake and to concentrate the urine. In addition, it has an action within the body to regulate blood pressure through its action on arterial smooth muscle and an action on metabolism through its enhancement of glycogen conversion to glucose in the liver. Oxytocin, receptors of which are found on uterine smooth muscle and on mammary smooth muscle, can cause milk letdown via contraction of the mammary smooth muscle and cause uterine contractions during birth. The hypothalamus also controls release of hormones from the anterior pituitary gland such as ACTH, prolactin, LH (Luteinizing Hormone), GH (Growth Hormone), TSH (Thyroid Stimulating Hormone), FSH (Follicle Stimulating Hormone) and beta-endorphin. Thus, for example, the ability to control LH secretion may lead to control of fertility, in females, or testosterone production in males. Testosterone production may be utilized for treatment of conditions such as low libido in males or for treatment of muscle wasting diseases or conditions, such as aging. Testosterone reduction may be utilized for treatment of conditions such as prostate cancer.

Control of behavior hypothalamic functions is also feasible by use of the vomeropherins according to the present invention. It is known that the hypothalamus controls such behavioral outputs as fear, rage, pleasure and circadian rhythms which regulate sleep and wakefulness. Other functions controlled by the hypothalamus include appetite, thirst, sympathetic functions such as, flight and fight, and functions such as cardiovascular control, thermoregulation and visceral functions such as control of the gut muscle and acid secretion for digestion. Thus, while there is a multitude of sensory inputs into the hypothalamus from various parts of the anatomy it is believed that the vomeropherins of the present invention provide, for the first time, a way of stimulating through the nasal cavity by inhalation to contact the epithelial cells in the VNO, a method of stimulating functions of the hypothalamus discussed above.

"Pregnane steroids" are aliphatic polycyclic hydrocarbons characterized by a four-ring steroidal structure with a methylation at the 10- and 13-positions and ethylation (including unsaturated groups) at the 17-position. A pregnane is a subset of pregnanes commonly understood to mean that the compound has at least one double bond. Furthermore, all derivatives which have the structural characteristics described above are also referred to generically as pregnane steroids.

A "cholane steroid" is an aliphatic polycyclic hydrocarbon characterized by a four-ring steroid structure, with methylation at the 10- and 13-positions and a 2-pentyl group (including unsaturated groups) at the 17-position.

A "chemoreceptor" is a receptor molecule displayed on the surface of a "chemosensory" neuroepithelial cell which binds in a stereospecific fashion to a particular ligand or ligands. This specific binding initiates a signal transduction which initiates an afferent nerve impulse. Chemoreceptors are found, inter alia, in taste buds, olfactory epithelium and vomeronasal tissue.

"Pregnene steroids", as the term is used herein, are aliphatic polycyclic hydrocarbons with a four-ring steroidal structure, at least one double bond in the A-ring, methylation at the 10-position and 13-position, ethylation (including unsaturated groups) at the 17-position and an oxo, hydroxyl or hydroxyl derivative such as alkoxy, ester, benzoate, cypionate, sulfate or glucuronide, at the 3-position. Derivatives which contain these structural characteristics are also referred to generically as pregnene steroids.

The following structure shows the four-ring steroidal structure common to steroids. For illustrative purposes, a side chain on the D-ring is shown for pregnane., In describing the location of groups and substituents, the following numbering system will be employed:

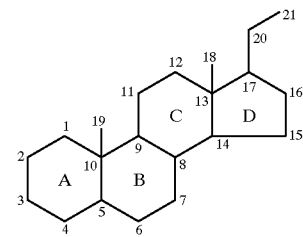

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to an individual in need of the drug. In the present case, a needy individual is one with a physiological or behavioral trait which is normally regulated by the hypothalamus and wherein it is desirable to affect the function of the hypothalamus or the trait. The effective amount of a given drug may vary depending upon the function to be affected, the desired effect, route of administration, and the like. For example, when the steroid is administered as a solution applied to the facial skin of a subject an effective concentration is from 1 microgram/ml to 100 µg/ml, preferably 10 to 50 µ/ml and most preferably 20 to 30 µg/ml. When the steroid is introduced directly into the VNO an effective amount is about 1 picogram to about 1 nanogram, more preferably about 10 picograms to about 50 picograms. When the steroid is administered to the nasal passage, by ointment, cream or aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammillary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the vomeropherin therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a vomeropherin) a summated change in cell surface receptor potential can be measured.

As used herein, "lower alkyl" means a braced or unbranched saturated hydrocarbon chain of 1 to 4 carbons, such as, for example, methyl, ethyl, n-propyl, i-butyl and the like. "Alkoxy" as used herein is used in its conventional sense to mean the group —OR wherein R is alkyl as herein defined.

A "pheromone" is a substance that provides chemical means of communication between members of the same species through secretion and peripheral chemoreception. In mammals pheromones are usually detected by receptors in the vomeronasal organ of the nose. Commonly, pheromones effect development, reproduction and related behaviors. A "vomeropherin" is a more general term which includes pheromones and describes a substance from any source which functions as a chemosensory messenger, binds to a specific vomeronasal neuroepithelial receptor, and induces a physiological or behavioral effect. The physiologic effect of a "vomeropherin" is mediated through the vomeronasal organ.

A picogram (pg) is equal to 0.001 nanograms (ng). A ng is equal to 0.001 micrograms ($\mu$g). A Ag is equal to 0.001 mg.

II. Modes for Carrying Out the Invention

A. Steroids useful in the Invention

The invention is directed to a group of certain steroids.

Syntheses are described herein for the following compounds as designated on the chart:

Chart 1 includes pregnanes to which the invention is directed, but do not limit its scope. The synthesis diagrams that follow depict intermediate and substructure syntheses for the preparation of these pregnanes:

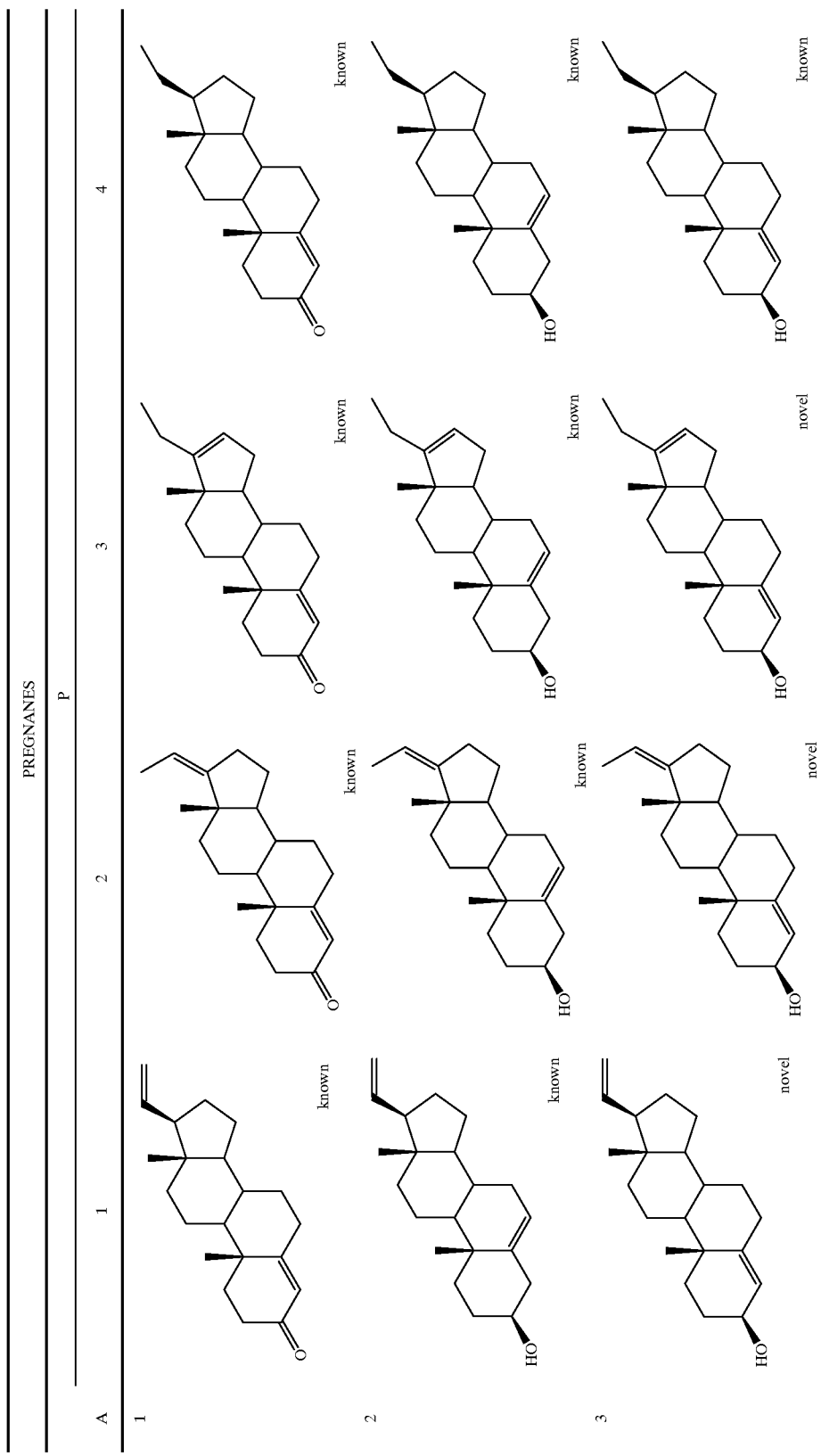

-continued
PREGNANES
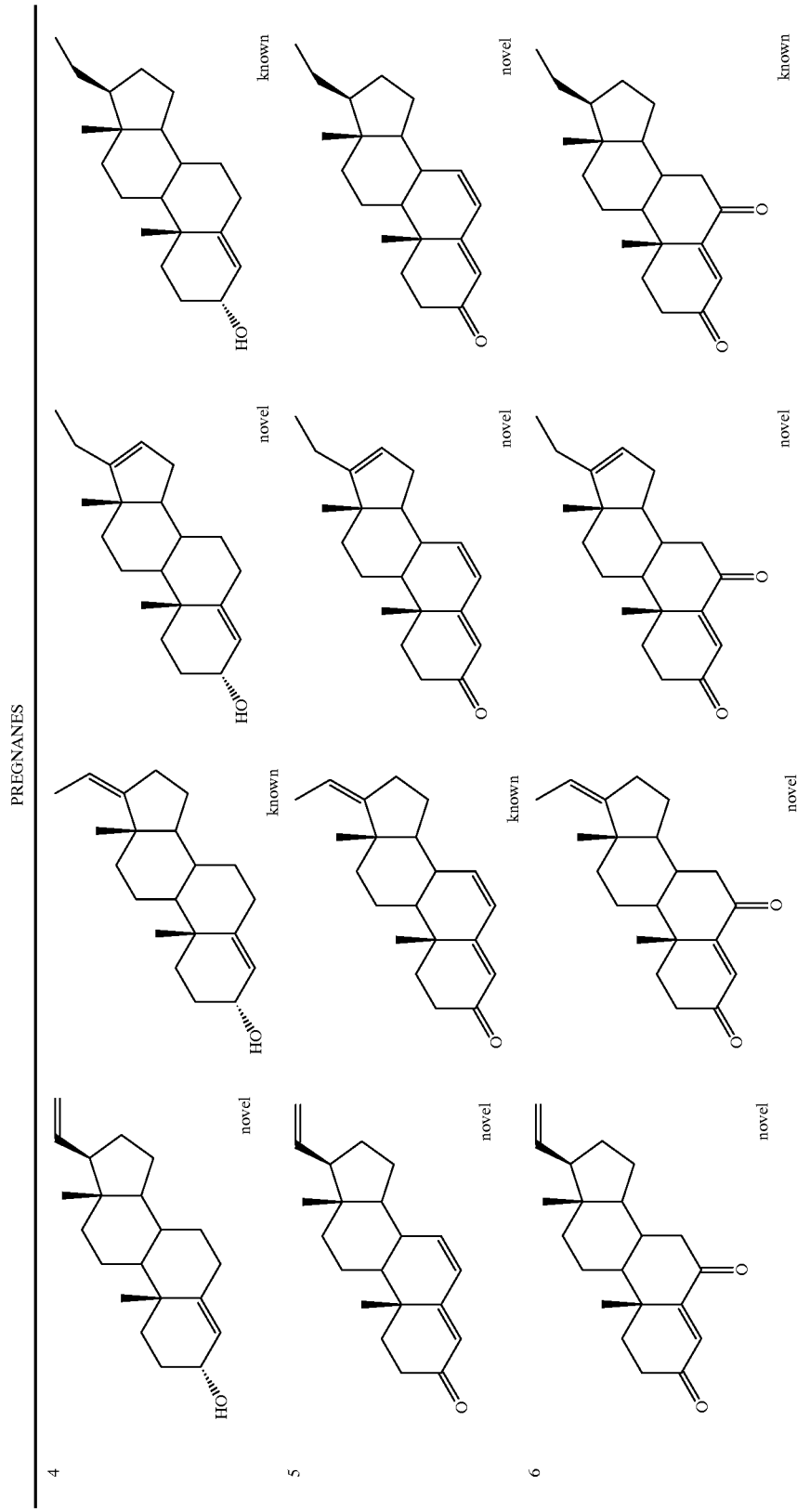

-continued
PREGNANES
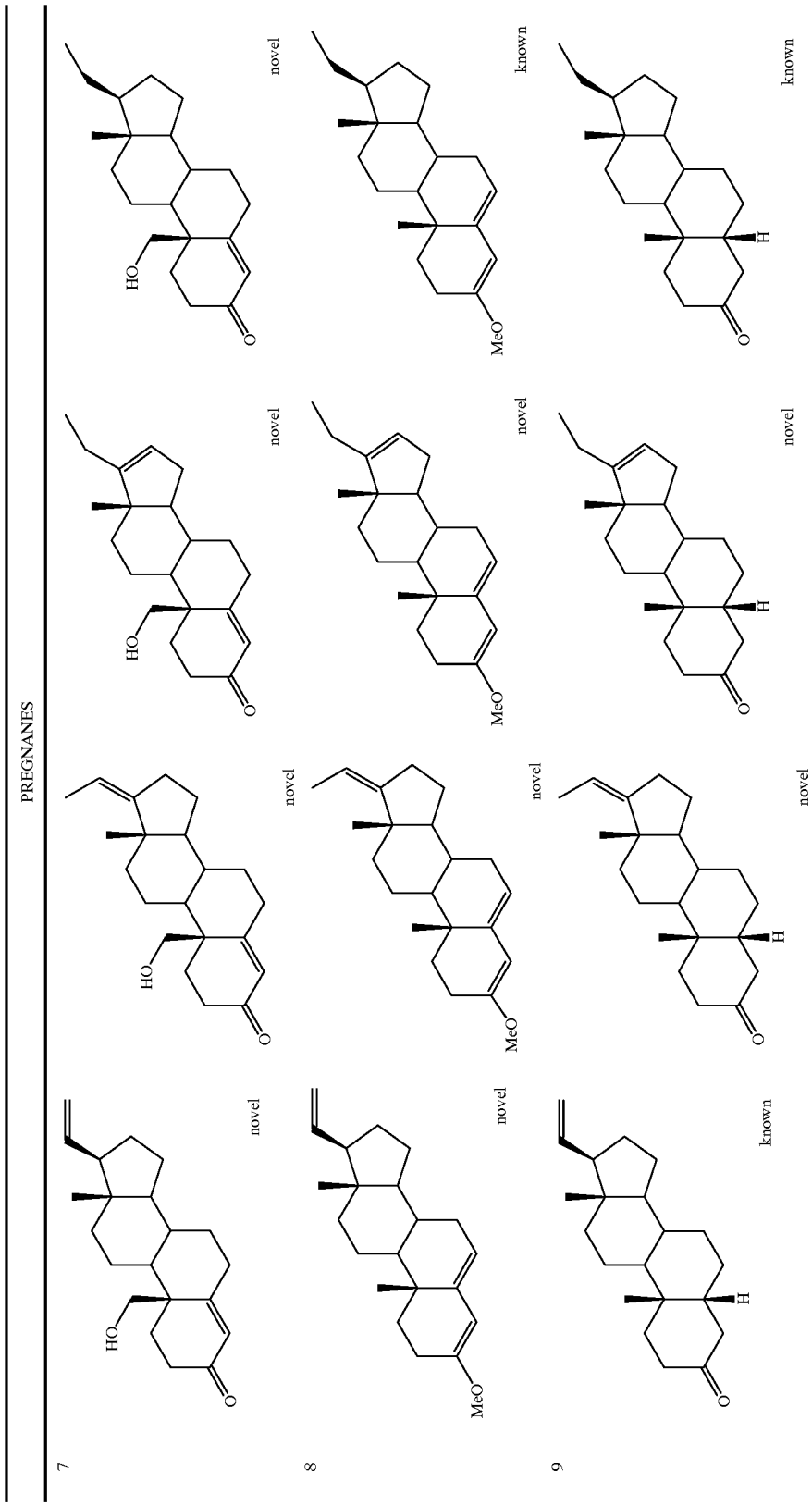

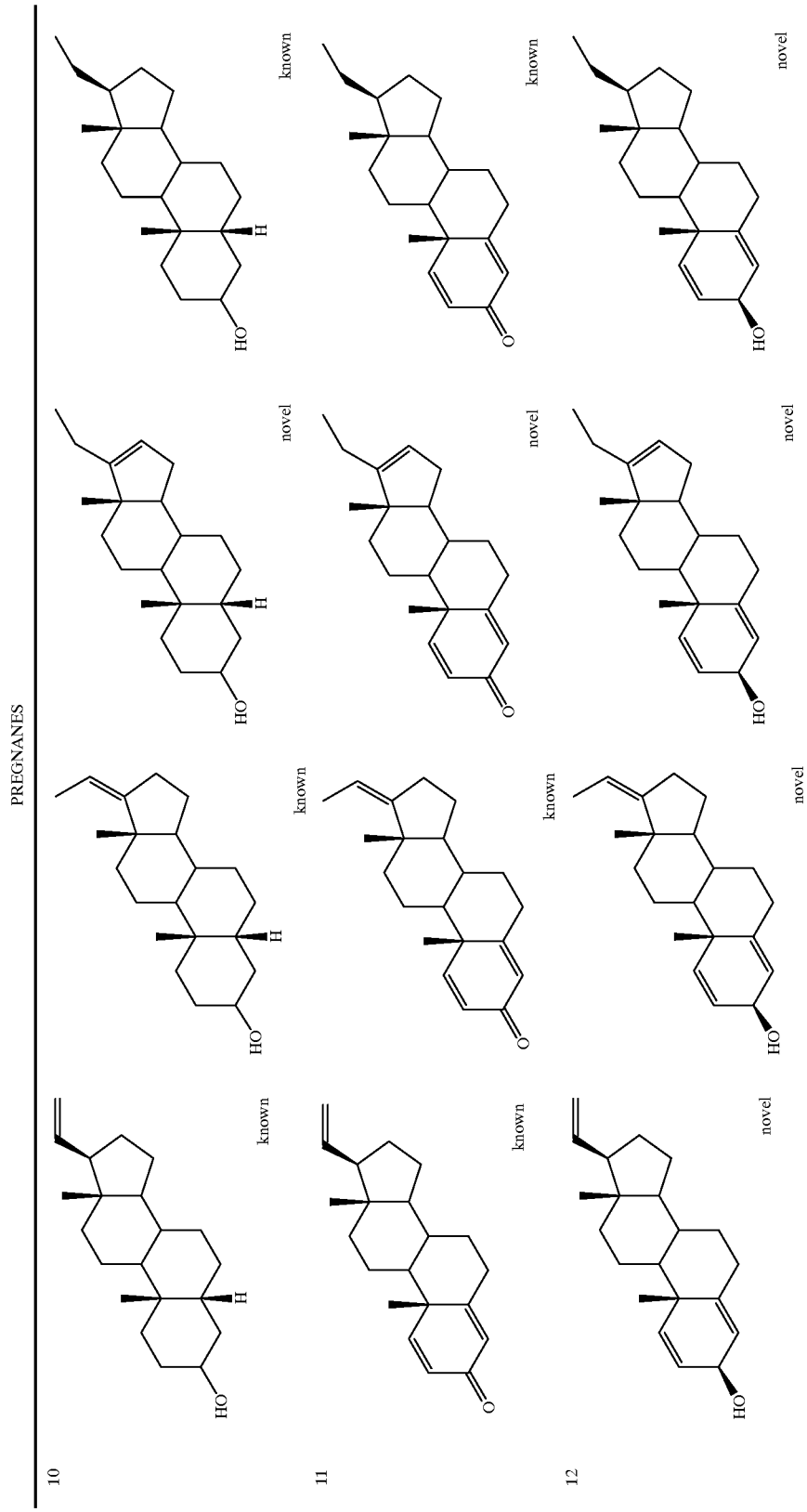
PREGNANES

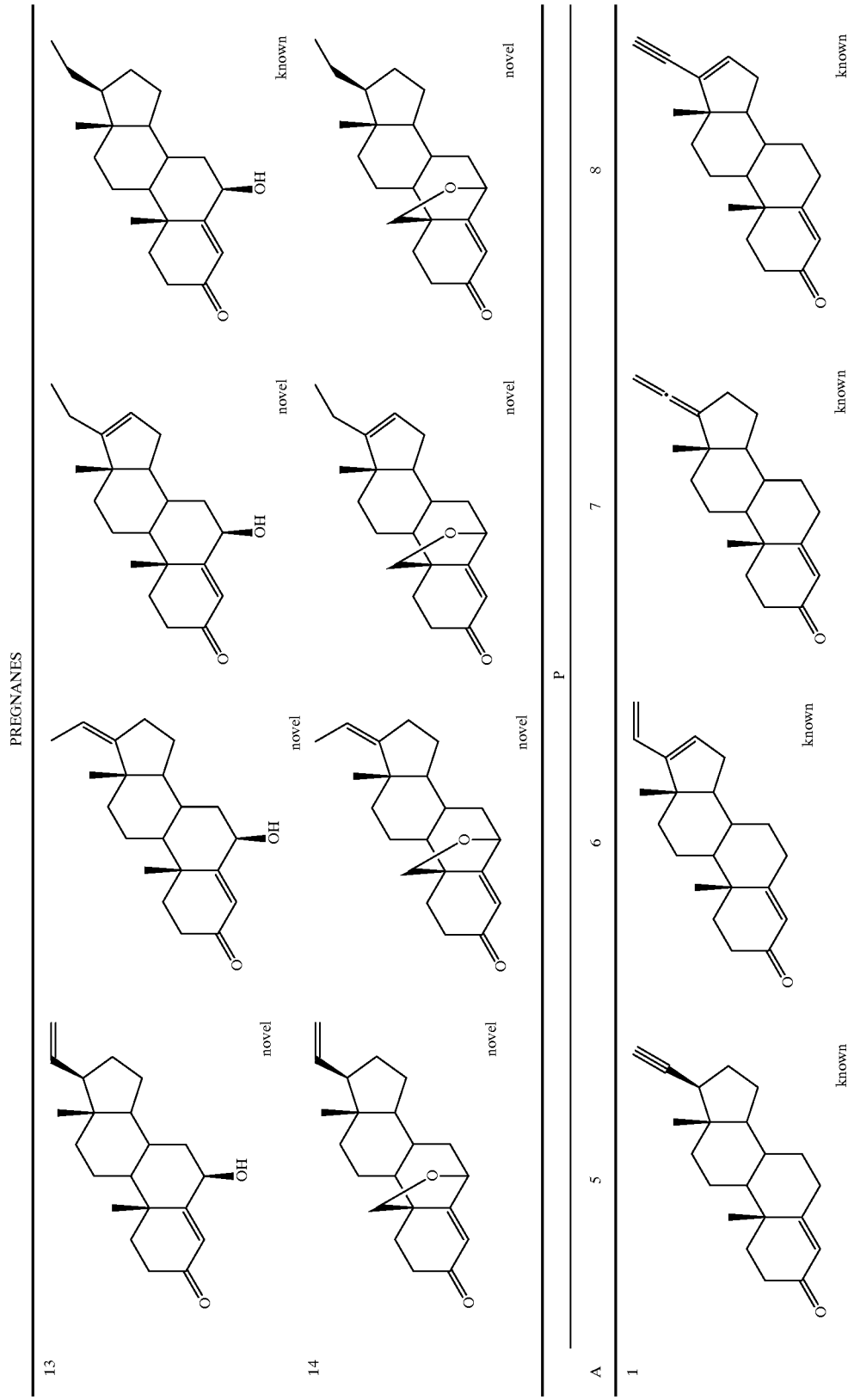

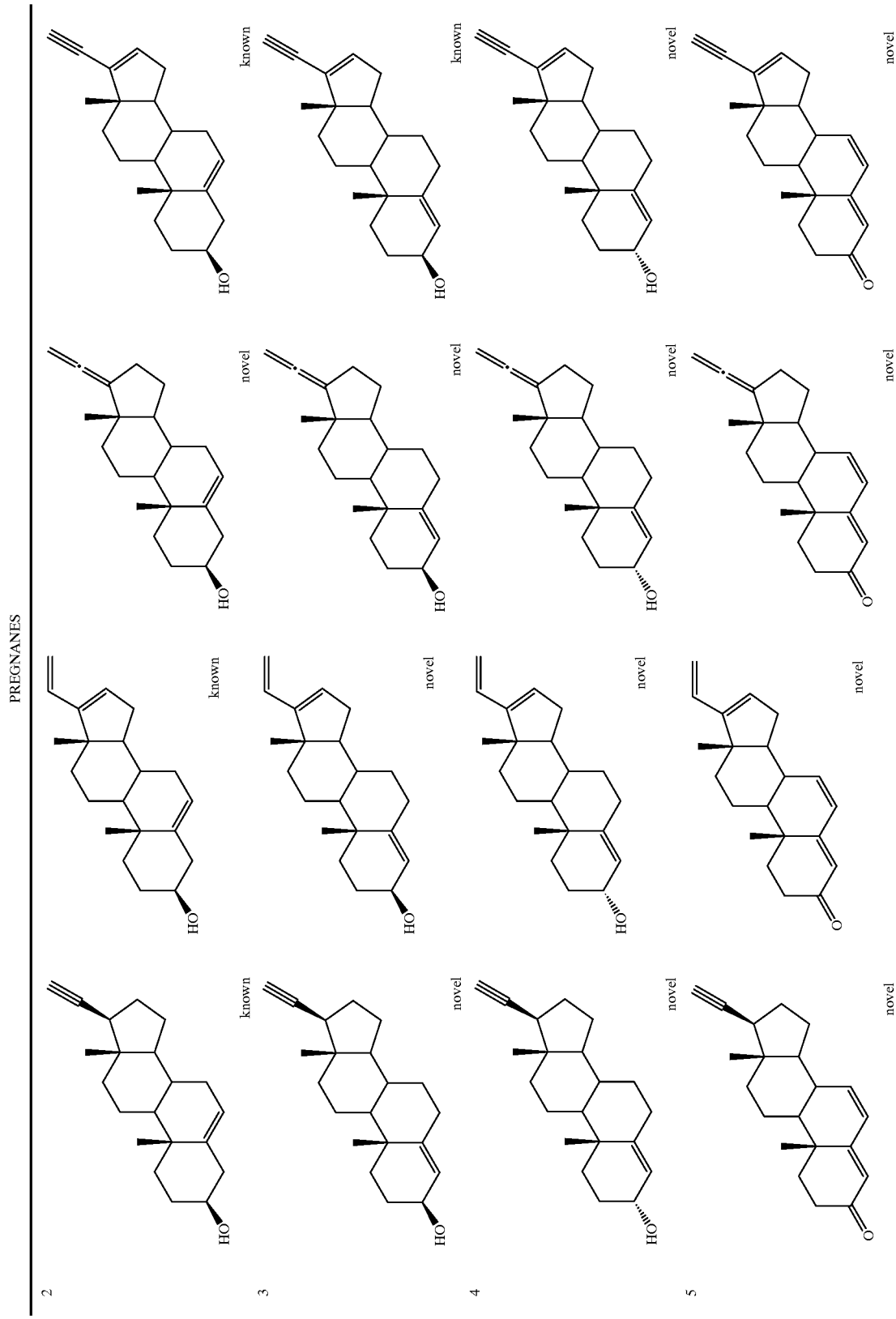

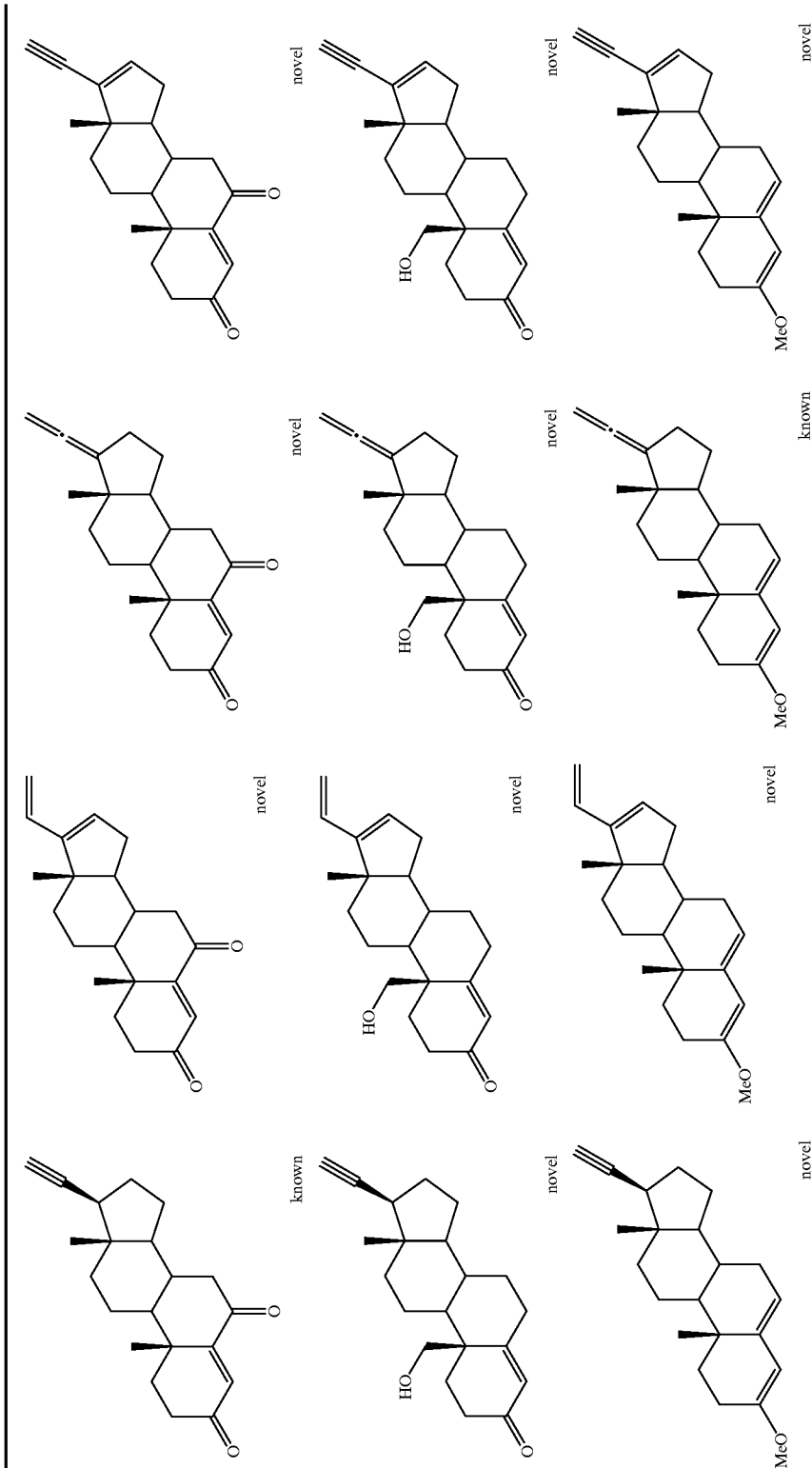

-continued
PREGNANES
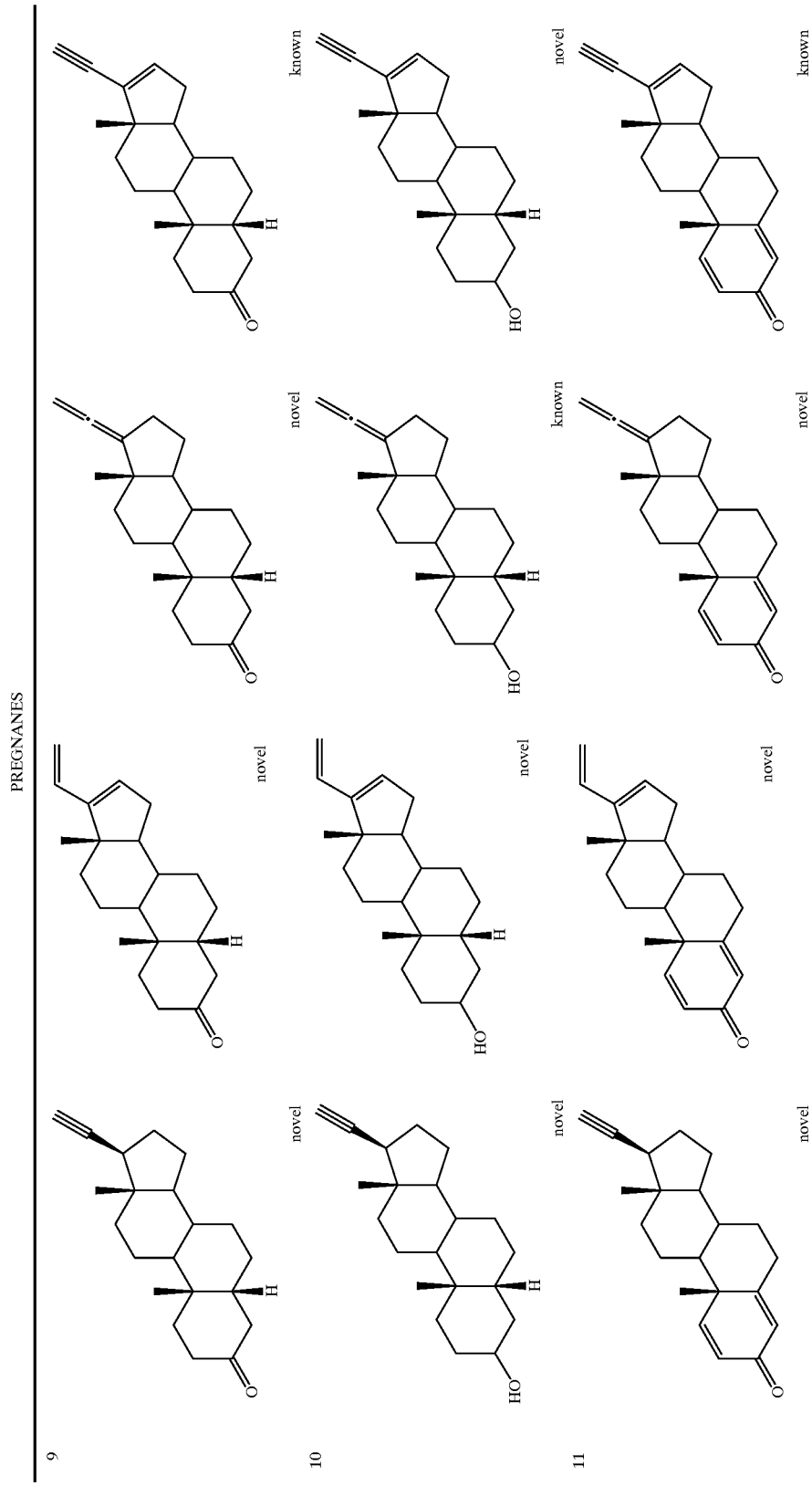

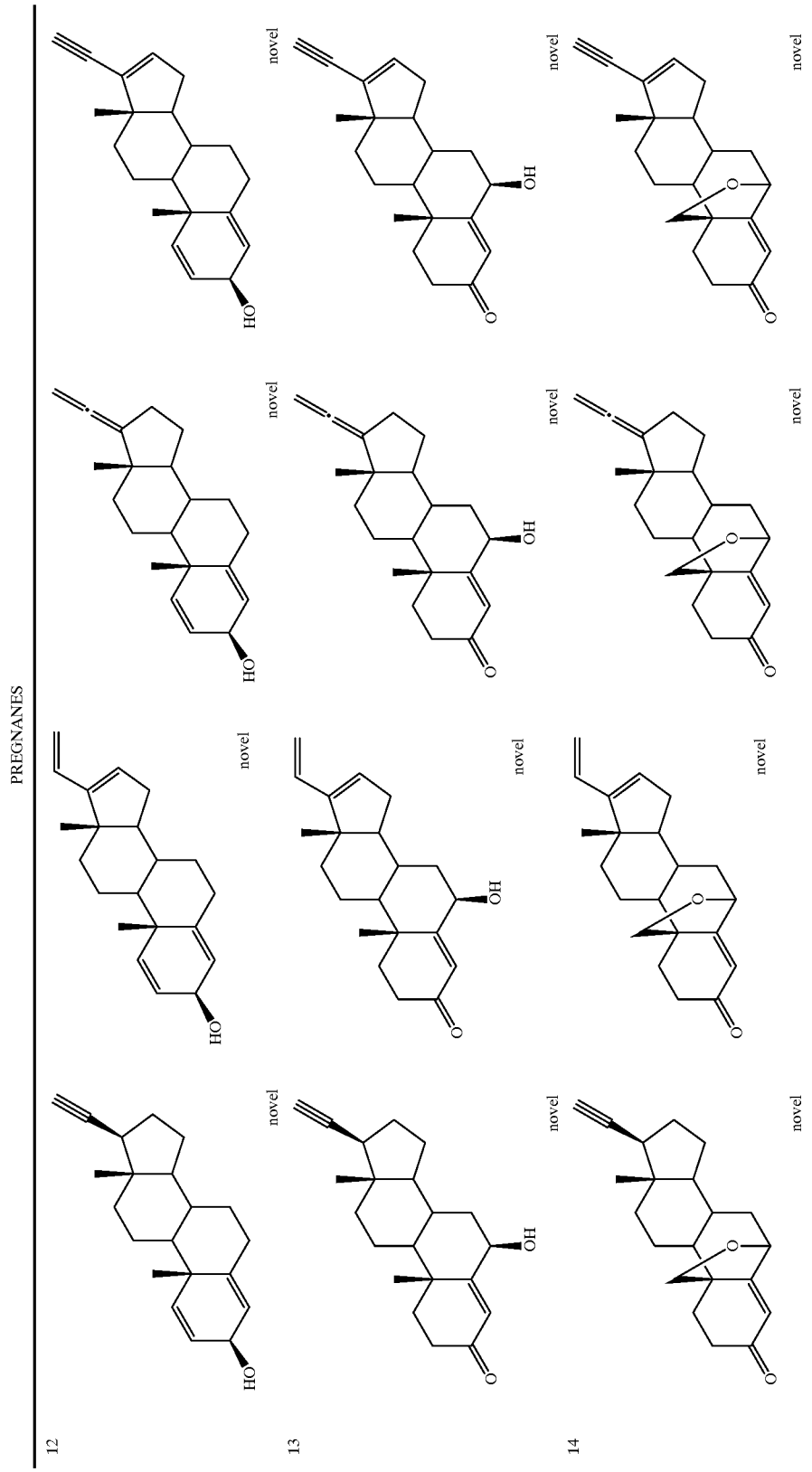

Substructure Synthesis

Referring to the preceding table, the following are exemplary syntheses for intermediates in a given row (A1 through A13) or column (P1 through P8).

Substructure Synthesis: Type A

A1:

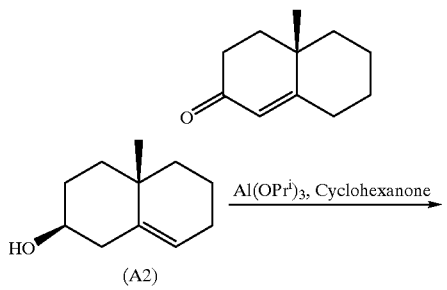

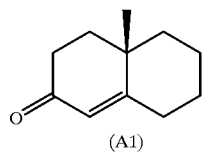
(A1)

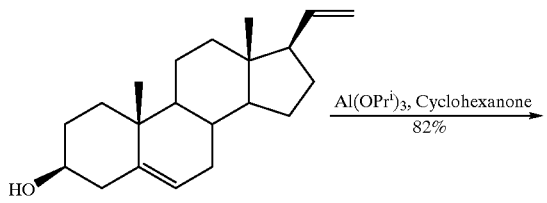

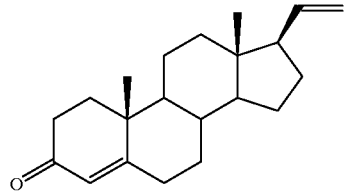

Percy L. Julian, Edwin W. Meyer and Helen C. Printy, J. Amer. Chem. Soc., 1948,70, 3, 887.

Also a commercially available substructure, for example, 17α-ethynyltestosterone.

A2:

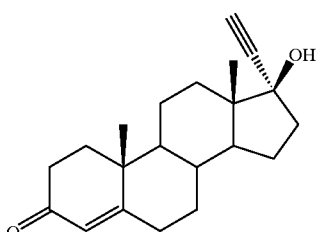

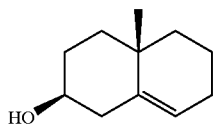

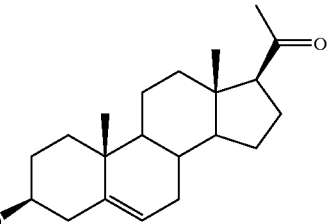

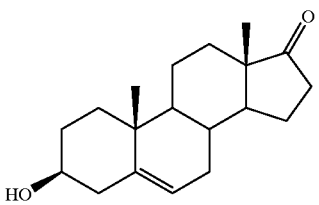

This is a commercially available substructure, for example, dehydroepiandrosterone, pregnenolone.

A3:

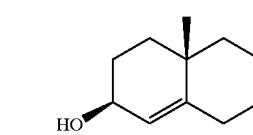

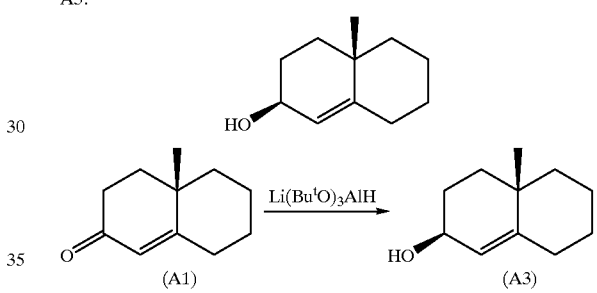

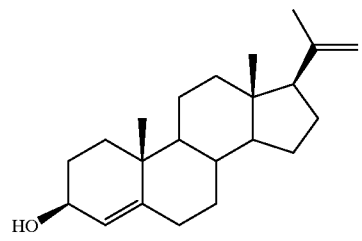

David G. Loughhead, J. Org. Chem., 1985, Vol. 50, No. 20, p. 3931.

A4:

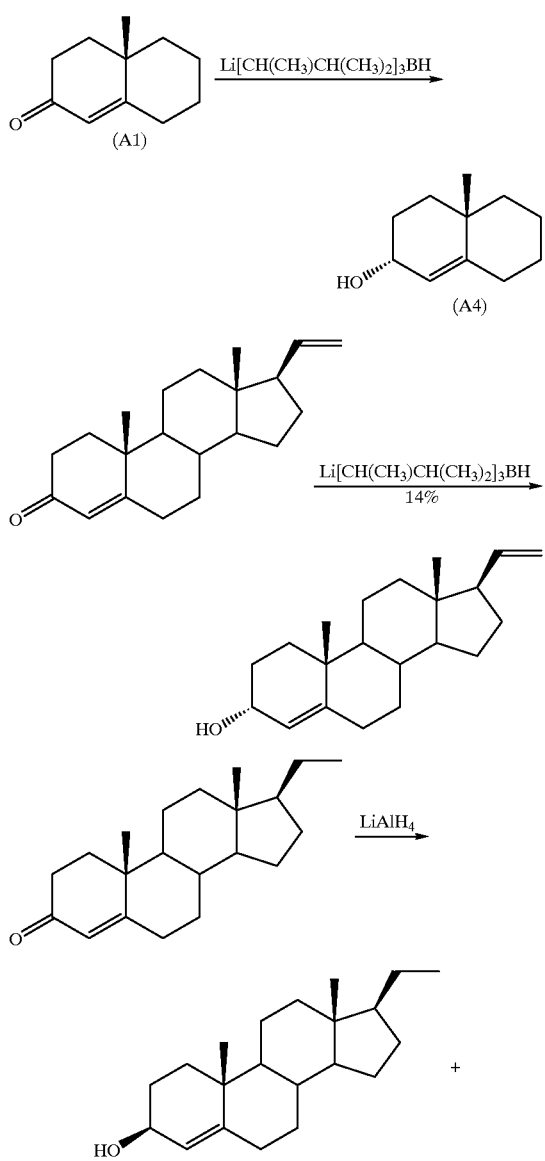
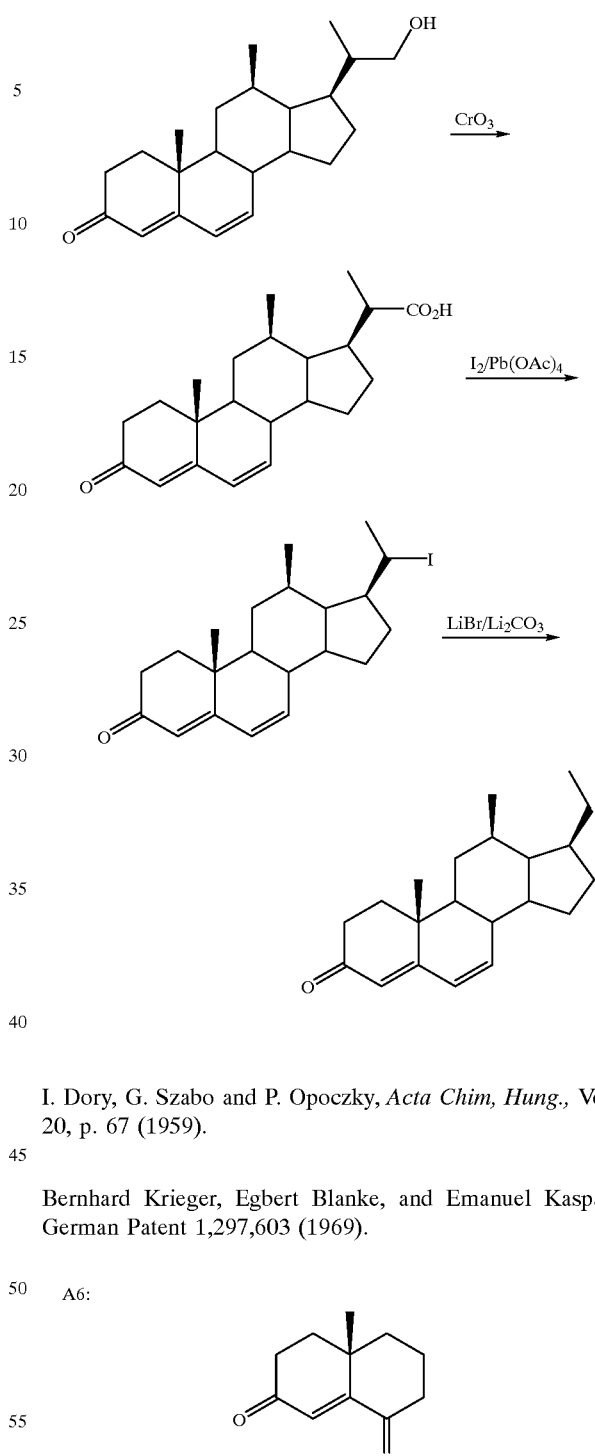
I. Z. Kabore, Q. Khuong-Huu, and A. Pancrazi, Tetrahedron, 1978, Vol. 34, p. 2807.
A5:
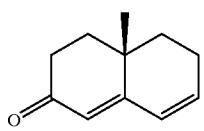
I. Dory, G. Szabo and P. Opoczky, *Acta Chim, Hung.*, Vol. 20, p. 67 (1959).
Bernhard Krieger, Egbert Blanke, and Emanuel Kaspar, German Patent 1,297,603 (1969).
A6:
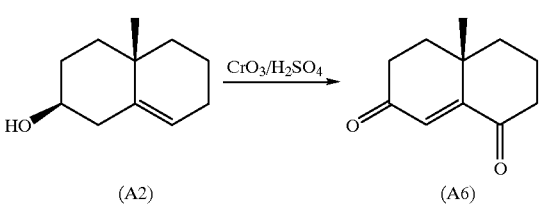

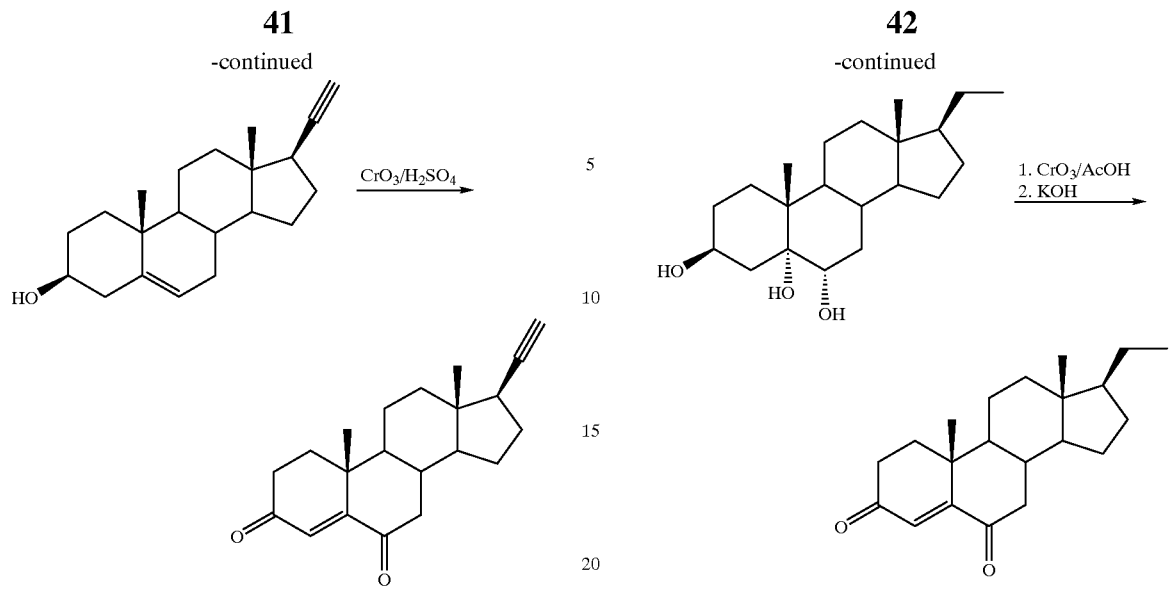
Alan M. Krubiner, Norman Gottfield, and Eugene P. Oliveto, J. Org. Chem., 1969, 34, 11, 3502.
Roberto Sciaky and Alberto Consonni, Gazz. Chim. Ital., 1962, 92, 730.
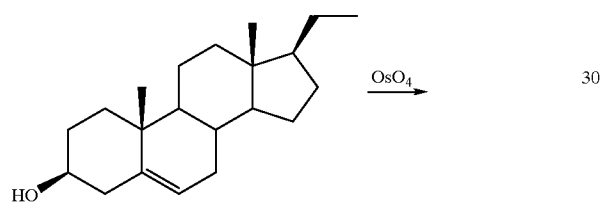
A7:
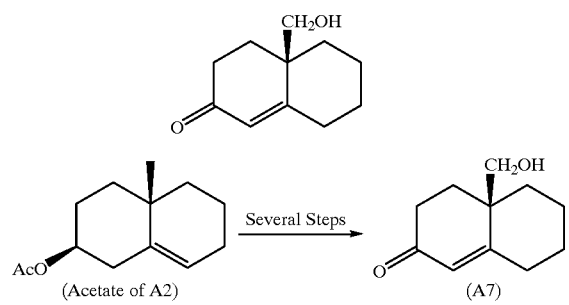
A8:
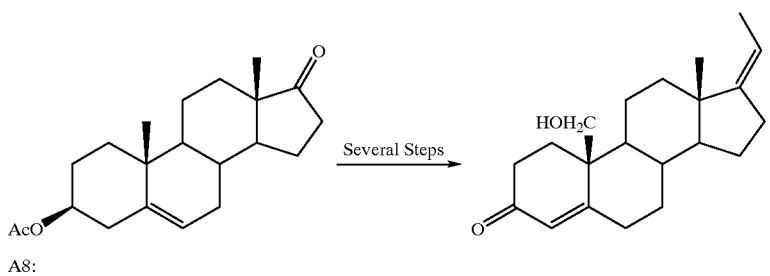
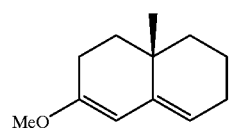

-continued
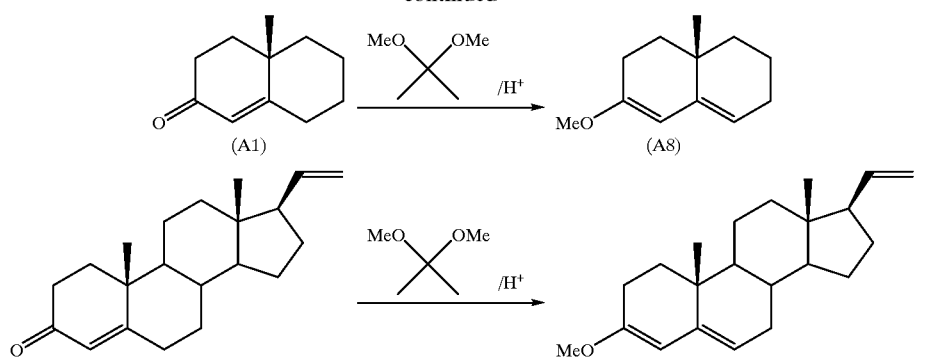
See example.
Also a commercially available substructure, for example, 17α-ethynyldihydrotestosterone.
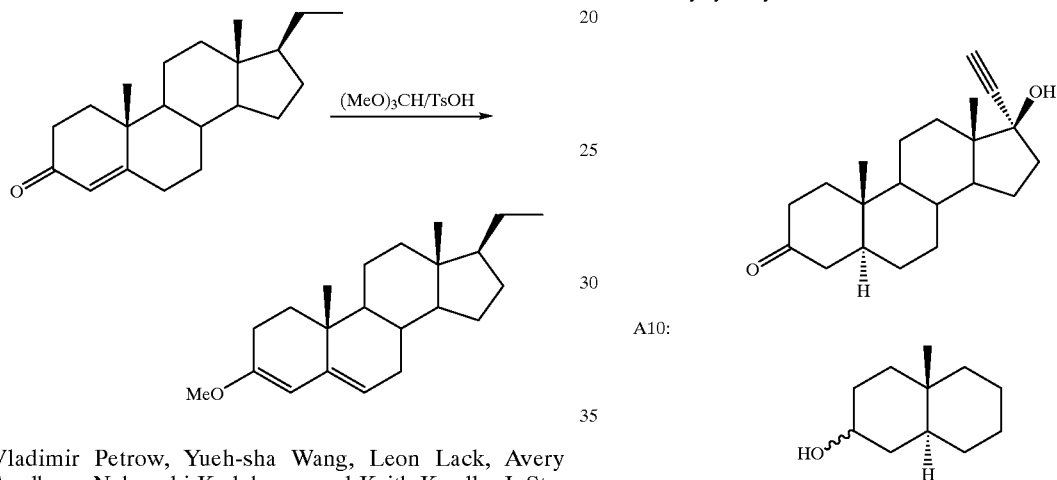
Vladimir Petrow, Yueh-sha Wang, Leon Lack, Avery Sandberg, Nobuyuki Kodohama, and Keith Kendle, J. Steroid Biochem., 1983, 19, 1491.
A9:
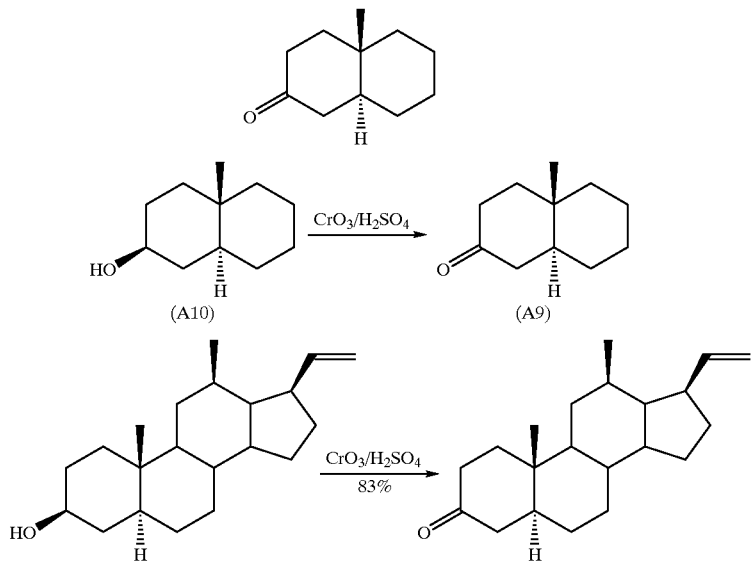
Steven R. Schow and Trevor C. McMorris, Steroids, 1977, Vol. 30, No. 3, p. 389.

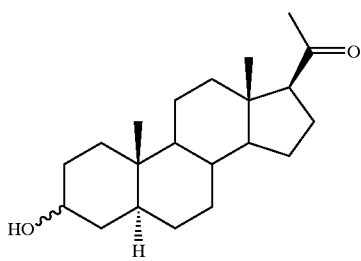
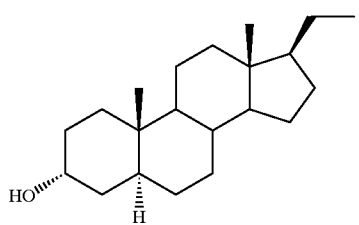
J. M. Kohli, A Zaman and A. R. Kidwai, Phytochemistry 1971, Vol. 10, p. 442.
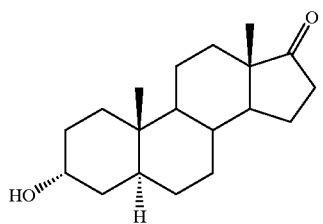
This is a commercially available substructure, for example, pregnanolone, androsterone.
A11:
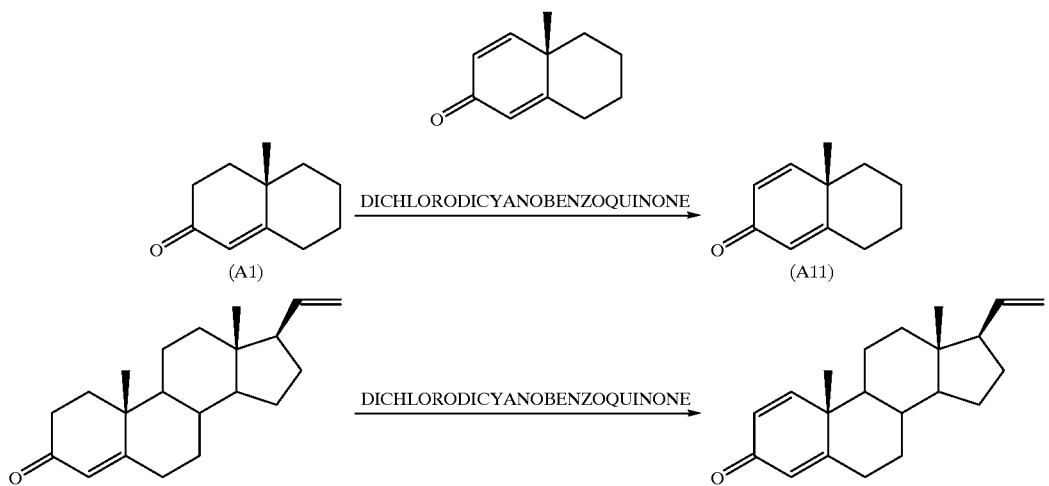
Also:
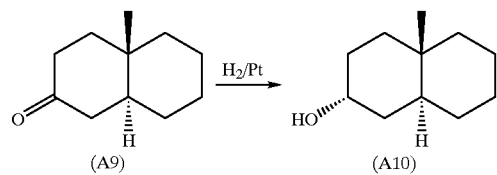
See example.
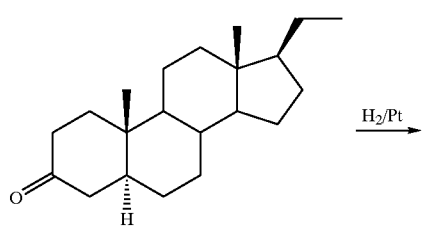
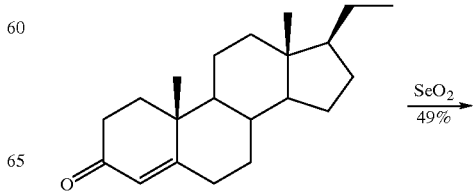

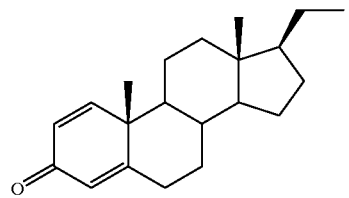
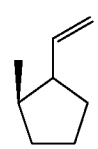
P1:
Substructure Syntheses: Type P
Frederick Brown and Carl Djerassi, J. Amer. Chem. Soc., 1980, 102, 2, 807.
A12:
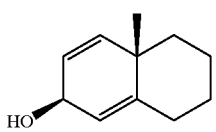
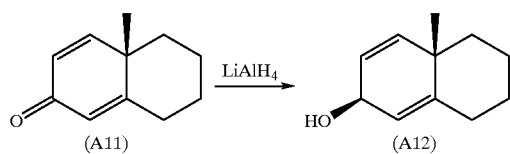
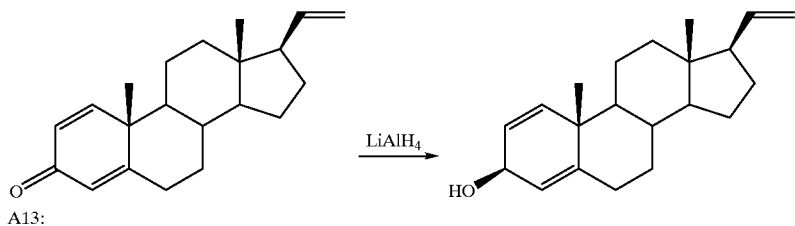
A13:
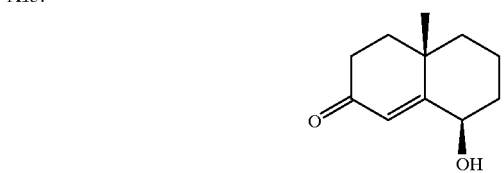
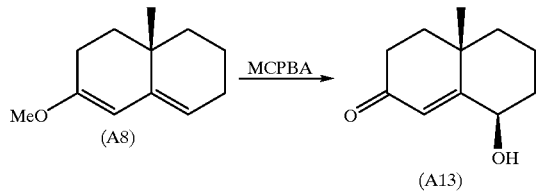
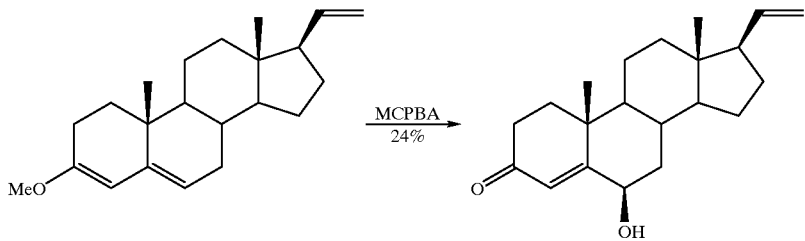

49
-continued
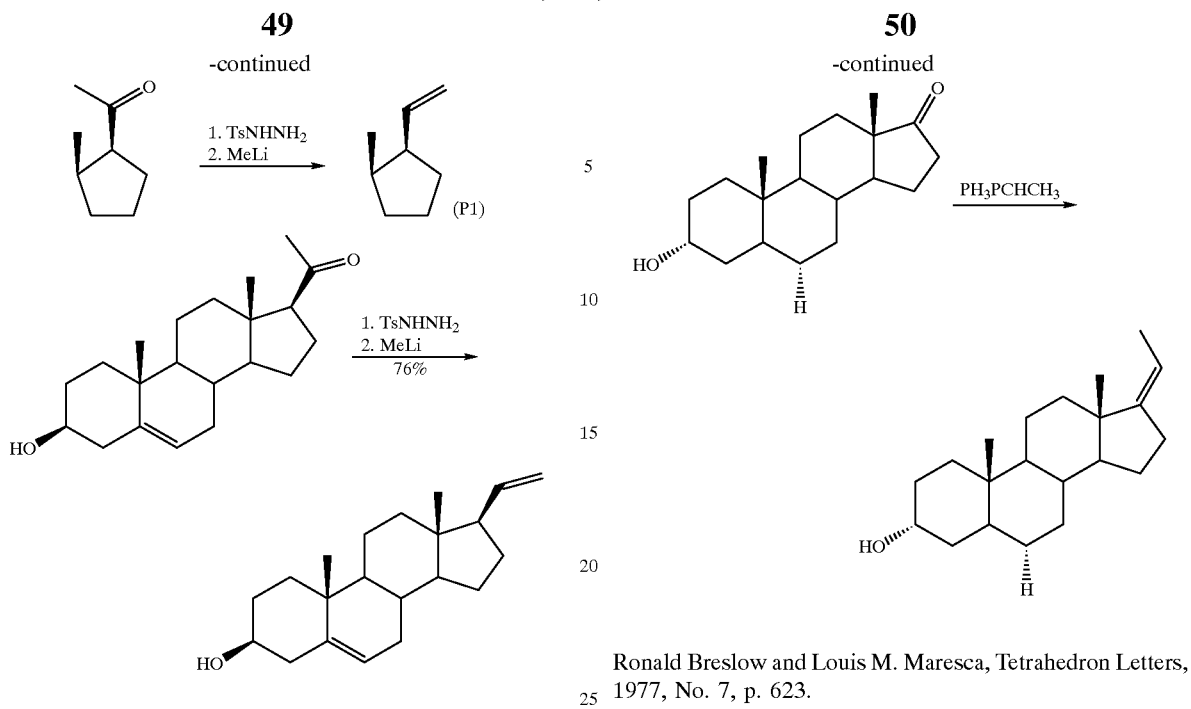
Ajay K. Bose and N. G. Steinberg, Synthesis, 1970, p. 595.
Steven R. Schow and Trevor C. McMorris, Steroids, 1977, vol. 30, No. 3, p. 389.
P2:
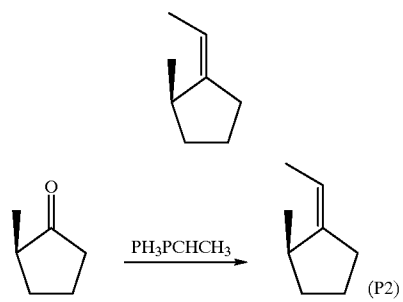
50
-continued
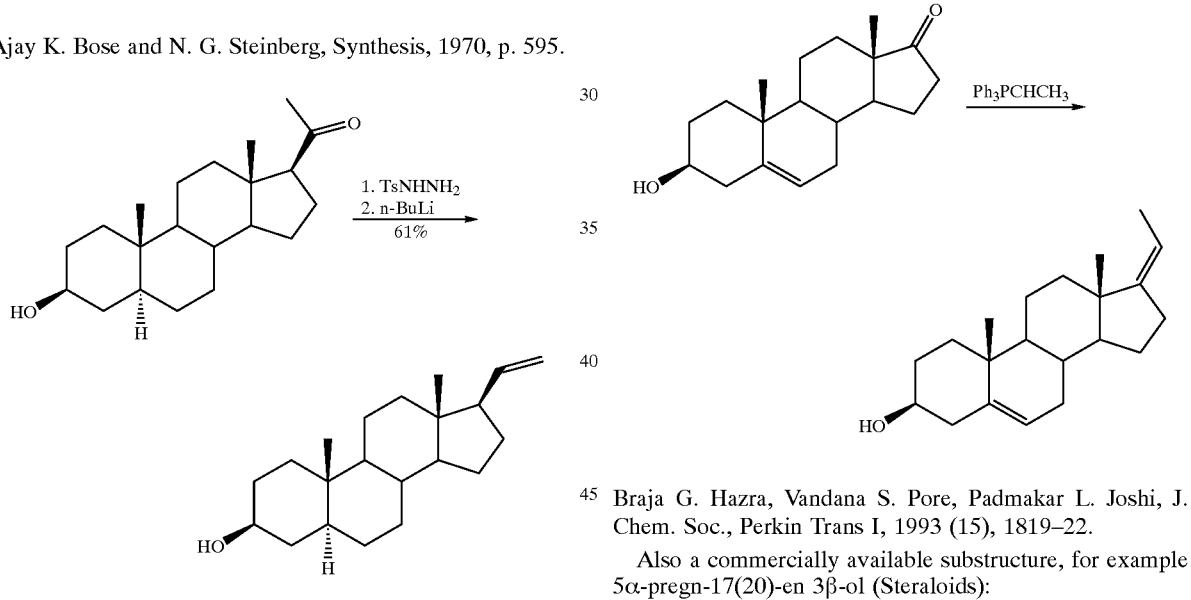
Ronald Breslow and Louis M. Maresca, Tetrahedron Letters, 1977, No. 7, p. 623.
Braja G. Hazra, Vandana S. Pore, Padmakar L. Joshi, J. Chem. Soc., Perkin Trans I, 1993 (15), 1819–22.
Also a commercially available substructure, for example 5α-pregn-17(20)-en 3β-ol (Steraloids):
P3:
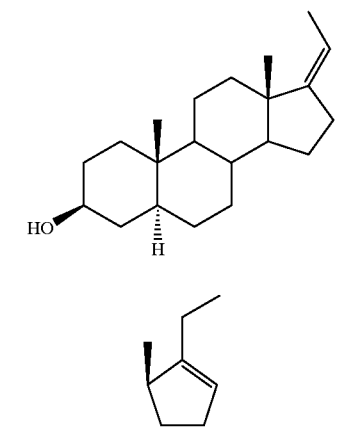

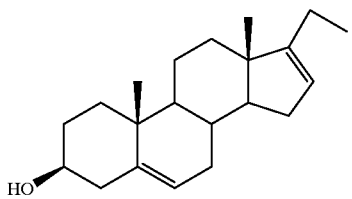

This is a commercially available substructure, for example pregna-5,16-dien-3β-ol (Steraloids).

When commercialy unavailable, synthesis proceeds as below:

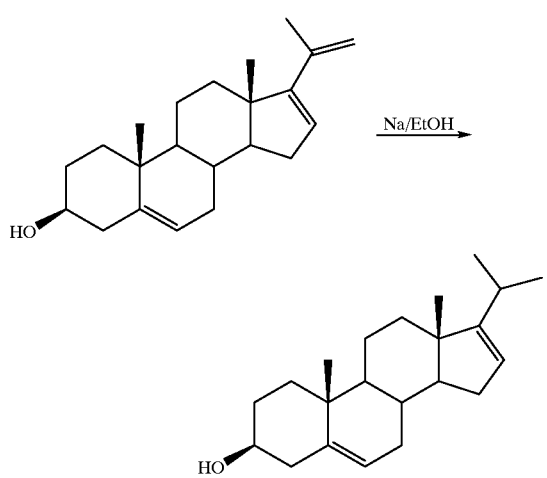

John P. Dusza and Werner Bergman, J. Org. Chem., 1960, 25, 79.

P4:

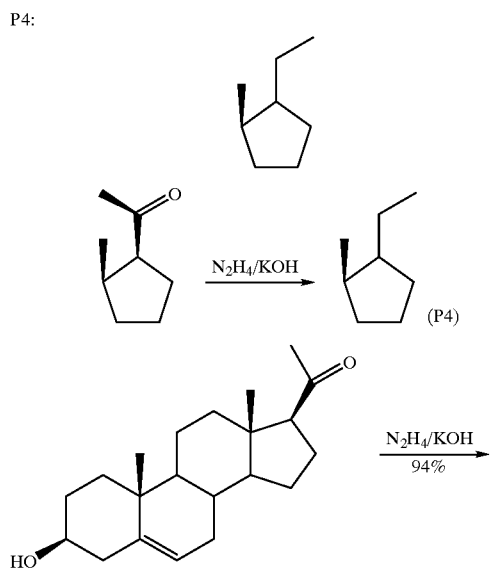

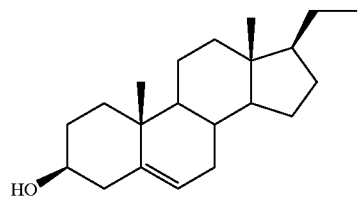

C. W. Shoppee, Ruth E. Lack, and B. C. Newman, J. Chem. Soc., 1964, p. 3388. Also a commercial available substructure, for example, 5α-pregnan-3β-ol (Steraloids):

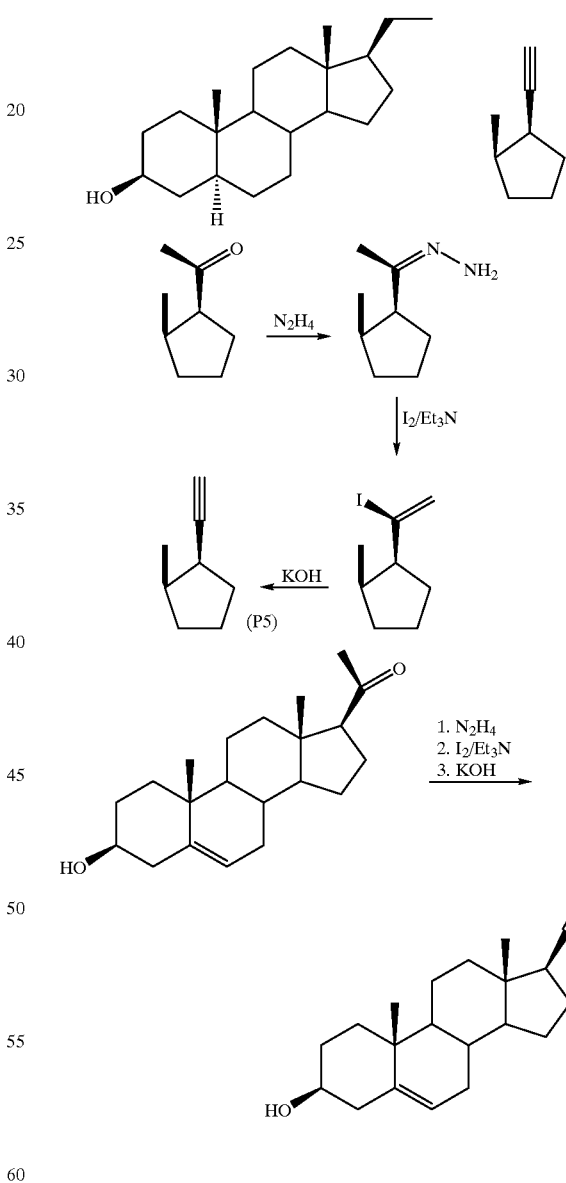

Alan M. Krubiner, Norman Gottfried, and Eugene P. Oliveto, J. Org. Chem., 1969, Vol. 34, No. 11, p. 3502.

P.6:
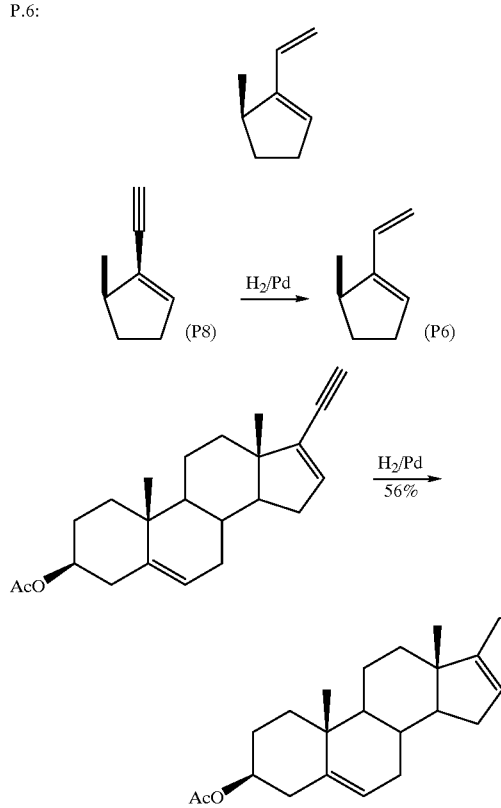
Eugene P. Oliveto, Corrine Gerold, and Lois Johnson, J. Am. Chem. Soc. 1951, 73, 5073.
P7:
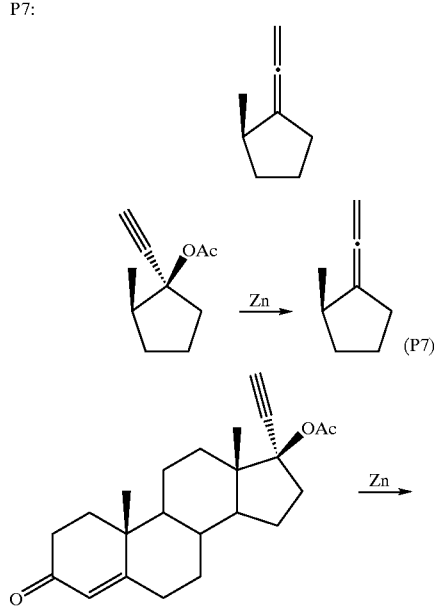
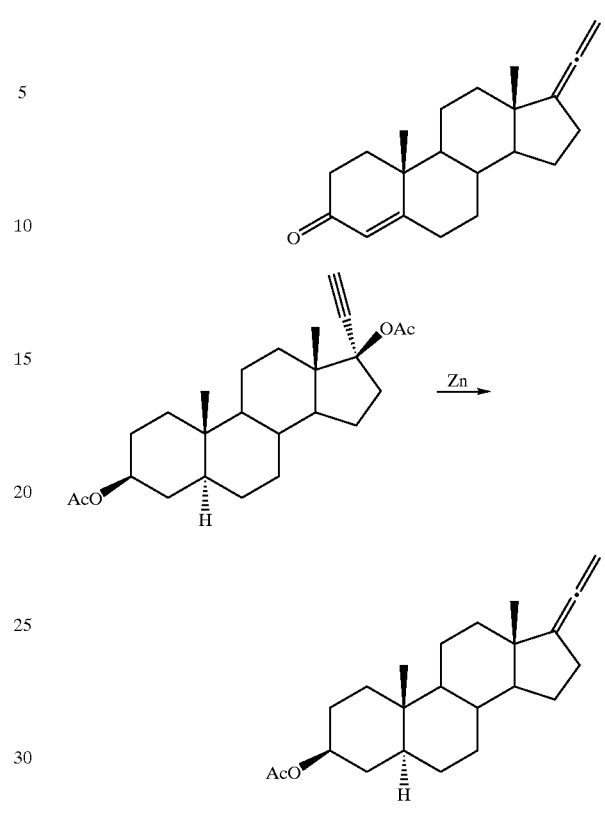
Pierre Crabble and Esperanza Valarde, U.S. Pat. No. 3,681,410, 1972.
P8:
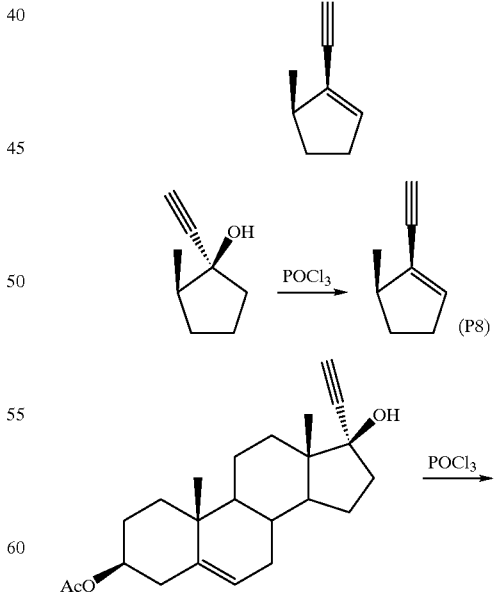

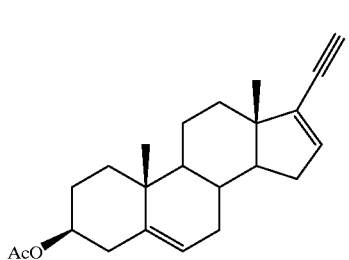

Maya Dvolaitsky Anna M. Giroud, and Jean Jacques, Bull. Soc. Chim. France, 1963, 62.

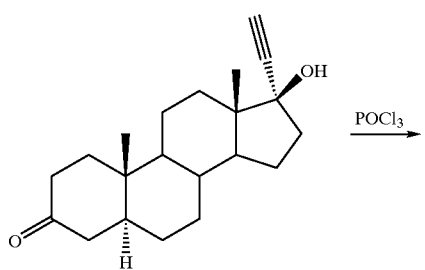

French Patent 1,536,034, 1968.

17α-Pregnanes

For substructures P1, P4, and P5, the normal configuration at the 17-position is β. However, the corresponding 17α analog may also be prepared by using 17α-pregnolone as the starting material. For example:

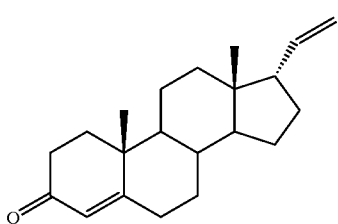

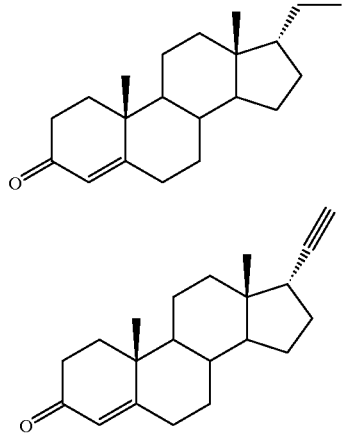

Alan M. Krubiner, Norman Gottfried, and Eugene P. Oliveto, J. Org. Chem., 1969, Vol. 34, No. 11, p. 3502.

Methylpregnanes

The following methodology enables a methyl group to be placed at the 20-position whenever allowed by the structure, namely with P1, P2, P3, P$_4$ and P6:

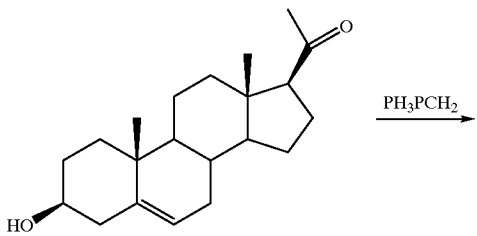

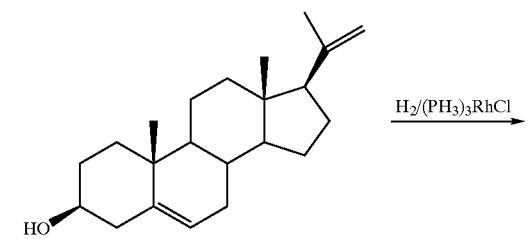

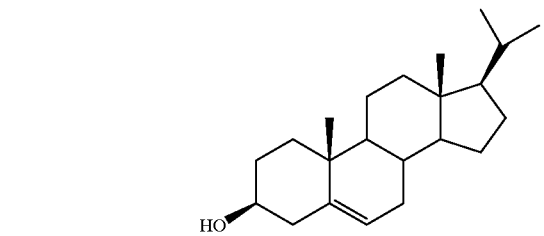

J. Bryan Jones and Keith D. Gordon, Can. J. Chem., 1972, vol. 50, p. 2712.

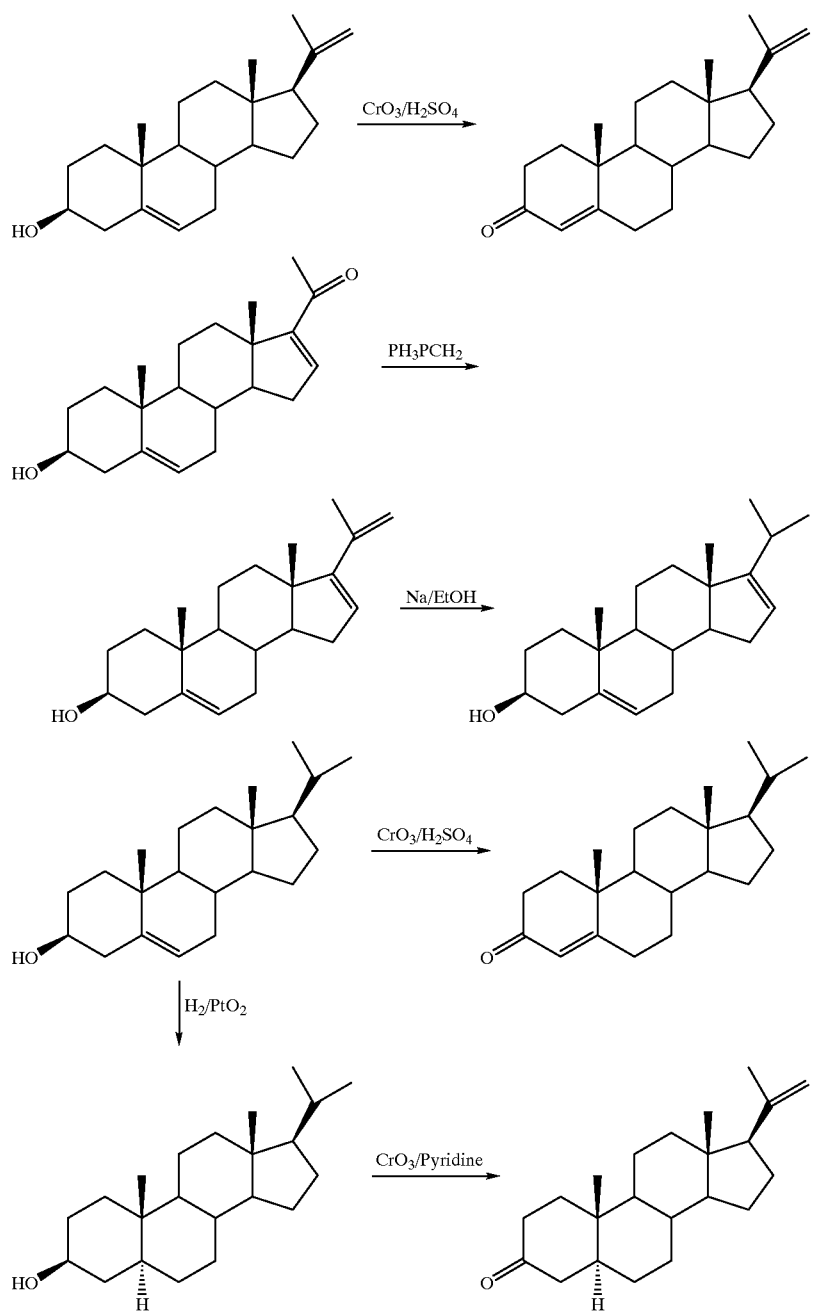
John P. Dusza and Werner Bergmann, J. Org. Chem., 1960, 25, 79.
-continued
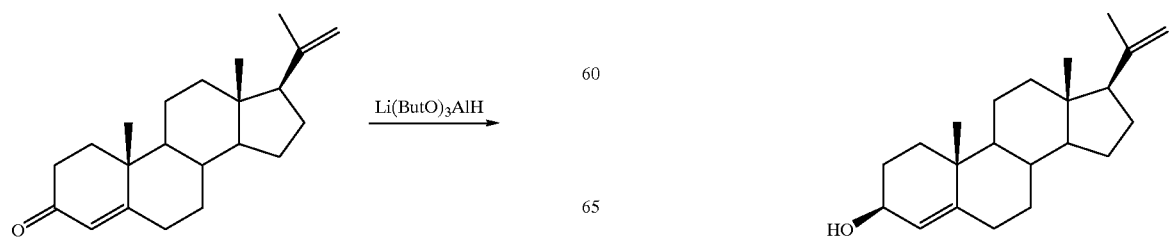

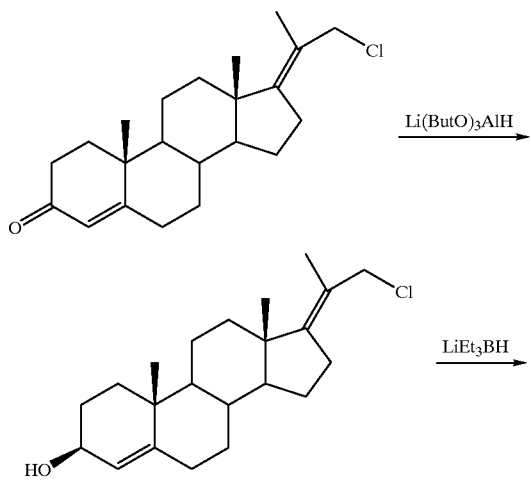
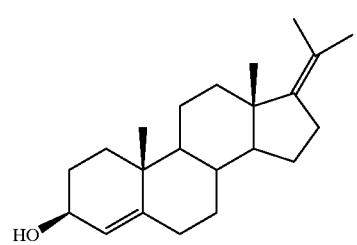
David G. Loughhead, J. Org. Chem., 1985, 50, 3931. U.S. Pat. No. 3,681,410 teaches preparation of 6α-methyl analogs:
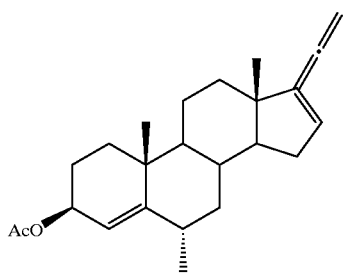
U.S. Pat. No. 3,492,318 teaches preparation of 18- and 21-methyl analogs:
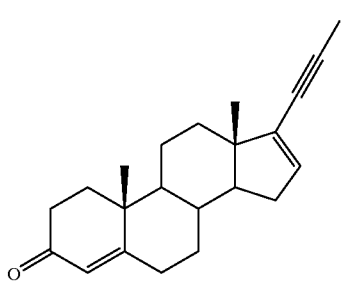
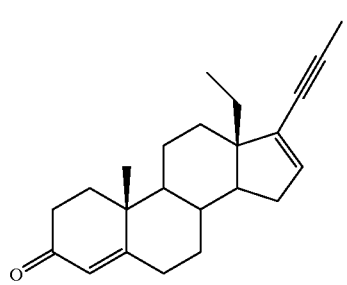
Certain methylated pregnenolone precursors are commercially available, vis 6,16α(β)-methyl:
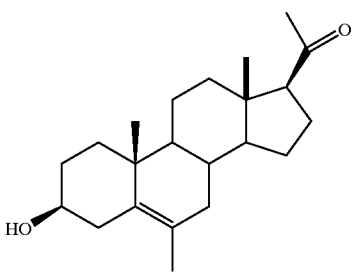
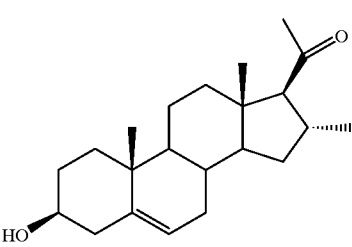
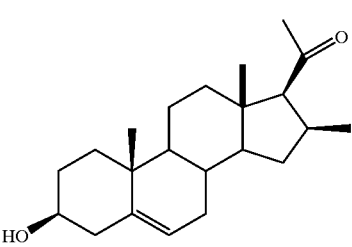
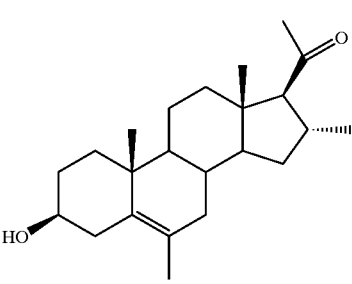
In addition 17α-methylpregnenolone is readily available: French patent 1,363,191:

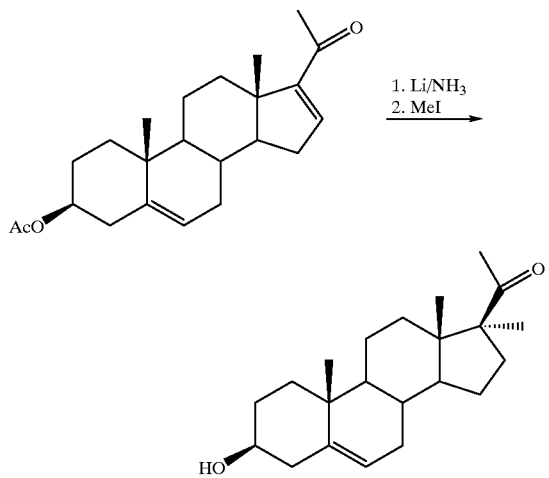

Therefore, compounds synthesized from pregnenolone may also be prepared with methyl groups at the 6, 16, or 17 positions by using the appropriate methylpregnenolone precursor.

Dimethyl compounds, such as the described 18, 21-dimethylpregna-4,16-dien-20-yn-3-one, may be prepared by one of three general methods:

The first method combines a methylated precursor, such as those in the 6, 16, or 17-positions, with methodology which introduces a methyl group, such as in the 20-position.

The second method uses a dimethylated precursor, such as the commercial available 6, 16α-dimethylpregnenolone.

The syntheses of other dimethylated pregnenolone precursors have been described, as in the following examples:

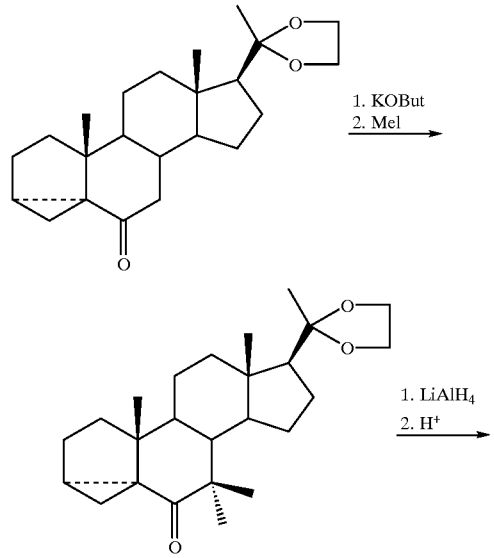

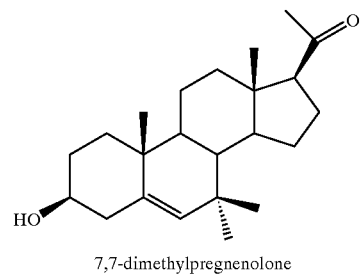

7,7-dimethylpregnenolone

Sylvestre Julia, Colette Neuville, and Pierre Simon, Bull. Soc. Chim. France, 1962, 1495.

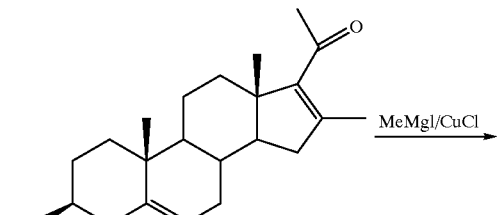

16, 16-dimethylpregnenolone acetate

Elliott Shapiro, Theodore Legatt, Lois Weber, Merl Steinberg, A. Watnick, M. Eisler, Marilyn Gilmore Hennessey, C. T. Coniglio, W. Charney, and Eugene P. Oliveto, J. Med. Pharm. Chem. 1962, 5, 975.

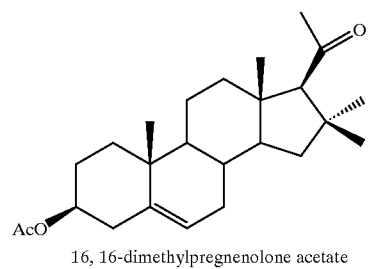

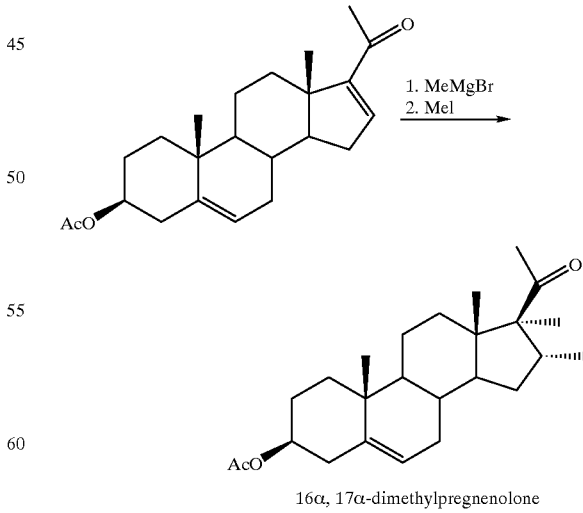

16α, 17α-dimethylpregnenolone

James Cairns, Colin L. Hewett, Robert T. Logan, George McGarry, Donald F. M. Stevenson, and Gilbert F. Woods, J. C. S. Perkin I. 1976, 1558.

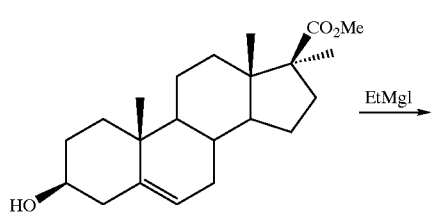

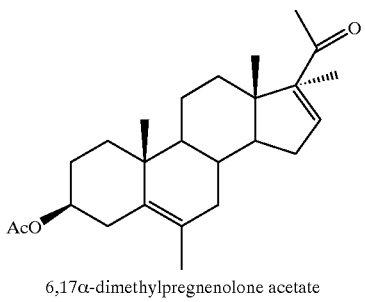

6,17α-dimethylpregnenolone acetate

Romano Deghenghi and Roger Gaudry, Tetrahedron Letters, 1962, No. 11, p. 489.

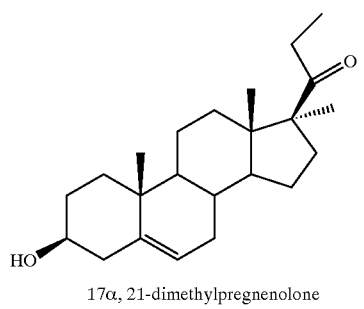

17α, 21-dimethylpregnenolone

R. Deghenghi and R. Gaudry, J. Amer. Chem. Soc., 1961, 4668.

British Patent 927,515:

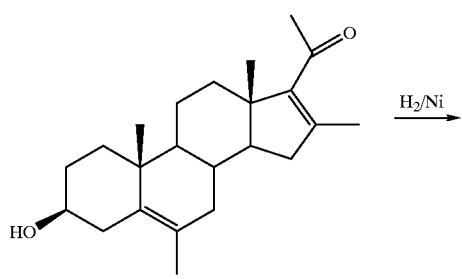

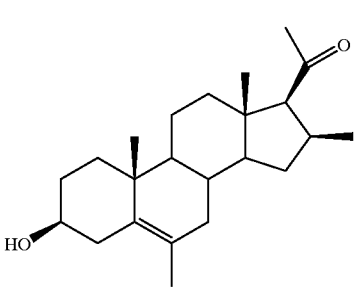

6, 16β-dimethylpregnenolone

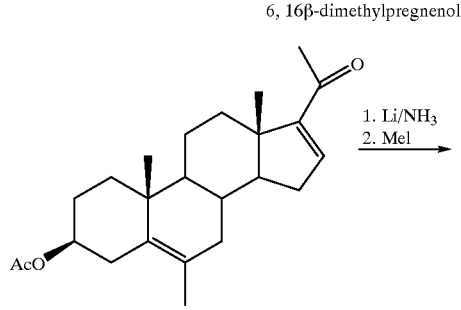

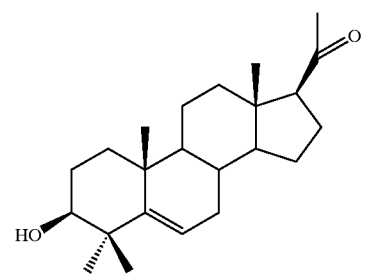

4,4-dimethylpregnenolone

W. J. Adams, D. K. Patel, V. Petrow, I. A. Stuart-Webb, and B. Sturgeon, J. Chem. Soc., 1956, 4490.

The third method starts with an unmethylated precursor, such as pregnenolone, and utilizes methodology which introduces two methyl groups, as in the following example:

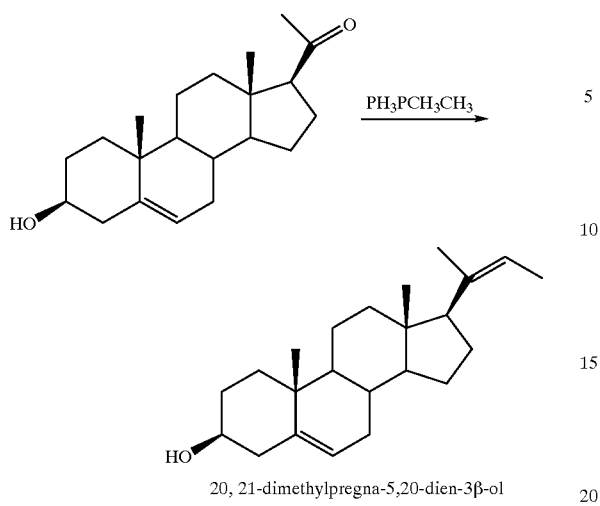
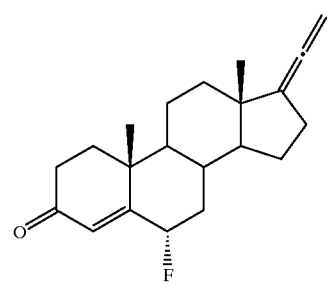
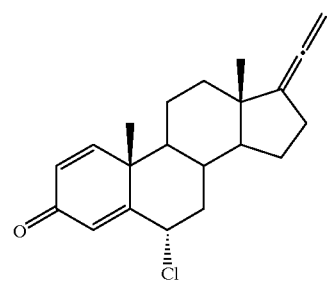
20,21-dimethylpregna-5,20-dien-3β-ol
The 20,21-dimethyl pregnanes are also known as 24-norcholanes. 24-norcholanes may alternatively be prepared by degradation of a cholane precursor, as in the following example:
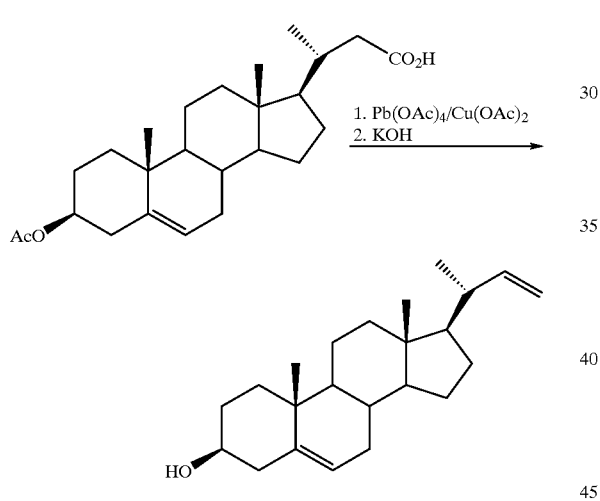
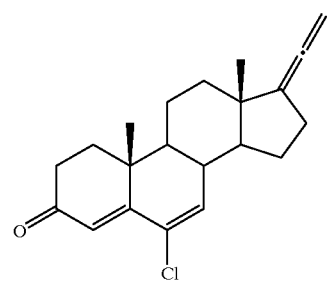
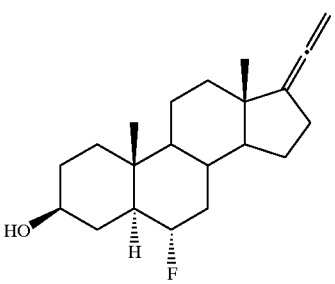
Yutaka Hirano, Tadashi Eguchi, Masaji Ishigmo, and Nubuo Ikakawa, Chem. Pharm. Bull., 1983, 31(2), 394.
Halopregnanes
U.S. Pat. No. 3,681,410 teaches the preparation of:
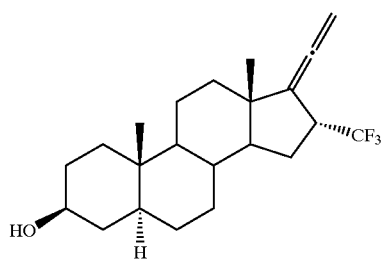
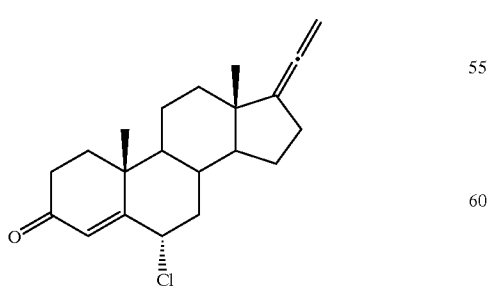

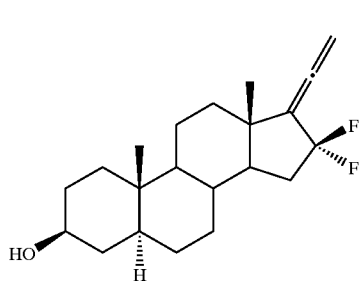

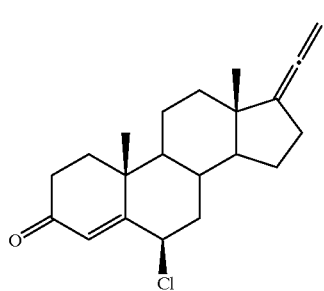

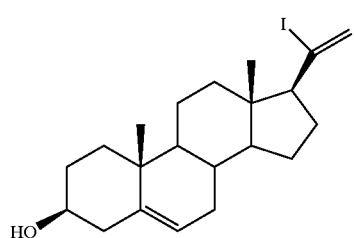

Derek H. R. Barton, George Bashiardes and Jean-Louis Fourrey, Tetrahedron Letters, 1983, vol. 24, 1605.

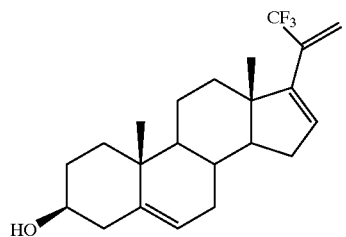

Biao Jiang and Yuanyao Xu, Tetrahedron Letters, 1992, vol. 33, 511.

Certain methylated pregnenolone precursors are commercially available, vis 6,16α(β)-methyl:

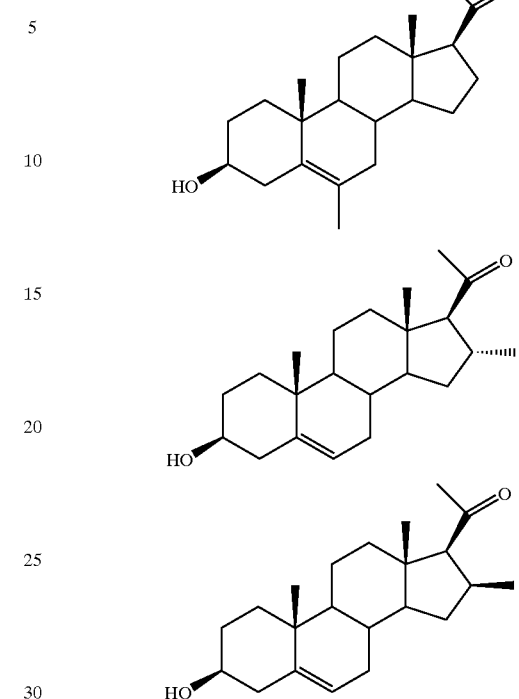

In addition 17α-methylpregnenolone is readily available: French patent 1,363,191:

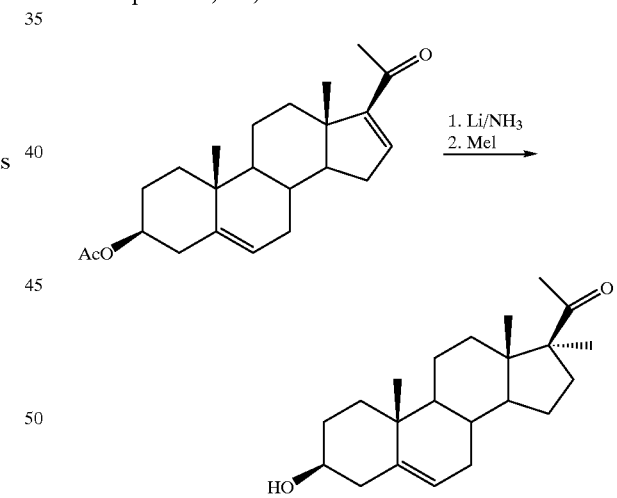

Therefore, compounds synthesized from pregnenolone may also be prepared with methyl groups at the 6, 16, or 17 positions by using the appropriate methylpregnenolone precursor.

CHART II

CHOLANES

|  | C |  |  |
|---|---|---|---|
| A | 1 | 2 | 3 |
| 1 | NOVEL | NOVEL | NOVEL |
| 2 | NOVEL | KNOWN | KNOWN |
| 3 | NOVEL | NOVEL | NOVEL |

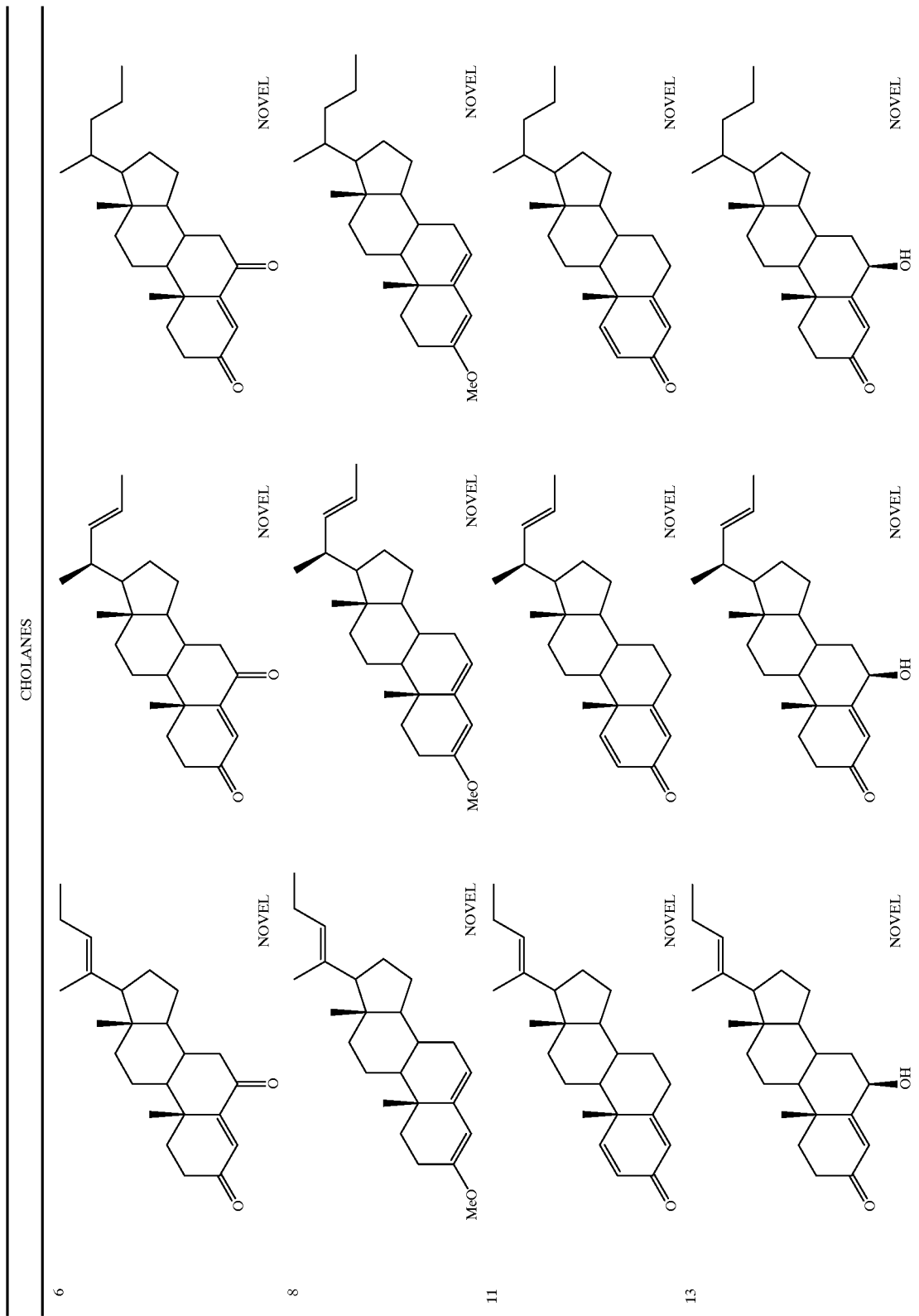

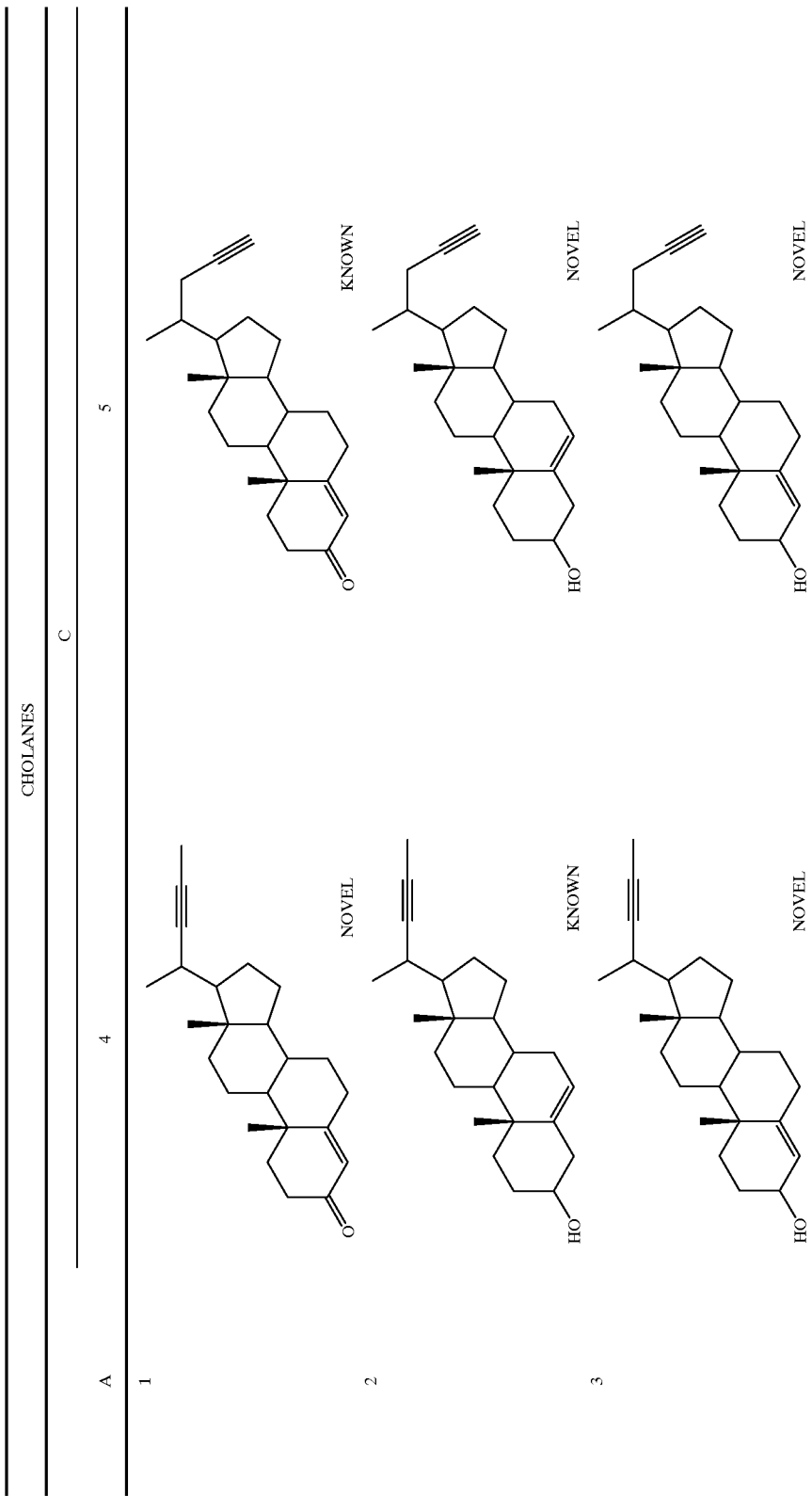

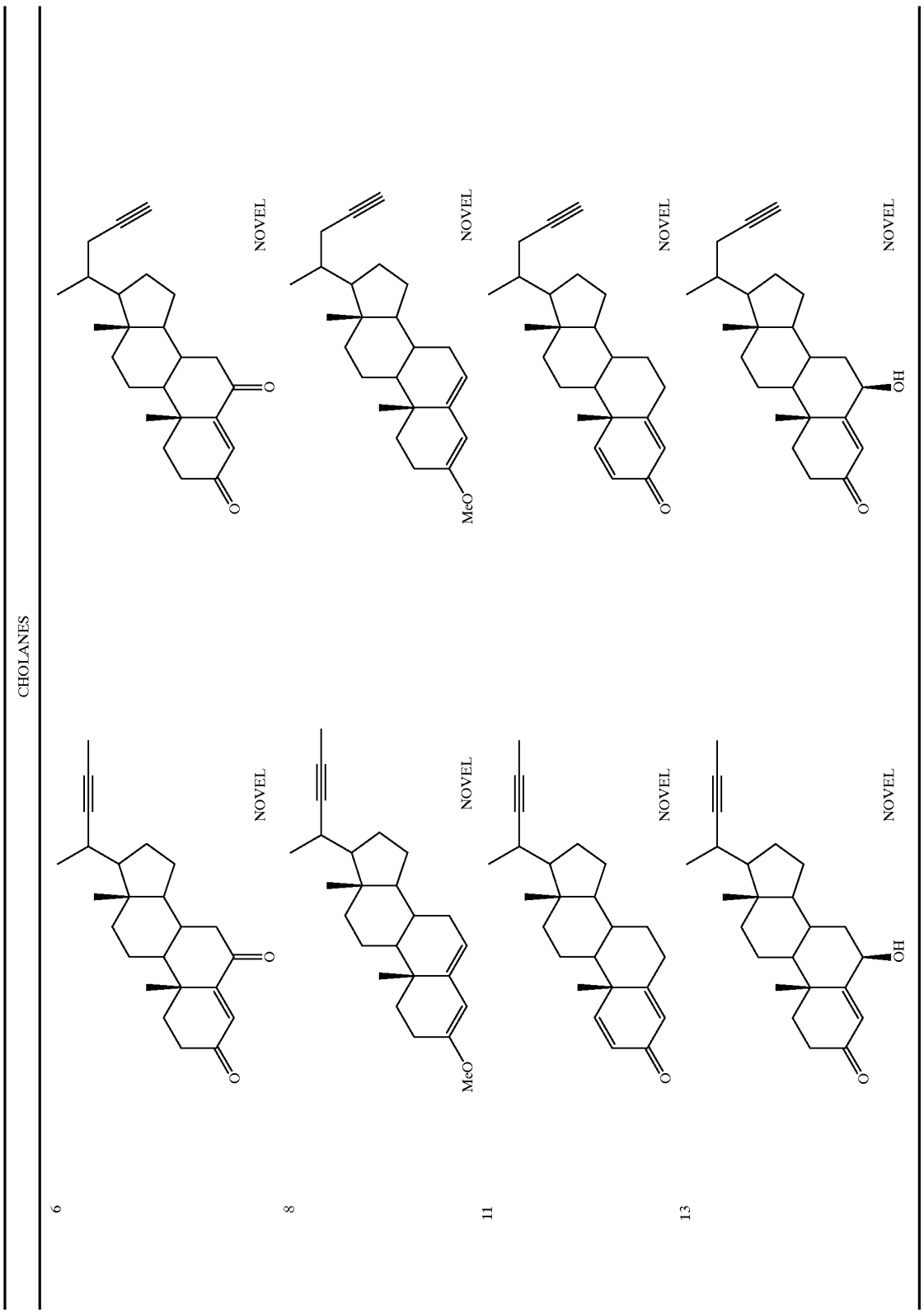

CHART II-continued
CHOLANES
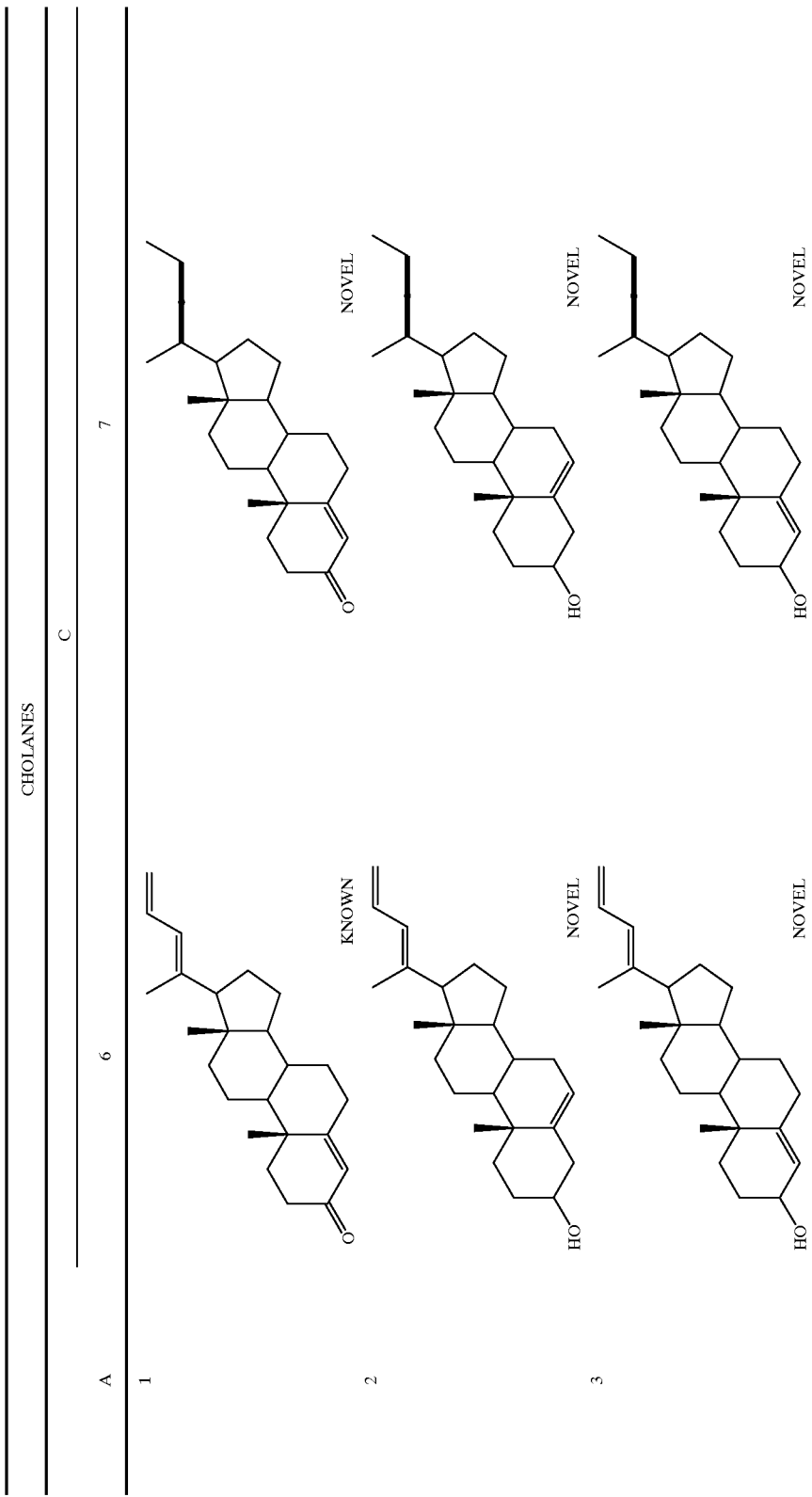

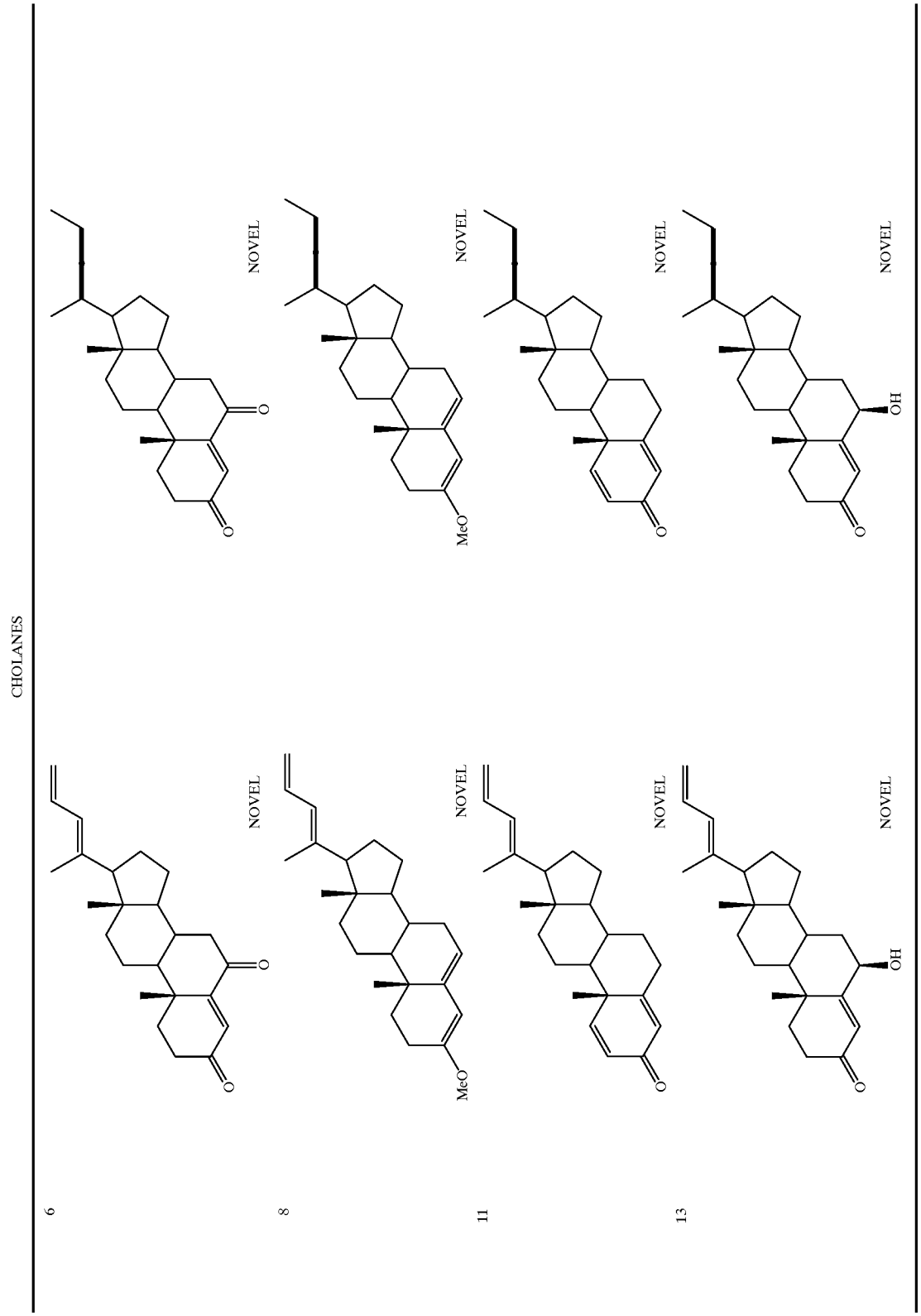

Substructure Syntheses
Referring to the preceding table, the following are exemplary syntheses for the substructures in a given row (A1 through A13) or column (C1 through C7).
Substructure Syntheses: Type A
A1:
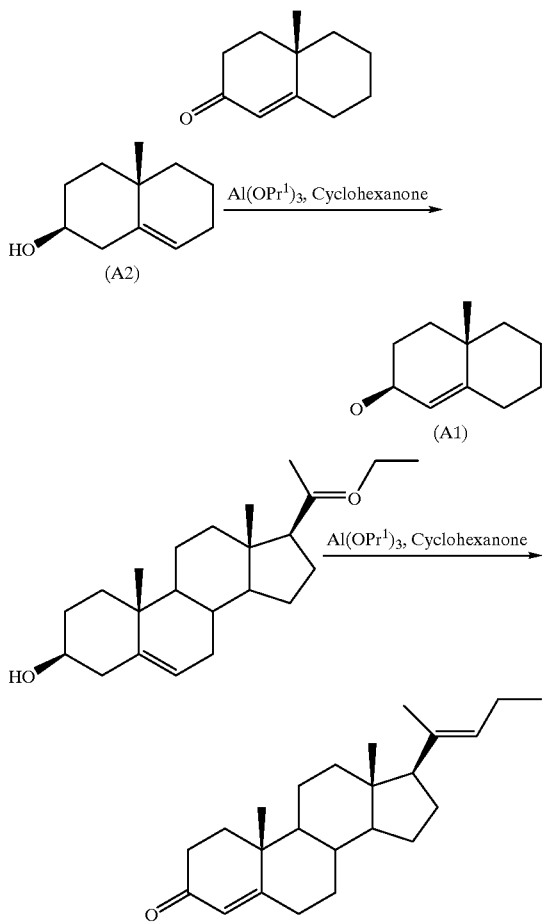
See example.
A2:
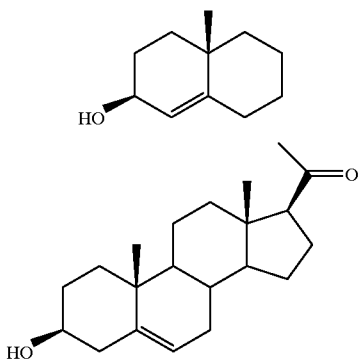
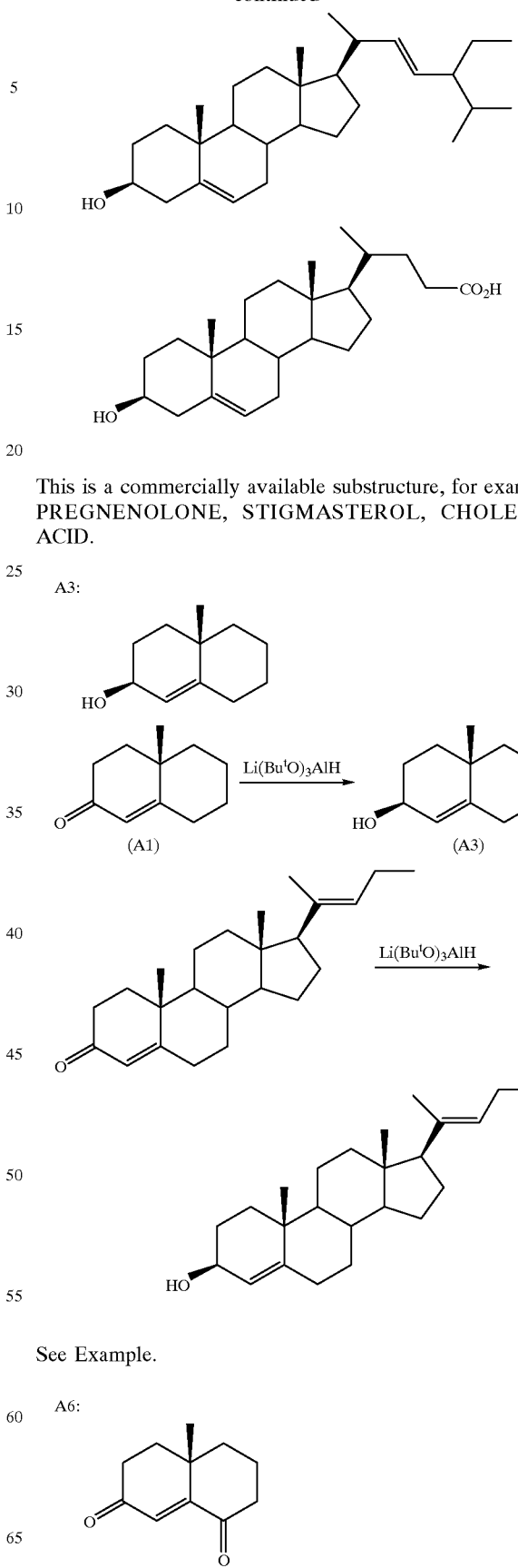
This is a commercially available substructure, for example PREGNENOLONE, STIGMASTEROL, CHOLENIC ACID.
A3:
See Example.
A6:

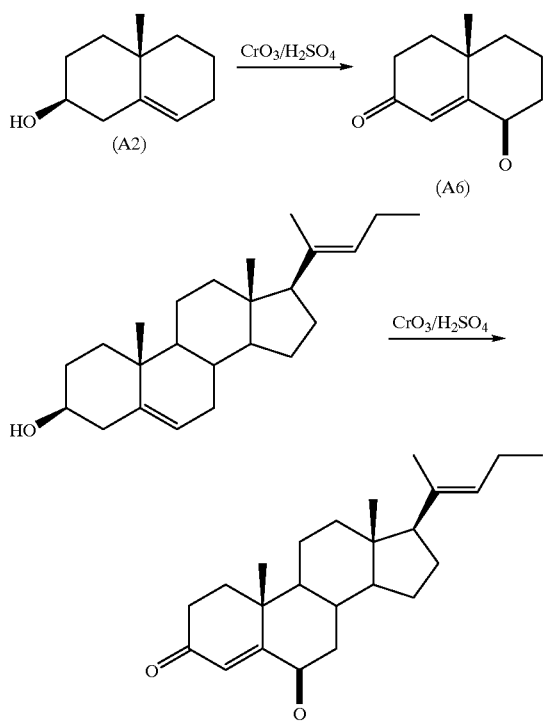
See example.
A8:
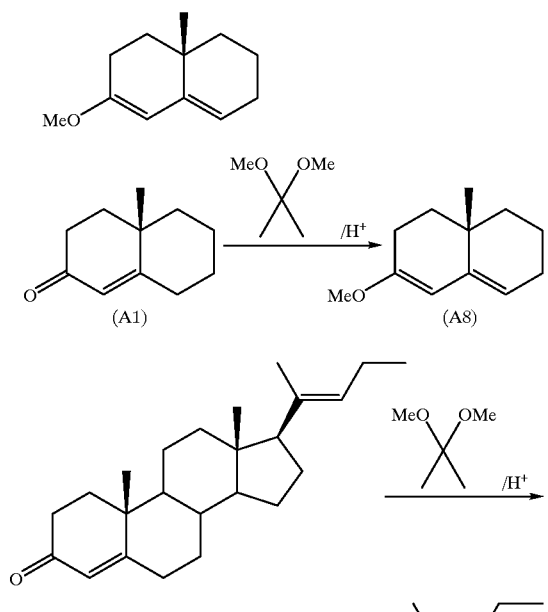
See example.
A11:
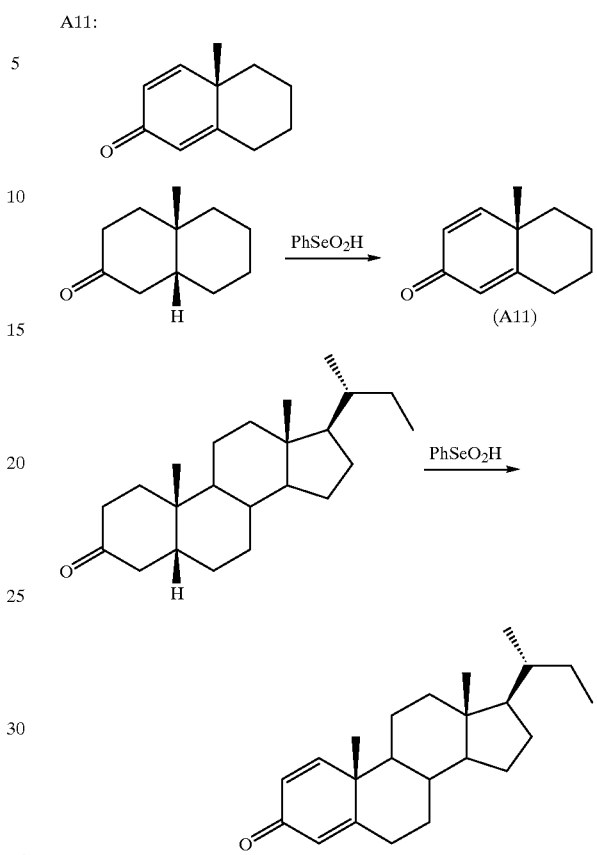
D. H. R. Barton, J. Boivin, D. Crich, and C. H. Hill, J. Chem. Soc. Perkin Trans. I, 1986, p. 1805.
A13:
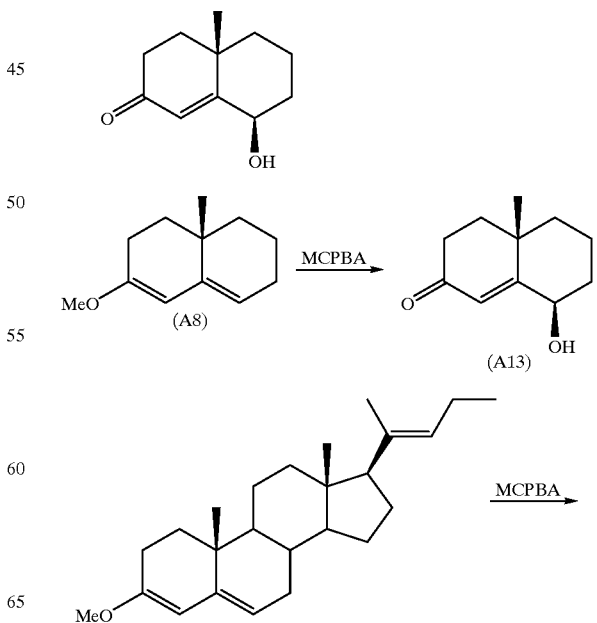

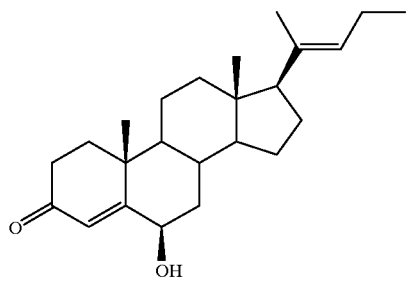
See example.
Substructure Syntheses: Type C
C1:
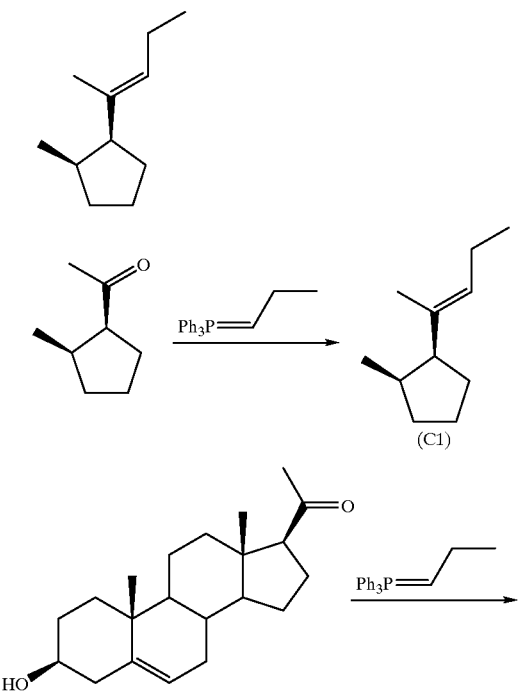
J. P. Schmit, M. Piraux, and J. F. Pilette, J. Org. Chem. 1975, Vol. 40, No. 11, p. 1586.
C2:
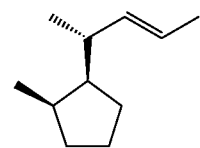
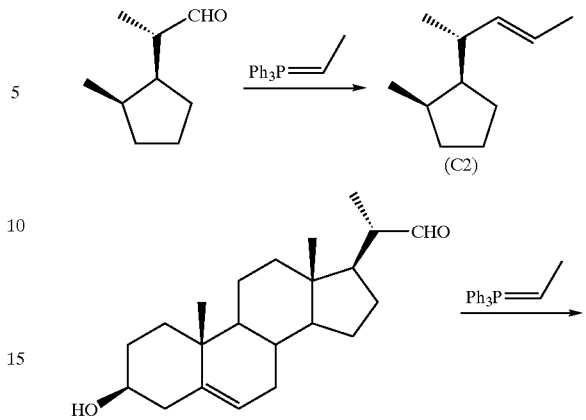
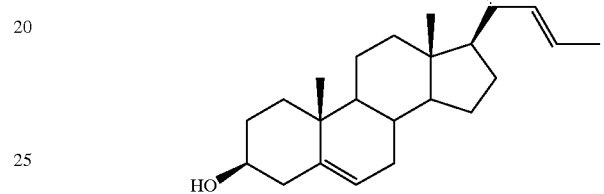
W. Bergmann and J. P. Dusza, J. Org. Chem., 1958, Vol. 23, p. 1245.
C3:
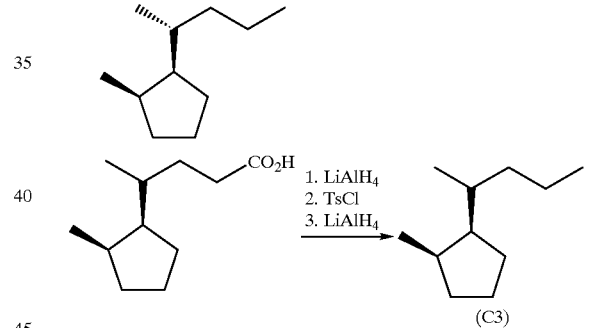
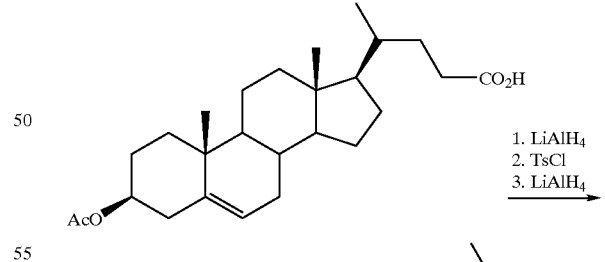
J. E. van Lier and L. L. Smith, J. Org. Chem., 1970, Vol. 36, No. 8, p. 2631.

C4:
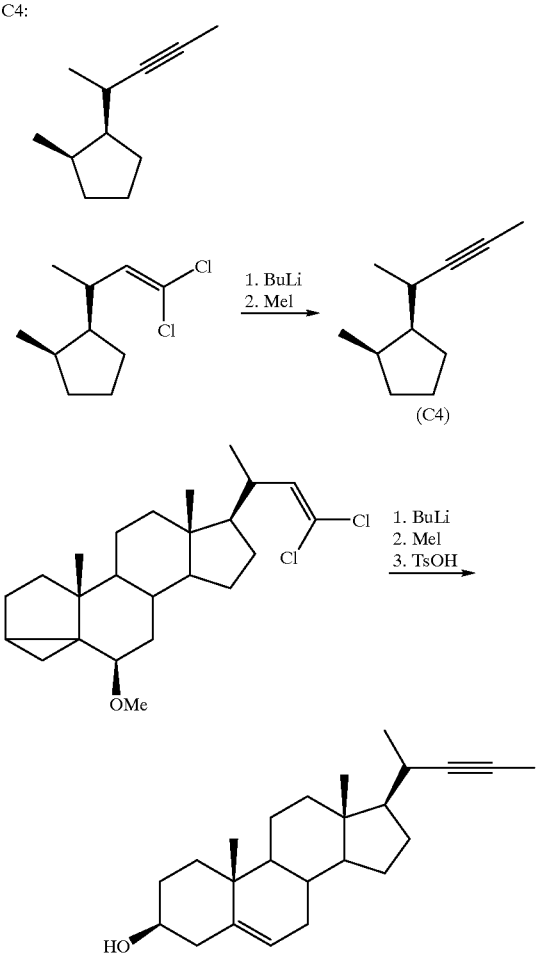
A. Burger, F. Colobert, C. Hetru, and B. Luu, Tetrahedron, 1988, Vol. 44, No. 4, p. 1141.
C5:
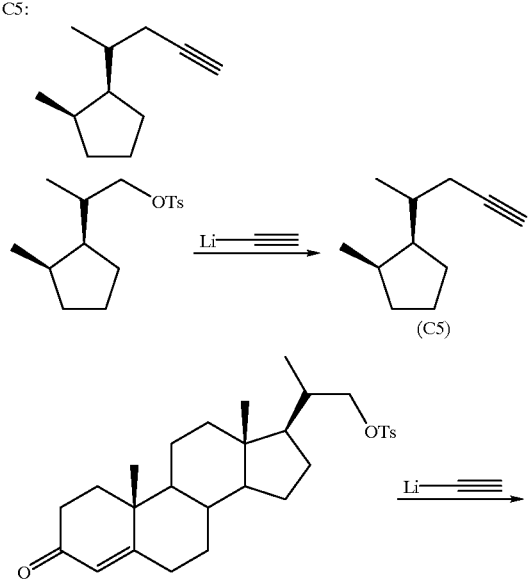
-continued
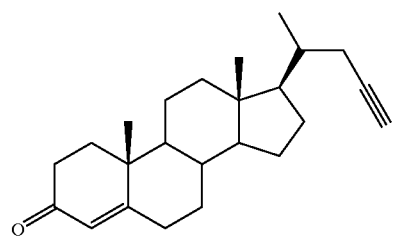
A. B. Turner, Chemistry and Industry, 1979, p. 385.
C6:
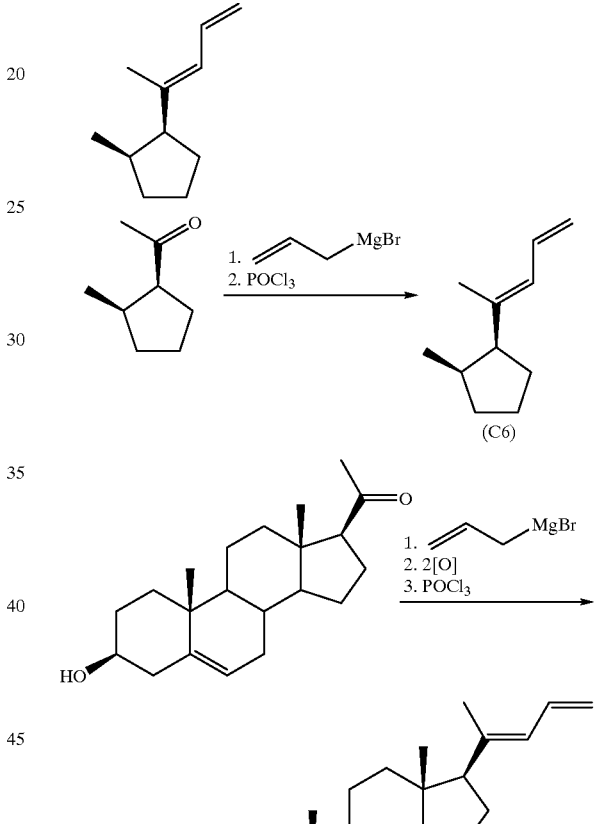
G. Stoeck and H. Stein, Germnan Patent No. 854,517, 1952.
C7:
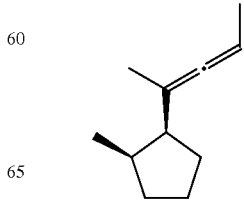

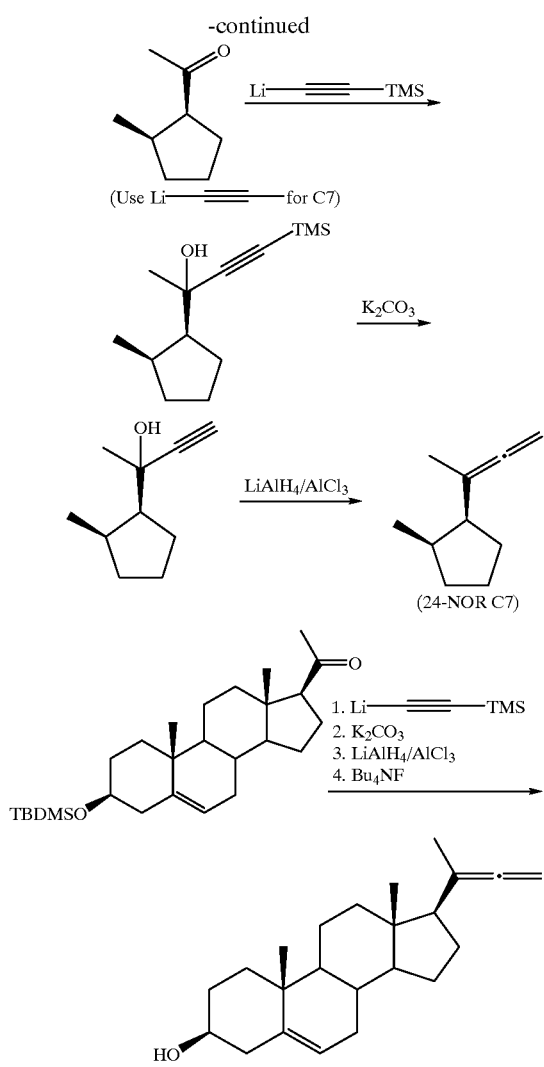

(24-NOR C7)

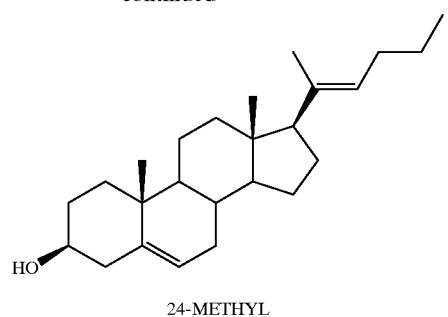

24-METHYL

J. P. Schmit, M. Piraux, and J. F. Pilette, J. Org. Chem., 1975, Vol. 40, No. 11, p. 1586.

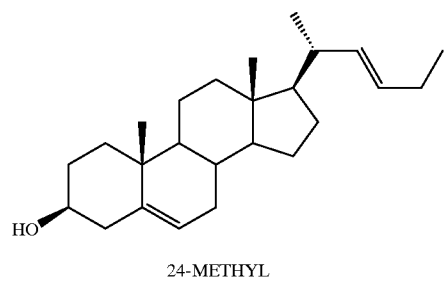

24-METHYL

Y. M. Sheikh and C. Djerassi, Steroids, 1975, Vol. 26(1), p. 129.

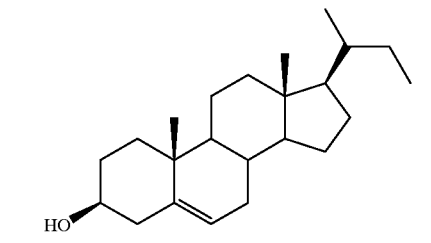

24-NOR

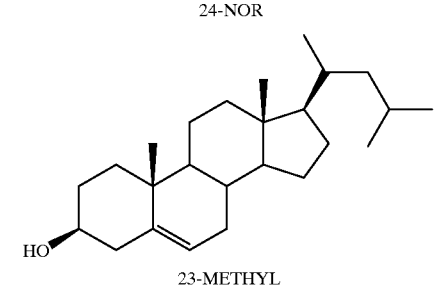

23-METHYL

A. Burger, J- P. Roussel, C. Hetru, J. A. Hoffmann, and B. Luu, Tetrahedron, 1989, Vol. 45, No. 1, p. 155.

24-Norcholanes and 24-Methylcholanes

Structures with the side chain shortened or lengthened by one carbon atom at the 24-position may be prepared using analogous methodology. 23-Methylcholanes are also available by similar means. Examples follow.

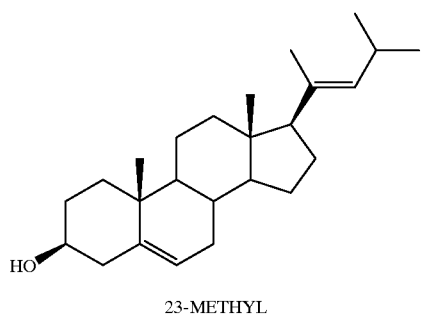

23-METHYL

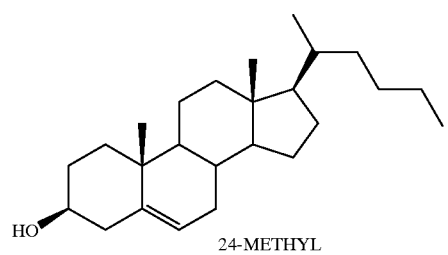

24-METHYL

M. Morisaki, M. Shibata, C. Duque, N. Imamura, and N. Ikekawa, Chem. Pharm. Bull., 1980, Vol. 28(2), p. 606.

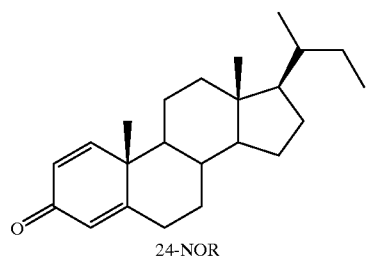

24-NOR

D. H. R. Barton, J. Boivin, D. Crich, and C. H. Hill, J. Chem. Soc. Perkin Trans. I, 1986, p. 1805.

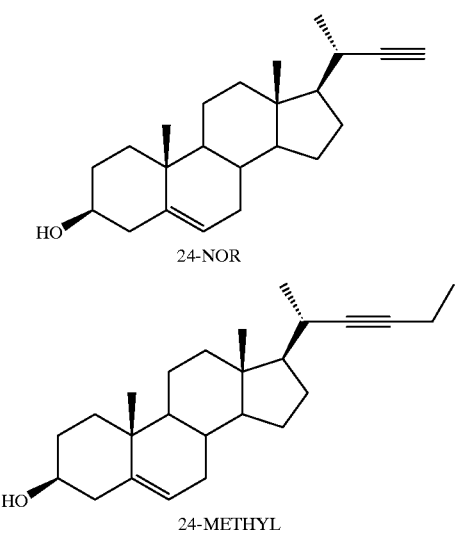

24-NOR

24-METHYL

A. Burger, F. Colobert, C. Hetru, and B. Luu, Tetrahedron, 1988, Vol. 44, No. 4, p. 1141.

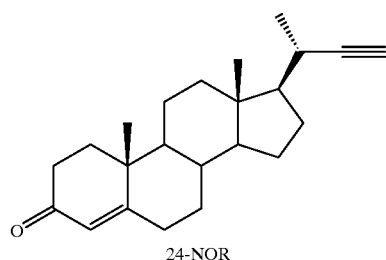

24-NOR

B. M. Trost, R. J. Kulawiec, and A. Hammes, Tetrahedron Letters, Vol. 34, No. 4, p. 587.

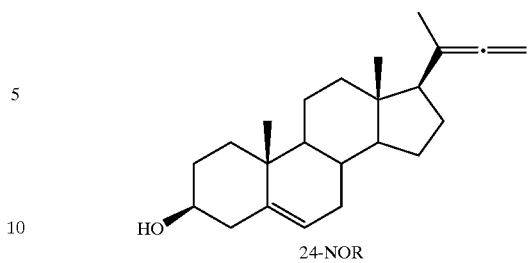

24-NOR

A. Burger, J- P. Roussel, C. Hetru, J. A. Moffmann, and B. Luu, Tetrahedron, 1989, Vol. 45, No. 1, p. 155.

C. Synthetic Methods

1. Preparation of 3-, 6-, 19-, 20- and 21-position derivatives.

Figure 1A:
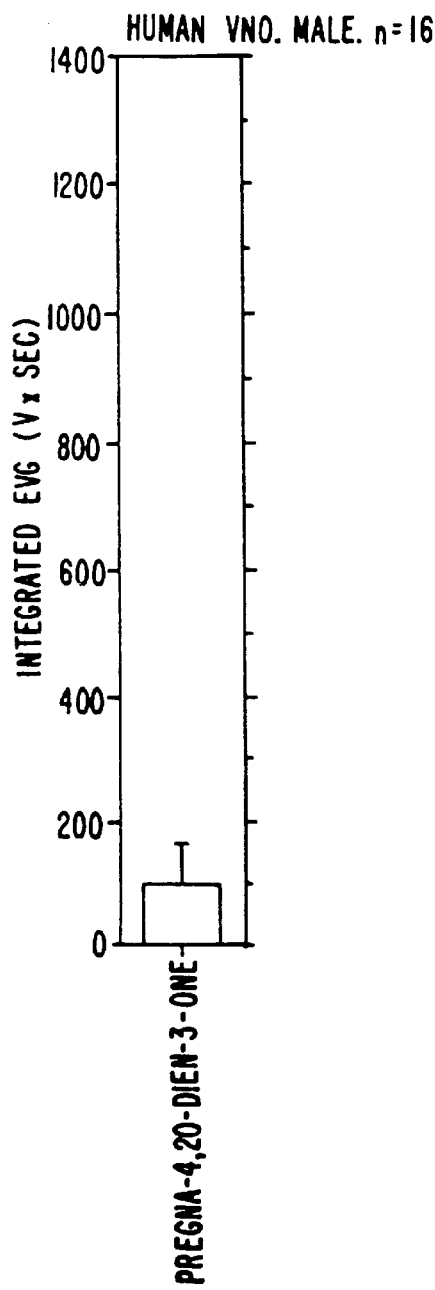
FIG. 1 is the data on the integrated EVG, GSR and ST for compound A1-P1 in males as tested according to Examples 16 and 17.
Figure 1B:
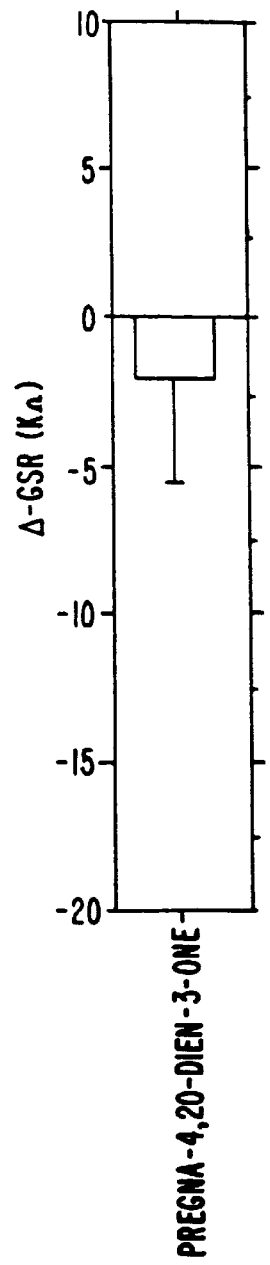
Figure 1C:
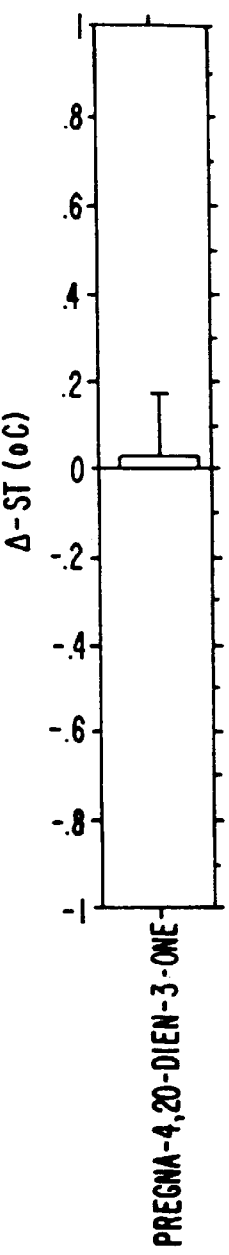

The compounds used in the methods of this invention are pregnane steroids substituted at the 3-, 6-, 19-, 20- and 21-positions. Many of the 3-substituted steroids are known compounds which may be derived from 3-oxo-steroids. As shown in FIG. 1, prena-4,20-diene-3-one (1) can be converted to a 3,5,20-triene ether (2) or 1,4,20-trien-3-one (3), which are respective starting materials for 6- and 3-substituted hydroxy derivatives.

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as NaH, KM or KOBut, silver oxide or barium oxide in polar, aphotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the work-up procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

2. Preparation of 19-OH derivatives.

Synthesis of 19-OH-pregna-4,17-diene-3-one.

A method of synthesizing this compound is provided in SCHEME 3.

In the following chart III, particularly preferred 19-nor-pregnanes are shown.

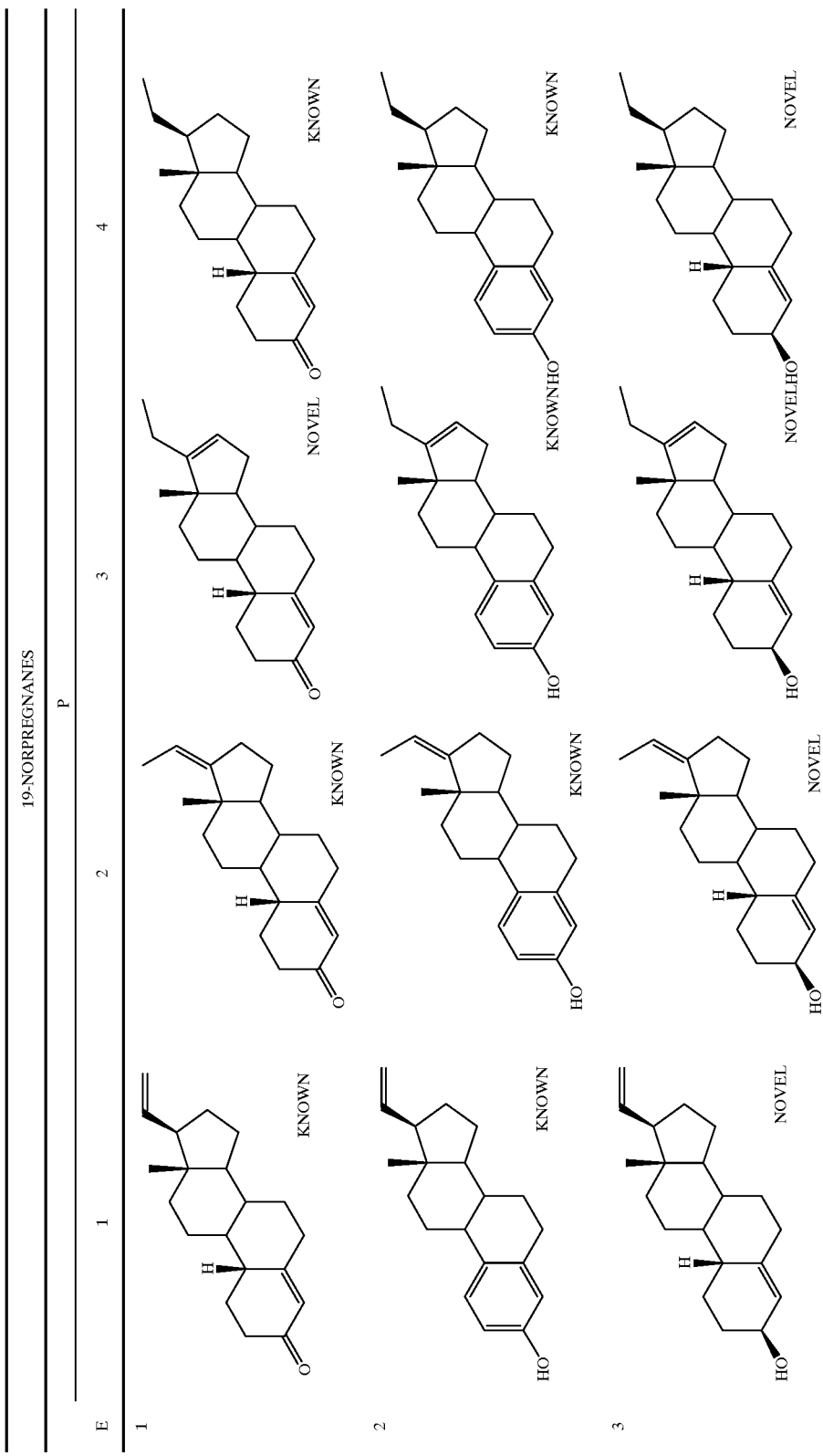

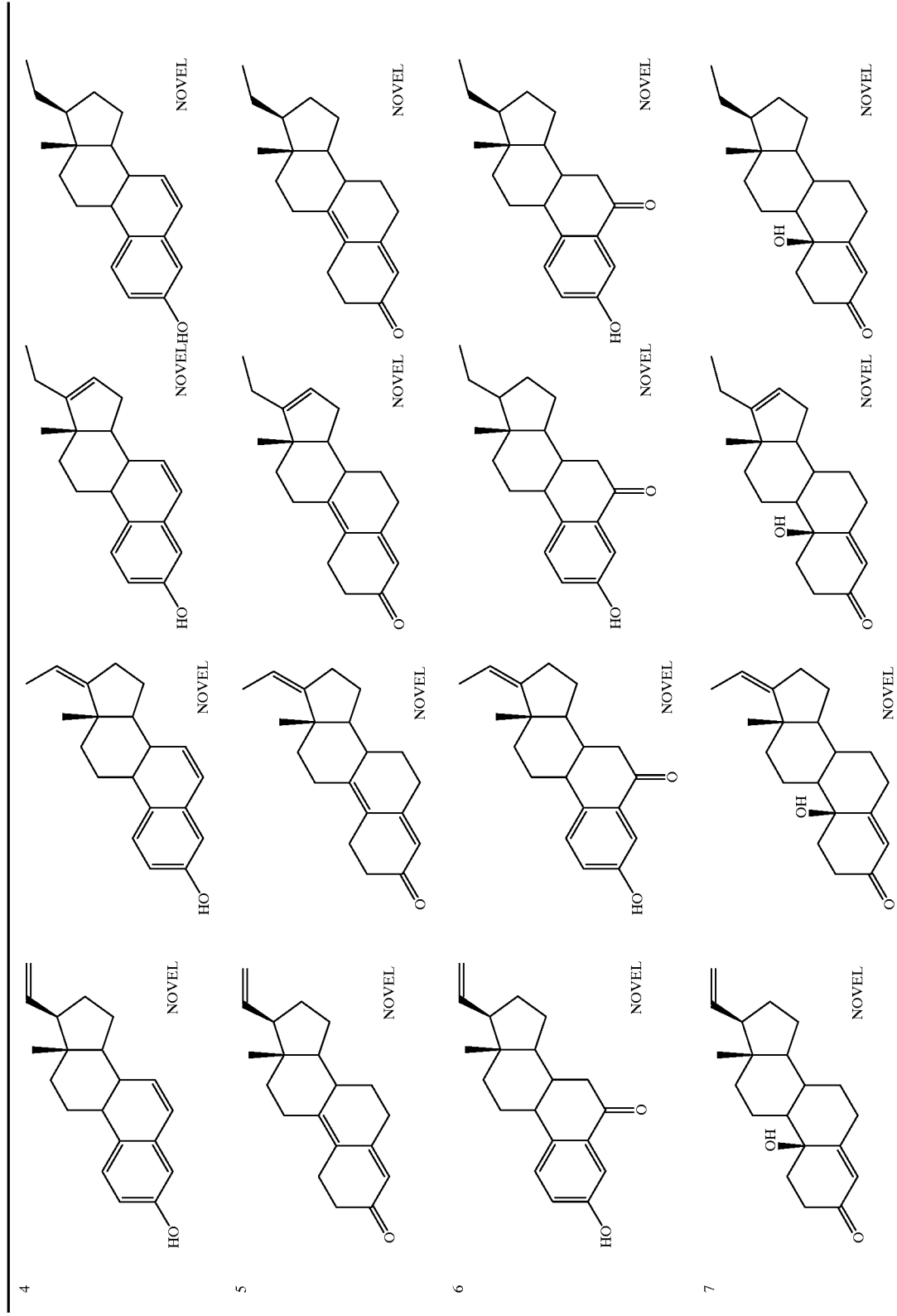

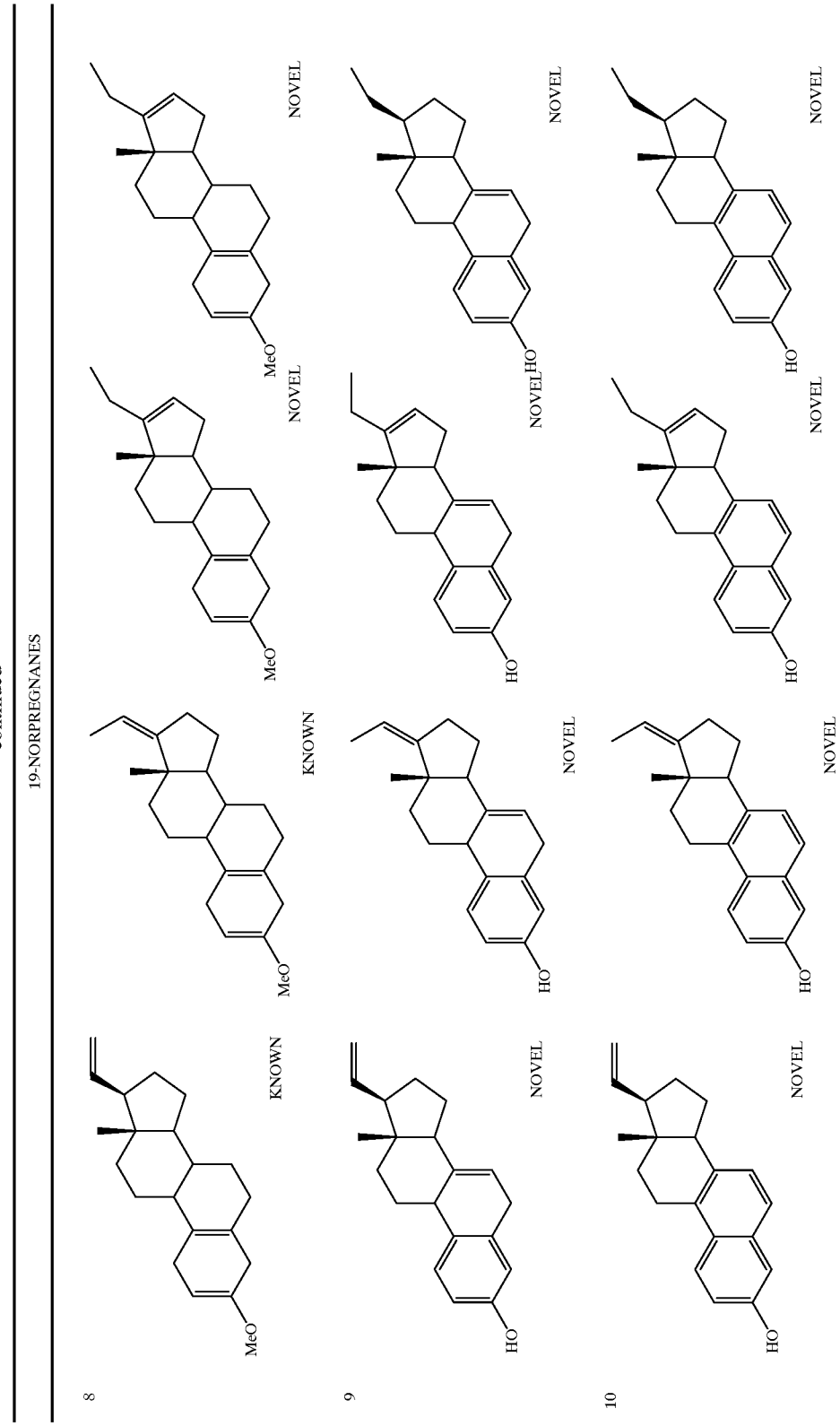

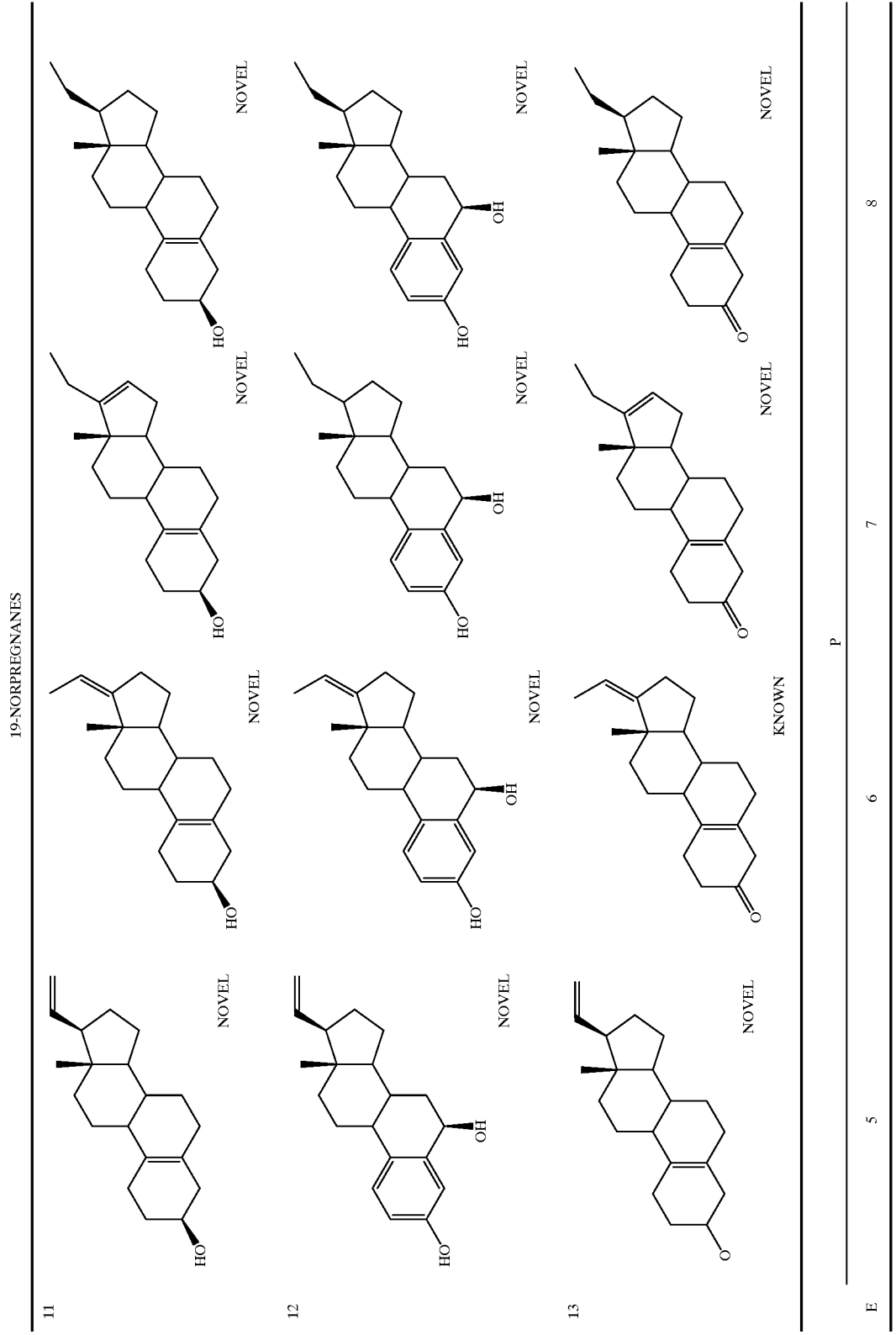

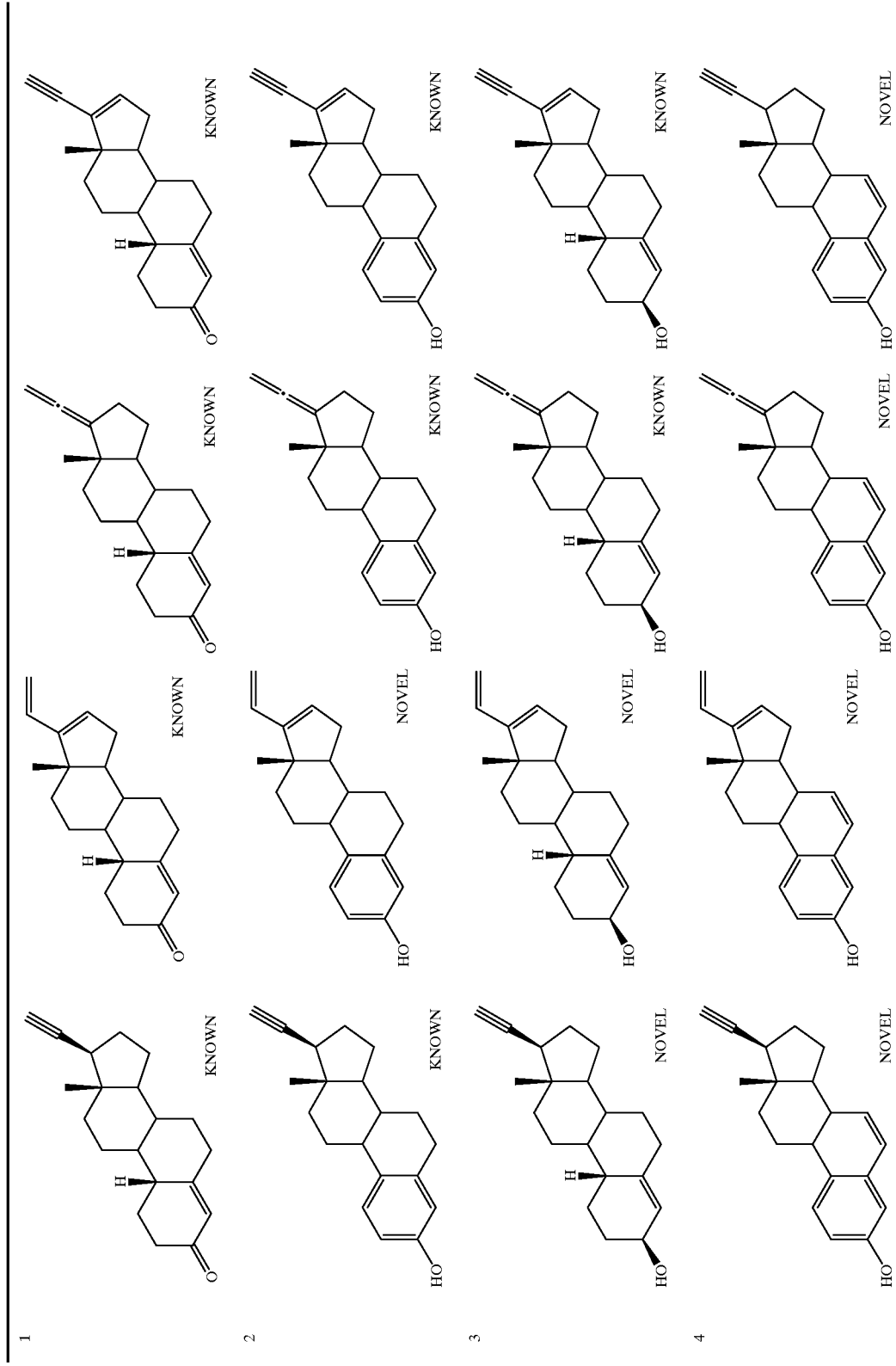

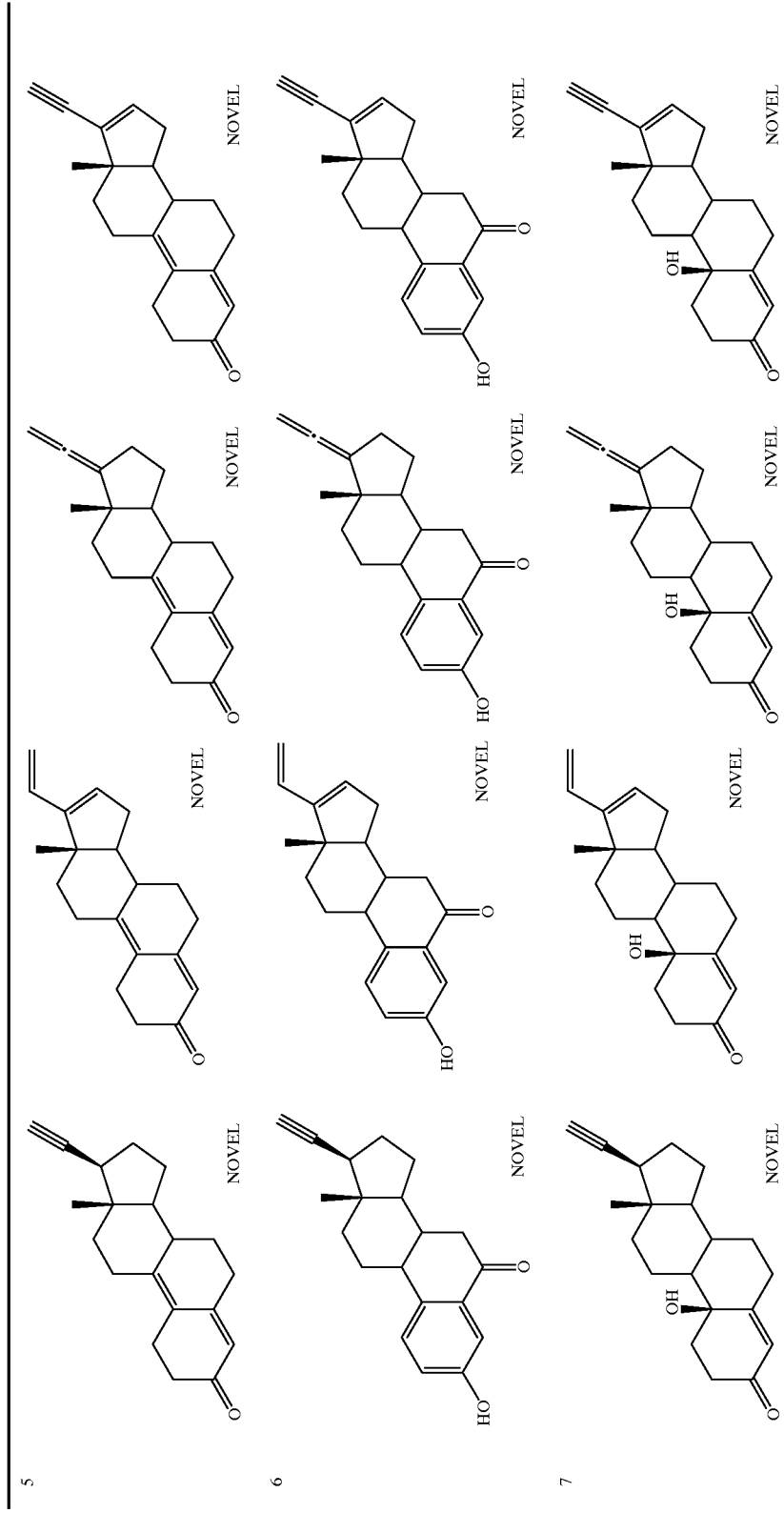

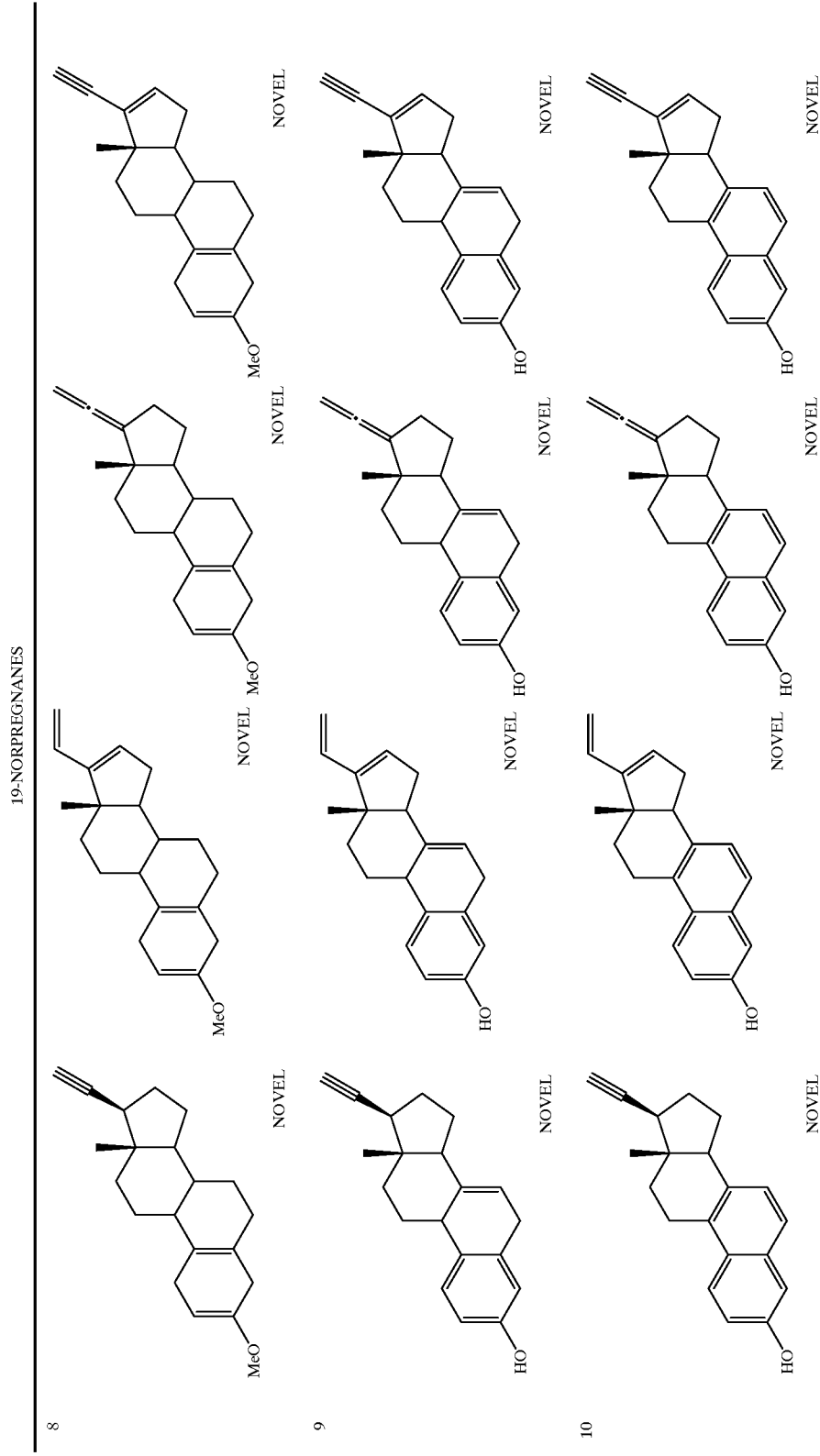

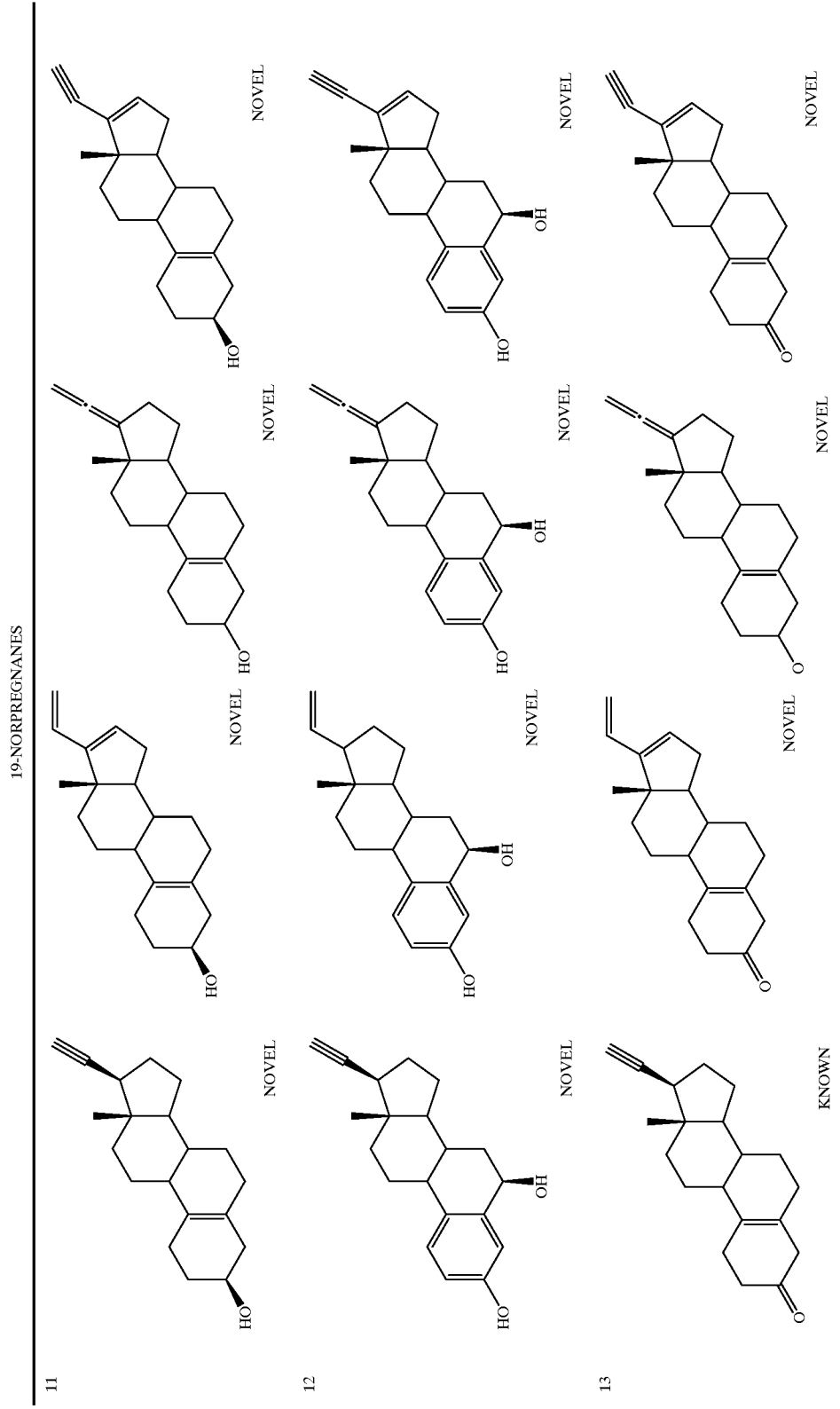

Substructure Syntheses: Type E

E1:

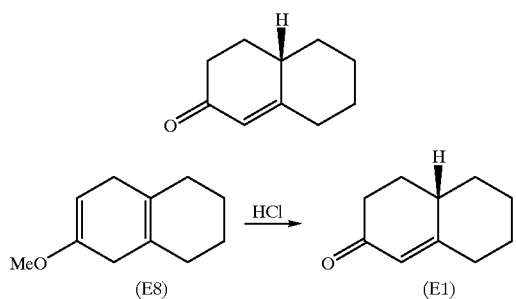

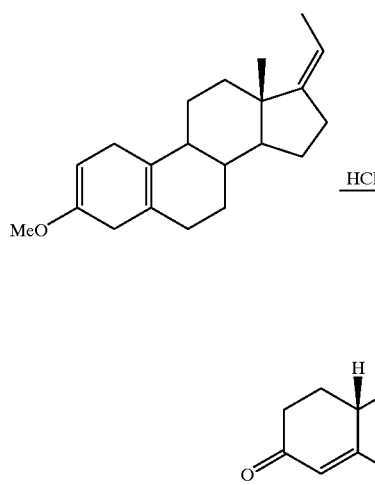

Frank B. Colton, Leonard N. Nysted, Byron Riegel, and Albert L. Raymond, J. Amer. Chem. Soc., 1957, 79, 1132.

Also a commercially available substructure, for example 17 α-ETHYNYL-19-NORTESTOSTERONE.

E2:

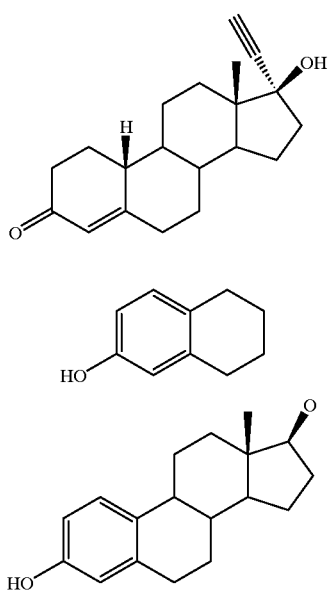

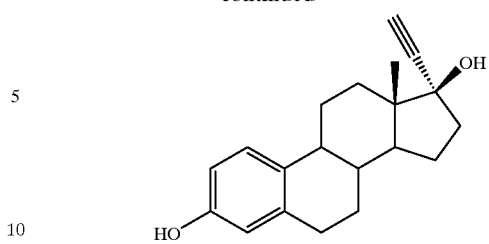

This is a commercially available substructure, for example ESTRONE, ETHYNYLESTRADIOL.

E3:

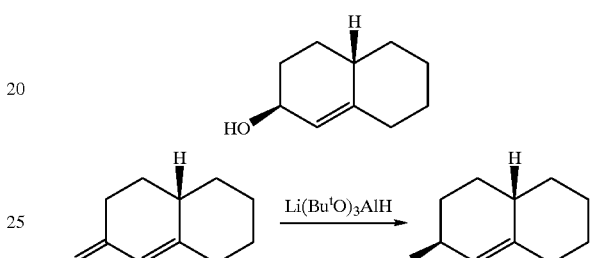

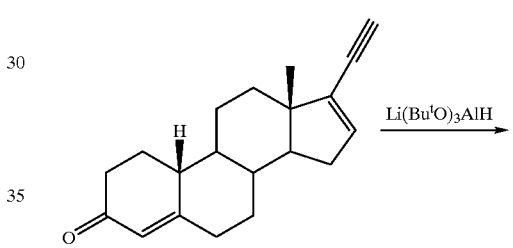

Pierre Crabble, U.S. Pat. No. 3,492,318, 1970.

E4:

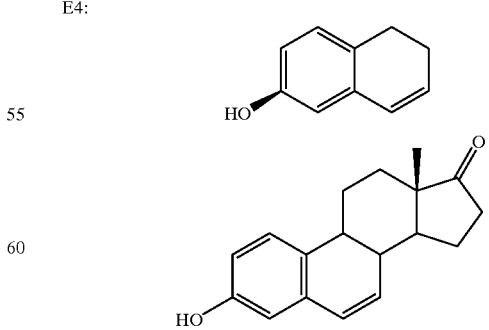

This is a commercially available substructure, for example 6-DEHYDROESTRONE.

E5:
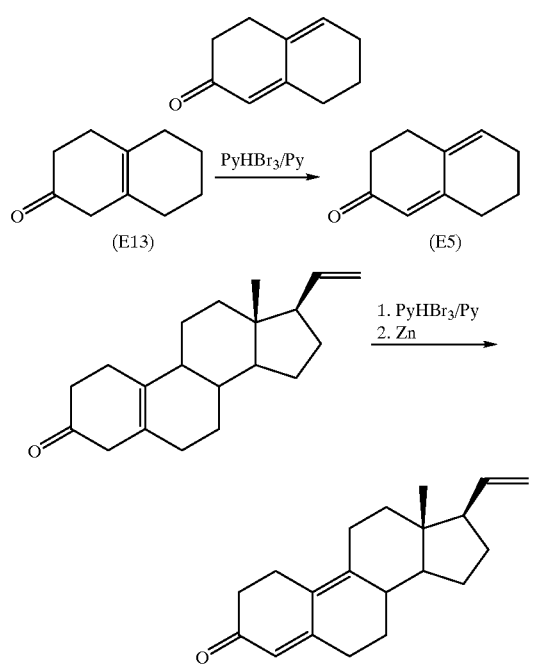
See example.
E6:
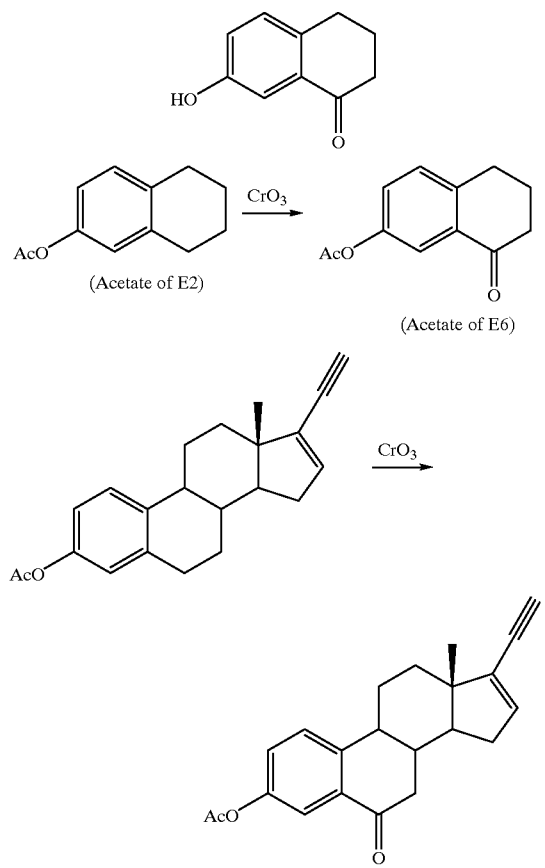
See example:
E7:
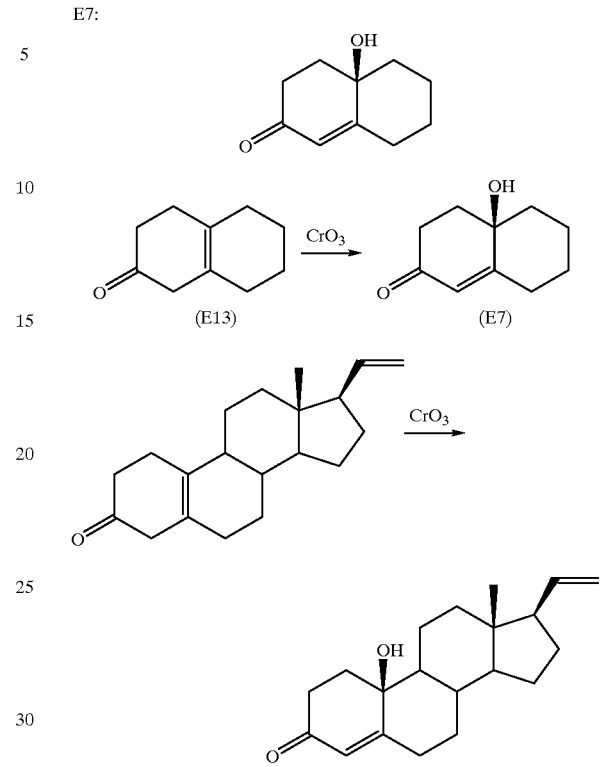
See example.
E8:
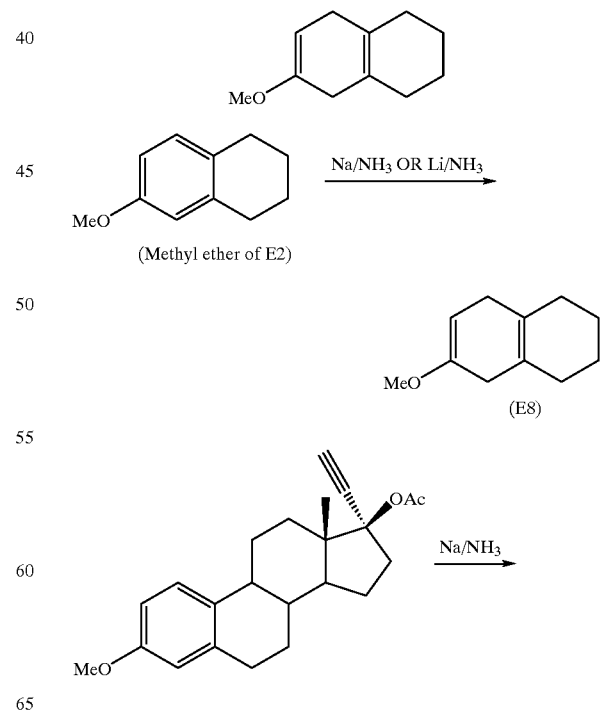

-continued
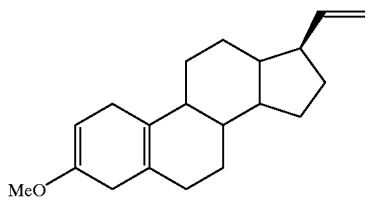
O. I. Fedorova, O. S. Anisimova, an G. S. Grinenko, Khim. Prir. Soedin., 1976, 2, 180.
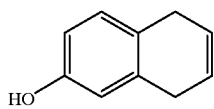
Frank B. Colton, Leonard H. Nysted, Byron Riegel, and Albert L. Raymond, J. Amer. Chem. Soc., 1957, 79, 1123.
E9:
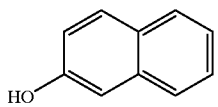
This is a commercially available substructure, for example EQUILIN.
E10:
-continued
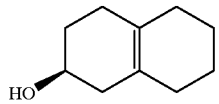
This is a commercially available substructure, for example EQUILENIN.
E11:
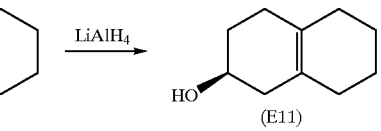
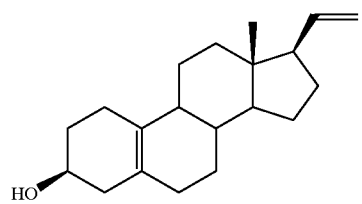
See example.
E12:
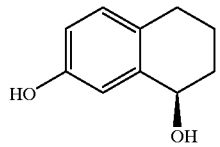
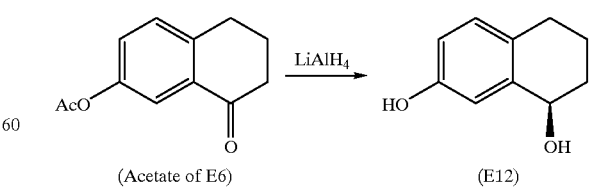

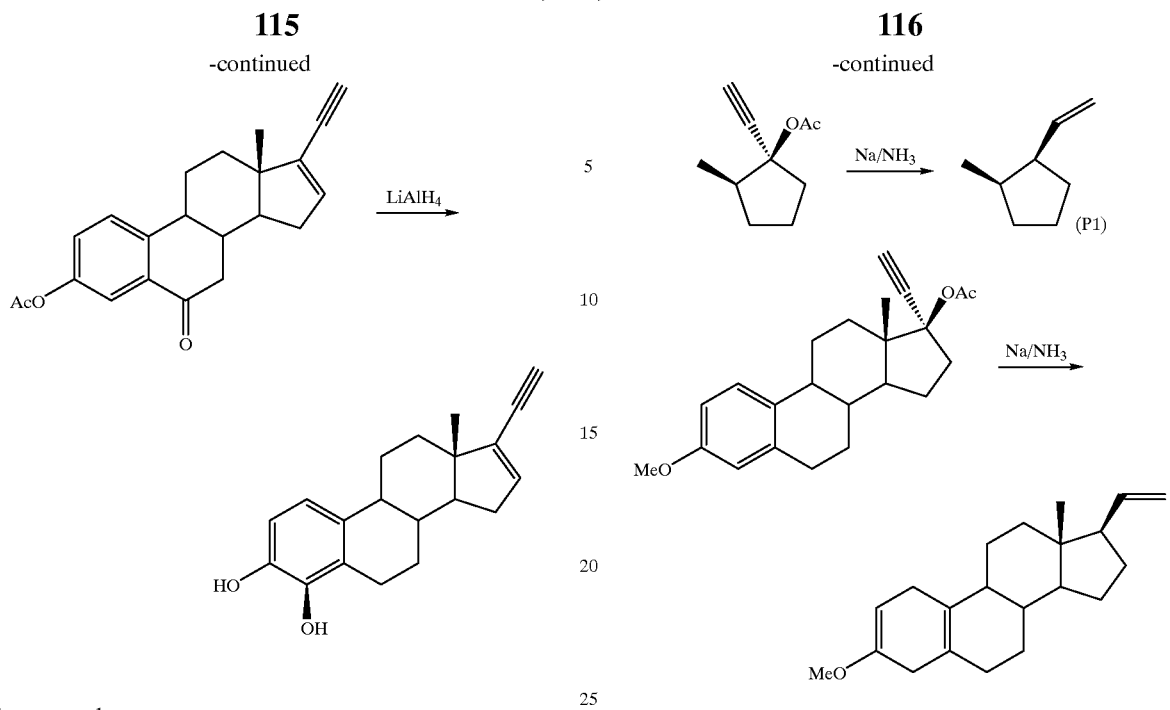
See example.
E13:
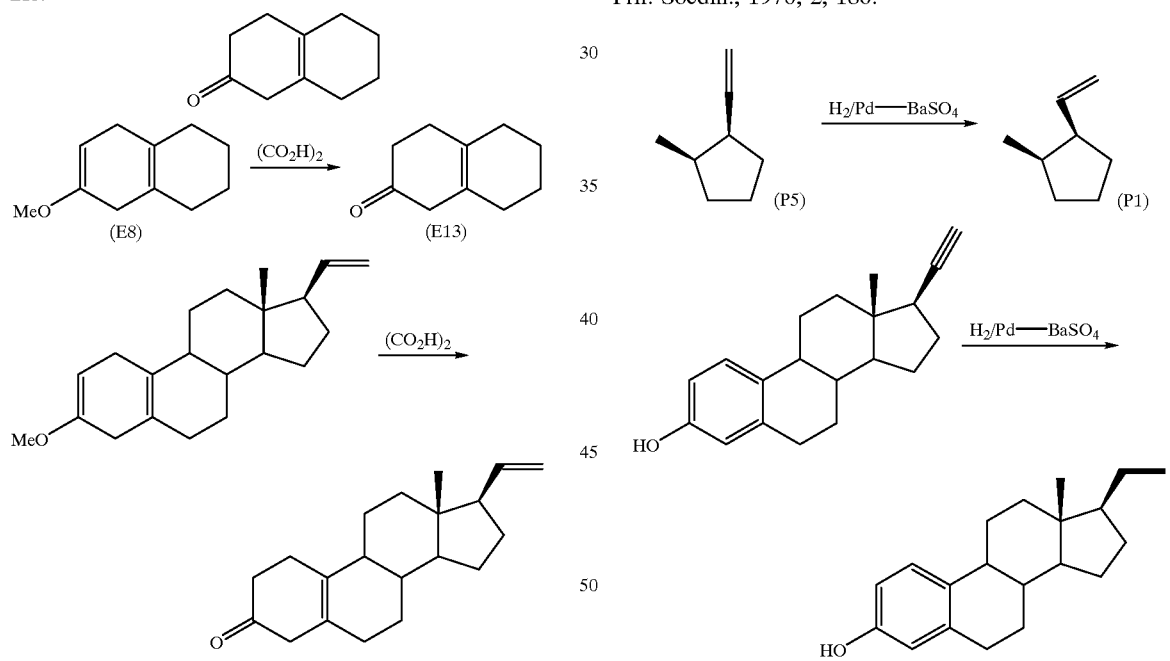
See Example.
Substructure Syntheses: Type P
P1:
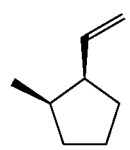
O. I. Fedorova, O. S. Anisimova, and G. S. Grinenko, Khim. Prir. Soedin., 1976, 2, 180.
Richard H. Peters, David F. Crowe, Mitchell A. Avery, Wesley K. M. Chong, and Masato Tanabe, J. Med. Chem., 1989, 32, 1642.
Also see example.
P2:
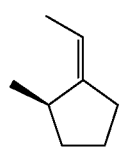

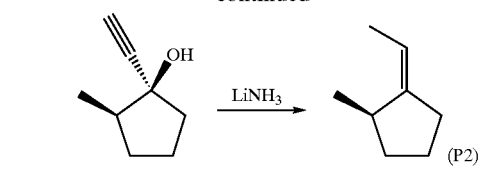
(P2)
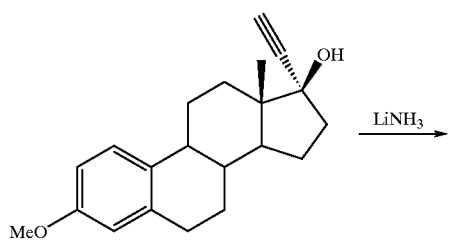
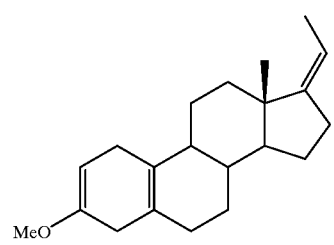
Frank F. Colton, Leonard N. Nysted, Bryon Riegel, and Albert L. Raymond, J. Amer. Chem. Soc., 1957, 79 1123.
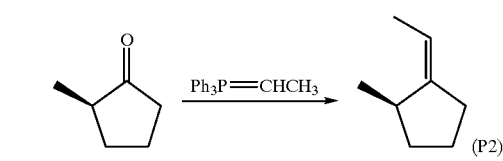
(P2)
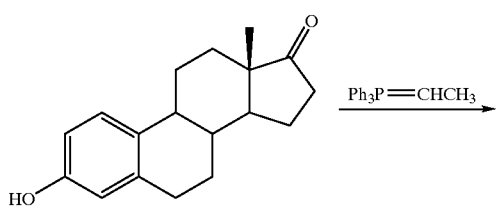
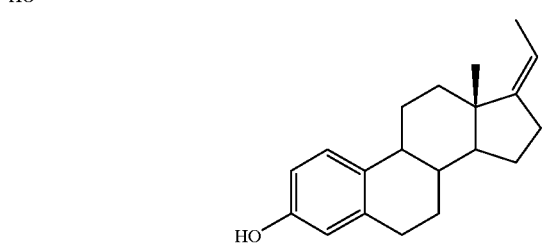
Richards H. Peters, David F. Crowe, Mitchell A. Avery, Wesley K. M. Chong, and Masato Tanabe, J. Med. Chem., 1989, 32, 1642.
P3:
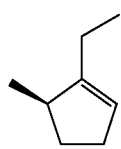
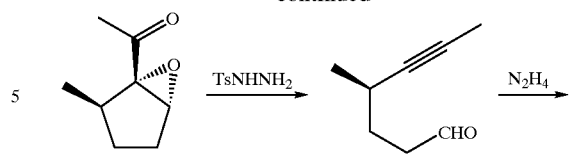
(P3)
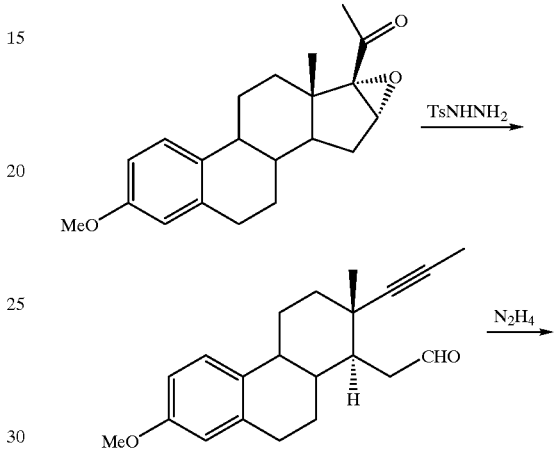
H. Kaufmann, P. Wieland, and J. Kalvoda, Helv. Chim. Acta., 1972, 55(2), 381.
P4:
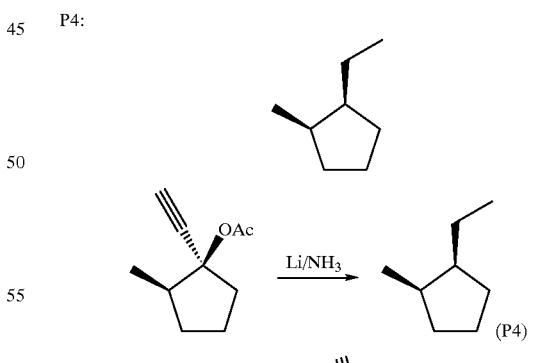
(P4)
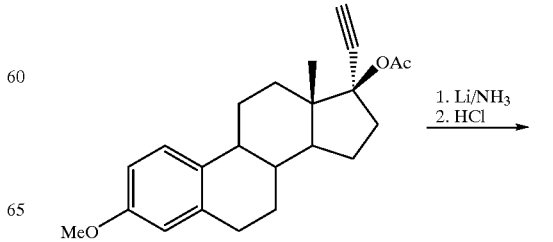
1. Li/NH$_3$
2. HCl

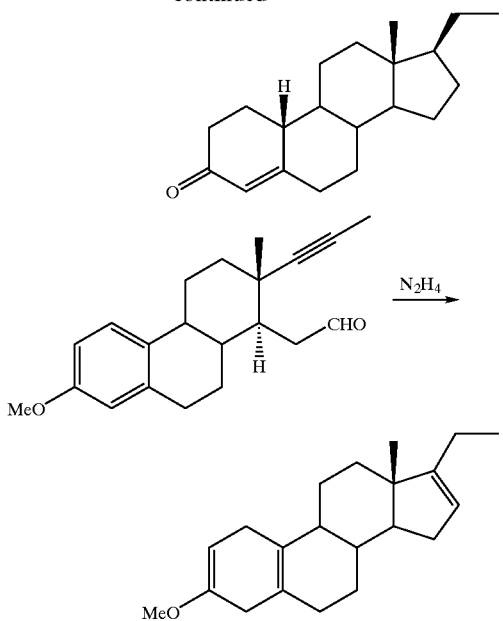
O. I. Fedorova, O. S. Anisimova, and G. S. Grinenko, Khim. Prir. Soedin., 1976, 2, 180.
Richard H. Peters, David F. Crowe, Mitchell A. Avery, Wesley K. M. Chong, and Masato Tanabe, J. Med. Chem., 1989, 32, 1642.
P5:
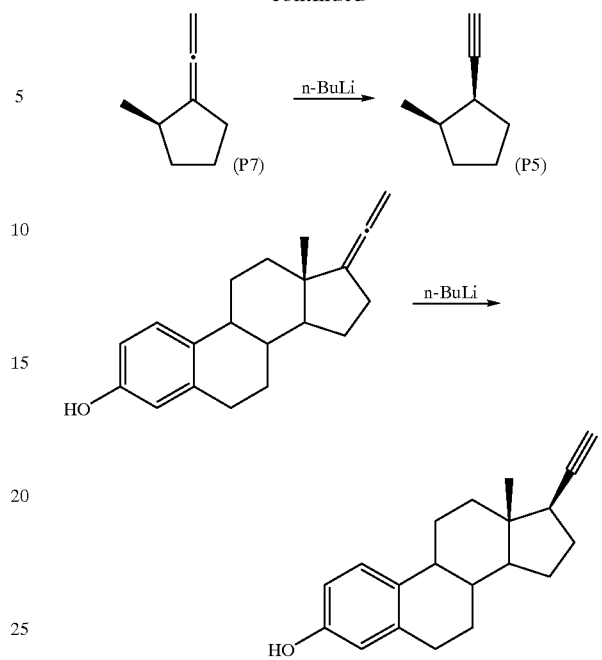
Peter Kaspar and Herbert Witzel, J. Steroid Biochem., 1985, Vol. 23, No. 3, p. 259.
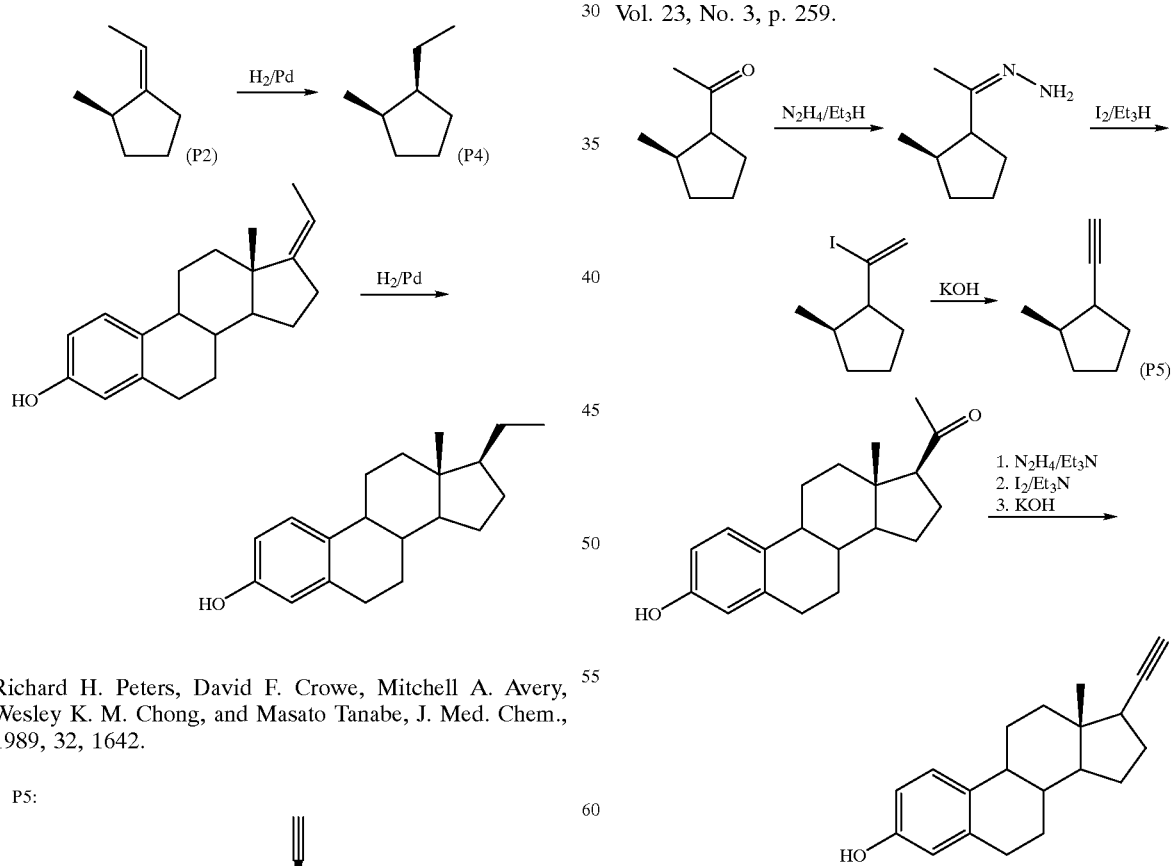
Richard H. Peters, David R. Crowe, Mitchell A. Avery, Wesley K. M. Chong, and Masato Tanabe, J. Med. Chem., 1989, 32, 1642.

P6:
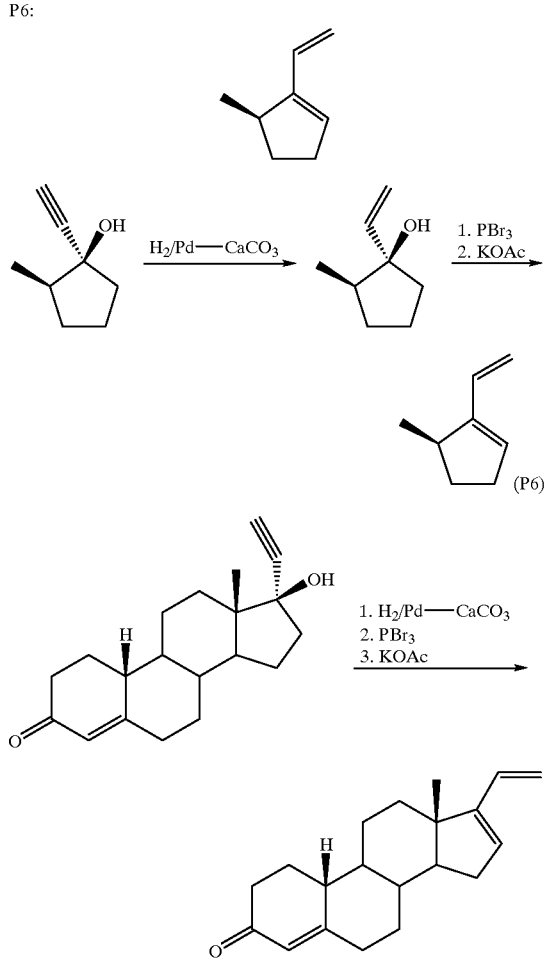
Frank B. Colton, U.S. Pat. No. 2,840,582, 1958.
P7:
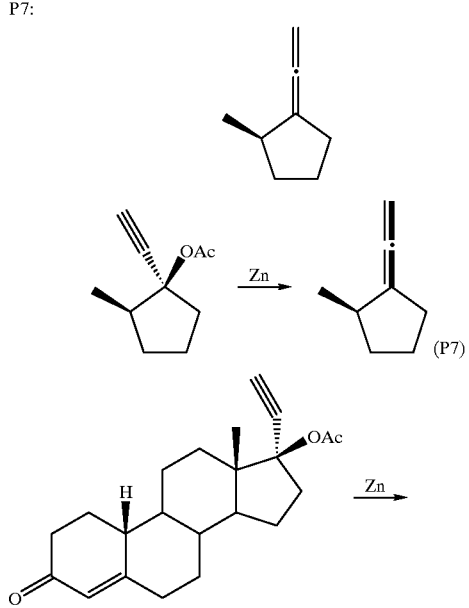
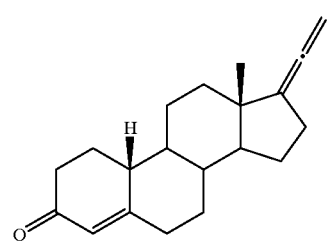
Pierre Crabble and Esperanza Velarde, U.S. Pat. No. 3,681,410, 1972.
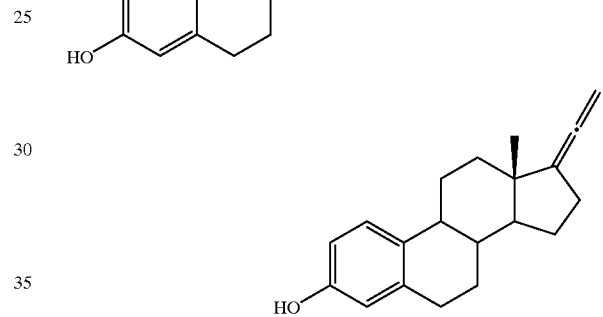
Peter Kaspar and Herbert Witzel, J. Steroid. Biochem., 1985, Vol. 23, No. 3, P. 259.
P8:
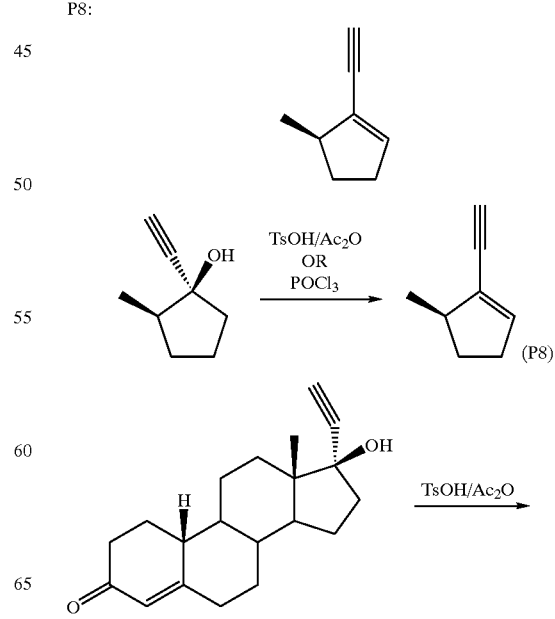

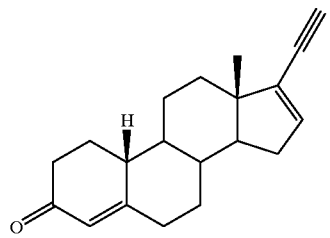
Pierre Crabble, U.S. Pat. No. 3,492,318, 1970.
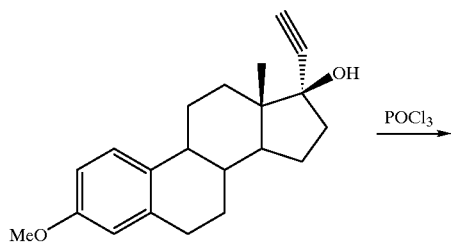
Klaus Prezewowsky and Rudolf Wiechert, U.S. Pat. No. 3,682,983, 1972.
Methylnorpregnanes
19-Norpregnanes in this-series may be prepared with a methyl group in the 6α, 7α, 18, 20, or 21 positions.
U.S. Pat. No. 3,681,410 teaches preparation of 6α-methyl analogs.
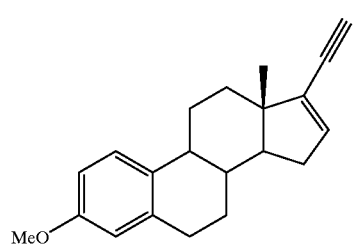
U.S. Pat. No. 3,682,983 teaches preparation of 18-methyl analogs.
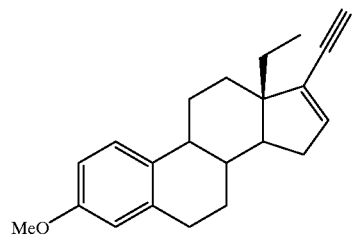
U.S. Pat. No. 3,492,318 teaches preparation of 7α, 18, and 21-methyl analogs.
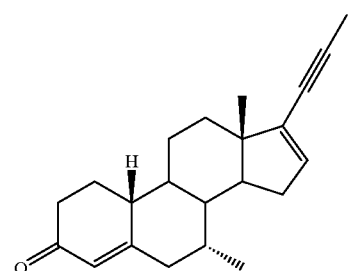
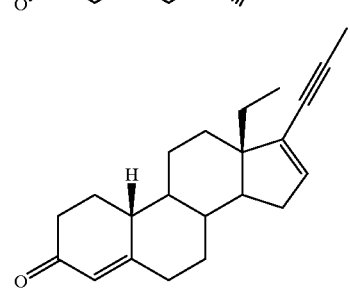
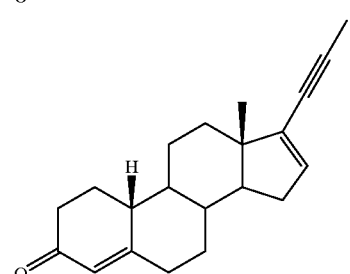
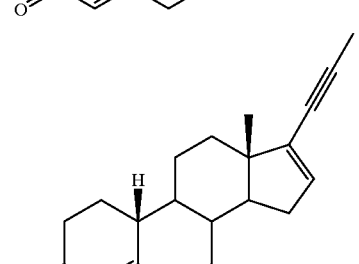

21-methyl analog:
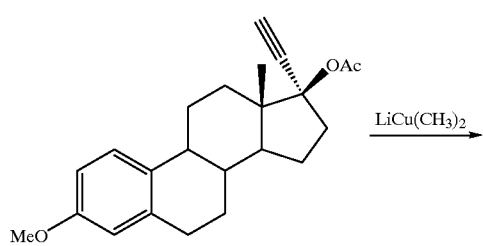
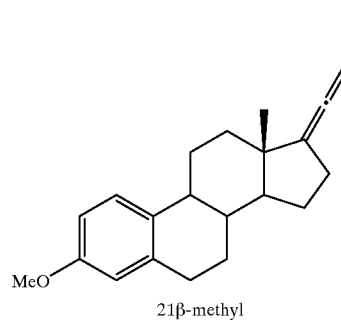
21β-methyl
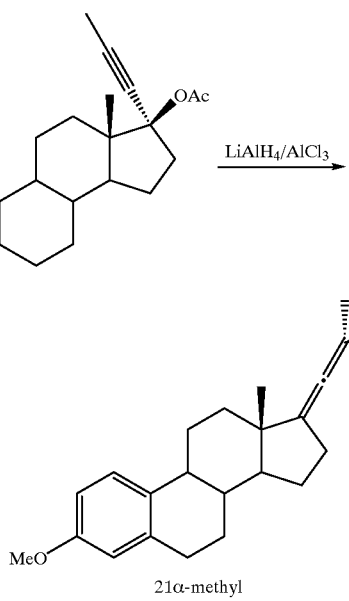
21α-methyl
L. A. Van Dijck, B. J. Lankwerden, J. G. C. M. Vermeer, and A. J. M. Weber, Recl. Trav. Chim. Pays-Bas Belg., 1971, 90, 801.
7α, 18, 20, and 21-methyl analogs.
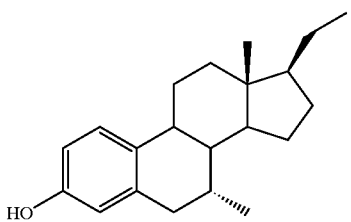
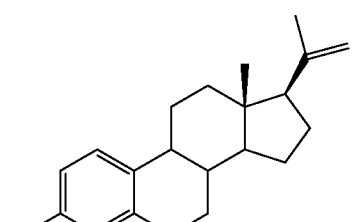
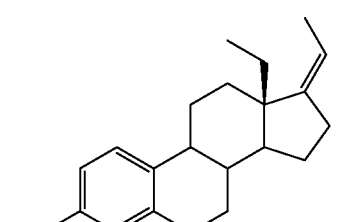
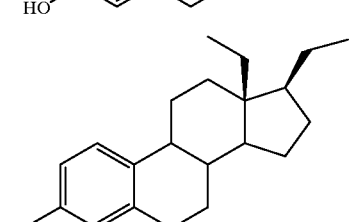
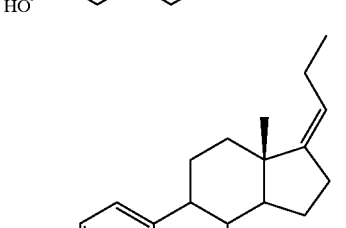
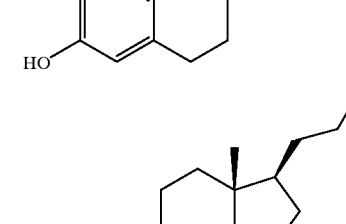
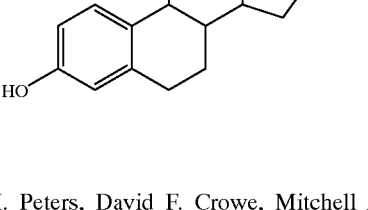
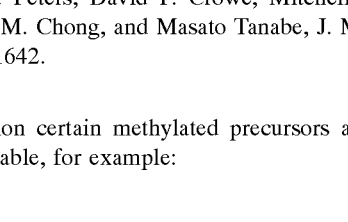
Richard H. Peters, David F. Crowe, Mitchell A. Averey, Wesley K. M. Chong, and Masato Tanabe, J. Med. Chem., 1989, 32, 1642.
In addition certain methylated precursors are commercially available, for example:

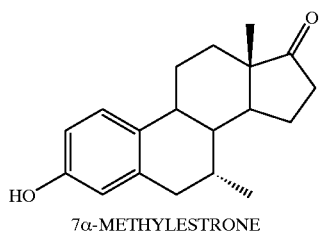

7α-METHYLESTRONE

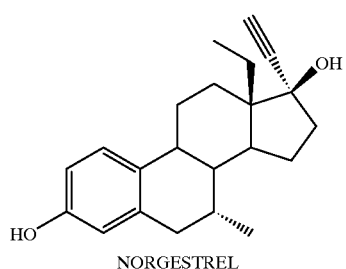

NORGESTREL

From these, 7α-methyl or 18-methyl analogs may be made of substances wherein estrone or 17α-ethynyl-19-nortestosterone (norethindrone) are the precursors, respectively.

Halonorpregnanes

U.S. Pat. No. 2,840,582 teaches the preparation of:

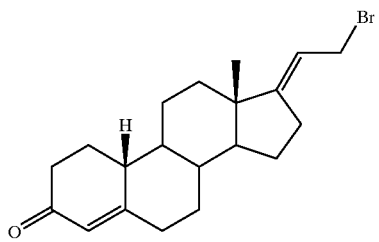

U.S. Pat. No. 3,681,410 teaches the preparation of:

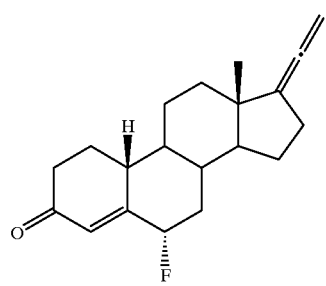

-continued

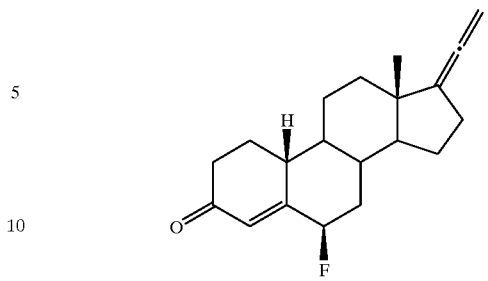

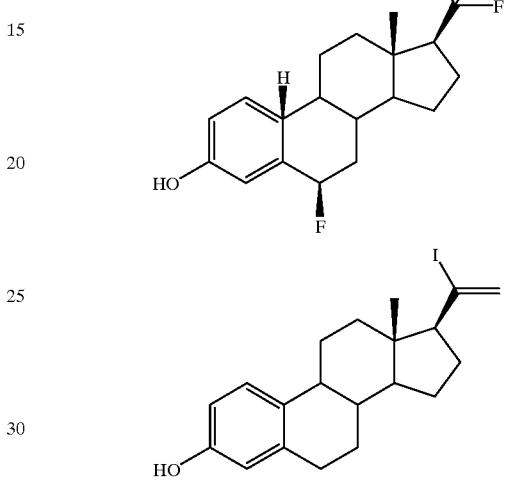

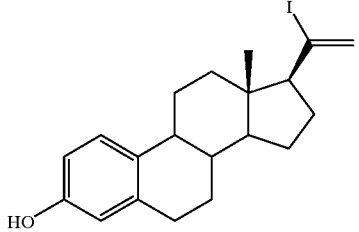

Richard H. Peters, David F. Crowe, Mitchell A. Avery, Wesley K. M. Chong, and Masato Tanabe, J. Med. Chem., 1989, 32, 1642.

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aphotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the workup procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

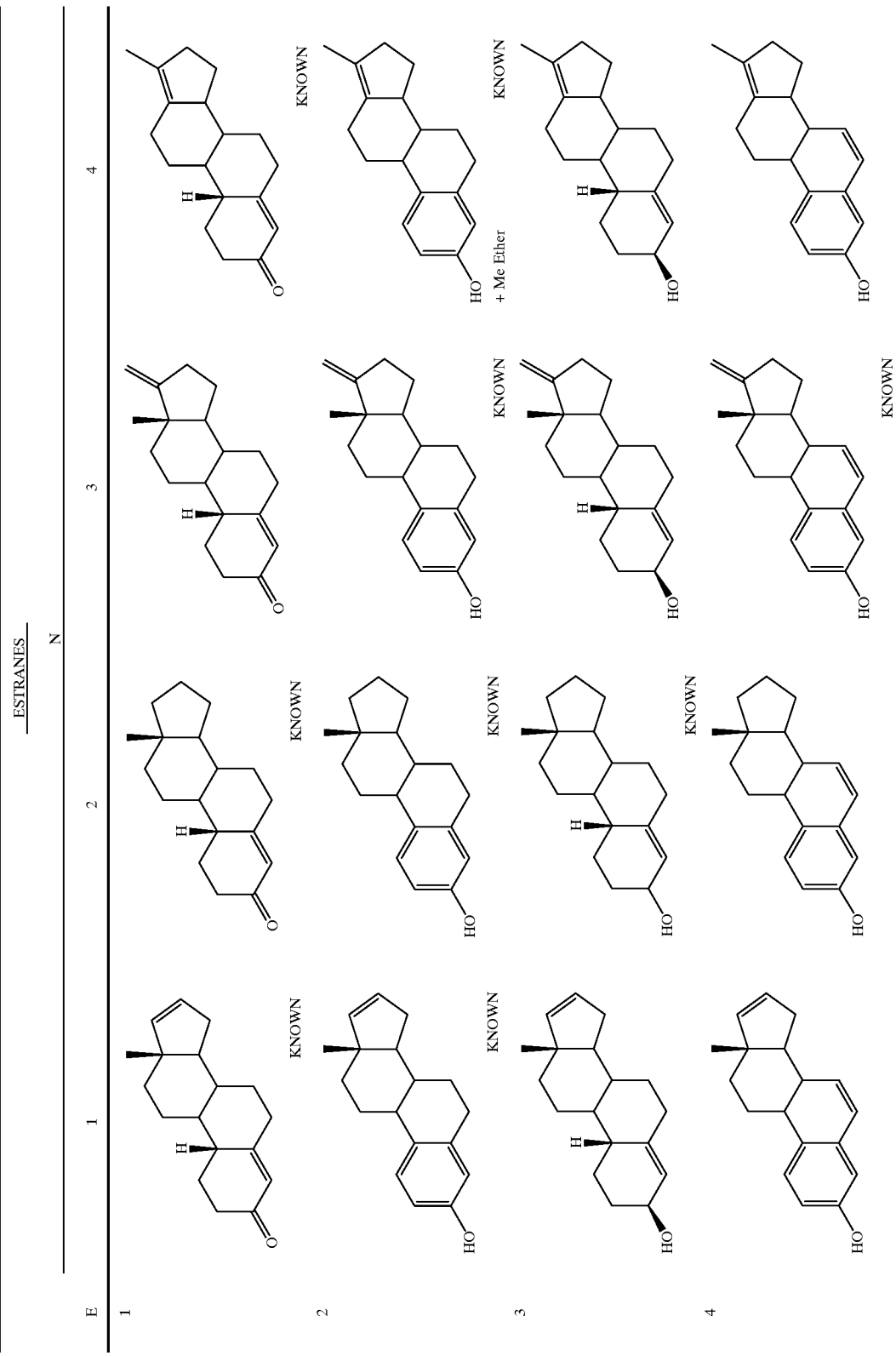

CHART IV-continued
ESTRANES
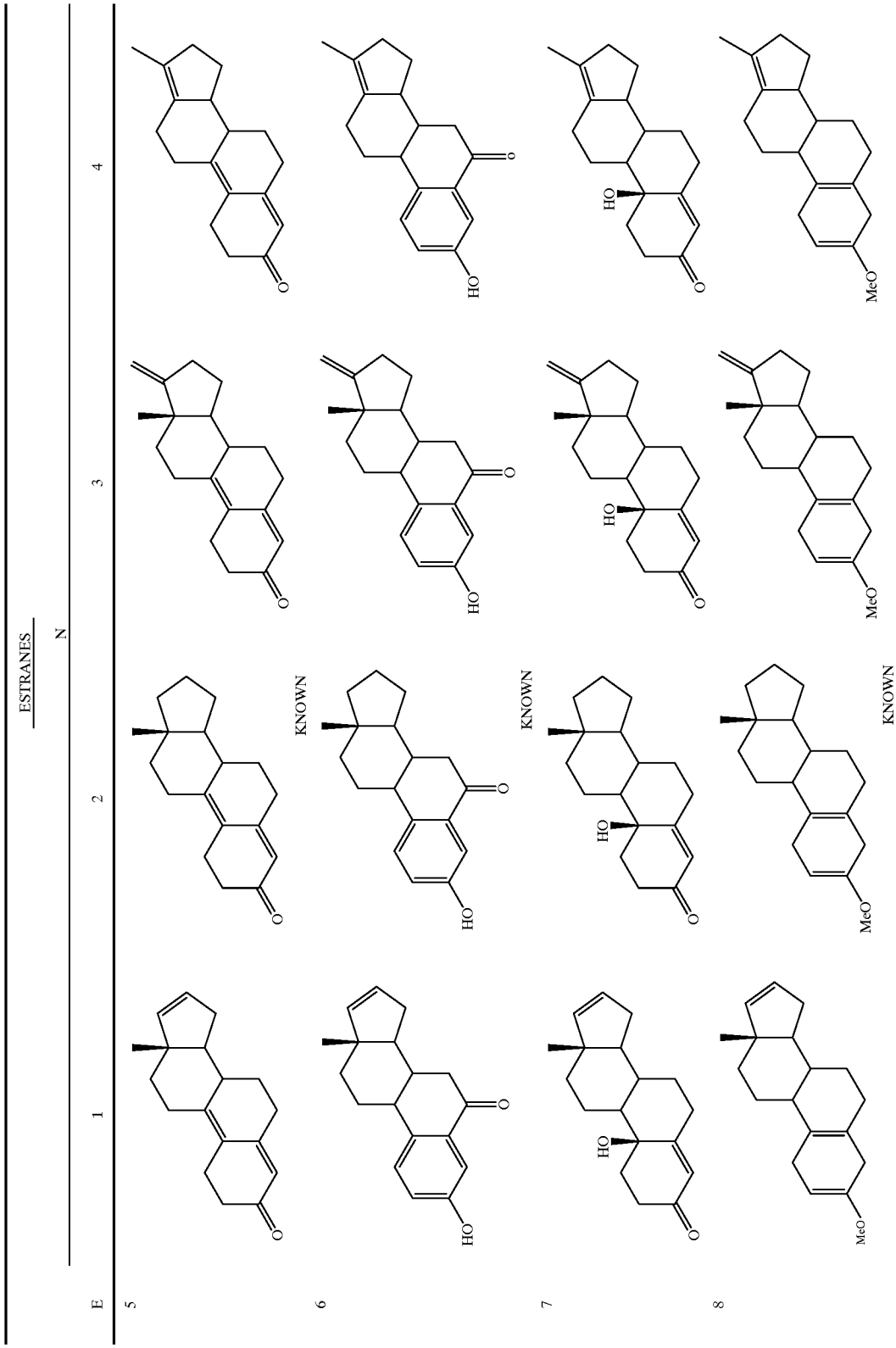

CHART IV-continued
ESTRANES
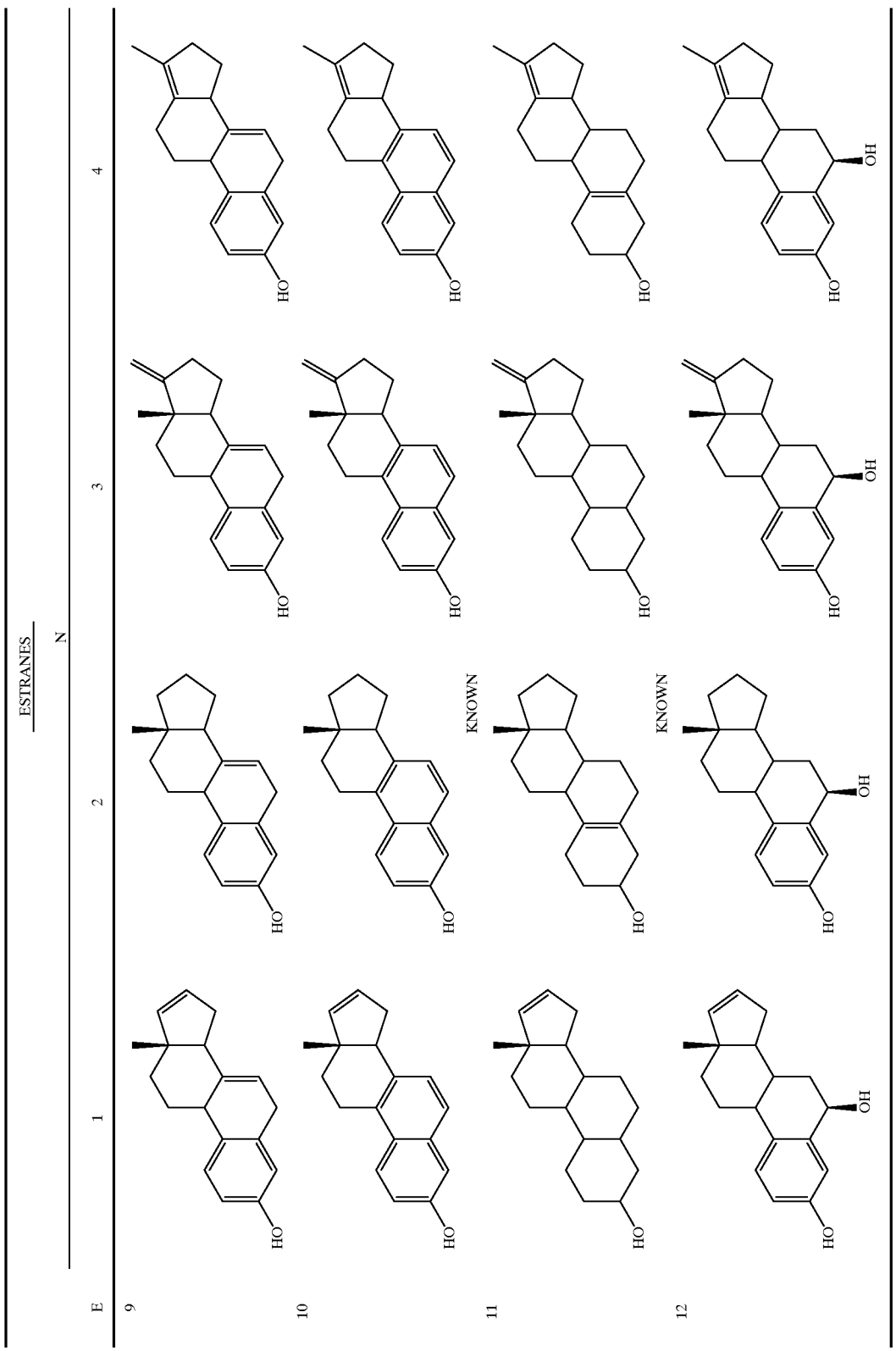

Substructure Syntheses
Referring to the preceding table, the following are exemplary syntheses for intermediates in a given row (E1 through E12) or column (N1 through N4).
Type E
E1:
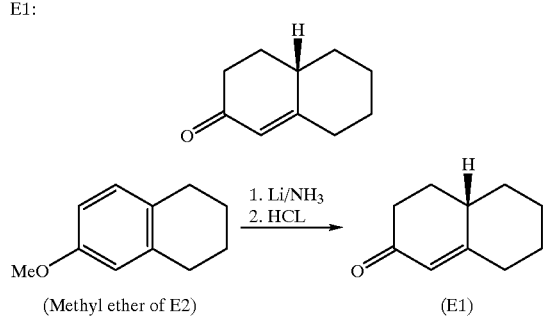
E2:
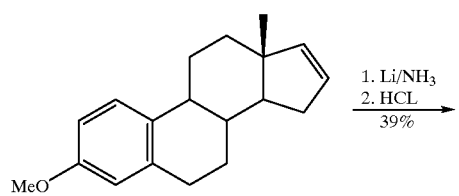
Commercially available substructure, for example, ESTRONE.
E3:
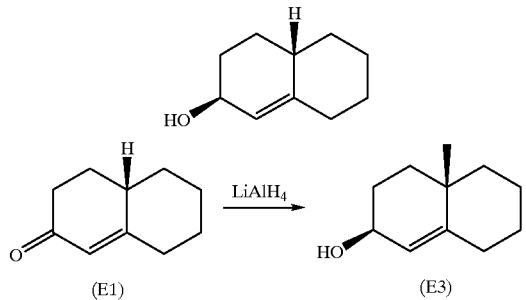
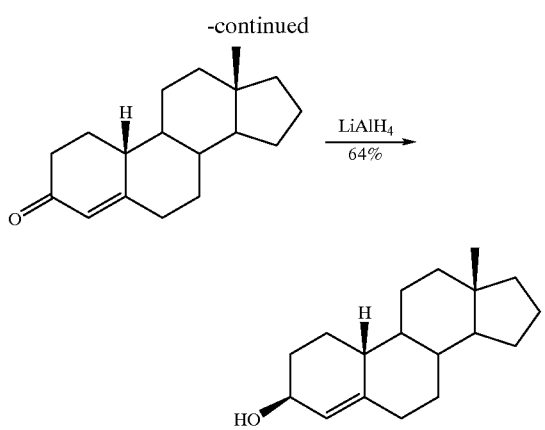
James R. Bull and Jan Floor, J. Chem. Sac. Perkin I, 1977 (7), 724.
E4:
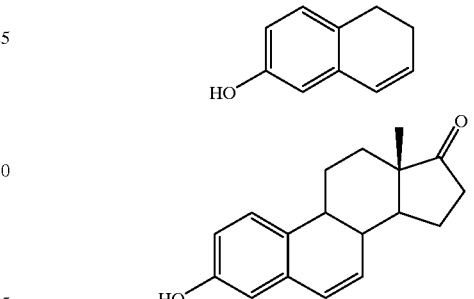
Commerically available substructure, for example, 6-DEHYDROESTRONE.
E5:
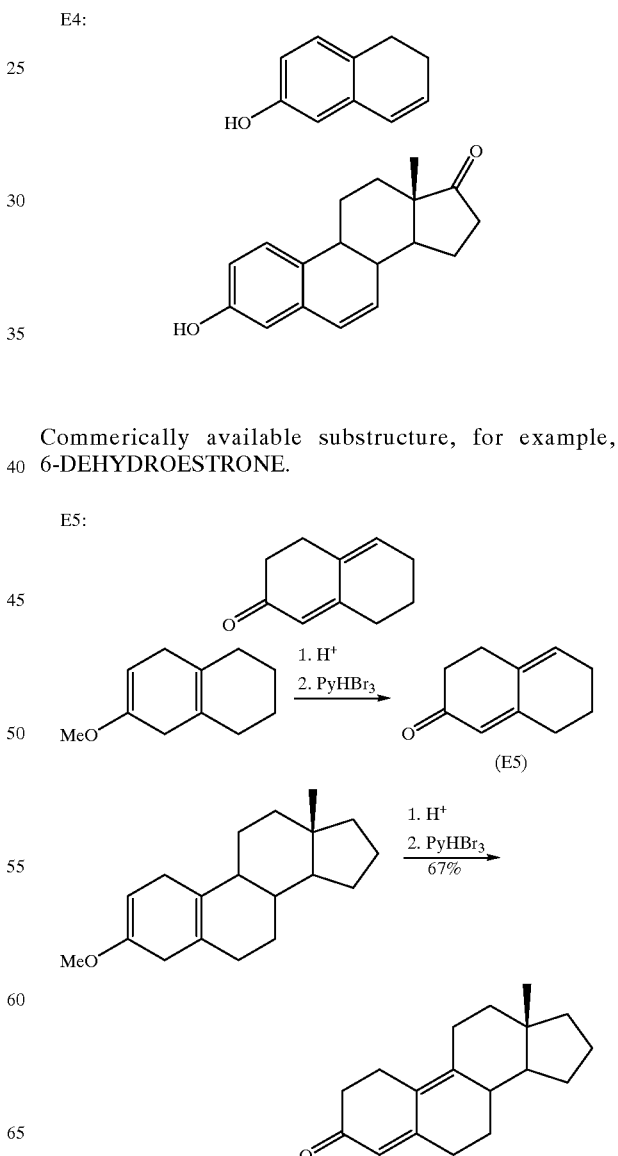

-continued
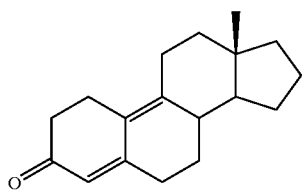
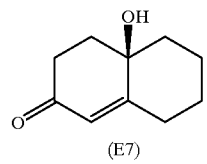
(E7)
V. I. Mel'nikova and K. K. Pivnitskii, Zhurnal Organickm-skoi Khisnii, 1974, Vol. 10, No. 5, pp. 1014–1019).
E6:
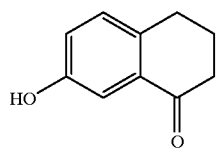
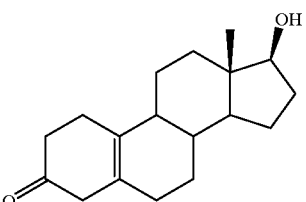
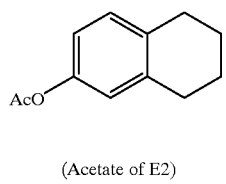 →CrO₃→ 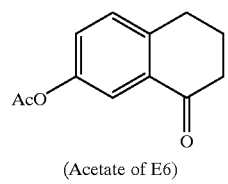
(Acetate of E2)      (Acetate of E6)
Michel Mauney and Jean Rigaudy, Bull. Soc. Chien, 1976, No. 11–12, 2021.
E8:
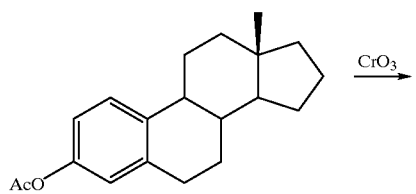
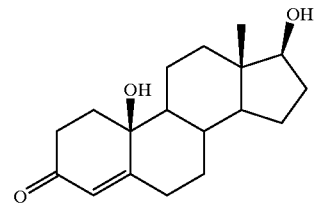
(Methyl ether of E2)      (E8)
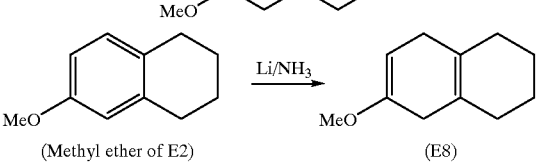
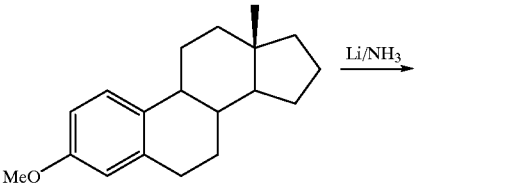
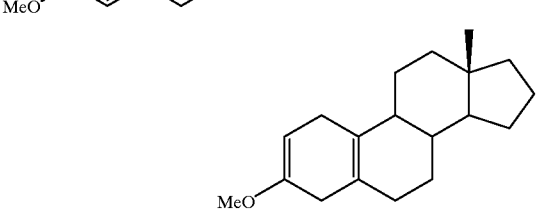
Hidetoshi Takagi, Ken-ichi Komatsu, and Itsuo Yoshisawa, Steroids, 1991, Vol. 56, p. 173.
E7:
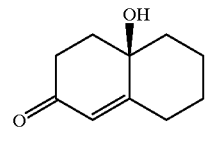
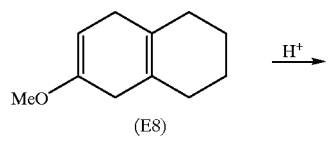
K. J. San, R. H. Blank, R. H. Evans, Jr., L. I. Feldman, and C. E. Holmbund, J. Org. Chem., 1964, 29, 2351.
E9:
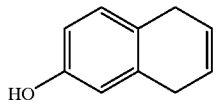

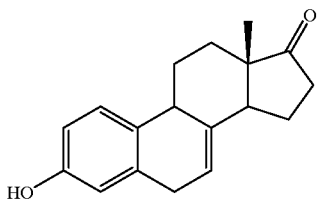
Commercially available substructure, as in EQUILIN.
E10:
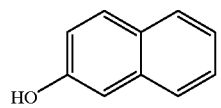
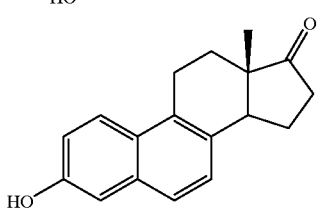
Commercially available substructure, as in EQUILENIN.
E11:
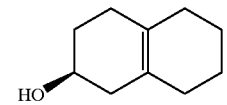
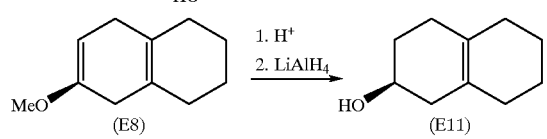
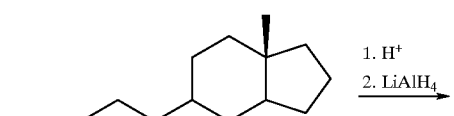
A. N. Cherkasov, A. M. Ponomarev, and X. K. Pivnitskii, Zhurnal Organiskeskoi Khimii, 1971, Vol. 7, No. 5, pp. 940–947.
E12:
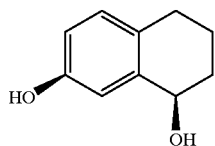
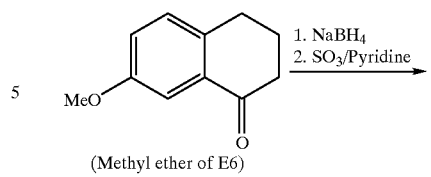
(Methyl ether of E6)
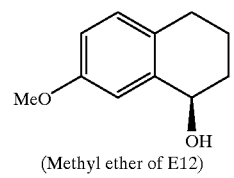
(Methyl ether of E12)
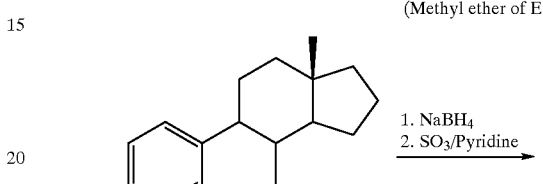
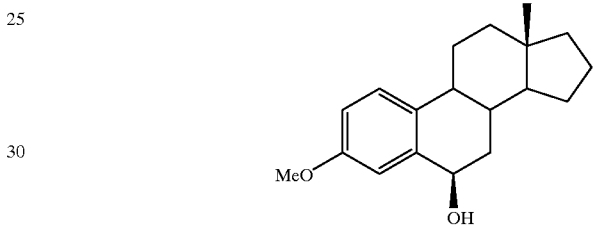
Hidetoshi Takagi, Ken-ichi Komatsu, and Itsuo Yoshisawa, Steroids, 1991, Vol. 56, p. 173.
Type N
N1:
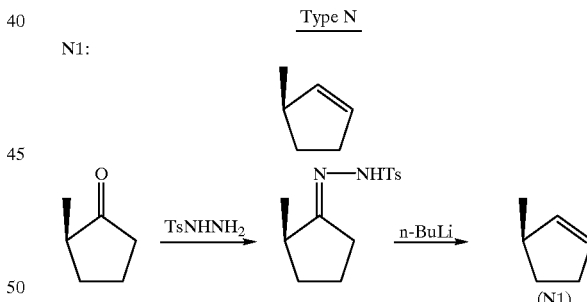
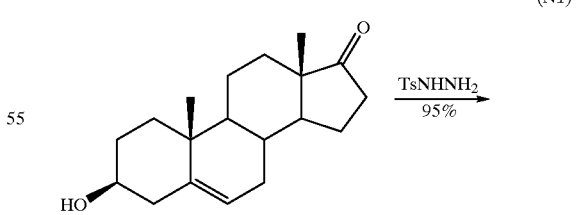
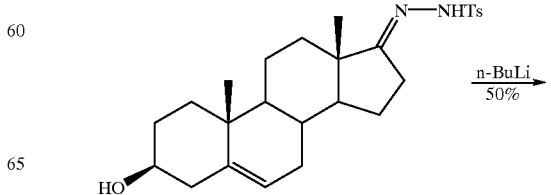

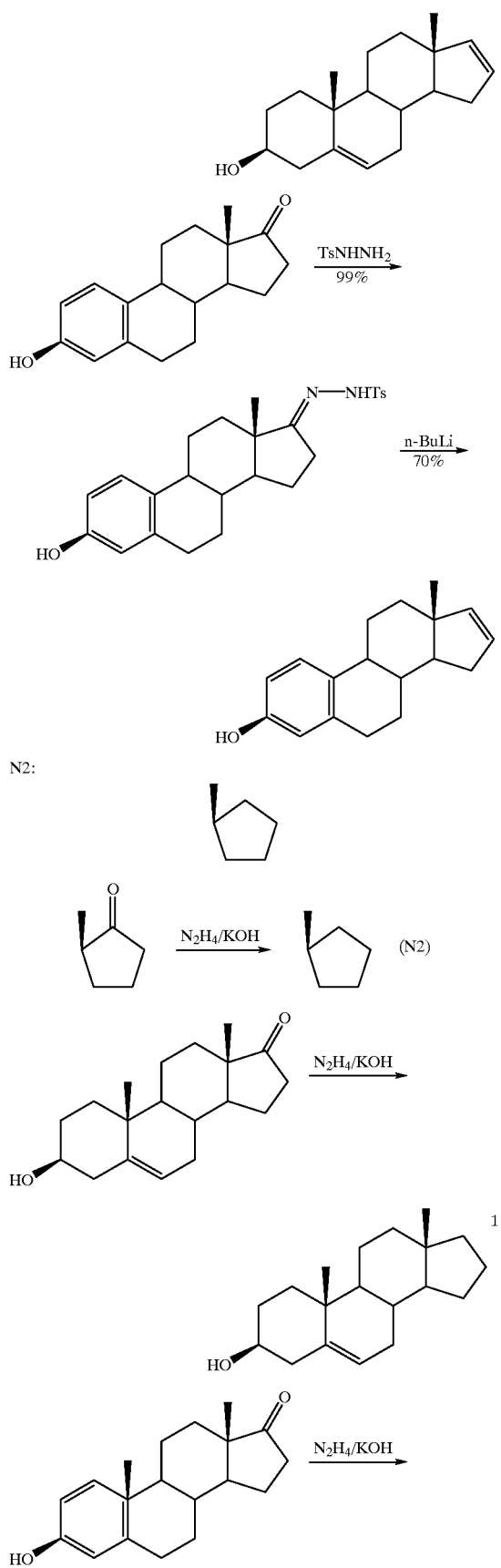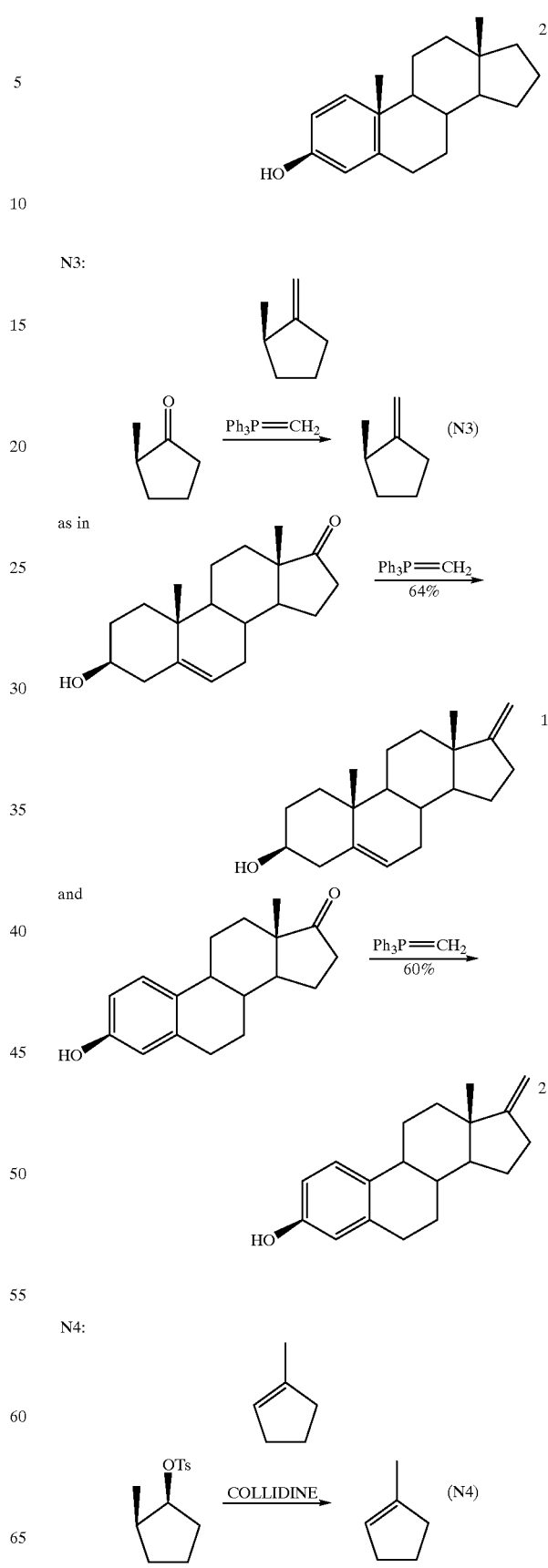

-continued as in 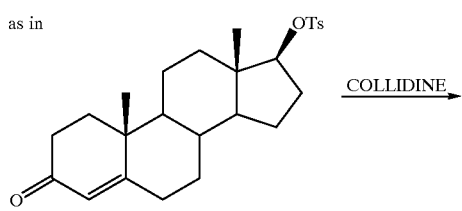

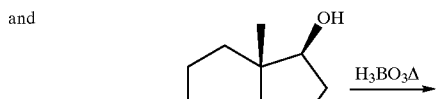 1 and 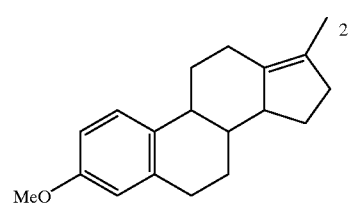

Methylestrenes

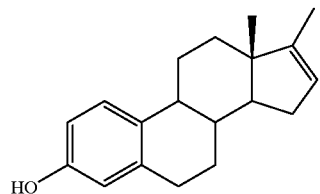

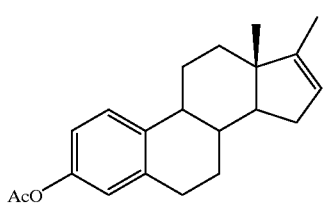

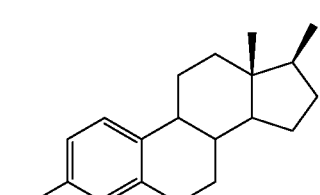

-continued

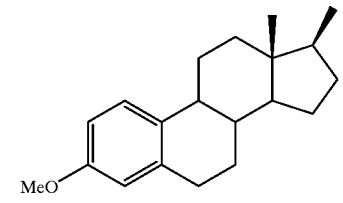

Harold J. Nicholas, J. Org. Chem., 1958, 23, 1747.

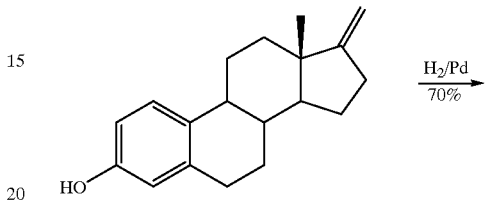

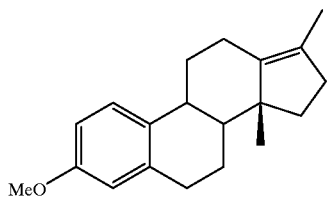
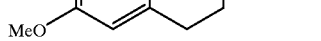

Richard H. Peters, David F. Crows, Mitchell A. Avery, Wesley K. M. Chong, and Masako Tanabe, J. Med. Chem., 1989, 32, 1642.

(RACEMIC)

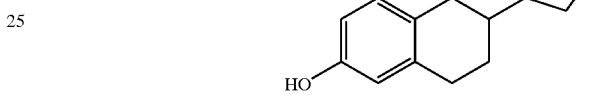

M. B. Green and F. J. Zeelen, Tetrahedron Letters, 1982, Vol. 23, No. 35, pp. 3611–3614.

Synthesisable compounds therefore include these, together with those derived from them; i.e., 17-Methyl-N1, 17β-Methyl-N2, or 14α-Methyl-N4, incombination with E1, E2, E3, E5, E6, E7, E8, E11 or E12.

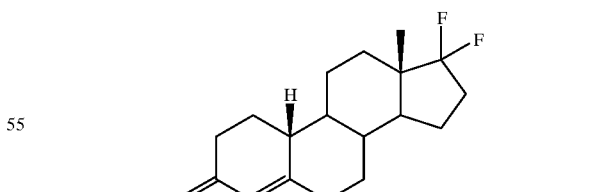

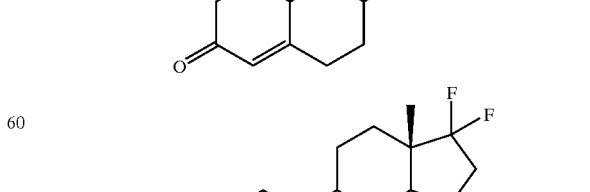

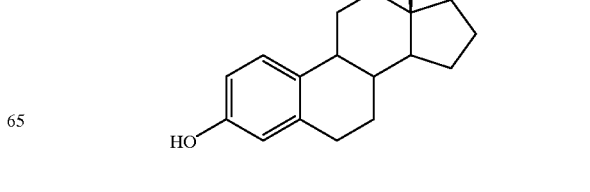

-continued

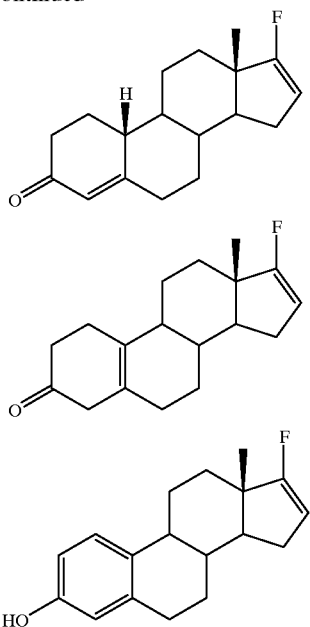

George A. Boswell in patent C.A. 70:58140g, following.

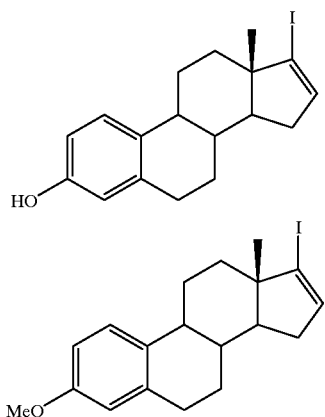

G. Michael Blackburn, Brian F. Taylor, and Andrew F. Worrall, Journal of Labelled Compounds and Radiopharmaceuticals, 1986, Vol. XXIII, No. 2, p. 197.

Synthesisable compounds therefore include these, together with those derived from them; i.e., 17-Fluoro-N1 in combination with E1, E2, E3, E5, E6, E7, E11 or E12. In addition, 17-Iodo-N1 in combination with E2, E6 or E12.

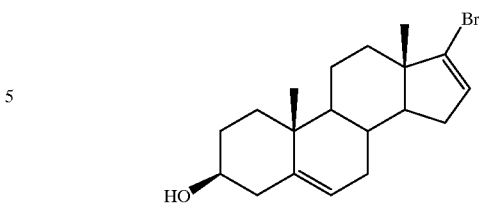

European Patent Application EP 208,497.

Synthesizable compounds therefore include these, together with those derived from them; i.e., (4-Chloro, 4-Bromo, 6α-Chloro, 6α-Bromo, 6β-Chloro, 6β-Bromo, or 6β-Iodo)-A1 in combination with N1, N2, N3, or N4. In addition, (17-Fluoro, 17-Chloro, 17-Bromo, or 17-Iodo)-N1 in combination with A1, A2, A3, A4, A5, A6, A8, A9, A10 or A11.

1. Preparation of 3-, 5-, 6-, 18- and 19-position derivatives.

The compounds used in the methods of this are Androstane steroids substituted at the 3-, 5-, 6-, 18- and 19-positions. Many of the 3- and 5-substituted steroids are known compounds which may be derived from 17-hydroxy- and 17-oxo-steroids (commercially available e.g. from Aldrich Chemical Co.) by elimination or reduction to the Δ16 homologue. The syntheses of most of these compounds are described by Ohloff (supra). As shown in FIG. 1, 17β-hydroxy-5α-Androstan-3-one (I) and methyl chloroformate (a) in pyridine gives the methyl carbonate, 17β-methoxycarbonyloxy-5α-Androstan-3-one (II) which provides a starting material for the 5α-Androst-16-en-(3-one and 3-ol) (Ohloff, supra at pg. 200).

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aphotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the workup procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

2. Preparation of 19-OH derivatives. Synthesis of 19-OH-Androsta-4,16-diene-3-one.

This compound has been disclosed as an intermediate in the synthesis of 19-oxo-3-aza-A-homo-5B-androstane (Habermehl, et al., Z. Naturforsch. (1970) 25b:191–195). A method of synthesizing this compound is provided.

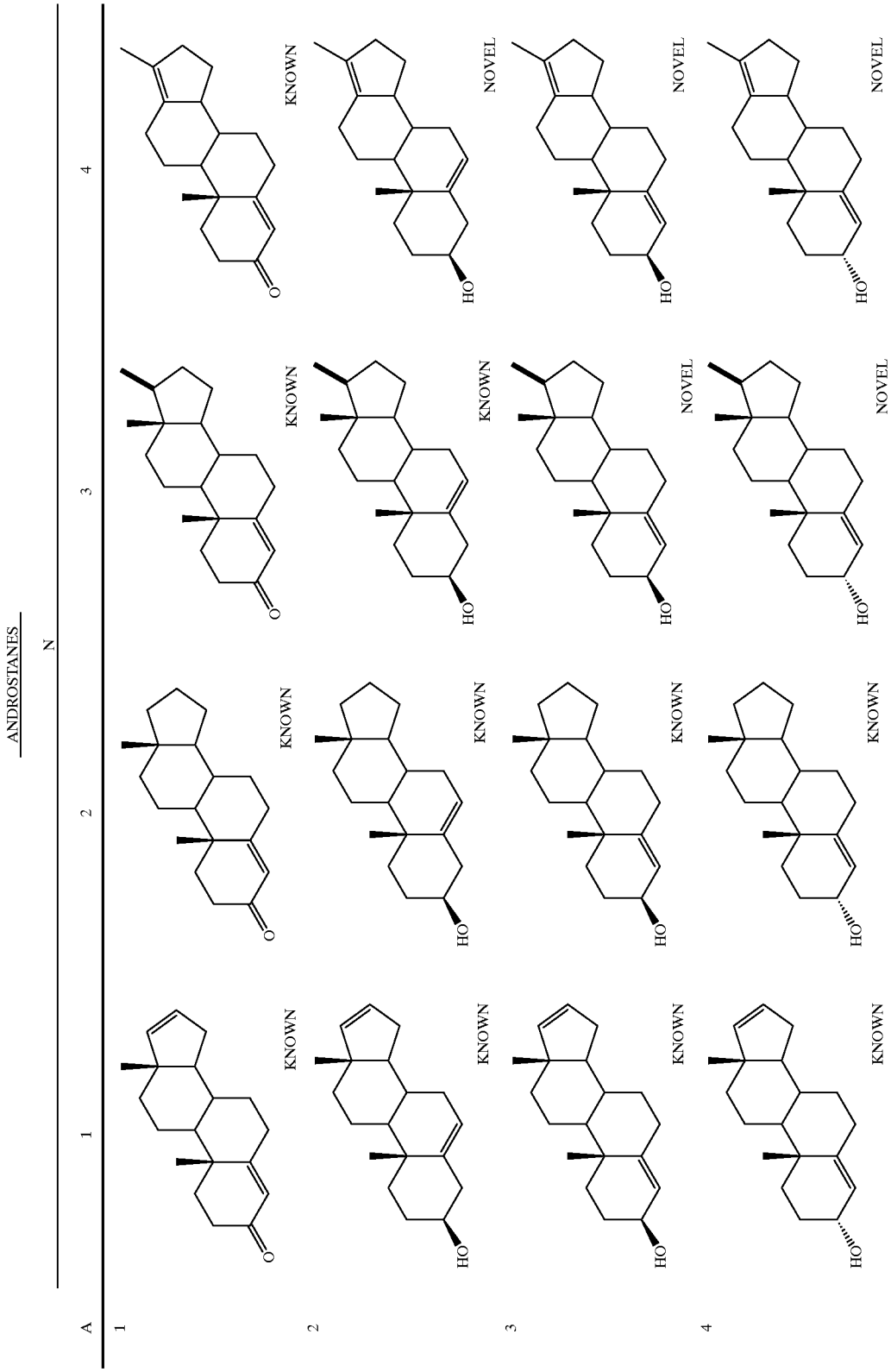

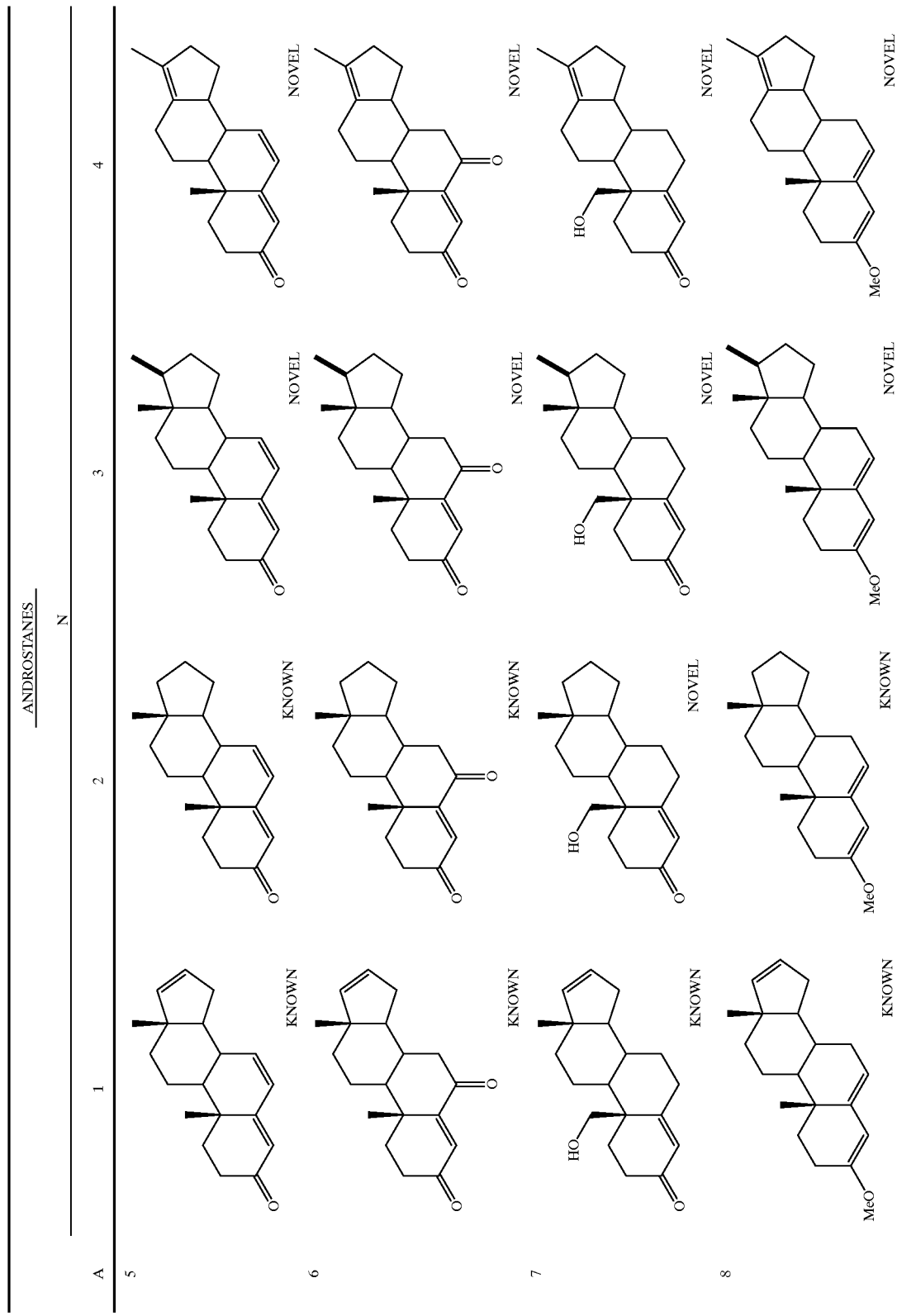

CHART V-continued
ANDROSTANES
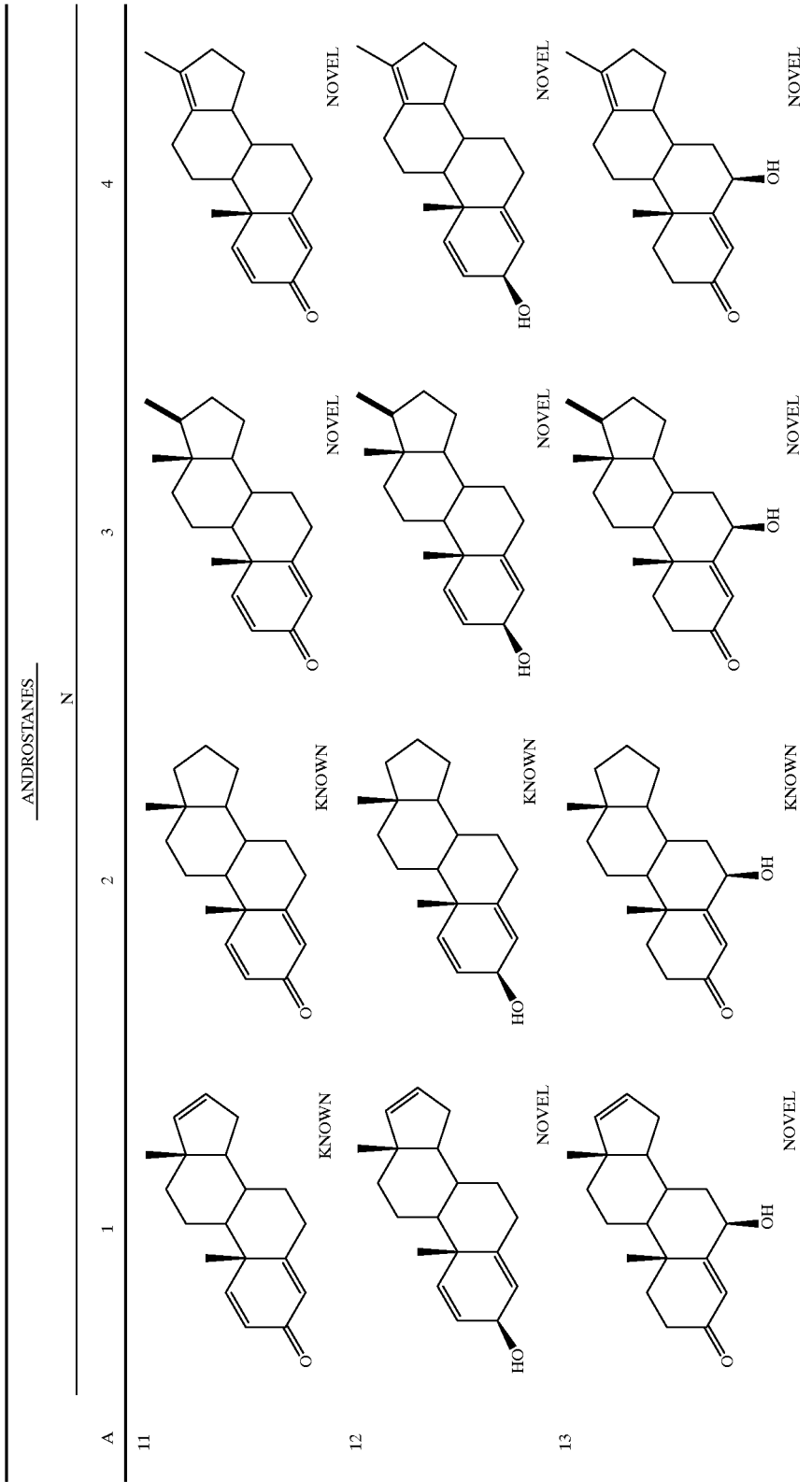

Novel Androstanes

17-METHYLENEANDROST-4-EN-3α-OL (A4/N3)
17-METHYLENEANDROST-4-EN-3β-OL (A3/N3)
6β-HYDROXYANDROSTA-4,16-DIEN-3-ONE (A13/N1)
6β-HYDROXY-17-METHYL-18-NORANDROSTA-4,13(17)-DIEN-3-ONE (A13/N4)
ANDROSTA-5,16-DIEN-3β,19-DIOL (19-HYDROXY DERIVATIVE OF A2/N1)
17-METHYLENEANDROST-4-ENE-3,6-DIONE (A6/N3)
17-METHYL-18-NORANDROSTA-4,13(17)-DIEN-3α-OL (A4/N4)
17-METHYL-18-NORANDROSTA-4,13 (17)-DIEN-3β-OL (A3/N4)
17β-METHYLANDROST-4-ENE-3,6-DIONE(17β METHYL derivative of A6/N2)
3-METHOXY-17-METHYLENEANDROSTA-3,5-DIENE (A8/N3)
6β-HYDROXY-17-METHYLENEANDROST-4-EN-3-ONE (A13/N3)
17-METHYLENEANDROSTA-1,4-DIEN-3-ONE (A11/N3)
6β-HYDROXYANDROSTA-1,4,16-TRIEN-3-ONE (6β-HYDROXY derivative of A11/N1)
6β-HYDROXY-17-METHYLENEANDROSTA-1,4-DIEN-3-ONE (6β-HYDROXY derivative of A11/N3)
17β-METHYLANDROST-4-EN-3α-OL (17β-METHYL derivative of A4/N2)
17β-METHYLANDROST-4-EN-3β-OL (17β-METHYL derivative of A3/N2)
3-METHOXY-17-METHYL-18-NORANDROSTA-3,5,13(17)-TRIENE (A8/N4)

Substructure Synthesis

Referring to the preceding CHART V, the following are exemplary syntheses for intermediates in a given row (A1 through A11) or column (N1 through N4).

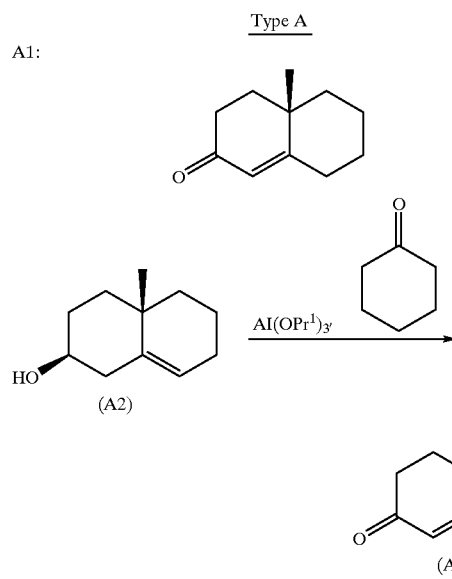

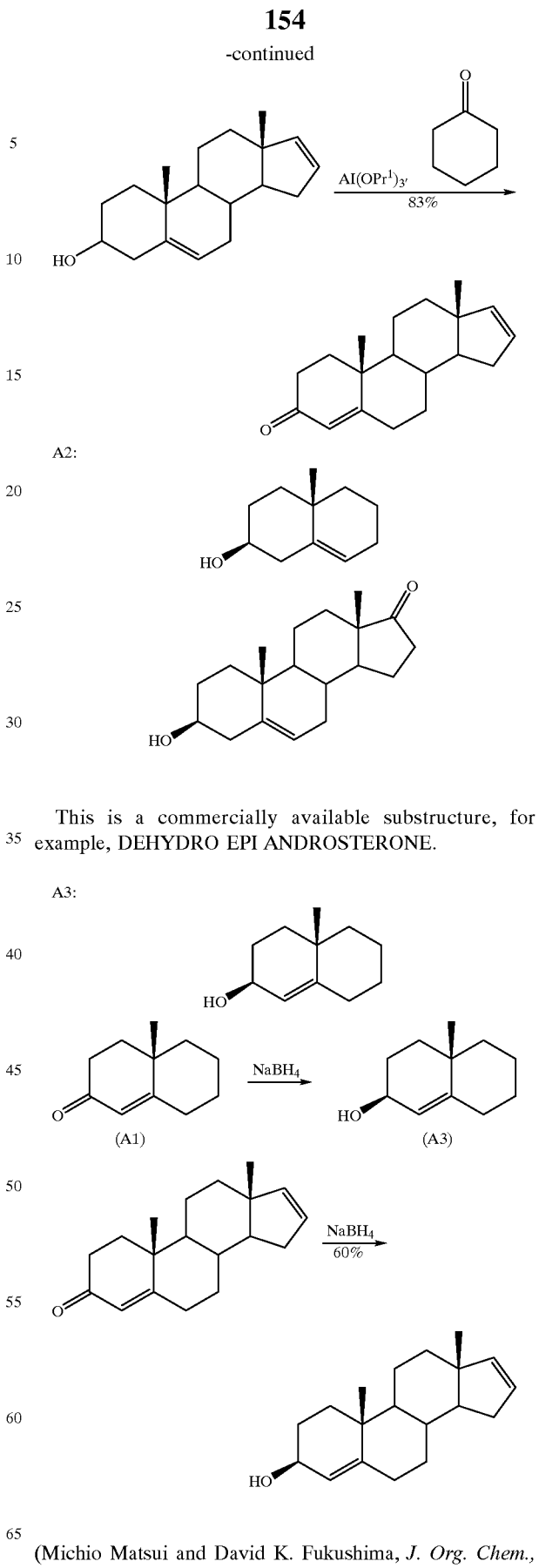

This is a commercially available substructure, for example, DEHYDRO EPI ANDROSTERONE.

(Michio Matsui and David K. Fukushima, *J. Org. Chem.*, 1970, Vol. 35, No. 3, p. 561–564).

A4:
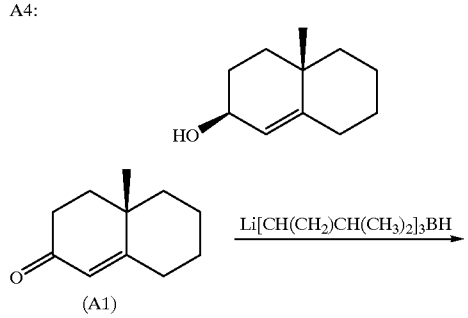
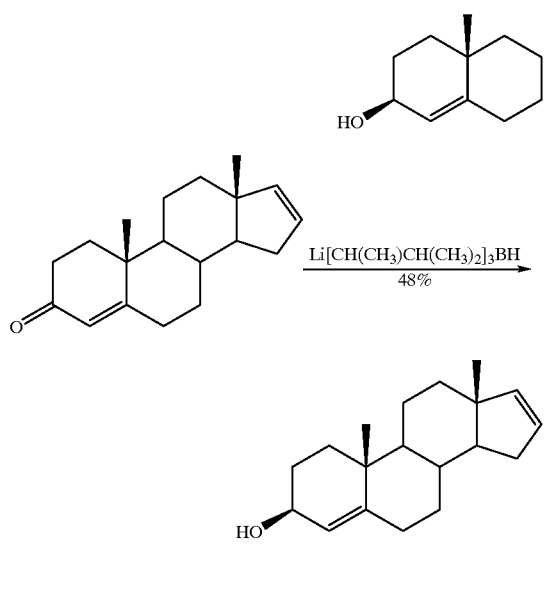
Ohloff, G. et al. (*Hevl. Chim. Acta* (1983) 66:192–217).
A5:
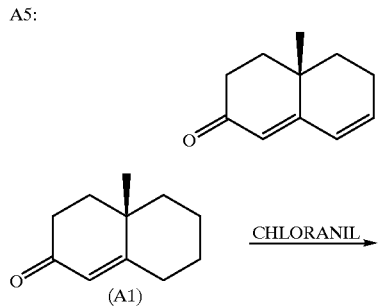
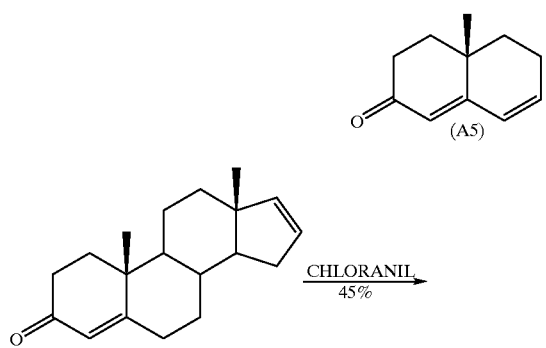
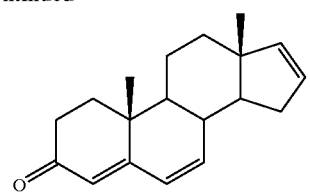
German Off. 2,631,915.
A6:
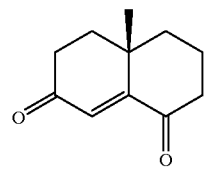
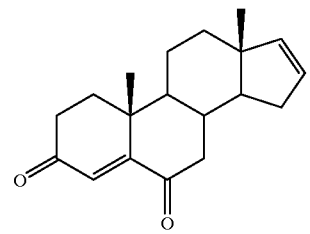
J. Romer, H. Wagner, and W. Sihade, Steroids, 1988, 51/5–6, p. 577–581.
A7:
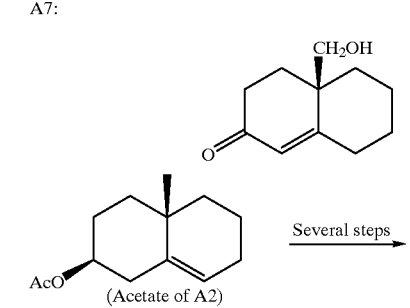

-continued
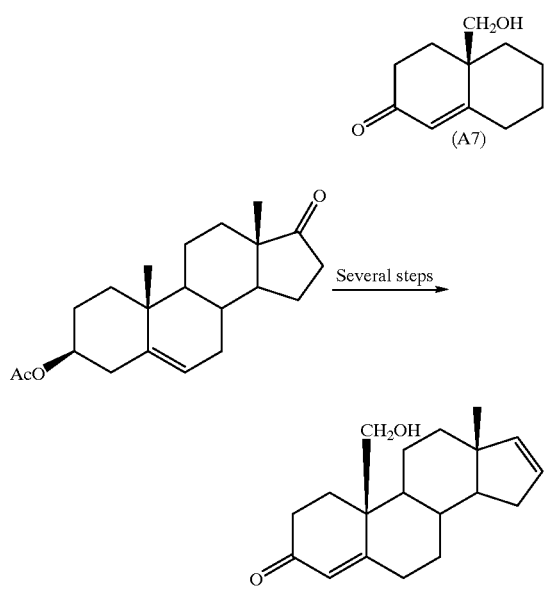
(Habermehl, et al., *Z. Naturforsch.* (1980) 256:191–195).
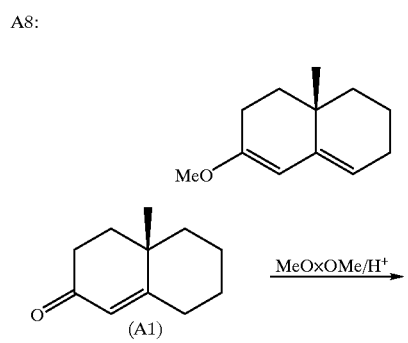
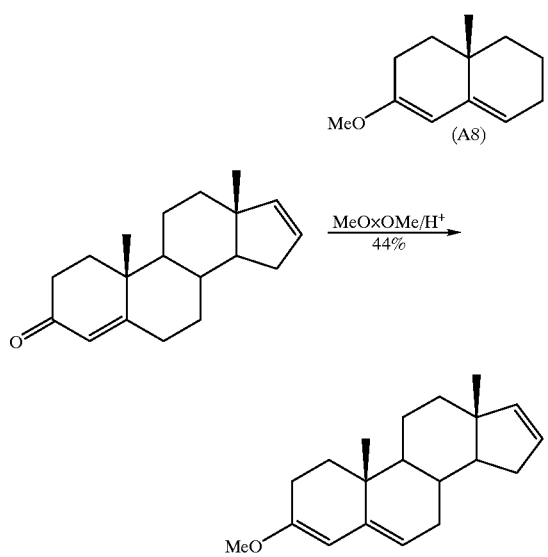
See Example 15.
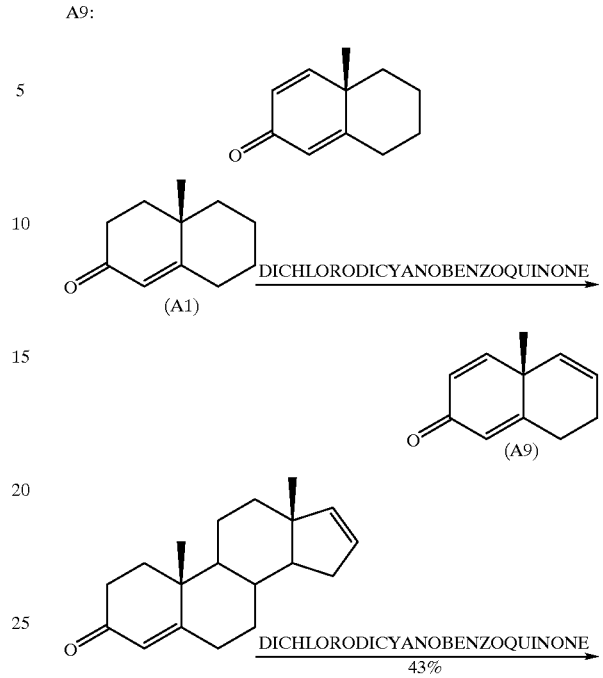
Ohloff, Gs et al. (*Helv. Chim. Acta* (1983) 66:192–217).
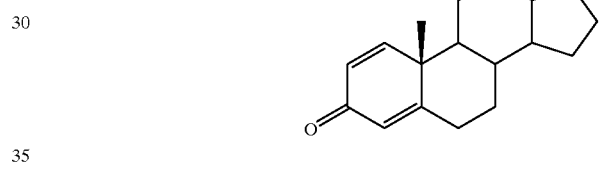

V. I. Mel'nikova and K. K. Pivnitskii, Zhurnal Organickeskoi Khisnii, 1972, Vol. 8, No. 1, pp. 68–74).
A11:
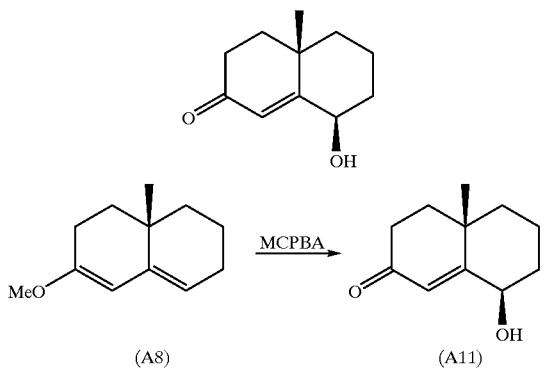
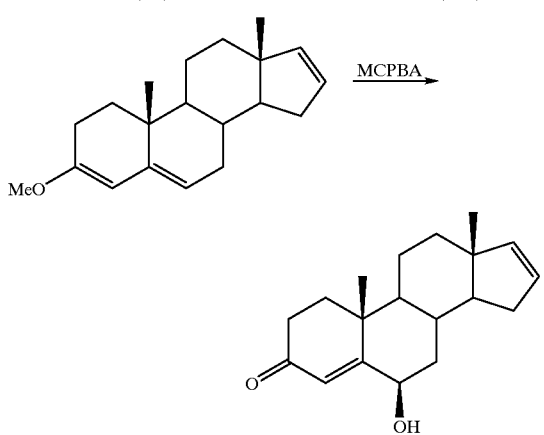
See Example 19.
Type N
N1:
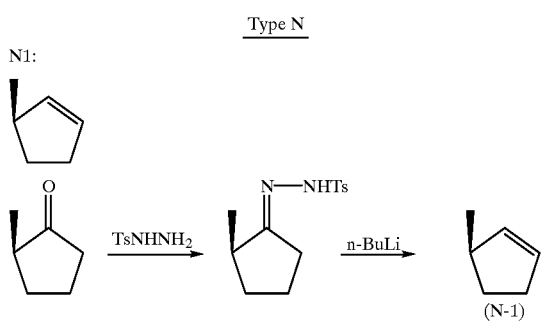
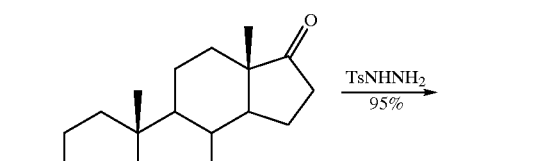
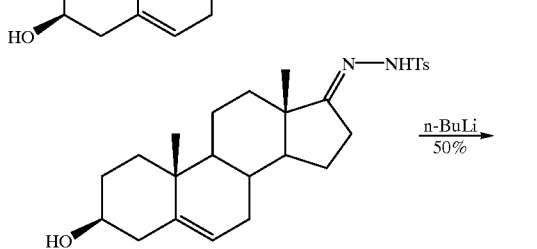
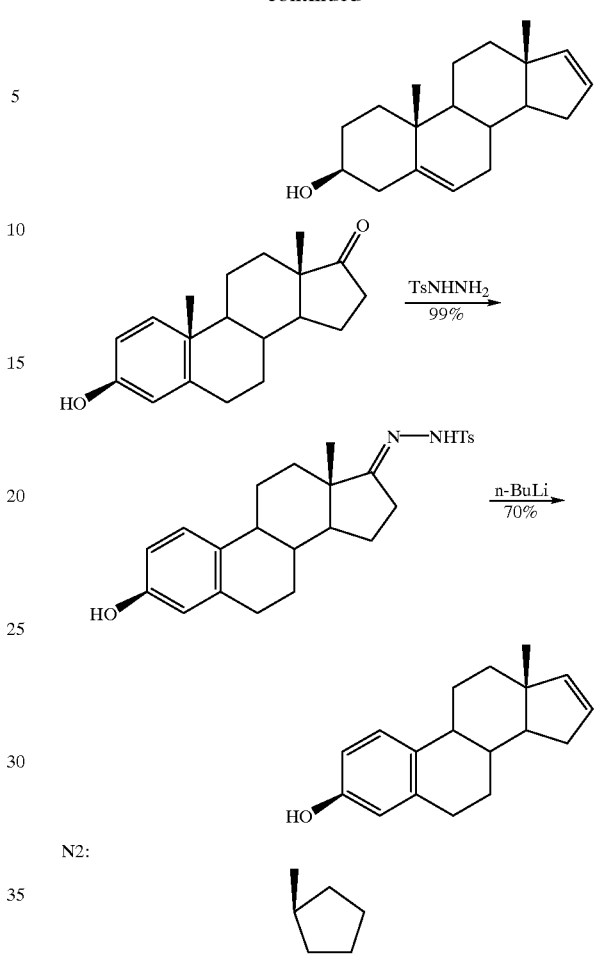
N2:
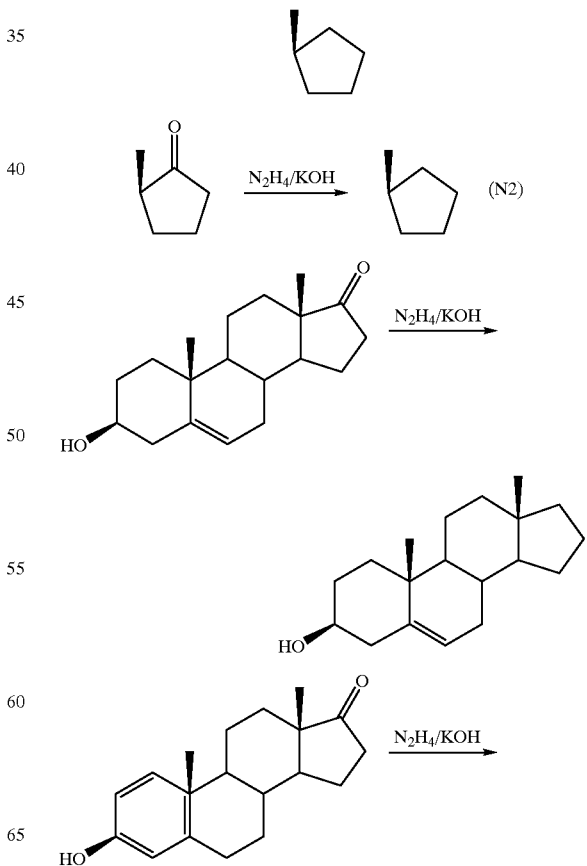

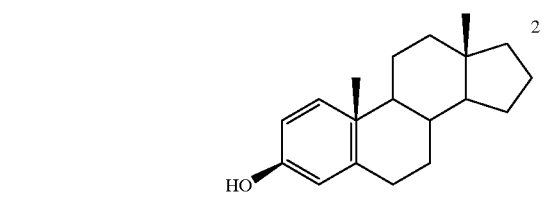
N3:
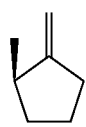
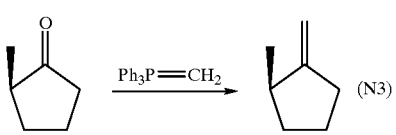
as in
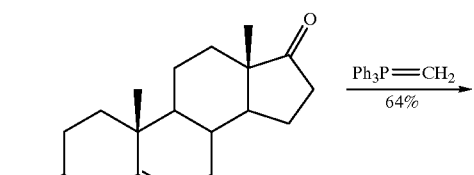
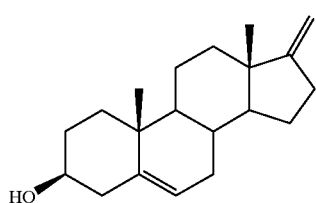
and
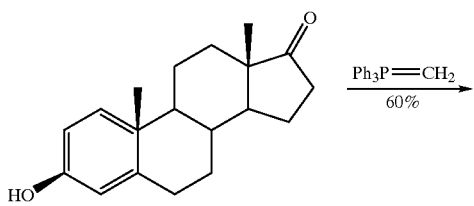
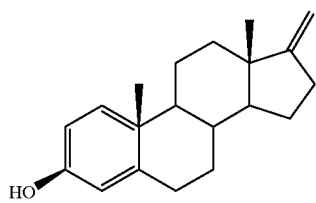
N4:
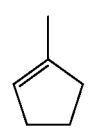
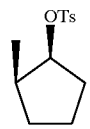
as in
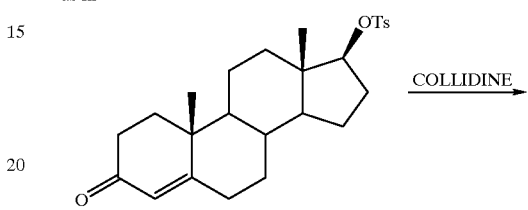
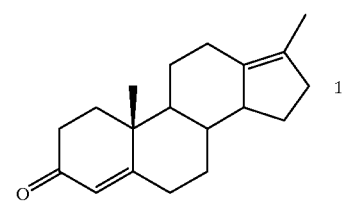
and
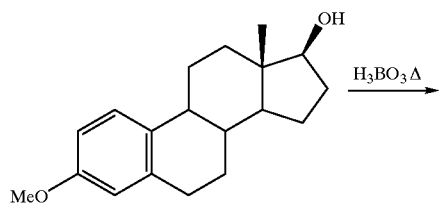
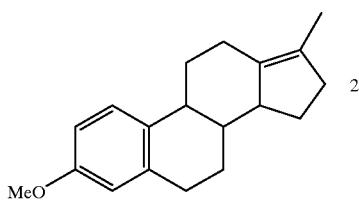
Methylandrostenes
German Off. 2,631,915 teaches preparation of
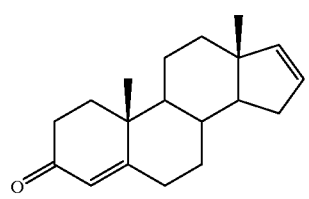

with a methyl group at any one of the following positions: 1α, 2α, 4, 6α, 6β, 7α, and 16.

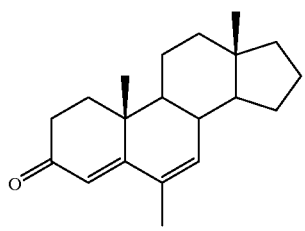

6-METHYLANDROSTA-4,6-DIEN-3-ONE

German Off. 2,428,679.

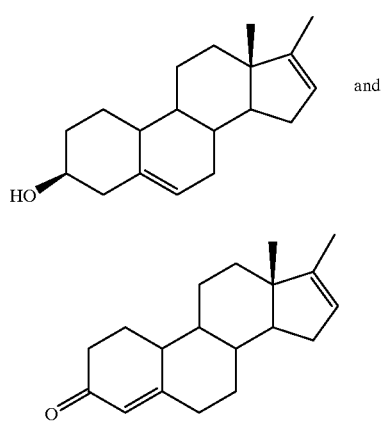
and

Daniel Bertin and Lucien Nedelac, Memoires Presentes a la Societe Chimique, 1964, No. 345, p. 2140. Synthesizable compounds therefore include these, together with those derived from them; i.e., N1 with methyl at 1α, 2α, 4, 6α, 6β, 7α, 16 or 17 combined with A1, A3, A4, A5, A8, A9, A10 or A11, as well as A2 or A6 with a 17-methyl.

Haloandrostenes

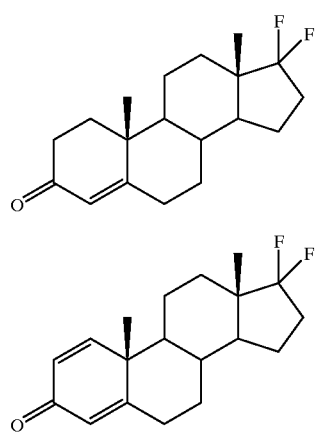

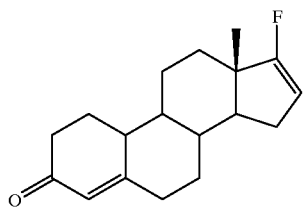

U.S. Pat. No. 3,413,321.

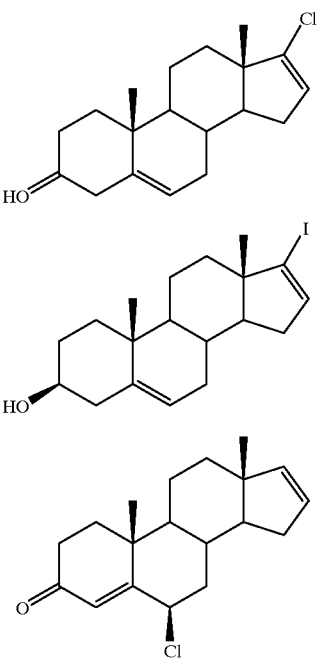

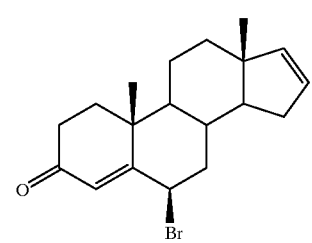

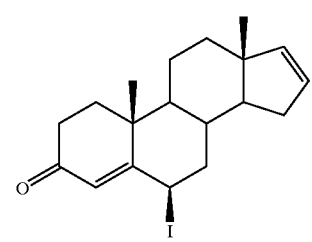

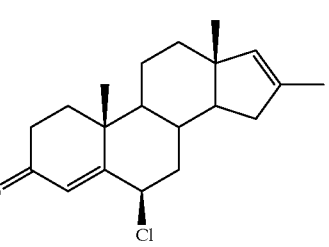

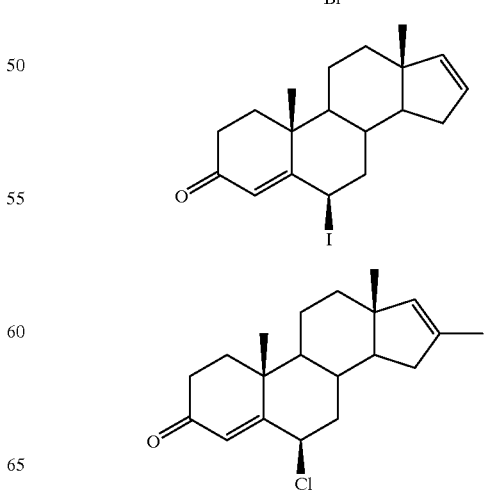

-continued
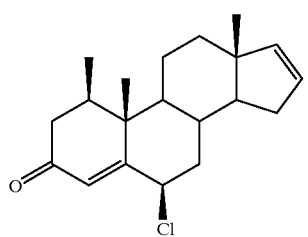
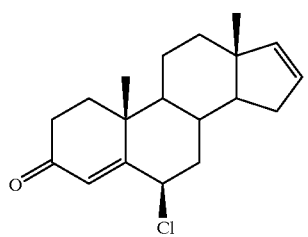
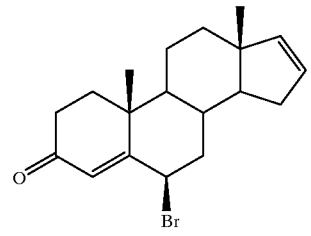
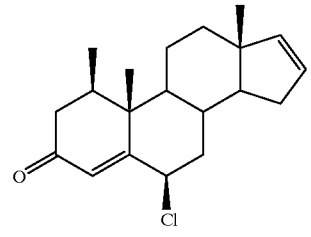
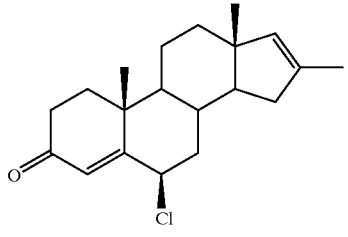
-continued
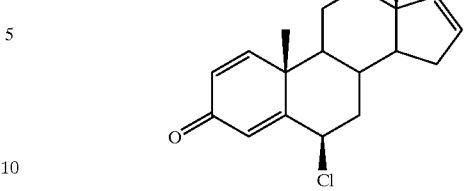
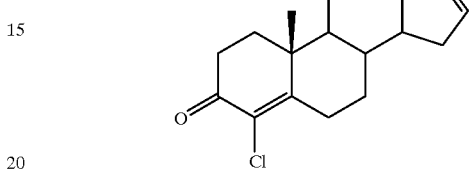
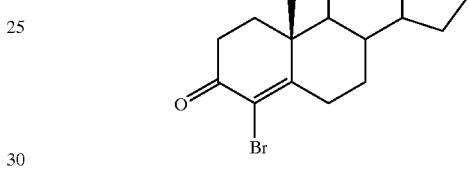
German Off. 2,631,915.

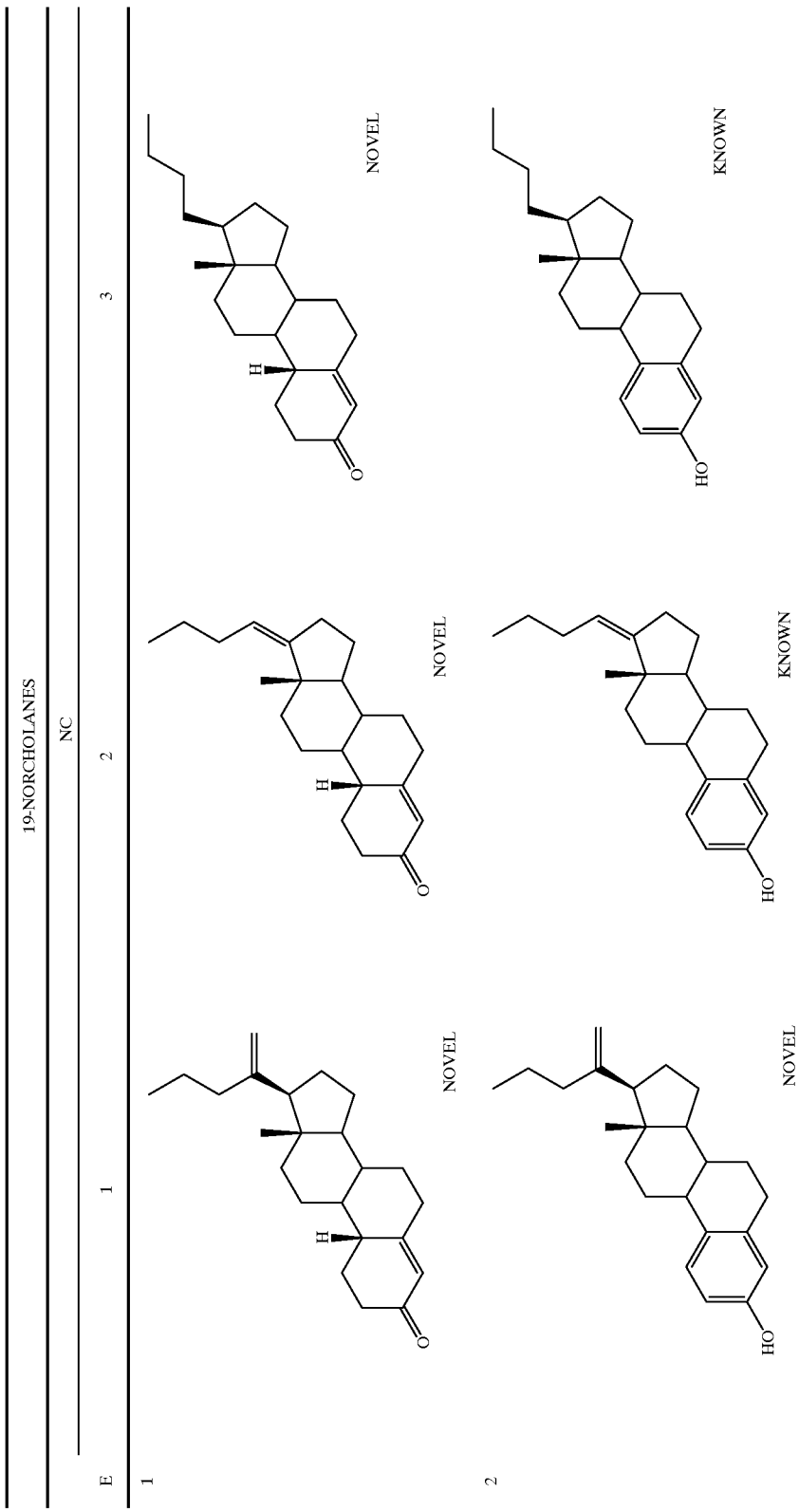

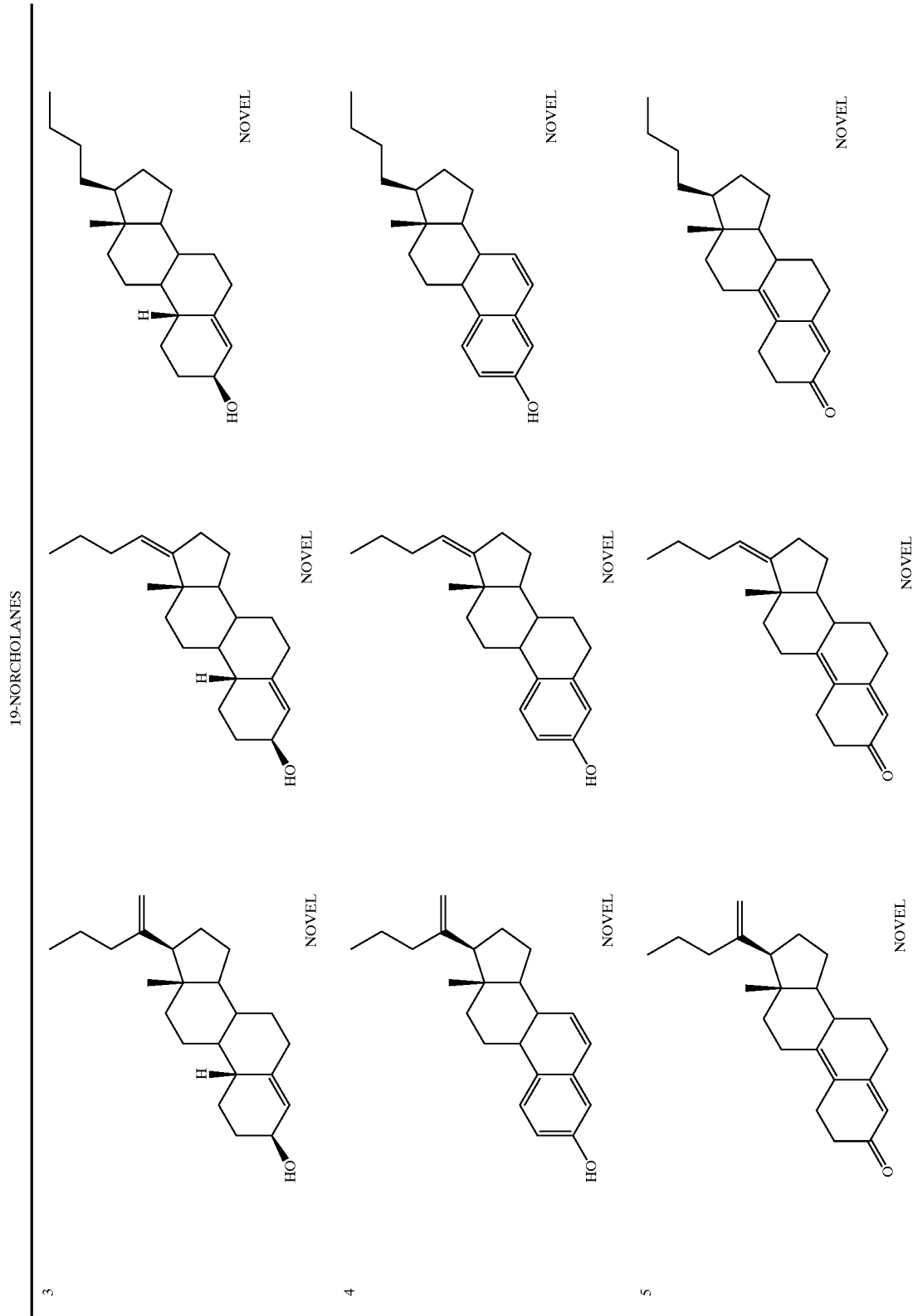

CHART VI-continued
19-NORCHOLANES
| | | |
|---|---|---|
| 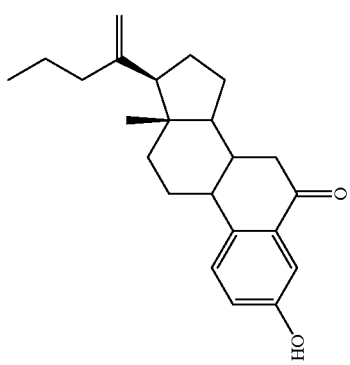 NOVEL | 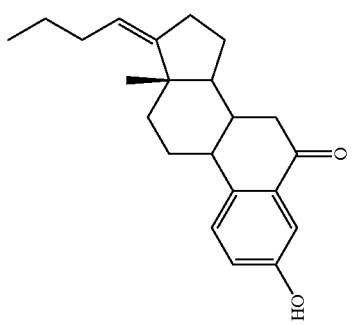 NOVEL | 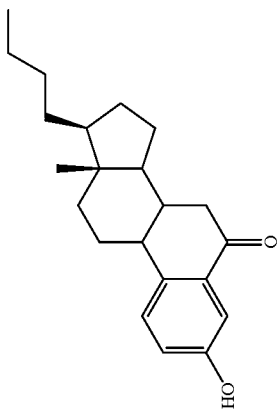 NOVEL |
| 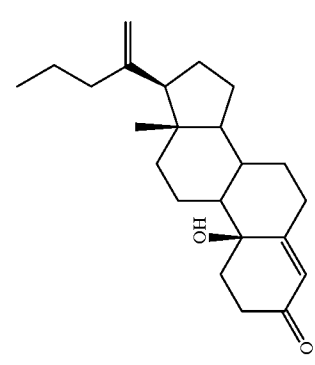 NOVEL | 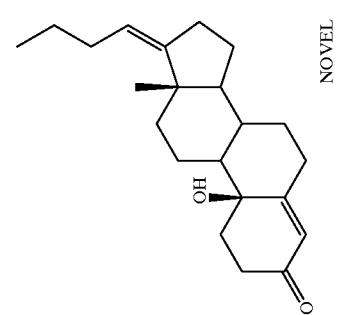 NOVEL | 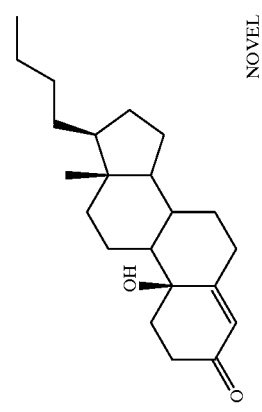 NOVEL |
6
7

CHART VI-continued
19-NORCHOLANES
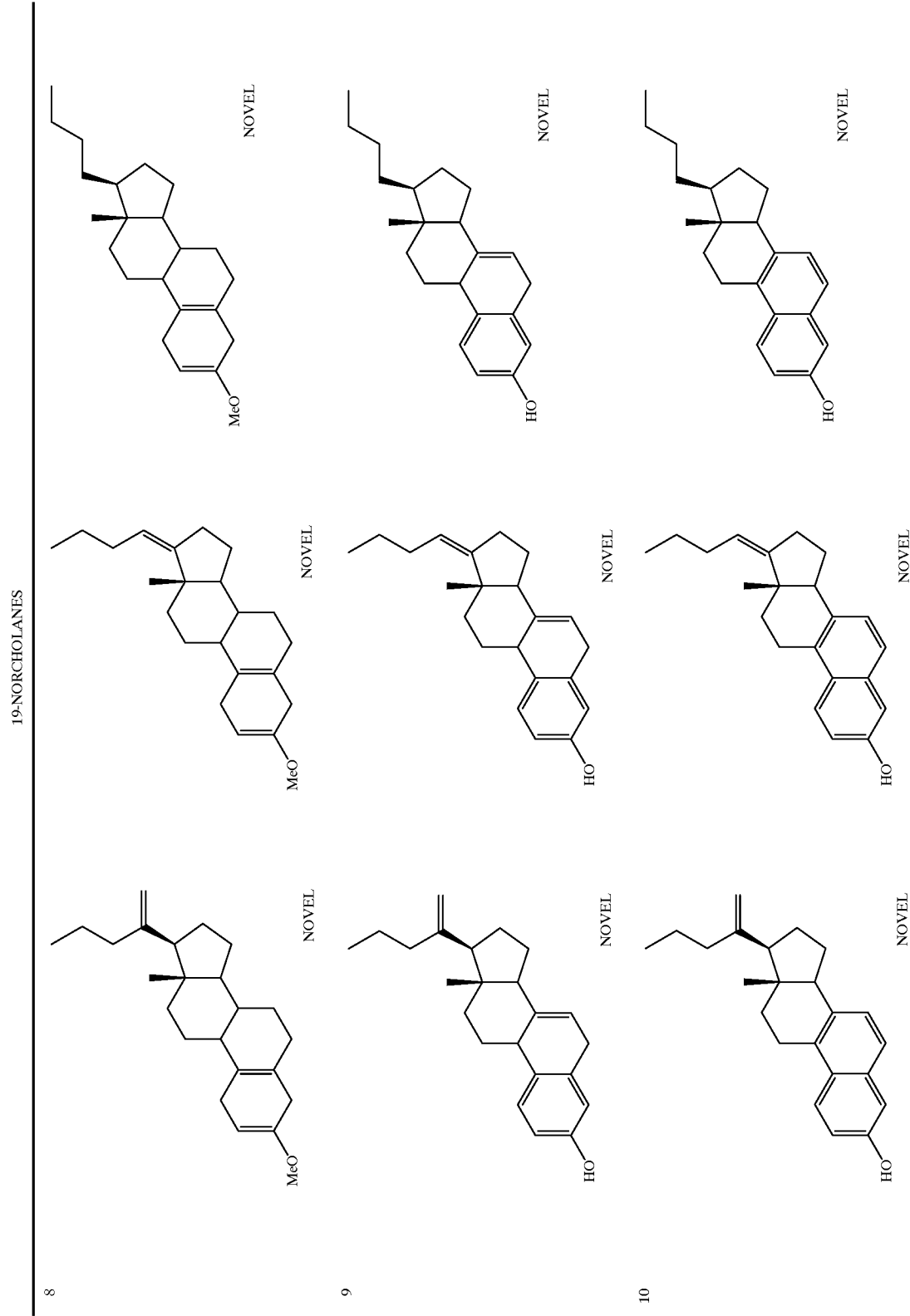
8
9
10

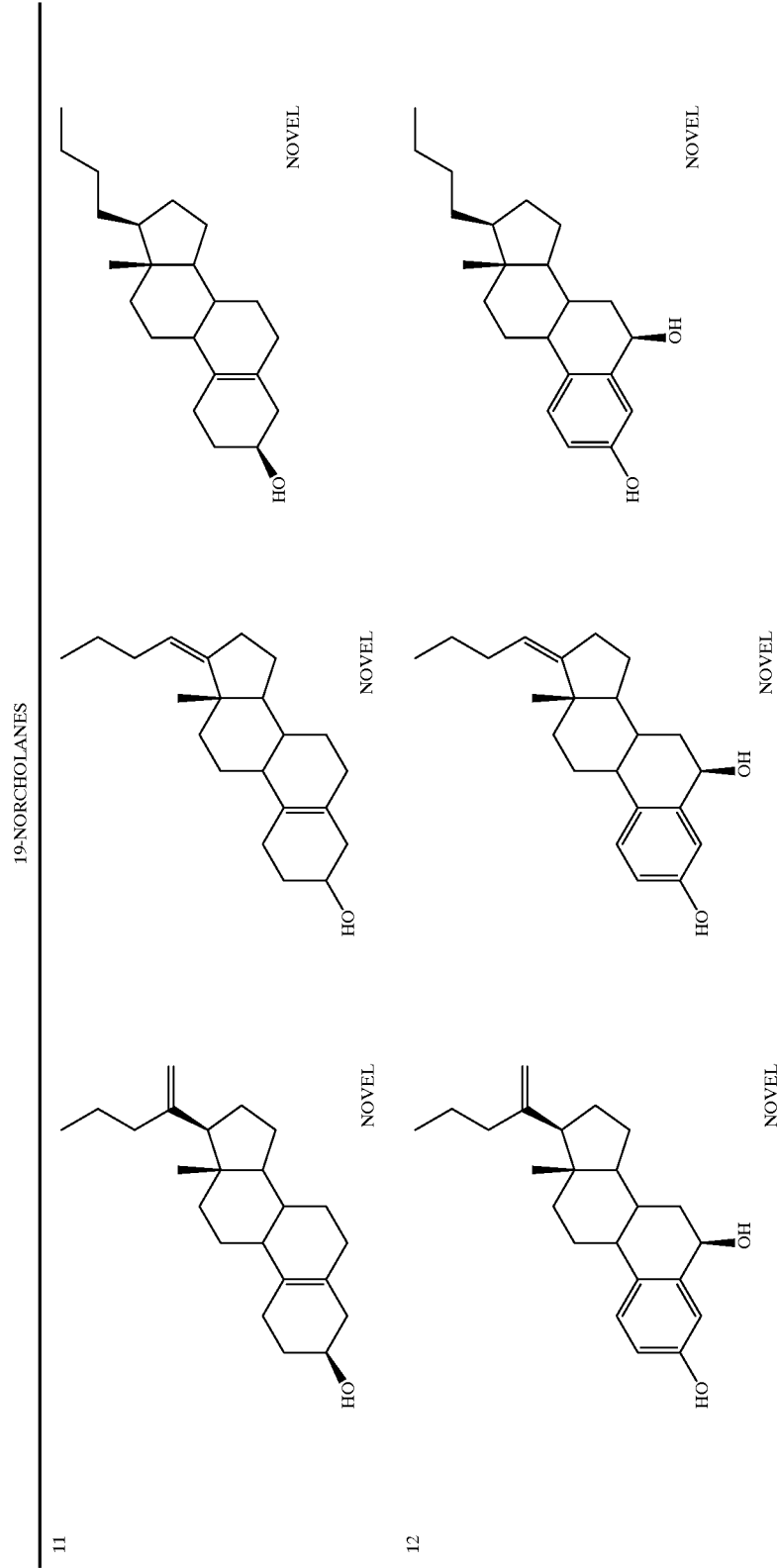
CHART VI-continued
19-NORCHOLANES

CHART VI-continued
19-NORCHOLANES
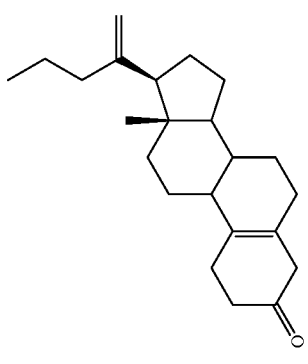
13 NOVEL
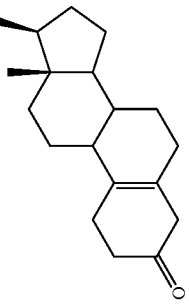
NOVEL
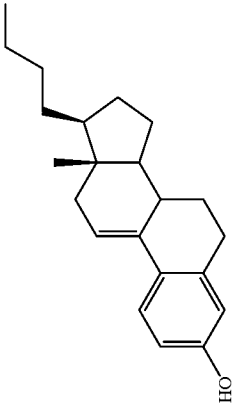
NOVEL
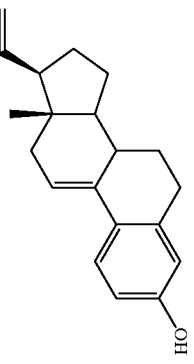
14 NOVEL
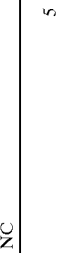
NOVEL
NOVEL
| E | 4 | NC | 5 |

CHART VI-continued
19-NORCHOLANES
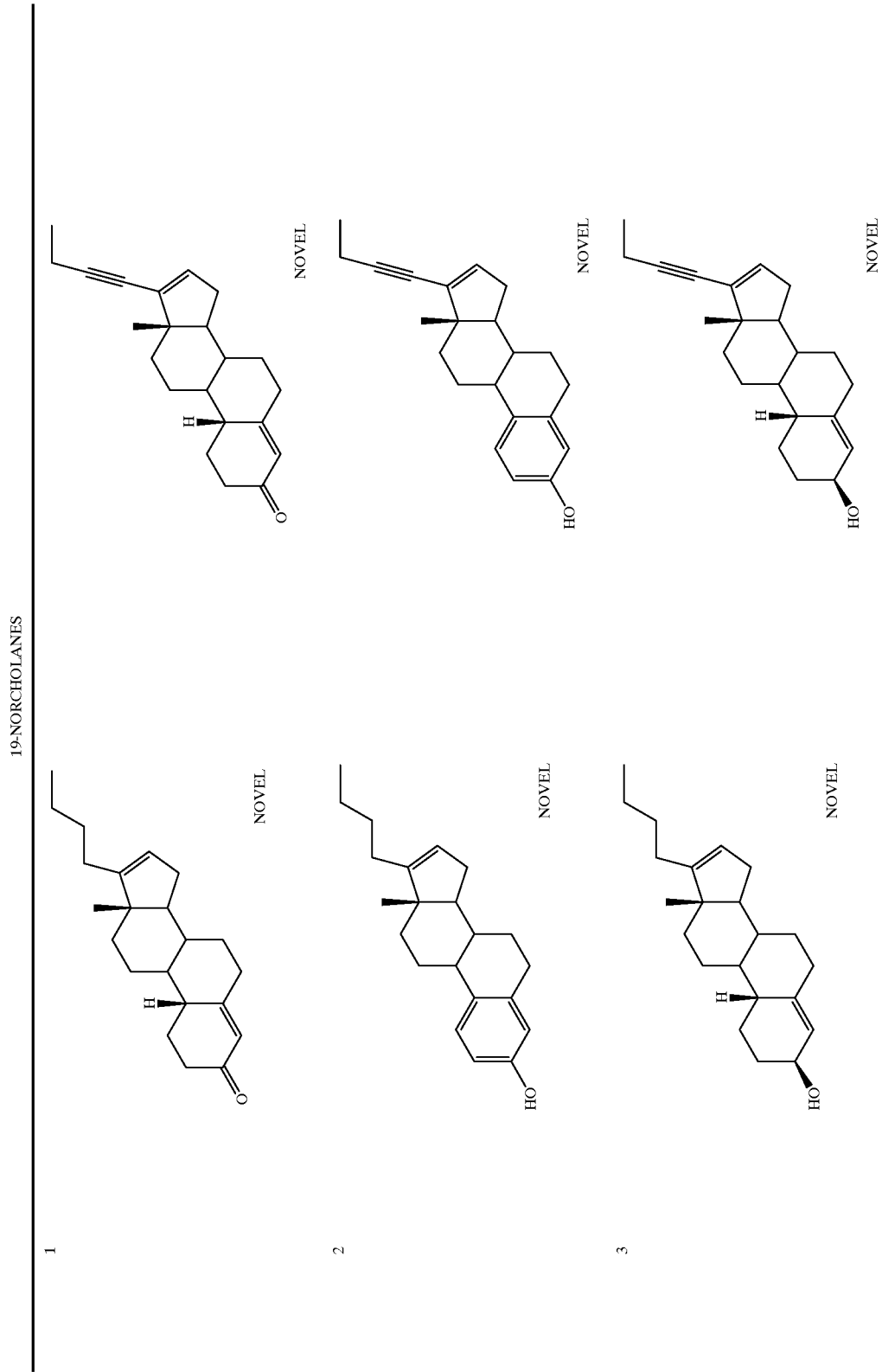

CHART VI-continued
19-NORCHOLANES
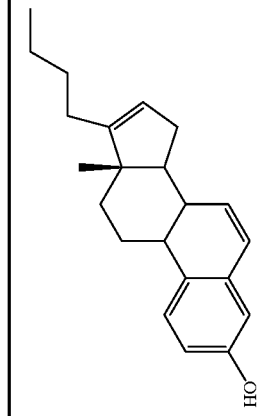
4
NOVEL
NOVEL
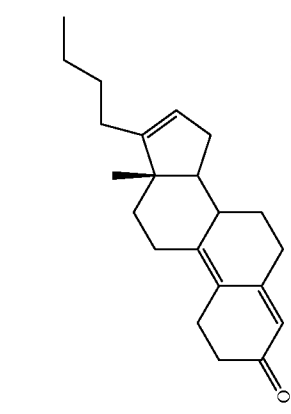
5
NOVEL
NOVEL
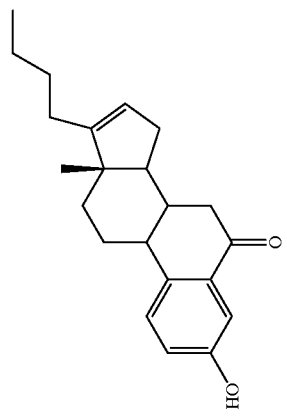
6
NOVEL
NOVEL

CHART VI-continued
19-NORCHOLANES
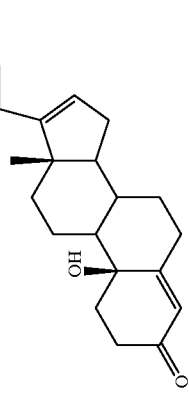
7
NOVEL
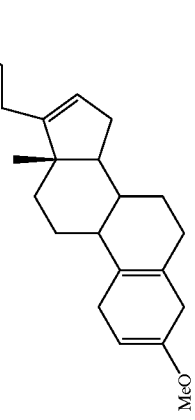
8
NOVEL
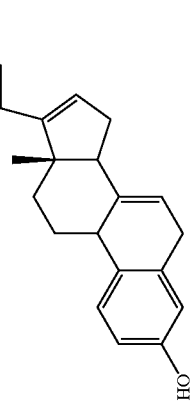
9
NOVEL CHART VI-continued
19-NORCHOLANES
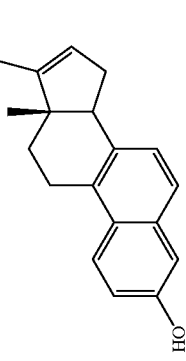
10 NOVEL
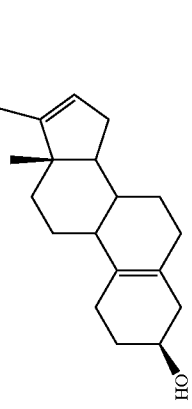
11 NOVEL
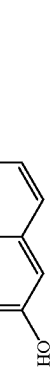
12 NOVEL
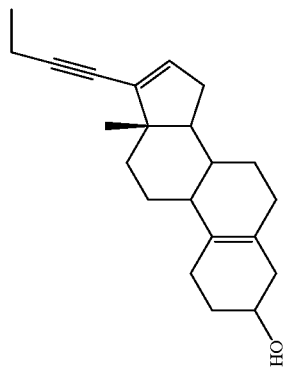
NOVEL
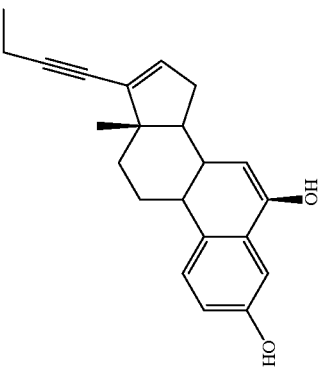
NOVEL
NOVEL CHART VI-continued
19-NORCHOLANES
13
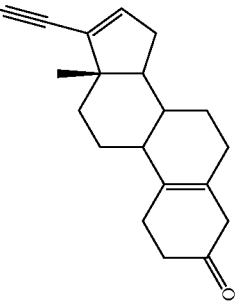
NOVEL
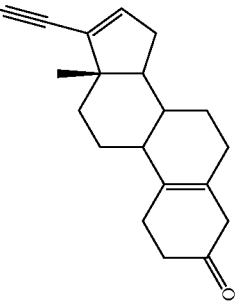
NOVEL
14
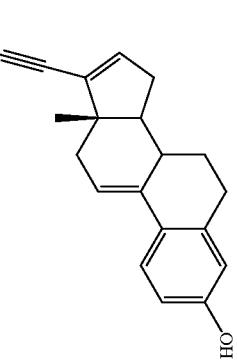
NOVEL
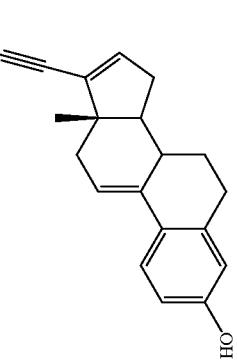
NOVEL
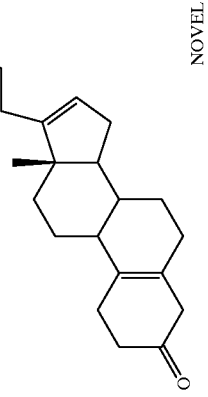
NOVEL
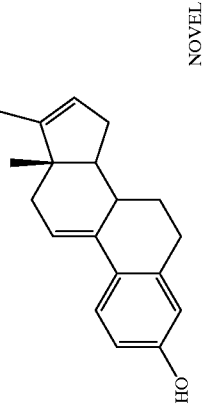
NOVEL

SUBSTRUCTURE SYNTHESES: TYPE E
E1:
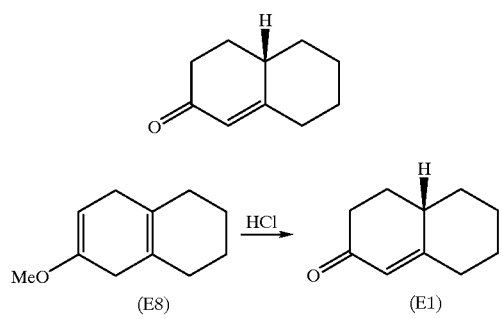
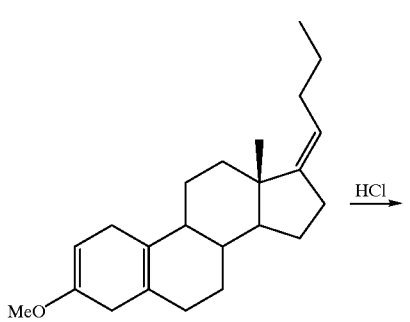
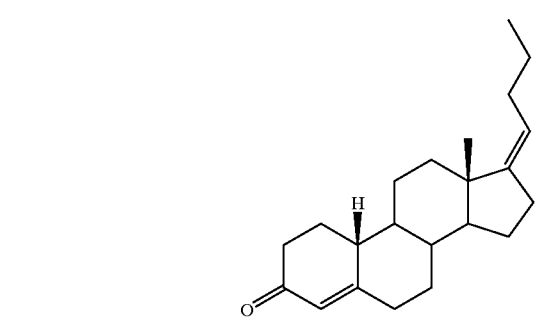
See Example.
E2:
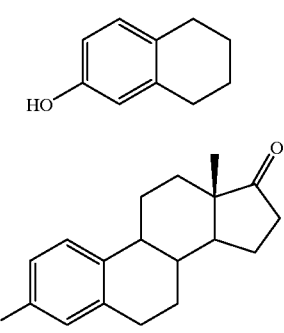
This is a commercially available substructure, for example ESTRONE.
E3:
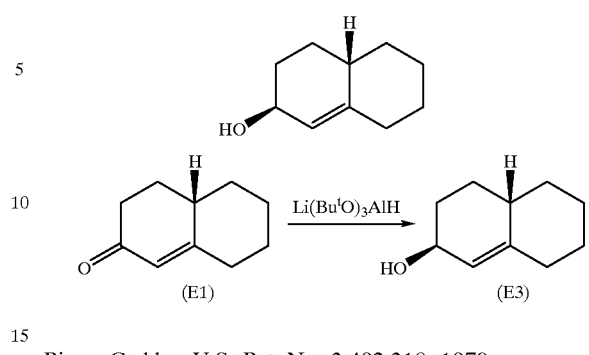
Pierre Crabbe, U.S. Pat. No. 3,492,318, 1970.
E4:
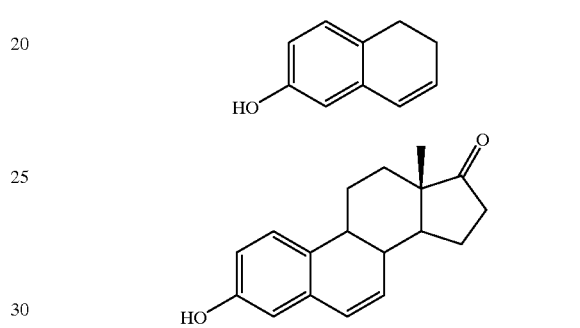
This is a commercially available substructure, for example 6-DEHYDROESTRONE.
E5:
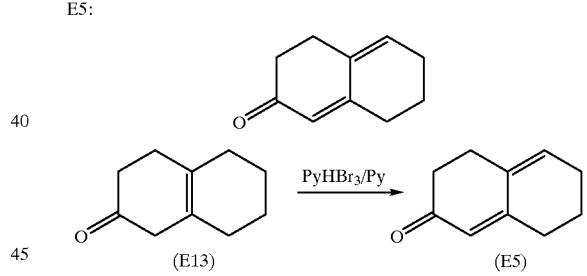
V. I. Melnikova and K. K. Pivnitskii, *Zhurnal Organicheskoi Khimii,* Vol. 10, No. 5, p. 1014, 1974.
E6:
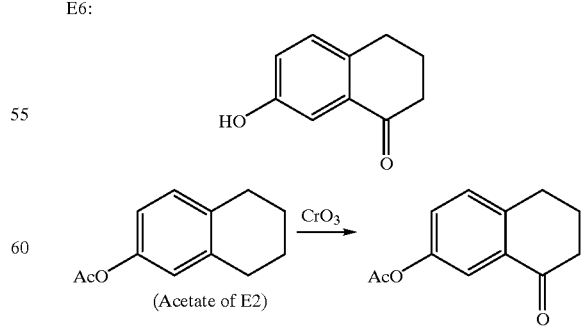

Hidetoshi Takagi, Ken-ichi Komatsu, and Hsuo Yoshizawa, *Steroids*, 1991, 56 173.

E7:

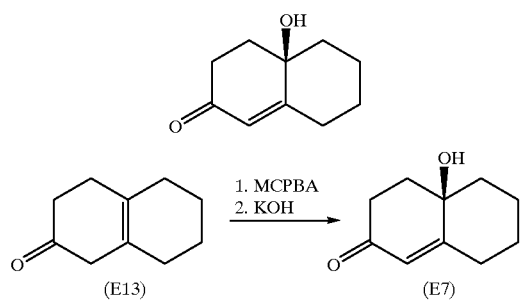

J. Perez Ruelas, J. Iriarte, F. Kinel, and Carl Djerassi, *J. Org. Chem.*, 7958, 23, 1744.

E8:

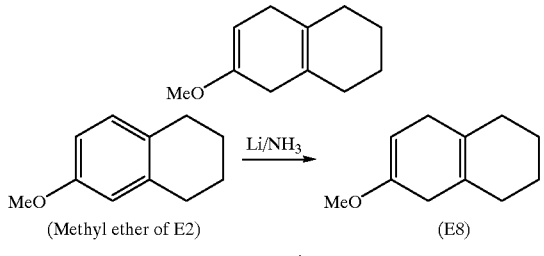

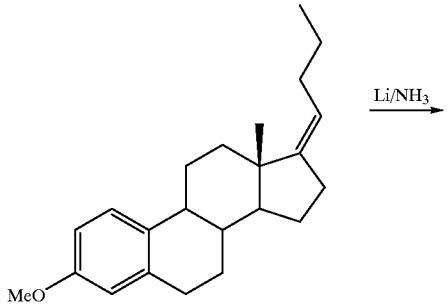

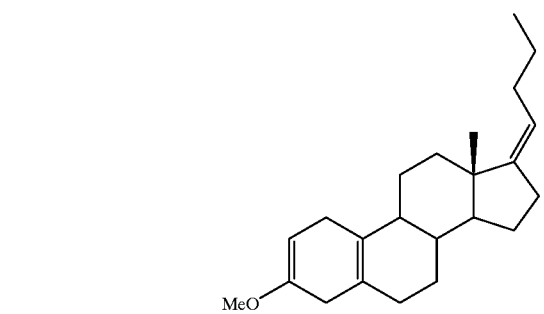

See Example.

E9:

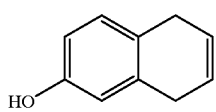

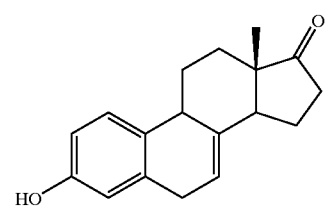

This is a commercially available substructure, for example EQUILIN.

E10:

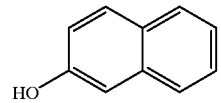

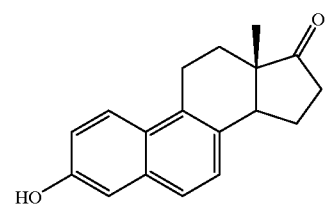

This is a commercially available substructure, for example EQUILENIN.

E11:

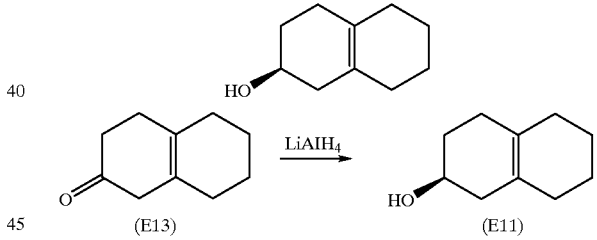

A. N. Cherkasov, A. M. Ponomarev, and K. K. Pivnitskii, *Zhurnal Organicheskoi Khimii*, Vol. 7, No. 5, p. 940, 1971.

E12:

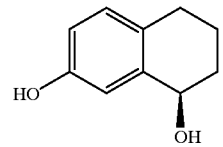

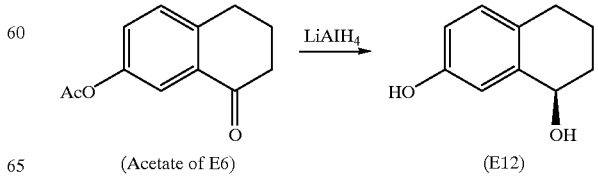

E13:
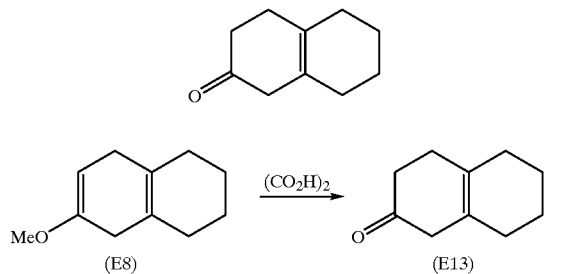
E14:
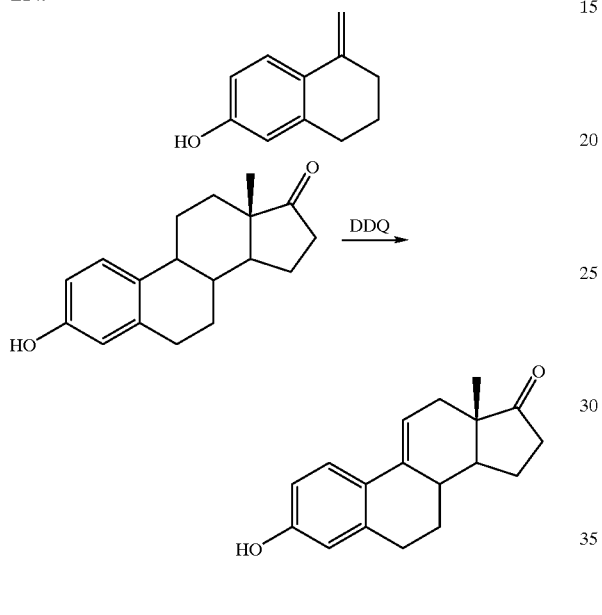
Elie Stephan, Regine Zen, Laurent Authier, and Gerard Jaouen, *Steroids*, 1995, 60, 809.
Substructure Syntheses: Type NC
NC1:
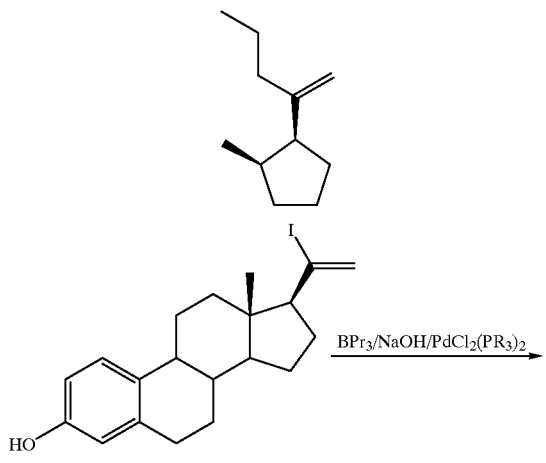
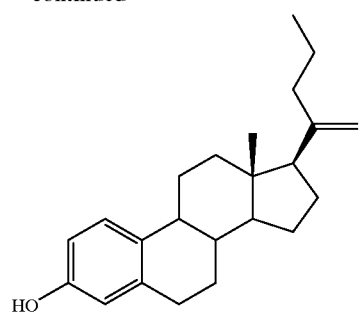
Gerard A. Potter, S. Elaine Barrie, Michael Jarman, and Martin G. Rowlands, *J. Med. Chem.*, 1995, 38, 2463.
NC2:
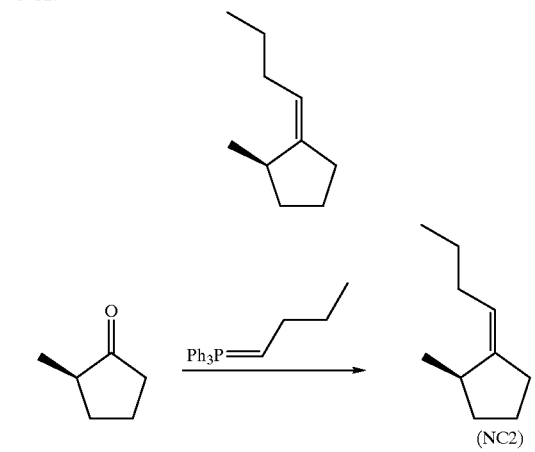
Richard H. Peters, David F. Crowe, Mitchell A. Avery, Wesley K. M. Chong, and Masate Tanabe, *J. Med. Chem.*, 1989, 32, 1642.

NC3:
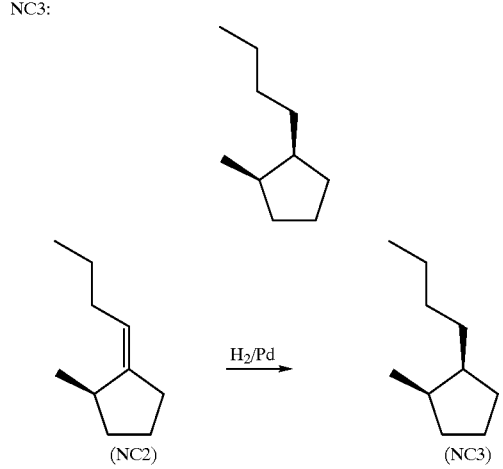
Richard H. Peters, David F. Crowe, Mitchell A. Avery, Wesley K. M. Chong, and Masate Tanabe, *J. Med Chem*, 1989, 32, 1642.
NC4:
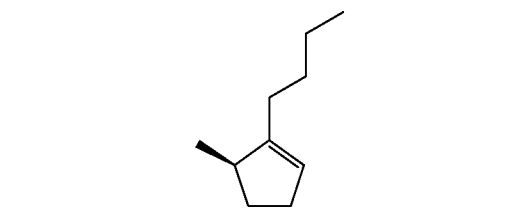
Gerard A. Potter, S. Elaine Barrie, Michael Jarman, and Martin G. Rowlands, *J. Med. Chem.*, 1995, 38, 2463.
NC5:
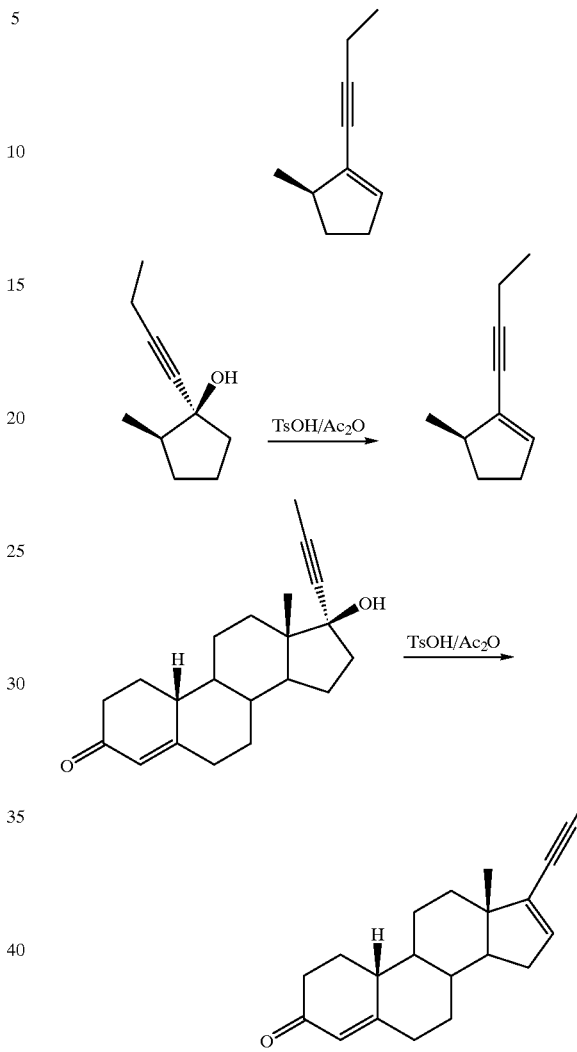
Pierre Crabbe, U.S. Pat. No. 3,492,318, 1970.
Methylnorcholanes
19-Norcholanes in this series may be prepared with a methyl group in the 1 or 7α positions.
Precursor of 1-Methyl analogs may be prepared as follows:
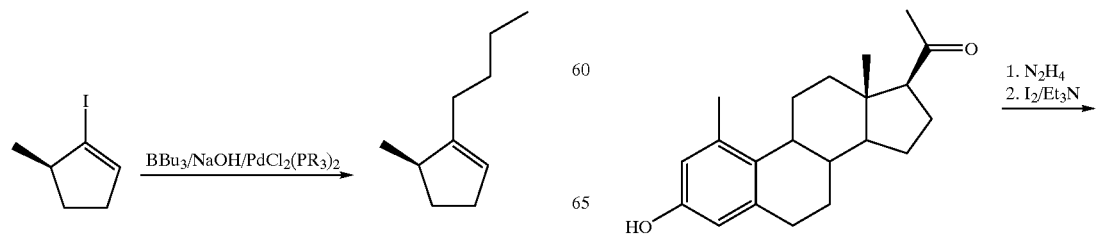

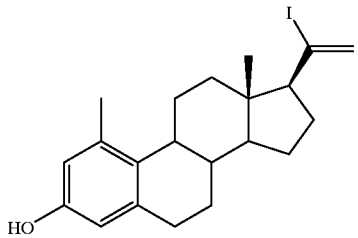

Starting material prepared according to Carl Djerassi, G. Rosenkanz, J. Iriarte, J. Berlin, and J. Romo, *J. Amer. Chem. Soc:* 1951, 73, 1523.

7α-Methyl analogs may be prepared from commercially available 7α-methylestrone.

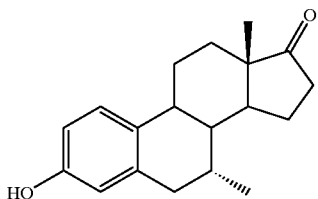

D. Methods of Use.

The methods of the invention are accomplished by means of the non-systemic, nasal administration of certain steroids, combinations of steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., non-invasively. Drug action is mediated through binding of the ligands, described herein, to specific receptors displayed by neuroepithelial cells in the nose, preferably in the VNO. This furthermore, the mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary. (See Johnson, et al., supra.)

The ligand substances described herein, or their sulfated, cypionated, benzoated, propionated, or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol. Alternatively, the active compound can be prepared as a creme or an ointment composition and applied topically within the nasal cavity. In addition, a vomeropherin may be administered as vapor contained in an air puff delivered to the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active compound(s). In addition, the compositions may include other medicinal agents, pharmaceutical agents, carriers, adjuvants, etc.

The most likely means of communication of a semichemical ligand is the inhalation of a naturally occurring pheromone present on the skin of another. Since these compounds are relatively nonvolatile, it is estimated that, even during intimate contact, a human subject would inhale picogram amounts of a naturally occurring steroid from the skin of another. From the amount inhaled it is estimated that only about 1% would reach the receptors of the vomeronasal organ.

The amount of vomeropherin administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response. When administered to the nasal cavity, the dosage is about 100 picograms to about 100 micrograms, preferably about 1 nanogram to about 10 micrograms, more preferably about 10 nanograms to 1 about microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates orbita, e.g., those sold under the trademarks "Arlacel C" (sorbitan sesquioleate), "Span 80" (sorbitan monoleate) and "Span 85" (sorbitan trioleate). The surfactant may constitute 0.1=20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

E. Antifertility Activity.

The steroid 19-norpregna-1,3,5(10)-trien-3-ol (compound $E2/P_4$ in the 19-norpregnane chart) was tested in the VNO of female rats. The EVG and vomeronasal nerve (VNn) discharge frequency are shown in FIGS. 97 and 98, respectively. This data shows stimulation of the VNO. The steroid $E2/P_4$ was shown to have postcoital antifertility activity when administered orally to female rats while having low hormonal activity (measured by estrogen-receptor binding). (Peters, et al., J. Med. Chem., 1989, 32,1642–52.) The data in FIGS. 97 and 98 suggest that this antifertility activity is explainable because $E2/P_4$ is not a hormone, but acts as a vomeropherin through stimulation of the VNO, which in turn affects the hypothalamus. Consistent with the rat model data, the compound $E2/P_4$ also shows VNO stimulation in women (see FIG. 118), and to a lesser extent, in men (see FIG. 140), and thus it is expected that the vomeropherins have antifertility activity in humans.

Stimulation of the hypothalamus via the VNO allows one to suppress release of LH and FSH. This can provide a clinical method for treatment of prostatic cancer, precocious puberty (in males and females), endometriosis, uterine leiomyoma, breast cancer, premenstrual syndrome and disfunctional uterine bleeding.

F. Measuring Affect, Mood and Character Trait.

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of related adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp. 1417. In: Medical Physiology. Vol. II Ed.: VB Mountcastle (1980); Wolfram Bouscein. Electrodermal Activity (Plenum Press 1992). In addition, non-verbal cues such as facial expression and body posture may be evaluated.

Treatment of Premenstrual Syndrome

Patients entered in the study (women 20–45 years old) participated in a recording session that takes place the day when PMDD symptoms are at the highest level (day 24 to 28 of the menstrual calendar). The entire procedure lasted approximately one hour in a quiet room with the subject laying supine.

The active ingredient used in the study was 16α,17α-epoxyestra-1,3,5(10)-trien-3-ol. The opening of the vomeronasal organ to the nose is identified at both sides of the nasal septum and a nasal probe (vomeronasal applicator) is positioned in one nostnl witb its output orifice pointing toward the VNO opening. One pulse of active substance, or placebo was delivered to the VNO. Following, the same procedure was repeated in the other nostril. The bilateral puffing of the vomeronasal organ was repeated 30 minutes after the first application.

The activation of the device delivers pulses of 200 μl, lasting 1 second. The quantity of active substance delivered in a pulse is 100 pg. The total quantity of active substance delivered to a patient's VNOs during the entire session is 400 pg (Table II).

TABLE II

Experimental protocol for randomized VNO stimulation.
n = 40 ($n_{control}$ = 20, $n_{test}$ = 20).

DAY 24 TO 28 OF MENSTRUAL CALENDAR

| SCREENING Menstrual calendar Interview Clinical diagnosis | Bilateral VNO stim. Single blind (placebo) | Bilateral VNO stim. Double blind (randomized) | Bilateral VNO stim. Double blind (randomized) (same as before) | No VNO stimulation |
|---|---|---|---|---|
| | Psychometric test Electrophysiology −10 | Psychometric test Electrophysiology 0 time (minutes) | Psychometric test Electrophysiology 30 | Psychometric test (answer at home) 5 hours |

Candidates were tested while they had clear PMDD symptomatology. This usually happens during day 24 to 28 of their menstrual calendar. The psychometric test (Table III) was presented ten minutes before, and thirty minutes after bilateral VNO stimulation with either the test substance or placebo (also, see Table II). After completion of the 30-minutes questionnaire, both VNOs were again stimulated with the same substance (vomeropherin, or placebo), and the patient was given again a similar psychometric test, to answer at home 5 hours after leaving the recording laboratory. Interviews of the patients the day after the study session indicated mood changes, feelings, and how she was perceived by other people, after the second puffing to the VNO.

Autonomic Reflexes and EEG

Several peripheral electrode leads attached to the patient's skin were used to study autonomic function and electroencephalogram (EEG). Recordings are produced 15 minutes before, and 30 minutes after stimulation of the VNO. Electrodermal activity (EDA), was recorded using two silver dectrode disks placed in the palmar skin of the major and annular finger (right hand). Electrocardiogram (ECG) was monitored from lead I (standard frontal-plane I). Respiratory frequency (RF) was recorded using a strain gauge placed around the lower thorax. The sinus respiratory physiological arrythmia was obtained from the correlation of RF and the ECG frequency. To assess changes in parasympathetic tone. Body temperature (BT) was taken from the external ear canal using a mini thermistor probe. A bipolar electromyographic recording (EMG) was accomplished with two electrodes placed in the chin. Electroencephalogram is recorded from CzA1 and T3A1 of the standard 10/20 system. All signals were amplified and digitized (Biopac Systems), and continuously monitored and stored using a computer (Macintosh LC-III). The autonomic function and EEG are recorded during the screening session and again in both double blind sessions, after VNO stimulation (see Table II).

Mood changes are evaluated in a scale from zero to four, using questionnaires. Autonomic function recorded before, and 30 minutes after the administration of placebo or test substance to the VNO, was processed using "aqknowledge" software (Biopac Systems). The significance of the results was assessed using t-tests and analysis of variance.

Fourteen patients diagnosed with PMDD were screened. Two patients responded to the placebo and were dropped from the study. Six of the patients received the steroid in their VNOs, and the other six received placebo. A summary of the results is shown in Table III.

The patient were asked to score a list of eleven PMDD symptoms before, and 30 minutes after stimulation of the VNO with the steroid (total dose=200 pg), or placebo. Bilateral stimulation of the VNO with placebo did not change significantly the magnitude of the symptoms, from control level (FIG. 210, shaded bars). However, 30 minutes after bilateral stimulation of the VNO with the steroid (total dose=200 pg), there was significant reduction of most PMDD symptoms (p=or<0.03). For some symptoms like "I feel like throwing things", and "I am angry", the improvement was significant at p=0.01. The score for other symptoms like "My mind feels cloudy", and "I feel the world would be better without me", was not different from control after administration of the steroid (p>0.05).

The analysis of autonomic function 30 minutes after stimulation of the VNO with the steroid shows changes of some reflexes, that correlatate with the mood improvement of the patient. The activity of skeletal muscles measured through the electromyogram (EMG), decreases thirty minutes after delivery of the steroid to the VNO, but not after administration of placebo (FIG. 211). Also, the frequency of electrodermal activity events, decreases after administration of the vomeropherin, but not after placebo (FIG. 212). Other autonomic reflexes do not show significant change. The electroencephalographic pattern does not change substantially from baseline, after administration of the steroid to the VNO. However, in four patients treated with the vomeropherin, there was increase in alpha cortical activity.

The score of PMDD symptoms was also studied five hours after the second application of vomeropherin to the VNO. At this time there was no significant difference with control. However, during the telephone interview done during the morning after the recording session, the patients referred feeling better after leaving the recording laboratory, and that this effect lasted from one to two hours.

Small quantities of the steroid (200 pg) delivered in vapor form to the VNO of patients suffering from PMDD, produced significant improvement. As shown in FIG. 210, the majority of the symptoms are decreased after 30 minutes of administration of the substance. This effect is not seen after administration of placebo to the VNO. Symptoms reduction is accompanied by relaxation, measured by decrease of the EMG and decrease of EDA frequency. Finally, the patients improvement is substantiated by verbal reports (telephone interview), obtained the morning after the recording session.

TABLE III

Summary of effects of vomeropherin in PMDD patients. n = 12

| Symptom | Improvement |
|---|---|
| I feel like running away | ++ |
| I feel like throwing things | ++++ |
| I am angry | ++++ |

TABLE III-continued

Summary of effects of vomeropherin in PMDD patients. n = 12

| Symptom | Improvement |
|---|---|
| I feel swollen up | +++ |
| My breasts hurt | ++ |
| I feel like crying | ++ |
| I feel overwhelmed | ++ |
| I get emotional easily | +++ |
| I blow up at little things | +++ |
| My mind feel cloudy | 0 |
| I feel the world would be better withiut me | 0 |
| Skeletal muscle relaxation | ++ |
| Electrodermal activity relaxation | ++ |
| Alpha brainwave activity | + |

Anxiety Tests

Eight patients were treated in the VNO with placebo and eleven were treated with androsta-4,16-dien-3β-ol. Scores on anxiety symptoms were taken using the convention Hamilton-A anxiety tests which measure the following:

| TOTAL HAMILTON-A | INSTANT HAMILTON-A | STATIC HAMILTON-A |
|---|---|---|
| anxious mood | anxious mood | fears |
| tension | tension | insomnia |
| fears | intellectual | depressed mood |
| insomnia | somatic (muscular) | gastrointestinal symptoms |
| intellectual | somatic (sensory) | genitourinary symptoms |
| depressed mood | cardiovascular symptoms | |
| somatic (muscular) | respiratory symptoms | |
| somatic (sensory) | autonomic symptoms | |
| cardiovascular symptoms | behavior at interview | |
| respiratory symptoms | | |
| gastrointestinal symptoms | | |
| genitourinary symptoms | | |
| autonomic symptoms | | |
| behavior at interview | | |

The results are summarized in FIGS. 213 through 218. In FIG. 213 the treated subjects (T) show an improvement over the control (C) in the instant, static and total Hamilton-A results. Referring to FIG. 214, only 25% of the subjects given placebo showed a Hamilton-A score drop of 45% or more, but 64% of the treated subjects showed a score drop of 45% or more.

FIG. 215 shows a significant decrease in respiratory frequency (RF) and cardiac frequency (CF) in treated anxious subjects compared to control.

FIG. 216 shows improved parasympathetic tone in treated anxious subjects as compared to control. This characteristic was measured through a standard test for physiologic sinus arrhythmia.

FIG. 217 shows an improved (decrease) on electrodermal activity (EDA) in treated anxious subjects as compared to control.

FIG. 218 shows an improved (increase) in body temperature in treated anxious subjects compared to control.

Electrovomerogram (EVG). FIG. 201A shows superimposed traces of EVGs recorded from a 25 year-old male subject. The ETA (estratetraenyl acetate) stimulus produced an EVG significantly different from control. The mean amplitude of the EVGs produced in all subjects studied was M=1.95 mV, S.D.=+0.8 mV, n=10). An air pulse carrying the same quantity of PDD induced a larger EVG. The mean amplitude for the same dose of PDD in all subjects recorded was M=3.6V, S.D.=0.7 mV, n=10).

The results of vomeropherins' action on the electrogram of the nasal respiratory mucosa are shown in FIG. 201B. The studies demonstrate that respiratory mucosa did not respond to either ETA or PDD (pregnadienedione) (p>0.1, n=10). The same vomeropherins when tested in the olfactory epithelium (unpublished observation) also showed no electrogram response.

FIG. 202 depicts ETA and PDD dose effect curves obtained in male subjects. Notice that for both vomeropherins the EVG amplitude increases as a function of the concentration, and dose-effect relationship for interstimulus intervals of 5 minutes is sigmoidal. The slope for ETA is not significantly different from that of PDD (p>0.02, n=20).

Autonomic reflexes produced by vomeropherins. Studies of the central nervous system (CNS) reflex response to VNO stimulation with air pulses containing ETA ($5 \times 10^{-9}$M), and PDD ($5 \times 10^{-9}$M) are shown in FIG. 203, discussed below.

Electrodermal activity (EDA). Both vomeropherins induced increase of skin conductance as compared to control (p<001). The effect of a single air pulse containing vomeropherin, either ETA or PDD, consisted of a transient monophasic wave, with a latency of $X_{Lat}$=520 ms, SD=110 ms. The mean peak amplitude of the effect for PDD was $X_{PDD}$=21.1 S, SD=19 $\mu$S, and for ETA it was $X_{ETA}$=22.01 $\mu$S, SD=13.6 $\mu$S. The average duration of the wave was 32 seconds. Vomeropherins ETA and PDD also changed the frequency of spontaneously occurring EDA events. After application of ETA or PDD, the frequency of waves decreased from 4.1 to 0.9.

Body temperature (BT). A single air pulse containing ETA produced a small but significant temperature increase ($X_{LTA}$=0.24° C., SD=0.1° C., p<0.02), that lasted about 2 minutes and then returned to baseline.

Cardiac frequency (CF). The heart rate was measured from the R-intervals of the EKG. The effect induced by both vomeropherins is significantly different in male subjects (p<0.01), (see FIG. 215). Compared to control values, ETA decreased cardiac frequency by $X_{ETA}$=-3.3 beats/min., SD=1 beat/min., while PDD increased cardiac rate by $X_{PDD}$=3.8 beats/min., SD=1.5 beats/min. These changes developed about 10 seconds after VNO stimulation with vomeropherins, and after approximately 2 minutes the heart rate returned to control values.

Respiratory frequency (RF). PDD induces a small but significant decrease in respiratory rate ($X_{RF}$=-2 cycles/min., SD=1 cycle/min. n=10) that appeared about 5 seconds after stimulation of the VNO and lasted for 1 minute.

Electroencephalogram (EEG). Electroencephalograms were recorded from the vertex $CzA_1$) and temporal region ($T_3A_1$), and epochs of four-minute duration were analyzed off line using the Fast Fourier Transform. Later, the ratio of alpha to beta brainwave activity (alpha/beta) was calculated in one epoch occurring before and another after administration of a vomeropherin to the VNO. PDD changed the alpha/beta ratio from control subjects 0.11 to treated subjects 1.85, while ETA changed the ratio from control subjects 0.14 to treated subjects 1.71. These effects were significantly different from control values ($p<0.02$).

The measurements of autonomic reflexes as described demonstrate that stimulation of the human VNO with vomeropherins triggers reflex activity in the central nervous system.

Plasma Levels of Pituitary Hormones and Testosterone. The effect of VNO stimulation with vomeropherins on plasma levels of pituitary hormones is shown in Tables II and III. Table II shows the characteristics of the pulsatile release of TSH, PRL, FSH, and LH in 10 subjects of Group B, before and during treatment with ETA.

In 10 normal male volunteers treated with ETA, no significant differences could be detected for TSH, PRL, and FSH when compared to normal placebo controls, ($p>0.05$). However, treated ETA subjects showed an increase in Mid Peaks and Peak Width measurements, control 79 vs. treated subjects 92 and control 45 vs. treated subjects 54, respectively ($p<0.05$). The number of peaks of LH for treated subjects was decreased significantly from 5.2 compared to control value of 6.8 ($p<0.05$).

In 10 male and 10 female subjects (Group C) PDD was administered at a concentration of $5\times10^{-9}$ M, every 10 minutes, during 6 hours. Pulsatility analysis was applied to the LH and FSH serum concentrations obtained at each sampling time. As shown in Table III, the mean area under the peaks (concentration/time) and the increment above basal were significantly reduced during the treatment with PDD for both gonadotropins but only in males without apparent changes in the female subpopulation.

In PDD treated males, FSH values were significantly decreased for both M. Area and I.A. Basal measurements: Treated 12.7 vs. Control 17.6, and Treated 0.63 vs. Control 0.89, respectively. Likewise, for the same group, LH values were significantly decreased for both M. Area and I.A. Basal measurements: Treated 44 vs. control 77 and Treated 1.4 vs. Control 2.0, respectively.

For all measurements as described, no statistically significant changes could be detected in female subjects treated with PDD. (Table III).

The major change was observed in the reduction of the increments above basal values particularly for LH (2.0 vs. 1.4 $p<0.009$).

Similarly to the findings during the administration of ETA, other pituitary hormones analyzed (PRL and TSH) did not show statistically significant changes either in their absolute concentrations or in the pulsatility characteristics.

Vomeropherins ETA and PDD appear to be gender specific both in their effect on the VNO and on hypothalamic responses. They significantly lower gonadotropin pulsatility in male, but not in female subjects (see Table III). This gender specific effect on the VNO (electrovomerogram) has been reported previously using naturally occurring vomeropherins (pheromones) from the human skin: Estra-1,3,5(10), 16-tetraen-3-ol specifically stimulates the human VNO in males, but not in females. However, Androsta-4,16-dien-3-one specifically stimulates the human VNO in females, but not in males.

The data provides support for a functional connection between the VNO and the basal forebrain. Furthermore, stimulation of the human VNO in males with ETA ($3\times10^{-9}$ M) significantly changes LH pulsatility, but not FSH. PDD ($5\times10^{-9}$ M) significantly changes LH and FSH pulsatility in males only. These findings open an opportunity to use a specific vomeropherin (chemically synthesized and not found in nature) that could be used in the treatment of certain diseases which are gender specific.

The release of LHRH and gonadotropins through exposure to semiochemicals of conspecifics of the opposite gender has been reported in several mammalian species (Beltramino et al, Neuroendocrinology 36 (1983):53–58, Coquelin, et al. J. Neuroscience 4 (1984):2230–2236. It was also shown in laboratory animals that VNO receptors are essential to trigger this neuroendocrine reflex (Johns 1978, Wysocki 2979, Meredith 1994). The present results here show that this neuroendocrine reflex is functional in humans and that it can be modulated through VNO receptor sites that are sensitive to vomeropherins. See Tables II and III in that there is the decrease in LH and FSH peak height, and frequency and increase in the peak interval. Therefore, ETA and PDD must be affecting vomeronasal afferent signals that modulate the pool of hypothalamic LHRH neurons.

Experimental studies in several animal species have demonstrated a close correlation between LH pulsatility and episodic GnRH release in hypothalamic-pituitary-portal blood (Veldhuis et al., J. Clin. Endocr. Metab., 64 (1987) :1275–1282). The pulsatile release of LH in normal men, post-menopausal women and young women studied throughout the menstrual cycle reflects episodic endogenous gonadotrophic releasing hormone (GnRH) action. Although variations in bioactive LH pulse amplitude can result from changes in either amplitude of the endogenous GnRH pulse signal and/or changes in pituitary gonadotropic-cell responsiveness, significant alterations in LH pulse frequency can be taken to reflect corresponding modulation of the hypothalamic GnRH pulse (Knobil, E. 1980, Recent Prog Horm Res 36:53). The changes observed in the amount and pattern of release of gonadotropins in male subjects during administration of femtomolar quantities of vomeropherins to the VNO result in a neuro-pharmacological effect at the hypothalamic/pituitary level.

Pulsatile release of LHRH from the preoptic hypothalamus drives the release of both gonadotropins (LH and FSH) from the pituitary (Yenand Jaffe, Textbook of Reproductive Endocrinology).

Data on several patients are shown for blood testosterone level (subjects 1, 2, 4 and 8, respectively, shown in FIGS. 204, 205, 206 and 207). Visit "A" shows the levels after administration of pregna-4,20-dien-3,6-dione to the VNO. Visit "B" shows testosterone levels after administration of a placebo. The slopes of the curves for levels after treatment with the pregnadiendione are statistically different from the slopes of the curves of the control. Also, in most instances, the levels of testosterone are lower after treatment of the pregnadiendione compared to the control. This shows the ability to affect blood testosterone level by administration of a vomeropherin to the VNO.

III. Examples

The following examples are intended to illustrate but not to limit the invention.

Abbreviations used in the examples are as follows: aq.= aqueous; RT.=room temperature; PE=petroleum ether (b.p. 50–70°); DMF=N,N=dimethylformamide; DMSO= dimethyl sulfoxide; THF=tetrahydrofuran.

SCHEME 1
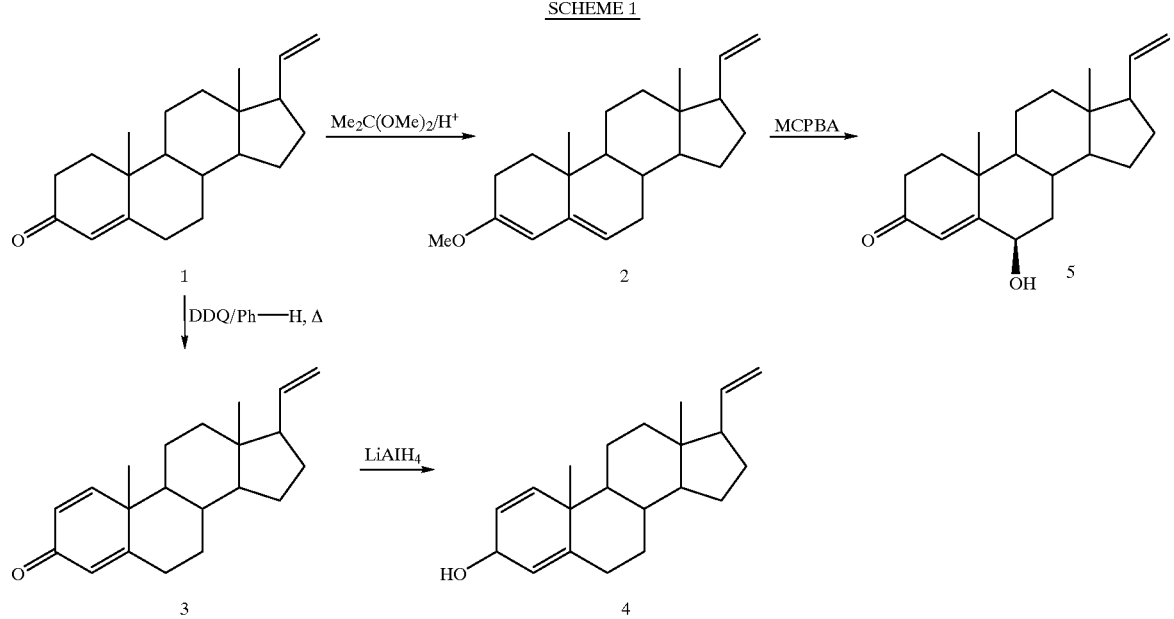
SCHEME 2
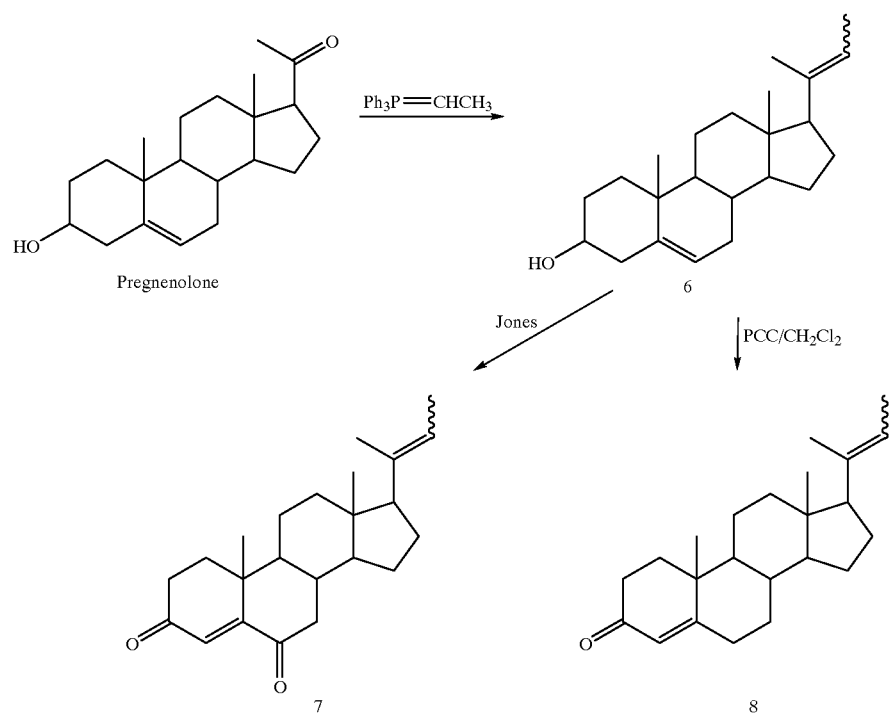

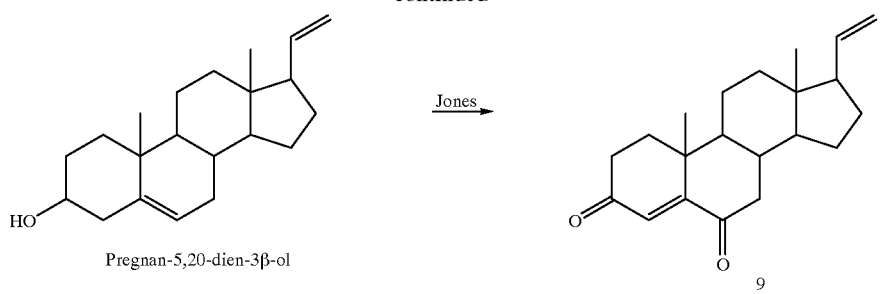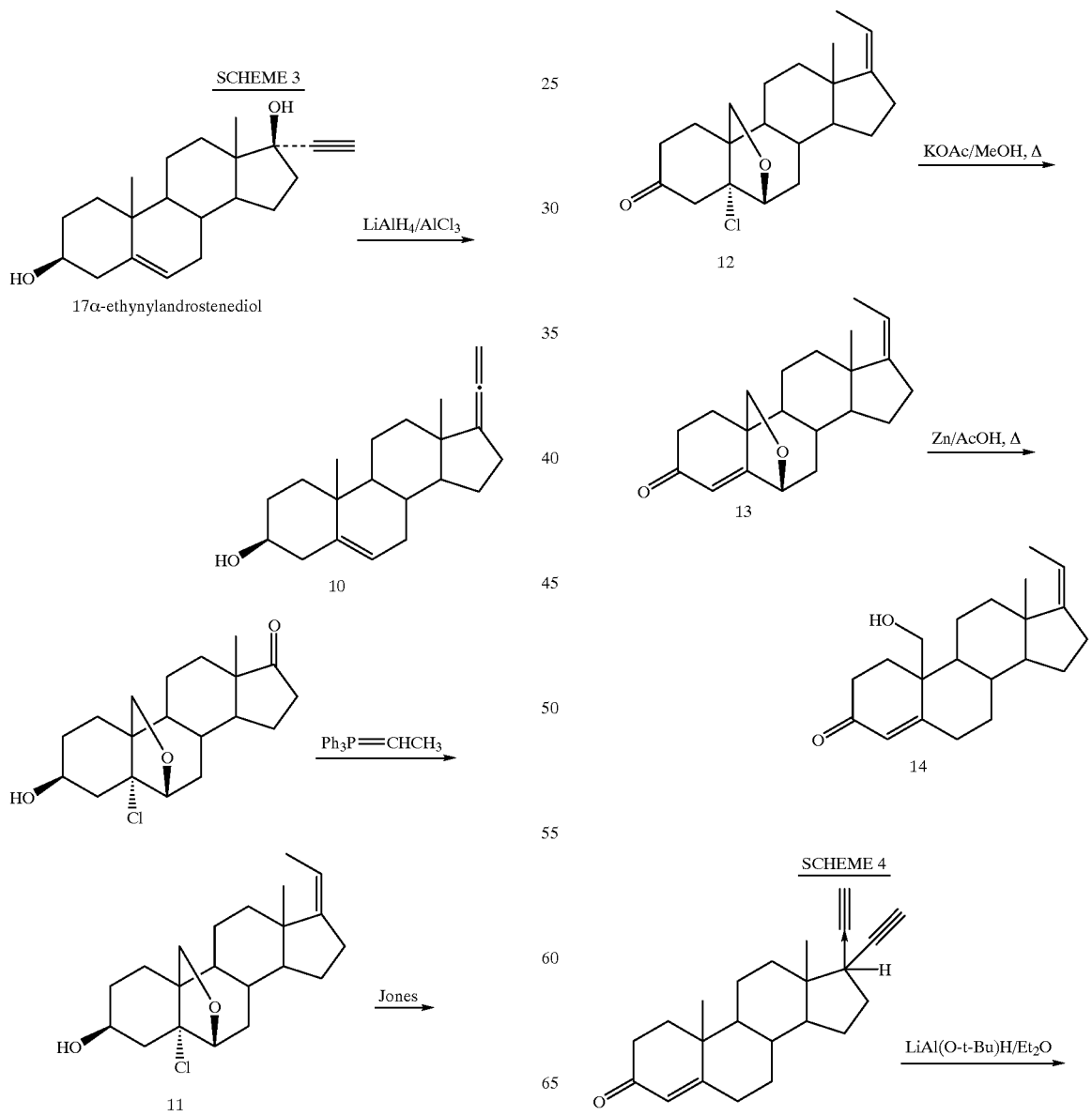

211
-continued
212
-continued
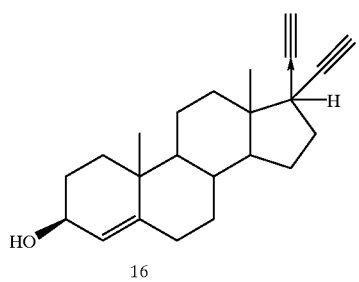
16
Scheme 5
Oxidation of pregnanes
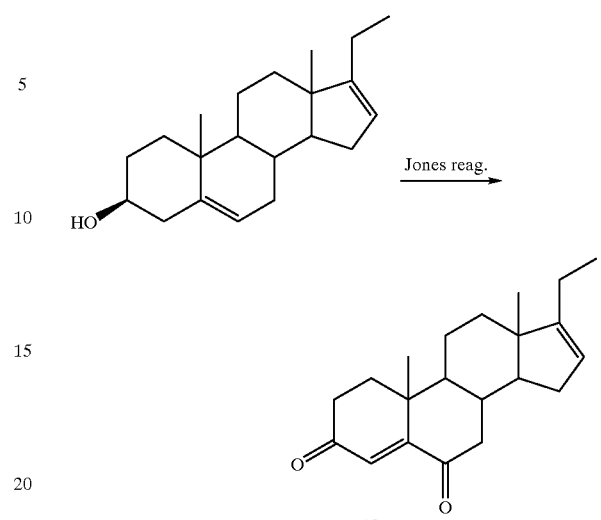
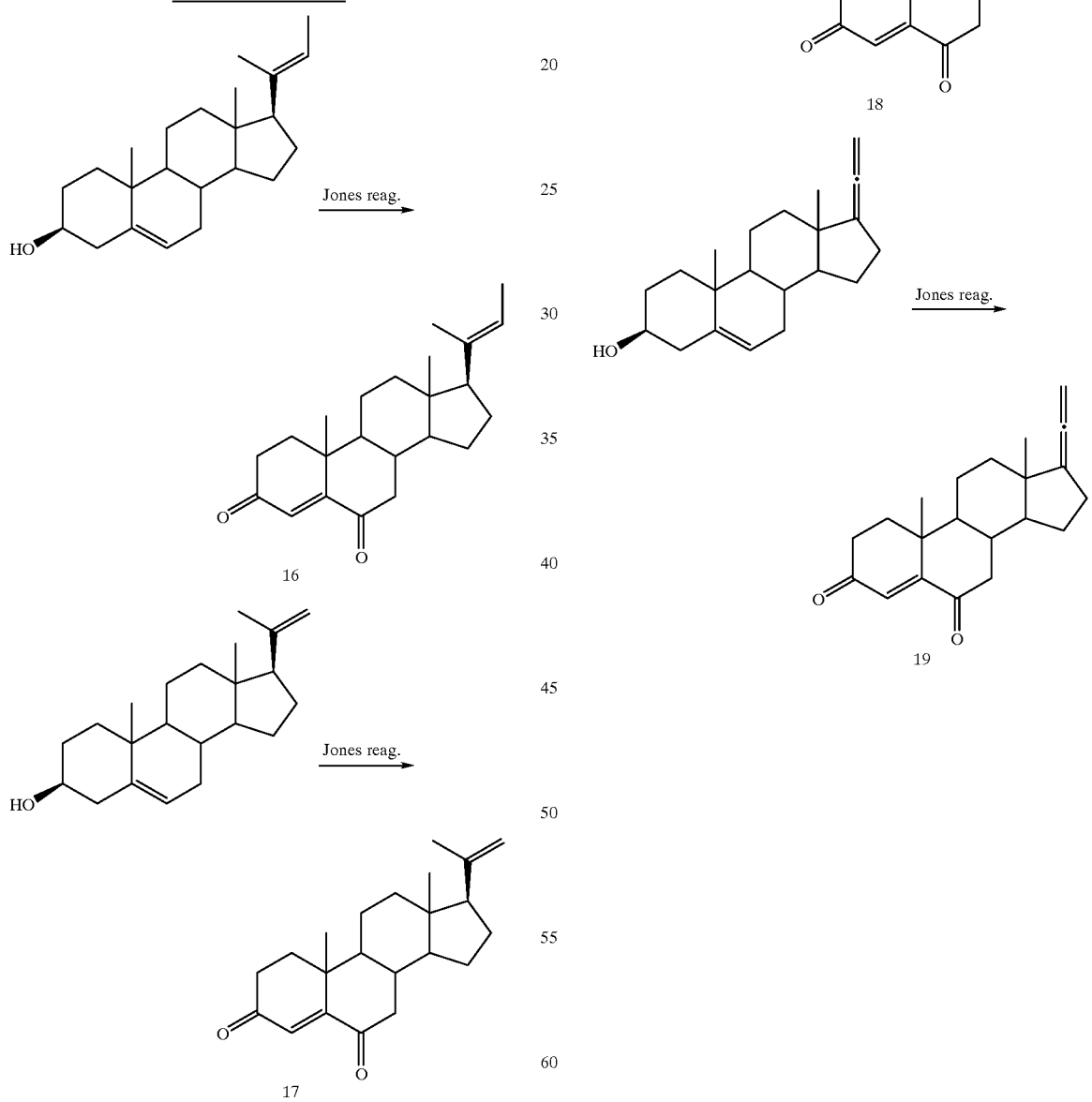

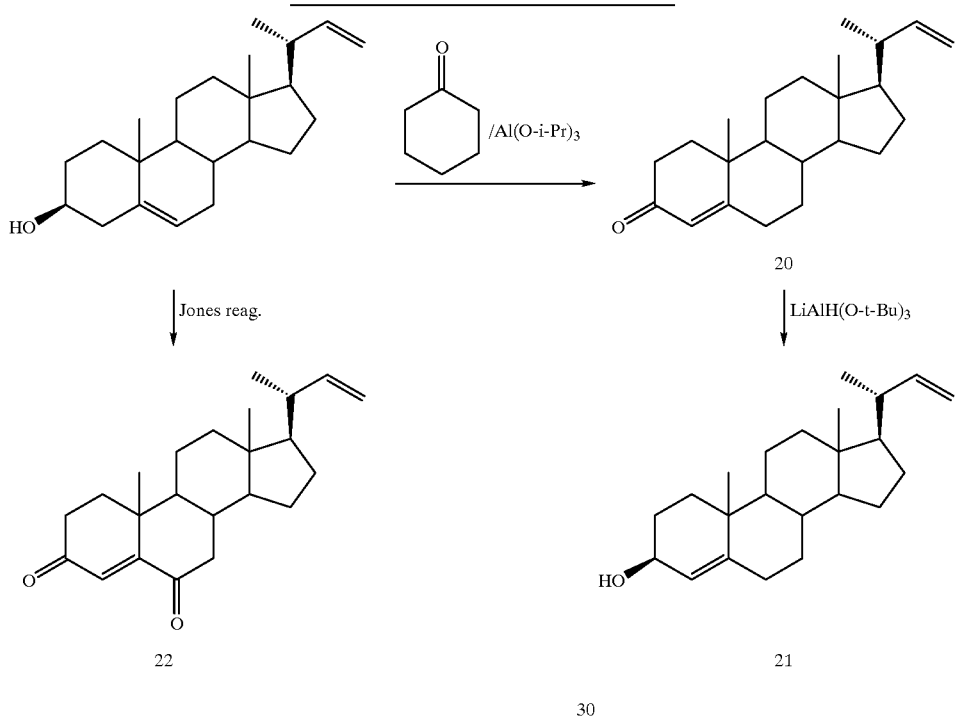
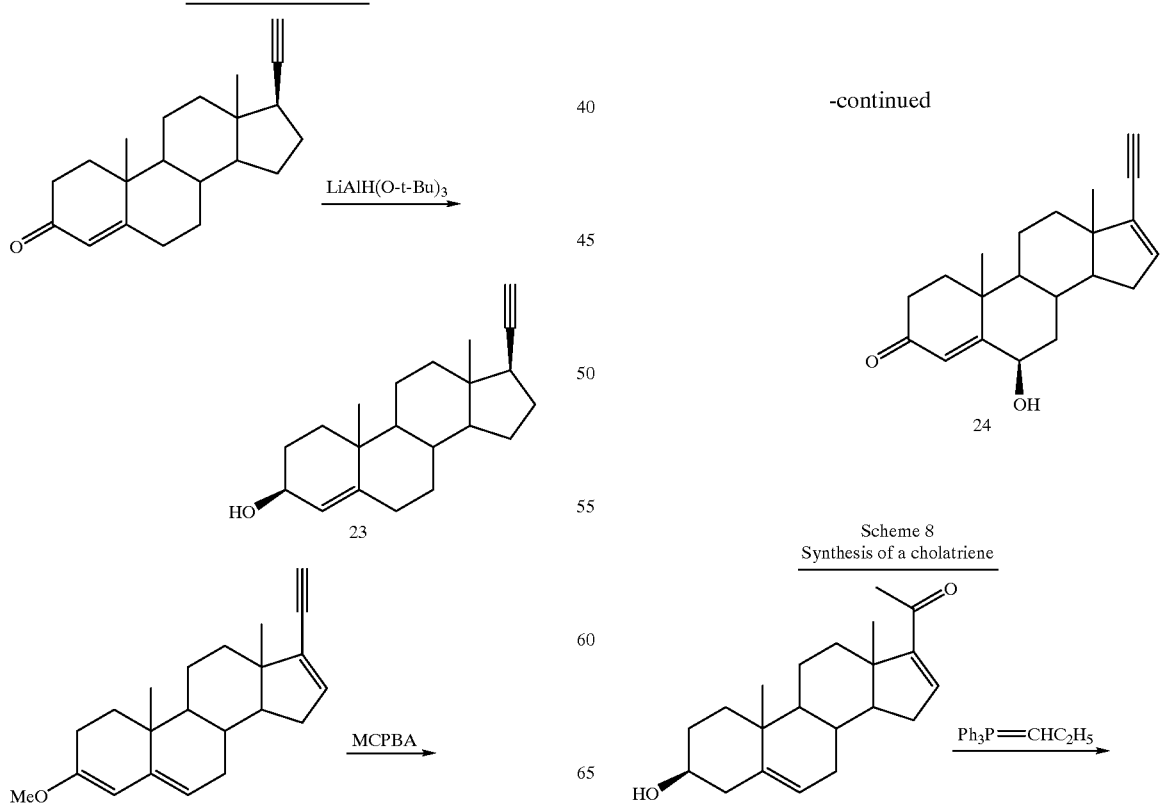

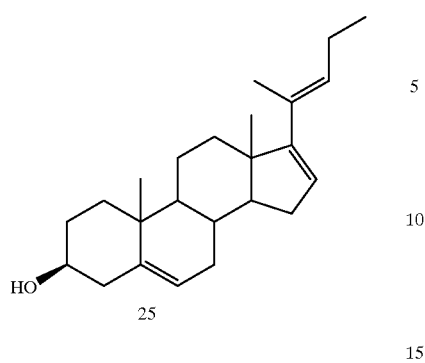
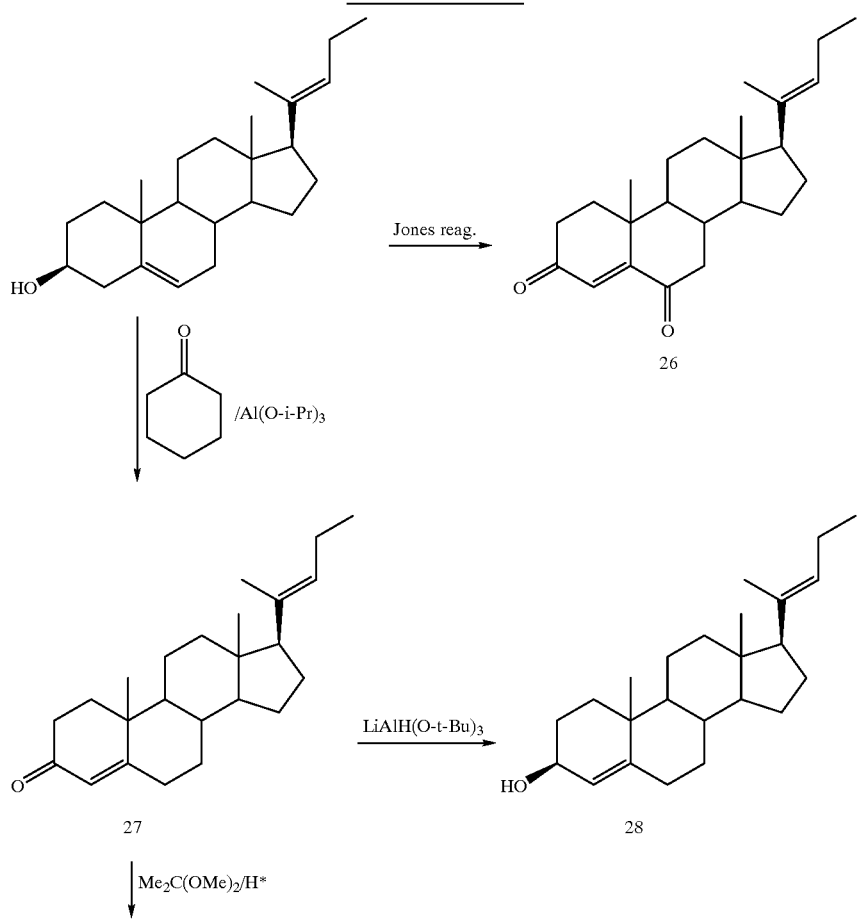
Scheme 9
Synthesis of Cholenes

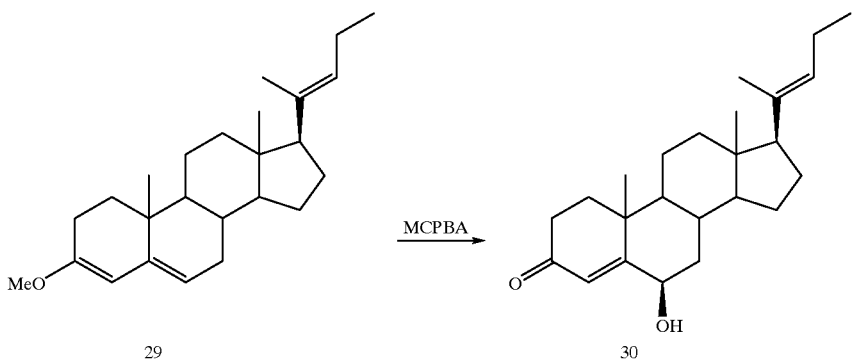

EXAMPLES

Example 1

Pregna-4,20-dien3α-(β-)-ol.

To a 1M solution of lithium trisiamylborohydride (5.0 ml, 5.0 mmole) at −78° C. under argon was added a solution of pregna-4,20-dien-3-one (1.10 g, 3.70 mmole) in dry THF (14 ml), with stirring, and the mixture was allowed to warm to room temperature. After 3 hours, the mixture was cooled to −78° C. and the following reagents were added sequentially: water (2 ml), ethanol (6 ml), 12% aqueous KOH solution (10 ml), and 3% hydrogen peroxide (50 ml). The mixture was allowed to warm to room temperature with stirring. After 2 hours, ethyl acetate (200 ml) was added and the stirring was continued. The organic layer was separated, and was washed with satd. NaHSO$_3$ solution, satd. NaHCO$_3$ solution, and satd. NaCl solution, dried (Na$_2$SO$_4$), and evaporated in vacuo to give 2.1 g crude material. This was purified by flash chromatography on 210 g silica gel (230–400 mesh), eluting with EtOAc/CH$_2$Cl$_2$ (5:95→7:93) to give three fractions. Fraction 1 (0.8 g) contained the impure 3α-alcohol. Fraction 2 (0.1 g) was a mixture of the 3α- and 3α-alcohols. Fraction 3 (0.25 g) was the pure 3β-alcohol (23%). Fraction 1 was repurified by flash chromatography on 80 g silica gel (230–400 mesh), eluting with EtOAc/hexane (10:90→15:85) to give 0.15 g pure 3α-alcohol (14%).

Example 2

Pregna-3,5 20-trien-3-yl methyl ether, 2.

Referring to SCHEME 1, compounds 2, 3, 4 and 5 were prepared as follows.

A solution of pregna-4,20-dien-3-one (1, 1.00 g 3.35 mmol) in 2,2-dimethoxypropane (5.0 Ml, 41 mmol) dimethylformamide (5.0 ml) and methanol (0.2 ml) was refluxed with catalytic p-toluenesulfonic acid monohydrate (26.9 mg, 0.141 mmol) for 2 h. After cooling, sodium bicarbonate (153.6 mg, 1.828 mmol) was added and the reaction mixture was partitioned between 75 ml of hexanes and 50 ml of ice water. The organic phase was washed twice with 50 ml portions of water and once with 50 ml of brine, after which it was filtered through a 17 mm high×30 mm diag. column of silica gel 60. Product was further eluted with 100 ml of hexanes. Concentration of the combined eluates and recrystallization from acetone/methanol gave lustrous very slightly yellow platelets (828.7 mg, 2.652 mmol, 79%) m.p. 111–114° C.

Example 3

Pregna-1,4,20-trien-3-one.

Pregna-4,20-dien-3-one (1, 1.19 g. 3.99 mmol) was refluxed for 24 h with 2,3-dichloro-5,6-dicyano-1,4-benzoquinone (DDQ, 2.72 g, 12.1 mmol) in 40 ml of benzene under Argon. The cooled suspension was diluted with ether and washed with two 100 ml portions of 5% (w/w) sodium hydroxide, two 100 ml portions of water and once with 100 ml of brine. Ether (100 ml) was added to the resulting emulsion, which was dried over sodium sulfate and then filtered through a column of sodium sulfate (20 g). After washing the residue twice with 50 ml portions of ether the combined filtrates were concentrated under reduced pressure and then flash chromatographed (25% ethyl acetate/hexanes on silica gel) to give a slightly yellow crystalline solid (0.26 g, 0.88 mmol, 226).

Example 4

Pregna-1,4,20-trien-3-ol, 4.

Pregna-1,4,20-trien-3-one (3, 0.26 g, 088 mmol) in 25 ml of anh. ether was reduced under argon atmosphere with lithium aluminum hydride (250.5 mg, 6.601 mmol) for 2 h and then quenched with 2.50 g of Glauber's salt. The resulting suspension was stirred 70 min., filtered, and washed twice with 50 ml portions of ether. After concentrating the combined filtrates under reduced pressure the residue was purified using preparative TLC (35% ethyl acetate/hexanes on alumina to give white needles (26.1 mg, 87.4 μmol, 10%) m.p. 98–128° C.

Example 5

Pregna-4,20-dien-6β-ol-3-one, 5.

m-Chloroperbenzoic acid (MCPBA, 77.4%, 763.4 mg, 3.42 mmol) suspended in 30 ml of 1,2-dimethoxyethane (DME), 6 ml of water and 2.4 ml of 5% (w/w) sodium hydroxide was added to a solution of pregna-3,5,20-trien-3-yl methyl ether (2, 400.3 mg, 1.281 mmol) in 20 ml of DME+2 ml of water over 85 min. with stirring. The reaction was continued 5 h and was then poured into 50 ml of saturated sodium bicarbonate. The mixture was extracted three times with 50 ml of ehter and the combined organic extracts were washed with 50 g of 5% (w/w) sodium thiosulfate pentahydrate +three 50 ml portions of brine, dried over magnesium sulfate, and filtered through Celite. After washing the residue with 10 ml of ether the combined filtrates were concentrated in vacuum. Flash chromatography (35% ethyl acetate/hexanes on silica gel) and preparative TLC (35% ethyl acetate/hexanes on silica gel) gave a difficulty separable mixture as white crystals (95.5 mg, 0.304 mmol, 24%).

Example 6

20,21-Dimethylpregna-5,20-dien-3β-ol, 6.

Referring to SCHEME 2, compounds 6, 7, 8 and 9 were prepared as follows.

Ethyltriphenylphosphonium bromide (25.99 g, 70.00 mmol) and potassium t-butoxide (7.86 g, 70.0 mmol) with 80 ml of anh. DMSO were stirred under Argon in oil bath at ca. 80° C. for 1 h, after which preen-5-en-3β-ol-20-one (4.43 g, 14.0 mmol) in 80 ml of warm anh. DMSO was added. The red suspension was stirred 1 h, removed from the heat and poured into 200 ml of ice-brine. The mixture was then extracted three times with 100 ml of ether and the combined organic extracts were washed with 100 ml of brine, dried over sodium sulfate, and filtered through Celite. After washing the residue with 50 ml of ether the combined filtrates were concentrated under reduced pressure. The yellow residue was taken up in 95% ethanol with heating, boiled briefly with 1 g of charcoal, and filtered through Celite. After cooling and filtration of the residue was recrystallized twice more from ethanol to give white crystals (1.746 g, 5.314 mmol, 38%), m.p. 140–145° C.

Example 7

20,21-Dimethylpregna-4,20-dien-3,6-dione, 7.

Jones reagent (2.67 M, 2.0 ml. 5.3 mmol) was added to a solution of 20,21 -dimethylpregna-5,20-dien-3β-ol (6, 460.1 mg, 1.400 mmol) in 50 ml of acetone and the reaction was stirred 45 min. After quenching with 2-propanol (1.0 ml) the mixture was poured into 100 ml of water and extracted three times with 50 ml of ethyl acetate. The combined organic extracts were washed with 50 ml of saturated sodium bicarbonate+50 ml of brine, dried over magnesium sulfate, and filtered through Celite. The residue was washed with 25 ml of ethyl acetate and the combined filtrates were concentrated under reduced pressure. Flash chromatography (25% ethyl acetate/hexanes on silica gel) and recrystallization of the residue from 95% ethanol gave yellow needles (138.2 mg, 0.4059 mmol, 29%), m.p. 172–178° C.

Example 8

20,21-Dimethylpregna-4,20-dien-3-one, 8.

20,21-Dimethylpregna-5,20-dien-3β-ol (6, 400.3 mg, 1.218 mmol) in 5 ml of methylene chloride was oxidized with pyridinium chlorochromate (525.4 mg 2.437 mmol) for 42 h. Ether (3.5 ml) was added and the suspension was filtered through a 5 mm dia.×60 mm high column of silica gel. The column was further eluted with 3.5 ml of ether and the combined filtrates were concentrated under reduced pressure. Flash chromatography of the resin followed by recrystallization from aqueous ethanol gave yellow crystals (43.6 mg, 0.134 mmol 11%). m.p. 157–165° C.

Example 9

Pregna-4,20-dien-3,6-dione 9.

A solution of pregna-5,20-dien-3β-ol (300.5 mg, 1.000 mmol) in 35 ml of acetone was cooled in an ice water bath and 2.67 M Jones reagent (0.71 ml, 1.9 mmol) was added. After stirring 1½ h a further 0.71 ml of Jones reagent were added and the reaction was continued 45 min, 2-Propanol (1.0 ml) was added and the mixture was poured into 100 ml of water. The mixture was then extracted twice with 50 ml of ethyl acetate and the combined organic extracts were washed with 50 ml of saturated sodium bicarbonate+50 ml of water +50 ml of brine and filtered through a 21 mm dia×22 mm high column of silica gel 60. The column was eluted further with 25 ml of ethyl acetate and the combined filtrates were concentrated under reduced pressure. Recrystallization of the residue from 95% ethanol gave a light yellow powder (104.6 mg, 0.3348 mmol 33%), m.p. 114–120° C.

Example 10

Pregna-5,17,20-trien-3β-ol, 10.

A solution of 17α-ethynylandrostenediol (439.4 mg, 1.397 mmol) in 10 ml of dry THF was added to a suspension of lithium aluminum hydride (106.5 mg, 2. mmol) and aluminum chloride (122.9 mg, 0.9220 mmol) in 10 ml of dry THF under argon. After refluxing 17 h the reaction mixture was quenched by stirring 2 h with sodium sulfate decahydrate (1.00 g, 3.10 mmol). The reaction was filtered and the residue washed with three 10 ml portions of THF. Concentration of the combined filtrates under reduced pressure gave 0.44 g of white solid, which was purified by flash chromatography (30% ethyl acetate/hexanes on silica gel) and twofold recrystallization from aqueous ethanol, giving lustrous white crystals (92.0 mg, 0.303 mmol, 22%), m.p. 144–149° C.

Example 11

5α-Chloro-6β,19-epoxypregn-17-en-3β-ol, 11.

Referring to SCHEME 3, compounds 11, 12, 13, and 14 were made as follows:

Ethyltriphenylphosphonium bromide (3.05 g, 8.22 mmol) and potassium t-butoxide (0.92 g, 8.2 mmol) were reacted under argon in anh. DMSO (9.2 ml) for 1 h in a 76–86° C. bath, following which 5α-chloro-6β,19-epoxyandrostan-3β-ol-17-one (555.9 mg, 1.640 mmol) in 9.2 ml of warm anh. DMSO was added and the mixture stirred a further 1 h. The reaction was then poured into 25 ml of ice-brine and extracted three times with 10 ml portions of ether. The combined organic extracts were washed with brine, dried over magnesium sulfate, and filtered through Celite. The residue was washed twice with 5 ml of ether and the combined filtrates were dried in vacuum. The residual yellow oil was purified by flash chromatography (60% ethyl acetate/hexanes on silica gel) to give a white syrupy solid (0.34 g, 0.97 mmol, 59%).

Example 12

5α-Chloro-6β,19-epoxypregn-17-en-3-one, 12.

A solution of 5α-chloro-6β,19-epoxypregn-17-en-3β-ol (11, 0.34 g, 0.97 mmol) in 35 ml of acetone was cooled in an ice-acetone bath and 0.47 ml of 2.67M Jones reagent were added. After stirring 40 min. the reaction was quenched with the addition of 0.5 ml of 2-propanol. Water (15 ml) was added, volatile components were removed under reduced pressure, and the mixture was extracted three times with 15 ml portions of methylene chloride. The combined organic extracts were washed with 15 ml of saturated sodium bicarbonate+15 ml of brine, dried over magnesium sulfate, and filtered through Celite. After washing the residue twice with 5 ml of methylene chloride the combined filtrates were dried in vacuum. The residue was flash chromatographed on silica gel using 30% ethyl acetate/hexanes as eluent to give a white crystalline solid (0.34 g, 0.97 mmol, quantitative).

Example 13

6β,19-Epoxypregn-4,17-dien-3-one, 13.

5α-chloro-6β,19-epoxypregn-17-en-3-one (12, 0.34 g, 0.97 mmol) was dissolved with warming in 10 ml of anh. methanol, potassium acetate (0.60 g, 6.1 mmol) was added, and 6.5 ml of solvent were distilled off at room pressure. The residue was concentrated under reduced pressure, taken up in 25 ml of water, and extracted three times with 10 ml portions of methylene chloride. The combined organic extracts were dried over magnesium sulfate and filtered through Celite. The residue was washed with 10 ml of methylene chloride and the combined filtrates concentrated under reduced pressure to give a white crystalline solid

Example 14
Pregna-4,17-dien-19-ol-3-one, 14.

To a solution of 6β,19-epoxypregna-4,17-dien-3-one (290.0 mg, 0.9281 mmol) in 10 ml of glacial acetic acid was added zinc dust (1.12 g, 17.1 mg-atom) activated by stirring 2 min. with 10% hydrochloric acid followed by washing with water and acetone. The suspension was stirred vigorously for 10 min. in a 99–102° C. and was then filtered through Celite. The residue was washed 4 times with 10 ml of acetic acid and the combined filtrates were concentrated in vacuum. The residue was taken up in 50 ml of ethyl acetate, washed with 50 ml of water+50 ml of saturated sodium bicarbonate+50 ml of brine, dried over magnesium sulfate, and filtered through Celite. The residue was washed with 10 ml of ethyl acetate and the combined filtrates dried in vacuum. The residue was recrystallized from ethyl acetate to give white crystals (46.4 mg, 0.148 mmol, 16%), m.p. 192–195° C.

Example 15
Pregn-4-en-3β-ol-20-yne, 15.

Pregn-4-en-3β-ol-20-yne, 15: Pregna-4-en-3-on-20-yne (200.1 mg, 0.6750 mmol) and lithium aluminum tri(t-butoxy)hydride (343.8 mg, 1.352 mmol) were suspended in 3.6 ml of anhydrous ether. After reacting 4 h, a further 343.5 mg (1.351 mmol) of hydride were added and the reaction was allowed to continue 16 h. See Scheme 4. After quenching with sodium sulfate decahydrate (3.41 g) the reaction mixture was agitated 15 min. and then filtered through diatomaceous earth. The residue was extracted 5 times with 10 ml portions of ether and the combined filtrates were concentrated under reduced pressure. Flash chromatography of the residue (25% ethyl acetate/hexanes on silica gel) followed by recrystallization from aqueous ethanol yielded a white powder (85.0 mg, 0.285 mmol, 42%), m.p. 120.5–123.5° C.

Example 16
20,21-Dimethylpregna-4,20E-diene-3,6-dione, 16.

Jones reagent (2.67 M, 1.75 ml, 4.67 mmol) was added to a solution of 20,21-dimethylpregna-5,20E-dien-3β-ol (400.0 mg, 1.281 mmol) in 45 ml of acetone and the reaction was stirred 30 min. The mixture was then poured into 85 ml of water and extracted three times with 40 ml portions of ethyl acetate. The combined organic extracts were washed with 40 ml of saturated sodium bicarbonate+40 ml of brine, dried over magnesium sulfate, and filtered through diatomaceous earth. The residue was washed with 10 ml of ethyl acetate and the combined filtrates were concentrated under reduced pressure. Flash chromatography (20% ethyl acetate/hexanes on silica gel) of the residue followed by recrystallization from aqueous ethanol gave light yellow needles (119.1 mg, 0.3497 mmol, 29%), m.p. 171–173° C. TLC (20% ethyl acetate/hexanes on silica gel) showed a major component at $R_f$ 0.17 with a minor contaminant at $R_f$ 0.24.

Example 17
20-Methylpregna-4,20-diene-3,6-dione, 17.

Jones reagent (2.67 M, 1.83 ml, 4.89 mmol) was added to a solution of 20-methylpregna-5,20-dien-3β-ol (400.0 mg, 1.272 mmol) in 45 ml of acetone and the reaction was stirred 20 min. After quenching with 2-propanol (0.91 ml) the mixture was poured into 85 ml of water and extracted three times with 40 ml portions of ethyl acetate. The combined organic extracts were washed with 40 ml of saturated sodium bicarbonate+40 ml of brine, dried over magnesium sulfate, and filtered through diatomaceous earth. The residue was washed with 25 ml of ethyl acetate and the combined filtrates were concentrated under reduced pressure. Recrystallization of the solid residue from aqueous ethanol gave yellow crystals (235.0 mg, 0.7298 mmol, 57%), m.p. 148–150° C. TLC (20% ethyl acetate/hexanes on silica gel) showed a major product at $R_f$ 0.24 with a minor impurity at the origin.

Example 18
Pregna-4,16-diene-3,6-dione, 18.

Jones reagent (2.67 M, 0.23 ml, 0.61 mmol) was added to a solution of pregna-5,16-dien-3β-ol (45.5 mg, 0.151 mmol) in 5 ml of acetone and the mixture was stirred 20 min. After quenching with 2-propanol (0.11 ml) 10 ml of water were added and the mixture was extracted three times with 5 ml portions of ethyl acetate. The combined organic extracts were washed with 5 ml of saturated sodium+5 ml of brine, dried over magnesium sulfate, and filtered through diatomaceous earth. The residue was washed with 5 ml of ethyl acetate and the combined filtrates were concentrated under reduced pressure. Preparative TLC (25% ethyl acetate/hexanes on silica gel) of the residue gave a light yellow solid (10.6 mg, 33.9 μmol, 22%) homogeneous to TLC ($R_f$ 0.41, 25% ethyl acetate/hexanes on silica gel; starting material $R_f$ 0.30).

Example 19
Pregna-4,17,20-triene-3,6-dione, 19.

Jones reagent (2.67 M, 1.03 ml 2.75 mmol) was added to pregna-5,17,20-trien-3β-ol (214.5 mg, 0.7187 mmol) in 25 ml of acetone and the mixture was stirred 20 min. After quenching with 2-propanol (0.52 ml), the mixture was poured into 50 ml of water and extracted three times with 25 ml portions of ethyl acetate. The combined organic extracts were washed with 25 ml of saturated sodium bicarbonate+25 ml of brine, dried over magnesium sulfate, and filtered through diatomaceous earth. The residue was washed with 10 ml of ethyl acetate and the combined filtrates were concentrated under reduced pressure. Recrystallization with concomitant treatment with charcoal in aqueous ethanol gave light yellow needles (67.7 mg, 0.218 mmol, 30%), m.p. 140–143. TLC (25% ethyl acetate/hexanes on silica gel) shows product at $R_f$ 0.43 with minor contaminants at $R_f$ 0.86, 0.14, 0.08, and 0.00 (pregna-5,17-dien-3β-ol $R_f$ 0.32).

Example 20
21-Methylene-20(R)-methylpregn-4-en-3-one, 20.

Aluminum isopropoxide (0.39 g, 1.9 mmol) in 3.6 ml of hot toluene was added to a solution of 21-methylene-20(R)-methylpregn-5-en-3β-ol (208.2 mg, 0.6337 mmol) in cyclohexanone (3.6 ml, 35 mmol) and 18 ml of toluene, and the mixture was refluxed with exclusion of moisture for 2 h. After cooling in ice, 0.92 ml of water and 2.2 ml of 3.6 N sulfuric acid were added and the mixture was shaken 1 min. Further water (4.6 ml) was added, the mixture was shaken 5 min., and the aqueous phase was discarded. Volatile components were removed by azeotropic/steam distillation and the resulting aqueous suspension was extracted three times with 5 ml portions of methylene chloride. The combined organic extracts were filtered through a small column of sodium sulfate resting on a bed of diatomaceous earth, all of which was contained in a Pasteur pipette. The residue was washed with 5 ml of methylene chloride and the combined filtrates were concentrated under reduced pressure. Recrystallization of the residual film gave white needles (152.7 mg, 0.4677 mmol, 74%), m.p. 138–139° C. TLC (25% ethyl (290.0 mg, 0.9281 mmol, 96%) homogeneous to TLC (60% ethyl acetate/hexanes on silica gel; $R_f$ 0.61).

Example 21
21-Methylene-20(R)-methylpregn-4-en-3β-ol, 21.

A suspension of 21-methylene-20(R)-methylpregn-4-en-3-one (5, 100.0 mg, 0.3063 mmol) and lithium tri-t-butoxyaluminohydride (319.4 mg, 1.256 mmol) in 5 ml of anh. THF was stirred under argon for 6 h, after which water (48 μL), 15% (w/w) sodium hydroxide (48 μL), and water (143 μL) were added. The mixture was filtered through diatomaceous earth and the residue was extracted four times with 5 ml aliquots of THF. Concentration of the combined filtrates under reduced pressure and two-fold recrystallization from aqueous ethanol gave white platelets (42.6 mg, 0.130 mmol, 42%), m.p. 121–123° C. TLC (25% ethyl acetate/hexanes on silica gel) shows major product at $R_f$ 0.38 and minor product at $R_f$ 0.43 (starting material $R_f$ 0.50).

Example 22
21-Methylene-20(R)-methylpregn-4-ene-3,6-dione, 22.

Jones reagent (2.67 M, 0.68 ml, 1.8 mmol) was added to 21-methylene-20(R)-methylpregn-5-en-3β-ol (149.8 mg, 0.4560 mmol) in 15 ml of acetone and the reaction was stirred 20 min. After quenching with 2-propanol (0.34 ml), the mixture was poured into 30 ml of water and extracted three times with 15 ml portions of ethyl acetate. The combined organic extracts were washed with 15 ml of saturated sodium bicarbonate+15 ml of brine, dried over magnesium sulfate, and filtered through diatomaceous earth. The residue was washed with 10 ml of ethyl acetate and the combined filtrates were concentrated under reduced pressure. Preparative TLC of the residue (25% ethyl acetate/hexanes on silica gel GF, 1000μ) gave a yellow, crystalline solid (49.7 mg, 0.146 mmol, 32%) homogeneous to TLC (25% ethyl acetate/hexanes; $R_f$ 0.47; starting material $R_f$ 0.35).

Example 23
Pregn-4-en-3β-ol-20-yne, 23.

Lithium tri-t-butoxyaluminohydride (343.8 mg, 1.352 mmol) was added to preen-4-en-3-on-20-yne (200.1 mg, 0.6750 mmol) suspended in 3.6 ml of anh. ether and the mixture was stirred 4 h. Additional hydride (343.5 mg, 1.351 mmol) was added and the reaction was stirred a further 16 h. Glauber's salt (3.41 g) was added and the suspension was agitated 15 min. The mixture was filtered through diatomaceous earth and the residue was extracted five times with 10 ml portions of ether. Concentration of the combined filtrates under reduced pressure followed by flash chromatography (25% ethyl acetate/hexanes on silica gel) and recrystallization from aqueous ethanol gave a white powder (85.0 mg, 0.285 mmol, 42%), m.p. 120.5–123.5° C. TLC (25% ethyl acetate/hexanes on silica gel) showed product ($R_f$ 0.23) contaminated with traces of what appeared to be starting material ($R_f$ 0.29).

Example 24
Pregn-4,16-dien-6β-ol-3-on-20-yne, 24.

3-chloroperbenzoic acid (290.0 mg, 1.680 mmol) in 9.4 ml of 1,2-dimethoxyethane+3.6 ml of water was added to a suspension of pregna-3,5,16-trien-20-yn-3-yl methyl ether (471.0 mg, 1.527 mmol) in 1,2-dimethoxyethane (9.4 ml) and the reaction was stirred 30 min. The mixture was poured into 50 ml of saturated sodium bicarbonate and extracted three times with 50 ml of ethyl acetate. The combined organic extracts were washed with 50 g of 5% (w/w) sodium thiosulfate pentahydrate+three 50 ml aliquouts of brine, dried over magnesium sulfate, and filtered through diatomaceous earth. The residue was washed with 25 ml of ethyl acetate and the combined filtrates were concentrated under reduced pressure. Flash chromatography (50% ethyl acetate/hexanes on silica gel) of the residue, followed by recrystallization from aqueous ethanol gave a light yellow solid (145.9 mg, 0.4700 mmol, 31%), m.p.>300° C.

Example 25
Chola-5,16,20(22)-trien-3β-ol, 25.

A suspension of propyltriphenylphosphonium bromide (12.13 g, 31.48 mmol) and potassium t-butoxide (3.54 g, 31.5 mmol) in anh. DMSO (35 ml) under argon atmosphere was placed in an oil bath (72–87° C.) and then stirred 1 h. Pregna-5,16-dien-3β-ol-20-one (1.9807 g, 6.298 mmol) in 35 ml of warm anh. DMSO was added and the reaction was stirred 90 min. The mixture was then poured into 90 ml of ice-brine and extracted with three 45 portions of ether. The combined organic extracts were washed with 45 ml of brine, dried over sodium sulfate, and filtered. The residue was washed with 10 ml of ether and the combined filtrates were concentrated under reduced pressure. Flash chromatography (20% ethyl acetate/hexanes on silica gel) of the resulting oil gave an amber resin (103.6 mg, 0.3042 mmol, 4.8%).

Example 26
Chola-4-20(22)E-diene-4,6-dione, 26.

Jones reagent (2.67 M, 1.26 ml, 3.36 mmol) was added to chola-5,20(22)E-dien-3β-ol (300.0 mg, 0.8758 mmol) in 30 ml of acetone and the reaction was stirred 20 min. After quenching with 2-propanol (0.63 ml), the mixture was poured into 60 ml of water and extracted three times with 30 ml portions of ethyl acetate. The combined organic extracts were washed with 30 ml of saturated sodium bicarbonate+30 ml of brine, dried over magnesium sulfate, and filtered through diatomaceous earth. The residue was washed with 10 ml of ethyl acetate and the combined filtrates were concentrated under reduced pressure. Recrystallization from aqueous ethanol gave a yellow solid (139.3 mg, 0.3929 mmol, 45%), m.p. 109–116° C. TLC (25% ethyl acetate/hexanes on silica gel) shows a major product ($R_f$ 0.45) with contaminants at $R_f$ 0.24, 0.1, and 0.08 (chola-4,20(22)E-dien-3-one $R_f$ 0.49).

Example 27
Chola-4,20(22)E-dien-3-one, 27.

Aluminum isopropoxide (2.82 g, 13.8 mmol) in 26 ml of hot toluene was added to chola-5,20(22)E-dien-3β-ol (1.5777 g, 4.605 mmol) in cyclohexanone (26 ml, 0.25 mol)+130 ml of toluene and the reaction was refluxed 4 h with exclusion of moisture. After cooling, water (6.7 ml) and 3.6 N sulfuric acid (16 ml) were added and the mixture was shaken 1 min. Further water (32 ml) was added, the mixture was shaken 5 min., and the aqueous layer was discarded. The volatile components were removed by azeotropic/steam distillation and the resulting aqueous suspension was extracted three times with 20 ml portions of methylene chloride. The combined organic extracts were dried over magnesium sulfate and filtered through diatomaceous earth. The residue was washed with 10 ml of methylene chloride and the combined filtrates were concentrated under reduced pressure. Recrystallization from aqueous ethanol with concomitant treatment with charcoal gave light yellow crystals (1.3317 g, 3.9104 mmol, 85%), m.p. 133–135° C. TLC (25% ethyl acetate/hexanes on silica gel) showed the product was homogeneous ($R_f$ 0.49; starting material $R_f$ 0.31).

Example 28
Chola-4,20(22)E-dien-3β-ol, 28.

A suspension of chola-4,20(22)E-dien-3-one (3, 400.0 mg, 1.175 mmol) and lithium tri-t-butoxyaluminohydride (1.2250 g, 4.8158 mmol) in 15 ml of anh. ether was stirred under argon for 8 h. Glauber's salt (6.07 g) was added, the mixture was stirred 5 min., and was then filtered through diatomaceous earth. The residue was extracted five times with 15 ml portions of ether and the combined filtrates were concentrated under reduced pressure. Preparative TLC (5% ethyl acetate/methylene chloride on silica gel, 1000μ) of the residue gave a light yellow solid (49.9 mg, 0.146 mmol, 12%) homogeneous to TLC (5% ethyl acetate/methylene chloride on silica gel, $R_f$ 0.34; pregna-5,20-dien-3β-ol $R_f$ 0.26).

Example 29
Chola-3,5,20(22)E-trien-3-yl methyl ether, 29.

A mixture of chola-4,20(22)E-dien-3-one (808.6 mg, 2.374 mmol), 2,2-dimethoxypropane (3.1 ml, 25 mmol), dimethylformamide (3.1 ml), methanol (0.13 ml), and p-toluenesulfonic acid monohydrate (28.0 mg, 0.147 mmol) was refluxed 4 h with exclusion of moisture. After cooling, sodium bicarbonate (0.17 g) was added and the mixture was partitioned between 30 ml of water and 50 ml of ether. The organic layer was washed with 30 ml of brine, dried over magnesium sulfate, and filtered through diatomaceous earth. The residue was washed with 10 ml of ether and the combined filtrates were concentrated under reduced pressure. Recrystallization of the resulting solid from acetone gave a light yellow solid (453.8 mg, 1.280 mmol, 54%), m.p. 94–96° C. TLC (10% ethyl acetate/hexanes on silica gel) showed product at $R_f$ 0.62 with a trace of starting material ($R_f$ 0.14).

Example 30
Chola-4,20(22)E-dien-6β-ol-3-one, 30.

3-Chloroperbenzoic acid (183.0 mg, 1.060 mmol) in 5.9 ml of 1,2-dimethoxyethane+2.3 ml of water was added to chola-3,5,20(22)E-trien-3-yl methyl ether in 5.9 ml of 1,2-dimethoxyethane over 2½ min. After stirring the reaction a further ½ h, it was poured into 30 ml of saturated sodium bicarbonate and extracted three times with 30 ml portions of ethyl acetate. The combined organic extracts were washed with 30 g of 5% (w/w) sodium thiosulfate pentahydrate+ three 30 ml portions of brine, dried over magnesium sulfate, and filtered through diatomaceous earth. The residue was washed with 10 ml of ethyl acetate and the combined filtrates were concentrated under reduced pressure. Flash chromatography (60% ethyl acetate/hexanes on silica gel) of the resulting solid and subsequent preparative TLC (50% ethyl acetate/hexanes on silica gel) of the resulting solid and subsequent preparative TLC (50% ethyl acetate/hexanes on silica gel, 1000μ) gave a white crystalline solid (114.3 mg, 0.3206 mmol, 33%) consisting of two components by TLC (50% ethyl acetate/hexanes on silica gel; major $R_f$ 0.48, minor $R_f$ 0.41; chola-4,20(22)E-dien-3-one $R_f$ 0.74).

Example 31
Measurement of Autonomic Responses to Stimulation of the VNO.

Figure 2:
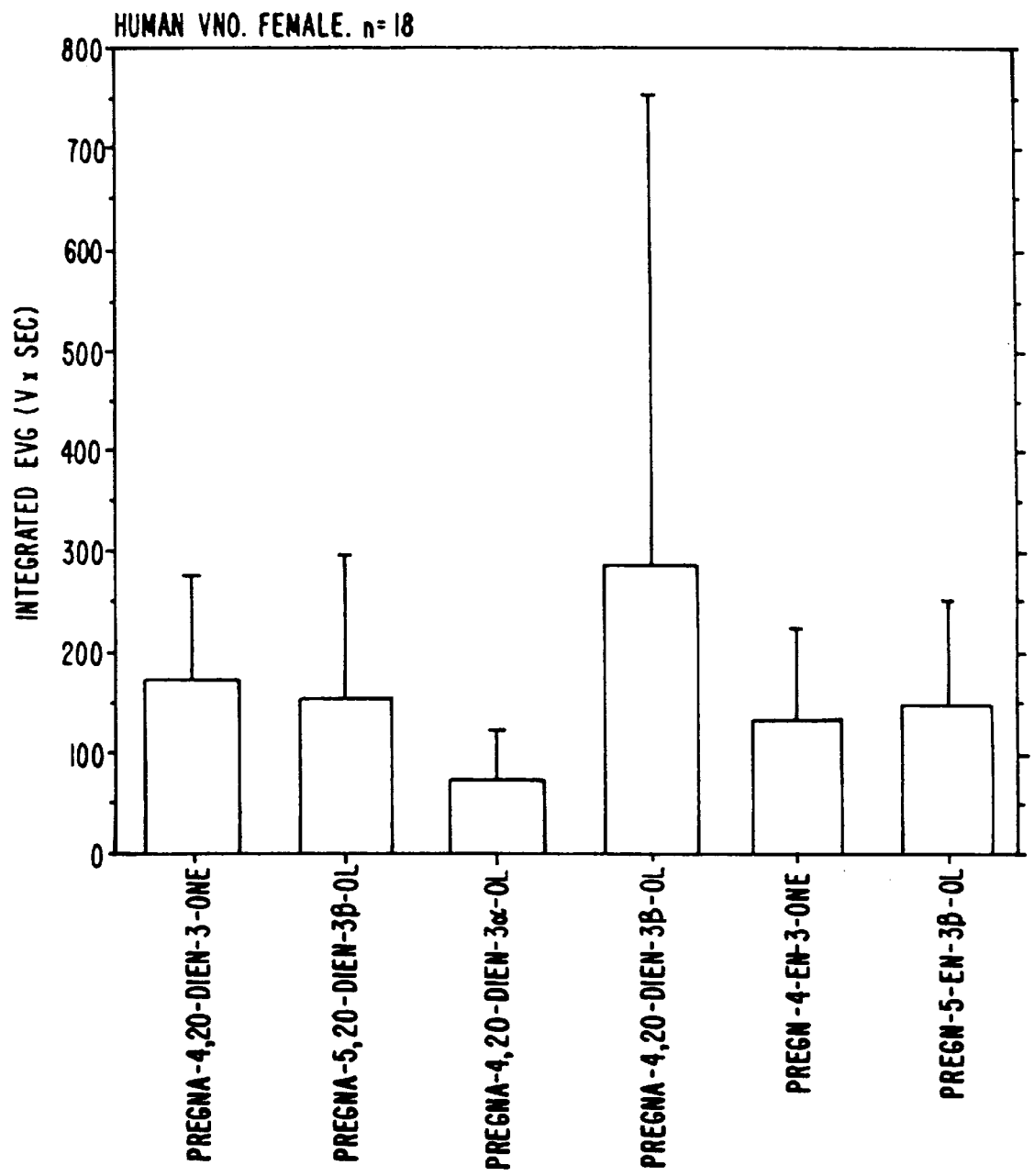
FIG. 2 is the data for the integrated EVG for compounds A1-P1, A2-P1, A4-P1, A3-P1, A1-P4, A2-P4 in females.
Figure 3:
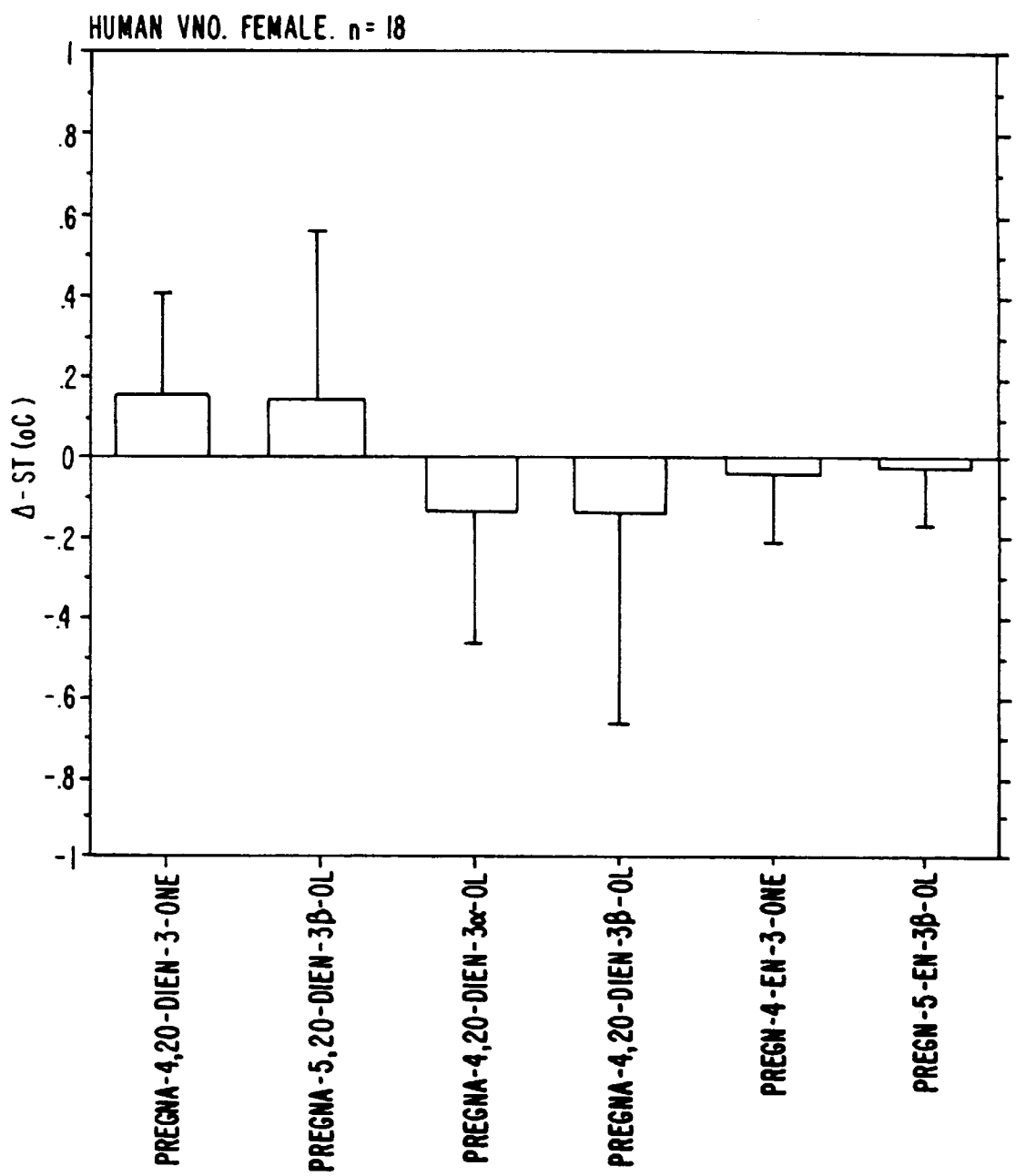
FIG. 3 is the data for the ST measurements of compounds A1-P1, A2-P1, A4-P1, A3-P1, A1-P4, A2-$P_4$ in females.
Figure 58:
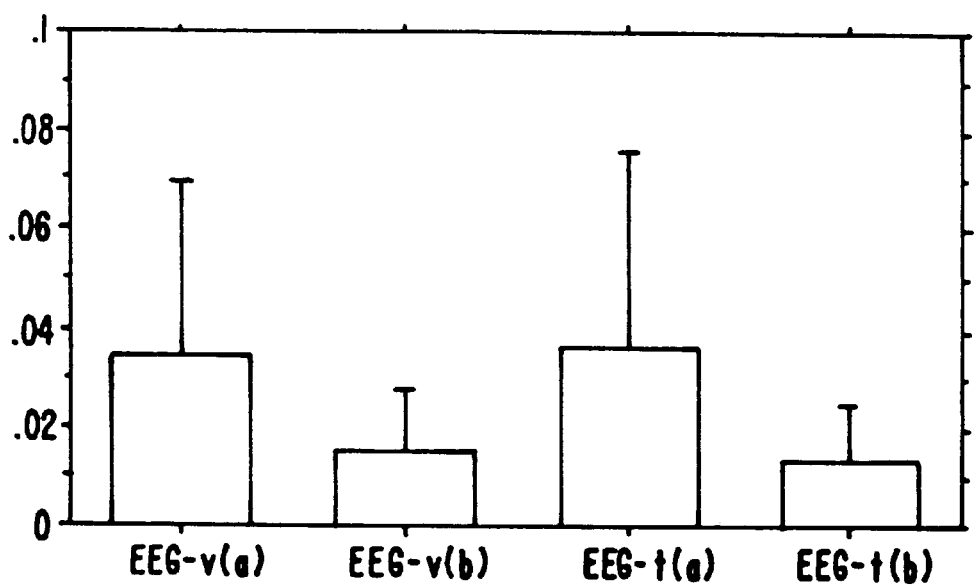
Figure 59:
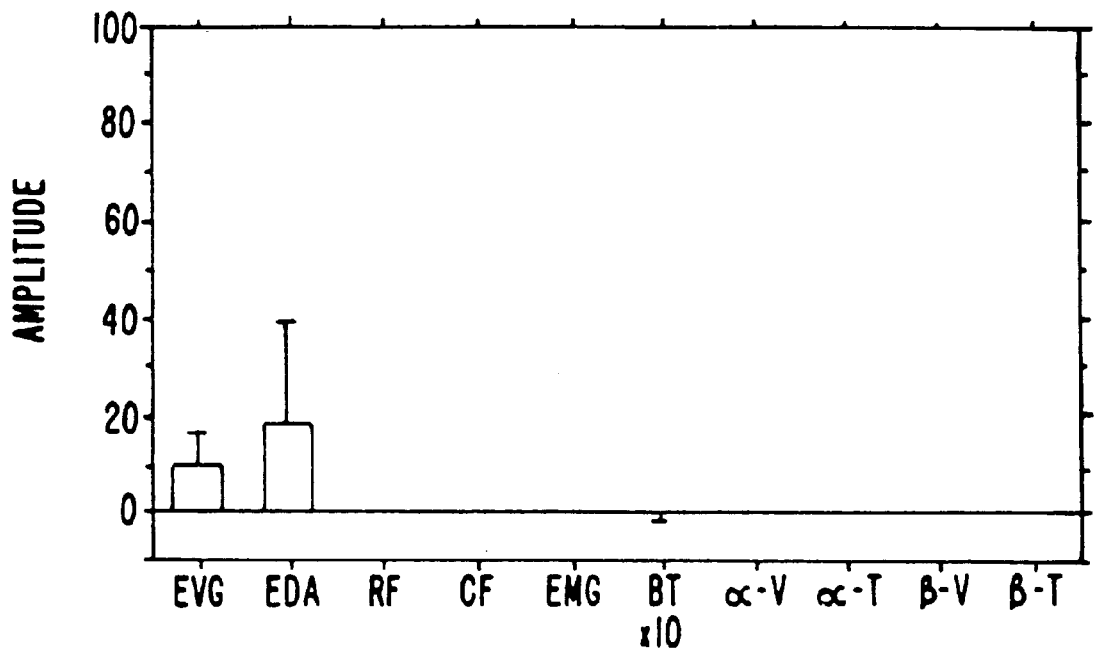
FIG. 59 shows EVG, EDA and BT data of measurements in women of compound A3/P1.
Figure 60:
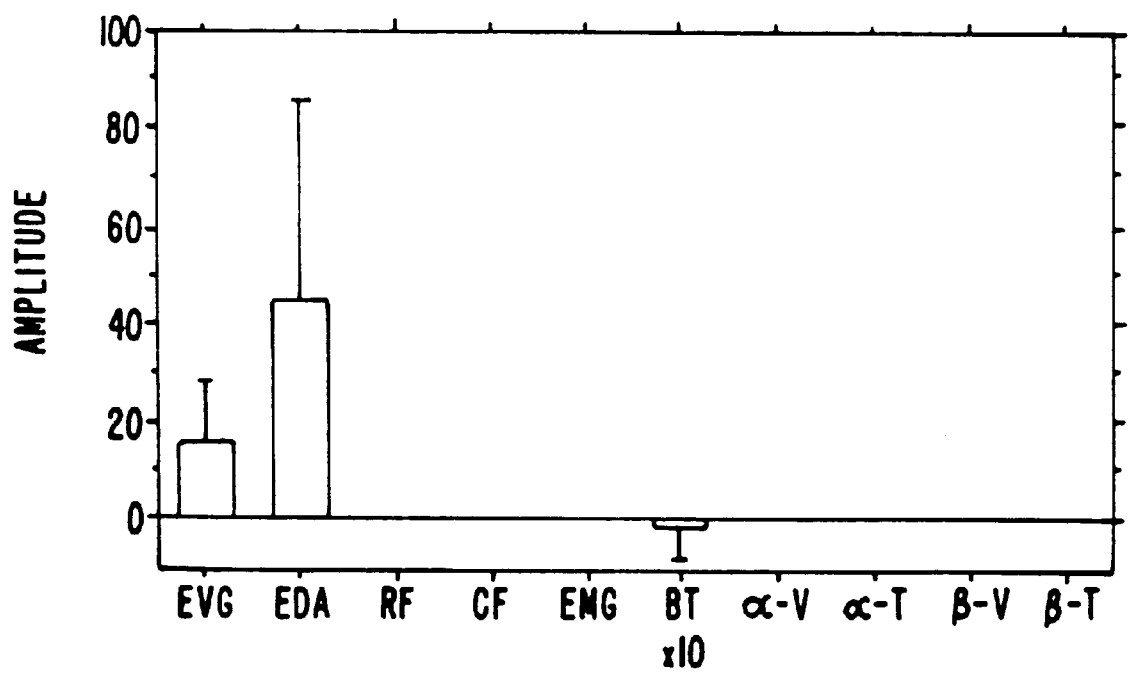
FIG. 60 shows EVG, EDA and BT data of measurements in women of compound A4/P1.
Figure 61:
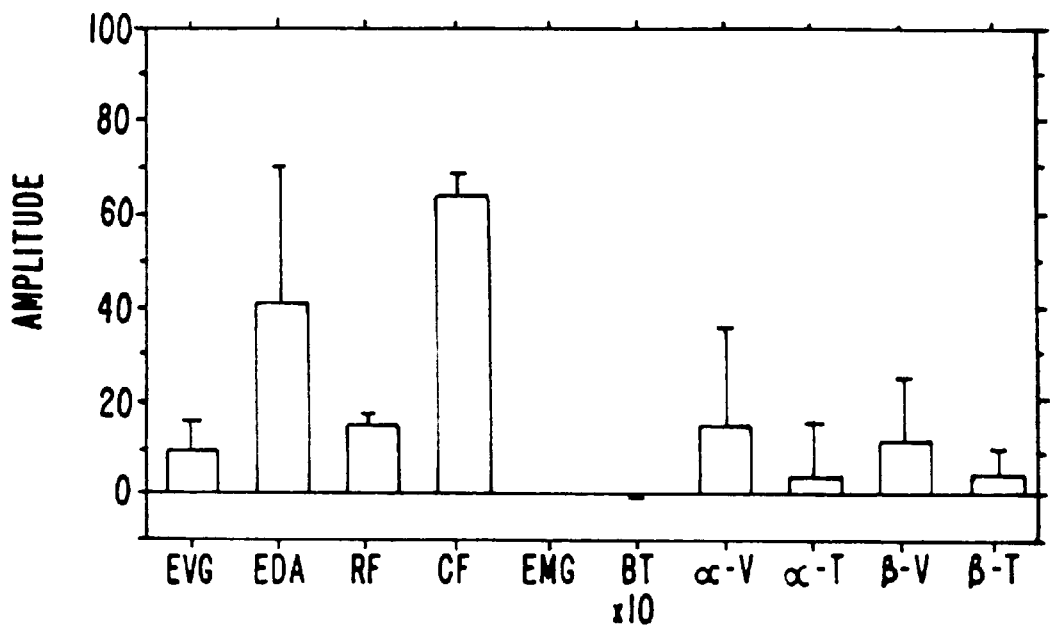
FIGS. 61 and 62 show data of measurements in men and women, respectively, of compound A8/P1.
Figure 62:
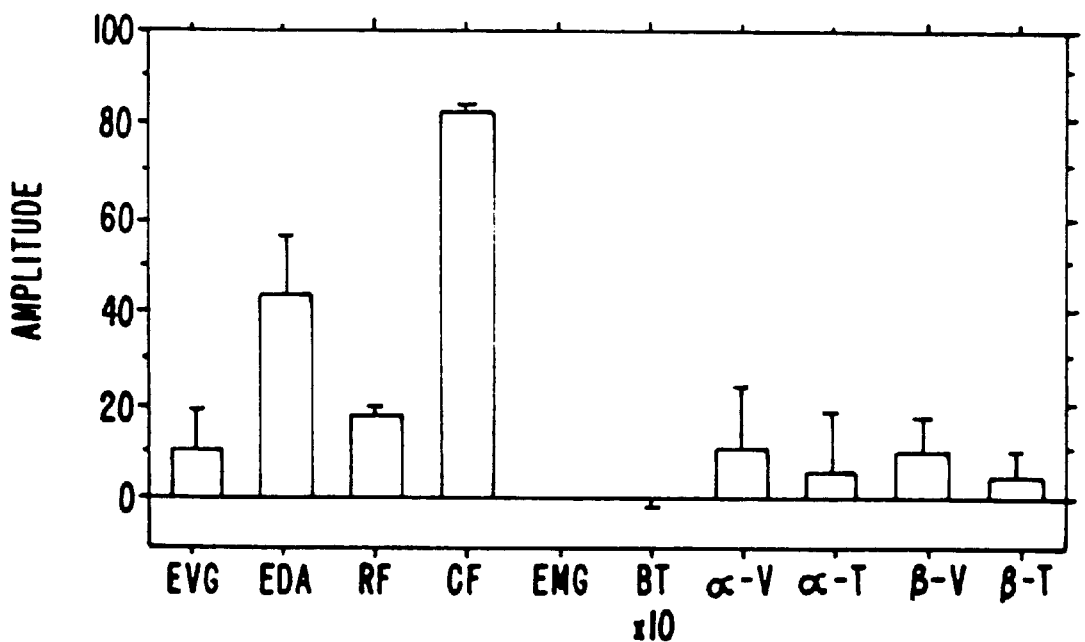
Figure 63:
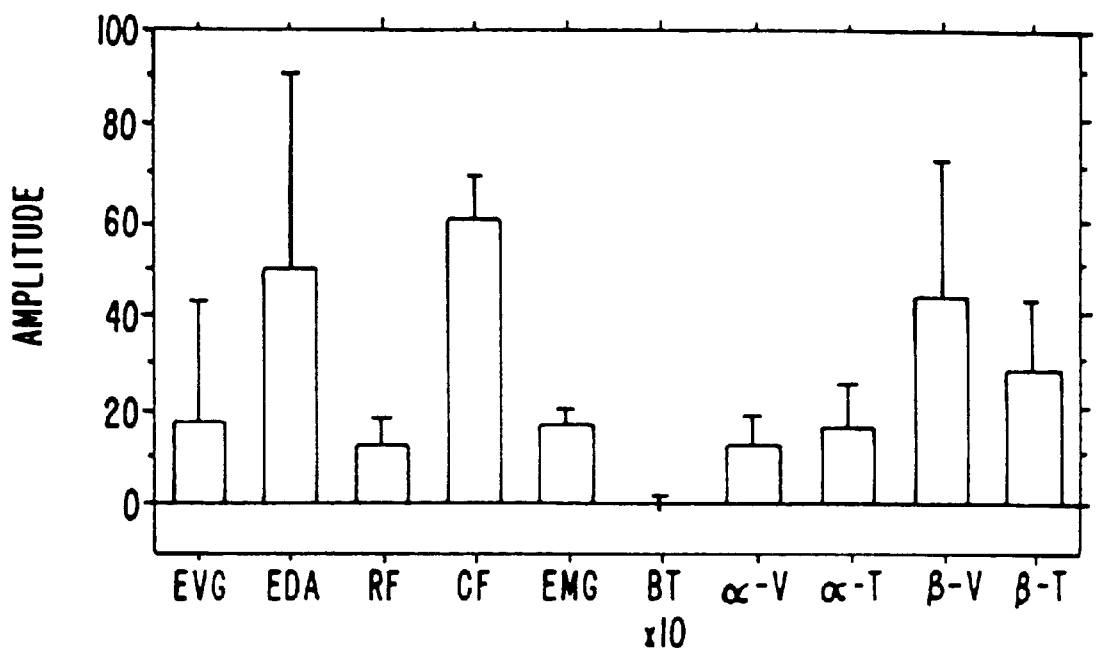
FIGS. 63 and 64 show data of measurements in men and women, respectively, of compound A13/P8.
Figure 64:
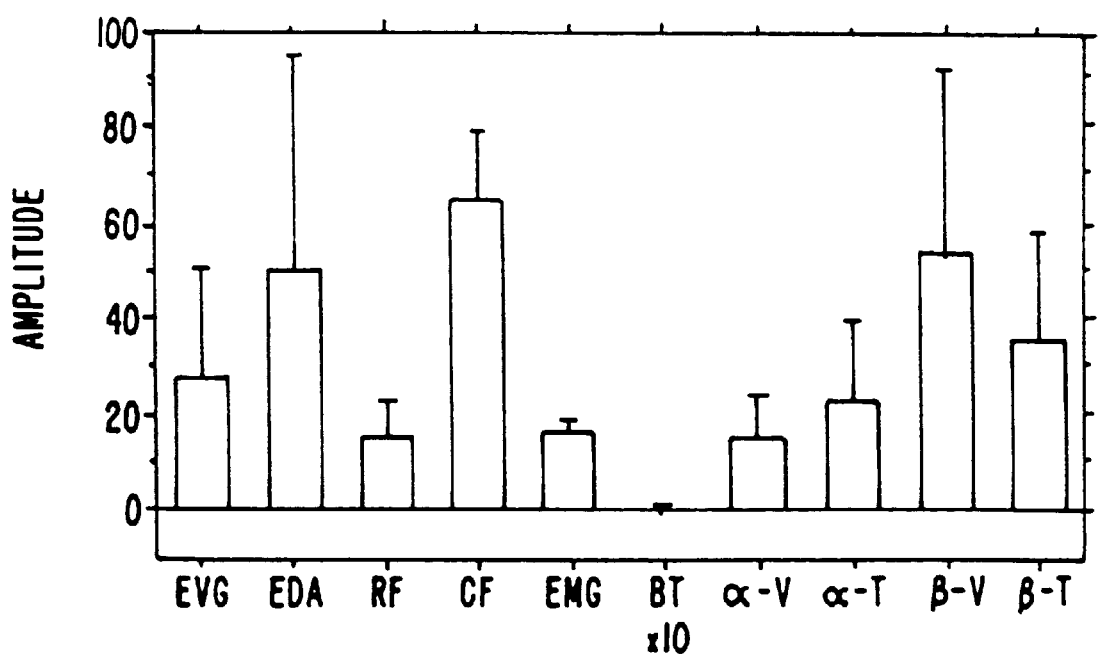
Figure 65:
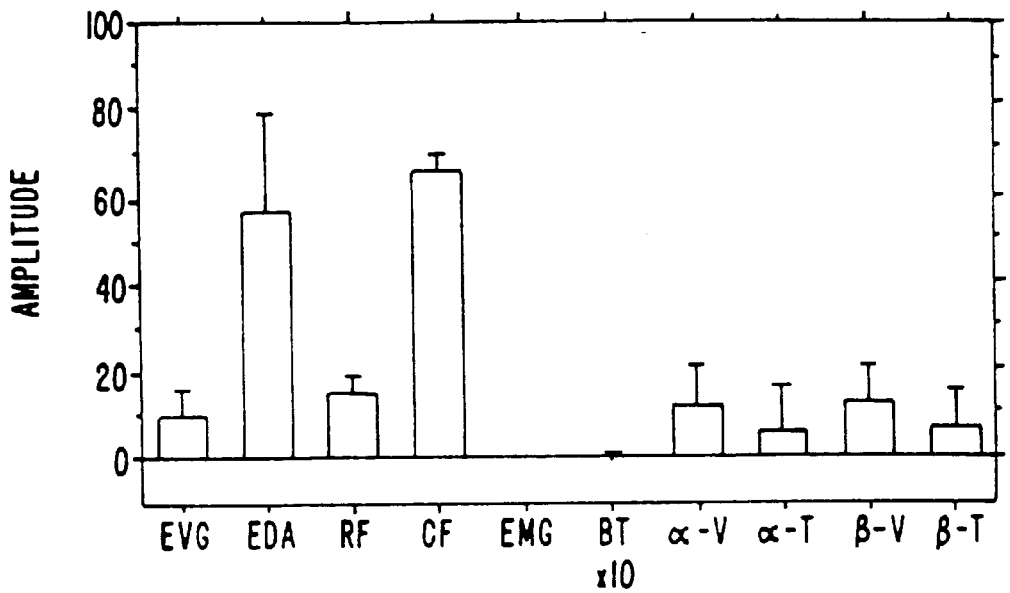
FIGS. 65 and 66 show data of measurements in men and women, respectively, of compound A6/P1.
Figure 66:
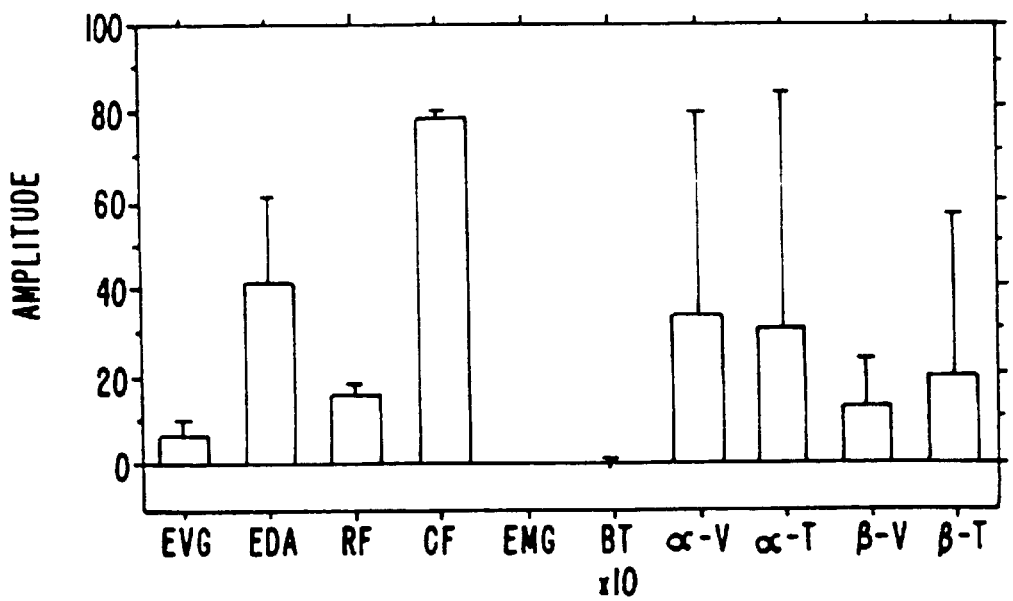
Figure 67:
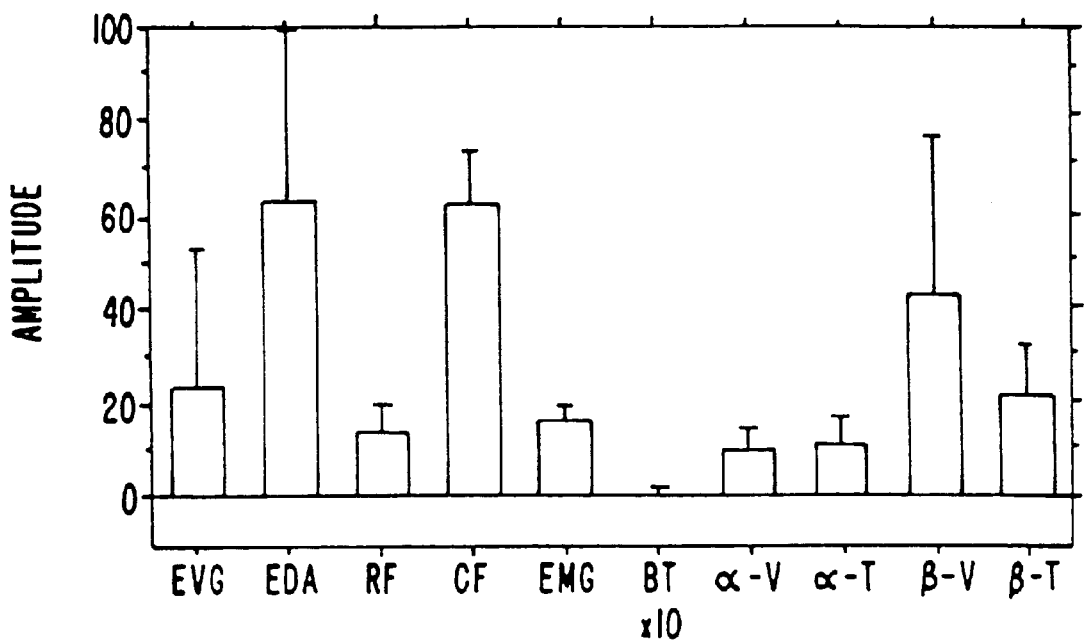
FIGS. 67 and 68 show data of measurements in men and women, respectively, of the 20-methyl derivative of compound A6/P1.
Figure 68:
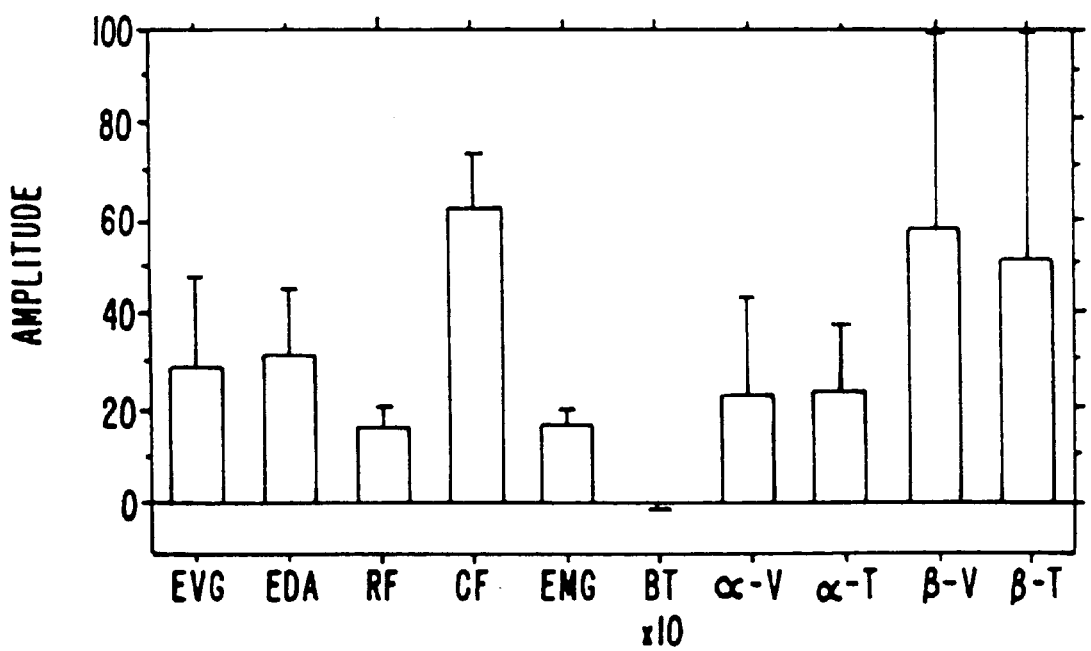
Figure 69:
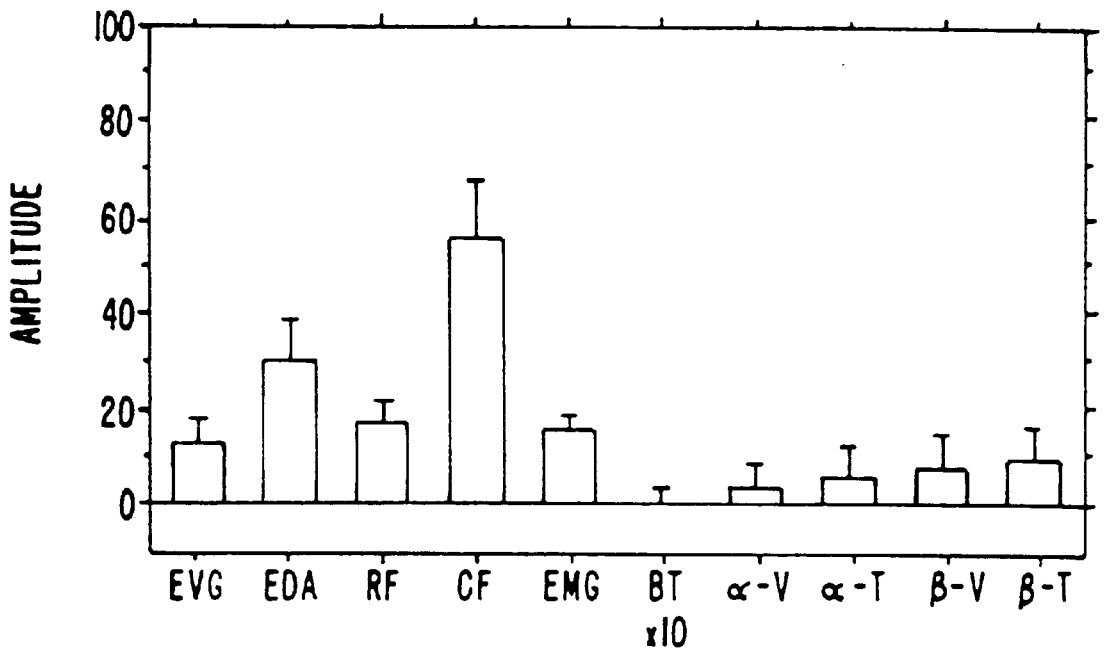
FIGS. 69 and 70 show data of measurements in men and women, respectively, of the 20,21-dimethyl derivative of compound A1/P1.
Figure 70:
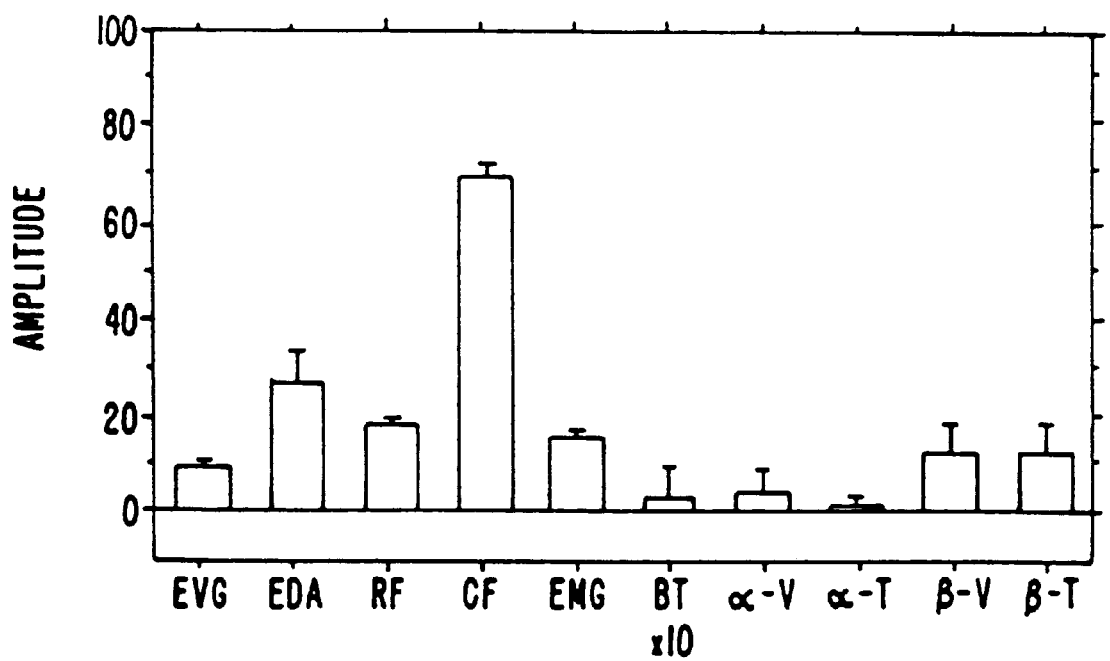
Figure 71:
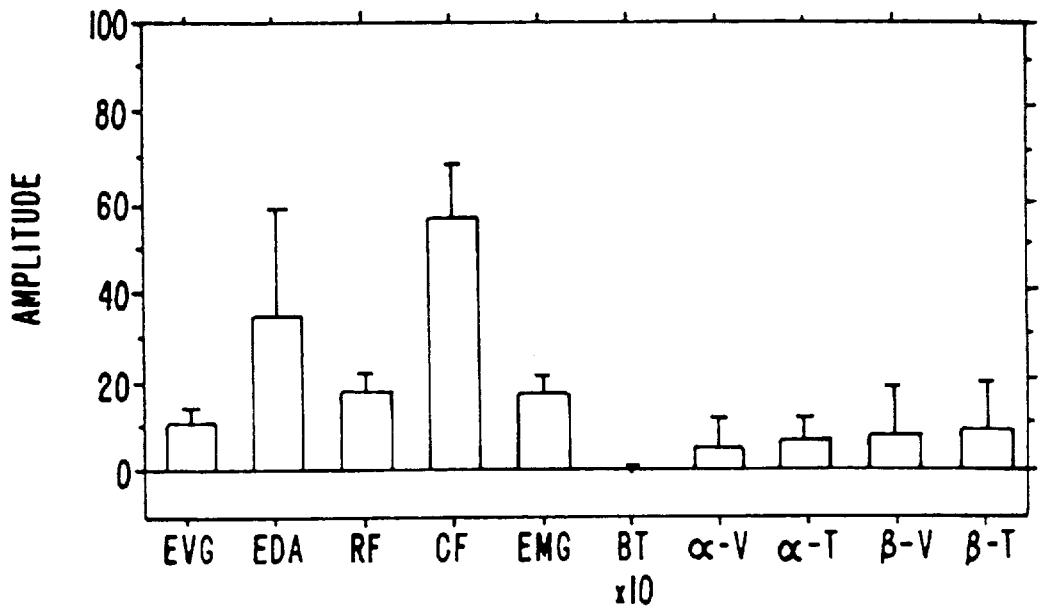
FIGS. 71 and 72 show data of measurements in men and women, respectively, of the 20,21-dimethyl derivative of compound A6/P1.
Figure 72:
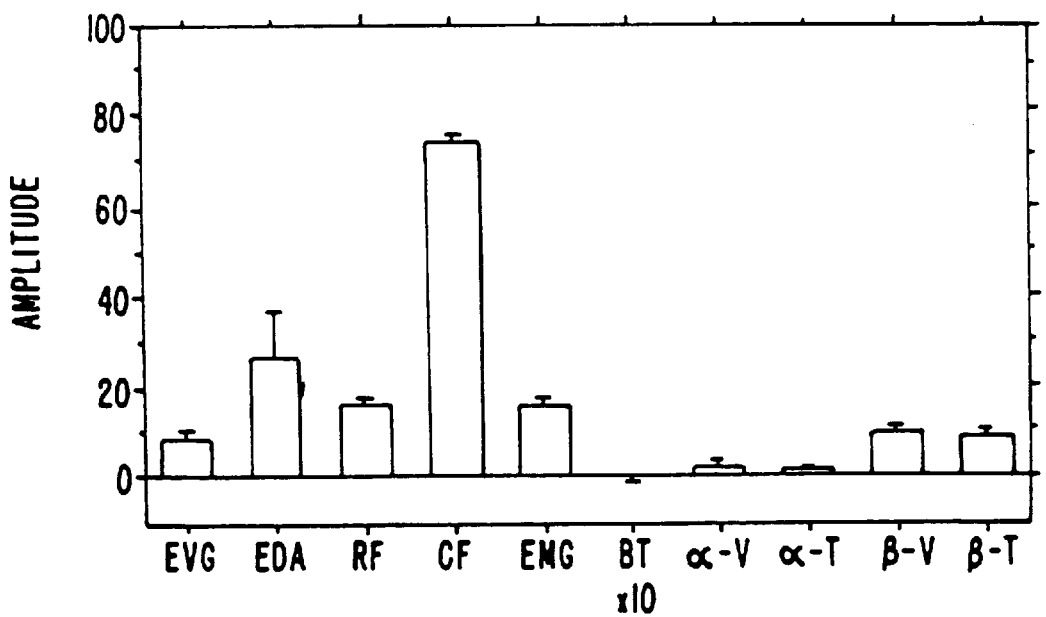
Figure 73:
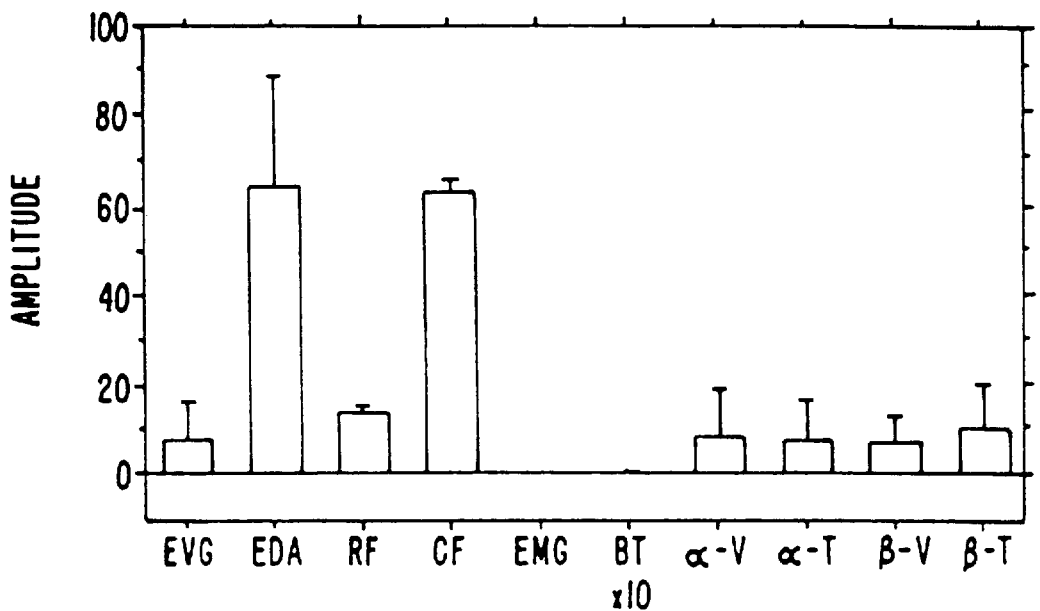
FIGS. 73 and 74 show the data of measurements in men and women, respectively, of compound A14/P2.
Figure 74:
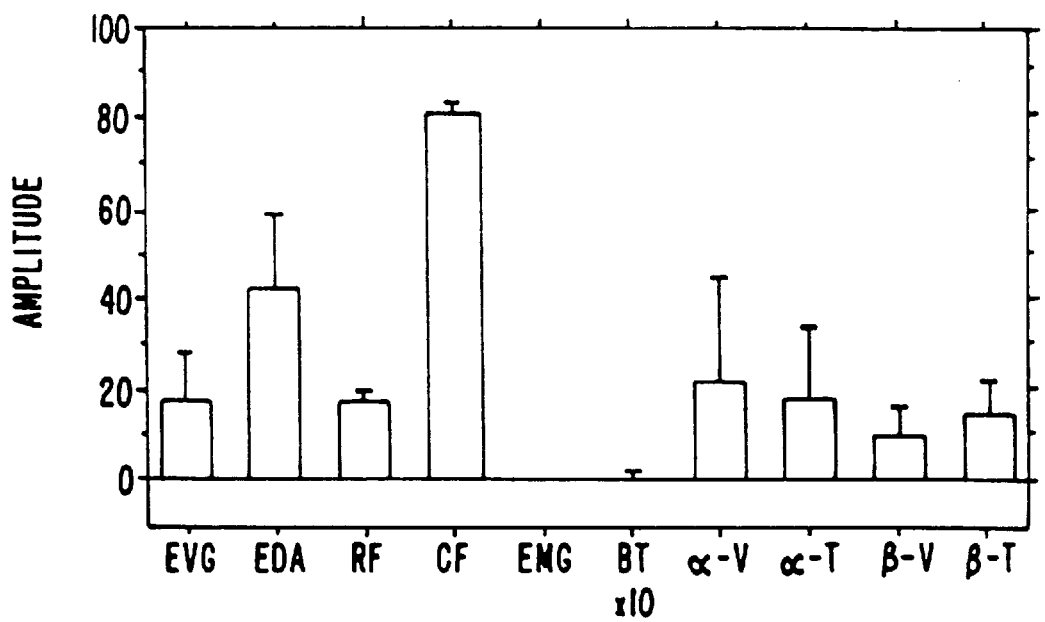
Figure 75:
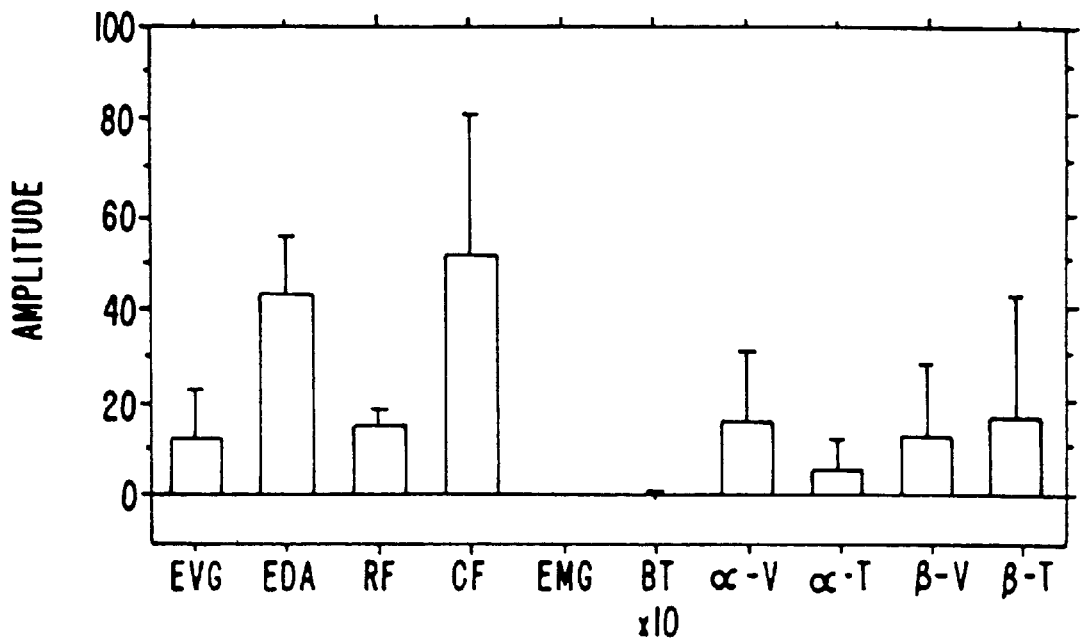
FIGS. 75 and 76 show the data of measurements in men and women, respectively, of compound A12/P1.
Figure 76:
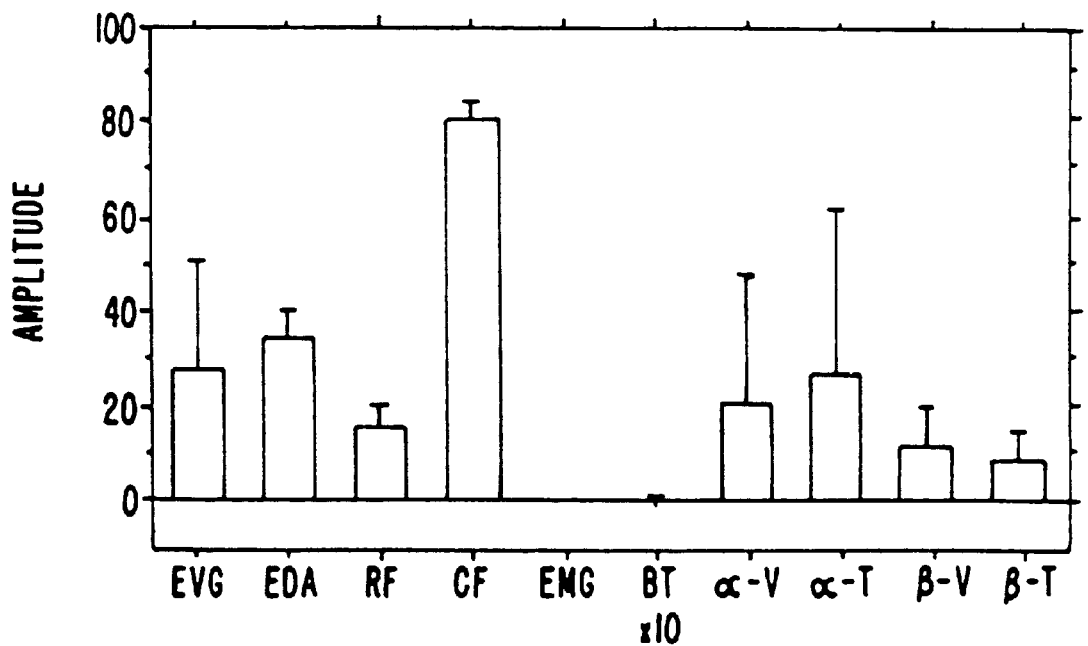
Figure 77:
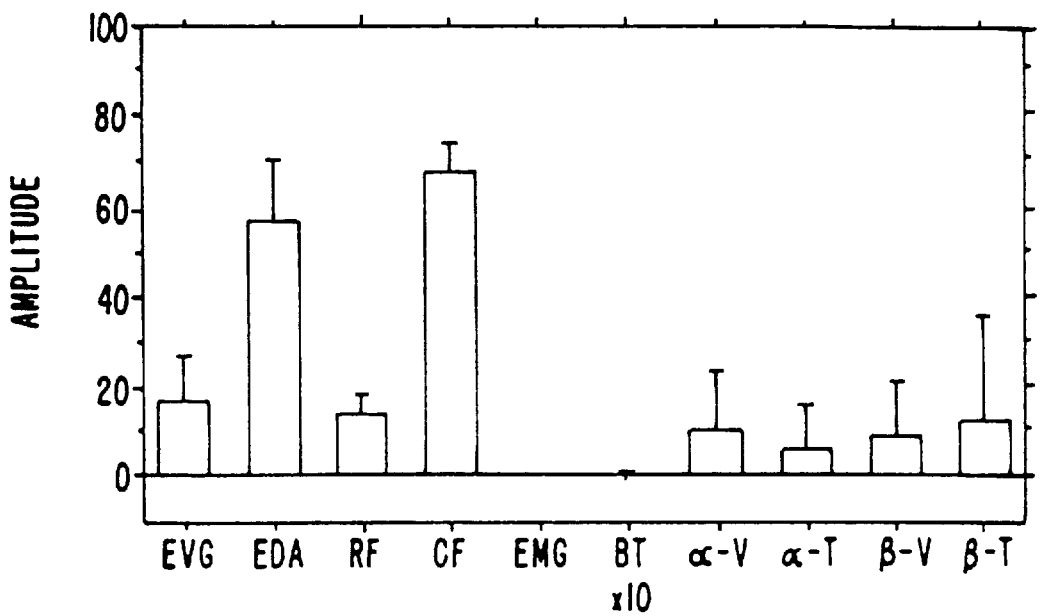
FIGS. 77 and 78 show the data of measurements in men and women, respectively, of compound A7/P2.
Figure 78:
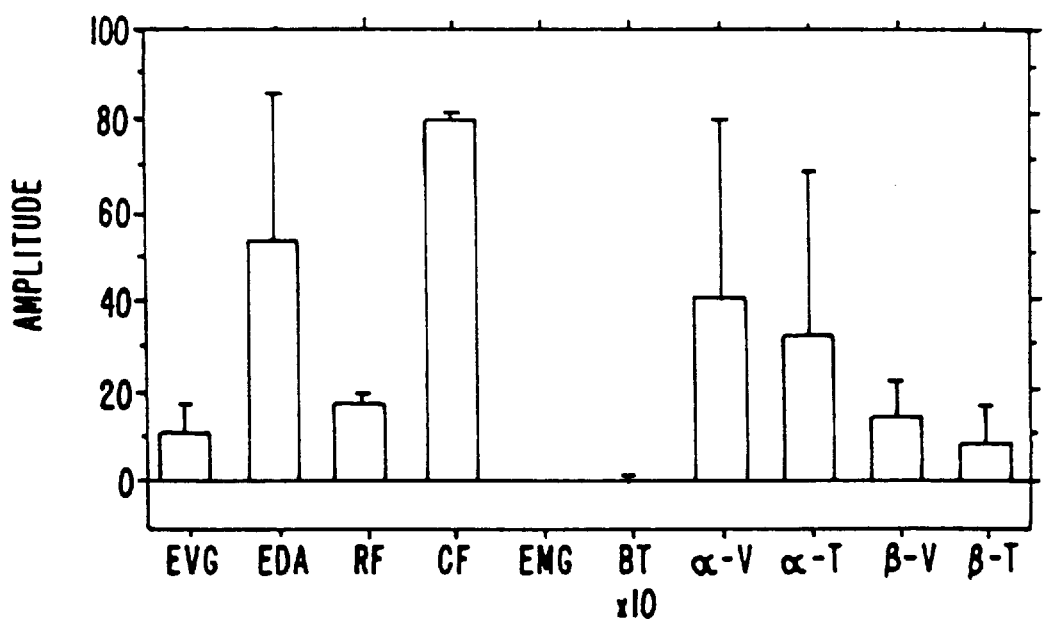
Figure 79:
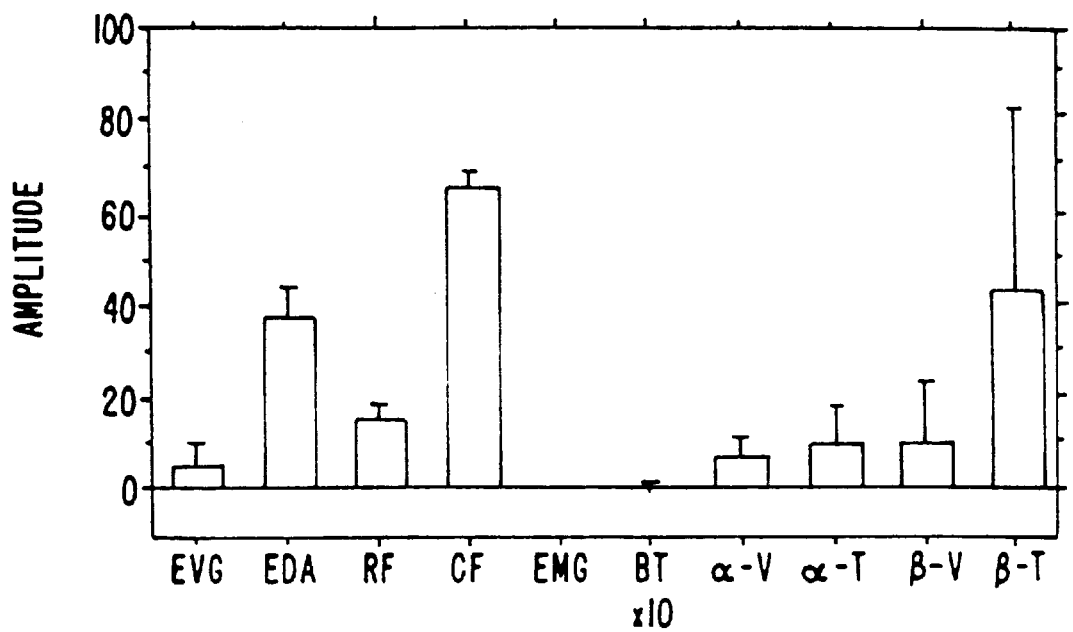
FIGS. 79 and 80 show the data of measurements in men and women, respectively, of compound A13/P1.
Figure 80:
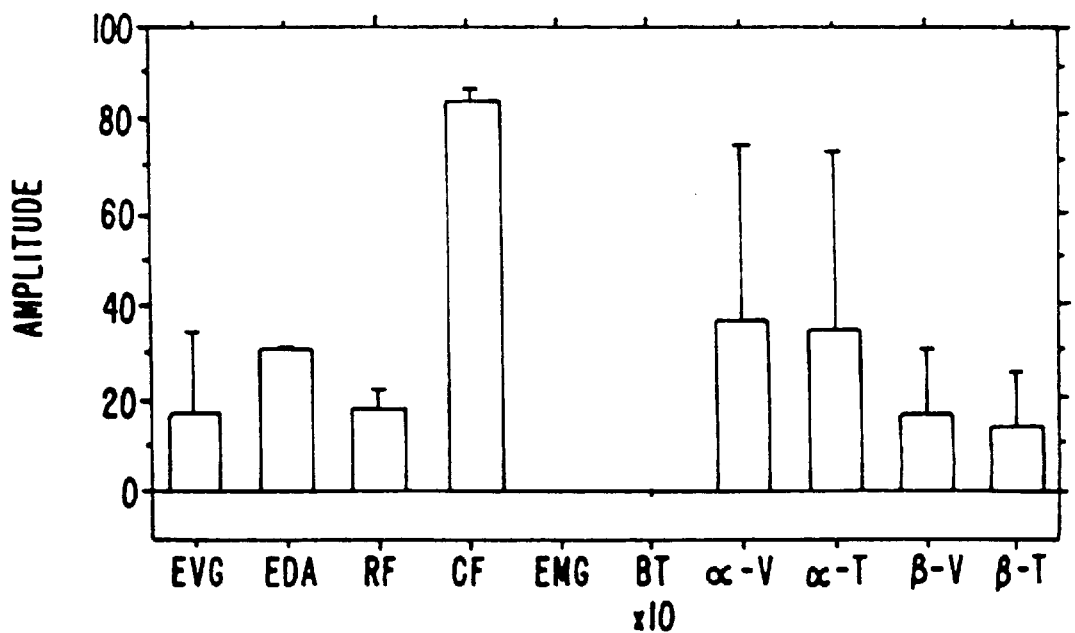
Figure 81:
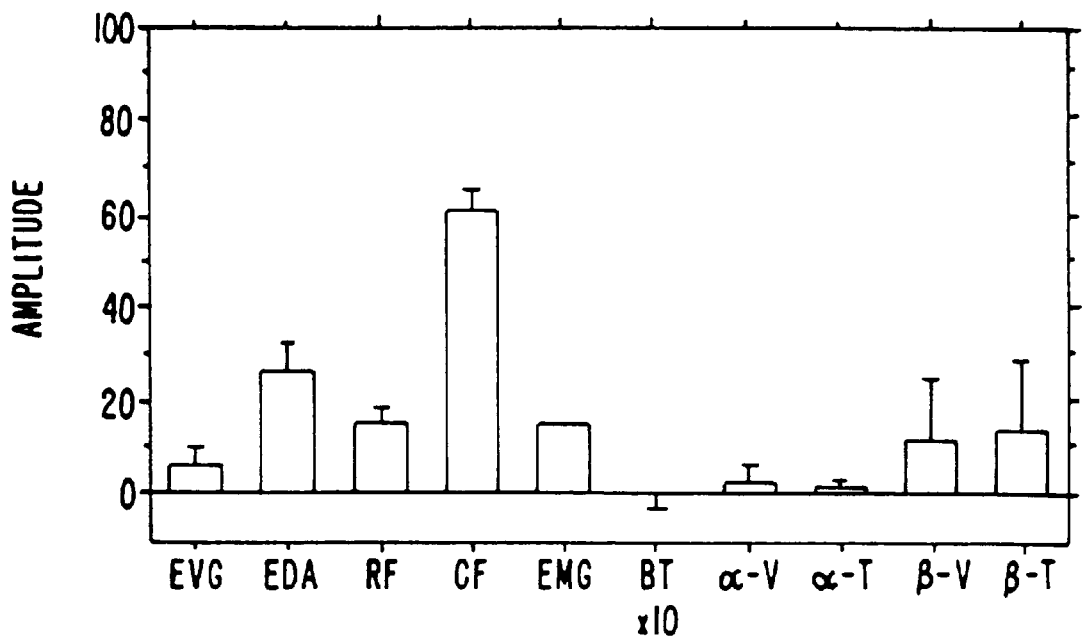
FIGS. 81 and 82 show the data of measurements in men and women, respectively, of compound A2/P7.
Figure 82:
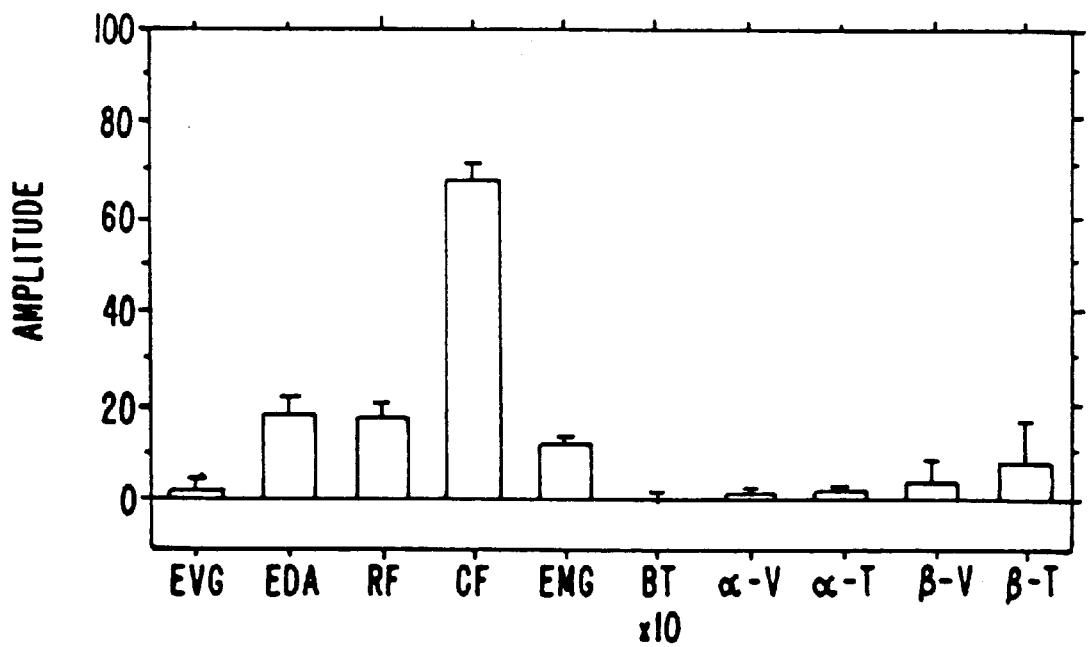
Figure 83:
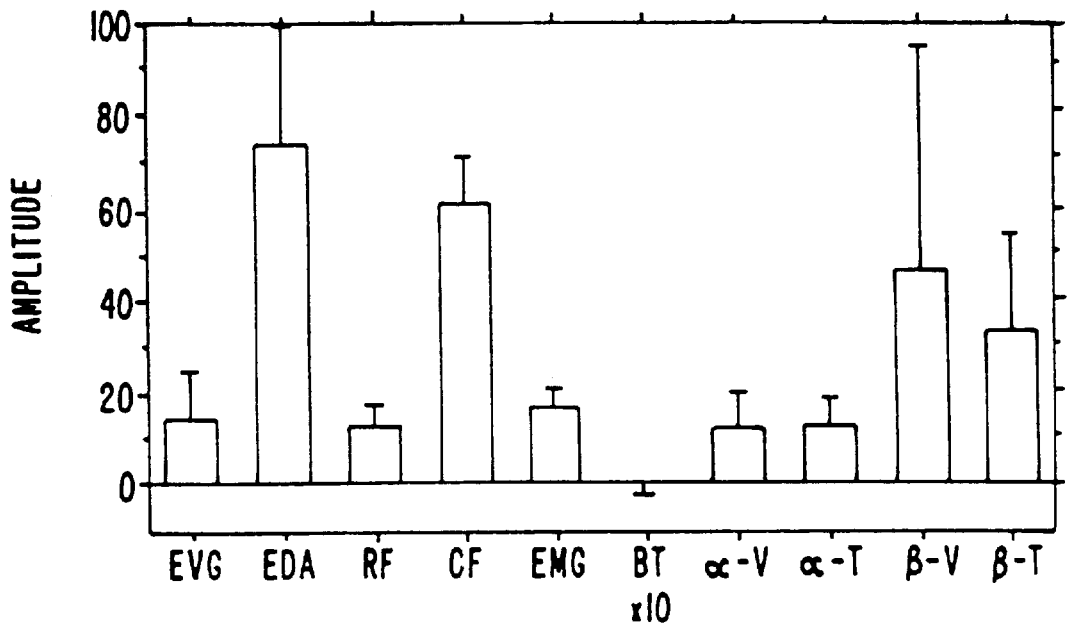
FIGS. 83 and 84 show the data of measurements in men and women, respectively, of compound A3/P5.
Figure 84:
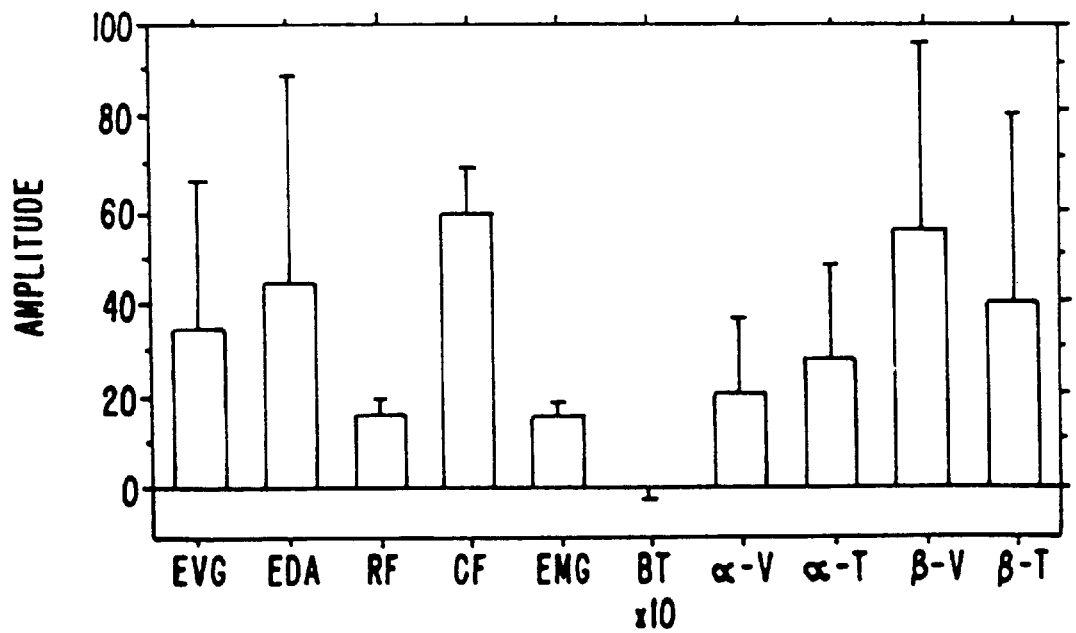
Figure 85:
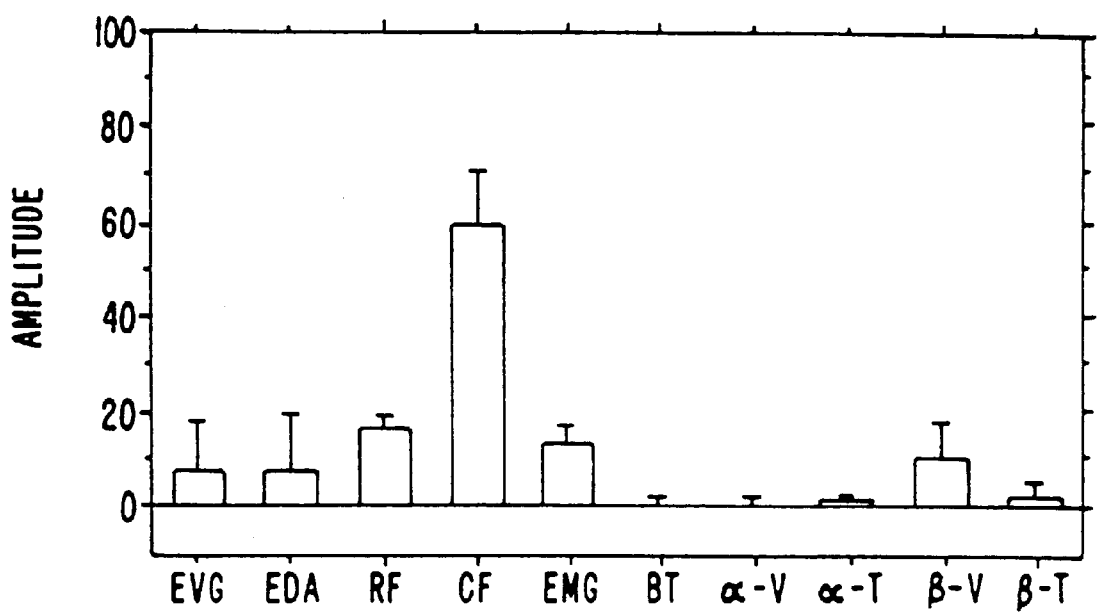
FIGS. 85–96 refer to the cholanes on Chart II.
Figure 86:
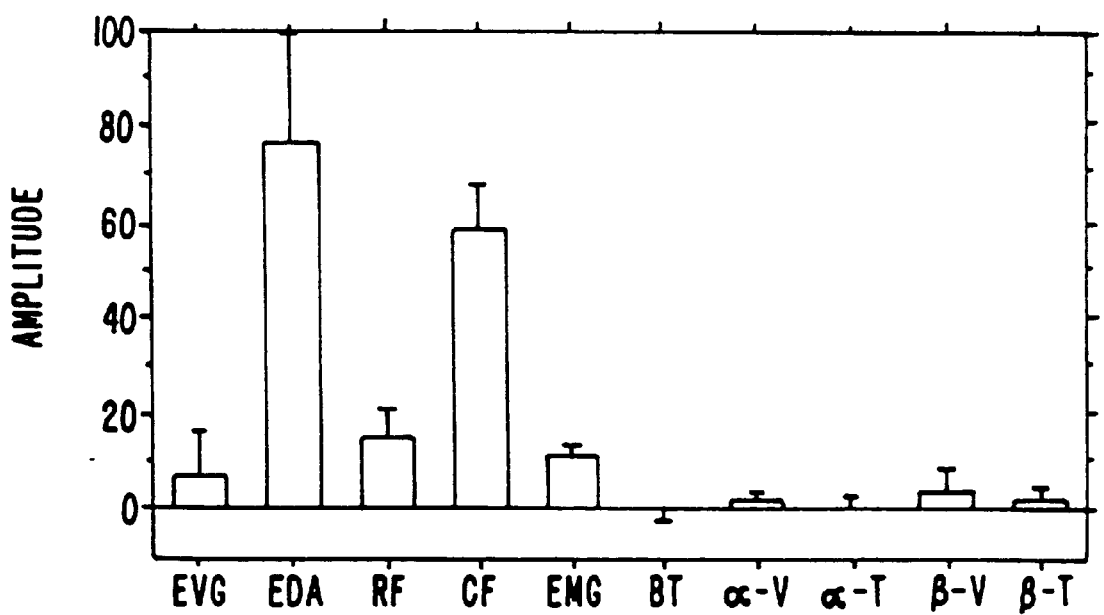
Figure 87:
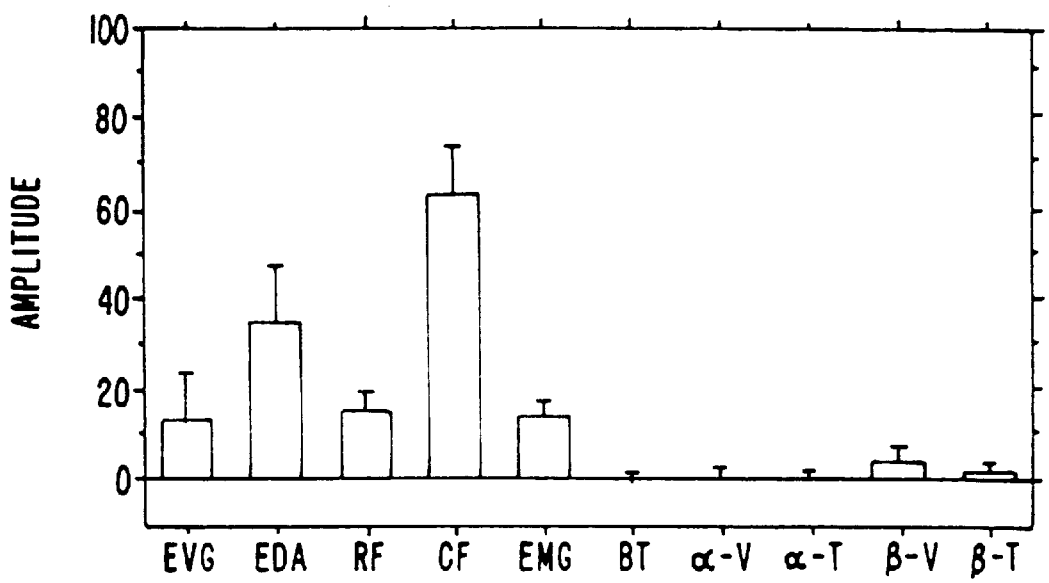
Figure 88:
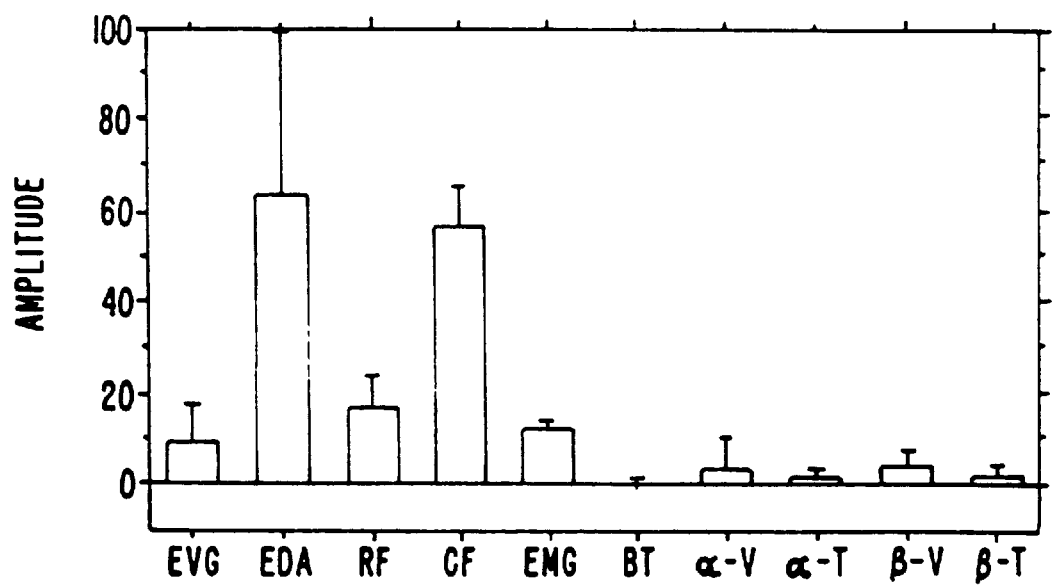
Figure 89:
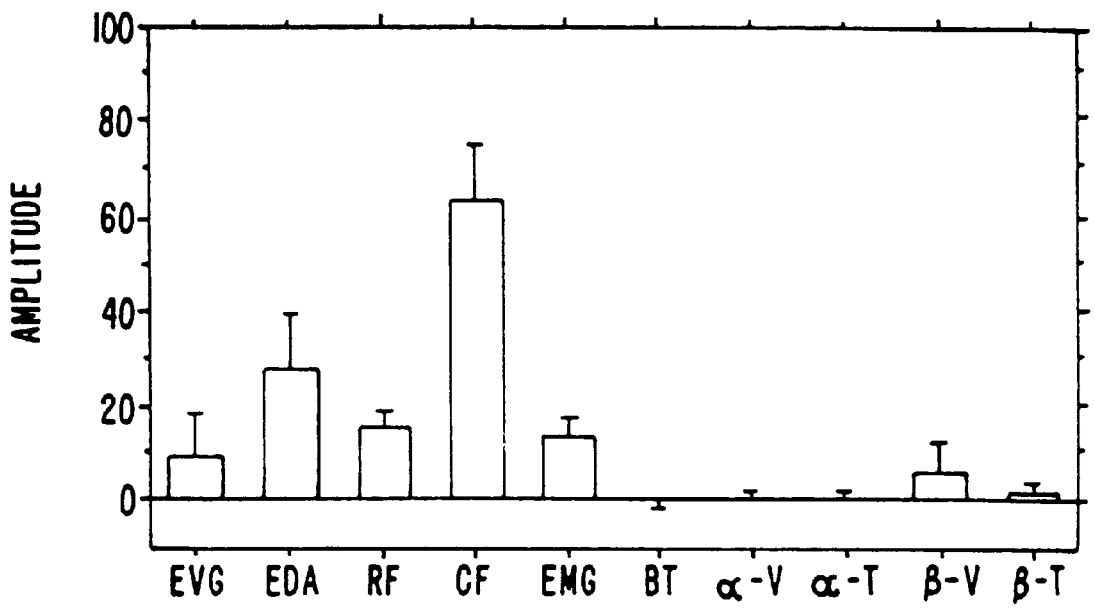
Figure 90:
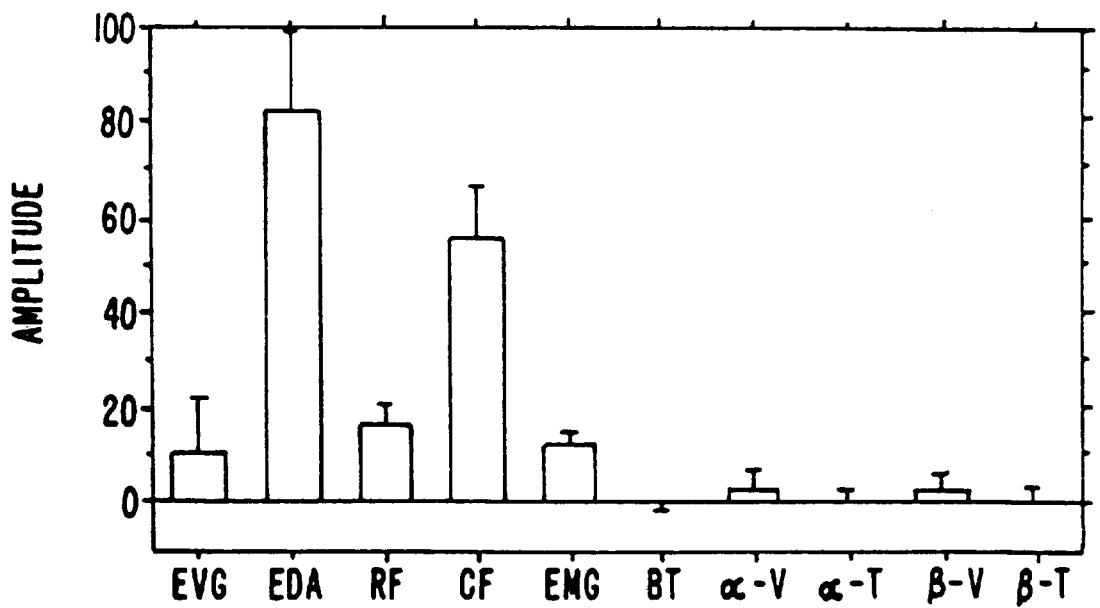
Figure 91:
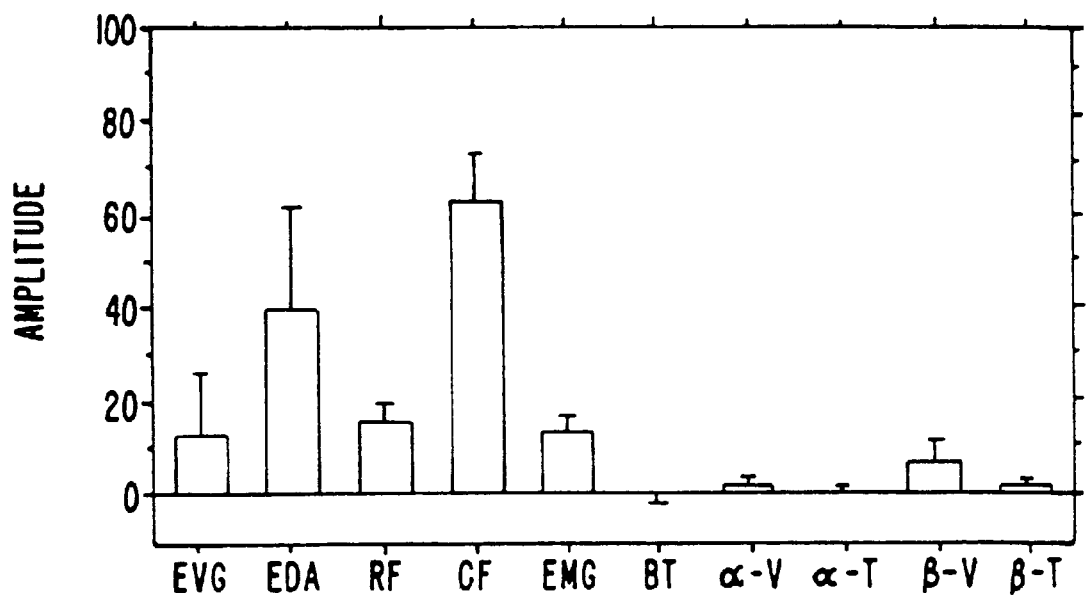
Figure 92:
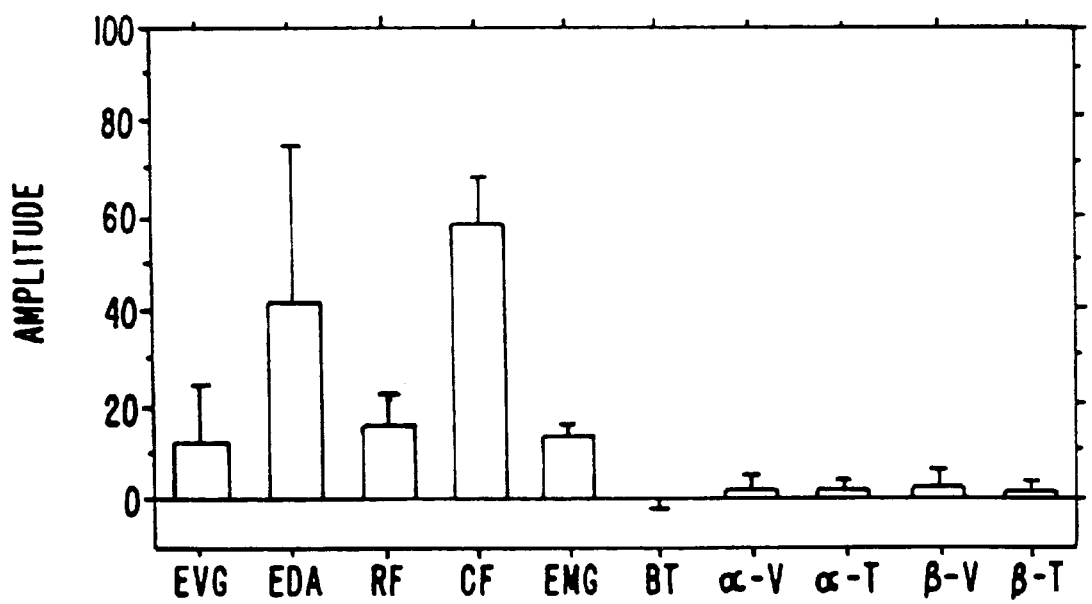
Figure 93:
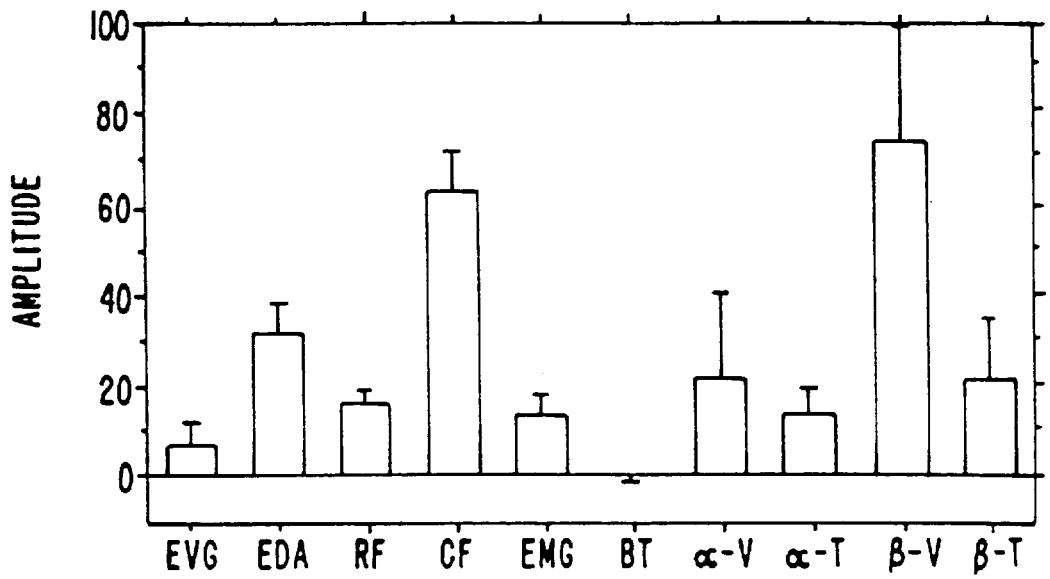
Figure 94:
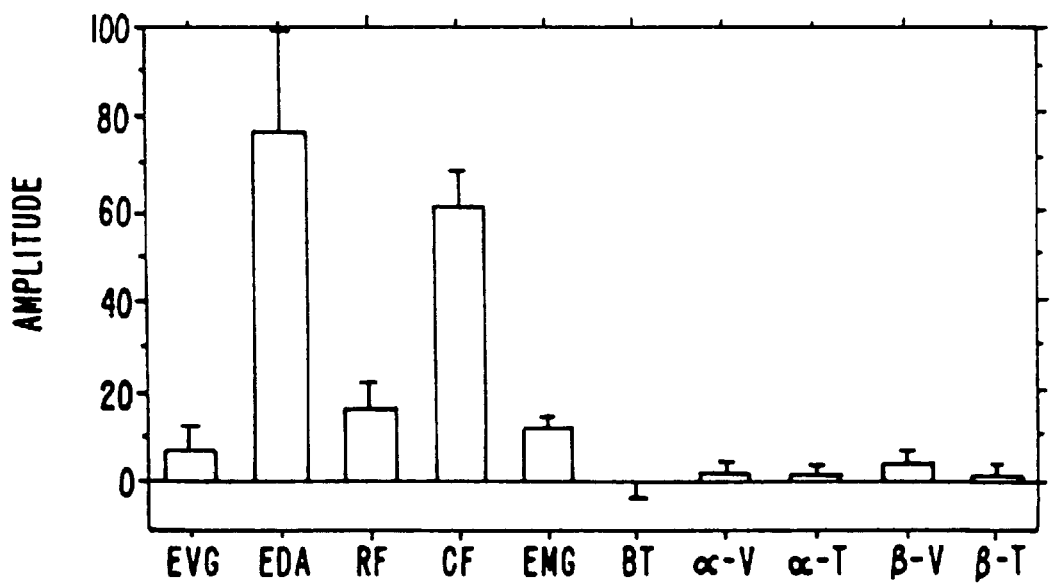
Figure 95:
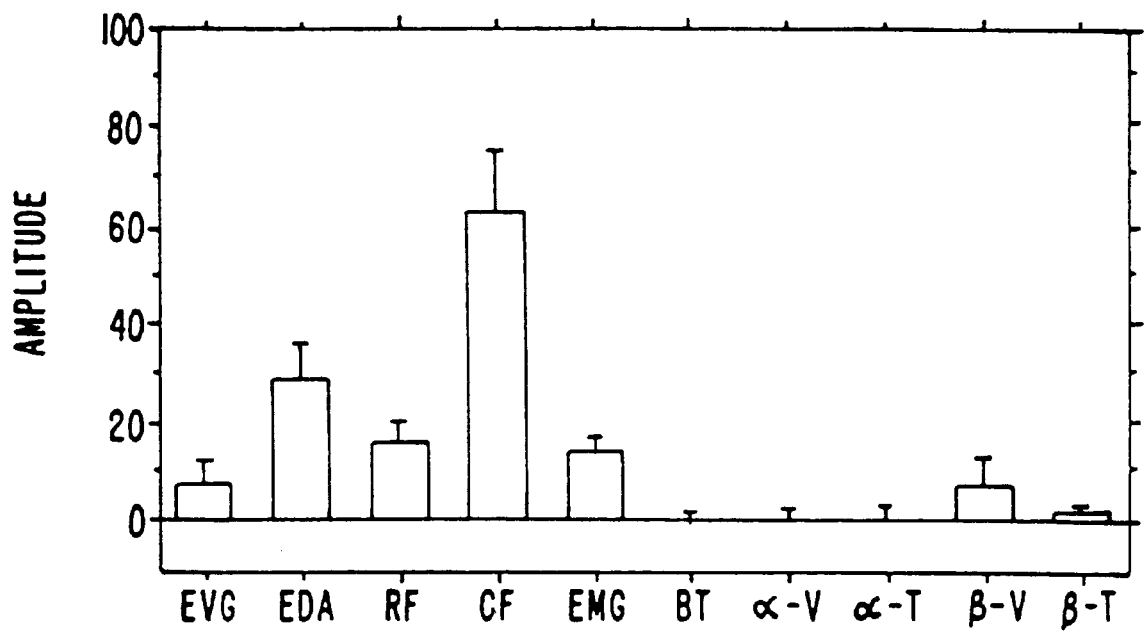
Figure 96:
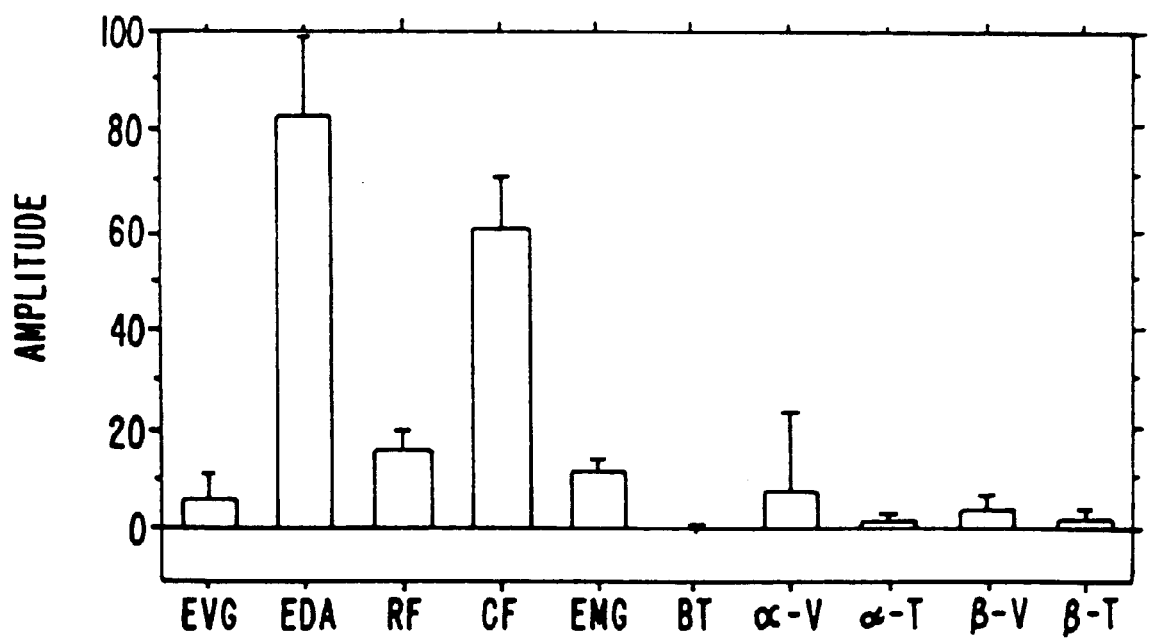
Figure 97:
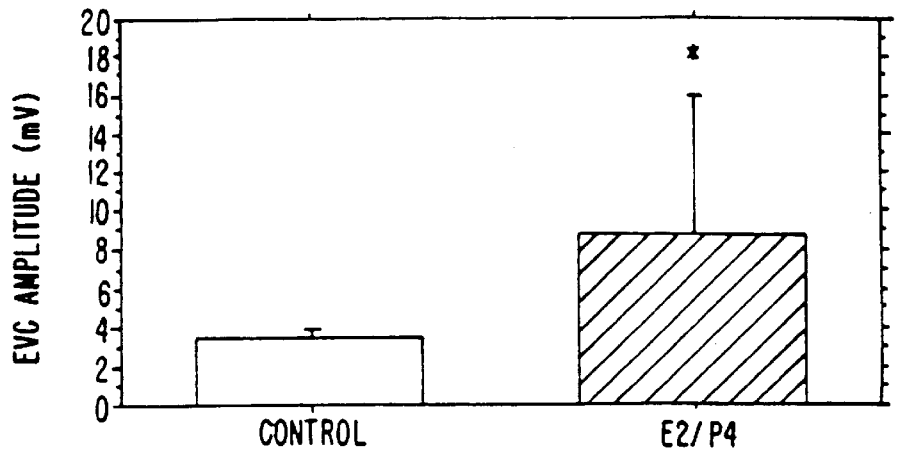
FIG. 97 and FIG. 98 show the EVG and vomeronasal nerve discharge frequency, respectively, of steroid E2/P4 and control, in female rats.
Figure 98:
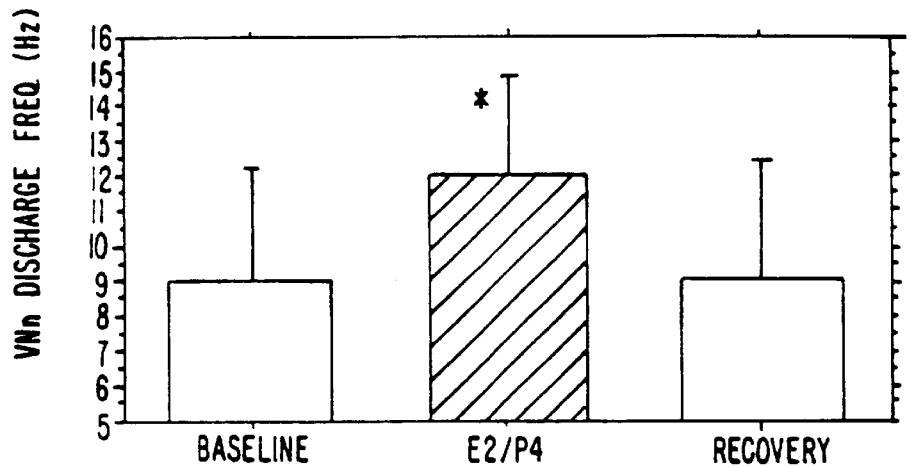
Figure 99:
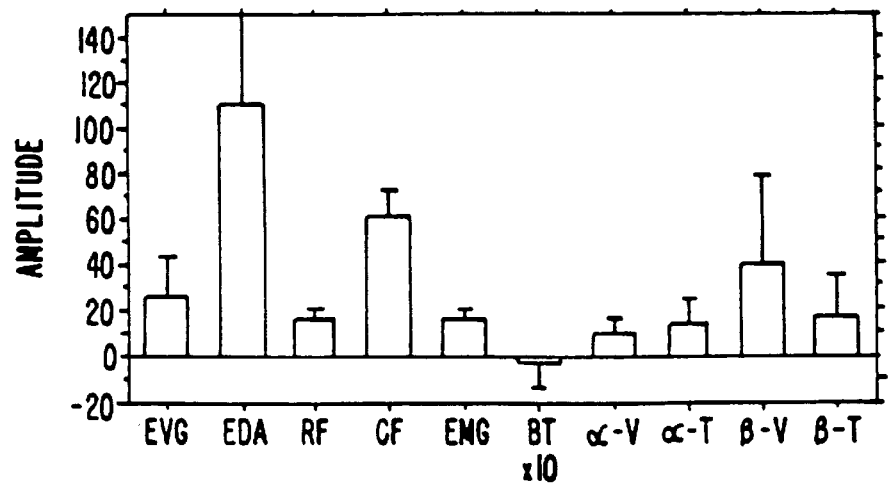
FIGS. 99 through 120 show the EVG, EDA, RF, CF, EMG, BT and EEG (alpha-V, alpha-T, beta-V and beta-T) data of administration of designated 19-nor-steroids in the VNO women.
Figure 100:
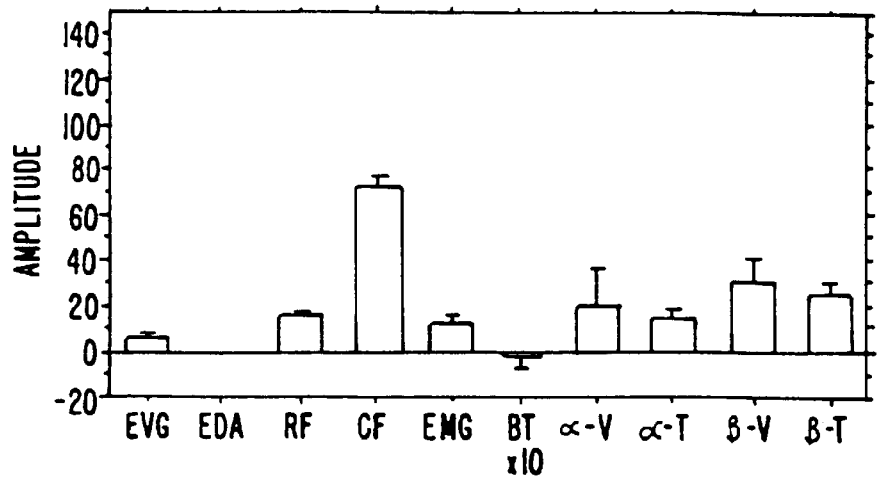
Figure 101:
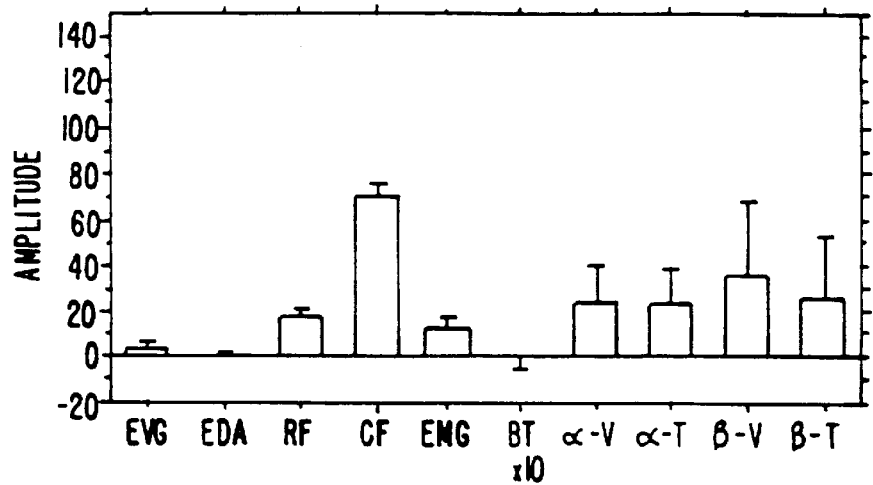
Figure 102:
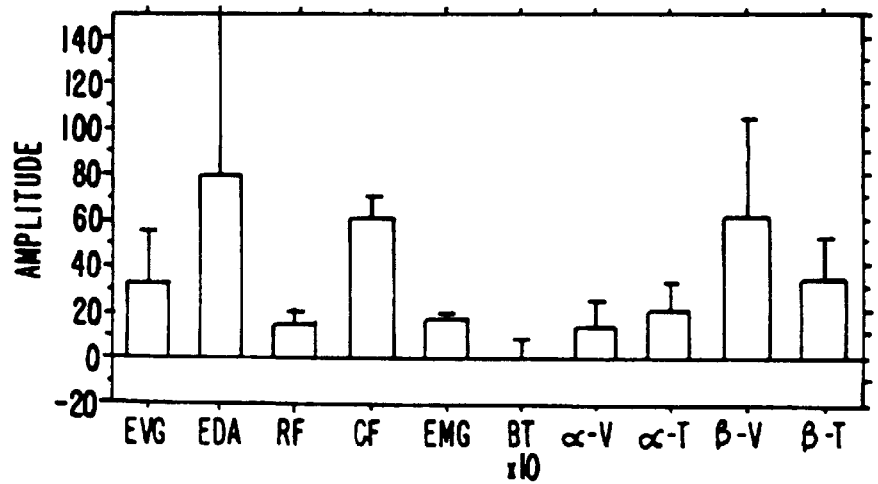
Figure 103:
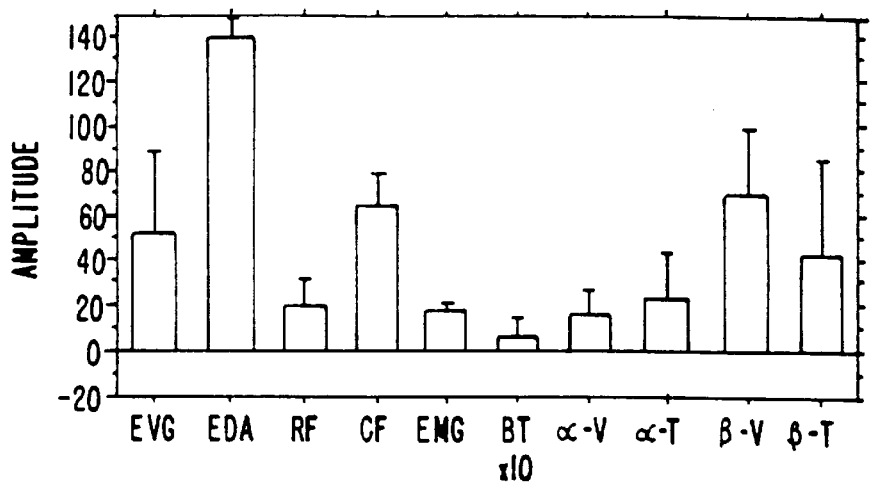
Figure 104:
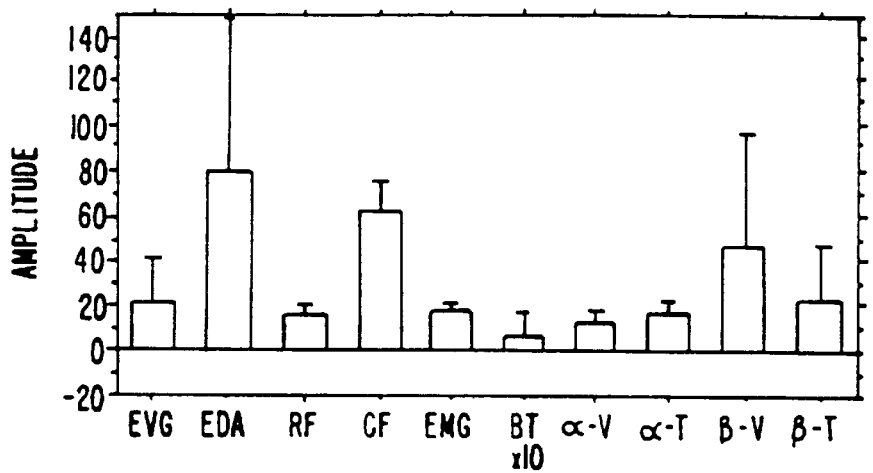
Figure 105:
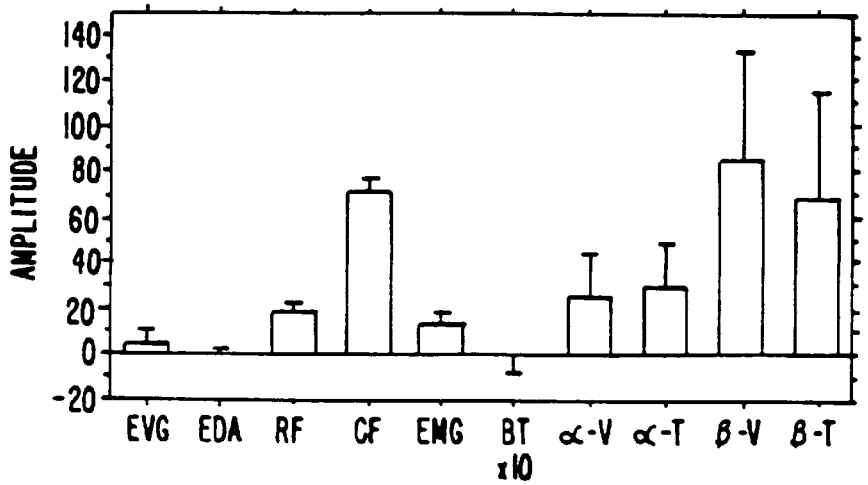
Figure 106:
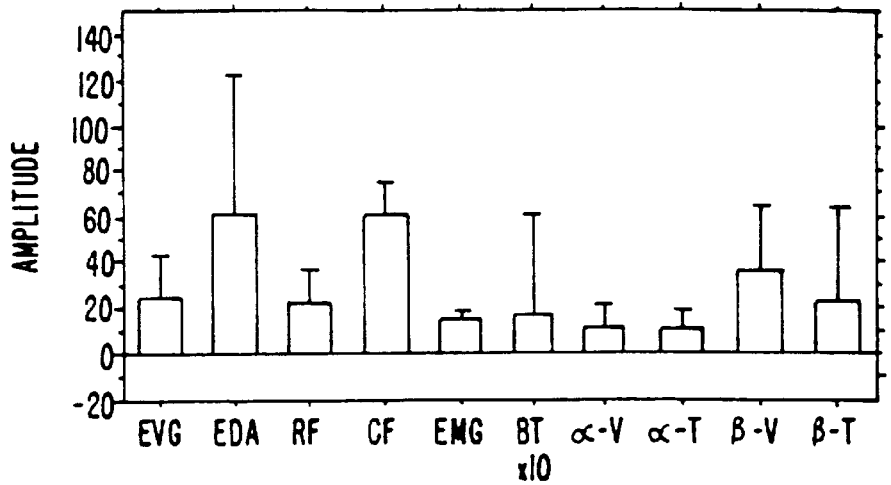
Figure 107:
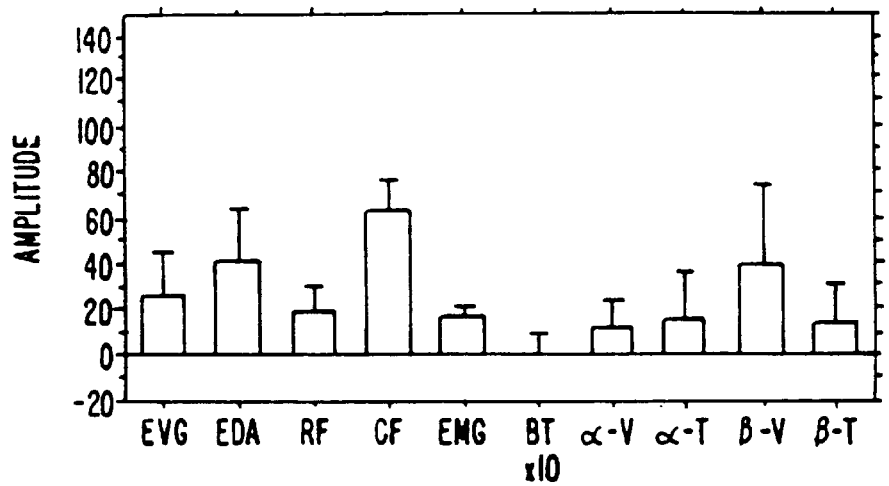
Figure 108:
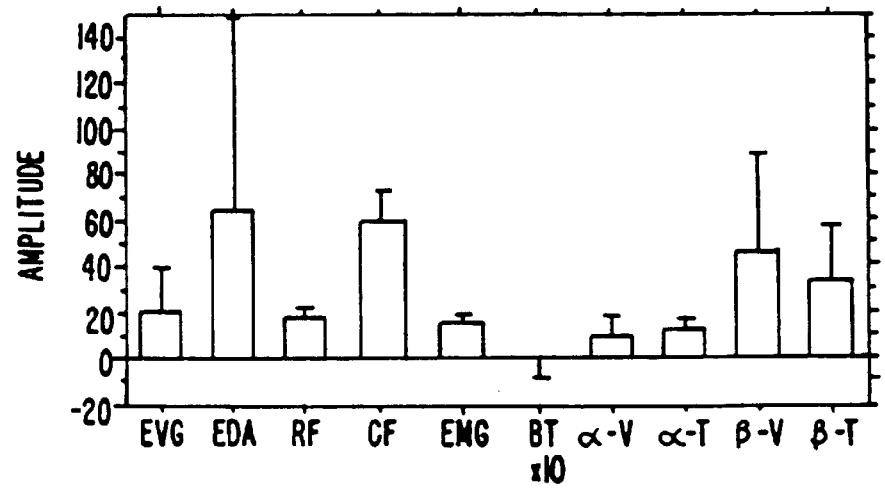
Figure 109:
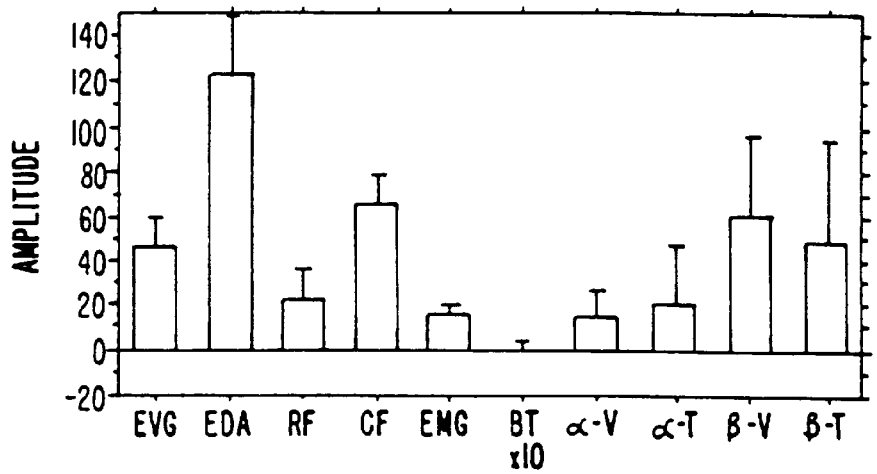
Figure 110:
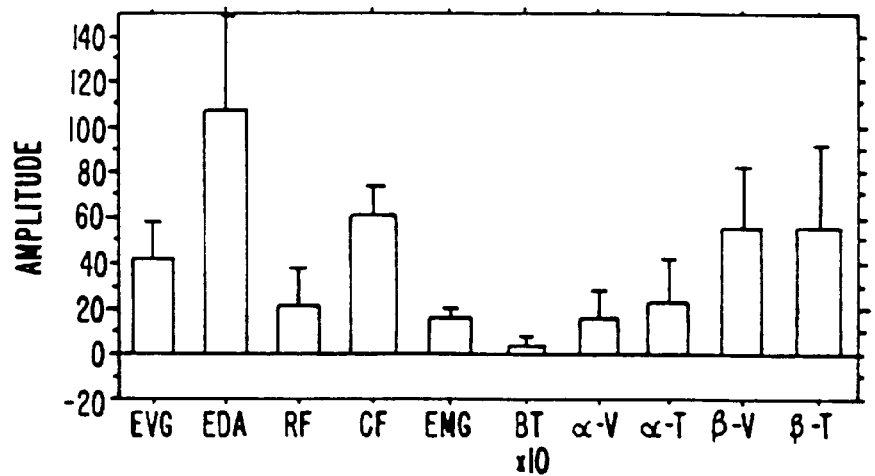
Figure 111:
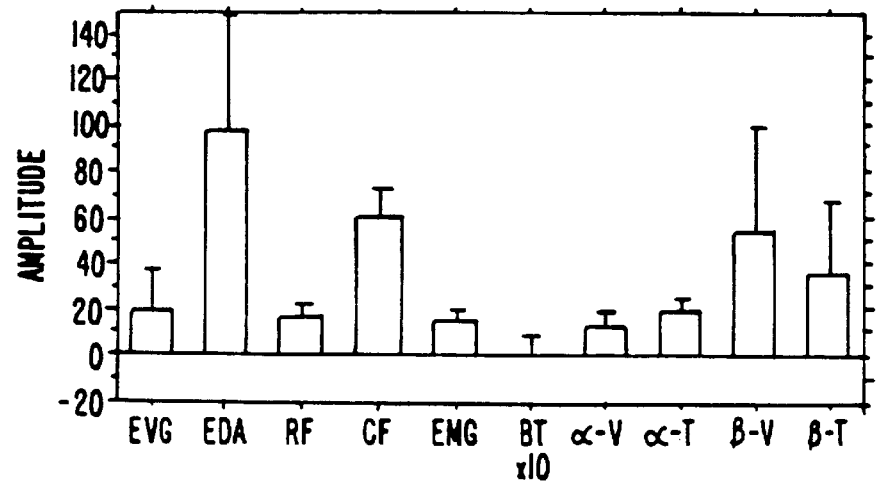
Figure 112:
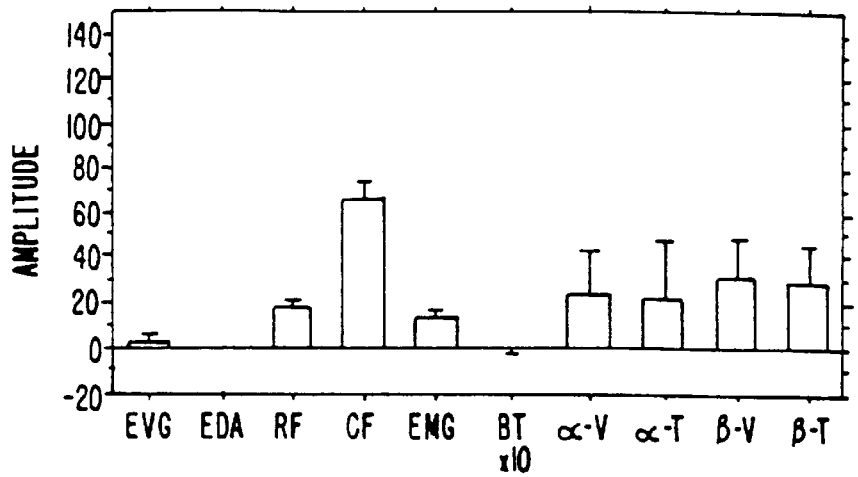
Figure 113:
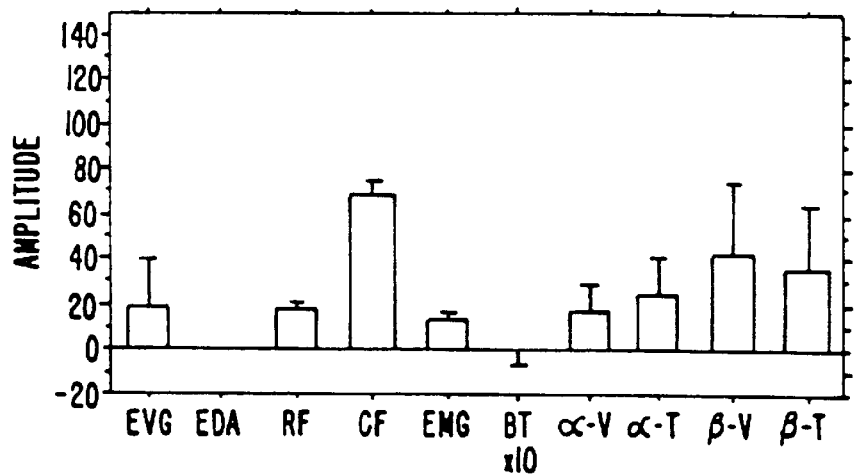
Figure 114:
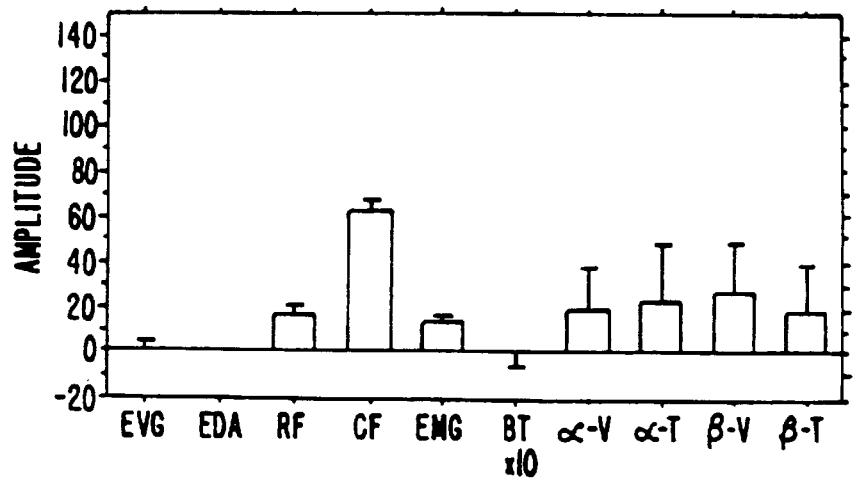
Figure 115:
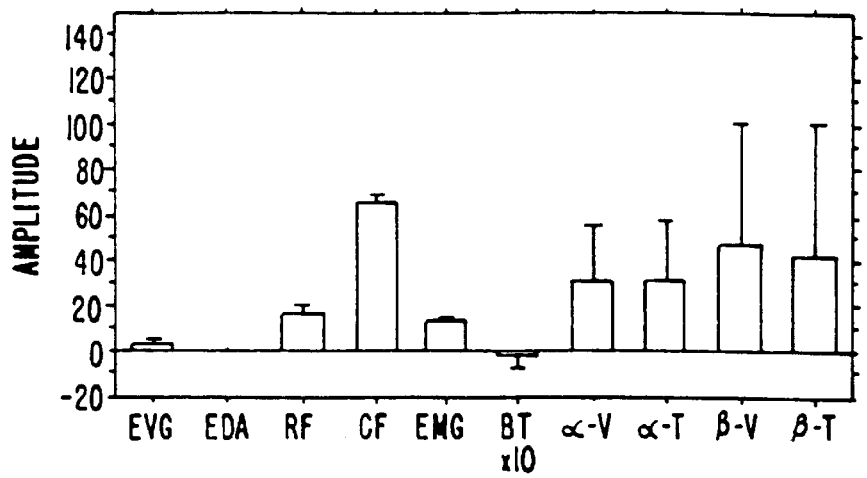
Figure 116:
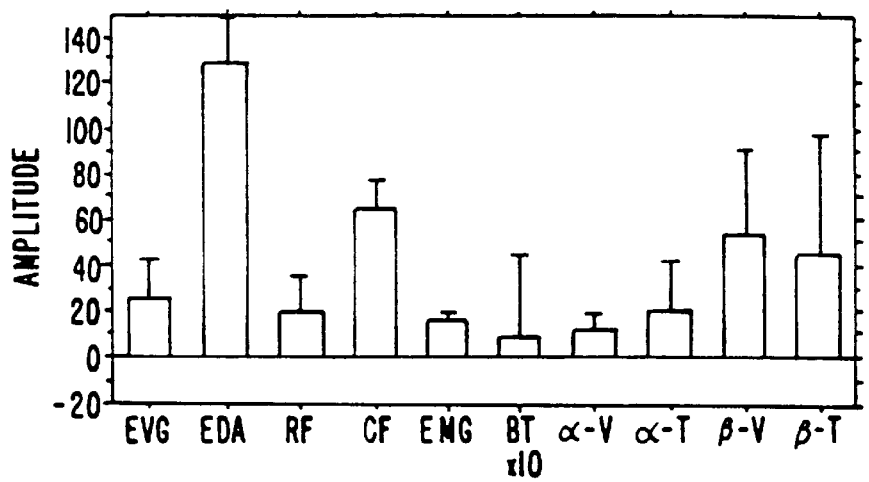
Figure 117:
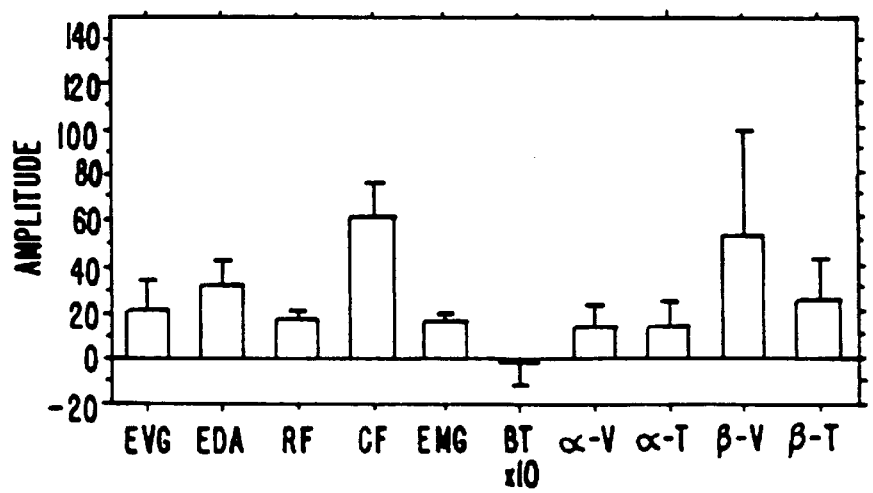
Figure 118:
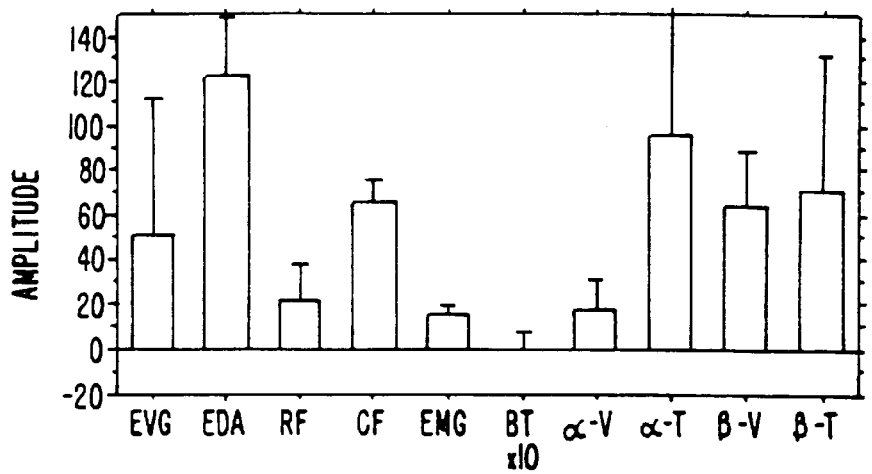
Figure 119:
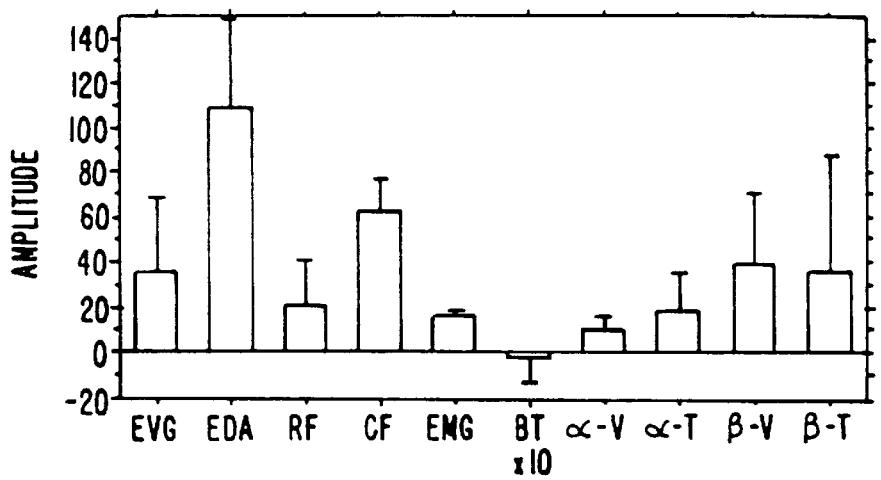
Figure 120:
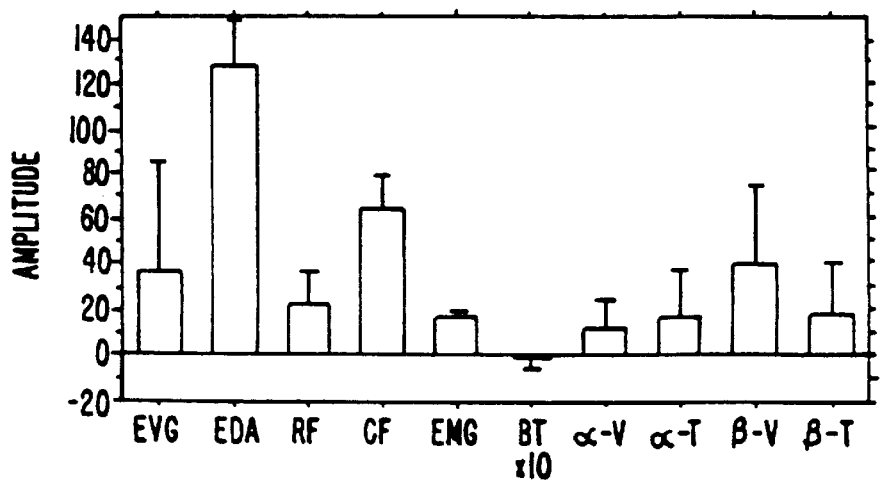
Figure 121:
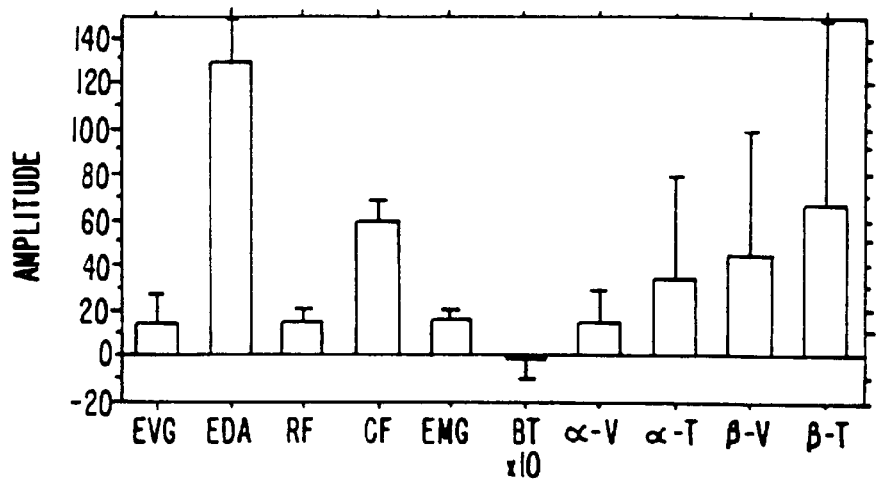
FIGS. 121 through 142 show the EVG, EDA, RF, CF, EMG, BT and EEG data of administration of designated 19-nor-steroids in the VNO of men.
Figure 122:
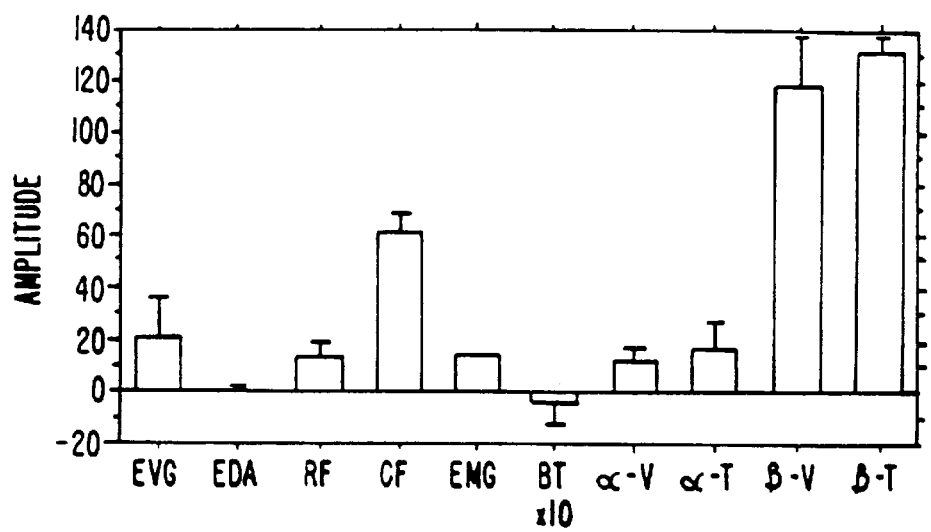
Figure 123:
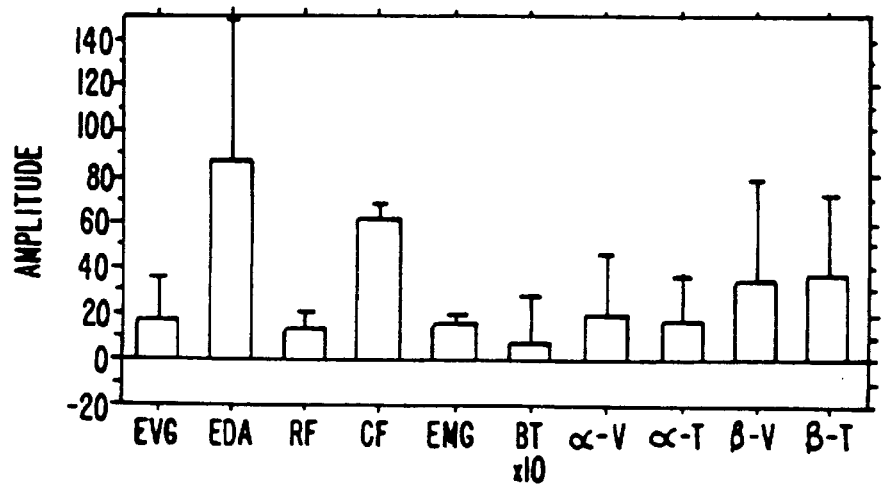
Figure 124:
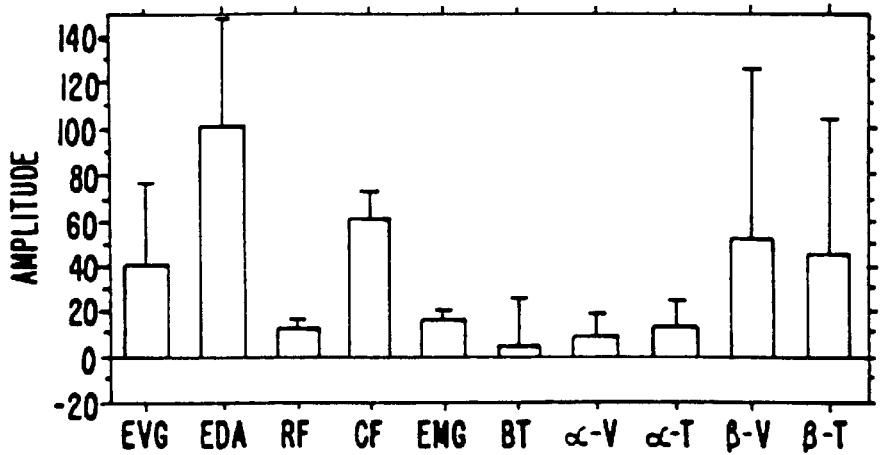
Figure 125:
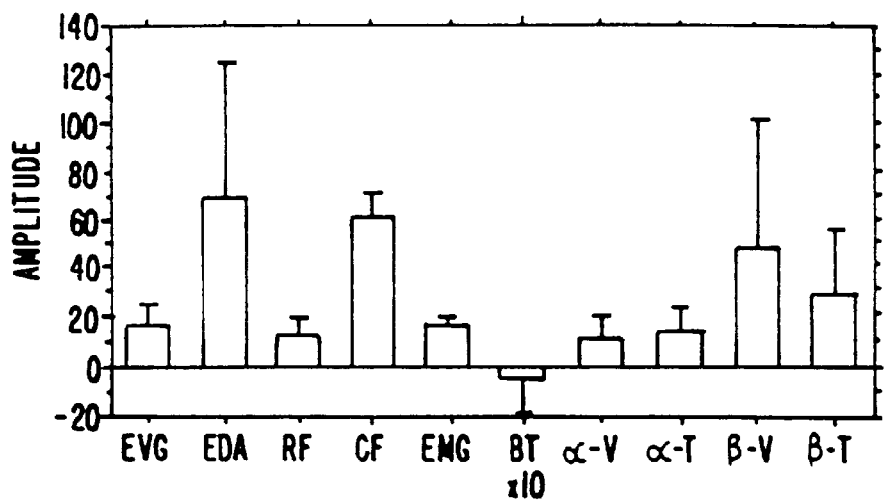
Figure 126:
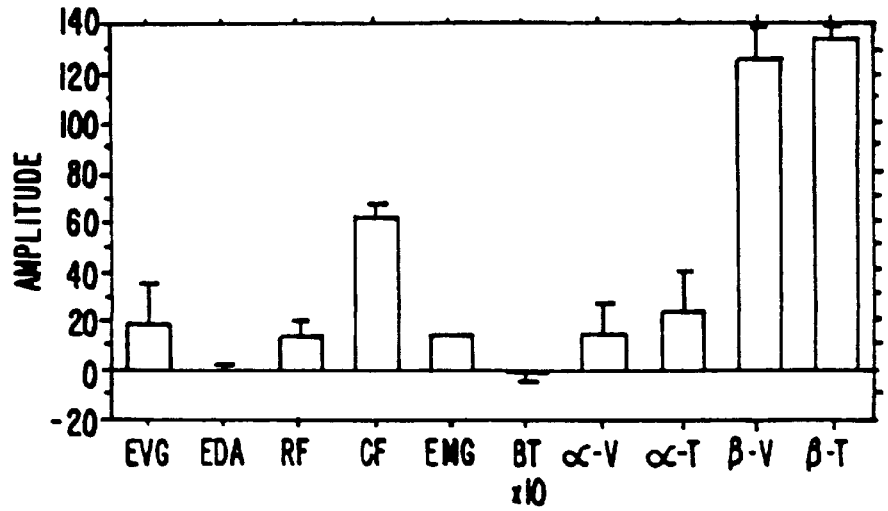
Figure 127:
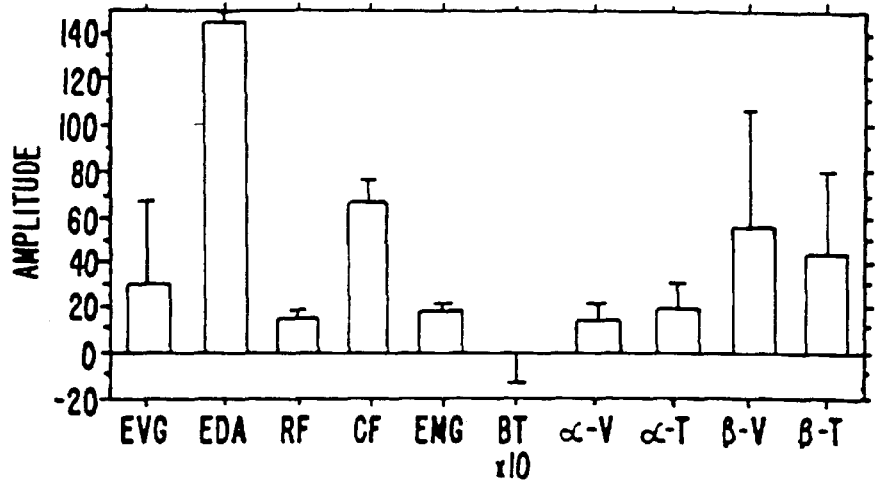
Figure 128:
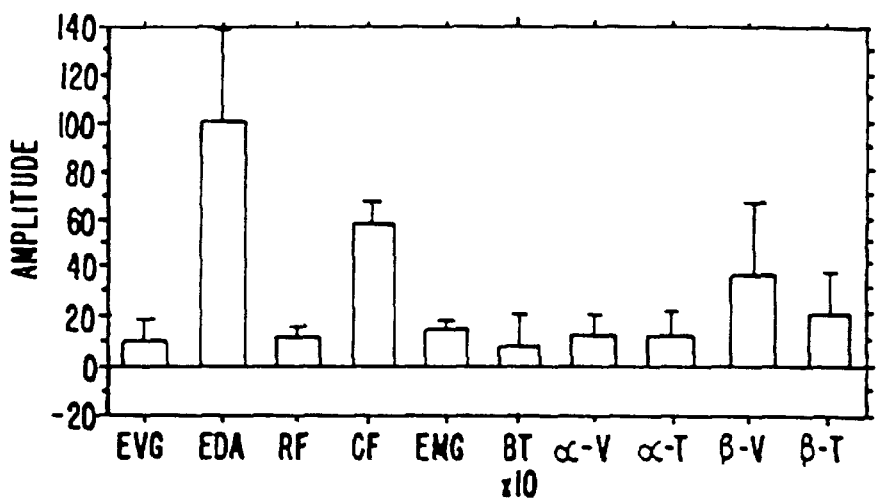
Figure 129:
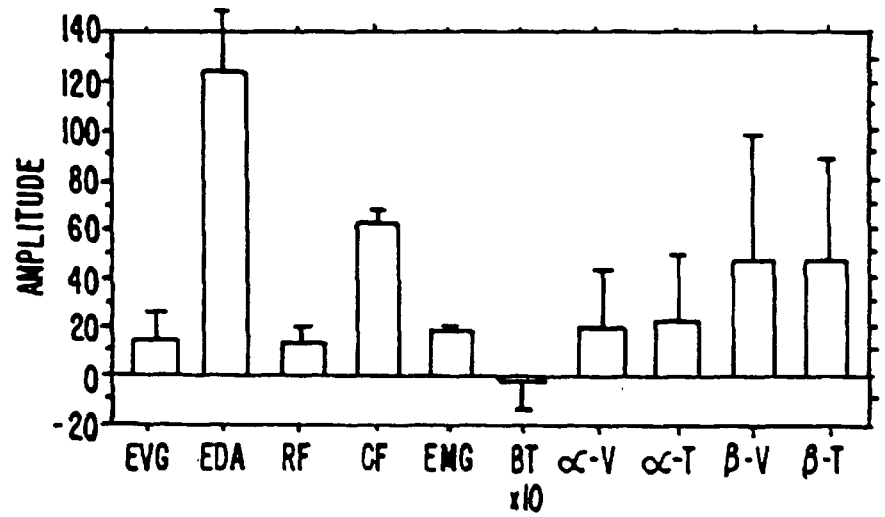
Figure 130:
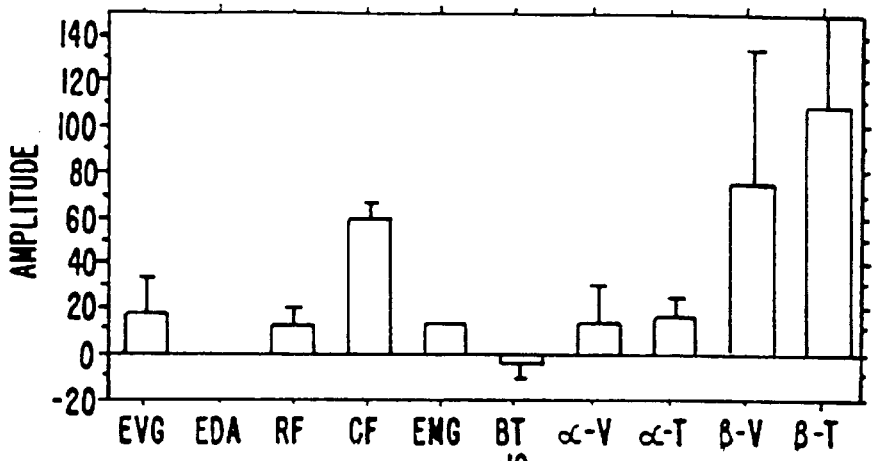
Figure 131:
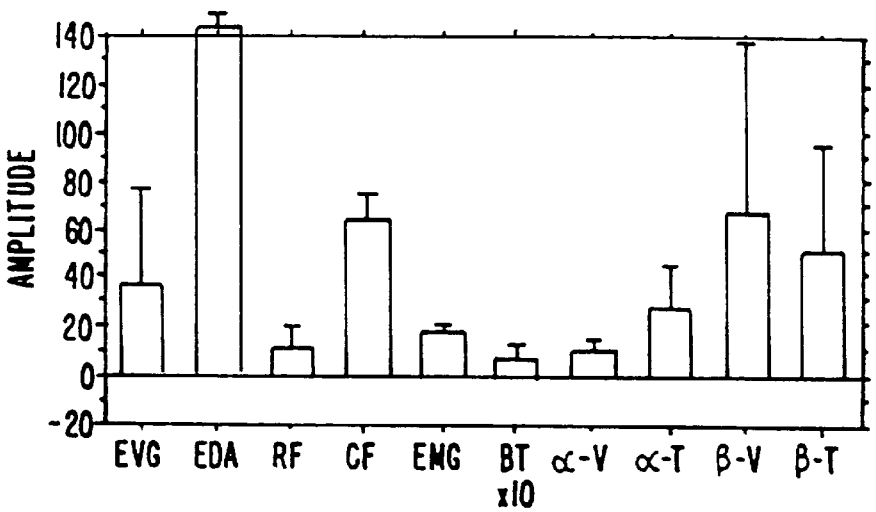
Figure 132:
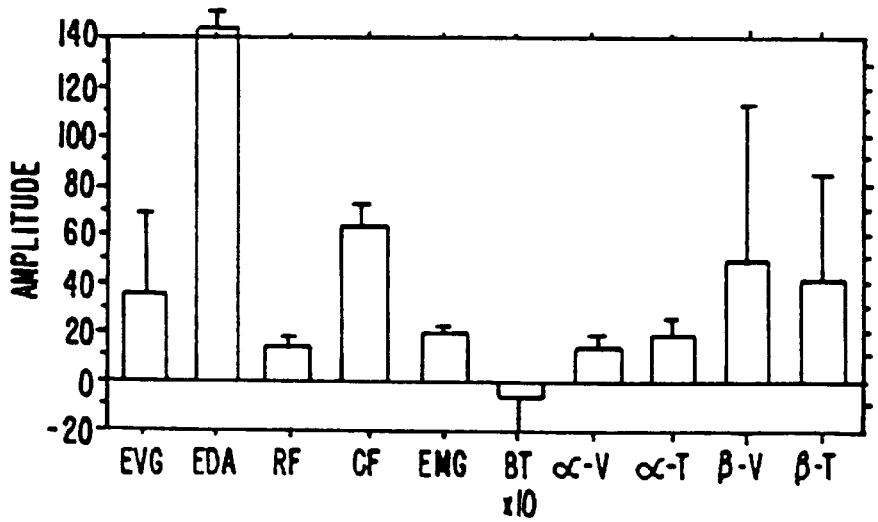
Figure 133:
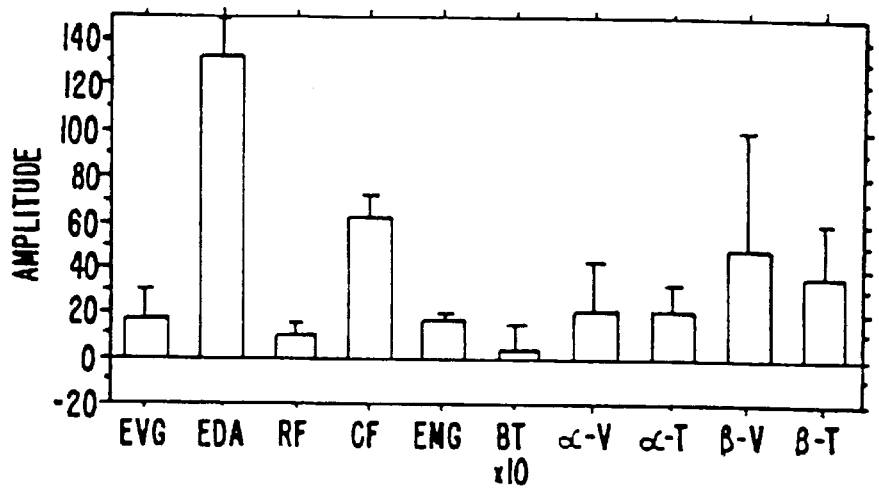
Figure 134:
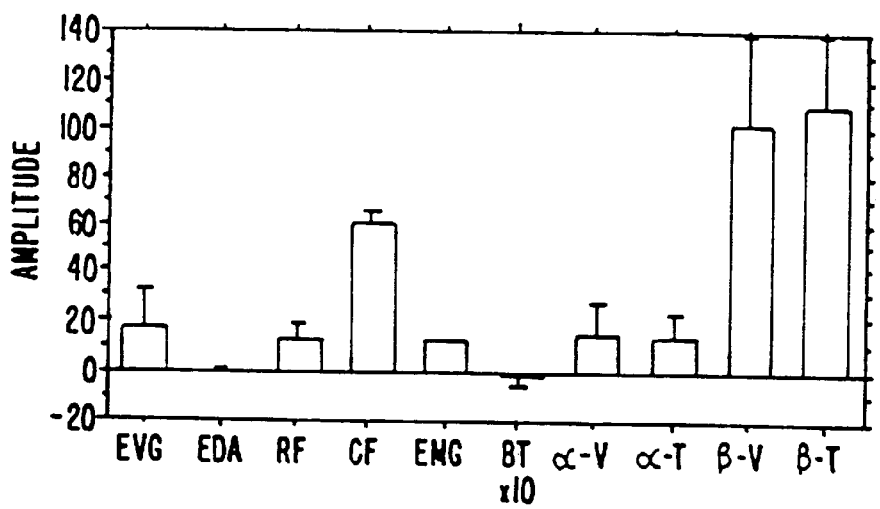
Figure 135:
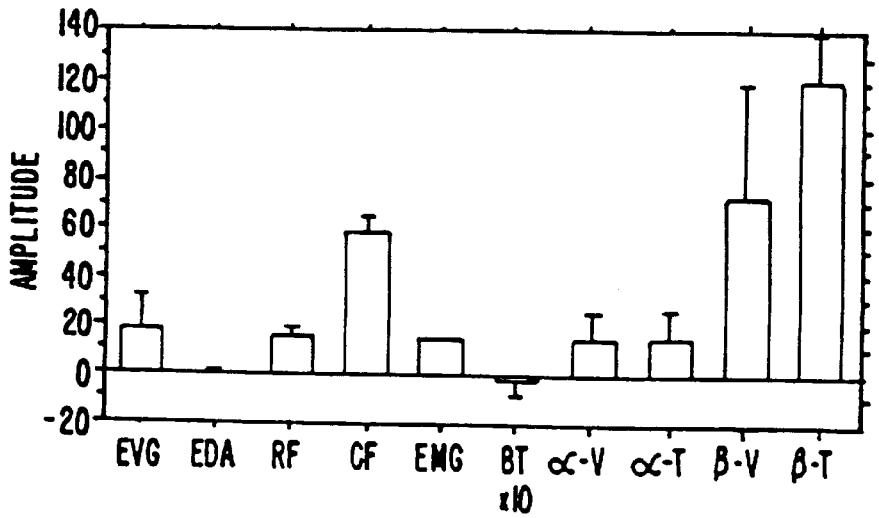
Figure 136:
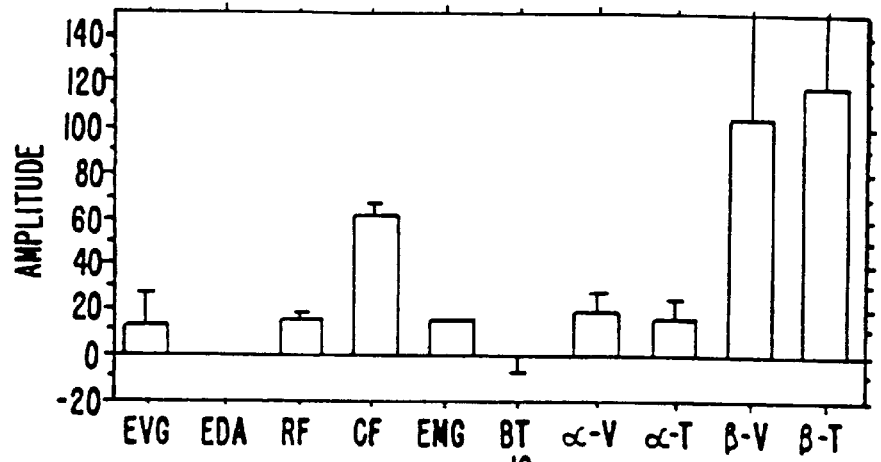
Figure 137:
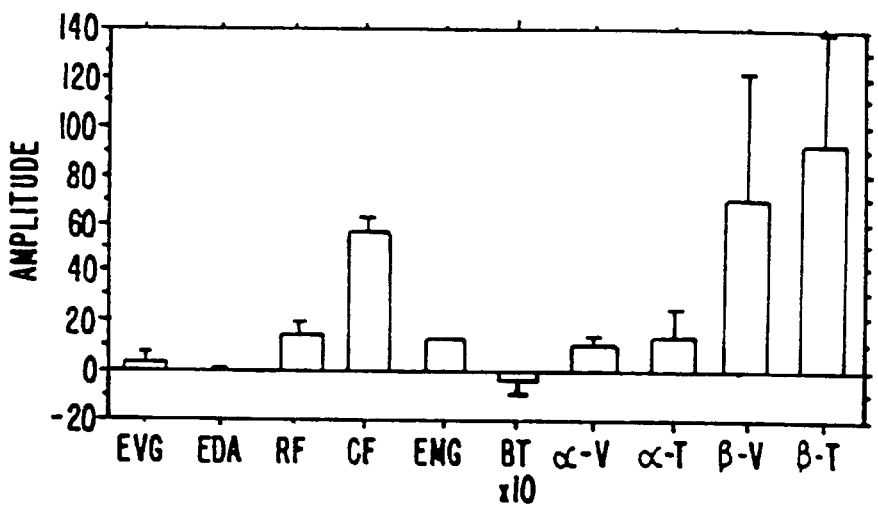
Figure 138:
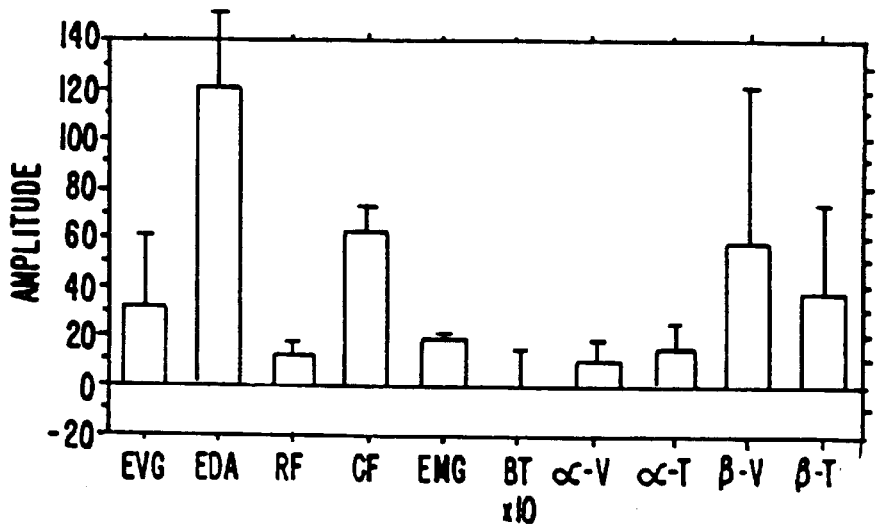
Figure 139:
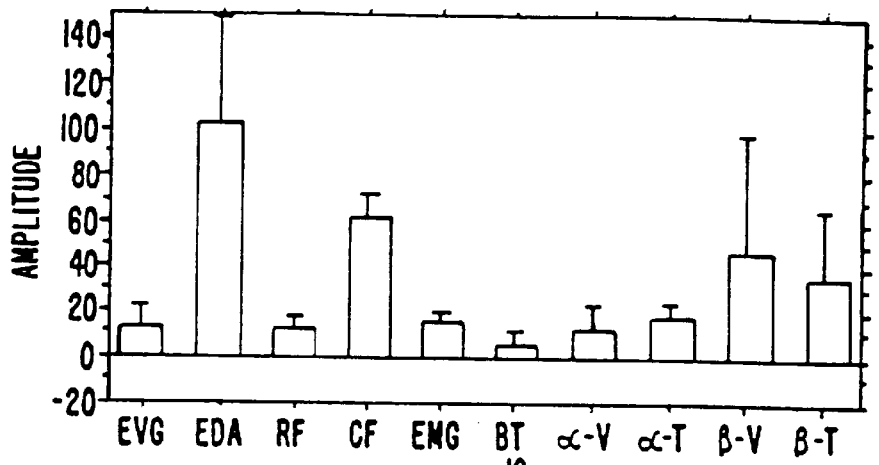
Figure 140:
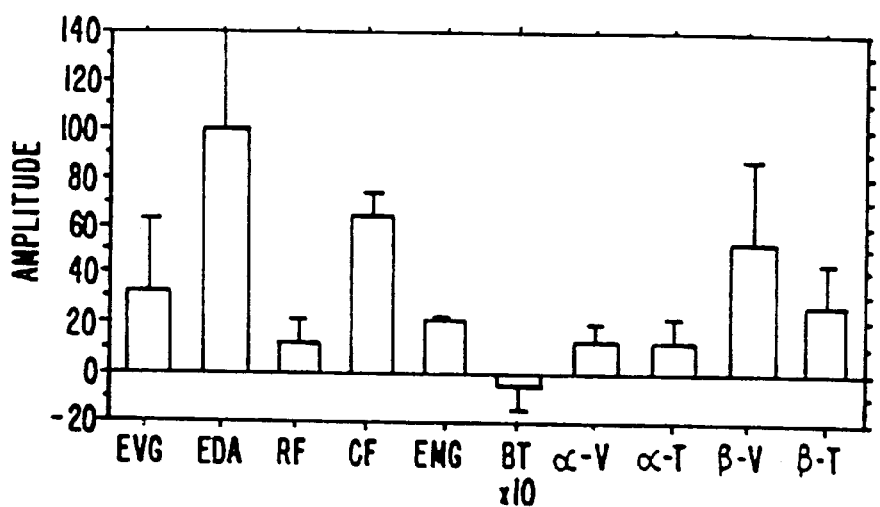
Figure 141:
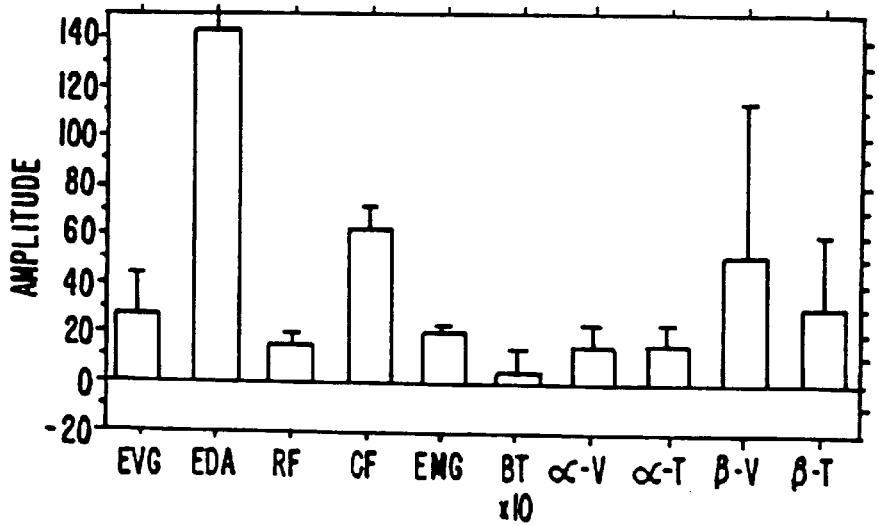
Figure 142:
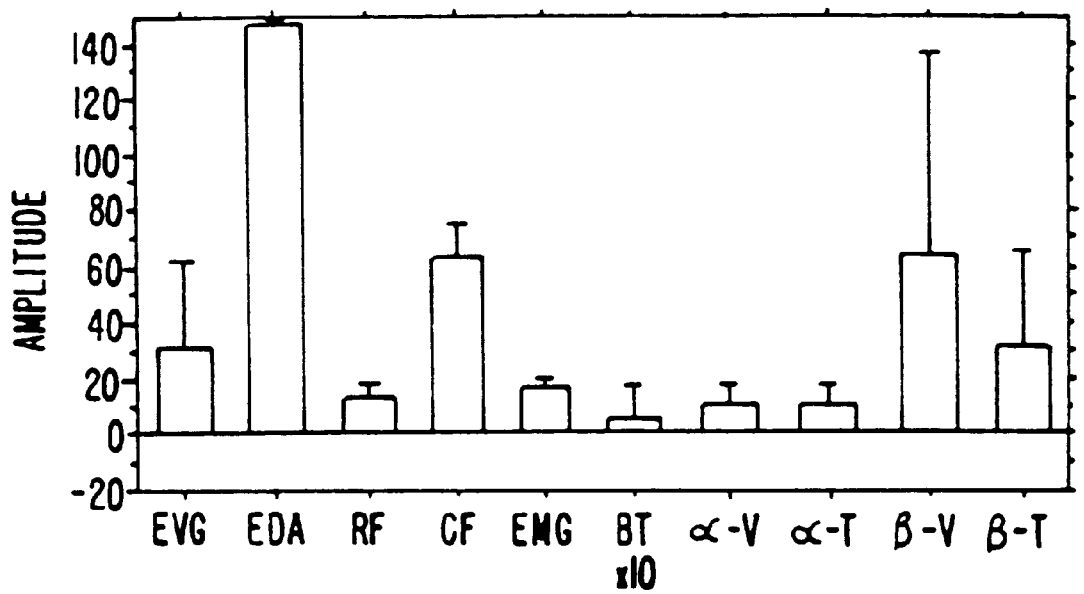
Figure 143:
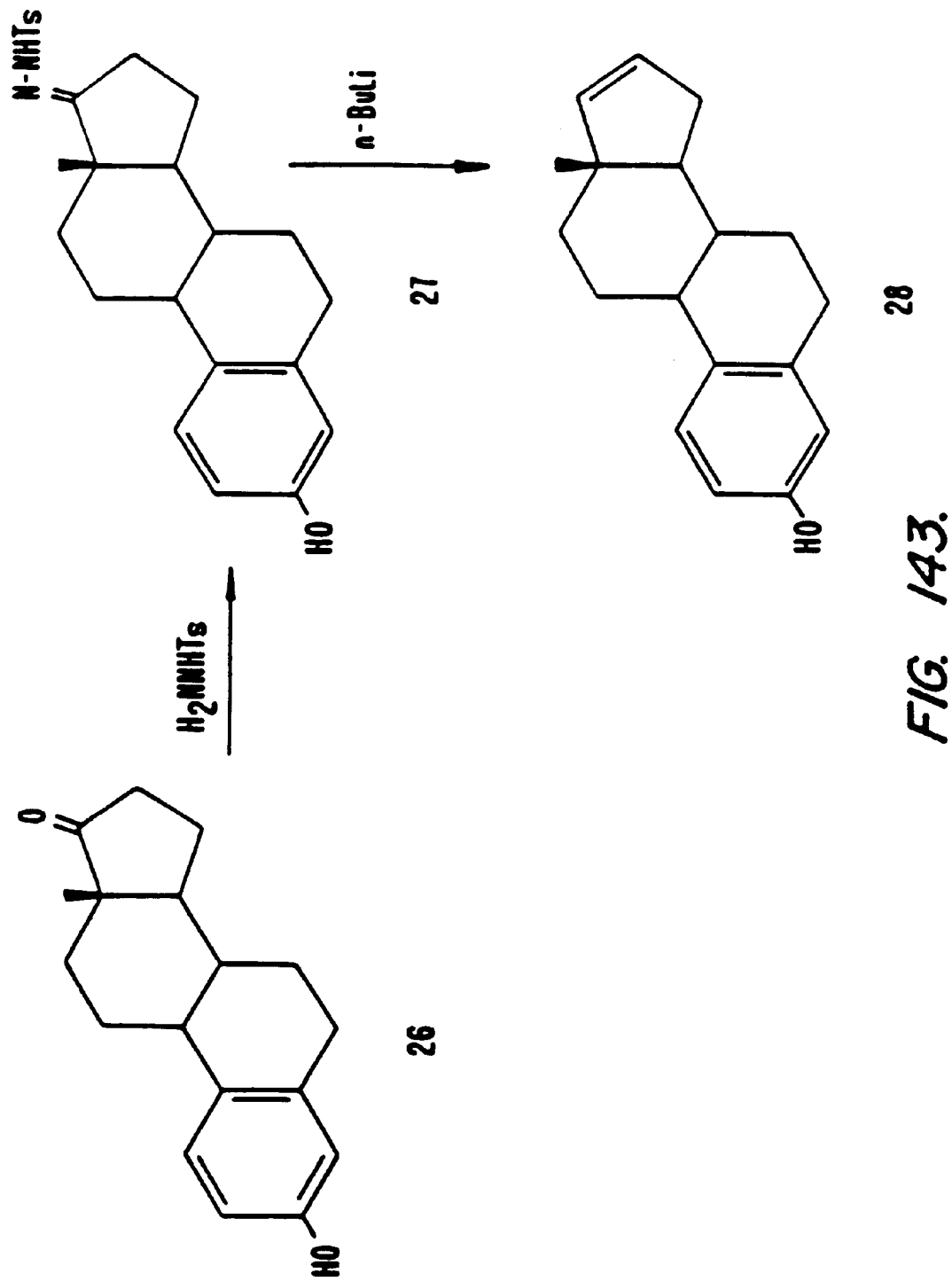
FIG. 143 illustrates the synthesis of 1, 3,5 (10), 16-Estratetraen-3-ol.
Figure 144A:
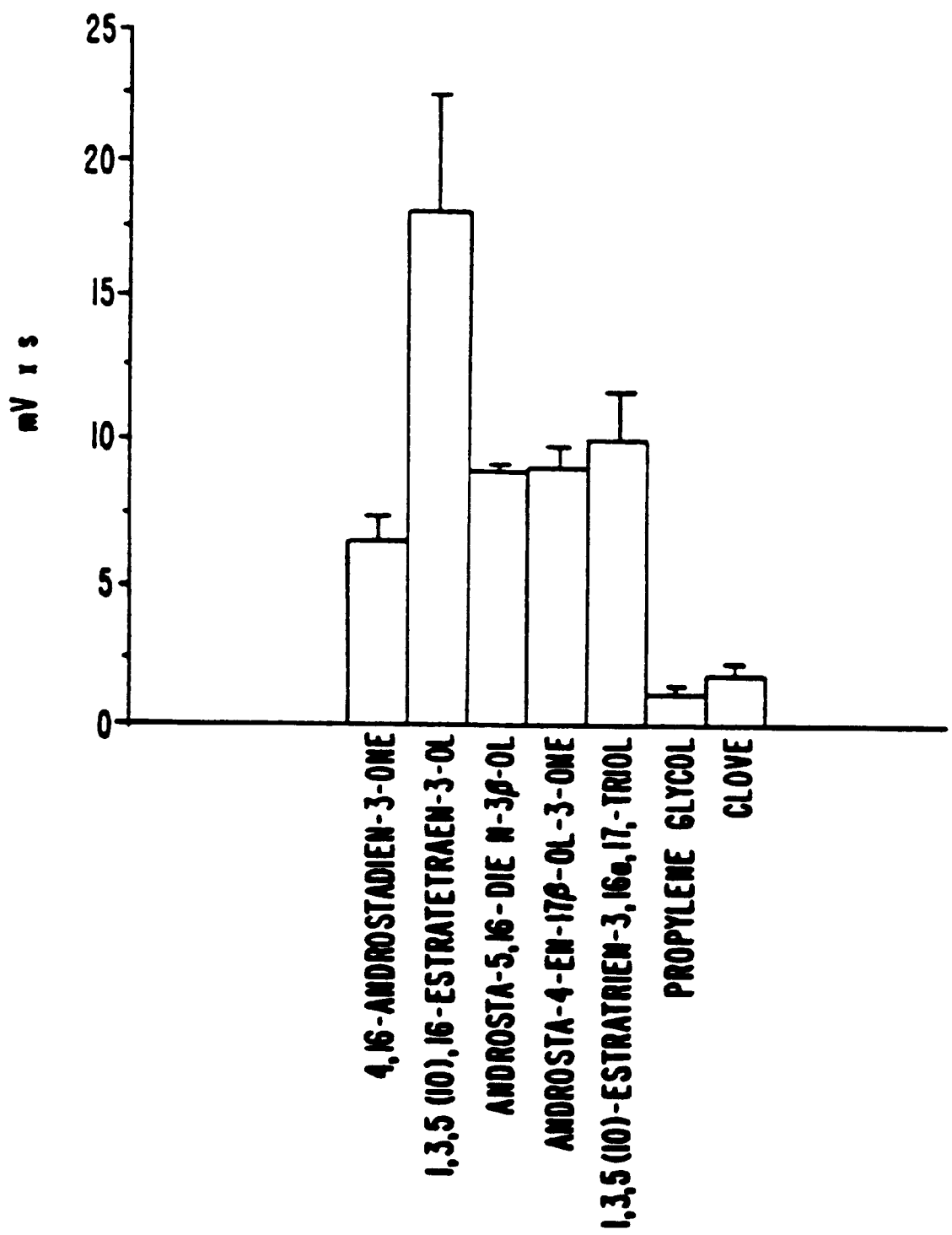
Figure 144C:
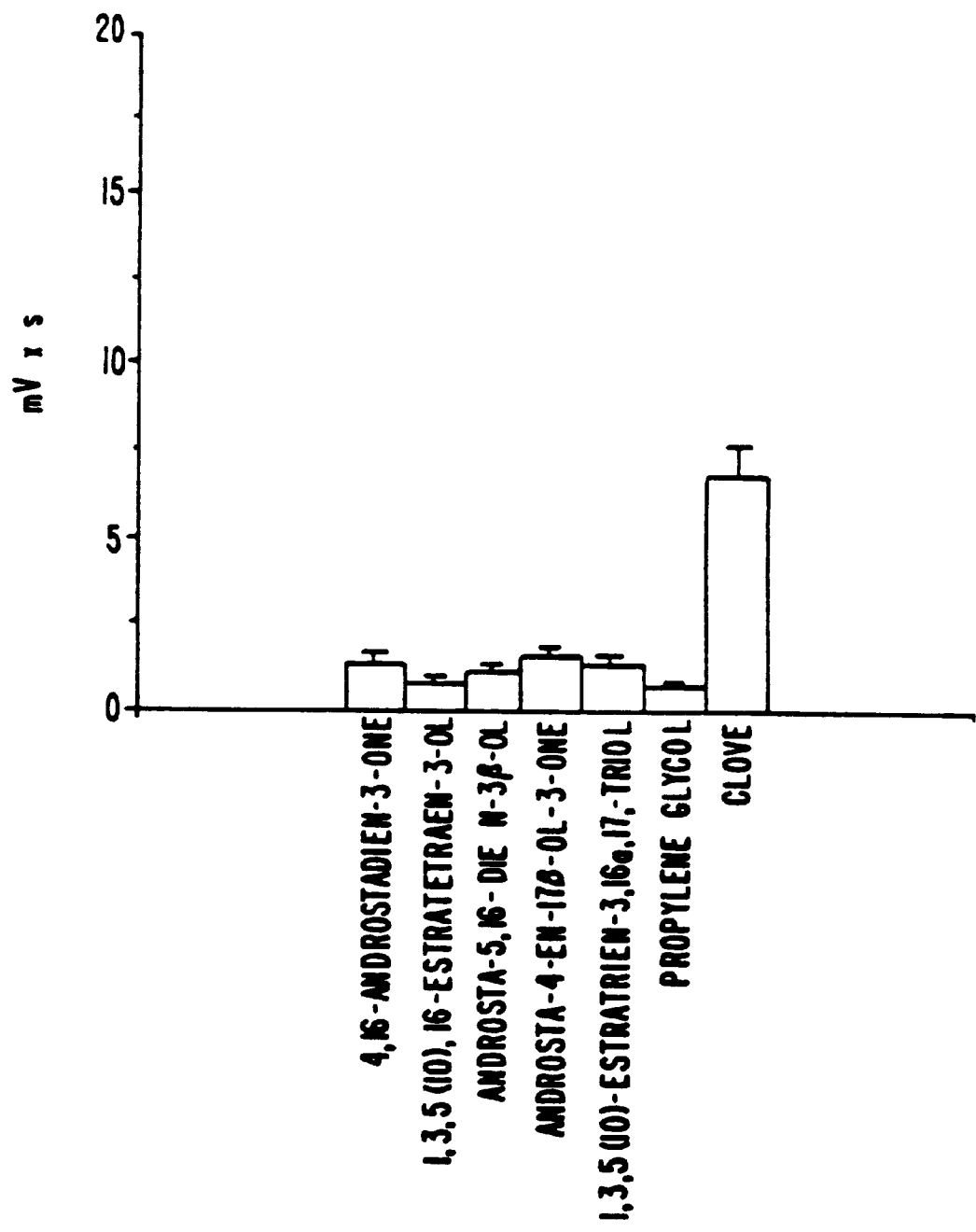
Figure 145A:
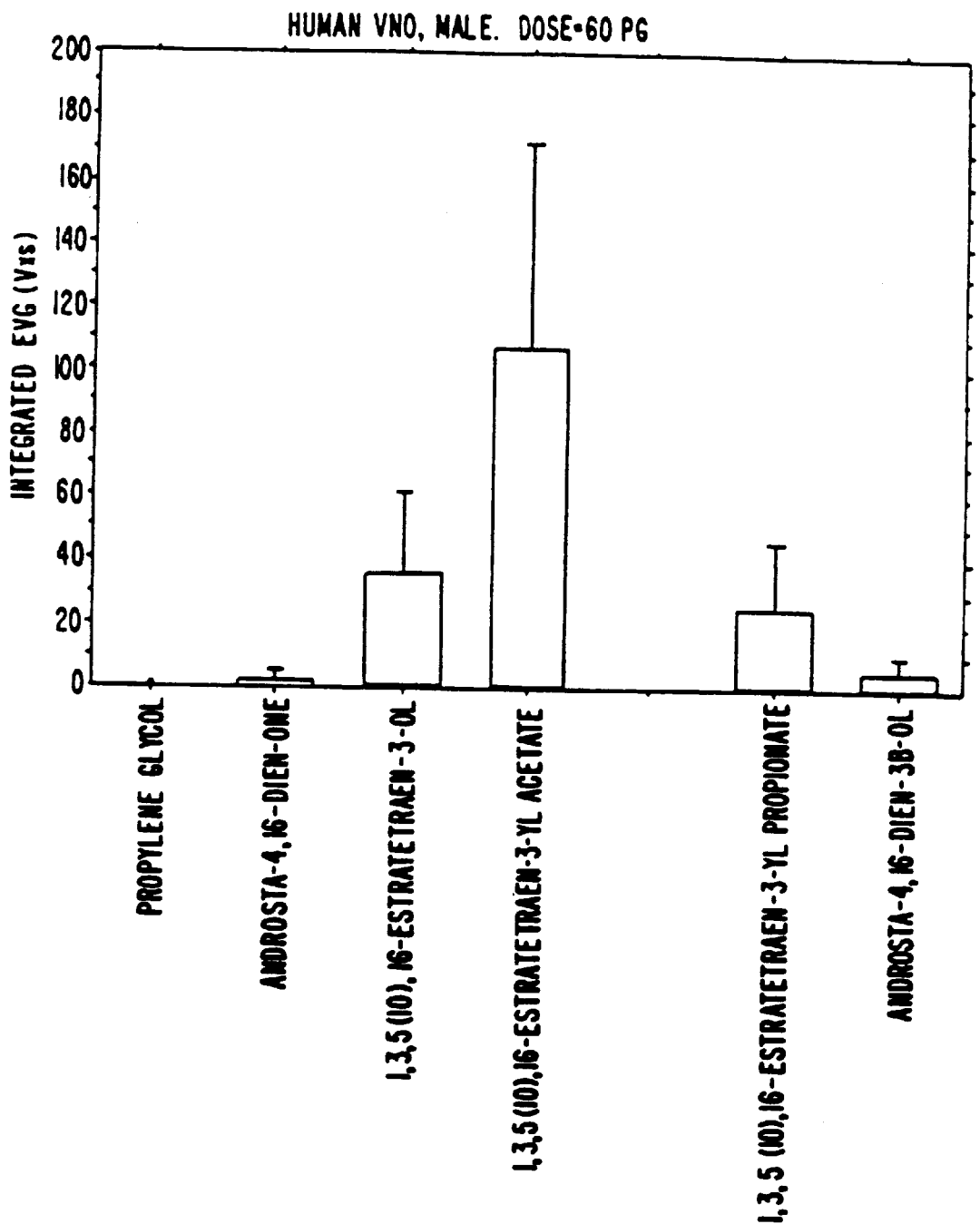
FIG. 145 is a graphic representation of the electrophysiological effect of the localized administration of particular steroids to the vomeronasal organ of male (145A) and female (145B) subjects.
Figure 145B:
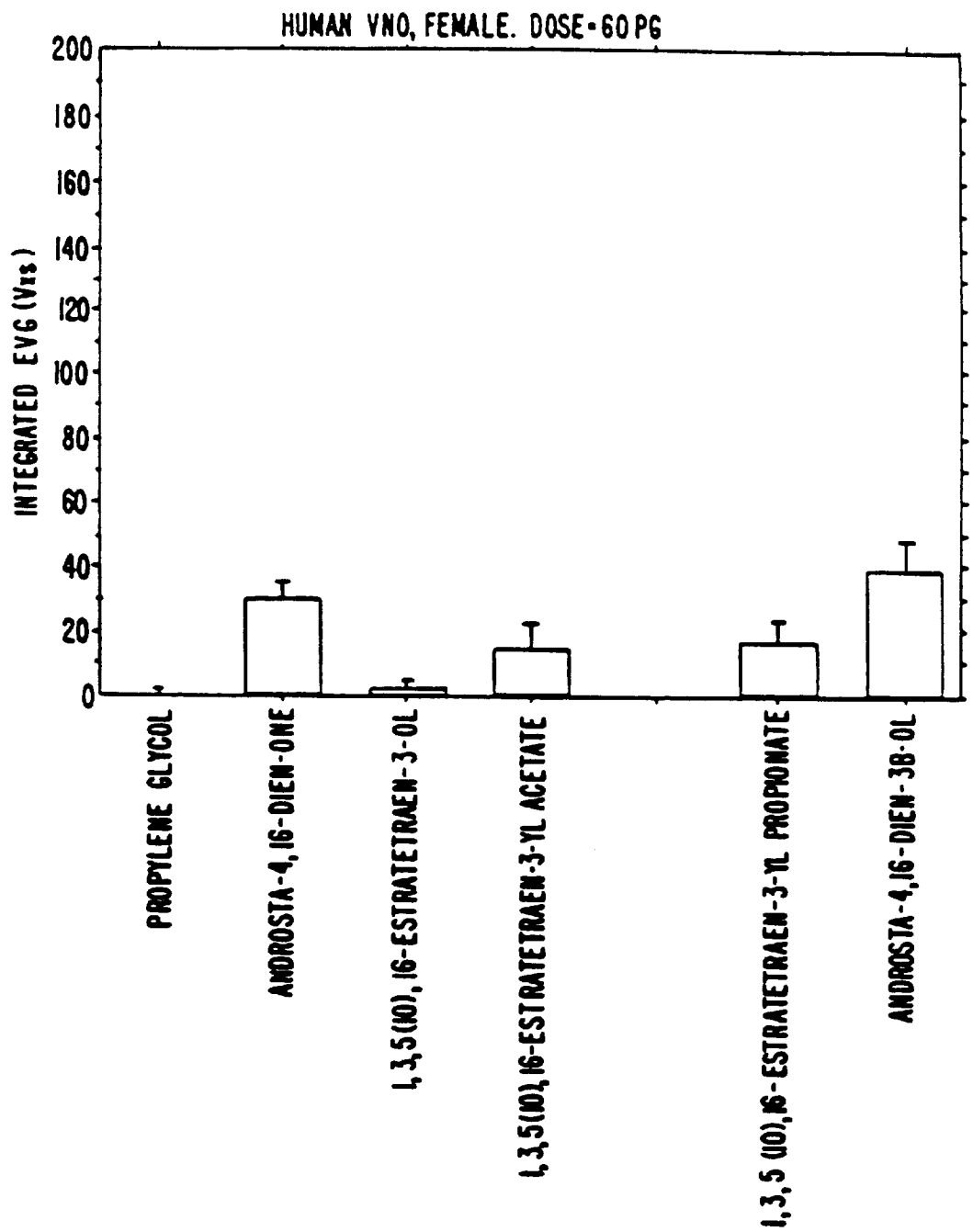
Figure 146:
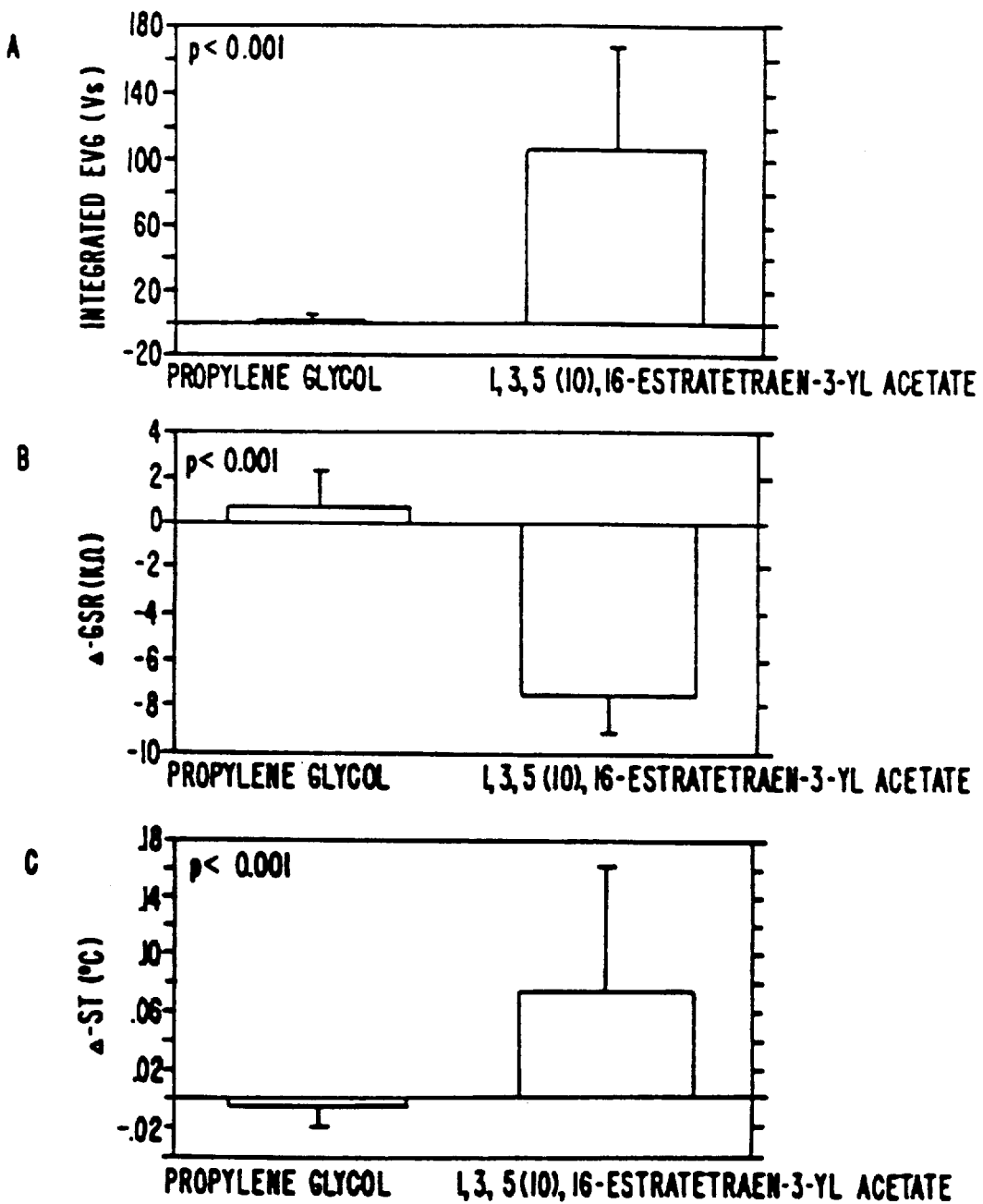
FIG. 146 depicts various autonomic responses of male subjects to 1,3,5(10), 16-Estratetraen-3-yl acetate. A=receptor potential of the vomeronasal neuroepithelium; B=change in galvanic skin response (K-ohms); C=change in skin temperature (degrees C.).
Figure 147:
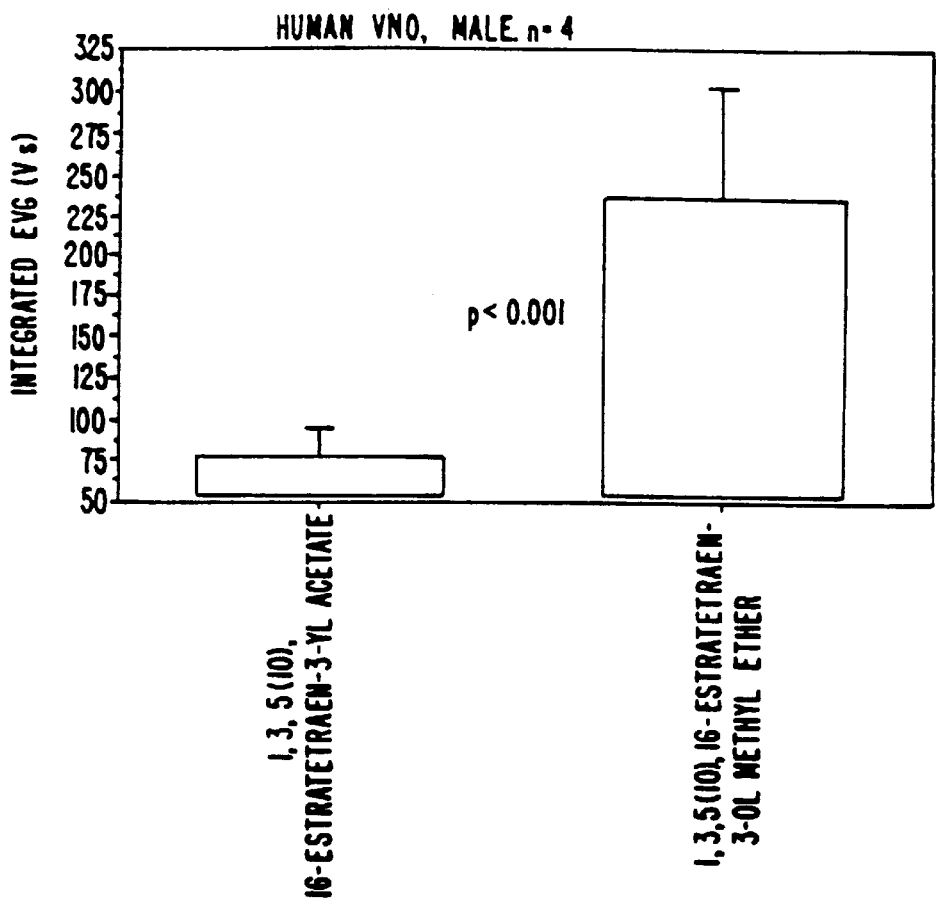
FIG. 147 depicts comparative changes in potential of the VNO after exposure to the methyl 5 ether and the acetate of 1,3,5(10),16-Estratetraen-3-ol.
Figure 148:
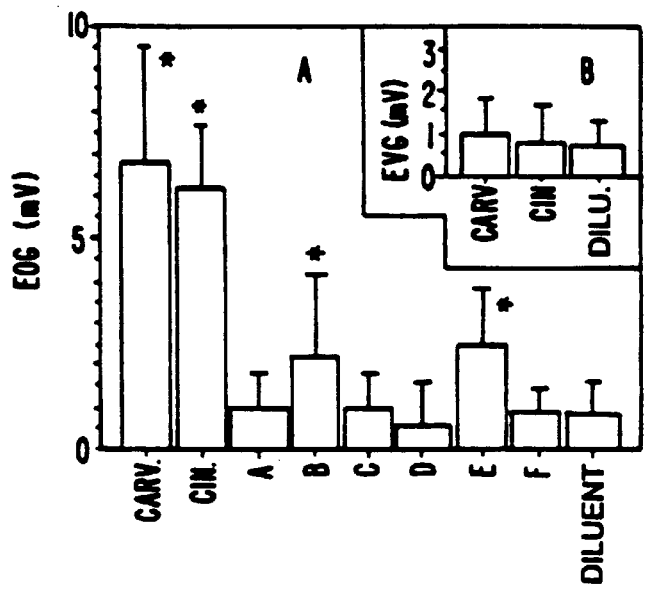
FIG. 148 depicts sexual dimorphism in local and autonomic responses to the stimulation of the VNO with vomeropherins. Various vomeropherins (200 10 fmoles) and the diluent control were administered to 30 male and 30 female subjects (ages 20 to 45 ) as described. Bars indicate the mean response of the population.
Figure 149:
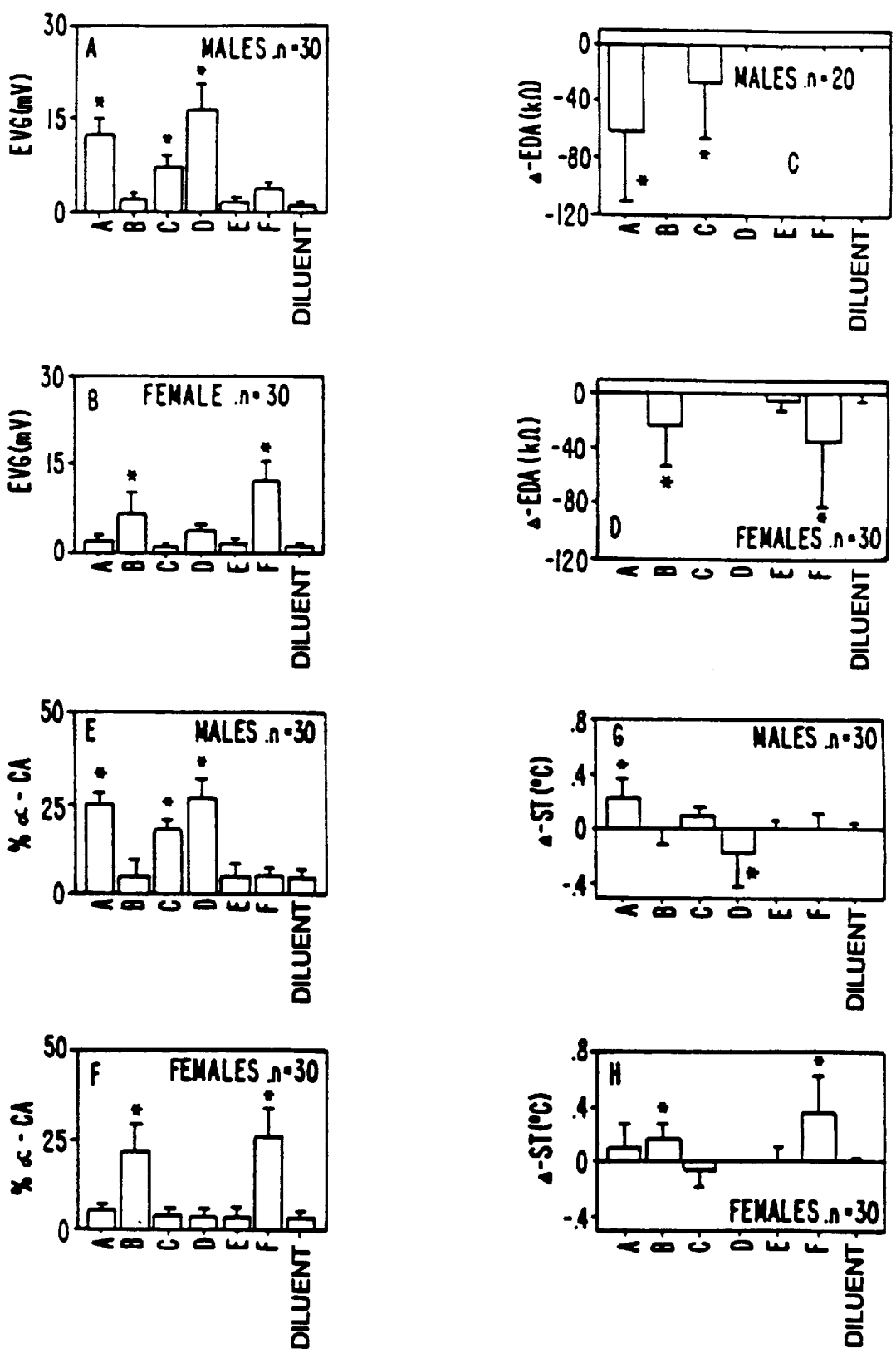
FIG. 149 depicts electro-olfactograms of male and female subjects induced by stimulation of the OE with olfactants and vomeropherins A: 400 fmoles of the olfactants 1-carvone and cineole as well as 200 fmoles of the vomeropherins A, B, C, D and F; and the 10 stereoisomer E were applied separately as one second pulses to the OE of 20 subjects (both male and female) and each EOG response was recorded as described. The olfactants as well as E and B produced significant (p<0.01) local response. B: 400 fmoles of the olfactants 1-carvone and cineole do not induce a significant EVG response when delivered to the VNO of male and female subjects.
Figure 150:
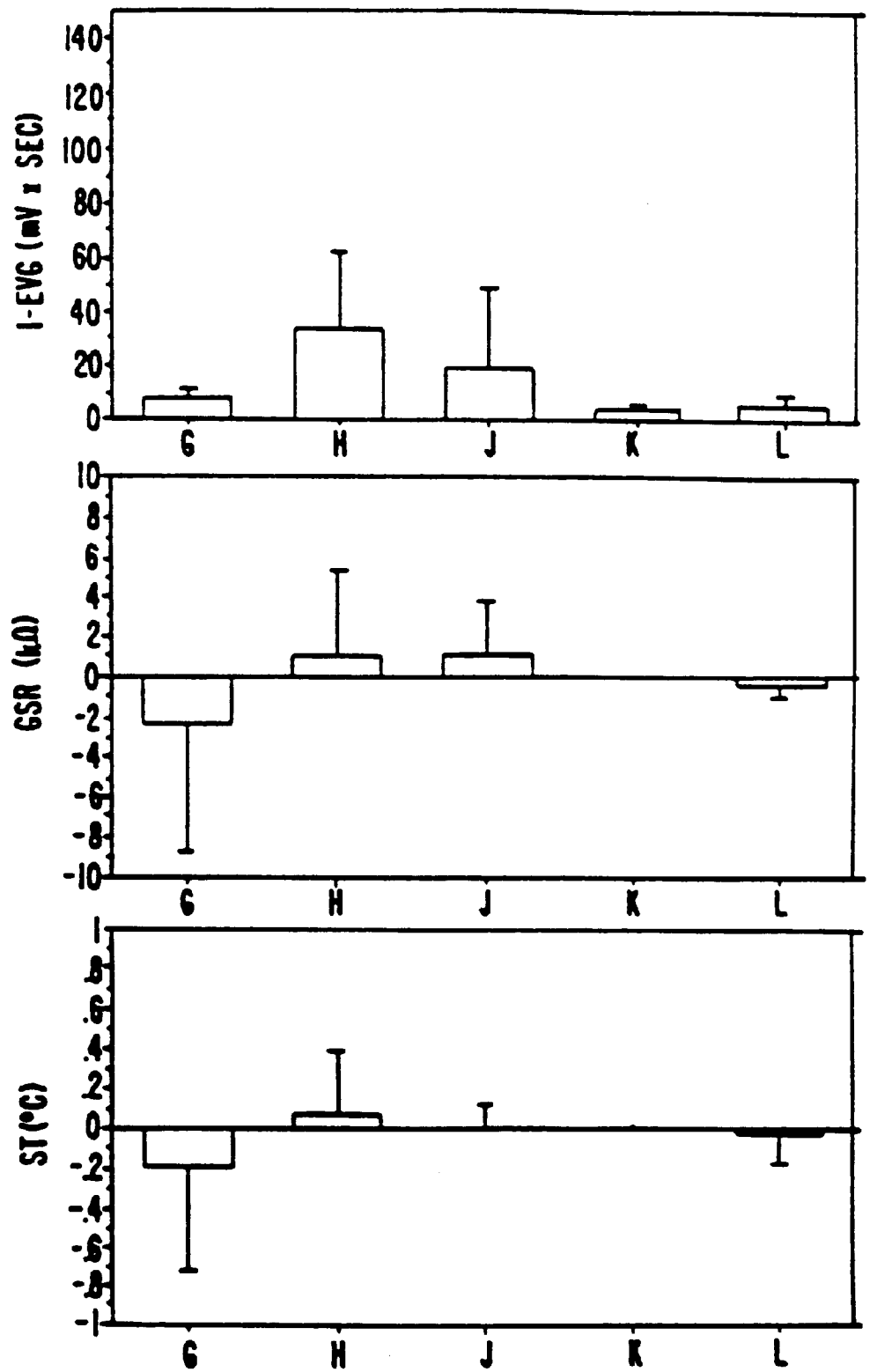
FIG. 150 depicts the electrophysiological effect of the following vomeropherins on the vomeronasal organ of 20 female subjects.
Figure 151:
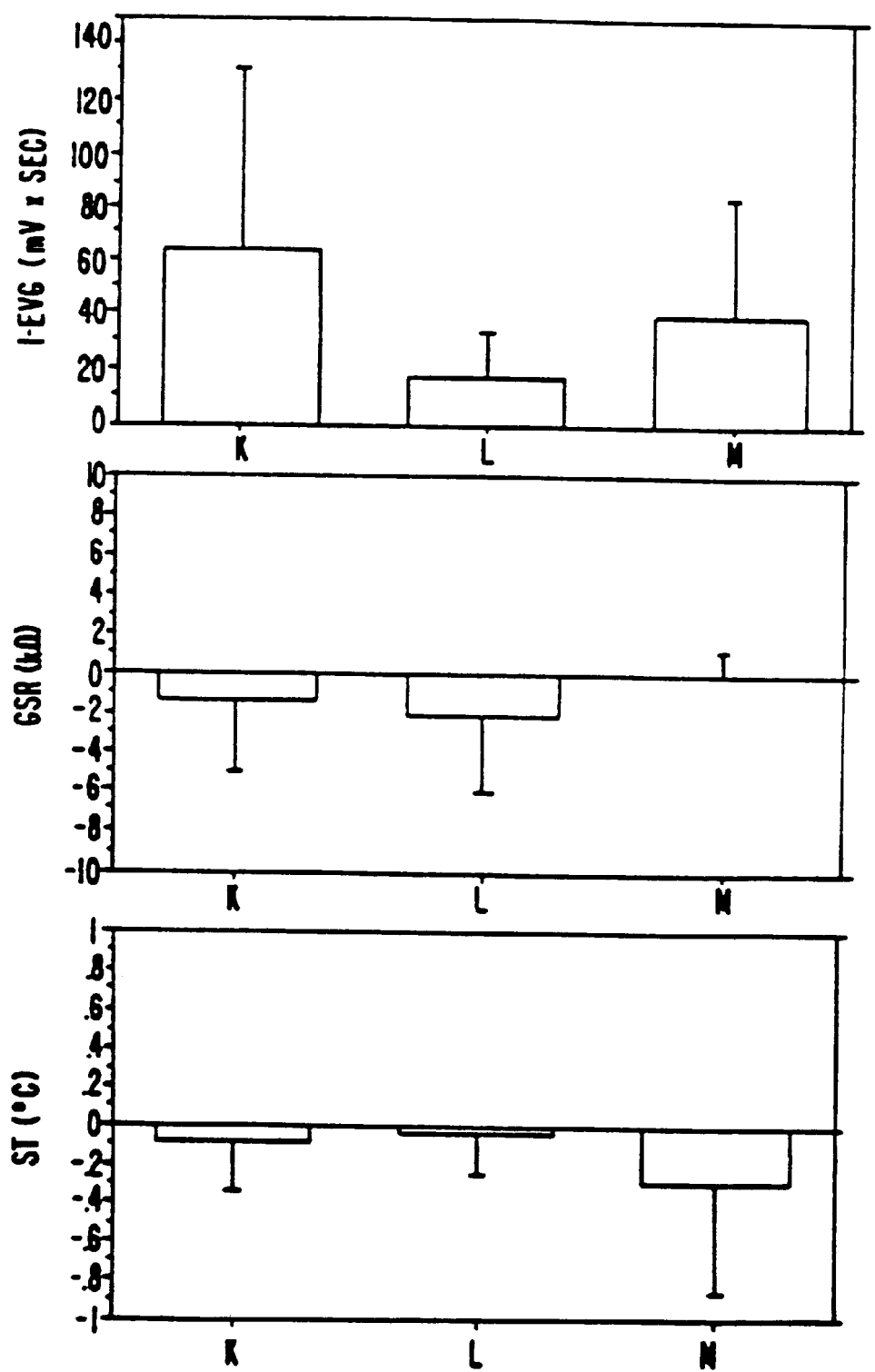
FIG. 151 depicts the electrophysiological effect of vomeropherins on the vomeronasal organ of 20 male subjects.

Various autonomic parameters were monitored as
A1-P3 Pregna-4,16-dien-3-one
A2-P3 Pregna-5,16-dien-3β-ol
A8-P1 3-Methoxy-pregna-3,5,20-triens
A6-P1 Pregna-4,20-dien-3,6-dione
  20,21-Dimethylpregna-5,20-dien-3β-01
  20,21-Dimethylpregna-5,20-dien-3-one
A14-P2 6β,19-Epoxypregna-4,17-dien-3-one
A7-P2 19-Hydroxy-pregna-4,17(20)-dien-3-one
A13-P1 Pregna-4,20-dien-6β-ol-3-one
A11-P1 Pregna-1,4,20-trien-3-one
A1-P1 Pregna-4,20-dien-3-one
A2-P1 Pregna-5,20-dien-3β-ol
A4-P1 Pregna-4,20-3α-ol
A3-P1 Pregna-4,20-3β-ol
A1-$P_4$ Preen-4-en-3-one
A2-$P_4$ Preen-5-en-3β-ol was administered to 24 female and 24 male subjects using the procedure described in Example 32. Propylene glycol was also administered as a control. When compared to a propylene glycol control, the test compounds induced a significant change in the integrated receptor potential in the VNO, galvanic skin response (GSR), skin temperature (ST), the percentage of cortical alpha wave activity as measured by electroencephalogram (EEG), electrocardiogram (EKG) and respiratory frequency (RF). The results are shown in FIGS. 2 through 58. Additional tests were performed on other pregnane derivatives, the results of which are shown in FIGS. 59–84. The results of tests on cholane derivatives are shown in FIGS. 85–96.

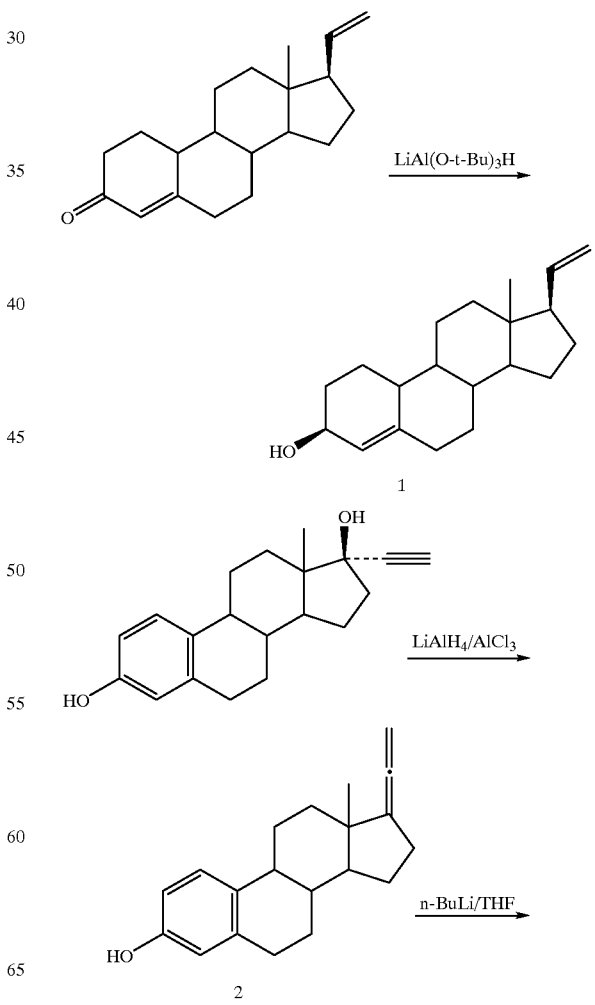

SCHEME 10.
Syntheses of 19-norpregnanes

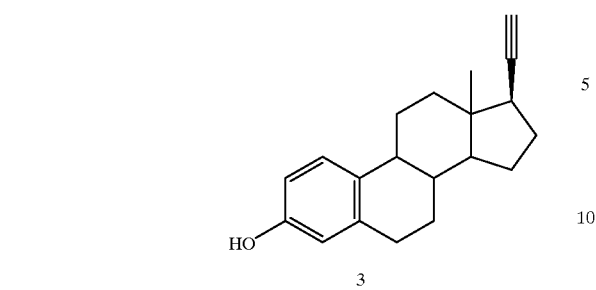
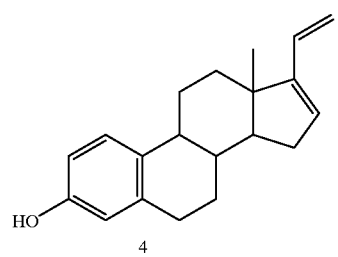
SCHEME 11.
Syntheses of further norpregnanes
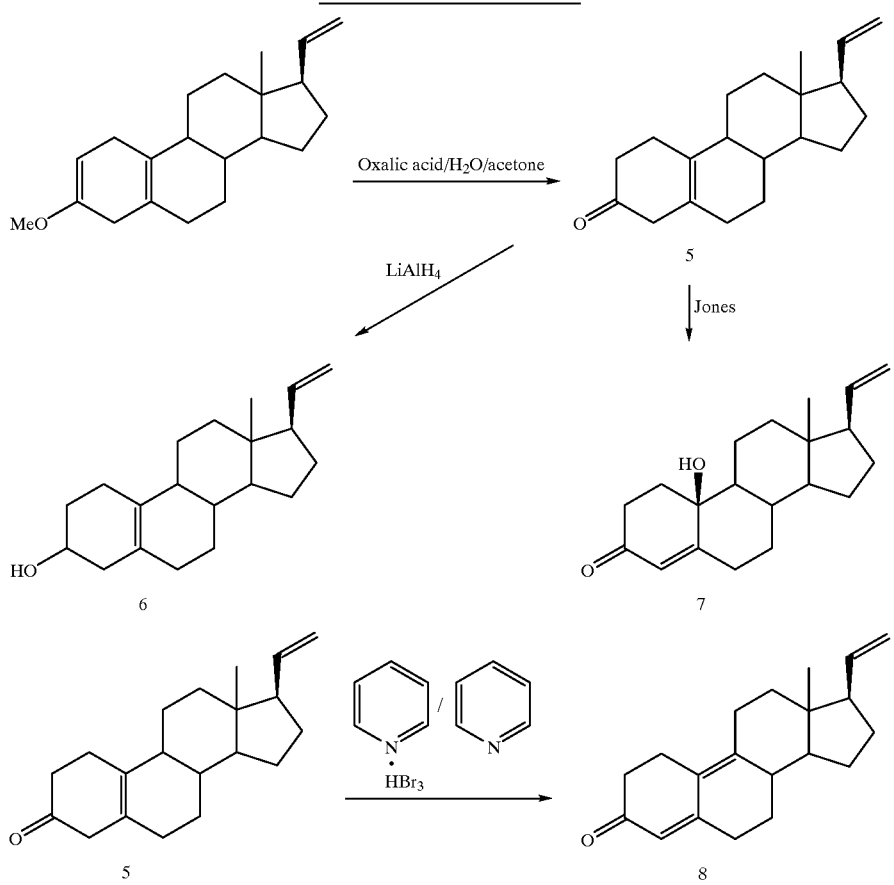

SCHEME 12.
Further syntheses of norpregnanes
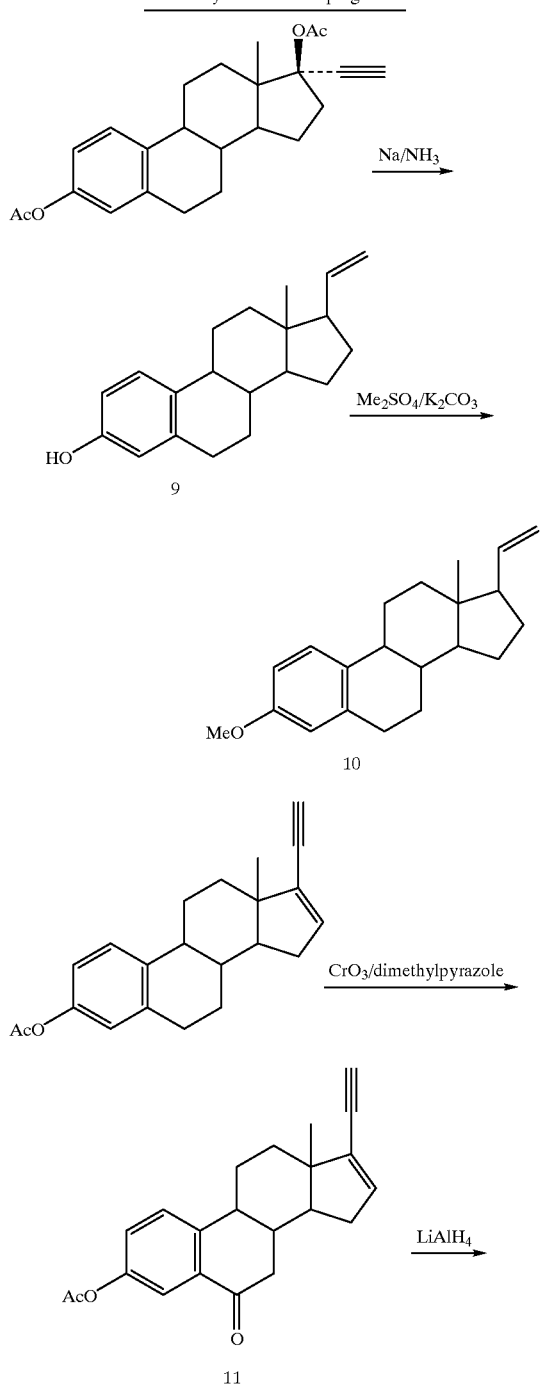
SCHEME 13.
17-Ethylenation of ketones
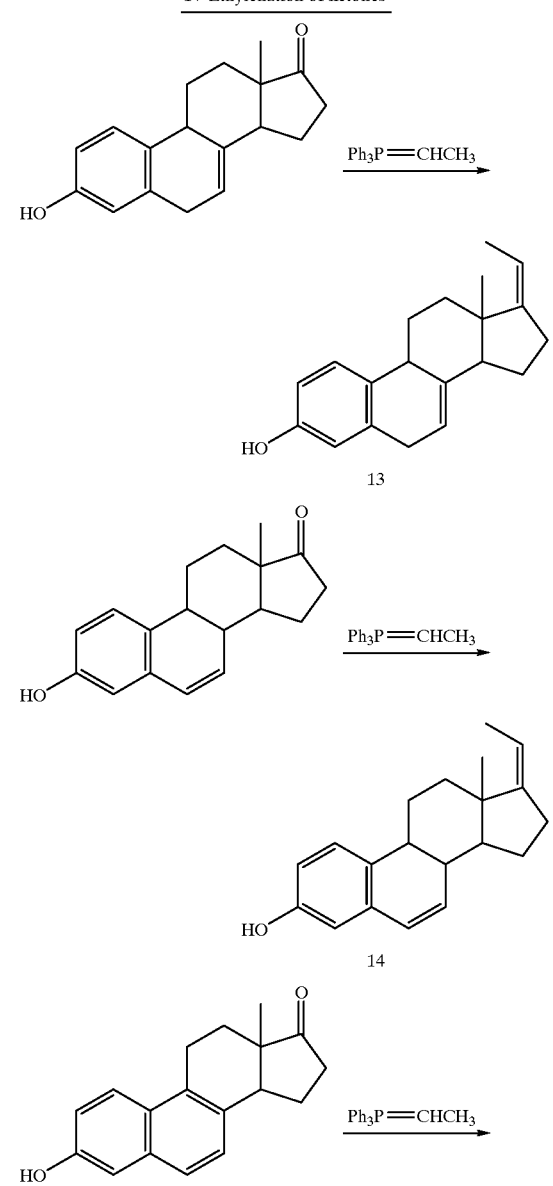
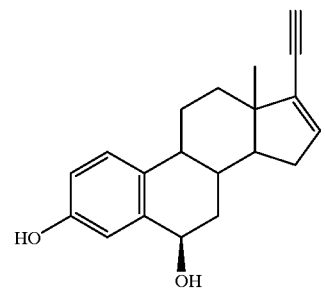

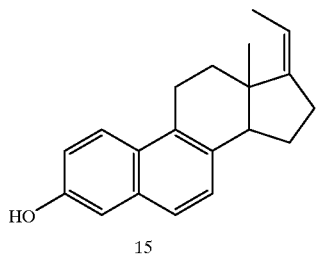

Example 32
19-Norpregna-4,20-dien-3β-ol.

A suspension of 19-norpregna-4,20-dien-3-one (0.38 g, 13 mmol) and lithium tri-t-butoxyaluminohydride (1.36 g, 5.35 mmol) in 20 ml of anh. ether was stirred S h at room temperature, which Glauber's salt (6.74 g) was added. The resulting mixture was stirred 5 min. and then filtered through a glass frit. The residue was washed with 5 20 ml portions of ether and the combined filtrates were concentrated under reduced pressure. The crude product was purified by preparative TLC on silica gel GF using 5% ethyl acetate/methylene chloride as eluent to give a yellow resin (39.6 mg, 0.138 mmol, 11%) homogeneous to TLC (56 ethyl acetate/methylene chloride on silica gel; $R_f$ 0.29).

Example 33
19-Norpregna-1,3,5(10),17,20-pentaen-3-ol.

To a suspension of lithium aluminum hydride (LAH, 256.1 mg, 6.748 mmol) and aluminum chloride (296.8 mq, 2.227 mmol) in 20 ml of anh. ether under argon was added ethinylestradiol (1.0000 g, in 20 ml anh. ether. After refluxing 20 h the reaction was quenched with the addition of Glauber's salt (2.00 g) and stirring a further 2 h. The mixture was then filtered through diatomaceous earth and the residue was washed with 3 10 ml portions of ethyl acetate. Concentration of the combined filtrates, flash chromatography on silica gel with 15% ethyl acetate/hexanes, and twofold recrystallization from aqueous ethanol gave slightly tan needles (367.5 mg, 1.311 mmol, 39%), m.p. 132–133° C., homogeneous to TLC (20% ethyl acetate/hexanes on silica gel; $R_f$ 0.36; estra-1,3,5(10),16-tetraen-3-ol $R_f$ 0.36).

Example 34
19-Norpregna-1,3,5(1)-trien-3-ol-20β-yne.

To a cooled (dry ice/acetone bath) solution of 19-norpregna-1,3,5(10),17,20-pentaen-3-ol (2, 280.4 mg, 1.000 mmol) in 28 ml of anh. THF under argon was added n-BuLi (2.5 M in hexane, 1.2 ml, 3.0 mmol) over 10 min. Stirring was continued for 18 h, during which the reaction was allowed to gradually warm to 15 RT. The reaction was quenched with 25 ml of 1 N HCl and then extracted with 3 10 portions of ether. The combined organic extracts were washed with 25 ml of saturated sodium bicarbonate+25 ml of brine, dried over magnesium sulfate, and filtered through diatomaceous earth. The reside was washed with 10 ml of ether and the combined filtrates were concentrated under reduced pressure. Flash chromatography of the resulting yellow resin on silica gel with 20% ethyl acetate/hexanes, followed by recrystallization from aqueous ethanol gave fine, white needles (150.5 mg, 0.5367 mmol, 54%), m.p. 148–149° C., homogeneous to TLC (20% ethyl acetate/hexanes on silica gel; $R_f$ 0.34; starting material $R_f$ 0.37).

Example 35
19-Norpregna-1,3,5(10),16,20-pentaen-3-ol.

19-Norpreana-1,3,5(10),16-tetraen-3-ol-20-yne (200.0 mg, 0.7184 mmol) in 9 ml anh. THF was added to approx. 30 ml of anh. ammonia. Sodium (0.07 g, 3 mg-atom) was added in small pieces and the reaction was stirred 1 h, during which the color disappeared. Abs. ethanol (3 ml) was added and the mixture was allowed to warm to RT overnight. HCl (1 N, 20 ml) was added the mixture was extracted three times with 10 ml portions of methylene chloride. The combined organic extracts were washed with 10 ml of brine, dried over magnesium sulfate, is and filtered through diatomaceous earth. The reside was washed with 10 ml of methylene chloride and the combined filtrates were concentrated under reduced pressure. Preparative TLC (silica gel GF, with 20% ethyl acetate/hexanes) of the resulting amber resin, followed by recrystallization from benzene/hexanes gave an off-white powder, m.p. 123–125° C. TLC (20% ethyl acetate/hexanes) showed a major product ($R_f$ 0.38) with a minor contaminant ($R_f$ 0.04).

Example 36
19-Norpregna-5(10),20-dien-3-one.

19-Norpregna-2,5(10),20-trien-3-yl methyl ether (750.0 mg, 2.513 mmol) was dissolved in 80 ml of acetone and oxalic acid (0.88 g, 7.0 mmol) in 12 ml of water was added. Further acetone (20 ml) was added to bring most of the precipitate back into solution and the reaction was stirred 6 h. Following saturated sodium bicarbonate quench (30 ml) the reaction mixture was twice with 40 ml portions of ethyl acetate. The combined organic lo extracts were washed twice with 50 ml portions of brine, dried over magnesium sulfate, and filtered through diatomaceous earth. The reside was washed with 25 ml of ethyl acetate and the combined filtrates were concentrated under reduced pressure. Flash chromatography (10% ethyl acetate/hexanes on 15 silica gel) gave a colorless resin (0.54 g, 1.9 mmol, 76%).

Example 37
19-Norpregna-5(10),20-dien-3-ol.

To an ethereal (8.4 ml) solution of 19-norpregna-5(10), 20-dien-3-one (0.42 g, 1.5 mmol) was added 69.7 mg (1.84 mmol) of LAH and the reaction was stirred 30 min. Glauber's salt (2.79 g) was added and the suspension was stirred an additional 10 ml. The mixture was then filtered through diatomaceous earth and the residue was extracted with 435 ml portions of ether. The combined filtrates were concentrated under reduced pressure and the resulting oil was flash chromatographed (20% ethyl acetate/hexanec on silica gel) to give an off-white foam (0.38 g, 1.3 mmol, 88%).

Example 38
19-Norpregna-4,20-dien-10β-ol-3-one.

19-Norpregna-5(10),20-dien-3-one (5,0.45 g, 1.6 mmol) in DMF (5.7 ml) was cooled in an ice-acetone bath and Jones reagent (2.67 M, 0.19 ml, 0.51 mmol) was added. After stirring 1½ h a further 0.19 ml of Jones reagent were added. Stirring was continued 45 min., after which 0.38 ml of Jones reagent were added. The reaction was quenched after stirring 1 more hour by the addition of 2-propanol (0.38 ml). Ethyl acetate (100 ml) was added and the mixture was washed with 3 50 ml portions of water+50 ml of brine, dried over magnesium sulfate, and filtered through diatomaceous earth. The residue was washed with 10 ml of ethyl acetate and the combined filtrates were concentrated under reduced pressure. Preparative TLC on alumina with 50% ethyl acetate/hexanes gave a white, crystalline fill (89.2 mg, 0.297 mmol, 19%). TLC (50% ethyl acetate/hexanes on silica gel)

showed mostly produce ($R_f$ 0.46), contaminated with a little starting material ($R_f$ 0.73).

Example 39
19-Norpregna-4,9(10),20-trien-3-one.

A solution of 19-Norpregna-5(10),20-dien-3-one (0.34 g, 1.2 mmol) in anh. Pyridine (4.0 ml, 49 mmol) was cooled in an ice-salt bath to S below −8° C. and solid pyridinium bromide perbromide (1.26 g, 3.94 mmol) was added at such a rate that the reaction temperature did not exceed −2° C. After stirring 1 min., 0.20 g of phenol were added, the cold bath was removed, and the reaction was stirred at RT for 24 h. Ethyl acetate (50 ml) was 10 added and the mixture was washed with 50 ml of 1 N HCl+25 ml of saturated $CuSO_4$ +25 ml of 5% sodium hydroxide+25 ml of water+25 ml of brine. The mixture was then dried over sodium sulfate for 4 h and afterwards filtered through a glass frit. The residue was washed with 10 ml of ethyl acetate and 15 the combined filtrates were concentrated under reduced pressure. The resulting dark syrup (512.8 mg) was taken up in 8 ml of abs. ethanol, zinc dust (260.8 mg, 3.990 mg-atom) was added, and the suspension was refluxed ½ h. The reduction mixture was filtered through cotton and the residue was washed with 10 ml of ethanol. Concentration of the combined filtrates and two-fold purification by preparative TLC, first on silica gel GF (1000μ, 20% ethyl acetate/hexanes as eluent) then on alumina GF (1000μ, 20% ethyl acetate/hexanes), gave a nearly colorless resin (152.8 mg, 0.5410 mmol, 45%) homogeneous to TLC ($R_f$ 0.22, 10% ethyl acetate/hexanes on silica gel; pregna-4,20-dien-3-one $R_f$ 0.25).

Example 40
19-Norpregna-1,3.5(10),20-tetraen-3-ol.

Ethynylestradiol diacetate (2.0004 g, 5.2576 mmol) in 100 ml of anh. THF was added to approx. 140 ml of anh. $NH_3$ and sodium (1.88 g, 81.8 mg-atom) was added in small slivers over 5 min. After stirring the dark blue solution 1 h, abs. ethanol was added and the reaction was allowed to gradually warm to RT overnight. 100 ml of 1 N HCl were added, the layers were separated, and the aqueous layer was extracted twice with 50 ml portions of ether. The combined organic phases were washed with 3 100 ml portions of brine, derived over magnesium sulfate, and filtered through diatomaceous earth. The residue was washed with 25 ml of ether and the combined filtrates were concentrated under reduced pressure. The residue was taken up in 25 ml of methylene chloride, dried over sodium sulfate, and filtered through diatomaceous earth. The residue was washed twice with 10 ml portions of methylene in chloride and the combined filtrates were concentrated under reduced pressure. Flash chromatography (15% ethyl acetate/hexanes on silica gel) gave a white, crystalline solid with yellow spots (0.86 g, 3.0 mmol, 58%).

Example 41
19-Norpregna-1,3.5(10),20-tetraen-3-yl methyl ether.

To crude 19-Norpregna-1,3,5(10),20-tetraen-3-ol (9, 0.86 g, 3.0 mmol) in 75 ml of 90% ethanol was added 5 potassium carbonate (6.73 g, 55.2 mmol) and the suspension was refluxed ½ h. Dimethyl sulfate (0.75 ml) was added and the reaction was refluxed a further ½ h. Dimethyl sulfate was added in 3 1.8 ml aliquots (total=6.15 ml, 65.0 mmol) over 1 h, and reflux was continued for ½ h. Ice water (65 ml) was added and the mixture was cooled in an ice bath and stirred for 2 h. The suspension was centrifuged and then filtered through a coarse frit. The residue was washed with 50 ml of water+50 ml of 5% sodium hydroxide+3 50 ml portions of water. The residue was recrystallized from aqueous ethanol to give fine white needles, m.p. 108.5–110° C. (lit.m.p. 108–110° C.).

Example 42
19-Norpregna-1,3,5(10),16-tetraen-6-on-20-yn-3-yl-acetate.

Chromium trioxide (2.68 g, 2.68 mmol) was suspended in 40 ml of methylene chloride and the suspension was cooled in an ice-salt bath to −8° C. 3,5-Dimethylpyrazole (2.58 g, 26.8 mmol) was added and the suspension was stirred 20 min. 19-Norpregna-1,3,5(10),16-tetraen-20-yn-3-yl acetate (0.86 g, 2.7 mmol) was added over 5 min., so that the reaction temperature did not exceed −7° C. After stirring an additional 2 h, the reaction mixture was poured through a 30 mm×116 mm column of silica gel and elution was continued under pressure with methylene chloride. Concentration of appropriate fractions gave a brown film (0.16 g, 0.48 mmol, 186).

Example 43
19-Norpregna-1,3,5(10),16-tetraene-3,6β-diol-20-yne.

Crude 19-nonpregna-1,3,5(10),16-tetraen-6-on-20-yn-3-yl acetate (11, 0.16 g, 048 mmol) was suspended in 20 anh. ether, LAH (36.7 mg, 0967 mmol) was added, and the mixture was refluxed with exclusion of water for 18 h. After cooling, 1.22 g of Glauber's salt were added and the suspension was stirred ½ h. The mixture was filtered through diatomaceous earth and the residue was washed with 4 10 ml portions of hot Concentration of the combined filtrates, ethyl acetate, followed by purification by preparative TLC (50% ethyl acetate/hexanes on silica gel GF, 1000μ) gave a white solid (26.0 mg, 88.3 mmol, 18%) homogeneous to TLC (50% ethyl acetate/hexanes on silica gel; $R_f$ 0.48).

Example 44
19-Norpregna-1,3,5(10),17-tetraen-3-ol.

Ethyltriphenylphosphonium bromice (1.3947 g, 3.7572 mmol) and potassium t-butoxide (422.5 mg, 3.765 mmol) suspended in anh. DMSO (4.1 ml) under argon were placed in an oil bath (80–84° C.) and stirred 1 h. Equilin (200.2 mg, 0.7459 mmol) in 4.1 ml of anh. DMSO was added and the reaction was stirred a further hour. After cooling, 25 ml of ice-1 N HCl was added and the mixture was extracted three times with 20 ml portions of ether. The combined organic extracts were washed with 25 ml of saturated sodium bicarbonate+25 ml of brine, dried over magnesium sulfate, and filtered through diatomaceous earth. The residue was washed with 10 ml of ether and the combined filtrates were concentrated under reduced pressure. Flash chromatography (20% ethyl acetate/hexanes on silica gel) followed by preparative TLC (20% ethyl acetate/hexanes on silica gel GF, 1000μ) gave a slightly yellow resin (182.9 mg, 15 0.6523 mmol, 87%) homogeneous to TLC (20% ethyl acetate/hexanes $R_f$ 0.42).

Example 45
19-Norpregna-1,3,5(10),617-pentaen-3-ol.

Ethyltriphenylphosphonium bromide (1.3945 g, 3.7561 mmol) and potassium $_1$-butoxide (422.8 mq, 3.768 mmol) suspended in 4. J ml of anh. DMSO under argon were placed in a 77–79° C. bath and were stirred 1 h. 6-Dehydroestrone (200.4 mg, 0.7466 mmol) in 4.1 ml of anh. DMSO was added and the reaction was stirred in 1 h. The reaction mixture was allowed to cool and was then poured into 25 ml o fice-1 N HCl. The mixture was extracted three times with 20 ml of ether and the combined organic extracts were washed with 25 ml of saturated sodium bicarbonate+25 ml of brine, dried over magnesium sulfate, and filtered through diatomaceous earth. The residue was washed with 10 ml of ether and the combined filtrates were concentrated under reduced pressure. Flash chromatography (15% ethyl acetate/ hexanes) and preparative TLC (15% ethyl acetate/hexanes on silica gel GF, 1000µ) gave an off-white crystalline solid (212.9 mg, >100%) homogeneous to TLC (15% ethyl acetate/hexanes on silica gel, $R_f$ 0.21).

Example 46

19-Norpregna-1,3,5(10),6,8,17-hexaen-3-ol.

Ethyltriphenylphosphonium bromide (1.3945 g, 3.7561 mmol) and potassium t-butoxide (422.3 mg, 3.763 mmol) suspended in 4.1 ml of anh. DMSO under argon were placed in an oil bath (74–83° C.) and the reaction was stirred 1 h. Equilenin (200.2 mg, 0.7518 mmol) in 4.1 ml of anh. DMSO was added and the reaction mixture was stirred a further hour. The mixture was poured into 25 ml of ice-1 N HCl and extracted three times with 20 ml portions of ether. The combined organic extracts were washed with 25 ml of saturated sodium bicarbonate+25 ml of brine, dried over magnesium sulfate, and filtered through diatomaceous earth. The residue was washed with 10 ml of ether and the combined filtrates were concentrated under reduced pressure. Flash chromatography (20% ethyl acetate/hexanes) and preparative TLC (20% ethyl acetate/hexanes on silica gel GF, 1000µ) gave a light yellow, crystalline wax (180.6 mg, 0.6487 mmol, 86%) homogeneous to TLC.

Example 47

The following study compares the effect of 23 vomeropherins with 19-norpregnane structure, and placebo (propylene glycol), on autonomic activity and EEG. Twelve healthy human subjects (6 women and 6 men), ages 19 to 29 participated in this study. All substances were delivered airborne to the vomeronasal organ (VNO) puff lasting 5 seconds. For this purpose we use a miniprobe electrode described elsewhere, that allowed local stimulation and simultaneous recording of the organ's electrovomerogram (EVG). The parameters recorded were: electrodermal activity (EDA), respiratory frequency (RF), electrocardiogram (CF), electromyogram (EMG), body temperature (BT), and EEG from CzA1 and T3A1. Autonomic activity, EEG and EVG were recorded using surface electrodes. All the techniques used were noninvasive. The procedure was done in two recording sessions each lasting one hour. The electrical recordings were amplified, digitized, and monitored and stored in a computer. Processing and analysis of the results were done offline.

The data on the tests on the women is shown in FIGS. 99–120, and the data on the men is shown in FIGS. 121–142.

The results were summarized in the following tables showing the overall effect of each vomeropherin already subtracted from control. An arbitrary score from 0 to 5 was assigned to compare the activity of the compounds relative to each other, but virtually all of the compounds tested had some effect.

These results show that the effect of some vomeropherins on autonomic activity and EEG is significantly different from placebo. Also shown is that some substances do not have significantly different effects in both genders.

Example 48

Synthesis of Estra-1,3,5(10),16-tetraen-3-ol.

The following method of synthesis is depicted in FIG. 1:

Estrone p-Toluenesulfonylhydrazone

Estrone (270 g, 1.00 mole) and p-toluenesulfonylhydrazide (232.8 g, 1.25 mole) in dry methanol (2.5 liters) were heated under reflux for 20 hours. The mixture was transferred to a conical flask and allowed to cool. The crystalline product was filtered off under suction and washed with methanol (300 ml). Further crops of product were obtained by sequentially evaporating the filtrate to 2000 ml, 800 ml and 400 ml, and allowing to crystallize each time. Total yield was 433.5 g (99%).

1,3,5(10),16-Estratetraen-3-ol

Estrone p-toluenesulfonylhydrazone (219.9 g, 500 m mole) in dry tetrahydrofuran (8.0 liters) was cooled in a sodium chloride/ice bath. The mixture was mechanically stirred while n-butyl lithium (800 ml of a 2.5 M solution in hexane, 2.00 mole) was added via double-ended needle. The mixture was stirred at room temperature for 3 days. Ice (250 g) was added, followed by saturated ammonium chloride solution (500 ml). The phases were mixed by stirring and then allowed to settle. The aqueous phase was removed via aspiration with teflon tube and extracted with ether (500 ml). The two organic phases were sequentially washed with the same batch of saturated sodium bicarbonate solution (500 ml) followed by saturated sodium chloride solution (500 ml). The organic layers were dried ($MgSO_4$) and evaporated in vacuo to give crude product. This was subjected to flash filtration on 500 g silica gel 60, 230–400 mesh, eluting with ethyl acetate/hexane (25.75, 2.5 liters) The filtrate was evaporated in vacuo to give crystalline material. The product was recrystallized from methanol (300 ml)/water (75 ml) washing with methanol (80 ml)/water (20 ml). Further recrystallization from ethyl acetate/hexane (12.5:87.5) gave pure product (88.9 g, 70%).

Example 49

Synthesis of Acyl derivatives of 1,3,5(10), 16-Estratetraen-3-ol.

To 1,3,5(10),16-Estratetraen-3-ol (254 mg, 1.00 Mmole) in ether (10 ml) is added acetic anhydride (0.25 ml) (or propionic anhydride for the propionate) followed by pyridine (0.25 ml) and the mixture is stirred at room temperature for 16 hours. The mixture is poured into ice/water and extracted with ether (2×20 ml). The organic extracts are washed with water, saturated copper sulfate solution, water, and saturated sodium chloride solution, dried ($MgSO_4$) and evaporated in vacuo to give the pure product (192 mg, 65%).

Example 50

Synthesis of Estra-4,16-dien-3-one.

To estra-1,3,5(10), 16-tetraene-3-methyl ether (551.5 mg., 2.055 mmol) in 8.6 ml of anhydrous THF, approximately 30 ml of anhydrous ammonia, and 6.76 g of t-butyl alcohol was added lithium wire (0.24 g, 35 mg-atom) cut in small pieces. The reaction mixture was refluxed 4½ h under argon, after which methanol (2.3 ml) was added and the ammonia was allowed to boil off overnight. The residue was dissolved in 25 Ml of methanol and was acidified to approximately Ph 1 with 5N HCl. After heating in an oil bath between 55 and 70 C for 15 min. the cooed hydrolysis mixture was partitioned between 25 ml of water and 50 ml of ethyl acetate and the aqueous phase was extracted with 25 ml of ethyl acetate. The combined organic extracts were washed with 25 ml of saturated sodium bicarbonate and 25 ml of brine, dried over magnesium sulfate, and filtered. Removal of solvent under reduced pressure yielded 0.57 g of oily residue which was purified by flash chromatography on silica gel (eluent: 15% ethyl acetate/hexane) followed by recrystallization from pentane to give crystals (206.1 mg, 39%) homogeneous to TLC, m.p. 67–71° C.

Example 51

Synthesis of Estra-2,5(10),16-triene-3-methyl ether.

To Estra-1,3,5(10),16-tetraene-3-methyl ether (1.22 g, 4.54 mmole) in 19 ml of anhydrous THF, 14.99 g of t-butyl alcohol, and approximately 70 ml of anhydrous ammonia was added lithium wire (0.53 g, 76 mg-atom) cut in small pieces. After refluxing under argon for 6 h the reaction was quenched with 5 ml of methanol and ammolonia was allowed to boil off overnight. A suspension of the residue in 100 ml of water was extracted twice with 100 ml portions of ethyl acetate and the combined organic extracts were washed with brine and dried over magnesium sulfate. Following solvent removal under reduced pressure the residue was flash chromatographed on silica gel using 1% ethyl acetate/hexane as eluent and then recrystallized from abs. ethanol to give fluffy white crystals (884.1 mg, 3.269 mmole, 72%), m.p. 72–73 C, homogeneous to TLC.

Example 52

Synthesis of Estra-5(10),16-dien-3-one.

Estra-2,5(10), 16-triene-3-methyl ether (2) (646.3 mg, 2.390 mmole), dissolved in 50 ml of acetone was hydrolyzed for 6 h at room temperature using oxalic acid dihydrate (0.84 g, 6.7 mmole). The reaction mixture was quenched with 25 ml of saturated sodium bicarbonate and then extracted twice with 25 ml portions of ethyl acetate. The combined organic extracts were washed twice with 25 ml of brine, dried over magnesium sulfate, filtered, and concentrated under reduced pressure. The residue was recrystallized from hexane to give product (462.5 mg, 1.804 mmole, 75%), m.p. 112–116° C.

Example 53

Synthesis of Estra-5(10),16-dien-3-ols (4).

Estra-5(10),16-dien-3-one (3) (301.1 mg, 1.174 mmole), in 6 ml of anhydrous ether was reduced for 1 h at room temperature using lithium aluminum hydride (50.0 mg, 1.32 mmole). After quenching with sodium sulfate decahydrate (2.00 g) for 10 min. the suspension was filtered through Celite and the residue washed with four 25 ml portion of ether. The combined filtrates were concentrated under reduced pressure and purified by flash chromatography (silica gel, 5% ethyl acetate/hexanes eluent) with subsequent preparative TLC of mixed fractions. The more polar product could be recrystallized with considerable loss from aqueous ethanol to give 4.8 m mg of solid. The less polar product was recrystallized from aqueous methanol to give white crystals (59.5 mg), m.p. 98–100° C. Total yield was 64.3 mg (0.249 mmol, 21%).

Example 54

Synthesis of Estra-4,9,16-trien-3-one.

Estra-5(10,16-dien-3-one (3) (0.38 g, 1.5 mmole), in pyridine (5.0 ml, 62 mmol) was cooled in an ice-salt bath to −13 C and pyridinium bromide perbromide (1.58 g, 4.94 mmole) was added in small portions so that T<−4 C. After swirling 1 min. phenol (0.25 g, 2.7 mmole) was added and reaction continued 24 h at room temperature. Ethyl acetate (50 ml) was added and the reaction mixture was washed with 25 ml of 1N HCl, two 25 ml portions of saturated copper sulfate, 25 ml of 5% sodium hydroxide, and 25 ml of brine. After drying our magnesium sulfate, filtration, and concentration under reduced pressure the residue was taken up in 10 ml of abs. ethanol, granular zinc (0.33 g, 5.0 mg-atom) was added, and the mixture was refluxed ½ h. The supernatant was removed, the residue was washed with 10 ml of abs. ethanol, and the combined supernatants were concentrated under reduced pressure. The resulting resin was flash chromatographed on silica gel using 15% ethyl acetate/hexane as eluent. Appropriate fractions were pooled, concentrated, and then recrystallized from hexane to give solid product (117.5 mg, 0.4619 mmol, 31%), m.p. 87–92° C.

Example 55

Synthesis of Estra-1,3,5(10),16-tetraen-6-one-3-acetate.

Chromium trioxide (13.40 g, 0.1340 mol) was suspended in 200 ml of methylene chloride and then cooled to 10° C. in an ice-salt bath. 3,5Dimethylpyrazole (12.90 g, 0.1342 mol) was added and the mixture was stirred 20 min. Estra-1,3,5(10),16tetraen-3-yl acetate (4.00 g, 13.5 mmol) in a chilled solution of 20 ml of methylene chloride was added and action stirred 2 h, during which time T<−8° C. Mixture was then filtered through 200 g of silica gel and the product was eluted with further methylene chloride. After combining and concentrating appropriate fractions the crude product was flash chromatographed on silica gel using 15% ethyl acetate/hexane as eluent. Pooling of appropriate fractions and concentration under reduced pressure yielded a white solid (0.92 g, 3.0 mmol, 22%), m.p. 87–103° C.

Example 56

Synthesis of Estra-1,3,5(10),16-tetraen-3-ol-6-one.

Estra-1,3,5(10),16-tetraen-6-one-3-acetate (203.1 mg, 0.6543 mmol) in 30 of methanol was saponified with 1.5 ml of 5% (w/w) sodium hydroxide for 40 min. The reaction mixture was concentrated under reduced pressure, taken up in 50 ml of water, neutralized with 1N HCl, and extracted three times with 25 ml portions of methylene chloride. The combined organic extracts were washed with 50 ml of brine, dried over magnesium sulfate, filtered, and concentrated to give a white solid which was purified by recrystallization from benzene/hexane and preparative TLC to give white crystalline solid (52.8 mg, 0.197 mmol, 30%), m.p. 188–191° C.

Example 57

Synthesis of Estra-1,3,5(10),16-tetraen-6α-ol-3-yl acetate.

Estra-1,3,5(10),16-tetraen-6-one-3-yl-acetate (421.4 mg, 1.358 mmol), suspended in 35 ml of 95% ethanol was reduced with sodium borohydride (98.8 mg, 2.61 mmol) for lo min. at room temperature. After concentrating under reduced pressure the residue was suspended in 25 ml of water, neutralized with 1N HCl, and extracted three times with 25 ml portions of methylene chloride. The combined organic extracts were washed with 25 ml of brine, dried over magnesium sulfate filtered, and concentrated. The resulting white foam was flash chromatographed on silica gel using 25% ethyl acetate/hexane as eluent. Combining fractions and concentration gave a white solid (0.12 g, 0.38 mmol, 28%), m.p. 209–212° C.

Example 58

Synthesis of Estra-1,3,5(10),16-tetraene-3 6-diol.

To a suspension of lithium aluminum hydride (LAH, 95%, 46.9 mg, 1.17 mmol) in 5 ml of anhydrous THF was added estra-1,3,5(10),16-tetraen-6-one-3-yl-acetate (6) (422.9 mg, 1.360 mmol) in 5 ml of anhydrous THF dropwise, with stirring. The reaction was stirred 50 min., after which further LAH (46.5 mg, 1.16 mmol) was added and the reaction stirred 22 h. After refluxing 4 h TLC still showed starting material. The reaction was quenched with 0.5 ml of water +0.5 ml of 20% (w/w) sulfuric acid and concentrated under reduced pressure. The residue was extracted four times with 10 ml portions of hot ethyl acetate and filtered through Celite. The combined filtrates were concentrated and purified twice by flash chromatography to give solid product (0.05 g, 0.2 mmol, 10%), m.p. 150–157° C.

Example 59
Synthesis of Estra-1 3.5(10).7-tetraen-3-ol.

To a suspension of equilin (100.2 mg, 0.3733 mmol) in 2 ml of diethylene glycol were added hydrazine (59 μL, 1.9 mmol) and potassium hydroxide (0.04 g, 0.7 mmol). The mixture was stirred in an oil bath at 200–214° C. for 2 h, after which the cooled reaction was diluted with 10 ml of water, neutralized with 1N HCl, and extracted three times with 25 ml of ether. The combined organic extracts were washed with 10 ml of brine, dried over magnesium sulfate, filtered, concentrated, and purified by preparative TLC (silica gel, 15% ethyl acetate/hexane eluent) to give a yellow resin.

Product was further purified by decolorizing with charcoal and recrystallization from aqueous ethanol to give tan crystals (13.2 mg, 51.9 μM, 14%), m.p. 130–134° C.

Example 60
Synthesis of 20-Homoestra-1,3,5(10), 6,8,17-hexaen-3-ol.

A suspension of triphenylmethylphosphonium bromide (671.0 mg, 1.878 mg) and potassium t-butoxide (212.1 mg, 1.890 mmol) in 2.1 ml of anhydrous DMSO was heated in a 76–86° C. bath under argon for 1 h, after which equilenin (100.1 mg, 0.3579 mmol) in 2.1 ml of anh. DMSO was added and the green solution was stirred 1 h. After cooling 10 ml of ice-1N HCl were added and the mixture was extracted with three 10 ml portions of ether. The combined organic extracts were washed with 10 ml of saturated sodium bicarbonate+10 ml of brine, dried over magnesium sulfate, filtered through Celite, and concentrated under reduced pressure. The residual orange oil was purified by preparative TLC (silica gel, 25% ethyl acetate/hexane) to give product (75.5 mg, 0.286 mmol, 76%) homogeneous to TLC, m.p. 113–121° C.

Example 61
Synthesis of 20-Homoestra-1.3.5(10), 6,8,17-hexaen-3-ol.

Estra-1,3,5(10),6-tetraen-3-ol-17-one (91.1 mg, 0.339 mmol), hydrazine (54 μL, 1.7 mmol), and potassium hydroxide (0.06 g) in 1.8 ml of diethylene glycol were heated in a 200° C. bath under argon for 2 h. After cooling to RT 10 ml of water were added and the solution was acidified to pH≈2 with 1N HCl. The resulting suspension was extracted three times with 10 ml of ether and the combined organic extracts were washed with 10 ml of brine, dried over magnesium sulfate, filtered through Celite, and concentrated under reduced pressure. The crude solid was purified by preparative TLC (25% ethyl acetate/hexane on silica gel) to give product homogeneous to TLC (5.9 mg, 23 mmol, 70%).

Example 62
Synthesis of Estra-4 16-dien-3-ol.

To estra-4,16-dien-3-one, (1) (87.2 mg, 0.340 mmol) in 1.7 ml of anh. ether was added lithium aluminum hydride (15.0 mg, 0.395 mmol) and the suspension was stirred 17 min. Reaction was then agitated 10 min. with 0.50 g of sodium sulfate decahydrate and filtered through Celite. The residue was washed with three 10 ml portions of ether and the combined filtrates were concentrated under reduced pressure. Preparative TLC (5% ethyl acetate/dichloromethane on silica gel) gave crude product (50.0 mg) as a yellow resin. This could be rechromatographed until sufficiently pure.

Example 63
Estra-4,16-dien-3-one.

This synthesis is depicted in FIG. 153. 19-Nor-testosterone (XIX) is commercially available, e.g., from Chemical Dynamics Corp. It provides the starting material for 19-Nor-16-androstene derivatives. 19-Nor-testosterone (XIX) was converted into the acetate (Hartman, J. A. et al., *J. Am. Chem. Soc.* (1956) 78:5662) with acetanhydride and pyridine. (a) A solution of this acetate (4.8 g, 15.17 mmol) in toluene (10 ml) was pyrolyzed (b) at 540° (200 Torr, slow N2-stream) in a glass tube packed with quartz pieces. Chromatography of the crude pyrolysate (3.1 g) on silica gel (150 g) with $CH_2Cl_2$ gave 1.1 g (28%) of the homogenous oily ketone 9; +57.9° (C 1) ([27]: m.p. 71–73°). -IR. ($CHCl_3$): 1660s, 1615m, 1585w, -$^1$H-NMR. (90 MHz): 0.84 (s, 3H); 5.82 (m, 2H); 5.87 (br. s, 1H).

Example 64
Estr-16-en-3-one

This synthesis is depicted in FIG. 153. 19-nor-testosterone was reduced to 19-nor-5a-Androstan-17-ol-3-one (XX) with lithium and ammonia (c) according to the method of Villotti, R., et al. (*J. Am. Chem. Soc.* (1960) 82:5693). Androsta-5a,17-diol-3-one (XX) was converted into the acetate (Hartman, J. A. et al., *J. Am. Chem. Soc.* (1956) 78:5662) with acetanhydride and pyridine (a). A solution of 17B-acetoxy-5a-Estran-3-one (8.0 g, 25.1 mmol) in octane/acetone 10:1 (22 ml) was pyrolyzed (b) at 550° (200 Torr, slow $N_2$-stream) Chromatography of the crude product (5.4 g) on silica gel (600 g) with $CH_2Cl_2$ and recrystallization of the homogenous fractions from PE gave 3.13 g (48.3%) of the pure ketone 10. M.p. 51–54°, [a]-+ 72.8° (C 1.0). -IR. ($CHCl_3$): 1705s, 1585w, -$^1$H-NMR. (90 MHz): 0.79 (s, 3H); 5.71 (m, 1H); 5.87 (m, 1H).

Example 65
Estra-16-en-3o-ol.

This synthesis is depicted in FIG. 153. L-Selectride (d, lithium tri(sec-butyl)hydridoborate, 4 ml of a 1 M solution in THF, 4 mmol) was added dropwise at 0° to a solution of ketone 10 (800 mg, 3.10 mmol) in dry ether (5 ml). After stirring for 1-h at 0°, water was added (10 ml). The boranes were oxidized by adding 10% aq. NaOH-solution (5 ml), followed by 306 aq. H2O2-solution (3 ml) and stirring for 3 h at RT. After workup (ether), the crude product (790 mg, Ca. 9:1 mixture of 11 and 12) was chromatographed on silica gel with CH2Cl2to give 700 mg (87%) of pure alcohol 11. M.p. 119–120°–123–124° (from PE), [a]D+40.6° (C=1.0). -IR. (CHCl3): 3640m, 3500 br., 1585w. -1H-NMR. (90 MHz): 0.78 (s, 3H); 4.09 (m, w½≈8, 1H); 5.71 (m, 1H), 5.87 (m, 1H)

Example 66
Estra-16-en-3B-ol.

This synthesis is depicted in FIG. 153. A solution of the ketone 10 (800 mg, 3.10 mmol) in dry ether (5 ml) was added dropwise at RT. to a slurry of LiAlH4 (38 mg, 1 mmol) in ether (3 ml) (e). After 1 h, the mixture was hydrolyzed with 10% aq. $H_2SO_4$. After workup (ether), the crude product (802 mg, 9:1-mixture of 12 and 11) was chromatographed on silica gel with $CH_2Cl_2$. A small fraction of 11 (70 mg) was eluted first, followed by the main fraction of 12 (705 mg, 87%). M.p. 113–115°, [a]-+36.3° (C=1.0). -IR. (CHCl3): 3640m, 3500 br., 1585w. -$^1$H-NMR. (90 MHz): 0.78 (s, 3H); 3.60 (m, w½≈(m, 20, 1H); 5.71 (m, 1H), 5.87 (m, 1H).

Example 67
Alternative Synthesis of Estra-4 16-dien-3-one

Estra-4,16-dien-3-one: To estra-1,3,5(10),16-tetraene-3-methyl ether (551.S mg, 2.055 mmol) in 8.6 ml of anhydrous THF, approximately 30 ml of anhydrous ammonia, and 6.76 g of t-butyl alcohol was added lithium wire (0.24 g, 35 mg-atom) cut in small pieces. The reaction mixture was refluxed 4½ h under argon, after which methanol (2.3 ml) was added and the ammolonia was allowed to boil off overnight. The residue was dissolved in 25 ml of methanol and was acidified to approximately pH 1 with 5N HCl. After heating in an oil bath between 55 and 70° C. for 15 min. the cooled hydrolysis mixture was partitioned between 25 ml of water and S0 ml of ethyl acetate and the aqueous phase was extracted with 2S ml of ethyl acetate. The combined organic extracts were washed with 25 ml of saturated sodium bicarbonate and 25 ml of brine, dried over magnesium sulfate, and filtered. Removal of solvent under reduced pressure yielded 0.57 q of oily residue which was purified by flash chromatography on silica gel (eluent: 15% ethyl acetate/hexane) followed by recrystallization from pentane to give crystals (206.1 mg, 39% homogeneous to TLC, m.p. 67–71° C.

Example 68

Estra-2,5(10),16-triene-3-methyl ether, 2.

Figure 12:
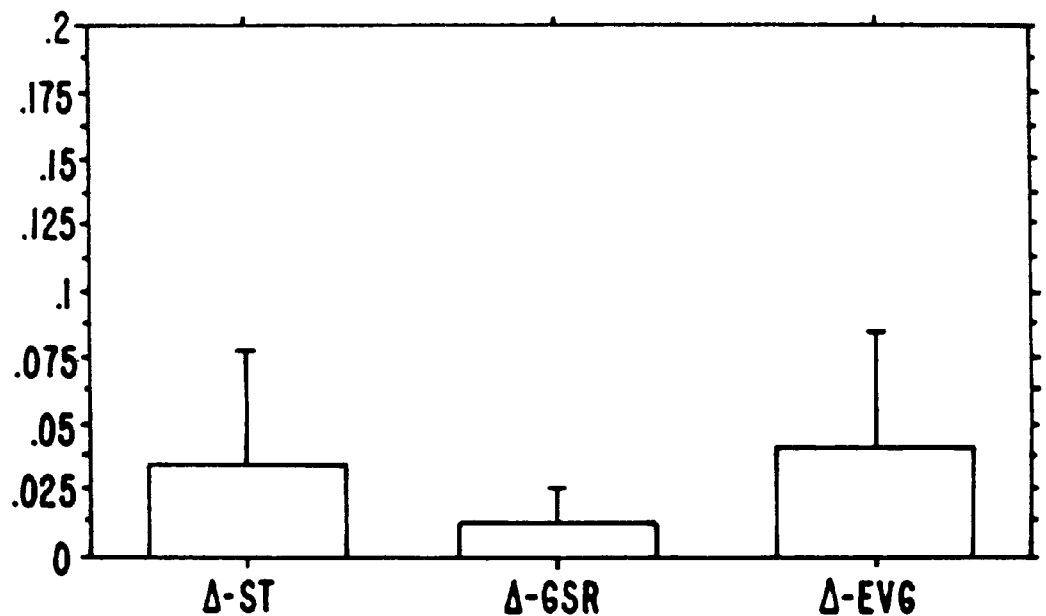

To estra-1,3,5(10),16-tetraene-3-methyl ether (1.22 g, 4.54 mmol) in 19 ml of anhydrous THF, 14.99 g of t-butyl alcohol, and approximately 70 ml of anhydrous ammonia was added lithium wire (0.53 g, 76 mg-atom) cut in small pieces. See FIG. 12. After refluxing under argon for 6 h the reaction was quenched with 5 ml of methanol and ammolonia was allowed to boil off overnight. A suspension of the residue in 100 ml of water was extracted twice with 100 ml portions of ethyl acetate and the combined organic extracts were washed with brine and dried over magnesium sulfate. Following solvent removal under reduced pressure the residue was flash chromatographed on silica gel using 1% ethyl acetate/hexane as eluent and then recrystallized from abs. ethanol to give fluffy white crystals (884.1 mg, 3.269 mmol, 72%), m.p. 72–73° C., homogeneous to TLC.

Example 69

Estra-5(10).16-dien-3-one, 3.

Estra-2,5(10),16-triene-3-methyl ether, 2 (646.3 mg, 2.390 mmol), dissolved in 50 ml of acetone was hydrolyzed for 6 h at room temperature using oxalic acid dihydrate (0.84 g, 6.7 mmol). See FIG. 12. The reaction mixture was quenched with 25 ml of saturated sodium bicarbonate and then extracted twice with 25 ml portions of ethyl acetate. The combined organic extracts were washed twice with 25 ml of brine, dried over magnesium sulfate, filtered, and concentrated under reduced pressure. The residue was recrystallized from hexane to give product (462.5 mg, 1.804 mmol, 75%), m.p. 112–116° C.

Example 70

Estra-5(10),16-dien-3-ols.

Estra-5(10),16-dien-3-one, 3 (301.1 mg, 1.174 mmol), in 6 ml of anhydrous ether was reduced for 1 h at room temperature using lithium aluminum hydride (50.0 mg, 1.32 mmol). See FIG. 155. After quenching with sodium sulfate decahydrate (2.00 g) for 10 min. the suspension was filtered through Celite and the residue washed with four 25 ml portions of ether. The combined filtrates were concentrated under reduced pressure and purified by flash chromatography (silica gel, 5% ethyl acetatethexanes eluent) with subsequent preparative TLC of mixed fractions. The more polar product could be recrystallized with considerable loss from aqueous ethanol to give 4.8 mg of solid. The less polar product was recrystallized from aqueous methanol to give white crystals (59.5 mg), m.p. 98–100° C. Total yield was 64.3 mg (0.249 mmol, 21 S).

Example 71

Estra-4.9.16-trien-3-one.

Estra-5(10),16-dien-3-one, 3 (0.38 g, 1.5 mmol), in pyridine (5.0 ml, 62 mmol) was cooled in an ice-salt bath to 13° C. and pyridinium bromide perbromide (1.58 g, 4.94 mmol) was added in small portions so that T<–4° C. After swirling 1 min. phenol (0.25 g, 2.7 mmol) was added and reaction continued 24 h at room temperature. See FIG. 12. Ethyl acetate (50 ml) was added and the reaction mixture was washed with 25 ml of 1N HCl, two 25 ml portions of saturated copper sulfate, 25 ml of 5% sodium hydroxide, and 25 ml of brine. After drying over magnesium sulfate, filtration, and concentration under reduced pressure the residue was taken up in 10 ml of abs. ethanol, granular zinc (0.33 g, 5.0 mg-atom) was added, and the mixture was refluxed ½ h. The supernatant was removed, the residue was washed with 10 ml of abs. ethanol, and the combined supernatants were concentrated under reduced pressure. The resulting resin was flash chromatographed on silica gel using 15% ethyl acetate/hexane as eluent. Appropriate fractions were pooled, concentrated, and then recrystallized from hexane to give solid product (117.S mg, 0.4619 mmol, 31%), m.p. 87–92° C.

Example 72

Estra-1,3,5(10),16-tetraen-6-one-3-acetate.

Figure 13:
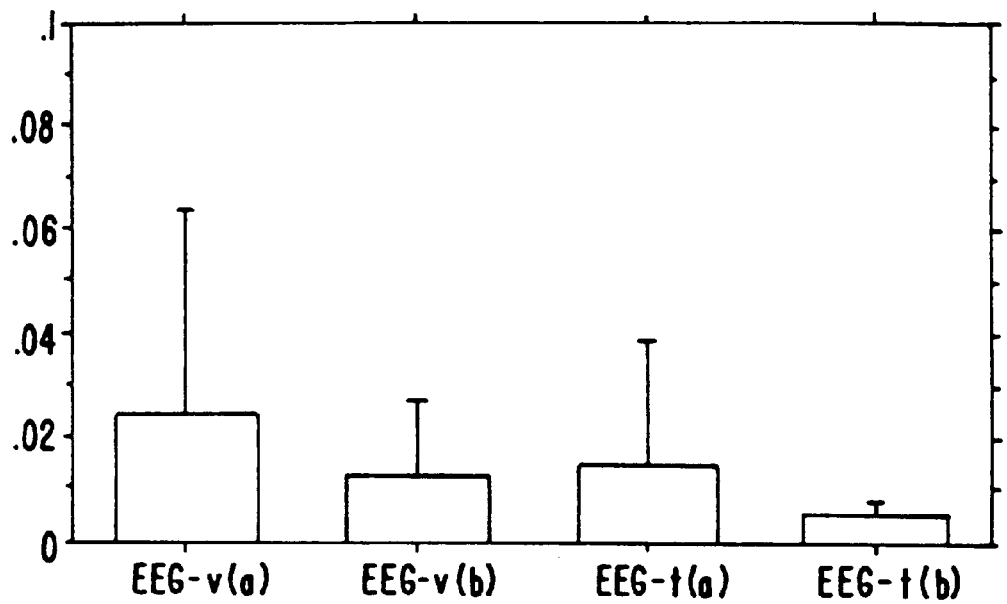
FIGS. 13 and 14 show the data of the EEG measurements in males and females, respectively, for compound A2-P3.
Figure 14:
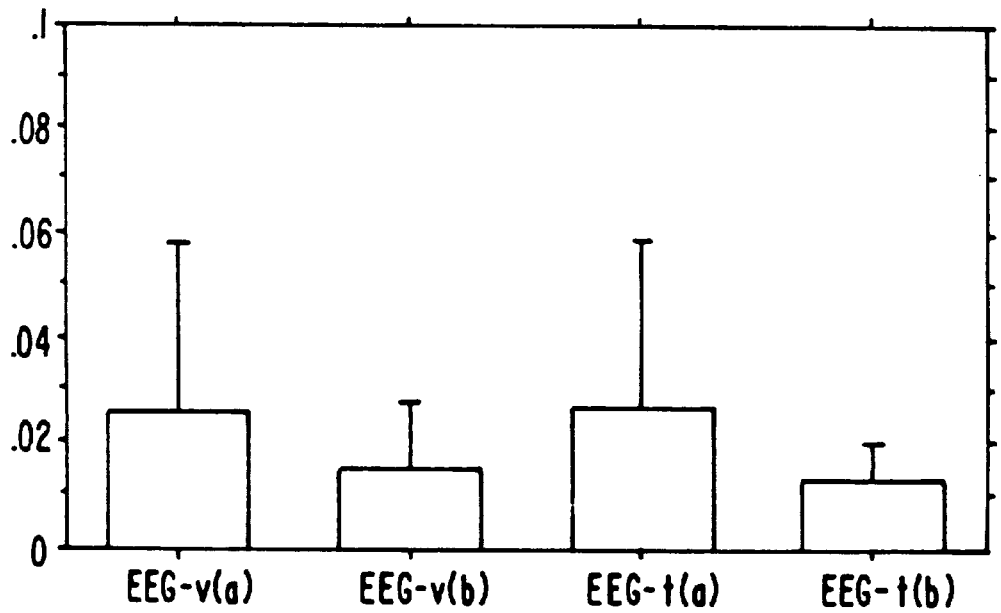

Chromium trioxide (13.40 g, 0.1340 mol) was suspended in 200 ml of methylene chloride and then cooled to –10° C. in an ice-salt bath. 3,5-Dimethylpyrazole (12.90 g, 0.1342 mol) was added and the mixture was stirred 20 min. See FIG. 13. Estra-1,3,5(10),16-tetraen-3-yl acetate (4.00 g, 13.5 mmol) in a chilled solution of 20 ml of methylene chloride was added and the reaction stirred 2 h, during which time T→–8° C. The mixture was then filtered through 200 g of silica gel and the product was eluted with further methylene chloride. After combining and concentrating appropriate fractions the crude product was flash chromatographed on silica gel using 15% ethyl acetate/hexane as eluent. Pooling of appropriate fractions and concentration under reduced pressure yielded a white solid (0.92 g, 3.0 mmol, 22%), m.p. 87–103° C.

Example 73

Estra-1,3,5(10),16-tetraen-3-ol-6-one.

Estra-1,3,5(10),16-tetraen-6-one-3-acetate (203.1 mg, 0.6543 mmol) in 30 of methanol was saponified with 1.5 ml of 5% (w/w) sodium hydroxide for 40 min. See FIG. 156. The reaction mixture was concentrated under reduced pressure, taken up in 50 ml of water, neutralized with 1N HCl, and extracted three times with 25 ml portions of methylene chloride. The combined organic extracts were washed with 50 ml of brine, dried over magnesium sulfate, filtered, and concentrated to give a white solid which was purified by recrystallization from benzene/hexane and preparative TLC to give white crystalline solid (52.8 mg, 0.197 mmol, 30%), m.p. 188–191° C.

Example 74

Estra-1,3,5(10),16-tetraen-6c-ol-3-yl acetate.

Estra-1,3,5(10),16-tetraen-6-one-3-yl acetate, 6 (421.4 mg, 1.358 mmol), suspended in 35 ml of 95% ethanol was reduced with sodium borohydride (98.8 mg, 2.61 mmol) for 100 min. at room temperature. See FIG. 13. After concentrating under reduced pressure the residue was suspended in 25 ml of water, neutralized with 1N HCl, and extracted three times with 25 ml portions of methylene chloride. The combined organic extracts were washed with 25 ml of brine, dried over magnesium 30 sulfate, filtered, and concentrated.

The resulting white foam was flash chromatographed on silica gel using 25% ethyl acetate/hexane as eluent. Combining fractions and concentration gave a white solid (0.12 g, 0.38 mmol, 28%), m.p. 209–212° C.

Example 75

Estra-1,3,5(10),16-tetraen-3,6-diol.

To a suspension of lithium aluminum hydride (LAH, 95%, 46.9 mg, 1.17 mmol) in 5 ml of anhydrous THF was added estra-1,3,5(10),16-tetraen-6-one-3-yl acetate, 6 (422.9 mg, 1.360 mmol) in 5 ml of anhydrous THF dropwise, with stirring. See FIG. 156. The reaction was stirred 50 min., after which further LAH (46.5 mg, 1.16 mmol) was added and the reaction stirred 22 h. After refluxing 4 h TLC still showed starting material. The reaction was quenched with 0.5 ml of water+0.5 ml of 20% (w/w) sulfuric acid and concentrated under reduced pressure. The residue was extracted four times with 10 ml portions of hot ethyl acetate and filtered through Celite. The combined filtrates were concentrated and purified twice by flash chromatography to give solid product (0.05 g, 0.2 mmol, 10%), m.p. 150–157° C.

Example 76

Estra-1,3,5(10),7-tetraen-3-ol.

To a suspension of equilin (100.2 mg, 0.3733 mmol) in 2 ml of diethylene glycol were added hydrazine (59 $\mu$L, 1.9 mmol) and potassium hydroxide (0.04 g, 0.7 mmol). See FIG. 157. The mixture was stirred in an oil bath at 200–214° C. for 2 h, after which the cooled reaction was diluted with 10 ml of water, neutralized with 1N HCl, and extracted three times with 25 ml of ether. The combined organic extracts were washed with 10 ml of brine, dried over magnesium sulfate, filtered, concentrated, and purified by preparative TLC (silica gel, 15% ethyl acetate/hexane eluent) to give a yellow resin. Product was further purified by decolorizing with charcoal and recrystallization from aqueous ethanol to give tan crystals (13.2 mg, 51.9 $\mu$M, 14%), m.p. 130–134° C.

Example 77

20-Homoestra-1,3,5(10),6,8,17-hexaen-3-ol.

A suspension of triphenylmethylphosphonium bromide (671.0 mg, 1.878 mg) and potassium t-butoxide (212.1 mg, 1.890 mmol) in 2.1 ml of anhydrous DMSO was heated in a 76–86° C. bath under argon for 1 h, after which equilenin (100.1 mg, 0.3579 mmol) in 2.1 ml of anh. See FIG. 157. DMSO was added and the green solution was stirred 1 h. After cooling 10 ml of ice-1N HCl were added and the mixture was extracted with three 10 ml portions of ether. The combined organic extracts were washed with 10 ml of saturated sodium bicarbonate+10 ml of brine, dried over magnesium sulfate, filtered through Celite, concentrated and purified.

Example 78

Estra-1,3,5(10),6-tetraen-3-ol-17-(p-toluenesulfonyl)hydrazone.

Figure 15:
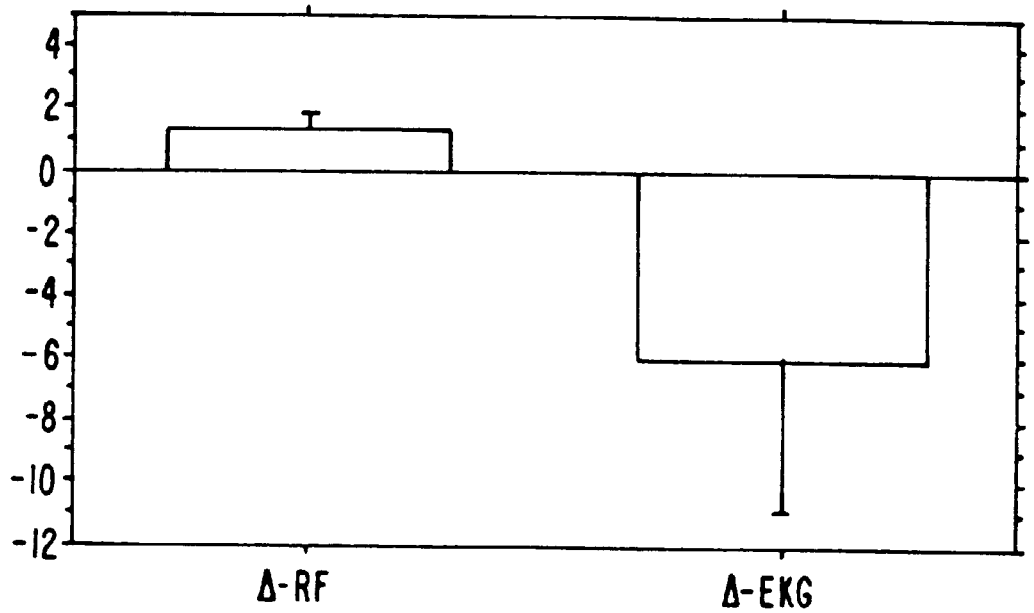
FIGS. 15 and 16 show the data for the RF and EKG measurements in males and females, respectively, for compound A2-P3.

A suspension of 6-dehydroestrone (538.0 mg, 2.004 mmol) and p-toluenesulfonylhydrazide (pTsNHNH$_2$, 466.6 mg, 2.506 mmol) in anh. methanol (5.4 ml) was refluxed 25 h with exclusion of moisture. See FIG. 15. After concentrating under reduced pressure the reaction residue was flash chromatographed (50% ethyl acetate/hexanes on silica gel) to give an off-white foam (942.5 mg), representing >100% yield.

Example 79

Estra-1,3,5(10),6-tetraen-3-ol-17-(p-toluenesulfonyl)hydrazone.

To a cooled (ice water bath) solution of crude estral,3,5(10),6-tetraen-3-ol-17-(p-toluenesulfonyl)hydrazone (1, 942.5 mg, $\leq$2.004 mmol) in tetrahydrofuran (THF) under argon was added n-butyllithium (2.5 M in hexane, 3.2 ml, 8.0 mmol) dropwise with stirring, over a period of 7 min. See FIG. 158. Stirring was continued 48 h, during which the reaction was allowed to gradually warm to room temperature. 50 ml of 1 N hydrochloric acid were added and the reaction mixture was extracted with three 25 ml portions of ether. The combined organic extracts were washed with 50 ml of brine, dried over magnesium sulfate, and filtered through diatomaceous earth. The residue was washed with 10 ml of ether and the combined filtrates were concentrated under reduced pressure. Crude product was purified by flash chromatography (20% ethyl acetate/hexanes on silica gel) and preparative TLC (20% ethyl acetate/hexanes on silica gel GF, 1000% thickness) to give a white, crystalline film (134.5 mg, 0.5331 mmol, 27%) homogeneous to TLC (20% ethyl acetate/hexanes on silica gel, R$_f$ 0.39).

Example 80

Estra- 1.3.5(10),6, 16-pentaen-3-yl-acetate.

A solution of estra-1,3,5(10),16-pentaen-3-ol(2, 97.9 mg, 0388 mmol) in anh. pyridine (1.3 ml, 16 mmol) and acetic anhydride (0.18 ml, 1.9 mmol) was stirred 24 h, after which ethyl acetate (15 ml) was added and the mixture washed with three 5 ml aliquots of 1 N hydrochloric acid+5 ml of saturated sodium bicarbonate+5 ml brine, dried over magnesium sulfate, and filtered through diatomaceous earth. See FIG. 15. The residue was washed with 5 ml of ethyl acetate and the combined filtrates were concentrated under reduced pressure. Preparative TLC (10% ethyl acetate/hexanes on silica gel GF, 1000 thickness) of the residue gave a slightly yellow crystalline solid (74.9 mg, 0.254 mmol, 66%) homogeneous to TLC (10% ethyl acetate/hexanes on silica gel, R, 0.40).

Example 81

Estra-1,3,5(10),7-tetraen-3-ol-17-(p-toluenesulfonyl)hydrazone.

Equilin (500.1 mg, 1.863 mmol) and p-TsNHNH$_2$ (433.7 mg, 2.329 mmol) suspended in anh. methanol (5.0 ml) were refluxed 24 h with exclusion of moisture. See FIG. 15. After concentrating under reduced pressure the residual reaction mixture was flash chromatographed (35% ethyl acetate/hexanes on silica gel) to give a white foam (899.9 mg) representing >100% yield.

Example 82

Estra-1,3,5(10),7,16-pentaen-3-ol.

To a cooled (ice water bath) solution of crude estra-1,3,5(10),7-tetraen-3-ol,-17-(p-toluenesulfonyl) hydrazone (4, 899.9 mg, $\leq$1.863 mmol) in anh. THF (20 ml) under argon was added n-butyllithium (2.5 M in hexane, 3.0 ml, 7.5 mmol) dropwise with stirring over a period of 3 min. See FIG. 15. Stirring was continued 48 h, during which the reaction was allowed to gradually warm to room temperature. The reaction was poured into 50 ml of 1 N hydrochloric acid and the mixture was extracted with three 25 ml portions of ether. The combined organic extracts were washed with 50 ml of brine, dried over magnesium sulfate, and filtered through diatomaceous earth. The residue was washed with 10 ml of ether and the combined filtrates were concentrated under reduced pressure. The product was flashed chromatographed (20% ethyl acetate/hexanes on silica gel) and decol-

Example 83
Estra-1,3,5(10),7,16-pentaen-3-yl acetate.

A solution of estra-1,3,5(10),7,16-pentaen-3-ol (5, 192.1 mg, 0.7612 mmol) in anh. pyridine (2.6 ml, 32 mmol) and acetic anhydride (0.36 ml, 3.8 mmol) was stirred 6 h, after which 30 ml of ethyl acetate were added. The mixture was washed with three 10 ml portions of 1 N hydrochloric acid+10 ml of saturated sodium bicarbonate+10 ml of brine, dried over magnesium sulfate, and filtered through diatomaceous earth. See Example 15. The residue was washed with 10 ml of ethyl acetate and the combined filtrates were concentrated under reduced pressure. Preparative TLC (5% ethyl acetate/hexanes on silica gel GF, 1000μ thickness) and recrystallization from aqueous ethanol gave fine white needles (78.6 mg, 0.267 mmol, 35%), m.p. 77–80° C. TLC (4% ethyl acetate/hexanes on silica gel) showed 2 spots at $R_f$ 0.21 and 0.24.

Example 84
Estra-1,3,5(10),6,8-pentaen-3-ol-17-(p-toluenesulfonyl) hydrazone.

Figure 16:
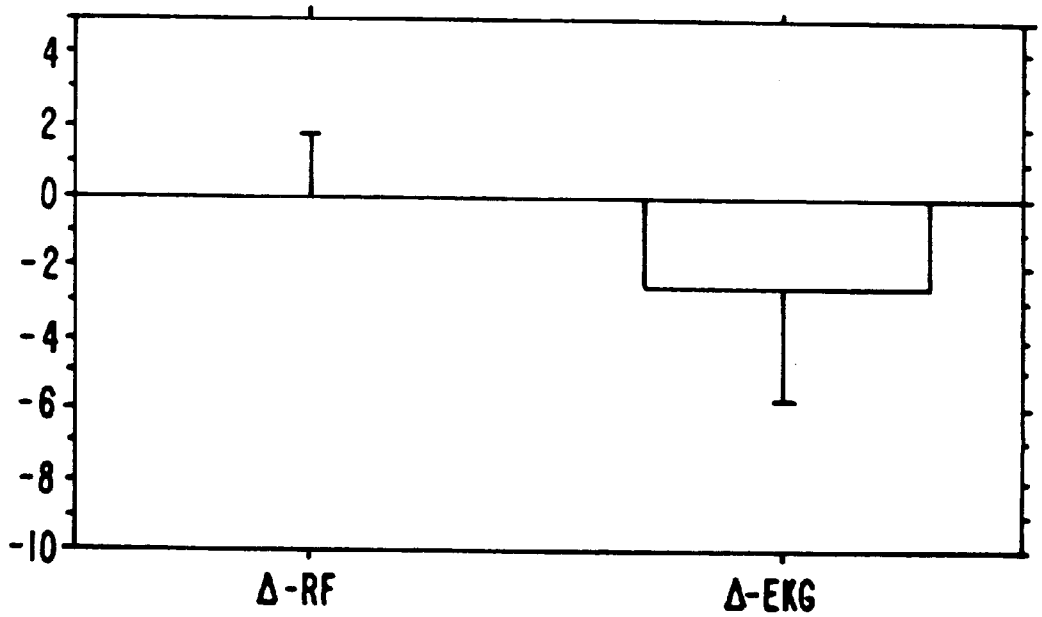

Equilenin (0.6559 mg, 2.463 mmol) and p-TsNHNH$_2$ (573.6 mg, 3.080 mmol) suspended in anh. methanol (8.2 ml) were refluxed 24 h with exclusion of moisture. See FIG. 16. After cooling and concentrating under reduced pressure the reaction mixture was flash chromatographed (35–40% ethyl acetate/hexanes 57%), m.p. 95–96° C. TLC (2% ethyl acetate/hexanes on silica gel) showed product ($R_f$ 0.1) contained a trace contaminant at the origin.

Example 85
Estra-1,3,5(10),6,8,16-hexaen-3-ol.

To a cooled (ice water bath) solution of crude estra-1,3,5(10)6,8-pentaen-3-ol 17-(p-toluenesuffonyl)hydrazone (7, 1.0887 g, ≦2463 mmol) in anh. THF (25 ml) under argon was added n-butyllithium (2.5 M in hexane, 3.9 ml, 9.8 mmol) dropwise with stirring over 2 min. See FIG. 159. Stirring was continued 3 days, during which the reaction was allowed to gradually warm to room temperature. 50 ml of 1N hydrochloric acid-ice were added and the mixture was extracted three times with 25 ml portions of ether. The combined organic extracts were washed with 50 ml of brine, dried over magnesium sulfate, and filtered through diatomaceous earth. The residue was washed 10 ml of ether and the combined filtrates were concentrated under reduced pressure. Flash chromatography (20% ethyl acetate/hexanes on silica gel) and recrystallization from aqueous ethanol with charcoal decolorization gave tan platelets (245.8 mg, 0.9819 mmol, 40%), m.p. 162–163° C.

Example 86
Estra-1,3,5(10),6,8,16-hexaen-3-yl acetate.

A solution of estra-1,3,5(10),6,8,16-hexaen-3-ol Q8, 148.8 mg, 0.5944 mmol) in anh. pyridine (2.0 ml, 25 mmol) and acetic anhydride (0.28 ml, 3.0 mmol) was stirred 6 h, after which ethyl acetate (20 ml) was added. See FIG. 159. The mixture was washed with three 10 ml portions of 1 N hydrochloric acid+10 ml of saturated sodium bicarbonate+ 10 ml of brine, dried over sodium sulfate, and filtered. The residue was washed with 5 ml of ethyl acetate and the combined filtrates were concentrated under reduced pressure. Recrystallization from 95% ethanol gave lustrous white platelets (99.4 mg, 0.340 mmol, 55%, m.p. 9596° C. TLC (2% ethyl acetate/hazanes on silica gel) showed product (Rf 0.1) contained a trace contaminant at the origin.

Example 87
17-Methylenestra-1,3,5110)-trien-3-ol.

A suspension of methyltriphenylphosphonium bromide (100.03 g, 0.28001 mol) and potassium t-butoxide (31.42 g, 0.2800 mol) in anh. dimethylsulfoxide (DMSO, 320 ml) under argon was stirred in an oil bath (68–81° C.) 1 h, after which estrone (15.14 g, 55.99 mmol) in anh. DMSO (320 ml) was added via syringe. See FIG. 160. Stirring was continued 1 h and the reaction allowed to cool. The mixture was poured into 800 ml of ice-1 N hydrochloric acid and then extracted three times with 400 ml aliquots of ether. The combined organic extracts were washed with 350 ml of saturated sodium bicarbonate+400 ml of brine, dried over sodium sulfate, and flash filtered through a 58 mm high×84 mm dia. column of silica gel (200–40 mesh). Product continued eluting with additional ether. Concentration of appropriate fractions under reduced pressure and three-fold recrystallization from aqueous ethanol gave very fine white needles (11.47 g, 42.73 mmol, 76%), m.p. 134–136° C., homogeneous to TLC (20% ethyl acetate/hexanes on silica gel, 0.45).

Example 88
17-Methylenestra-1,3,5(10)-trien-3-yl acetate.

A solution of 17-methylenestra-1,3,5(10)-trien-3-ol (10, 5.84 g, 21.8 mmol) in anh. pyridine (32 ml, 0.40 mol) and acetic anhydride (9.7 ml, 0.10 mol) was stirred 24, after which ethyl acetate (250 ml) was added. See FIG. 160. The mixture was washed with three 100 ml portions of 1 N hydrochloric acid+100 ml of saturated sodium bicarbonate+ 100 ml of saturated copper sulfate+100 ml of brine, dried over magnesium sulfate, and filtered through diatomaceous earth. The residue was washed with 25 ml of ethyl acetate and the combined filtrates were concentrated under reduced pressure. Recrystallization from aqueous ethanol gave lustrous white platelets (5.84 g, 18.8 mmol), m.p. 77–79° C.

Example 89
17-Methylenestra-1,3,5(10)-trien-6-on-3-yl acetate.

Figure 17:
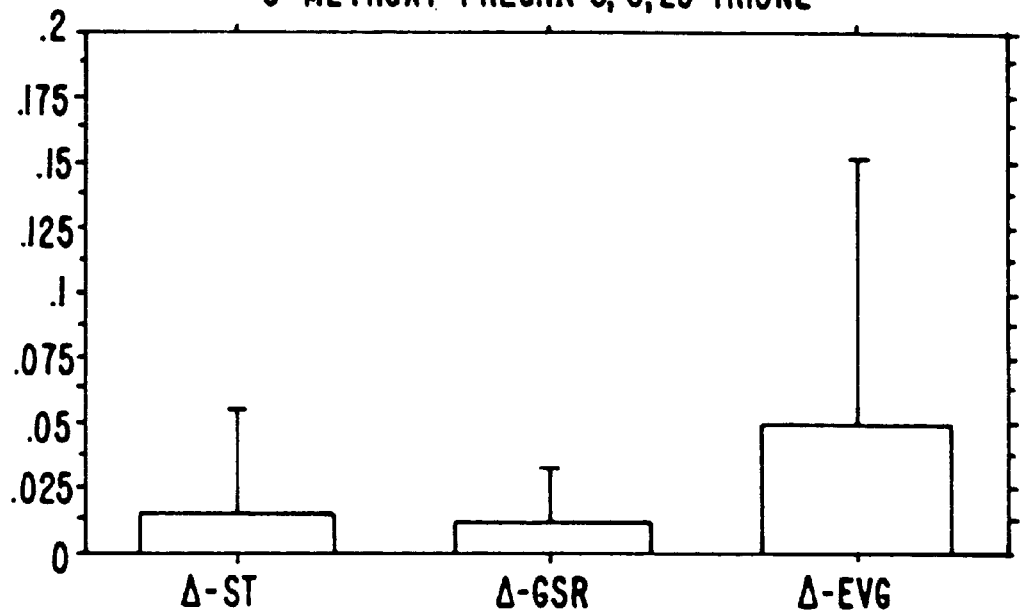
FIGS. 17 and 18 show the data of the ST, GSR and EVG measurements in males and females, respectively, for compound A8-P1.
Figure 18:
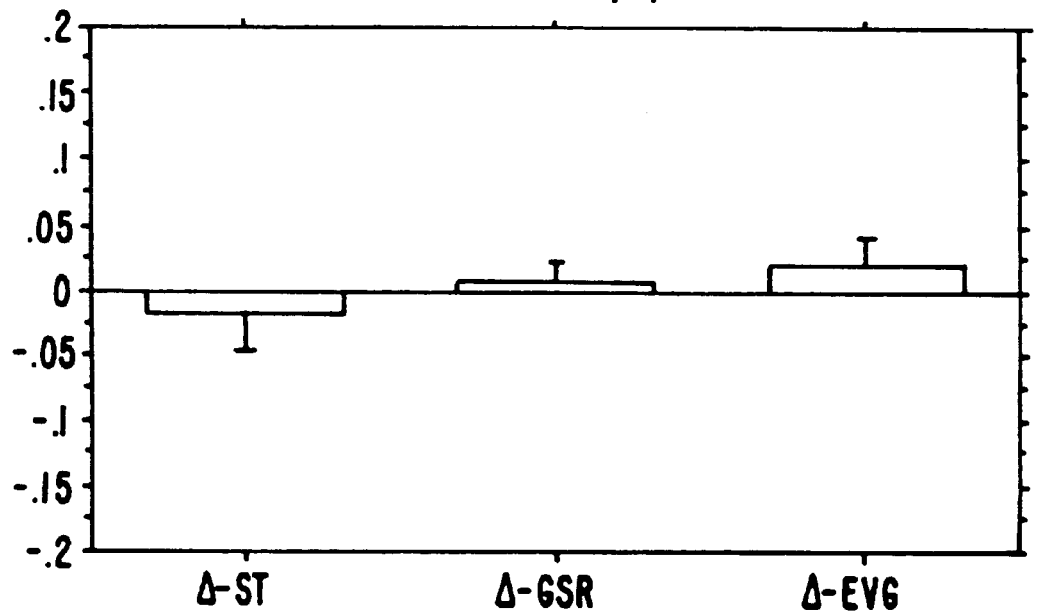
Figure 19:
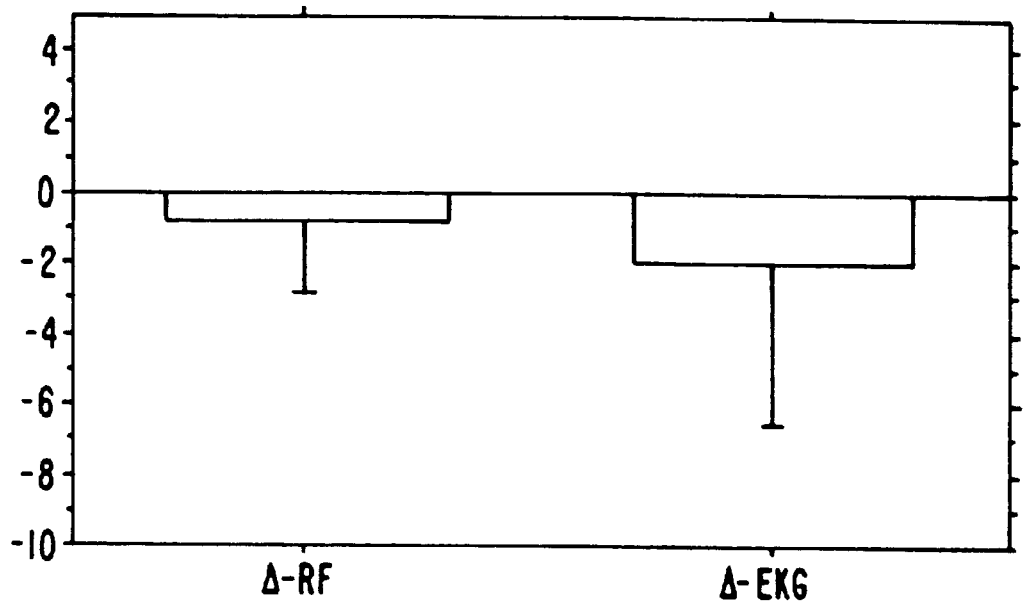
FIGS. 19 and 20 show the data of the RF and EKG measurements in males and females, respectively, for compound A8-P1.
Figure 20:
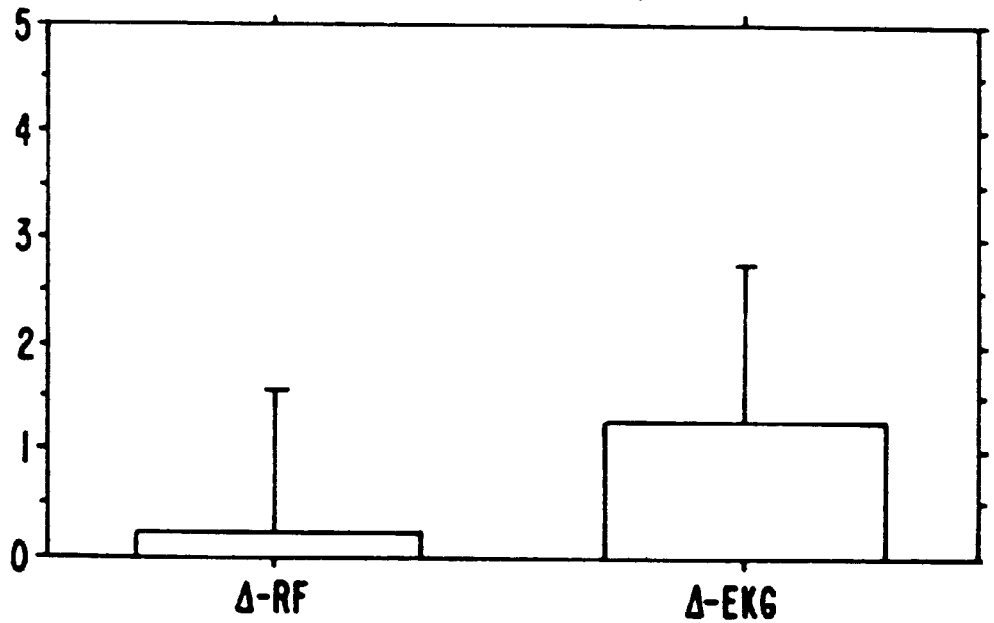
Figure 21:
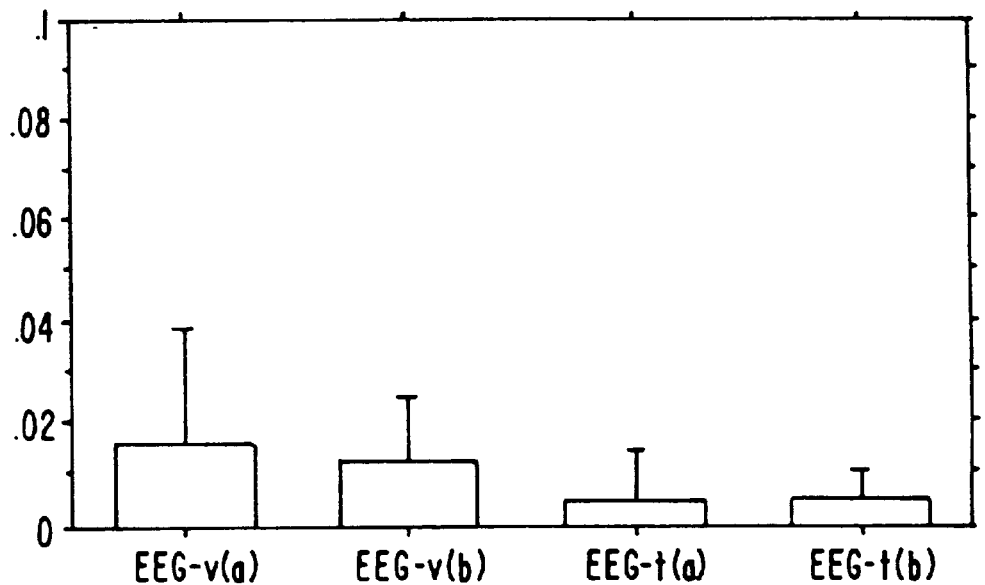
FIGS. 21 and 22 show the data for EEG measurements in males and females, respectively, for compound A8-P1.
Figure 22:
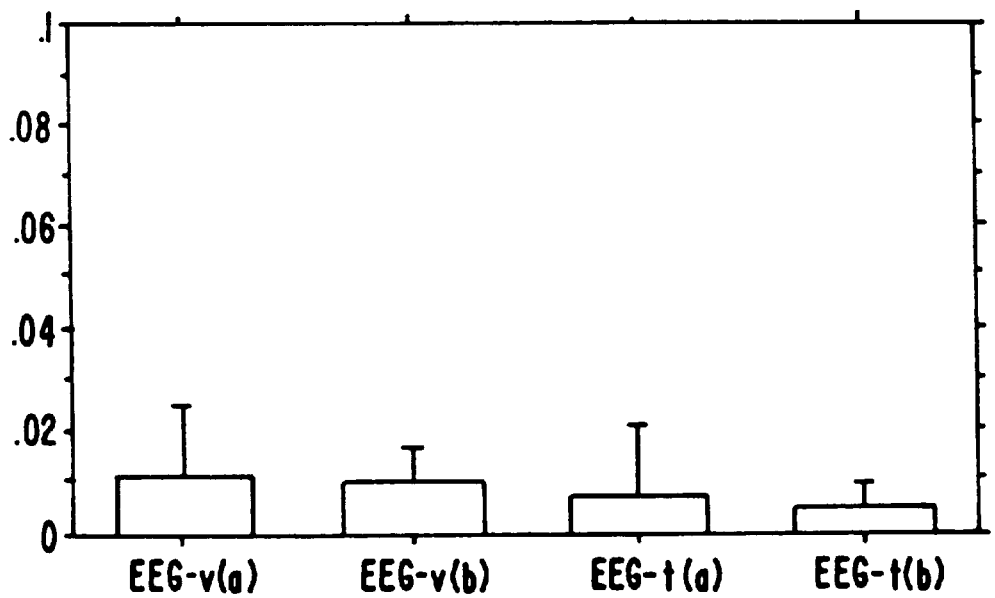
Figure 23:
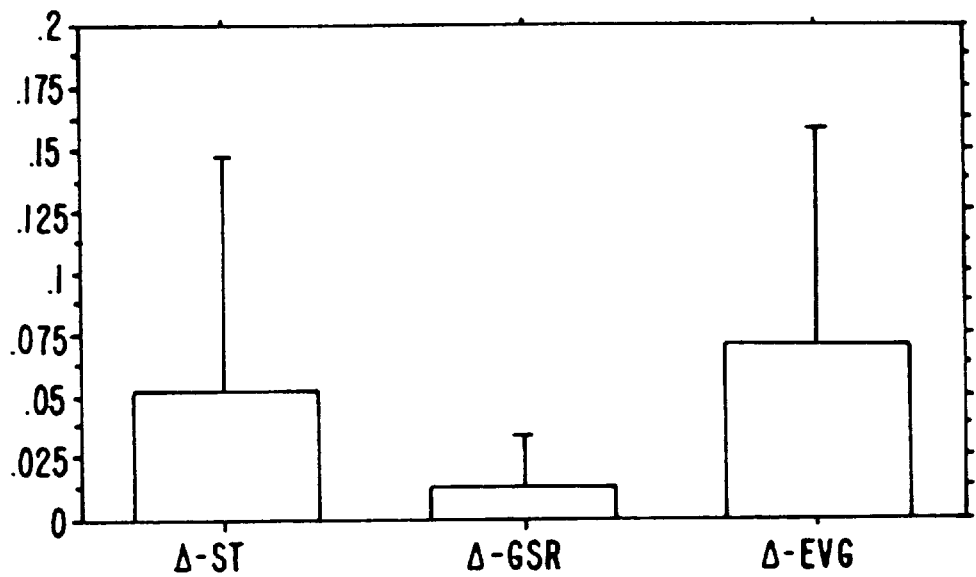
FIGS. 23 and 24 show the data for ST, GSR and EVG measurements in males and females, respectively, for compounds A6-P1.
Figure 24:
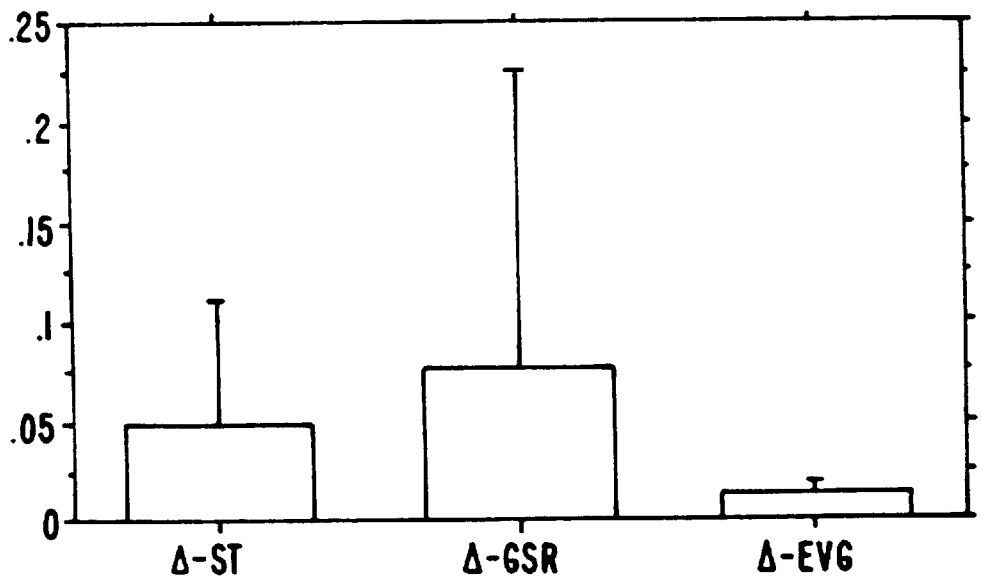
Figure 25:
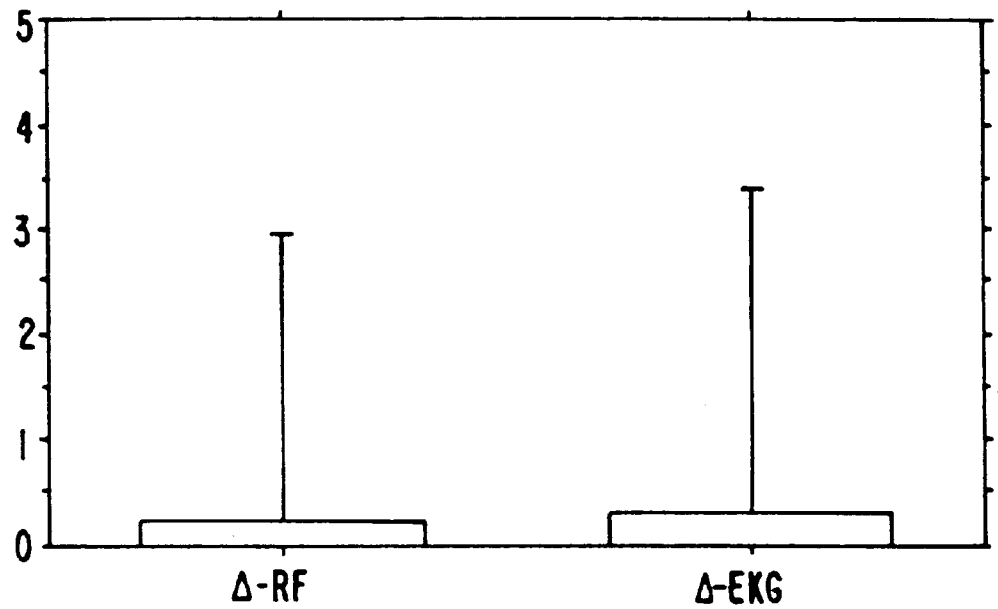
FIGS. 25 and 26 show the data for RF and EKG measurements in males and females, respectively, for compound A6-P1.
Figure 26:
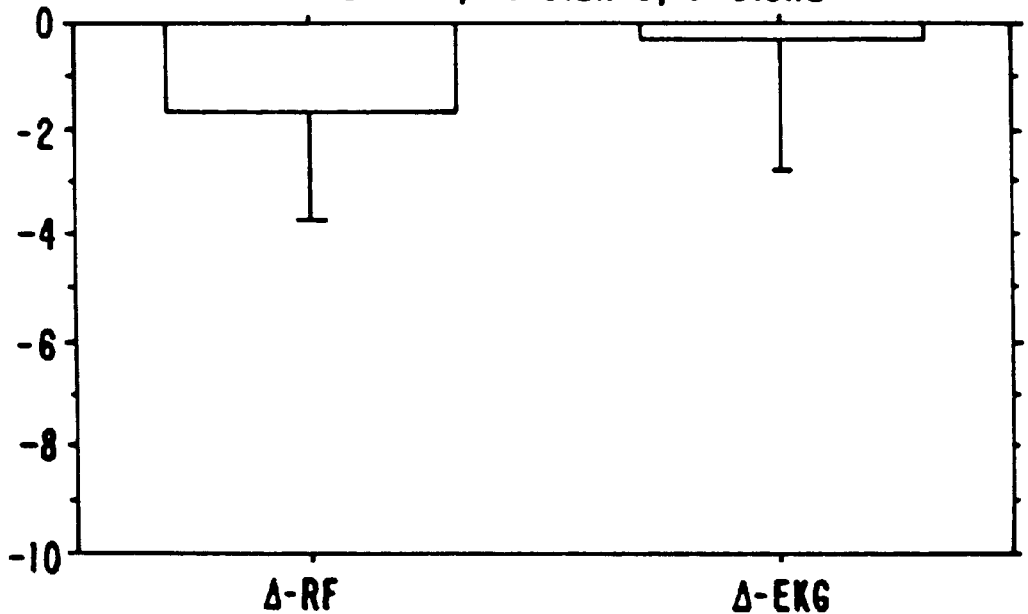
Figure 27:
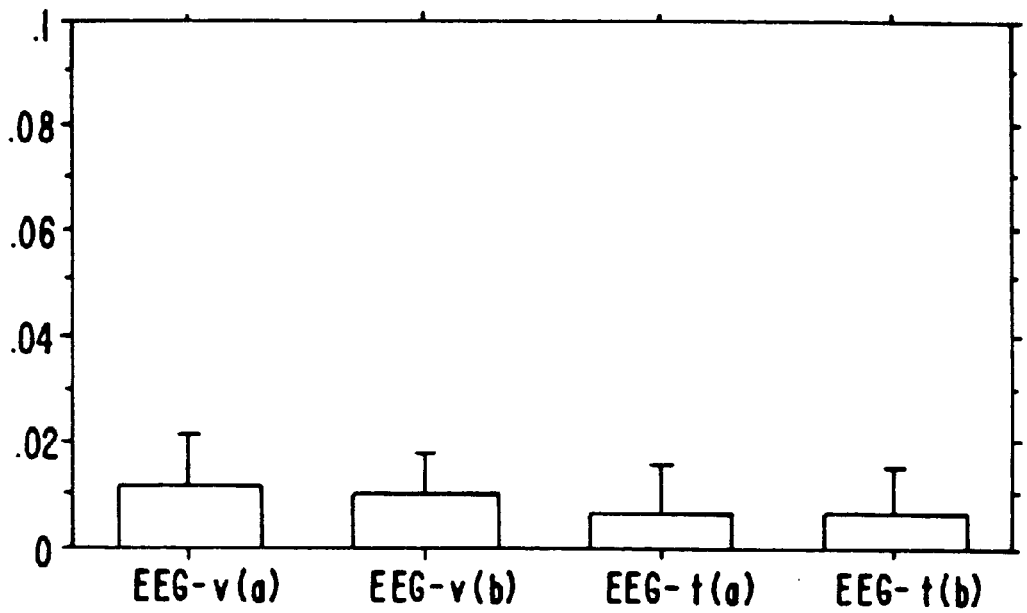
FIGS. 27 and 28 show the data for EEG measurements in males and females, respectively, for compound A6-P1.
Figure 28:
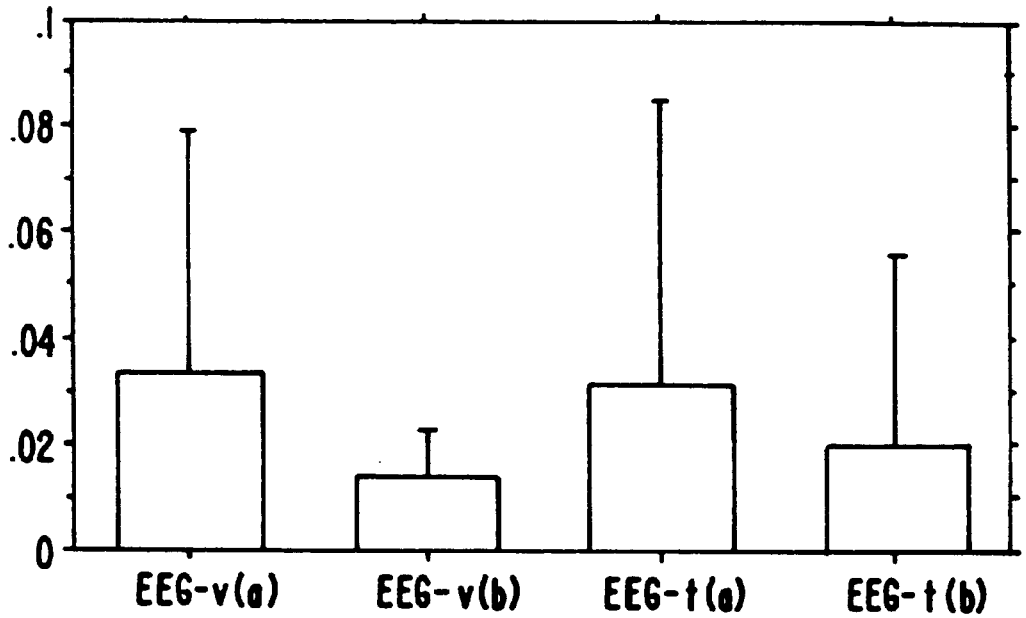
Figure 29:
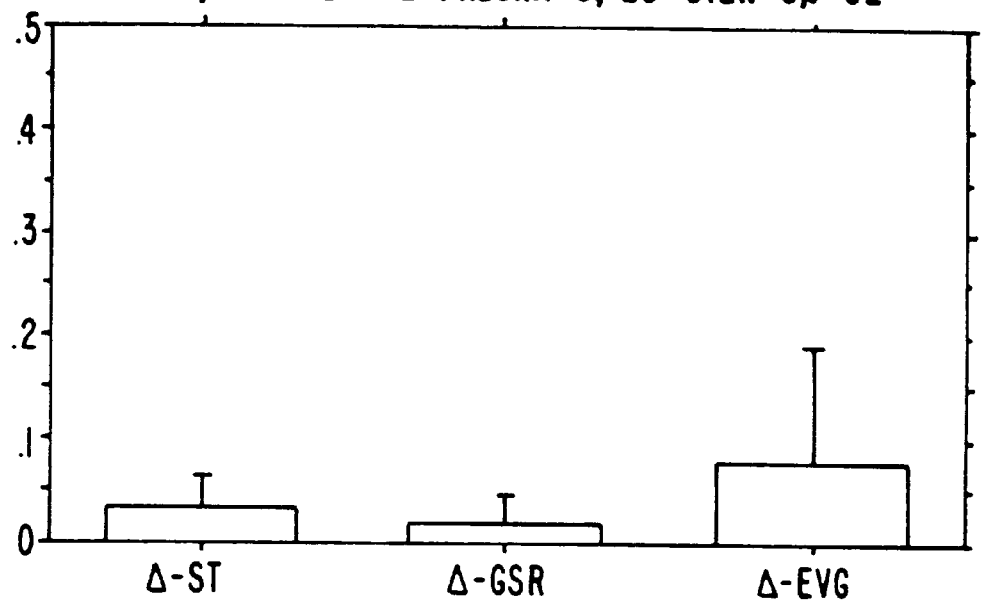
FIGS. 29, 30 and 31 show the data for ST, GSR, EVG, RF EKG and EEG measurements in males of 20,21-dimethylpregna-5,20-dien-3β-ol.
Figure 30:
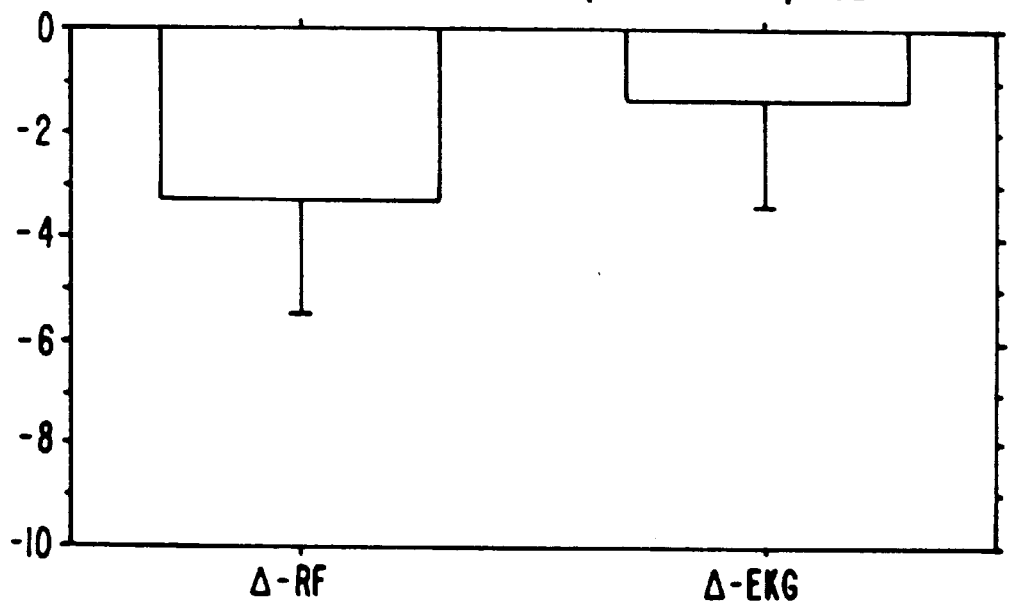
Figure 31:
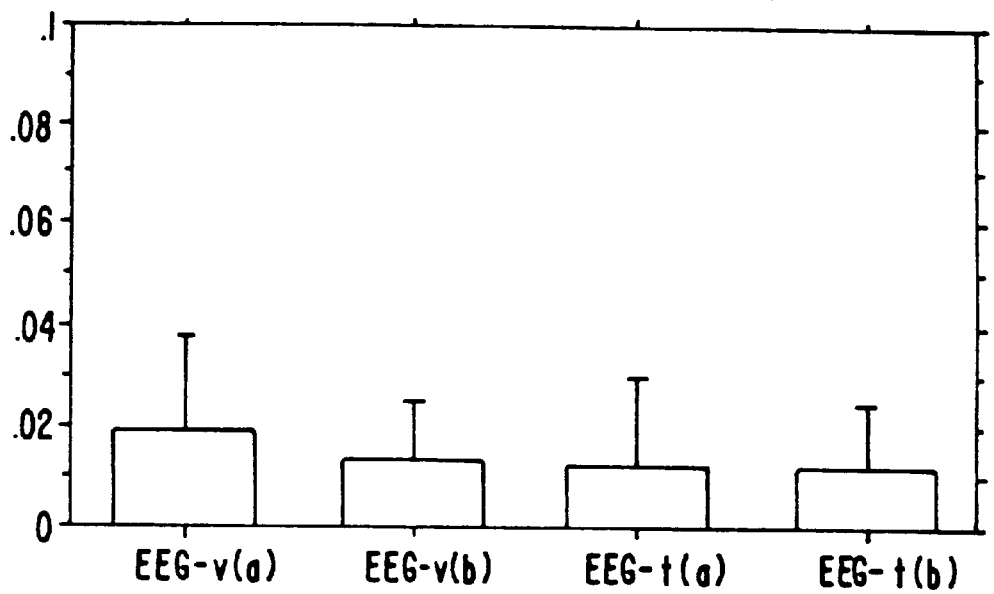
Figure 32:
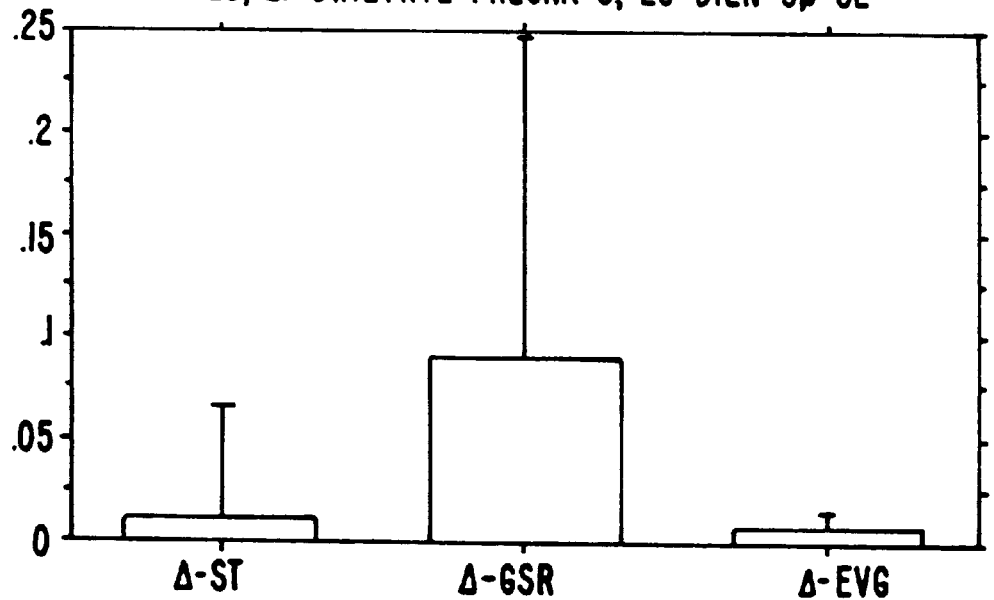
FIGS. 32, 33 and 34 show the data for the ST, GSR, EVG, RF KEG and EEG measurements in females of 20,21-dimethylpregna-5,20-dien-3β-ol.
Figure 33:
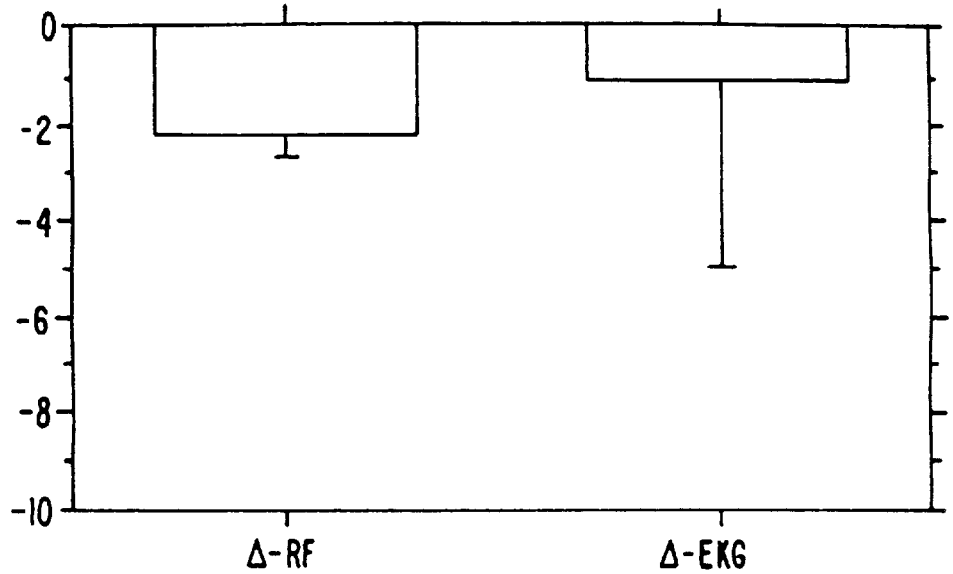
Figure 34:
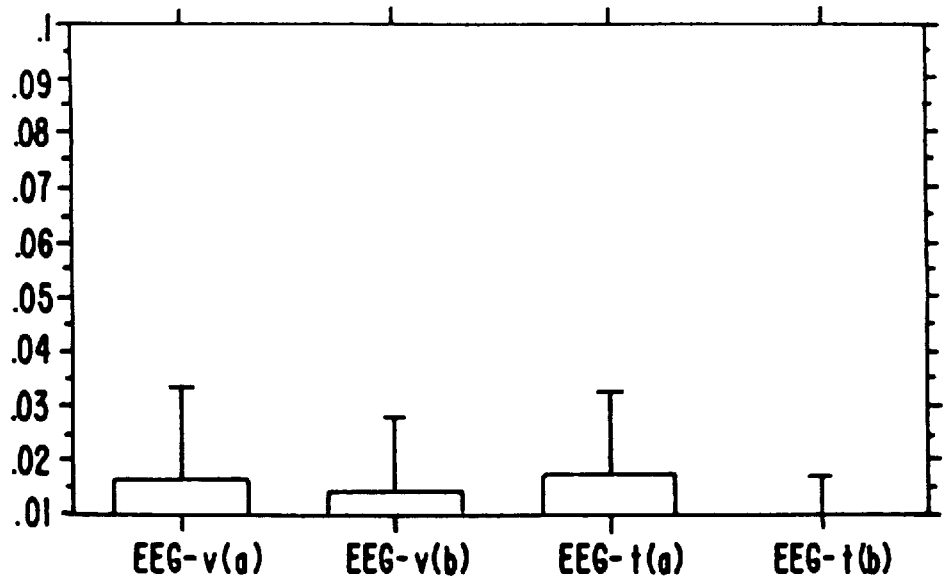
Figure 35:
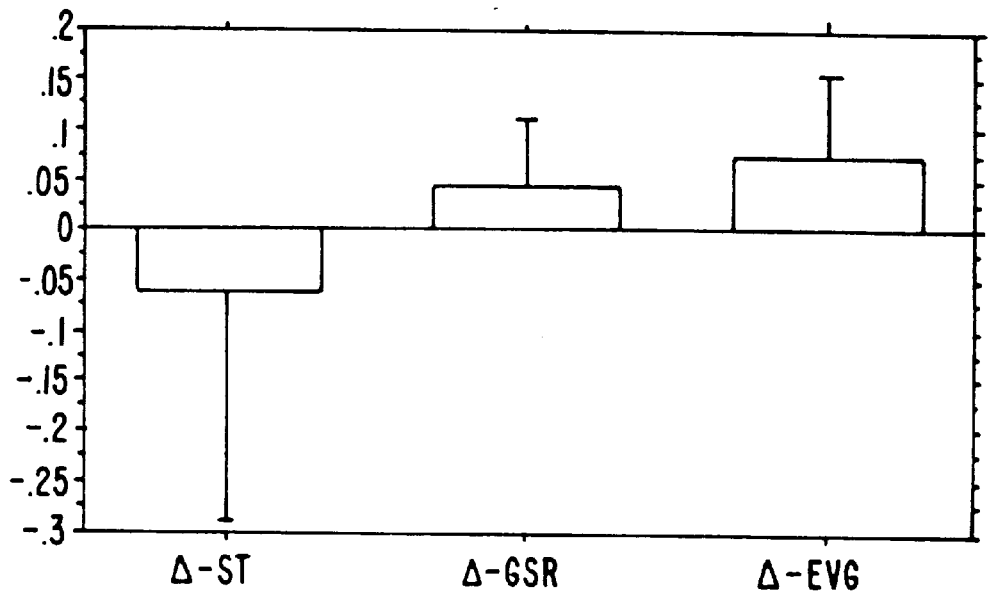
FIGS. 35, 36 and 37 show the data for the ST, GSR, EVG, RF KEG and EEG measurements in males of 20,21-dimethylpregna-5,20-dien-3-one.
Figure 36:
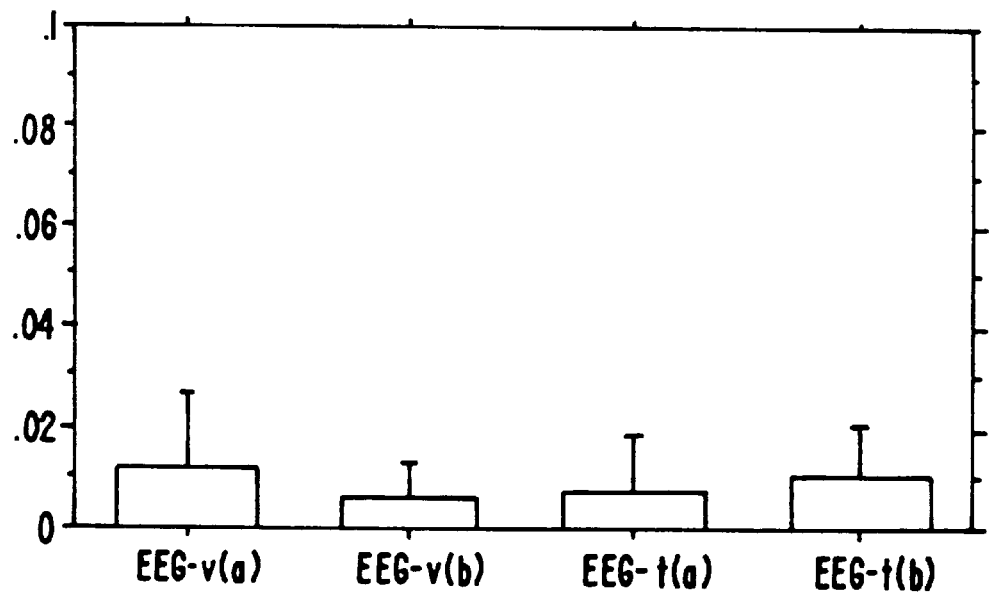
Figure 37:
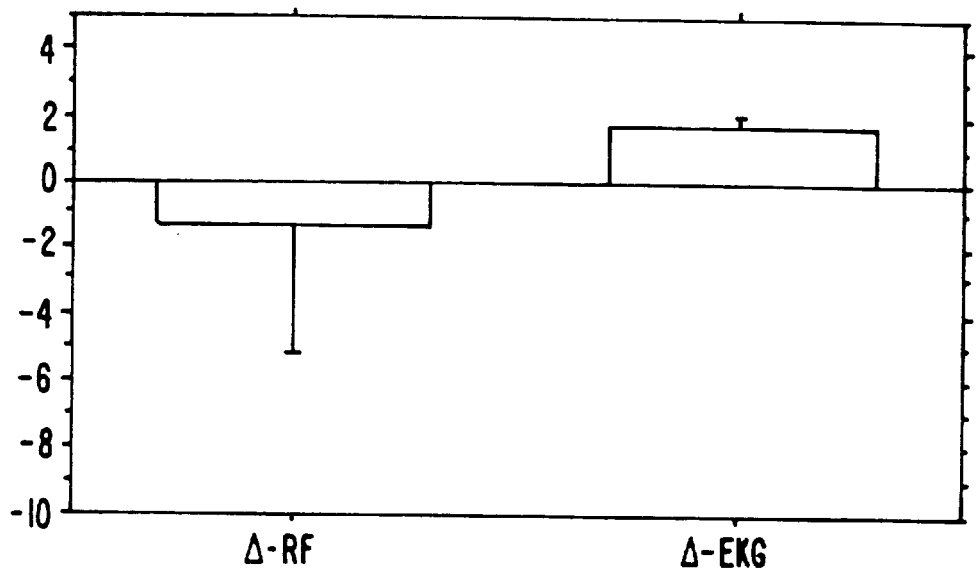
Figure 38:
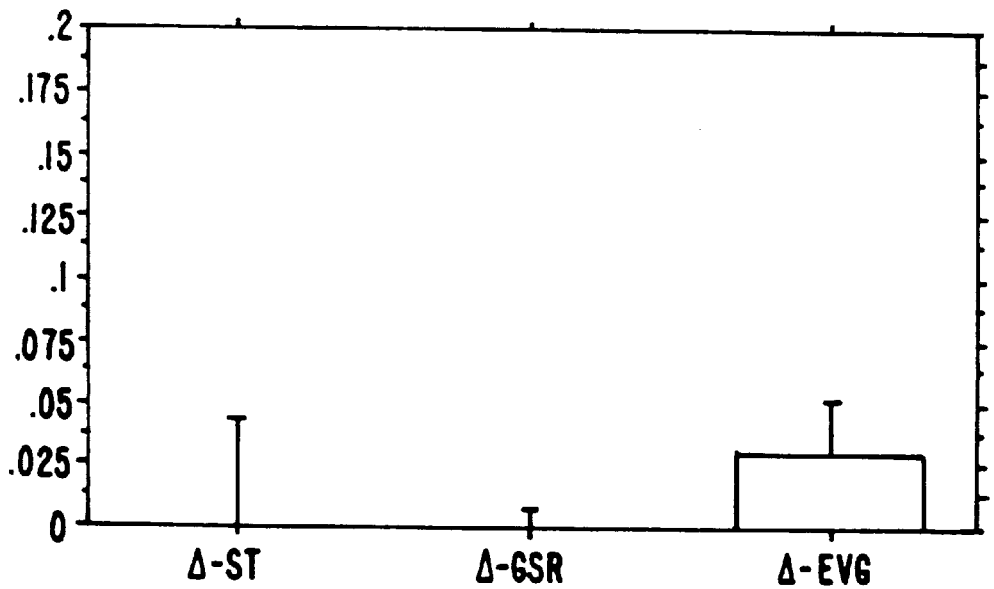
FIGS. 38, 39 and 40 show the ST, GSR, EVG, RF EKG and EEG measurements in females of 20,21-dimethylpregna-5,20-dien-3-one.
Figure 39:
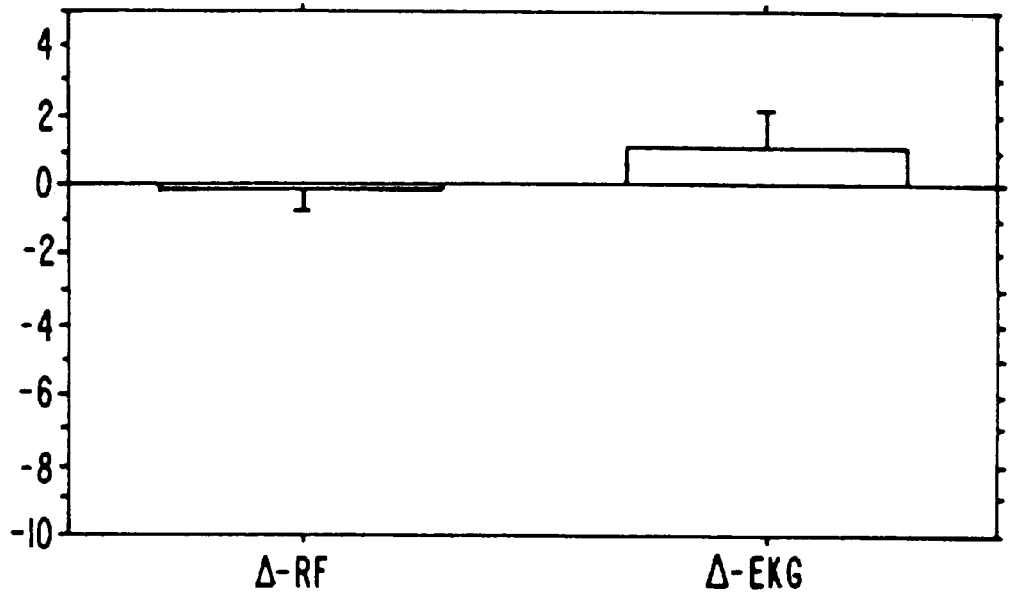
Figure 40:
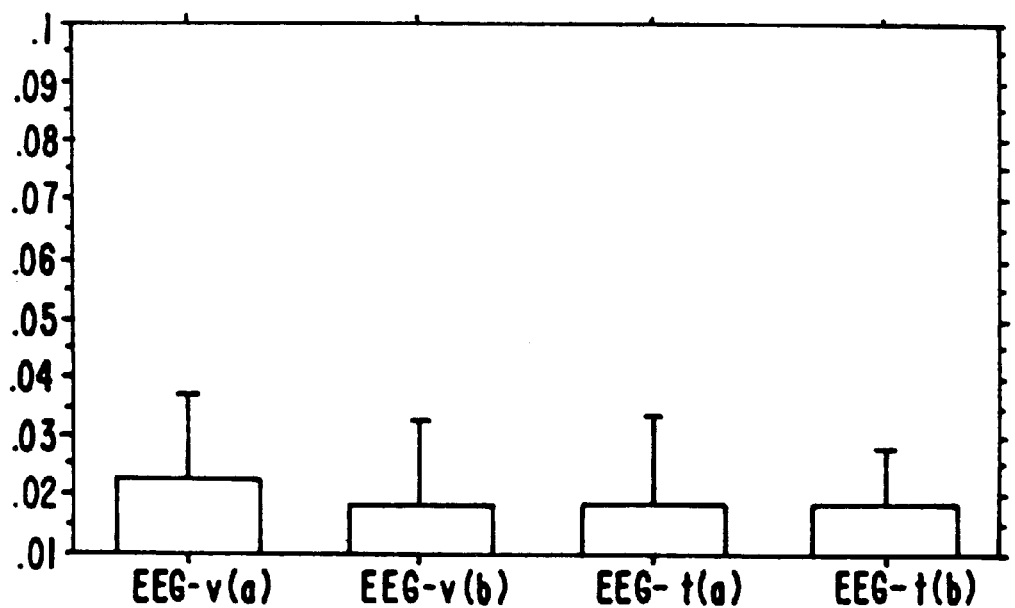
Figure 41:
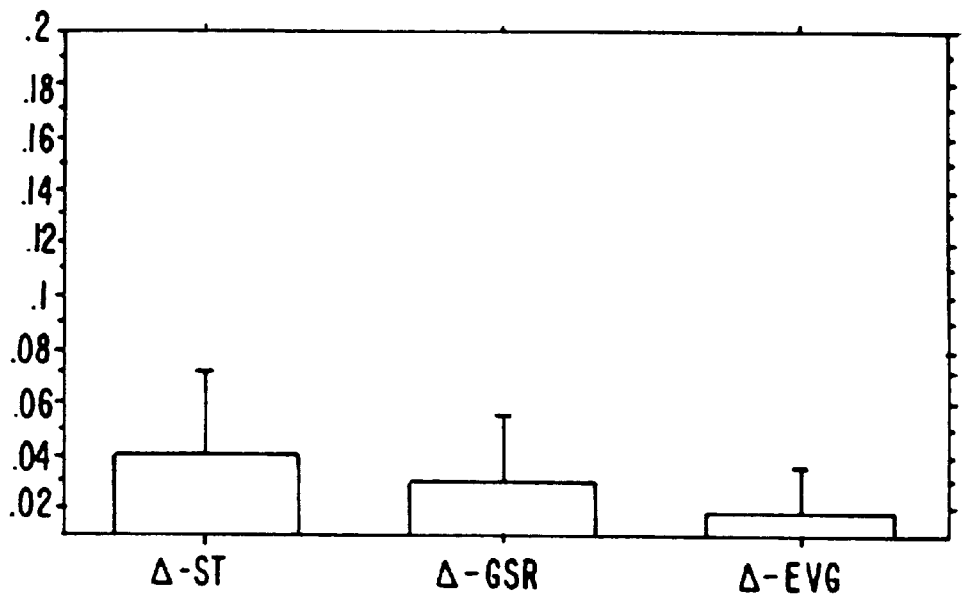
FIGS. 41, 42 and 43 show the ST, GSR, EVG, RF EKG and EEG measurements in males of compound A14-P2.
Figure 42:
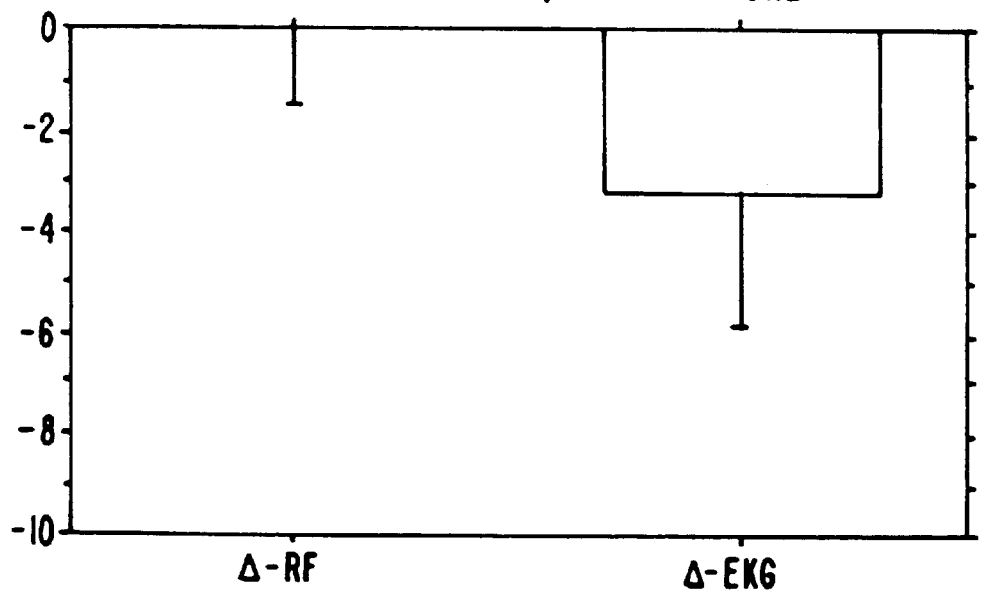
Figure 43:
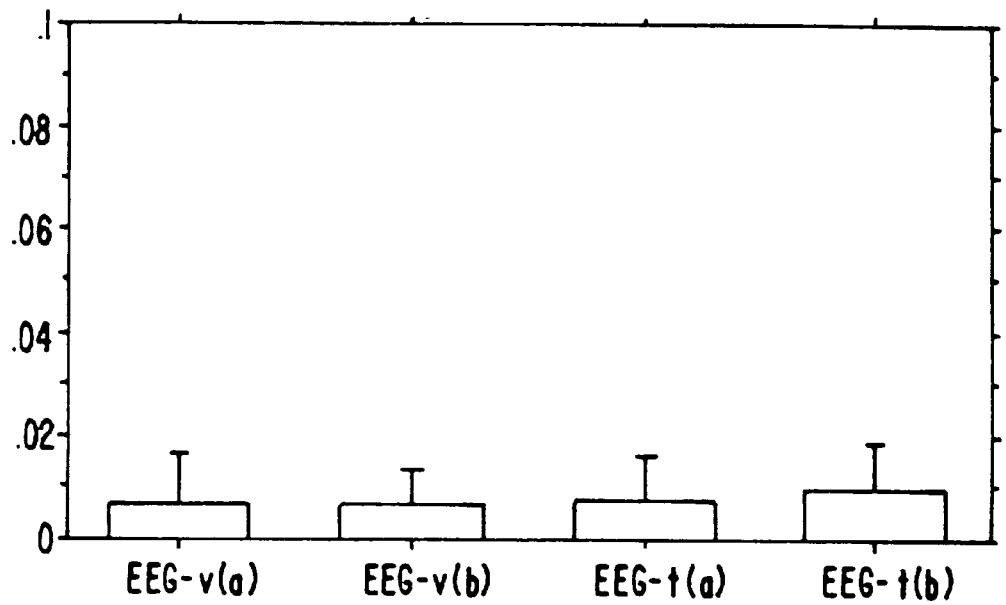
Figure 44:
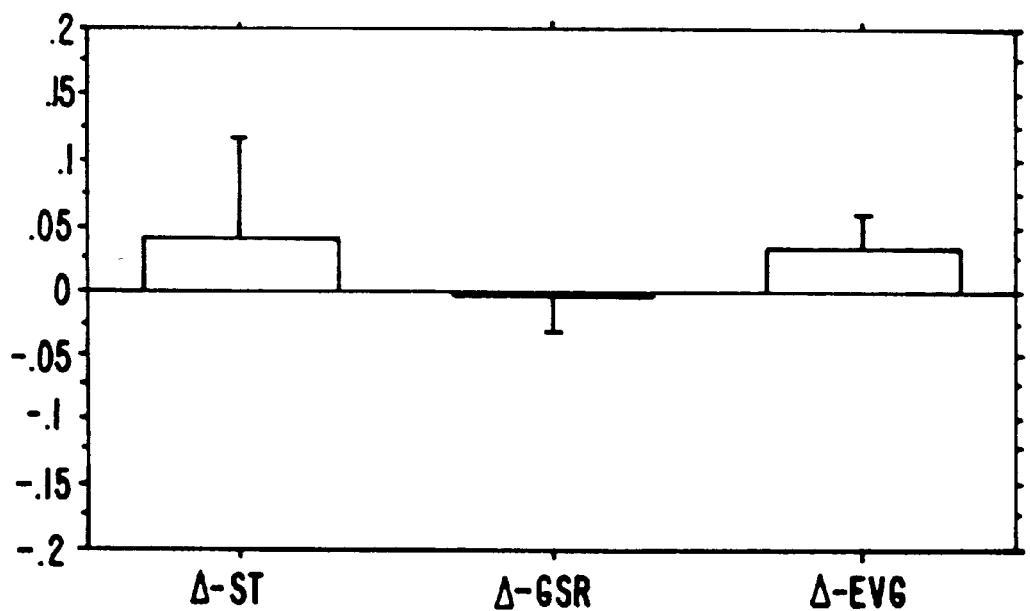
FIGS. 44, 45 and 46 show the ST, GSR, EVG, RF, EKG and EEG measurements in females of compound A14-P2.
Figure 45:
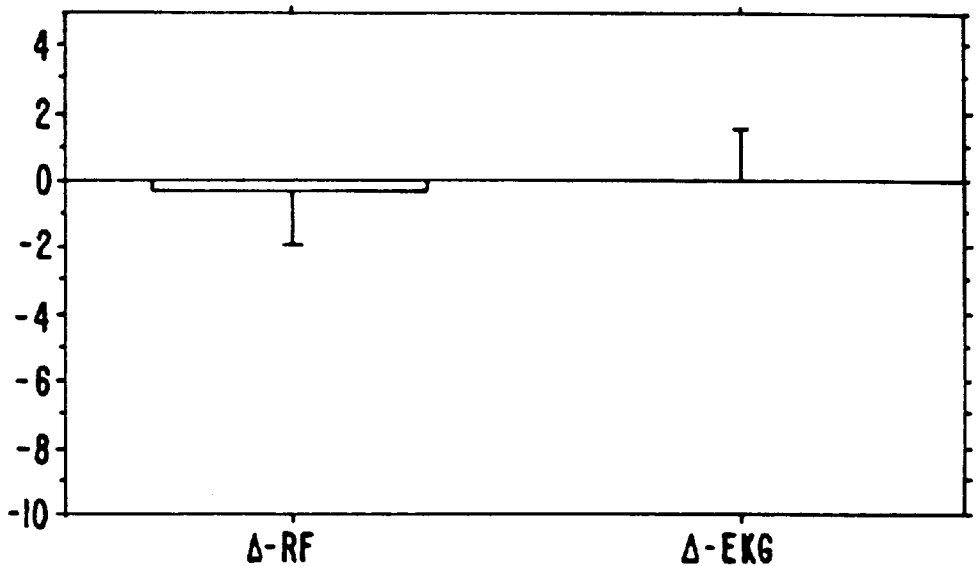
Figure 46:
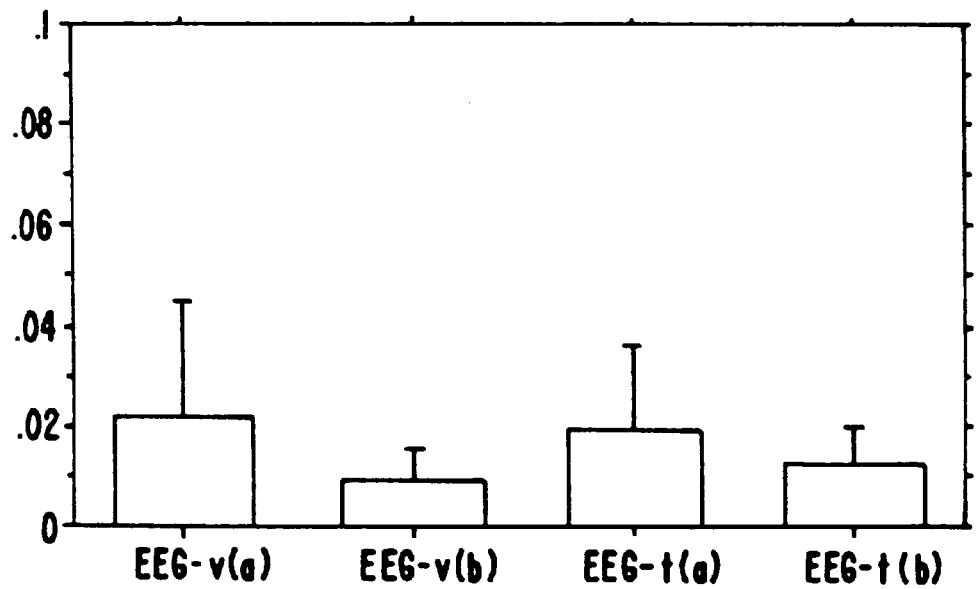
Figure 47:
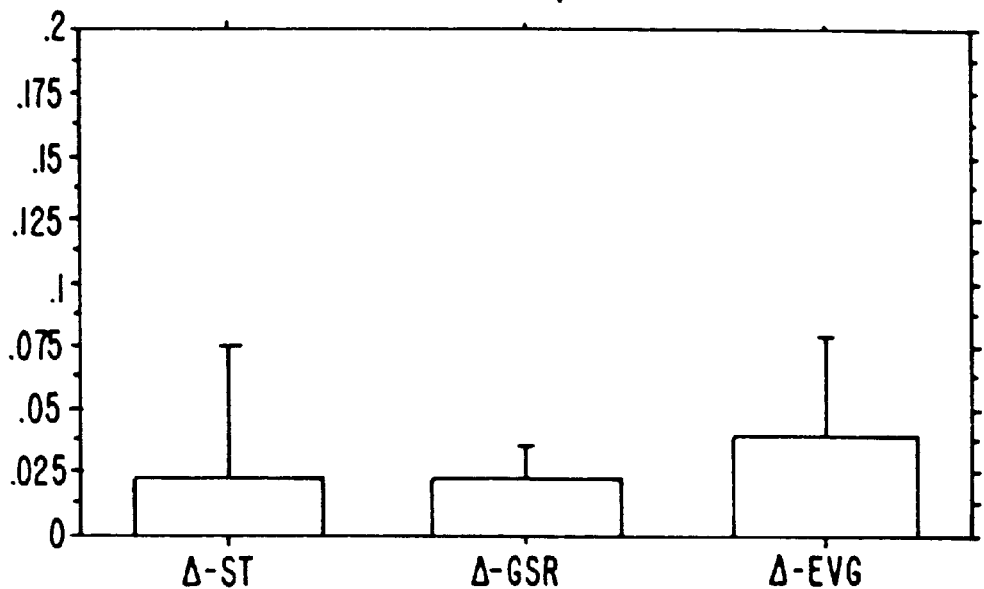
FIGS. 47, 48 and 49 show the ST, GSR, EVG, RF, EKG and EEG measurements in males of compound A7-P2.
Figure 48:
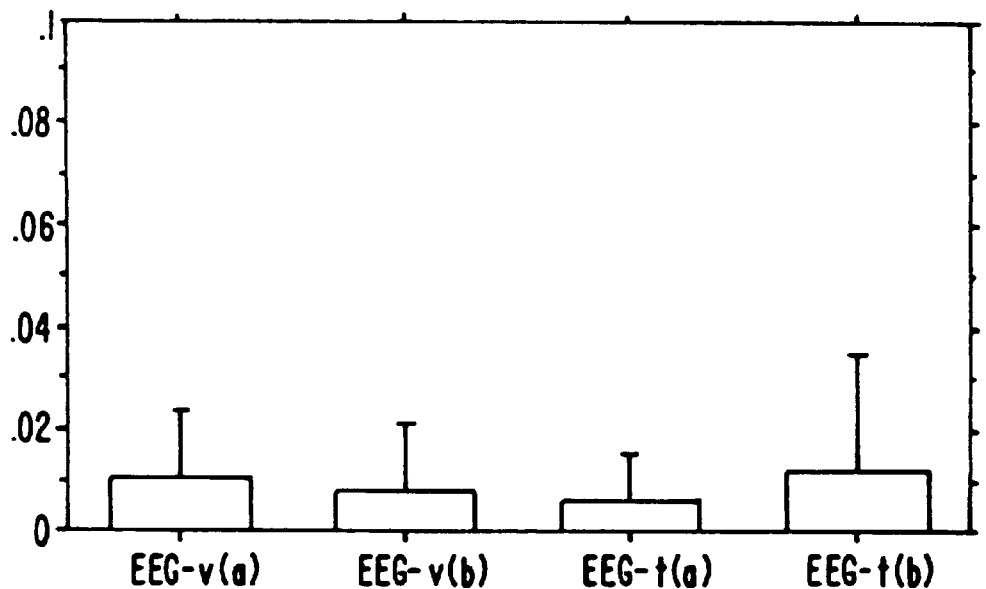
Figure 49:
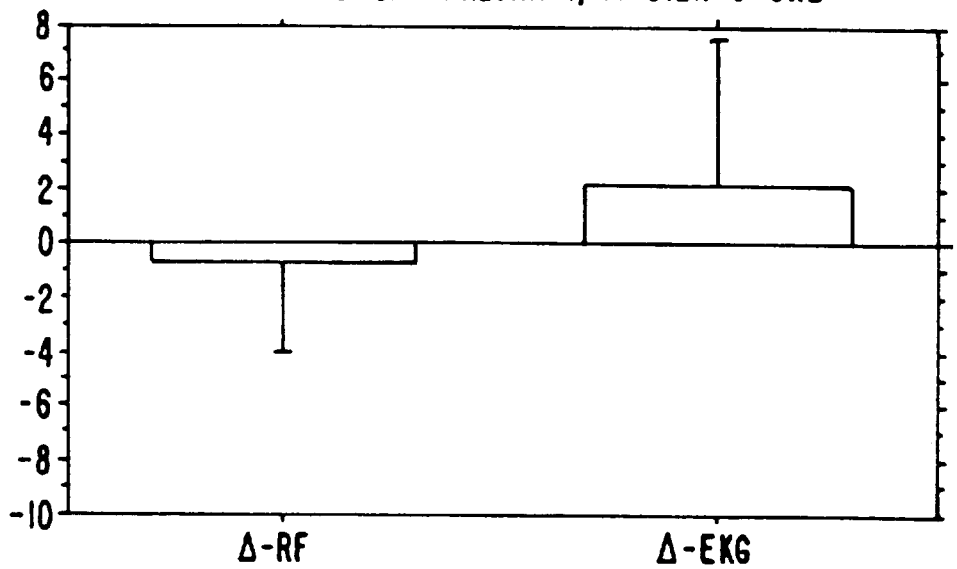
Figure 50:
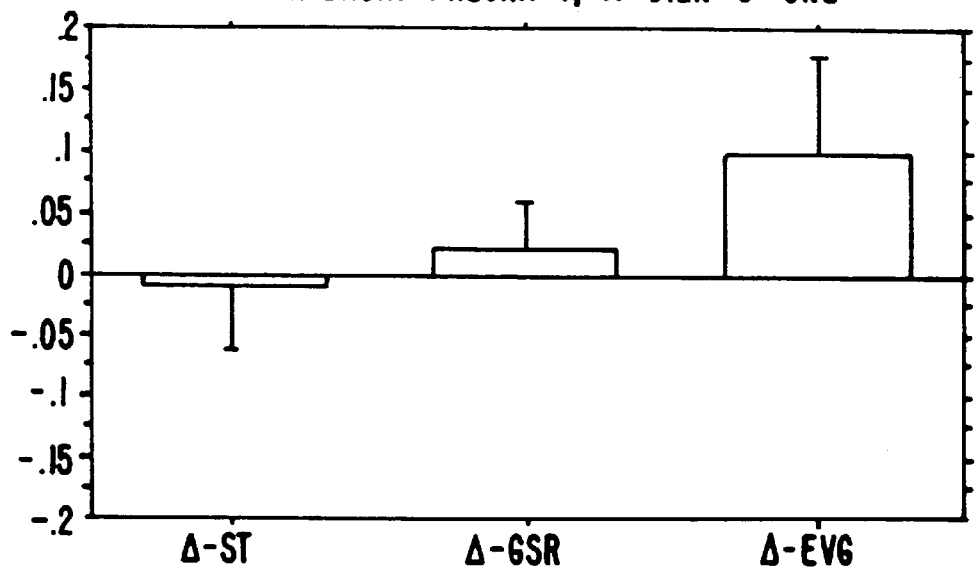
FIGS. 50, 51 and 52 show the ST, GSR, EVG, RF, EKG and EEG measurements in females of compound A7-P2.
Figure 51:
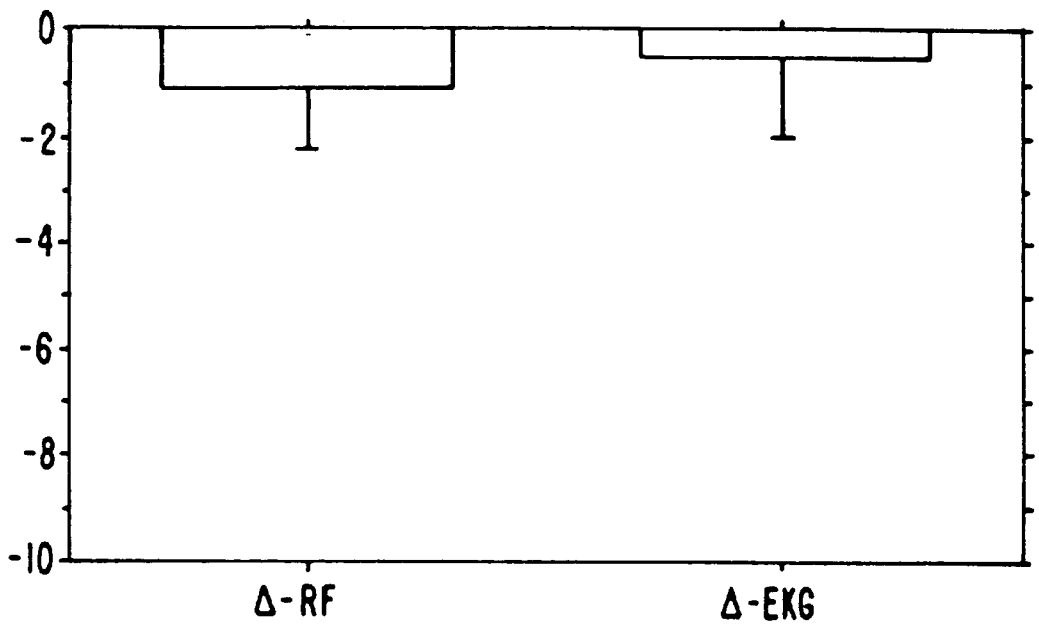
Figure 52:
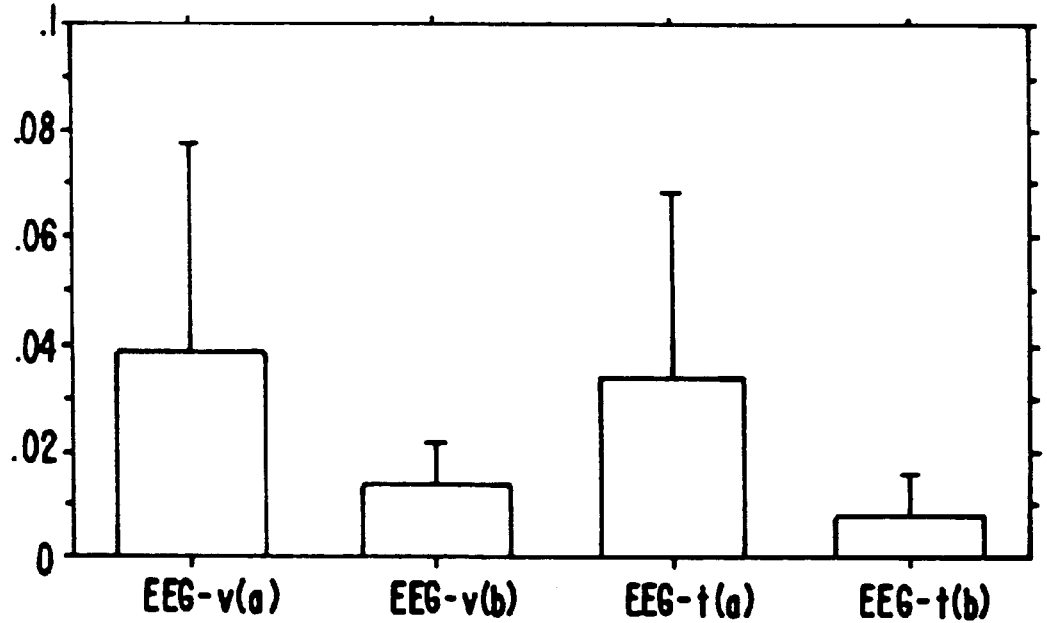
Figure 53:
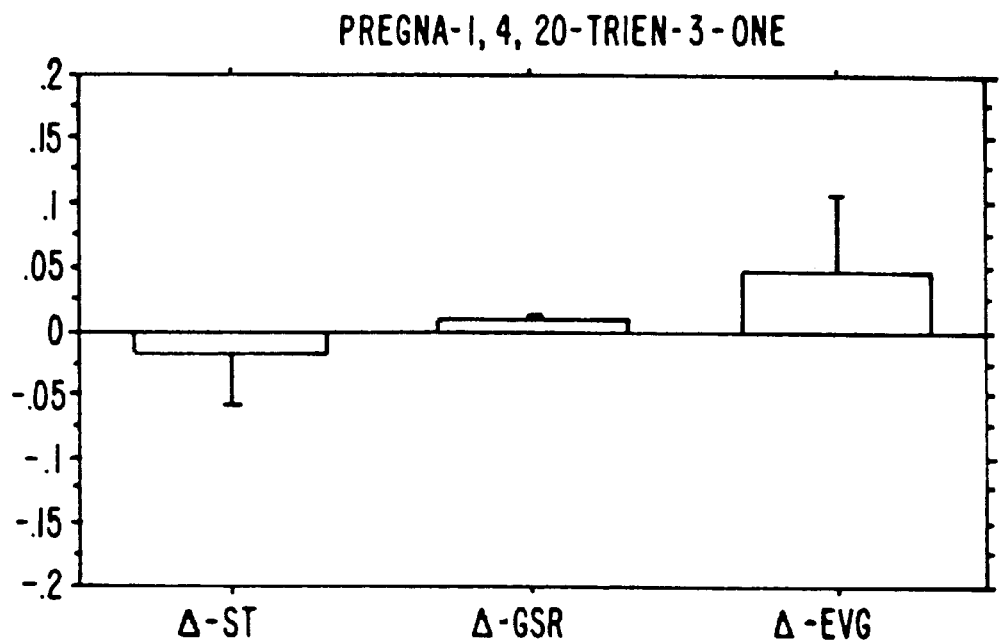
FIGS. 53 and 54 show the ST, GSR, EVG, EEG measurements in males of compound A11-P1.
Figure 54:
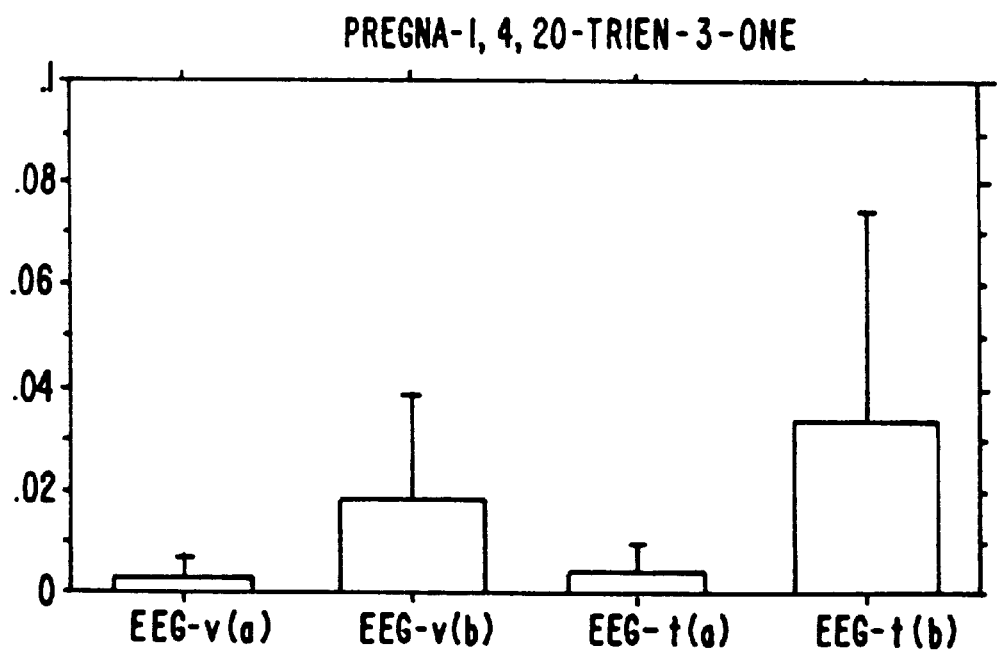
Figure 55:
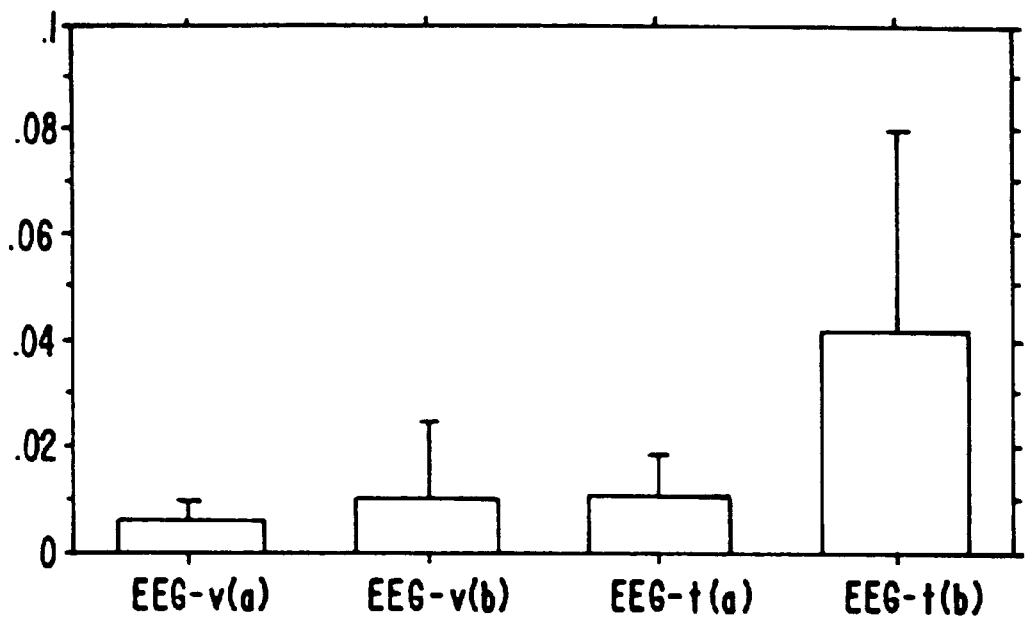
FIG. 55 shows the data of EEG measurements in males of compound A13-P1.
Figure 56:
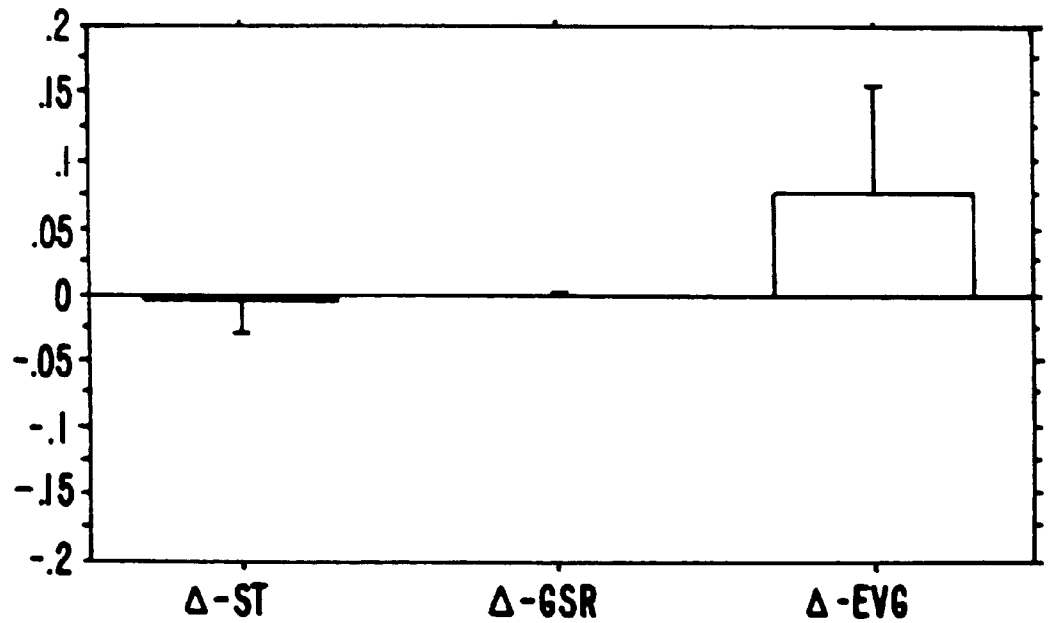
FIGS. 56, 57 and 58 show the data of measurements of ST, GSR, EVG, RF, EKG and EEG in females of compound A13-P1.
Figure 57:
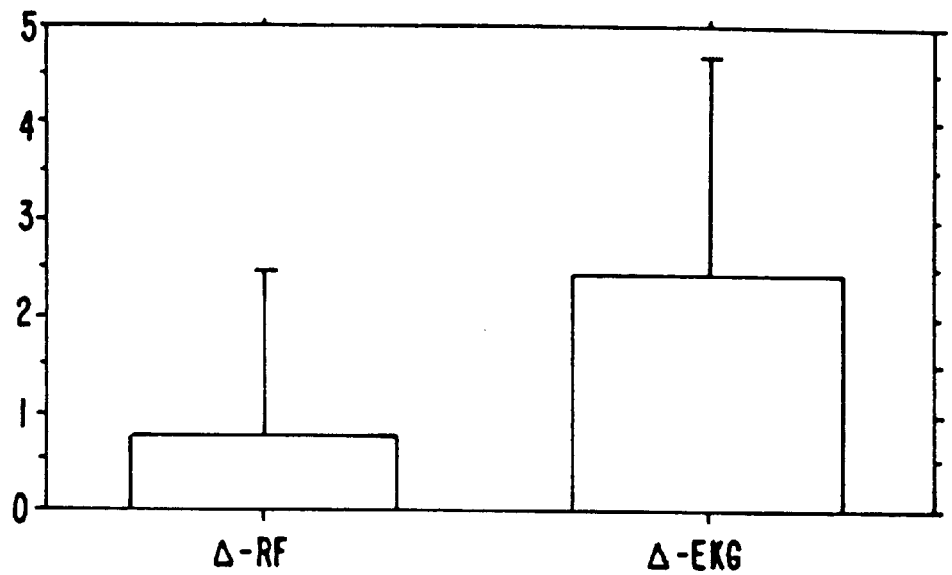

To a suspension of chromium trioxide (6.19 g. 61.9 mmol) cooled to −8° C. (ice-salt bath) in methylene chloride (100 ml) was added 2,4-dimethylpyrazole (5.95 g, 61.9 mmol). See FIG. 17. After stirring 20 min., a solution of 17-methylenestra-1,3,5(10)-trien-3-yl acetate (11, 2.0001 g, 6.4428 mmol) in 10 ml of chilled methylene chloride was added over a period of 2 min. so that the temperature did not reach −6° C. Stirring was continued 2 h and the mixture was then passed through a column of 100 g of silica gel (200–400 mesh). Product continued eluting with further methylene chloride. Pooling and concentration of appropriate fractions under reduced pressure gave crude product, which was further purified by two-fold recrystallization from aqueous ethanol to give lustrous off-white crystals (334.0 mg, 1.030 mmol, 16%), m.p. 91–94° C. TLC (25% ethyl acetate/ hexanes on silica gel) showed product ($R_f$ 0.47) with two minor contaminants at Rf 0.30 and 0.39.

Example 90
17-Methylenestra-1,3,5(10)-trien-3,6B-diol.

To a suspension of lithium aluminum hydride (53.6 mg, 1.41 mmol) in anh. THF (3.0 ml) under argon cooled in a dry ice/acetone bath was added 17 35 methylenestra-1,3,5(10)- trien-6-on-3-yl acetate (12, 251.7 mg, 0.7758 mmol) in anh. THF (3.0 ml) dropwise with stirring over 8 min. See FIG. 160. After stirring 2 h, the bath was removed and stirring continued a further hour. The reaction was quenched by stirring ½ h with Glauber's salt (1.78 g). The resulting mixture was applied to a short pad of diatomaceous earth and extracted four times with 10 ml portions of ethyl acetate. Continued extraction with five 10 ml portions of hot ethyl acetate and concentration of all extracts under reduced pressure gave a colorless film. Preparative TLC (40% ethyl acetate/hexanes on silica gel GF, $^{1000}$IL thickness) gave a white foam (15.3 mg, 53.8 ILmol, 7%). TLC (40% ethyl acetate/hexanes on silica gel) showed major ($R_f$ 0.29) and minor components ($R_f$ 0.37).

Example 91
17-Methylenestra-1,3,5(10)-trien-3-yl methyl ether.

To a stirred suspension of 17-methylenestra-1,3,5(10)-trien-3-ol (5.37 g, 20.0 mmol) and potassium carbonate (50.82 g, 0.3678 mol) at reflux in 90% ethanol (500 ml) was added dimethyl sulfate (5.0 ml, 53 mmol). After ½ h reflux additional dimethyl sulfate (36 ml, 0.38 mol, in three 12 ml aliquots) was added over the period of 1 h. See FIG. 160. The reaction was refluxed a further hour, following which 360 ml of water were added and the mixture was placed in the refrigerator overnight. The resulting suspension was filtered and washed with 80 ml of 60% methanol+three 80 ml portions of 5% (w/w) sodium hydroxide+three 80 ml portions of water. The residue was recrystallized from aqueous methanol to give white crystals (3.88 g, 13.7 mmol, 69%), m.p. 59–62° C. TLC (20% ethyl acetate/hexanes on silica gel) showed product ($R_f$ 0.63) with trace contaminants at $R_f$ 0.37 and at the origin.

Example 92
17-Methylenestra-2,5(10)-dien-3-yl methyl ether.

Approximately 70 ml of anh. ammonia was distilled through a KOH tower into a 250 ml flamedried 3-neck flask fitted with an inlet adapter, magnetic stirring bar, dry ice/acetone condenser, and V ground glass stopper. See FIG. 160. A solution of 17-methylenestra-1,3,5(10)-trien-3-yl methyl ether (14, 1.1297 g, 4.0001 mmol) and t-butyl alcohol (13.21 g, 0.1782 mol) in dry THF (17 ml) was added, followed by lithium wire (0.47 g, 68 mg-atom) cut in small pieces. After refluxing under argon for 6 h anh. methanol (6.6 ml) was added and the suspension was stirred overnight while allowing ammonia to boil off. Water (100 ml) was added and the suspension was extracted three times with 50 ml portions of methylene chloride. The combined organic extracts were washed with 100 ml of brine, dried over sodium sulfate, and filtered. The residue was washed with 25 ml of methylene chloride and the combined filtrates were concentrated under reduced pressure. The resulting light yellow oil was crystallized from aqueous ethanol to give lustrous white crystals (815.0 mg, 2.865 mmol, 72%), m.p. 77–78° C., homogeneous to TLC ($R_f$ 0.60, 10% ethyl acetate/hexanes on silica gel).

Example 93
17-Methylenestr-4-en-3-one.

Con. hydrochloric acid (6.0 ml) and water (6.0 ml) were added to a solution of 17-methylenestra-2,5(10)-dien-3-yl methyl ether (15, 702.8 mg. 2.471 mmol) in methanol (6 ml) and acetone (20 ml). See Example 160. After stirring 1 h, sodium bicarbonate (7.50 g) was added cautiously. The mixture was concentrated under reduced pressure once effervescence had ceased and water (50 ml) was added. The mixture was extracted three times with 25 ml portions of methylene chloride. The combined organic extracts were washed with 50 ml of brine, dried over magnesium sulfate, and filtered through diatomaceous earth. The residue was washed with 10 ml of methylene chloride and the combined filtrates were concentrated under reduced pressure. The product was purified by decolorization with charcoal, flash chromatography (20% ethyl acetate/hexanes on silica gel), and recrystallization from aqueous ethanol to give a white powder (302.8 mg. 1.120 mmol, 45%), m.p. 83–89° C.

Example 94
17-Methylenestr-4-en-3β-ol.

Lithium tri-t-butoxyaluminohydride (766.6 mg, 3.015 mmol) was added to a solution of 17-methylenestr-4-en-3-one (16, 203.7 mg, 0.7533 mmol) in 10 ml of anh. ether and the reaction was stirred 420 h. See FIG. 161. Glauber's salt (3.80 g) was added and the suspension was stirred an additional ½ h. The mixture was filtered through diatomaceous earth and the residue was washed five times with 10 ml portions of ether. The combined filtrates were concentrated under reduced pressure and then subjected to preparative TLC (5% ethyl acetate/methylene chloride on silica gel GF, 1000 thickness) to give white needles (60.2 mg. 0.221 mmol, 29%) homogeneous to TLC ($R_f$ 0.37, 5% ethyl acetate/methylene chloride on silica gel).

Example 95
17-Methylenestra-1,3,5(10),7-tetraen-3-ol.

Methyltriphenylphosphonium bromide (1.9967 g, 5.5892 mmol) and potassium t-butoxide (627.2 mg, 5.589 mmol) suspended in 6.1 ml of anh. DMSO under argon were lh in an oil bath (71–83° C., after which equilin (300.0 mg, 1.118 mmol) in 6.1 ml of anh. DMSO was added via syringe. See FIG. 161. After stirring a further 70 min., the reaction mixture was poured into 40 ml of ice water and extracted three times with 25 ml portions of ether. The combined organic extracts were washed with 25 ml of brine, dried over magnesium sulfate, and filtered through diatomaceous earth. The residue was washed with 10 ml of ether and the combined filtrates were concentrated under reduced pressure. Flash chromatography (15% ethyl acetate/hexanes on silica gel) followed by preparative TLC (20% ethyl acetate/hexanes on silica gel GF, 1000 g thickness) gave an opaque white film (162.3 mg, 0.6093 mmol, 54%).

Example 96
17-Methylenestra-1,3,5(10),7-tetraen-3-yl acetate.

Methyltriphenylphosphonium bromide (3.33 g, 9.32 mmol) and potassium t-butoxide (1.05 g, 9.36 mmol) suspended in 10 ml of anh. DMSO under argon was stirred 1 h in an oil bath (77–79° C.), following which equilin (500.0 mg, 1.863 mmol) in 10 ml of anh. DMSO was added via syringe. See FIG. 161. After stirring a further hour the cooled reaction mixture was poured into 50 ml of ice-1 N hydrochloric acid and extracted three times with 25 ml portions of ether. The combined organic extracts were washed with 25 ml of brine, dried over magnesium sulfate, and filtered through diatomaceous earth. The residue was washed with 10 ml of ether and combined filtrates concentrated under reduced pressure. The resulting light yellow syrup was taken up in anh. pyridine (6.3 ml, 78 mmol), acetic anhydride was added (0.88 ml, 9.3 mmol), and the reaction mixture was stirred 16 h. The mixture was then poured into 100 ml of 1 N hydrochloric acid and extracted three times with 50 ml portions of ether. The combined organic extracts were washed with 100 ml of saturated sodium bicarbonate+100 ml of brine, dried over magnesium sulfate, and filtered through diatomaceous earth. The residue was washed with 25 ml of ether and the combined filtrates were concentrated under reduced pressure. The crude acetate was flash chromatographed (5% ethyl acetate/hexanes on silica gel) to give a yellow resin (494.7 mg, 1,604 mmol, 86%).

Example 97
16α,7α-Epoxyestr-4-en-10β-ol-3-one.

To a frozen (dry ice/acetone) suspension of estra-5(10),16-dien-3-one (1, 115.7 mg, 0.4513 mmol) in chloroform (3 ml) was added m-chloroperbenzoic acid (MCPBA, 77.4%, 420.8 mq, 1.89 mEquiv. of peracid) suspended in ether 4.3 ml) and the mixture was stirred 2 h. The reaction was then stored in a refrigerator for 18 h, after which sodium thiosulfate pentahydrate [5% (w/w), 25 g] was added. After stirring 5 min., the mixture was extracted three times with 10 ml portions of ether. The combined organic extracts were washed with 25 ml of saturated sodium bicarbonate+25 ml of brine, dried over magnesium sulfate, and filtered through diatomaceous earth. The residue was washed with 10 ml of ether and the combined filtrates were concentrated under reduced pressure. TLC suggested the intermediate 5B,10B-epoxide had undergone partial elimination. Elimination was completed by refluxing the white crystalline residue for 1 h in 20 g of 5% (w/w) potassium hydroxide in anh. methanol. The reaction mixture was poured into 50 ml of ice water 5 and extracted with 50 ml of ether. The organic extract was washed twice with 50 ml portions of water, dried over sodium sulfate, and filtered through diatomaceous earth. The residue was washed with 20 ml of ether and the combined filtrates were concentrated under reduced pressure. The residue was subjected to preparative TLC (50% ethyl acetate/hexanes on silica gel GF, 1000μ thickness) to give a colorless resin (19.7 mg, 72.3 μmol, 166).

Example 98
18-Nor-17-methylestra-4,13(17)-dien-3-ol.

To a cooled (ice water bath) solution of 18-nor-17-methylestra-4,13(17)-dien-3-one (3, 0.23 g, 0.90 mmol) in anh. methanol (2.3 ml) was added sodium borohydride (0.23 g, 6.1 mmol) and the reaction was stirred for 2 h. See FIG. 162. Solvent was removed under reduced pressure and 10 ml of water were added to the residue. The mixture was then extracted three times with 10 ml portions of methylene chloride. The combined organic extracts were washed with 10 ml of brine, dried over magnesium sulfate, and filtered through diatomaceous earth. The residue was washed twice with 5 ml of methylene chloride and the combined filtrates were concentrated under reduced pressure. The resulting slightly yellow solid was purified by preparative TLC (5% ethyl acetate/methylene chloride on silica gel GF, 1000 thickness) to give a yellow solid (53.6 mg, 0.207 mmol, 23%) homogeneous to TLC (5% ethyl acetate/methylene chloride on silica gel; $R_f$ 0.32).

Example 99
Androsta-4,16-dien-3-one.

This synthesis is depicted in FIG. 178. Several methods are known for the conversion of testosterone into Androsta-4,16-dien-3-one (Brooksbank et al., Biochem. J. (1950) AZ:36). Alternatively, thermolysis (460°) of the methyl 15 carbonate of testosterone gives Androsta-4,16-dien-3-one in 90% yield. 17B-MethoxyCarbonyloxy-androst-4en-3-one (IV) was prepared from testosterone (III. Fluka) with methyl chloroformate/pyridine (a) in 76% yield (after recrystallization from MeOH). M.p. 140–141°, $[a]_D$=+95.4° (c=1.10) -IR. ($CDCl_3$): 1740s, 1665s, 1450s, 1280s, -$^1$H-NMR. (360 MHz): 0.87 (s, 3H); 1.20 (s, 3H); 3.77 (s, 3H); 4.53 (br. t, J 8, 1H); 5.75 (s, 1H). A solution of the methyl carbonate IV in toluene was pyrolyzed (b) as 25 described for I. Recrystallization of the crude product from acetone at RT. gave pure ketone 4 in 90% yield. M.p. 127–129.5°, $(a)_D$+118.9° (C=1.32) ([3]: m.p. 131.5–133.5° (hexane), $[a]_D$16=+123±3.5° (C=1.03)). -IR. ($CDCl_3$) 3050w, 1660s, 1615m. -$^1$H-NMR. (360 MHz): 0.82 (s, 3H); 1.22 (s, 3H); 5.70 (m, 1H); 5.73 (s, 1H); 5.84 (m, 1H).

Example 100
Androsta-4,16-dien-3α-ol (5) and -3β-ol.

These syntheses are depicted in FIG. 178. Androsta-4,16-dien-3-one (4) was reduced at −55° with 5 lithium tris (1,2-dimethylpropyl) hydridoborate in THF (c) as described for the preparation of 2 (FIG. 1). Chromatography on silica gel with $CH_2Cl_2$/ethyl acetate 9:1 gave pure axial alcohol 5 (48% yield) and pure equatorial alcohol 6 (48% yield). Analytical samples were further purified by recrystallization (from PE at −30° for 5, from cyclohexane at RT. for 6).

Data of 5. M.p. 77–79°, $[a]_D$+120.6° (C=1.26) -IR. ($CDCl_3$): 3620m, 3440m br., 1660m, 1595w.-$^1$H-NMR. (360 MHz): 0.79 (s, 3H); 1.02 (s, 3H); 4.07 (m, $w_{1/2}$≈10, 1H) 5.48 (d×d, J 5 and 2, 1H); 5.71 (m, 1H); 5.85 (m, 1H).

Data of 6. M.p. 116.1190, $[a]_D$+53.9° (C=1.28) ([47]: m.p. 116.1180, [$^8$)D+59.3° (C=0.4) -IR. ($CDCl_3$) 3610m, 3420m br., 3050m, 1660m, 1590w. -$^1$H-NMR. (360 MHz): 0.78 (s, 3H); 1.08 (s, 3H); 4.15 (m, $w_{1/2}$≈20, 1H); 5.30 (m, $w_{1/2}$≈5, 1H); 5.71 (m, 1H); 5.85 (m, 1H)

Example 101
Androsta-5,16-dien-3α-ol.

This synthesis is depicted in FIG. 179. To a solution of alcohol 8 (545 mg, 2.0 mmol) in acetone (100 ml) at 0° C. under $N_2$ was added rapidly Jones reagent (i, 1.5 ml, ca. 4 mmol). After 5 min., the mixture was poured into a dilute phosphate buffer (pH 7.2, 1200 ml) and extracted with ether. The extracts were washed with sat. aq. NaCl solution, dried ($Na_2SO_4$) and evaporated to give mainly Androsta-5,16-dien-3-one as an oil (567 mg). The crude product was dissolved in THF (7 ml) and reduced with lithium tris (1,2-dimethylpropyl) hydridoborate (c) at 0.550 as described for the preparation of 2. The crude product (530 mg) was chromatographed on silica gel (100 g) with $CH_2Cl_2$/ethyl acetate 4:1 to give 280 mg (51%) of pure a-alcohol 7 (eluted first) and 13 mg of 5 starting alcohol 8. A small sample of 7 was recrystallized from acetone/water at RT. M.p. 1380, [$^8$]D−77.5° (c=1.2. -IR. ($CDCl_3$): 3580m, 3430m, 1665w, 1590w, -$^1$H-NMR. (360 MHz) 0.80 (s, 3H); 1.06 (s, 3H); 4.02 (m, w,8, 1H); 5.44 (m, 1H); 5.72 (m, 1H); 5.86 (m, 1H)

Example 102
Androsta-5,16-dien-3B-ol.

Figure 4:
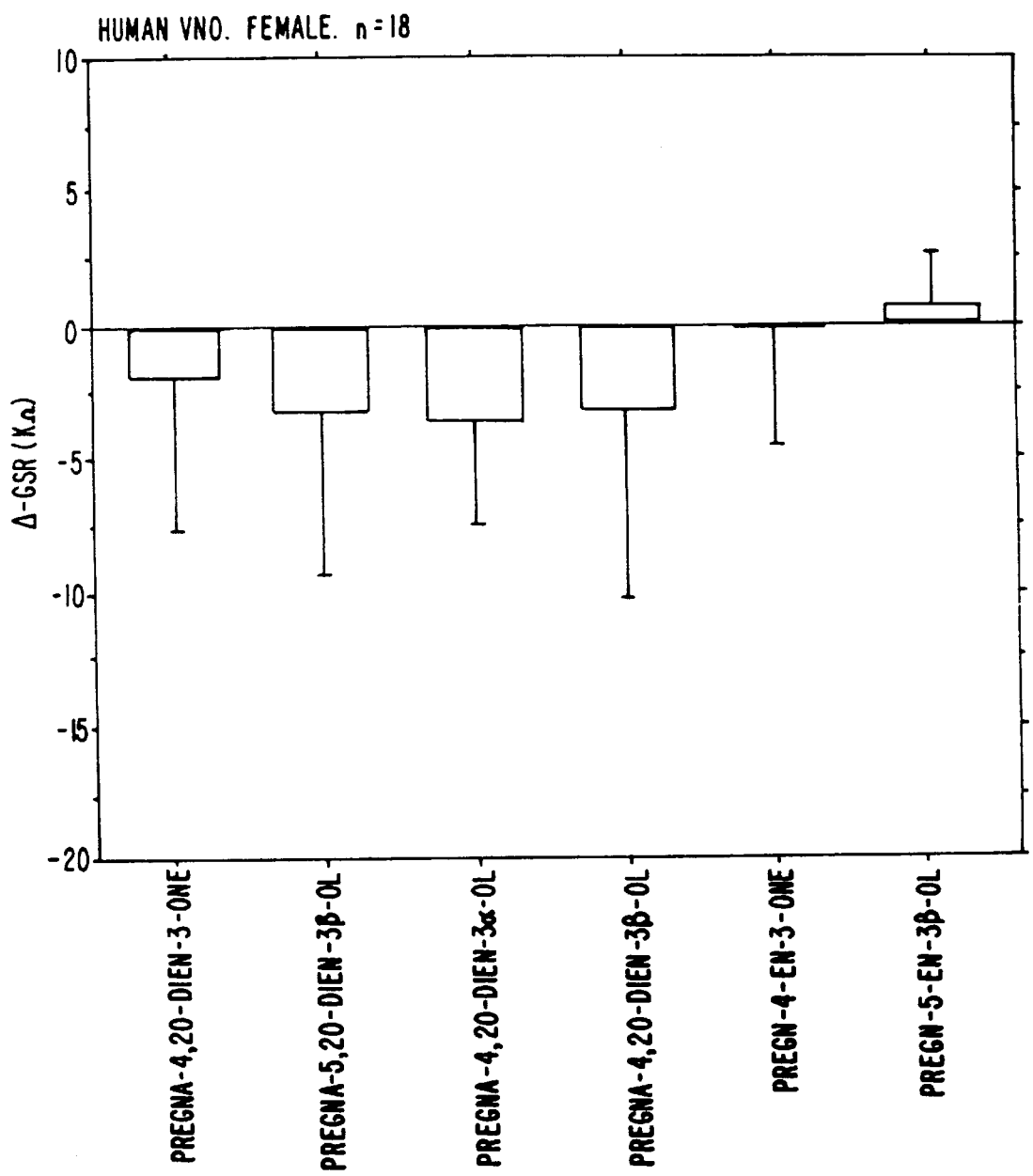
FIG. 4 is the data for the GSR measurements in females of compounds A1-P1, A2-P1, A4-P1, A3-P1, A1-P4, A2-P4.
Figure 5:
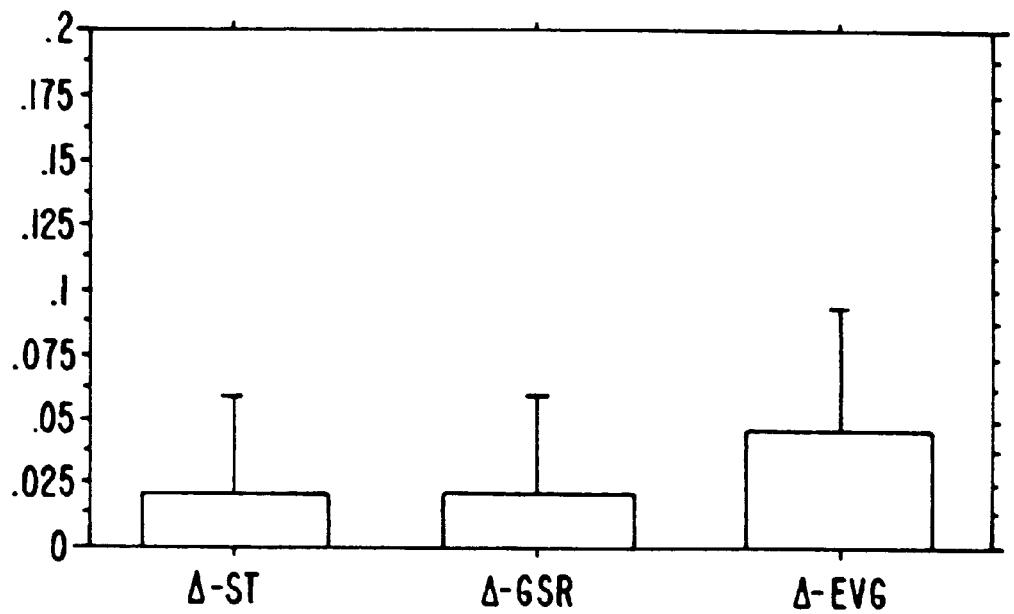
FIG. 5 is the data for ST, GSR and EVG measurements in females of compound A1-P3.
Figure 6:
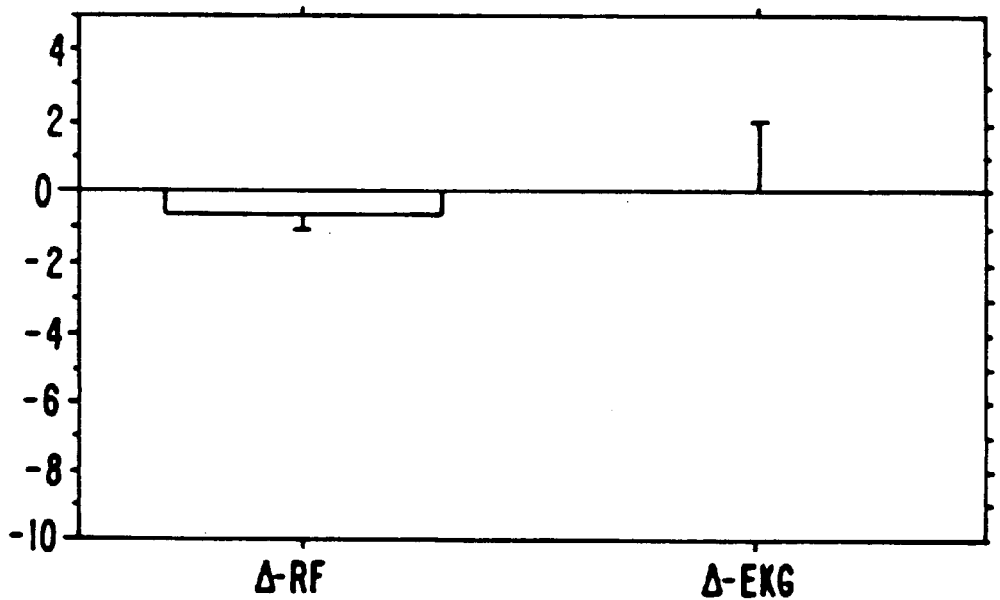
FIG. 6 is the data for RF and EKG measurements in females of compound A1-P3.
Figure 7:
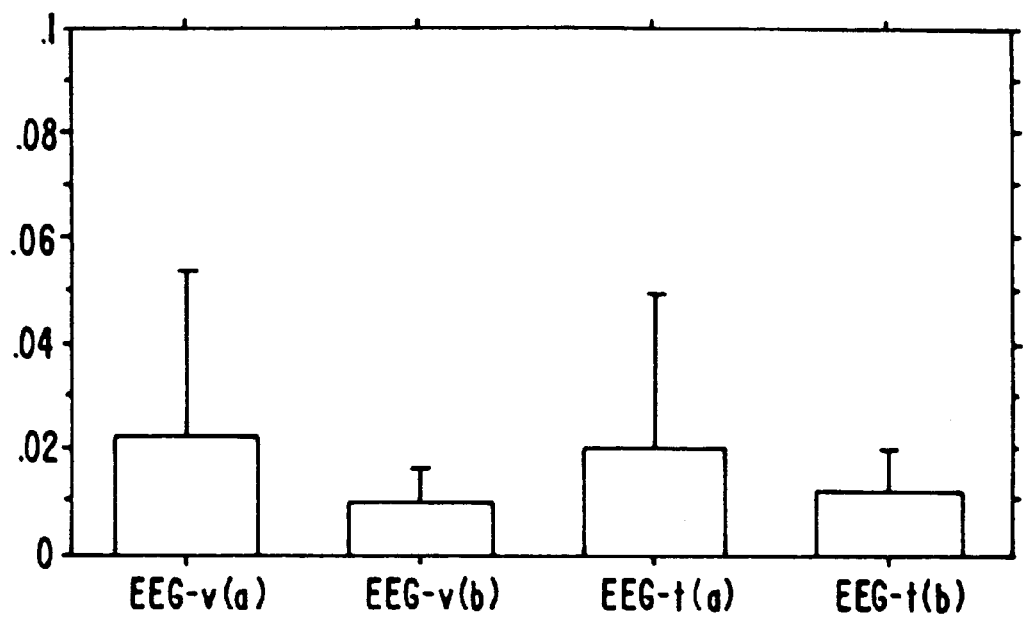
FIG. 7 is the data for EEG measurements in females of the compound A1-P3.
Figure 8:
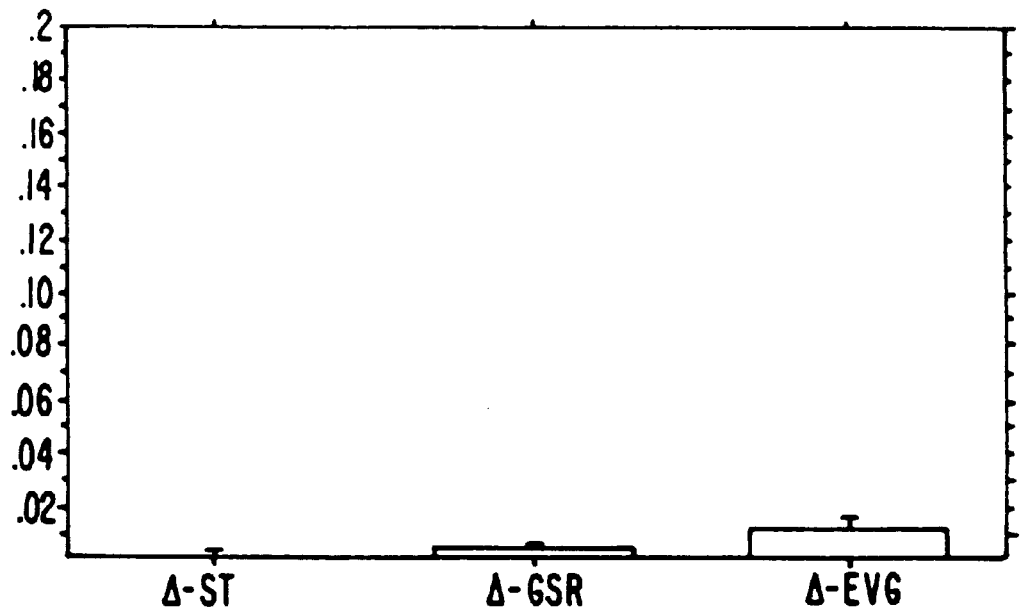
FIG. 8 is the data for the ST, GSR and EVG measurements in males of compound A1-P3.
Figure 9:
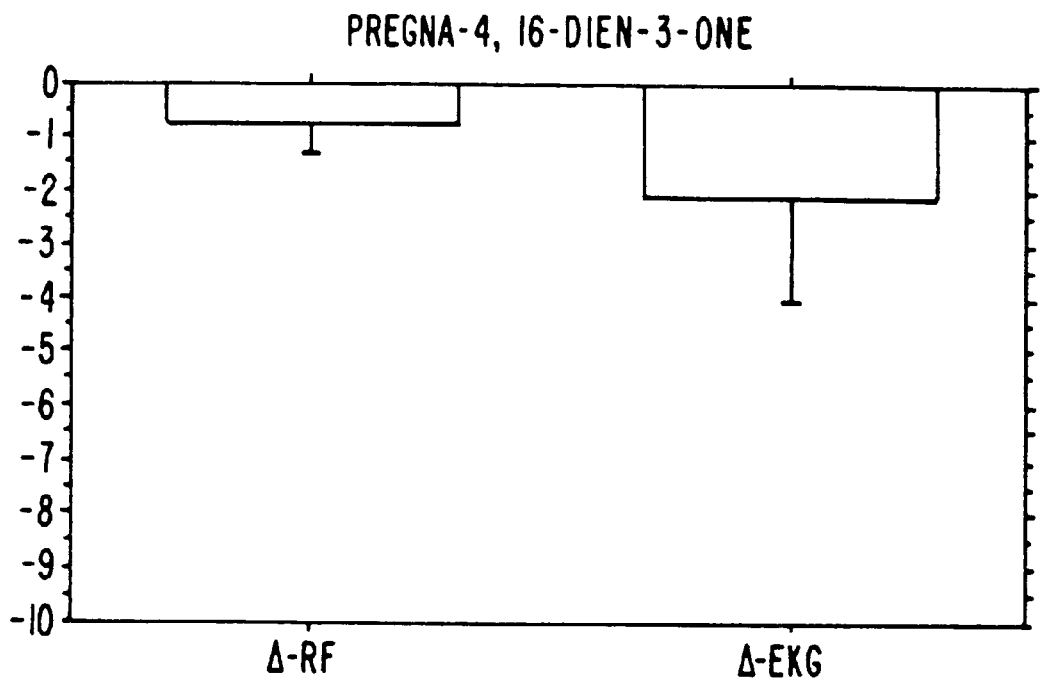
FIG. 9 is the data for the RF and EKG measurements in males of compound A1-P3.
Figure 10:
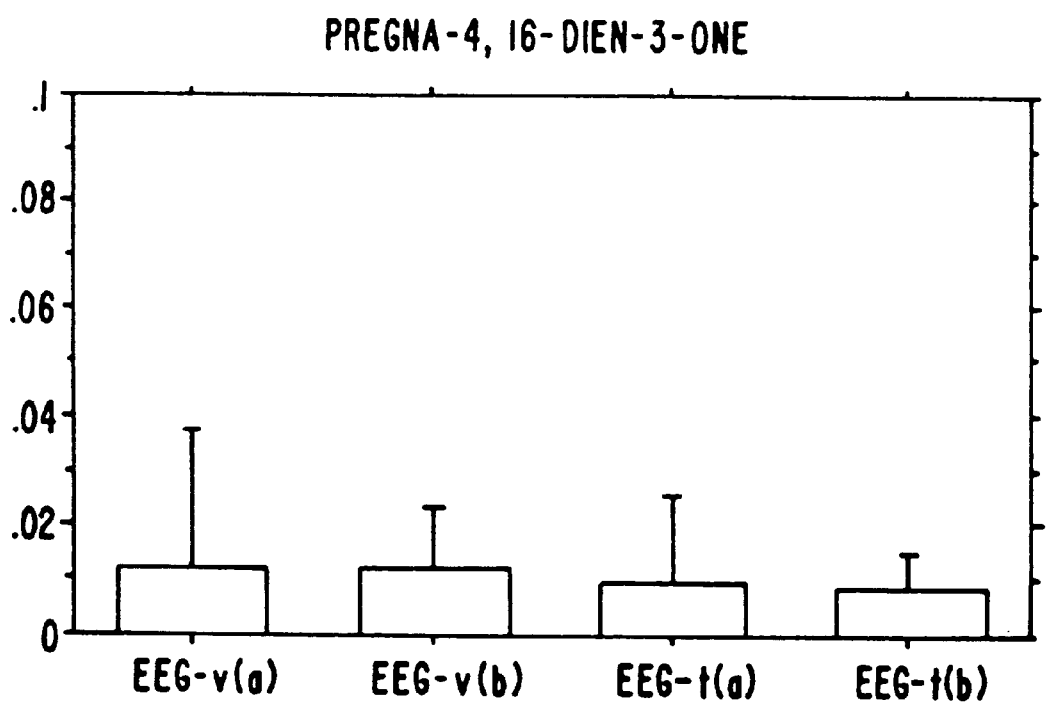
FIG. 10 is the data for the EEG measurements in males of compound A1-P3.
Figure 11:
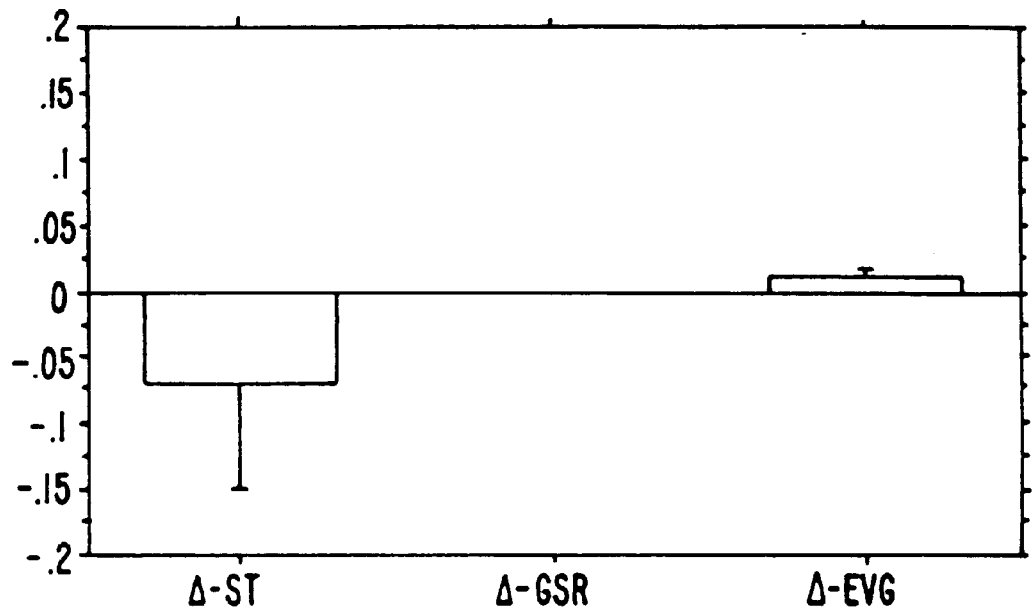
FIGS. 11 and 12 show the data of the ST, GSR and EVG measurements in males and females, respectively, for compound A2-P3.

This compound was prepared in 73% yield by a known procedure (Marx, A. F., et al., Ger. Offen. 2,631,915; Chem. Abst. 87:23614p (1977)) from commercial (Fluka) 3B-hydroxy-androst-5-en-17-one (VII). M.p. 137°, $[a]_D$=−71.9° (c=1.5) ([48]: m.p. 140–141°, $[a]_D$=68°. -IR. ($CDCl_3$): 3600m, 3420m br., 1670w, 1590w, -$^1$H-NMR. (360 MHz): 0.80 (s, 3H); 1.05 (s, 3H); 3.53 (m, $w_{1/2}$≈22, 1H); 5.38 (m, 1H); 5.72 (m, 1H); 5.86 (m, 1H). This synthesis is depicted in FIG. 4.

Example 103
Alternate synthesis of Androsta-4,16-dien-3-one.

The following method of synthesis is depicted in FIG. 180:

Dehydroepiandrosterone p-Toluenesulfonylhydrazone

Dehydroepiandrosterone (VII) (14.4 g, 50.0 m mole) and p-toluenesulfonylhydrazide (12.75 g, 68.5 m mole) in dry methanol (300 ml) were heated under reflux for 20 hours. The mixture was transferred to a conical flask and allowed to cool. The crystalline product was filtered under suction and washed with methanol (50 ml). Further crops of product were obtained by sequentially evaporating the filtrate to 75 ml and 20 ml, and allowing crystallization each time. Total yield was 21.6 g (95%).

Androsta-5,16-dien-3β-ol

Dehydroepiandrosterone p-toluenesulfonylhydrazone (22.8 g, 50.0 m mole) in dry tetrahydrofuran (1.0 liters) was cooled in a dry ice/isopropanol bath. The mixture was stirred while n-butyl lithium (125 ml of 1.6 M solution in hexane, 200 m mole) was added. The mixture was allowed to warm to room temperature and was stirred for 24 hours. Water (50 ml) was added with cooling in ice. The mixture was poured into saturated ammonium chloride solution/ice (500 ml) and extracted with ether (×2). The organic layers were washed with saturated sodium bicarbonate solution (500 ml) and saturated sodium chloride solution (500 ml), dried (MgSO$_4$) and evaporated in vacuo to give the crude product. This was purified by flash chromatography on 190 g silica gel 60, 230–400 mesh, eluting with ethyl acetate/hexane (20:80→50:50) to give crystalline material. The product was recrystallized from methanol (45 ml)/3%. hydrogen peroxide (8 ml) 25 washing with methanol (30 ml)/water (8 ml) to give pure product (6.75 g, 50%).

Androsta-4,16-dien-3-one

A solution of 10 g of Androsta-5,16-dien-3β-ol in 475 cc of toluene and 75 cc of 30 cyclohexanone was distilled (ca. 50 cc of distillate was collected) to eliminate moisture, 5 g of Al(OPr$^i$)$_3$ in 50 cc of toluene was added and the solution was refluxed for 1 hour. Water then was added, volatile components were removed by steam distillation and the residue was extracted with chloroform. Evaporation of the dried extract, followed by crystallization of the residue from chloroform-hexane, yielded 7.53 g of Androsta-4,165 dien-3-one (25). Another 0.97 g (total, 8.5 g, 86%) was obtained by chromatography of the mother liquor on neutral alumina.

Example 104

Synthesis of Androsta-3,5,16-trien-3-yl methyl ether.

To a partial solution of androsta-4,16-dien-3-one (1.00 g, 3.70 mmol) in 2.2 dimethoxypropane (5.0 ml, 41 mmol) and 5 ml DMF were added methanol (0.2 ml) and p-toluenesulfonic acid monohydrate (26.4 mg, 0.139 mmol). The mixture was refluxed 5 h, after which it was cooled and sodium bicarbonate (152.5 mg) was added. The suspension was partitioned between 50 ml of ice water and 50 ml of ethyl acetate. The organic layer was washed with two 50 ml portions of water+50 ml of brine, dried over 20 magnesium sulfate, filtered, and concentrated under reduced pressure. The residual oil was taken up in 50 ml of hot hexane and filtered through a 12 mm×30 mm column of silica gel 60 using 150 ml of hot hexane. The combined filtrates were concentrated under reduced pressure and recrystallized from acetone/methanol to give white crystals (468.0 mg, 1.645 mmol, 446), m.p. 83–92° C.

Example 105

Synthesis of 17-methylene-Androst-4-en-ols.

To 20-homoandrosta-4,17-dien-3-one (119.0 mg, 0.4184 mmol) in 5 ml of methanol were added sodium borohydride (6.0 mg, 0.16 mmol) and 77 μL of water. After stirring 2 h further sodium borohydride (32.0 mg, 0.846 mmol) was added and the mixture was stirred overnight. After concentrating under reduced (5% ethyl acetate/hexane on silica gel) to give a more polar (59.8 mg) and a less polar (1.7 mg) product.

Example 106

Synthesis of 17-methylene-6-oxo-Androsta-4-en-3-one.

To a cooled solution of 20-homoandrosta-5,17-dien-3-ol (399.4 mg, 1.394 mmol) in 50 ml of acetone was added 2.67M Jones reagent (2.0 ml, 5.3 mmol). After stirring 1 h the reaction was quenched with isopropanol (1.0 ml, 13 mmol) and poured into 100 ml of water. The mixture was extracted three times with 50 ml portions of ethyl acetate and the combined organic extracts were washed with 50 ml of saturated sodium bicarbonate+50 ml of brine. The organic phase was then dried over magnesium sulfate, filtered, and concentrated under reduced pressure. The residue was recrystallized from 95% ethanol to give an almost white powder (177.8 mg, 0.5958 mmol, 43%), m.p. 113–115° C.

Example 107

Synthesis of 6β-OH-Androsta-4,16-dien-3-one.

To a solution of androsta-3,5,16-trien-3-yl methyl ether, (12) (200.5 mg, 0.7049 mmol), in 5 ml of 1,2-dimethoxyethane (DME) and 1 ml of water was added m-chloroperbenzoic acid (MCPBA, 77.4%, 173.2 mg, 0.776 mmol) suspended in 5 ml of DME+1 ml of water+0.40 g of 5% (w/w) NaOH dropwise, with stirring, over a period of 90 min. After stirring 18 h further MCPBA (247.0 mg, 1.11 mmol) suspended in 10 ml of DME+2 ml of water+0.8 g of 5% (w/w) NaOH was added dropwise, with stirring, over 1½ h. The reaction mixture was stirred ½ h and then poured into 25 ml of saturated sodium bicarbonate. The aqueous mixture was extracted three times with 25 ml of ether and the combined organic extracts were washed with 50 g of 5% (w/w) sodium thiosulfate+three 50 ml portions of brine, dried over magnesium sulfate, filtered through Celite, and concentrated under reduced pressure. The resulting crystalline residue was purified by preparative TLC (35% ethyl acetate/hexane on silica gel) followed by two-fold recrystallization from aqueous ethanol to give lustrous white platelets (102.3 mg, 0.3571 mmol, 51%), m.p. 165–166° C.

Example 108

18-Nor-17-methylandrosta-4,13(17)-dien-3-ol.

Refer to FIG. 189. To a solution of 18-nor-17-methylandrosta-4,13(17)-dien-3-one (1, 378.2 mg, 1.399 mmol) in 7.5 ml of anh. ether were added 59.7 mg (1.57 mmol) of lithium aluminum hydride (LAH). After stirring the resulting suspension for 30 min. 2.00 g of Glauber's salt were added and the mixture was stirred a further 30 min. The mixture was then filtered and extracted with four 25 ml portions of ether. The combined filtrates were concentrated under reduced pressure and then subjected to preparative TLC (silica gel GF, 1000μ, 5% ethyl acetate/methylene chloride as eluent) to give a less polar fraction (R$_f$ 0.63, 34.5 mg, 0.127 mmol, 9%) and a more polar fraction (R$_f$ 0.45, 273.8 mg, 1.005 mmol, 72%).

Example 109

18-Nor-17-methylandrosta-3,5,13(17)-trien-3-yl methyl ether.

Refer to FIG. 189. A solution of 18-nor-17-methylandrosta-4,13(17)-dien-3-one (1, 0.86 g, 3.2 mmol) in 2,2-dimethoxypropane (4.3 ml, 35 mmol) and dimethylformamide (DMF, 4.3 ml) containing anh. methanol (0.17 ml) and p-toluenesulfonic acid monohydrate (21.3 mg) was refluxed 4 h and then allowed to cool. Sodium bicarbonate (0.13 g) was added and the mixture was partitioned between 65 ml of hexanes and 40 ml of ice water. The organic phase was washed with two 40 ml portions of water+40 ml of brine and then flash filtered through a 17 mm high×30 mm dia. column of silica gel (200–400 mesh). Concentration of the combined filtrates followed by recrystallization from acetone/95% ethanol gave bright yellow crystals (489.6 mg, 1.721 mmol, 54%), m.p. 95–101° C. TLC (10% ethyl acetate/hexanes on silica gel) showed a major product at R$_f$ 0.69 with a trace contaminant at the origin.

Example 110
18-Nor-17-methylandrosta-4,13(17)-dien-6e-ol-3-one.

Refer to FIG. 189. Reaction was carried out similar to the procedure of D. N. Kirk and J. M. Wiles, *J. Chem. Soc., Chem. Commun.* 1974, 927. To a stirred solution of 18-nor-17-methylandrosta-3,5,13(17)-trien-3-yl methyl ether (477.0 mg, 1.677 mmol) in 1,2-dimethoxyethane (DME, 26 ml) was added 77% m-chloroperbenzoic acid (MCPBA, 999.7 mg, 4.48 mEq) suspended in DME (39 ml), water (8 ml), and 5% (w/w) sodium hydroxide (7.1 ml), over a period of 88 min. After stirring 20 h the reaction mixture was poured into saturated sodium bicarbonate (50 ml) and extracted with three 50 ml portions of ether. The combined organic extracts were washed with 50 g of 5% (w/w) sodium thiosulfate pentahydrate+three 50 ml portions of brine, dried over magnesium sulfate, and filtered through diatomaceous earth. The residue was washed with 25 ml of ether and the combined filtrates were concentrated under reduced pressure to give a yellow syrup. Purification by preparative TLC (silica gel GF, 1000μ, 35% ethyl acetate/hexanes as eluent) gave an off-white crystalline film (132.1 mg, 0.4612 mmol, 28%) which TLC (35% ethyl acetate/hexanes on silica gel) showed contained a major component ($R_f$ 0.23) and a minor component ($R_f$ 0.18)

Example 111
17β-Methylandrost-4-en-3,6-dione.

Refer to FIG. 189. Jones reagent (2.67 M, 0.88 ml, 2.3 mmol) was added to a solution of 17β-methylandrost-5-en-3β-ol (5, 135.5 mg, 0.4697 mmol) (J. B. Jones and K. D. Gordon, *Can. J. Chem.* 1972, 50, 2712–2718) in acetone (15 ml) and the mixture was 10 stirred 45 min. The reaction was quenched with the addition of 2-propanol (0.44 ml). After stirring a further 10 min. the reaction mixture was poured into 30 ml of water and extracted with three 15 ml portions of ethyl acetate. The combined organic extracts were washed with 15 ml of saturated sodium bicarbonate+15 ml of brine, dried over magnesium sulfate, and filtered through diatomaceous earth. The residue was washed with 10 ml of ethyl acetate and the combined filtrates were concentrated under reduced pressure. Preparative TLC (silica gel GF, 1000μ, 25% ethyl acetate/hexanes as eluent), and recrystallization from aqueous ethanol gave lustrous off-white crystals (37.5 mg, 0.125 mmol, 27%), m.p. 94–95° C., homogeneous to TLC (25% ethyl acetate/hexanes on silica gel, $R_f$ 0.39).

Example 112
17β-Methylandrost-4-en-3-ol.

Refer to FIG. 189. LAH (21.3 mg, 0.561 mmol) was added to a solution of 17β-methylandrost-4-en-3-one (7, 143.2 mg, 0.4999 mmol) (J. B. Jones and K. D. Gordon, *Can. Chem.* 1972, 50, 2712–2718) in 2.8 ml of anh. ether. After stirring the suspension for 30 min. Glauber's salt (0.76 g) was added and the mixture stirred a further ½ h. Ether (10 ml) was added and the suspension was filtered through diatomaceous earth. The residue was washed with three 10 ml portions of ether and the combined filtrates were concentrated under reduced pressure. The crude product was separated by preparative TLC (silica gel GF, 1000μ, 5% ethyl acetate/methylene chloride as eluent) into a more polar component ($R_f$ 0.30, 77.9 mg, 0.270 mmol, 54%) and a less polar component (Rf 10 0.43, 10.3 mg, 0.0357 mmol, 7%).

Example 113
17-Methylenandrosta-3,5-dien-3-yl methyl ether.

Refer to FIG. 190. To 17-methylenandrost-4-en-3-one (9, 2.0000 g, 7.0314 mmol) in 2,2-dimethoxypropane (9.4 ml, 76 mmol) and DMF (9.4 ml) were added 0.37 ml of anh. methanol and 47.0 mg of p-toluenesulfonic acid. After refluxing 4 h the reaction mixture was allowed to cool and then partitioned between 140 ml of hexanes and 90 ml of water. The organic phase was washed with two 90 ml portions of water+90 ml of brine, dried over magnesium sulfate, and flash filtered through a 30 mm dia.×37 mm high column of silica gel (200–400 mesh). Product continued eluting with 200 ml of hexanes. Concentration of the combined filtrates under reduced pressure and recrystallization of the residue from acetone/methanol gave very slightly yellow platelets (1.5291 g, 5.1231 mmol, 73%), m.p. 97–99° C., homogeneous to TLC (25% ethyl acetate/hexanes on silica gel, $R_f$ 0.72).

Example 114
17-Methylenandrost-4-en-6β-ol-3-one.

Refer to FIG. 190. To a stirred solution of 17-methylenandrosta-3,5-dien-3-yl methyl ether (10, 500.1 mg, 1.676 mmol) in DME (10 ml) was added MCPBA (318.6 mg, 1.846 mmol) in DME (10 ml) and water (4 ml) over a period of 15 min. After stirring 30 min. the mixture was poured into 50 ml of saturated sodium bicarbonate and extracted with three 50 ml portions of ether. The combined organic extracts were washed with 50 g of 5% (w/w) sodium thiosulfate pentahydrate+three 50 ml portions of brine, dried over magnesium sulfate, and filtered through diatomaceous earth. The residue was washed with 25 ml of ether and the combined filtrates were concentrated under reduced pressure. Flash chromatography (45% ethyl acetate/hexanes on silica gel) followed by recrystallization from aqueous ethanol gave slightly yellow crystals (187.1 mg, 0.6228 mmol, 37%), m.p. 192–194° C., which TLC (35% ethyl acetate/hexanes on silica gel) showed consisted of major ($R_f$ 0.17) and minor ($R_f$ 0.13) components.

Example 115
17-Methylenandrosta-1,4-dien-3-one.

Refer to FIG. 190. A solution of 17-methylenandrost-4-en-3-one (9, 1.0001 g, 3.5160 mmol) and 2,3-dichloro-5,6-dicyano-1,4-benzoquinone (DDQ, 2.43 g, 10.7 mmol) in dioxane (60 ml, freshly distilled after overnight reflux over sodium) was refluxed 6 h and then cooled with swirling in tap water. Methyl t-butyl ether (MTBE, 50 ml) was added and the suspension was filtered through diatomaceous earth. The residue was washed with two 50 ml portions of MTBE and the combined filtrates were concentrated under reduced pressure. Flash chromatography of the residue (20% ethyl acetate/hexanes on silica gel) followed by recrystallization from 95% ethanol gave off-white crystals (498.9 mg, 1.767 mmol, 50%), m.p. 155–157° C.

Example 116
17-Methylenandrosta-1,3,5-trien-3-yl benzoate.

Refer to FIG. 190. Reaction was carried out in a procedure adapted from R. W. Draper et al., Arzneim.-Forsch. 1982, 32, 317–322, as follows: 17-Methylenandrosta-1,4-dien-3-one (12, 389.0 mg, 1.378 mmol), anh. pyridine (4.7 ml, 58 mmol), and benzoyl chloride (1.2 ml, 10 mmol) under argon were stirred 18 h in an oil bath (68–73° C.). After cooling in ice the reaction mixture was poured into 40 ml of ice-1 N MCl and extracted with three 20 ml portions of methylene chloride. The combined organic extracts were washed with 40 ml of cold 1 N HCl+40 ml of saturated sodium bicarbonate+40 ml of brine, dried over magnesium sulfate, and filtered through diatomaceous earth. The residue was washed with 10 ml of methylene chloride and the combined filtrates were concentrated under reduced pressure. Flash chromatography (4% ethyl acetate/hexanes on silica gel) gave a yellow solid (0.43 g, 1.1 mmol, 81%).

Example 117
17-Methylenandrosta-1,4-dien-6β-ol-3-one.

Refer to FIG. 190. Reaction was carried out in a procedure adapted from R. W. Draper et al., Arznoim.-Forsch. 1982, 32, 317–322, as follows: MCPBA (211.4 mg, 1.225 mmol) in DME (6.6 ml) and 30 water (2.7 ml) was added to 17-methylenandrosta-1,3,5-trien-3-yl benzoate (13, 0.43 g, 1.1 mmol) in 6.6 ml of DME over a period 20 min. with stirring. Stirring was continued 30 min. and the reaction mixture was then poured into 35 ml of saturated sodium bicarbonate. The mixture was extracted with three 35 ml portions of ethyl acetate. The combined organic extracts were washed with 35 g of 5% sodium s thiosulfate pentahydrate+three 35 ml portions of brine, dried over magnesium sulfate, and filtered through diatomaceous earth. The residue was washed with 10 ml of ethyl acetate and the combined filtrates were concentrated under reduced pressure. Preparative TLC (silica gel GF, 1000μ, 50% ethyl acetate/hexanes as eluent) gave a yellow crystalline solid (83.7 mg, 0.280 mmol, 25%) homogeneous to TLC (50% ethyl acetate/hexanes on silica gel, $R_f$ 0.50).

Example 118
Androsta-1,4,16-trien-68-ol-3-one.

Refer to FIG. 190. Androsta-1,4,16-trien-3-one (15, 500.0 mg, 1.863 mmol), anh. pyridine (6.4 ml, 79 mmol), and benzoyl chloride (1.6 ml, 14 mmol) under argon were placed in an oil bath (70–73° C.) and stirred 18 h. After cooling in ice the mixture was poured into 50 ml of ice-1 N HCl and extracted with three 25 ml portions of methylene chloride. The combined organic extracts were washed with 50 ml of cold 1 N HCl+50 ml of saturated sodium bicarbonate+50 ml of brine, dried over magnesium sulfate, and filtered through diatomaceous earth. The residue was washed with 10 ml of methylene chloride and the combined filtrates were concentrated under reduced pressure. Flash chromatography (2% ethyl acetate/hexanes on silica gel) gave yellow crystals (0.47 g, 1.3 mmol, 68%) of intermediate benzoate. This was taken up in chloroform (30 ml) with MCPBA (240.0 mg, 1.391 mmol). After stirring 1 h further MCPBA (239.5 mg, 1.388 mmol) was added and the reaction was stirred another hour. The mixture was then washed with 30 g of 5% (w/w) sodium thiosulfate pentahydrate+30 ml of saturated sodium bicarbonate+30 ml of brine, dried over magnesium sulfate, and filtered through diatomaceous earth. The residue was washed with 10 ml of chloroform and the combined filtrates were concentrated under reduced pressure. Flash chromatography (40–45% ethyl acetate/hexanes on silica gel) gave a yellow resin (106.1 mg, 0.3731 mmol, 29%), which TLC (40% ethyl acetate/hexanes on silica gel) showed contained major ($R_f$ 0.34) and minor ($R_f$ 0.40) components.

Example 119
Androsta-4,16-dien-6β-ol-3-one.

To a solution of androsta-3,5,16-trien-3-yl methyl ether, 12 (200.5 mg, 0.7049 mmol), in 5 ml of 1,2-dimethoxyethane (DME) and 1 ml of water was added m-chloroperbenzoic acid (MCPBA, 77.4%, 173.2 mg, 0.776 mmol) suspended in 5 ml of DME+1 ml of water+0.40 g of 5% (w/w) NaOH dropwise, with stirring, over a period of 90 min. After stirring 18 h further MCPBA (247.0 mg, 1.11 mmol) suspended in 10 ml of DME+2 ml of water+0.8 g of 5% (w/w) NaOH was added dropwise, with stirring, over 1½ h. The reaction mixture was stirred ½ h and then poured into 25 ml of saturated sodium bicarbonate. The aqueous mixture was extracted three times with 25 ml of ether and the combined organic extracts were washed with 50 g of 5% (w/w) sodium thiosulfate+three 50 ml portions of brine, dried over magnesium sulfate, filtered through Celite, and concentrated under reduced pressure. The resulting crystalline residue was purified by preparative TLC (35% ethyl acetate/hexane on silica gel) followed by two-fold recrystallization from aqueous ethanol to give lustrous white platelets (102.3 mg, 0.3571 mmol, 51%), m.p. 165–166° C.

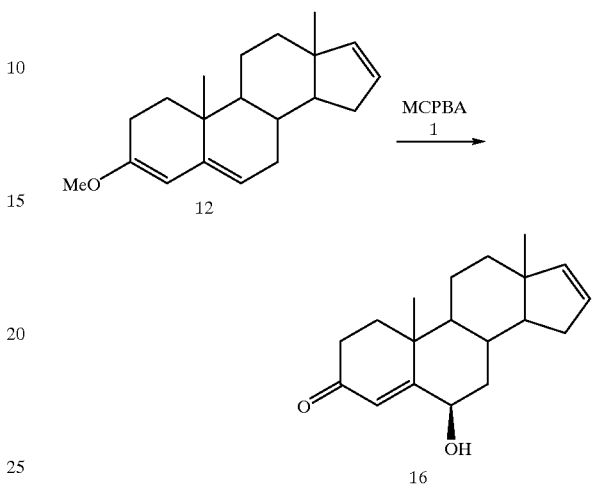

Example 120
20-Homoandrosta-4,17-dien-3-one.

Refer to FIG. 191. To a partial solution of 20-homoandrosta-5,17-dien-3-ol (1.0001 g, 3.4911 mmol) in 100 ml of toluene and 20 ml (0.19 mol) of cyclohexanone was added aluminum isopropoxide (2.00 g, 9.79 mmol) in 20 ml of warm toluene. After refluxing 4 h the cooled reaction mixture was shaken 1 min. with 5 ml of water and 12.5 ml of 3.6N sulfuric acid. The organic layer was washed with 50 ml of brine, dried over magnesium sulfate, filtered through Celite, and concentrated under reduced pressure. Following steam distillation to remove cyclohexanone the non-volatile residue was taken up in two 10 ml aliquots of dichloromethane, dried over magnesium sulfate, filtered, and concentrated. The oily residue was purified by flash Chromatography (15% ethyl acetatelhexane on silica gel) and recrystallization from aqueous acetone to give colorless needles (238.8 mg, 0.8400 mmol, 24%), m.p. 130–134° C. [lit. (B. S. Macdonald et al., Steroids 1971, 18, 753–766) m.p. 129–131° C].

Example 121
20-Homoandrosta-4,17-dien-3-ols.

Refer to FIG. 191. To 20-homoandrosta-4,17-dien-3-one (119.0 mg, 0.4184 mmol) in 5 ml of methanol were added sodium borohydride (6.0 mg, 0.16 mmol) and 77 ml of water. After stirring 2 h further sodium borohydride (32.0 mg, 0.846 mmol) was added and the mixture was stirred overnight. After concentrating under reduced pressure the residue was purified by preparative TLC (5% ethyl acetate/hexane on silica gel) to give a more polar (59.8 mg) and a less polar (1.7 mg) product.

Example 122
20-Homoandrosta-4,17-diene-3,6-dione.

Refer to FIG. 191. To a cooled solution of 20-homoandrosta-5,17-dien-3-ol (399.4 mg, 1.394 mmol) in 50 ml of acetone was added 2.67M Jones reagent (2.0 ml, 5.3 mmol). After stirring 1 h the reaction was quenched with isopropanol (1.0 ml, 13 mmol) and poured into 100 ml of water. The mixture was extracted three times with 50 ml portions of ethyl acetate and the combined organic extracts were washed with 50 ml of saturated sodium bicarbonate+50 ml of brine. The organic phase was then dried over magnesium sulfate, filtered, and concentrated under reduced pressure. The residue was recrystallized from 95% ethanol to give an almost white powder (177.8 mg, 0.5958 mmol, 43%), m.p. 113–115° C.

Example 123

6β,19-Epoxy-17-iodoandrosta-4,16-diene-3-ethylene ketal.

Refer to FIG. 192. A mixture of crude 6β,19-epoxy-5β-chloro-17-iodoandrost-16-ene (17, 1.38 g, 3.09 mmol) (G. Habermehl and A. Haaf, *Z. Naturforsch.* 1970, 25b, 191–195), ethylene glycol (0.97 g, 16 mmol), toluene (50 ml), and ptoluenesulfonic acid monohydrate (20.3 mg, 0.107 mmol) was refluxed 19 h with azeotropic removal of water (Deen-Stark). After cooling ethyl acetate (100 ml) was added and the reaction mixture was washed with 100 ml of saturated sodium bicarbonate+100 ml of brine. The organic phase was dried over magnesium sulfate and filtered through diatomaceous earth. The residue was washed with 25 ml of ethyl acetate and the combined filtrates were concentrated under reduced pressure to give a tan, crystalline solid (1.47 g). This residue was suspended in anh. methanol (40 ml), potassium acetate (2.44 g, 24.9 mmol) was added, and ca. 26 ml of methanol were distilled off. The remainder was concentrated under reduced pressure, water (50 ml) was added, and the mixture was extracted three times with 25 ml aliquots of methylene chloride. The dried (sodium sulfate) extracts were filtered through diatomaceous earth and the residue was washed with 10 ml of methylene chloride. Concentration of the combined filtrates under reduced pressure gave a yellow solid, which was purified further by flash chromatography (5–7.5–10% ethyl acetate/methylene chloride on silica gel) and recrystallization from methanol to give light yellow needles (914.6 mg, 2.013 mmol, 65%), m.p. 187–189° C. $^1$H-NMR: 6.13 $\partial$, 1H, dd, 16-H; 5.82 $\partial$, 1H, s, 4-H; 4.71 $\partial$, 1H, d, 6a-H; 4.22 $\partial$ and 3.53 $\partial$, 2H, AB, 19-H's; 4.10–3.28 $\partial$, 4M, mult., 3-ketal H's; 0.83 $\partial$, 3H, s, 18-Me.

Example 124

Androsta-4,16-dien-19-ol-3-one.

Refer to FIG. 192. Anh. ammonia (ca. 75 ml) was distilled through a KOH tower into a 250 ml flamedried 3-neck flask fitted with an inlet adapter, a magnetic stirring bar, a dry ice/acetone condenser, 35 and a stoDPer. A solution of 6β,19-epoxy-17-iodoandrosta-4,16-diene 3-ethylene ketal (18, 880.4 mg, 1.938 mmol) in dry tetrahydrofuran (THF, 45 ml) was added, followed by metallic sodium (0.20 g, 8.7 mg-atom) cut in small pieces. After stirring under argon pressure for 30 min. the reaction was quenched with the addition of abs. ethanol (1.0 ml). Ammonia was allowed to boil off overnight, 50 ml of water were added, and the mixture was extracted with three 25 ml portions of methylene chloride. The combined organic extracts were washed with 50 ml of brine, dried over magnesium sulfate, and filtered through diatomaceous earth. After washing the residue with 10 ml of methylene chloride the combined filtrates were concentrated under reduced pressure. The intermediate ketal proved remarkably unreactive, but was finally hydrolyzed by refluxing 18 h in 5 ml of chloroform and 2.5 ml of 4 N hydrochloric acid. To the cooled hydrolysis mixture ethyl acetate (50 ml) was added and the layers were separated. The organic phase was washed with 25 ml of saturated sodium bicarbonate+25 ml of brine, dried over magnesium sulfate, and filtered through diatomaceous earth. The residue was washed with 10 ml of ethyl acetate and the combined filtrates were concentrated under reduced pressure. The resulting brown foam was purified by flash chromatography (50% ethyl acetate/hexanes on silica gel) followed by preparative TLC (50% ethyl acetate/hexanes on silica gel GF, 1000μ thickness) to give a partially crystalline film (66.7 mg, 0.233 mmol, 12%). $^1$H-NMR: 5.92 $\partial$, 1H, s, 4-H; 5.87–5.64 $\partial$, 2H, mult., 16,17-H's; 4.10$\partial$ and 3.94 $\partial$, 2H, AB, 19-H's; 0.79 $\partial$, 3H, s, 18-Me.

Example 125

Androst-5-en-3β,19-diol-17-(p-toluenesulfonyl)hydrazone.

Refer to FIG. 193. A suspension of androst-5-en-3β,19-diol-17-one (1, commercially available from Research Plus, 512.5 mg, 5 1.684 mmol) and p-toluenesulfonylhydrazide (p-TsNHNH$_2$, 392.1 mg, 2.105 mmol) in 2-propanol (6.0 ml) was refluxed 24 h. To the cool reaction mixture were added 20 ml of ether and the solvent was removed under reduced pressure. The residue was taken up in 10 ml of ether and the solution was filtered through diatomaceous earth. 10 ml of hexanes were added to the filtrate and the suspension was concentrated under reduced pressure. Residue was taken up in 10 ml of hot benzene and the cooled suspension was filtered. The filtrate was concentrated under reduced pressure and then flash chromatographed (40% ethyl acetate/hexanes on silica gel) to give an opaque resin (0.69 g, 1.5 mmol, 87%).

Example 126

Androsta-5,16-dien-3β,19-diol.

Refer to FIG. 193. A solution of androst-5-en-3β,19-diol-17-(p-toluenesulfonyl)hydrazone (2, 0.69 g, 1.5 mmol) in anh. tetrahydrofuran (THF, 35 ml) was cooled in an ice/acetone bath under argon and n-butyllithium (2.5 in hexanes, 3.7 ml, 9.3 mmol) was added dropwise, with stirring, over the period of 1 min. The reaction mixture was stirred 4 days, during which time it was allowed to gradually warm to room temperature. The reaction was then poured into 50 ml of ice-saturated ammonium chloride and the layers were separated. The aqueous layer was extracted twice with 25 ml portion of ethyl acetate. The combined organic phases were washed with 25 ml of saturated sodium bicarbonate+25 ml of brine, dried over magnesium sulfate, and filtered through diatomaceous earth. The residue was washed with 10 ml of ethyl acetate and the combined filtrates were concentrated under reduced pressure. The residual yellow resin was flash chromatographed (50–55–60% ethyl acetate/hexanes on silica gel) and crystallized from methyl t-butyl ether/benzene to give fluffy white crystals (92.5 mg, 0.361 mmol, 24%), m.p. 169–171° C.

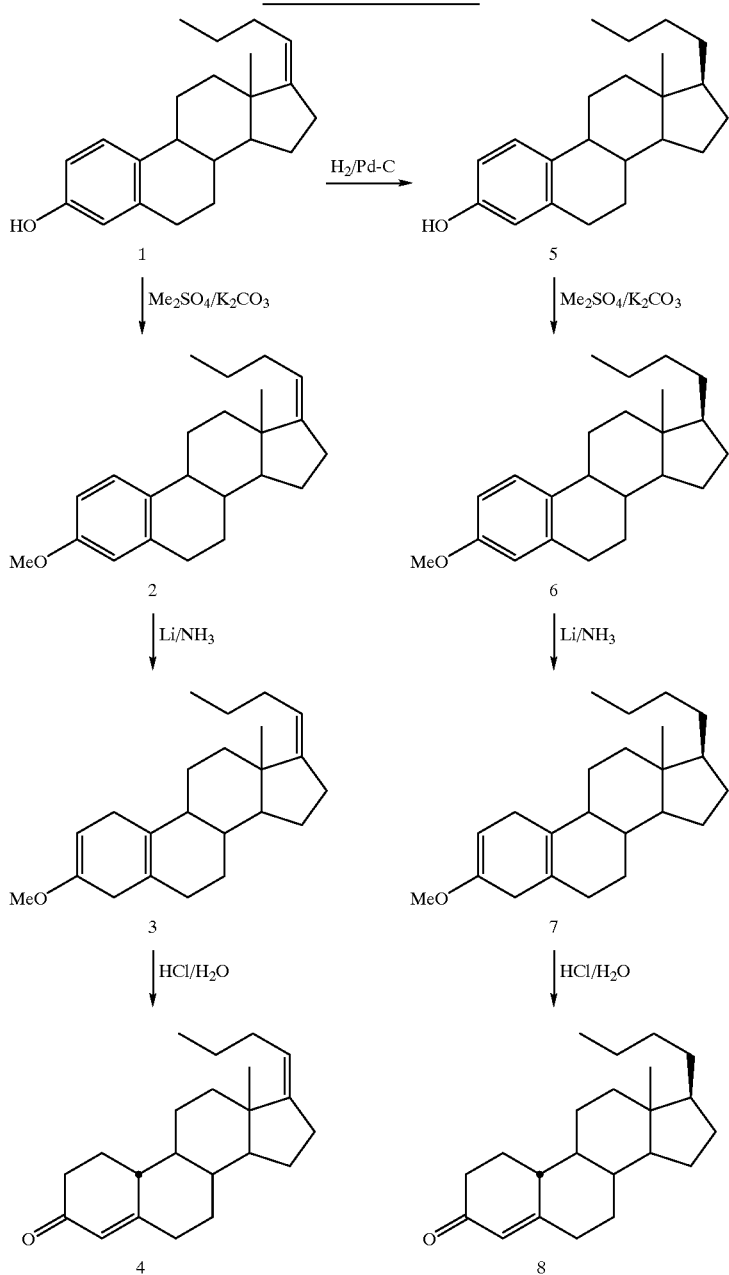

Scheme 14.
Synthesis of bisnorcholenes

Example 127
19,21-Bisnorchola-1,3,5(10) 17Z-tetraen-3-yl methyl ether, 2 (Scheme 14):

To a solution of 19,21-bisnorchola-1,3,5(10),17Z-tetraen-3β-ol (1, 1.0000 g, 3.2208 mmol) in 50 mL of acetone was added potassium carbonate (0.67 g, 4.8 mmol), and the resulting suspension was heated to reflux with exclusion of moisture. Dimethyl sulfate (0.76 mL, 8.0 mmol) was added and reaction was continued 22 h. The mixture was then poured into 50 mL of 5% (w/w) sodium hydroxide and extracted 3 times with 50 mL portions of ether. The combined organic extracts were washed 3 times with 50 mL portions of brine, dried over magnesium sulfate, and filtered through diatomaceous earth. The residue was washed with 25 mL of ether and the combined filtrates were concentrated under reduced pressure. Crystallization of the residual tan solid from 95% ethanol with intermediate treatment with charcoal yielded lustrous white platelets (753.1 mg, 2.321 mmol, 72%), m.p. 80.5–82° C., homogeneous to TLC (10% ethyl acetate/hexanes on silica gel; product $R_f$ 0.69; estra-1,3,5(10),16-tetraen-3-yl methyl ether $R_f$ 0.66).

Example 128
19,21-Bisnorchola-2,5(10),17Z-trien-3-yl methyl ether, 3 (Scheme 14):

A solution of 19,21-bisnorchola-1,3,5(10),17Z-tetraen-3-yl methyl ether (2, 450.0 mg, 1.387 mmol) in 13 mL of anh. THF+4.60 g (62.1 mmol) of t-butanol was added to ca. 50 mL of anh. ammonia, followed by 0.20 g (29 mg-atom) of lithium wire cut in small pieces. Reaction was continued for 7 h, after which 1.6 mL of methanol were added and ammonia was allowed to boil off overnight. 40 mL of water were added and the mixture was extracted 3 times with 40 mL portions of ether. The combined organic extracts were washed 3 times with 40 mL portions of brine, dried over magnesium sulfate, and filtered through Celite 503. The residue was washed with 10 mL of ether and the combined filtrates were concentrated under reduced pressure. Flash filtration of the resulting white platelets (hexanes–1% ethyl acetate/hexanes–2% ethyl acetate/hexanes) followed by recrystallization from 95% ethanol gave lustrous, fine, white platelets (329.7 mg, 1.010 mmol, 73%), m.p. 76–77° C. TLC (1% ethyl acetate/hexanes) showed this to be a mixture of the desired Birch product ($R_f$ 0.15) and starting material ($R_f$ 0.09).

Example 129
19,21-Bisnorchola-4,17Z-dien-3 one, 4 (Scheme 14):

To a solution of crude 19,21-bisnorchola-2,5(10),17Z-trien-3-yl methyl ether (3, 130 mg, 0.3981 mmol) in 35 mL of acetone were added 1.3 mL of methanol and 1.3 mL of con. (12.1 M) HCl. After stirring 1 h, 1.33 g of sodium bicarbonate+10 mL of water were added and the mixture was extracted 3 times with 5 mL portions of methylene chloride. The combined organic extracts were washed with 5 mL of brine, dried over sodium sulfate, and filtered through Celite 503. The residue was washed with 5 mL of methylene chloride and the combined filtrates were concentrated under reduced pressure. Preparative TLC (10% ethyl acetatelhexanes on alumina GF, 1000$\mu$) of the resulting yellow syrup produced a slightly yellow resin (293 mg, 93.7 $\mu$mol, 24%) homogeneous to TLC (10% ethyl acetate/hexanes on silica gel; product $R_f$ 0.1; estra-4,16-dien-3-one $R_f$ 0.1).

Example 130
19,21-Bisnorchola-1,3,5(10)-trien-3-yl methyl ether. 6 (Scheme 14):

To a solution of 19,21-bisnorchola-1,3,5(10)-trien-3-ol (5, 460.0 mg, 1.472 mmol) in 25 mL of acetone was added potassium carbonate (0.31 g, 2.2 mmol), and the suspension was heated to reflux with exclusion of moisture. Dimethyl sulfate (0.34 mL, 3.6 mmol) was added and reaction was continued for 20 h. The mixture was then poured into 25 mL of 5% (w/w) sodium hydroxide and extracted 3 times with 25 mL portions of ether. The combined organic extracts were washed 3 times with 25 mL portions of brine, dried over magnesium sulfate, and filtered through diatomaceous earth. The residue was washed with 10 mL of ether and the combined filtrates were concentrated under reduced pressure. Flash chromatography (10% ethyl acetate/hexanes on silica gel) gave a colorless syrup (0.43 g, 1.3 mmol, 89%).

Example 131
19,21-Bisnorchola-2,5(10)-dien-3-yl methyl ether, 7 (Scheme 14):

A solution of 19,21-bisnorchola-1,3,5(10)-trien-3-yl methyl ether (6, 0.36 g, 1.1 mmol) in 10 mL of anh. THF+3.68 g (49.6 mmol) of t-butanol was added to ca. 35 mL of anh. ammonia, followed by 0.16 g (23 mg atom) of lithium wire cut in small pieces. Reaction proceeded for 8 h and was then quenched with 1.3 mL of methanol. After allowing ammonia to boil off overnight, 30 mL of water were added and the mixture was extracted 3 times with 30 mL portions of ether. The combined organic extracts were washed 3 times with 30 mL portions of brine, dried over magnesium sulfate, and filtered through Celite 503. The residue was washed with 25 mL of ether and the combined filtrates were concentrated under reduced pressure to give a colorless syrup (0.33 g, 1.0 mmol, 91%) homogeneous to TLC (5% ethyl acetate/hexanes on silica gel; $R_f$ 0.69; starting material $R_f$ 0.56 0.49).

Example 132
19.21-Bisnorchol-4-en-3-one, 8 (Scheme 14):

To a solution of 19,21-bisnorchola-2,5(10)-dien-3-yl methyl ether (7, 0.27 g, 0.82 mmol) in 7.2 mL of acetone were added 2.3 mL of methanol and 2.3 mL of con. (12.1 M) HCl. After stirring 1 h, 2.75 g of sodium bicarbonate and 20 mL of water were added and the mixture was extracted 3 times with 10 mL portions of methylene chloride. The combined organic extracts were washed with 10 mL of brine, dried over sodium sulfate, and filtered through Celite 503. The residue was washed with 10 mL of methylene chloride and the combined filtrates were concentrated under reduced pressure. Preparative TLC (20% ethyl acetate/hexanes on alumina GF, 1000$\mu$) gave a light yellow syrup (125.6 mg, 0.3994 mmol, 49%) homogeneous to TLC (20% ethyl acetate/hexanes on silica gel; product $R_f$ 0.39; estra-4,16-dien-3-one $R_f$ 0–34).

Example 133
16$\alpha$,17$\alpha$-Epoxyestra-1,3,5(10)-trien-3-ol, 2 (Scheme 15):

To a solution of 1,3,5(10),16-estratetraen-3-ol (2,CAS No. [1150-90-9], 636.0 mg, 2.500 mmol) in 15 ml of 1,2-dimethoxyethane (DME) was added m-chloroperbenzoic acid (862.9) mg, 5,000 mmol) in 25 mL of DME over 3 minutes and the reaction was stirred for 6 h. The mixture was poured into 140 g of 5% (w/w) sodium thiosulfate pentahydrate and extracted three times with 100 mL portions of ethyl acetate. The combined organic extracts were washed with 100 mL of saturated sodium bicarbonate+ three 100 mL aliquots of saturated sodium chloride, dried over magnesium sulfate, and filtered through Celited 503. The residue was washed with 50 mL of ethyl acetate and the combined filtrates were concentrated under reduced pressure. Flash chromatography (20% ethyl acetate/hexanes on silica gel) of the resulting residue, followed by recysttalli-zation from ethyl acetate gave lustrous white platelets (349.9 mg, 1.294 mmol, 52%), m.p. 217–219° C. (lit. [Prelog, V., Ruzicka, L., and Wieland, P., (1945), "Steroids and Sexualhormone", (111.Mitteilung). Uberein neues Stereoi-someres des Oestriols., *Helv. Chem. Acta.* 28:250–256] m.p. 215° C.), homogeneous to TLC (20% ethyl acetate/hexanes on silica gel; $R_f$ 0.32; starting material $R_f$ 0.50).

Example 134
Estra-4,16-dien-10$\beta$-ol-3-one, 4 (Scheme 15):

To a solution of estra-5(10),16-dien-3-one (3, 256.4 mg, 1.000 mmol) in 6 ml of 1,2-dimethoxyethane (DME) was added MCPBA (189.8 MG, 1.100 mmol) in 6 mL of DME+2.4 mL of water. After stirring ½ h, the reaction mixture was poured into 30 g of 5% (w/w) sodium thiosul-fate pentahydrate and extracted three times with 30 mL aliquots of ethyl acetate. The combined organic extracts were washed with 30 mL of saturated sodium bicarbonate+ three 30 mL portions of brine, dried over magnesium sulfate, and filtered through diatomaceous earth. The residue was washed with 10 mL of ethyl acetate and the combined filtrates were concentrated under reduced pressure. To the resulting crystalline film was added 45 mL of 5% (w/v) potassium hydroxide in methanol and the mixture was refluxed with exclusion of moisture for 1 h, after which it was poured into 100 mL of ice water and extracted three times with 70 mL aliquots of ether. The combined ethereal extracts were washed three times with 70 mL portions of brine, dried over magnesium sulfate, and filtered through diatomaceous earth. The residue was washed with 25 mL of ether and the combined filtrates were concentrated under reduced pressure. Preparative TLC (50% ethyl acetate/hexanes on alumina GF, 1000μ) of the residual resin, followed by recystallization from aqueous ethanol gave light yellow needles (62.4 mg, 0.229 mmol, 23%), m.p. 156–166° C. TLC (50% ethyl acetate/hexanes on silica gel; estrone $R_f$ 0.59) showed a major product ($R_f$ 0.44) with minor contaminants at $R_f$ 0.62 and 0.73.

Example 134A

16α,17α-Epoxyestr-4-en-10β-ol-3-one,5 Scheme 15):

A solution of estra-5(10),16-dien-3-one was treated MCPBA as in Example 134, except that 4 equivalents of MCPBA are used instead of a slight excess of 1 equivalent. After refluxing, the resulting product in 5% (w/v) potassium hydroxide in methanol, and after work-up and purification as in Example 134, 16α,17α-epoxyestr-4-en-10β-ol-3-one was obtained.

maceous earth. The residue was washed with 25 mL of ether and the combined filtrates were concentrated under reduced pressure. The resulting crystalline syrup (presumably crude ether 1) was dissolved in 200 mL of acetone and oxalic acid dihydrate (2.88 g) in 38 mL of water was added. After stirring 7 h, the mixture was poured into 100 mL of saturated sodium bicarbonate and extracted 3 times with 100 mL aliquots of ether. The combined organic extracts were washed 3 times with 100 mL portions of brine, dried over magnesium sulfate, and filtered through diatomaceous earth. The residue was washed with 25 mL of ether and the combined filtrates were concentrated under reduced pressure. Two-fold crystallization of the resulting white solid from hexane yielded white crystals (1.2931 g, 5.0435 mmol, 62%), m.p. 117–119° C. TCL (10% ethyl acetate/hexane on silica gel; estratetraenol methyl ether $R_f$ 0.61(showed product (Rf 0.34) with a trace contaminant ($R_f$ 0.14).

Example 135A

16α,17α-Epoxyestr-4-en-108-ol-3-one,3 (Scheme 16):

Estra-5(10),16-dien-3-one (2, 270.4 mg, 1.055 mmol) in 6.7 mL of chloroform was cooled in an acetone/dry ice bath

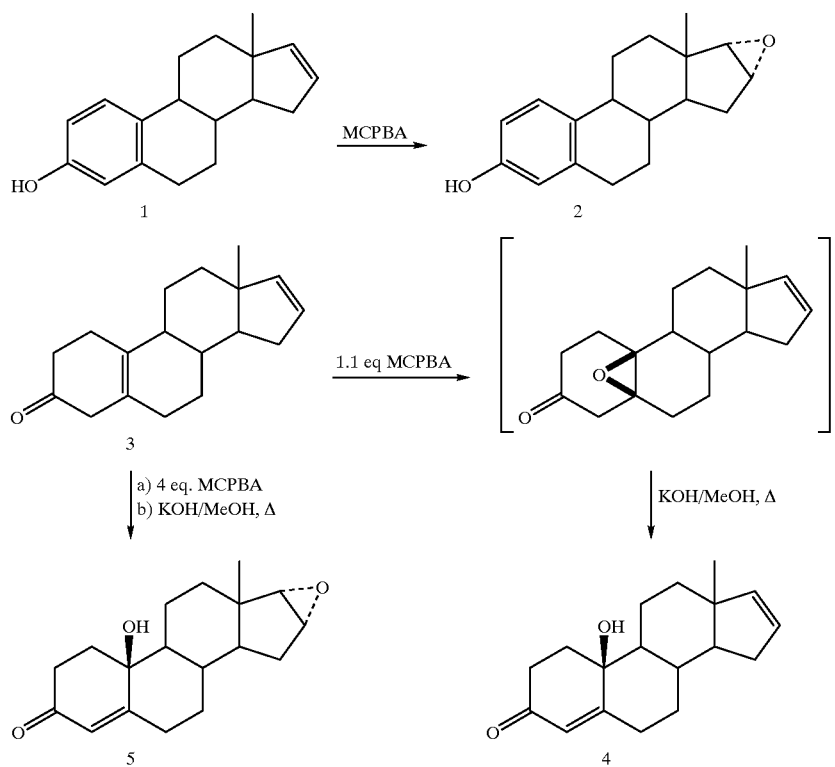

SCHEME 15.

Example 135

Estra-5(10),16-dien-3-one,2 (Scheme 16):

To approximately 200 ml of anh. ammonia was added estratetraenol methyl ether (2.20 g. 8.20 mmol) in 27.07 g (0.3652 mol) of t-butyl alcohol and 34 mL of anh. THF, followed by 1.01 g (0.146 g-atom) of lithium wire cut in small pieces. After refluxing 4 h, 9.2 mL of methanol were added and the ammonia was allowed to boil off overnight. Water (200 mL) was added and the mixture was extracted 3 times with 100 mL aliquots of ether. The combined organic extracts were washed twice with 100 mL portions of brine, dried over magnesium sulfate, and filtered through diatoand 3-chloroperoxybenzoic acid (724.8 mg, 4.200 mmol) in 7.4 mL of ether was added. After stirring 2 h, the mixture was placed in the refrigerator. After 18 h, the mixture was poured into 60 g of 5% (w/w) sodium thiosulfate pentahydrate and was extracted three times with 25 mL aliquots of ethyl acetate. The combined organic extracts were washed with 25 mL of saturated sodium bicarbonate+25 mL of brine, dried over magnesium sulfate, and filtered through diatomaceous earth. The residue was washed with 10 mL of ethyl acetate and the combined filtrates were concentrated under reduced pressure. To the resulting white solid were added 50 mL of 5% (w/v) potassium hydroxide in methanol and the mixture was refluxed 1 h with exclusion of moisture. After cooling, the mixture was poured into 100 mL of ice water and extracted three times with 70 mL aliquots of ether. The combined organic extracts were washed 3 times with 70 mL portions of brine, dried over magnesium sulfate, and filtered through diatomaceous earth. The residue was washed with 25 mL of ether and the combined filtrates were concentrated under reduced pressure. The resulting yellow resin was chromatographed twice on alumina GF preparative TLC plates (1000μ) to give a white crystalline solid (55.1 mg, 0.191 mmol, 18%).

age from 18 to 85 years. The studies were conducted without general or local anesthetics.

The catheter/electrodes were designed to deliver a localized stimulus and simultaneously record the response. In the case of VNO recording, the right nasal fossa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then

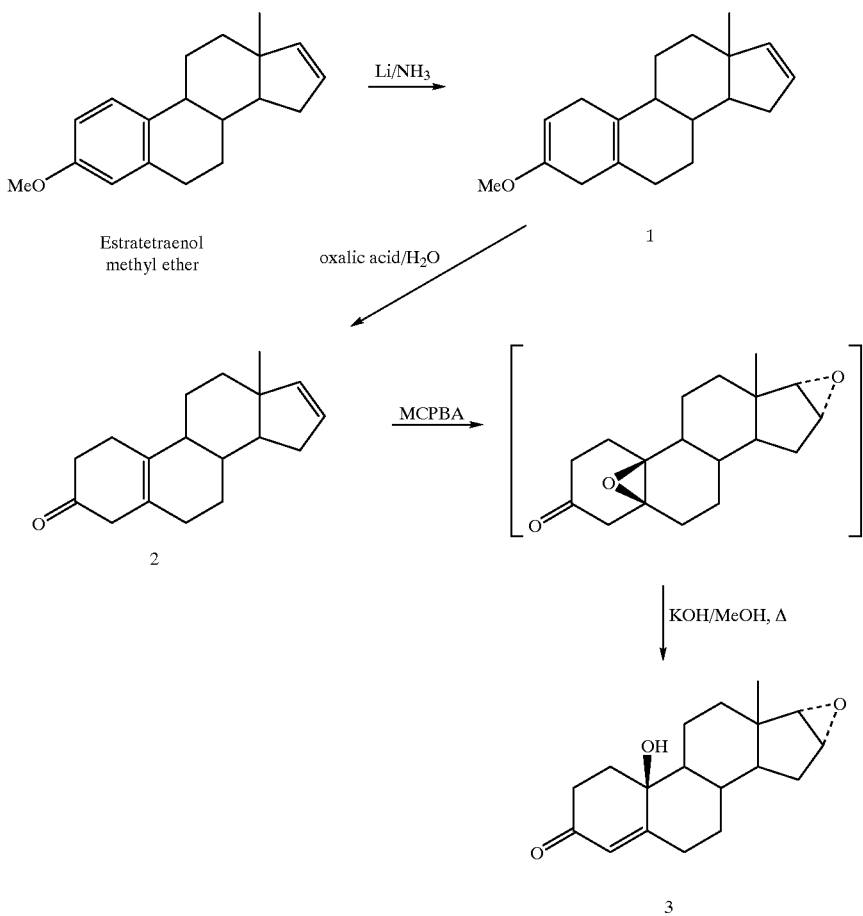

Example 136
Electrophysiology of Androstane Stimulation of the Human VNO and Olfactory Epithelium.

A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. This electrode and delivery system has been described by Monti and Grosser (*J. Steroid Biochem. and Molec. Biol.* (1991) 39:573) and in commonly owned, copending U.S. Ser. No. 07/771,414, incorporated herein by reference. The local response of the VNO and the OE showed a correlation with the concentration of the ligand stimulus.

The study was performed on ten clinically normal (screened) volunteers—2 males and 8 females, ranging in removed. In the case of the OE, recording the procedure was similar except the positioning of the catheter/electrode was gently placed deep in the lateral part of the medial nasal duct, reaching the olfactory mucosa.

Figure 180C:
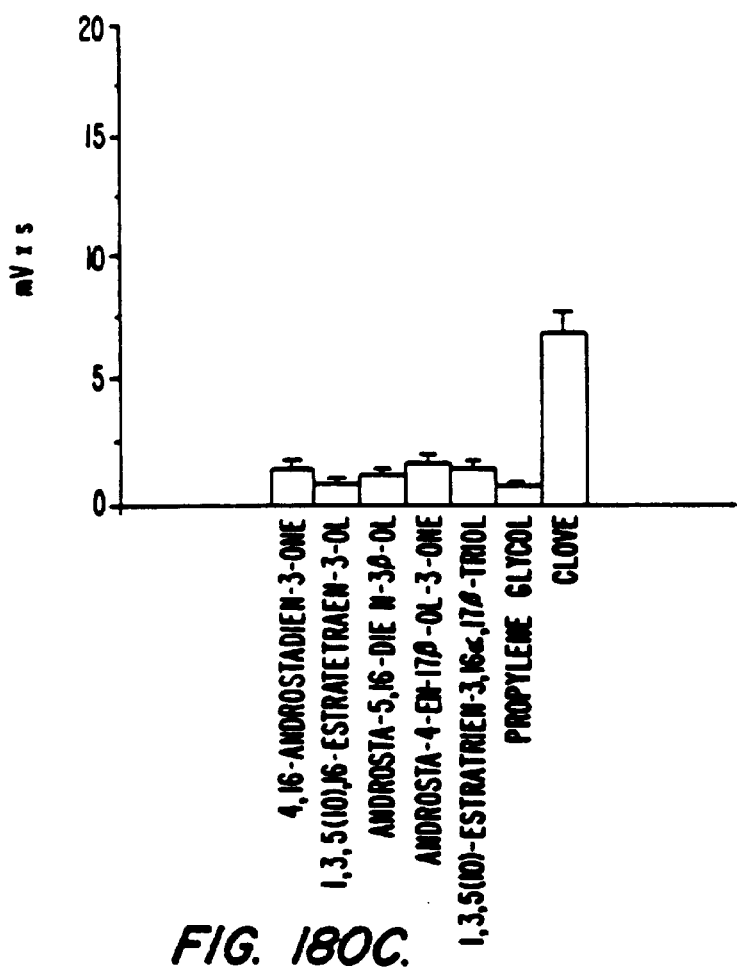

Localized gaseous stimulation was done through the catheter/electrode. A constant stream of clean, nonodorous, humidified air at room temperature was continuously passed through a channel of the stimulating system. The stimulating ligand substances were diluted in propylene glycol, mixed with the humidified air, and puffed for from 1 to 2 seconds through the catheter/electrode. It is estimated that this administration provides about pg of the steroid-ligand to the nasal cavity. The results of this study are presented in FIGS. 180A, 180B and 180C. The response is measured in millivolt-seconds (mV×s). Androsta-4,16-dien-3-one elicits a significantly stronger VNO response in females than do the other compounds tested (FIG. 180A). Furthermore, the VNO response to Androsta-4,16-dien-3-one is sexually dimorphic—twice as strong in females as it is in males (FIG. 180B). In contrast, the OE response in both males and females is low compared to a strong odorant such as clove (FIG. 180C).

Example 137
Measurement of the Change in Receptor Potential of the Neuroepithelium of the VNO in Response to Various Steroids.

Figure 181A:
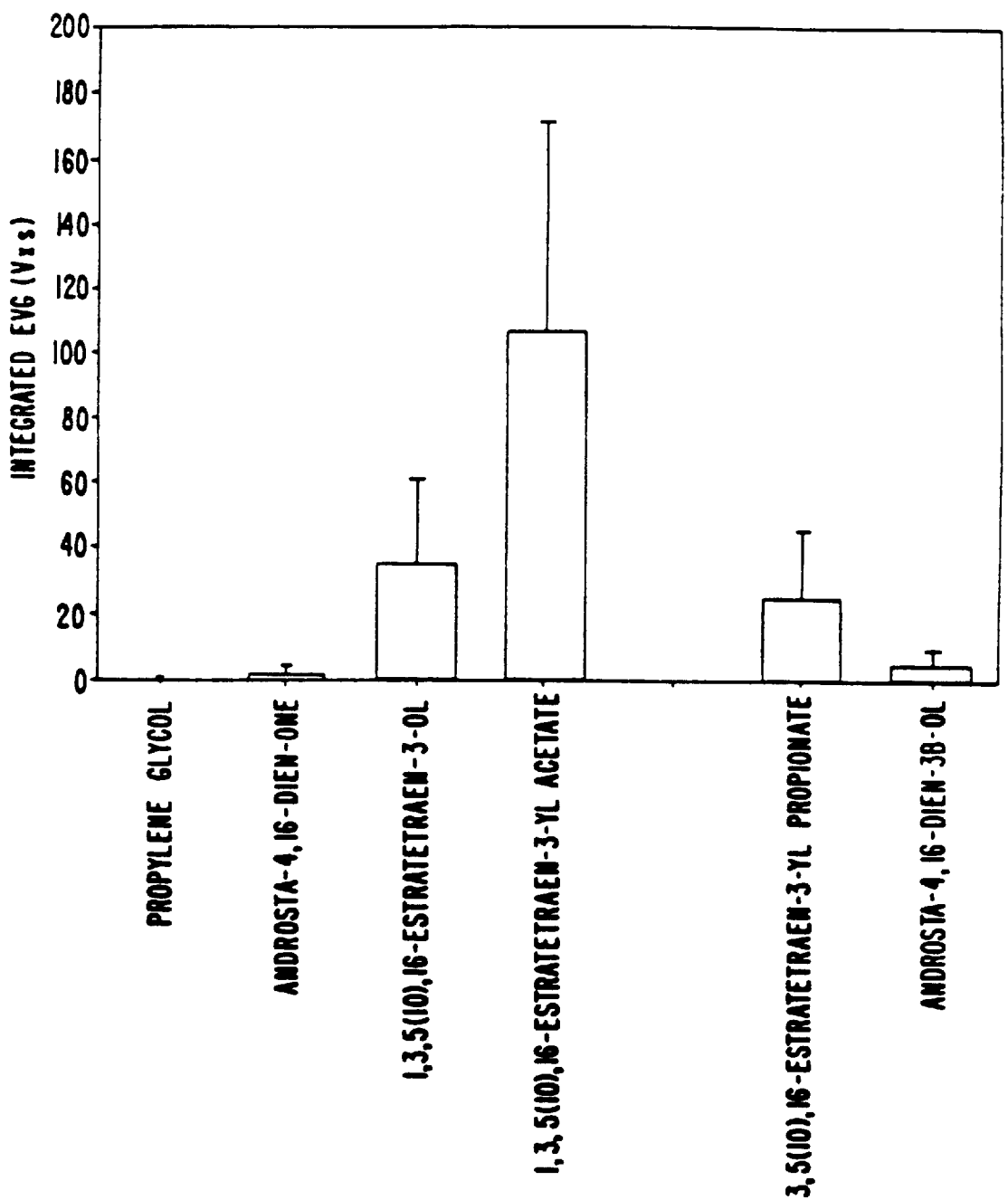
Figure 181B:
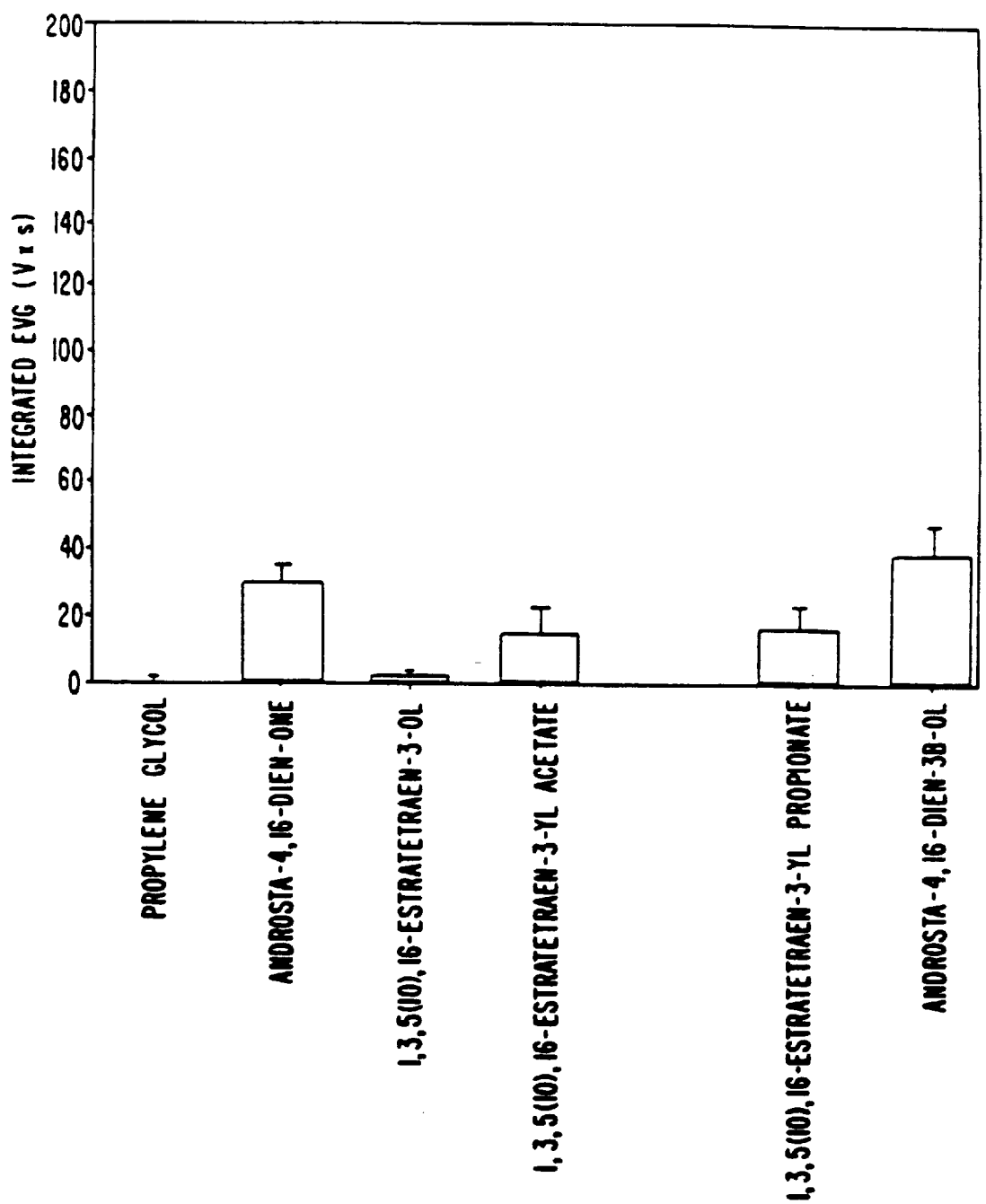
Figure 182A:
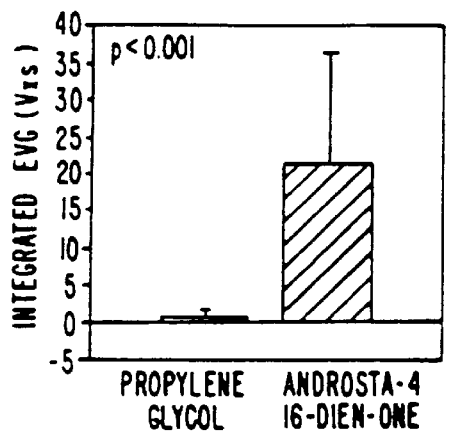
Figure 182B:
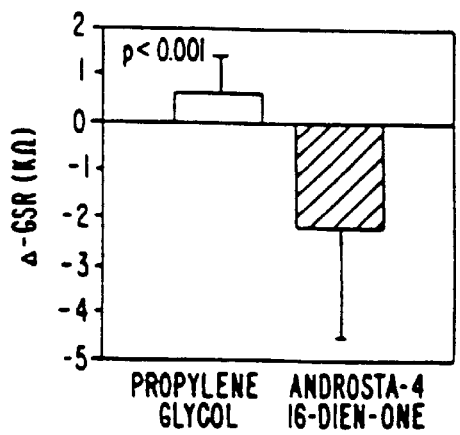
Figure 182C:
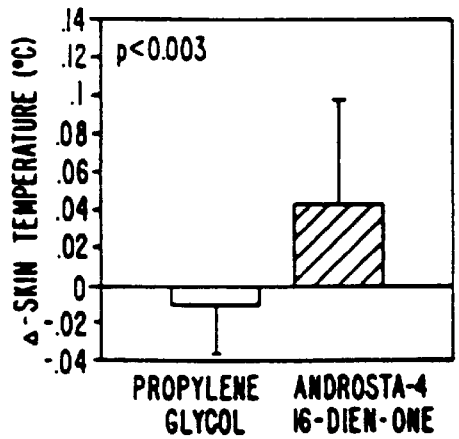
Figure 182D:
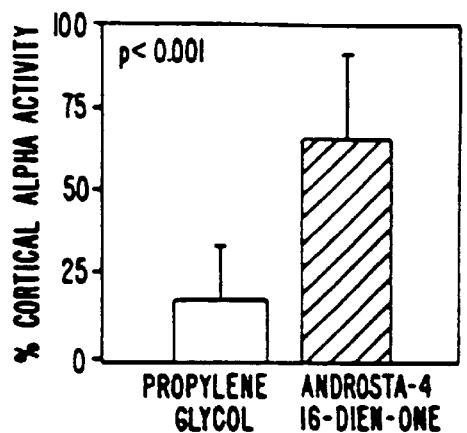
Figure 182E:
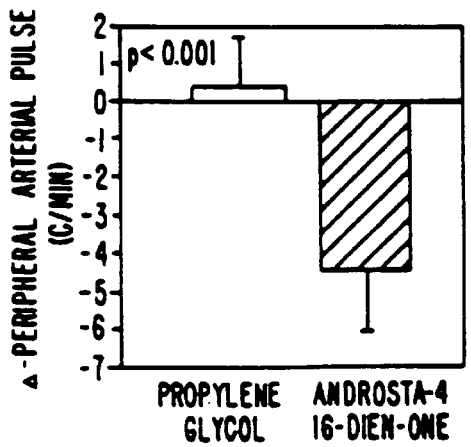
Figure 182F:
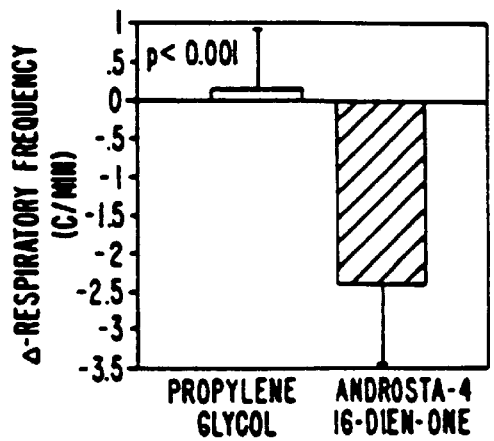

The change in receptor potential in response to five different ligands was measured in 40 female (FIG. 181A) and 40 male (FIG. 181B) subjects. Each subject was administered 60 µg of each of seven substances as indicated in the figure. The substances were administered separately for 1 second. The change in potential of the neuroepithelium of the VNO was recorded over time and the integral of the change in potential for each of the forty subjects was averaged. The results are shown in the figure. Comparison of FIGS. 181A and 181B show that each steroid is sexually dimorphic in its activity, and that some ligand substances are stronger in males while others are stronger in females.

Example 138
Measurement of Autonomic Responses to 16-Androstene Stimulation of the VNO.

Various autonomic parameters were monitored as Androsta-4,16-dien-3-one was administered to 40 female subjects. Propylene glycol was also administered as a control. The ligand was administered as a 1 second pulse. The change in autonomic function was first noted within 2 seconds and lasted for up to 45 seconds. As shown in FIG. 182, when compared to a propylene glycol control, the Androstane induced a significant change in the integrated receptor potential in the VNO (182A), galvanic skin response (182B), skin temperature (182C), the percentage of cortical alpha wave activity as measured by electroencephalogram (182D), peripheral arterial pulse (182E), and respiratory frequency (182F).

Example 139
Comparison of the Change in Receptor Potential Induced by Two Androstane Steroids.

60 picograms of each ligand steroid and of a propylene glycol control were administered to 5 female subjects. As shown in FIG. 183, Androsta-4,16-dien-3β-ol induced a greater change in receptor potential than did Androsta-4,16-dien-3-one.

Example 140
Psychophysiological Effect of Androstane Stimulation of the VNO.

The psychophysiological effect of Androstane stimulation of the VNO was measured by the coordinate administration of pheromone and questionnaire evaluation of the subject before and after administration. The questionnaire included a panel of adjectives used as part of the standard Derogatis Sexual Inventory evaluation.

The subjects were 40 women between the ages of 20 and 45, all in good health. The women were randomly assigned—20 exposed to placebo and 20 exposed to about 20 picograms of Androsta-4,16-dien-3-one. Subjects were given a 70 item questionnaire evaluating feeling states immediately before and 30 minutes after administration of either placebo or experimental substance. The 70 adjectives of the questionnaire were randomly administered and subsequently clustered for evaluation based on their relevance to each mood, feeling, or character trait. The results were as follows: Changes in feelings of social warmth, personal well-being, arousal/excitement, and aggression, from before administration to 30 minutes after administration, were not significant in those exposed to the 16-Androstene compared to the changes resulting from administration of the control. However, the decrease in negative affect (nervous, tense, ashamed, anxious, irritable, angry, enraged—T-test: $p<0.0001$, Anova: $p<0.04$), negative mood and character (sensitive, regretful, blameworthy, guilty, remorseful, sad, hopeless, resentful, worthless, miserable, unhappy, bitter, timid—T-test: $p<0.0004$, Anova: $p<0.06$), and overall negativity (the combination of affect and character—T-test: $p<0.0003$, Anova: $p<0.05$) were highly significant after 16-Androstene administration as compared to administration of the control.

Overall, these results suggest a sedative and/or anti-anxiety, and/or anti-depressant effect of Androsta-4 16-dien-3-one when administered intranasally.

Example 141
Electrophysiological Studies.

The following electrophysiological studies were performed in 60 clinically normal human volunteers of both sexes (30 male and 30 female) whose ages ranged from 20 to 45 years. No anesthetics were used, and female subjects were excluded if pregnant.

The stimulation and recording system consists of a "multifunctional miniprobe" described elsewhere (Monti-Bloch, L. and Grosner, B. l. (1991) "Effect of putative pheromones on the electrical activity of the human vomeronasal organ and olfactory 35 epithelium," *J. Steroid Biochem. Molec. Biol.* 39:573–582.). The recording electrode is a 0.3 mm silver ball attached to a small (0.1 mm) silver wire insulated with Teflon© the surface of the electrode is first treated to produce a silver chloride interface, and is then covered with gelatin. It is positioned within a small caliber Teflon© catheter (dia=S mm) such that the tip of the electrode protrudes approximately 2 mm. The Teflon© catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon© tube with a diameter of 2 mm surrounds the catheter-electrode assemblage, and its central end is connected to an aspirator that provides continuous suction of 3 ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNO, or on the surface of the olfactory or respiratory epithelium.

Electro-vomeronasogram (EVG): Recordings are carried out in a quiet room with the subject supine; the multi-functional miniprobe initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6× magnifying binocular loupe with halogen illumination is then used to introduce the tip of the Teflon© catheter and recording electrode assemblage into the VNO opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. Artifacts produced by respiratory movements are deleted by training the subjects to practice mouth breathing with velopharyngeal closure.

Chemosensory Stimulants: Olfactory test substances are cineole, and 1-carvone; vomeropherins are A, B, C, D, E and F, in FIGS. 180–184. Samples of vomeropherins in concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon©, glass or stainless steel and are carefully cleaned and sterilized before each use.

Electro-olfactoram (EOG): Olfactory recordings employed the same stimulating and recording multifunctional miniprobe as that used for the VNO. The tip was slowly introduced until the recording electrode touched the olfactory mucosa. Adequate placement was signaled by a depolarization in response to a pulse of the odorant test substance.

Cortical evoked activity was induced by VNO stimulation with vomeropherins, and olfactory stimulation with odorants delivered in 300 ms air pulses. It was recorded using standard electroencephalographic (EEG) electrodes placed at positions Cz-A1 and Tz-A1 of the international 10120 system; the ground electrode was placed on the mastoid process. Electrodermal activity (EDA) was recorded using standard 8 mm silver electrodes in contact with palmar skin of the medial and ring fingers respectively, through a conductive gel interface. Skin temperature (ST) was recorded by a small (1.0 mm) thermistor probe placed in the right ear lobe. Peripheral arterial pulse (PAP) was monitored with a plethysmograph attached to the tip of the index finger. Respiratory frequency (RF) was measured with an adjustable strain gauge placed around the lower thorax. All electrical signals were DC amplified, digitized (MP-100, Biopac Systems) and continuously monitored utilizing a computer. Statistical Analysis: EVGs or EOGS, peak-to-peak changes and frequency changes of other parameters were measured and statistically analyzed. The significance of the results was determined by either using paired t-tests or analysis of variance (ANOVA).

Effect of Vomeropherins on the EVG: Each of the vomeropherins was found to produce a sexually dimorphic receptor potential (FIGS. 184A and 184B). Recordings of the EVG were performed on 30 men and 30 women (ages 20 to 45). Vomeropherins were diluted and applied as 1 second pulses to the VNO with b minute intervals between pulses when questioned, the subjects were not able to "smell" or otherwise consciously detect any of the vomeropherins. This finding is in agreement with results previously reported (Monti-Bloch, L. and Grosser, B. 1. (1991) "Effect of putative pheromones on the electrical activity of the human vomeronasal organ and olfactory 5 epithelium," *J. Steroid Biochem. Molec. Biol.* 39:573–582) which indicated that neither olfactory nor vomeropherin test stimuli delivered to the VNO elicit a perceptible sensation at the delivered concentration.

FIG. 184A shows the average response of male subjects (ages 20 to 38) to the diluent, and to equimolar quantities (100 fmoles) of five vomeropherins (A, B, C, D and F), and to E, a stereoisomer of F. The profile of the response to each of the substances was similar in all subjects regardless of age, and no significant differences were revealed either by t-tests or by analysis of variance. For example, A, C and D produced significant effects ($M_{15}$=11.4 mV, SD=3.6 mV; $M_{76}$=6.4 mV, SD 2.5 mV, and $M_{84}$=15.1 mV, SD=4.9 mV; $p<0.01$), that were consistent in all individual cases. Other vomeropherins depolarized the VNO-receptors to a much lesser extent, but with consistent mean response amplitudes from individual to individual. Vomeropherins active in male subjects produced larger responses than the diluent ($p<0.001$). B, F and similar concentrations of olfactants induced significantly reduced responses in the male VNO (FIG. 184A and FIG. 185).

A similar experimental protocol was followed with the 30 female subjects (ages 20–45). Among the vomeropherins, F (100 fmoles) produced the most significant differences within the group (FIG. 184B). Here, A induced a small effect that was significantly different from F ($p<0.01$). In both populations of subjects, active vomeropherins induced receptor responses having large standard deviations (FIG. 184). When the frequency distribution of the effects of A and F was studied in males and females respectively, we found a bimodal distribution. The significance of this observation is being studied at 5 this point.

E, a stereoisomer of F, does not stimulate the VNO in female subjects while F does (FIG. 184B). This is a demonstration of the specificity of VNO recognition of vomeropherins. In this regard it is interesting to note that while F is a superior vomeropherin, E generates a stronger olfactory effect than does F (FIG. 184B and FIG. 185).

Results on the EVG amplitude tested in the VNO of men (FIG. 208) and women (FIG. 209) are shown for steroids E2/NC2, E1/NC2, E2/NC3, E1/NC3, methylated E2/NC2, methylated E2/NC3, and E8/NC3 on Chart VI.

Effects of Vomeropherins on the EOG: The summated receptor potential from the olfactory epithelium (OE) was recorded in 20 subjects: 10 males and 10 females. In contrast to the sensitivity of the VNO to vomeropherins, the OE is less sensitive to these substances. This is true for both males and females (FIG. 185A). The mean receptor potential amplitude ranged from 2.3 mV to 0.78 mV. In this study, B was the only vomeropherin having significant effect in the OE ($p<0.02$). Of the subjects questioned about odorant sensations following each stimulus presentation, 16 reported no olfactory sensation, while three males and one female described B as an unpleasant odor. This finding reveals that at the concentrations used in our study, most vomeropherins are not effective stimulants of the olfactory receptors, but do have a clear effect on vomeronasal receptors.

Effects of Olfactants on the EVG and EOG: In contract to vomeropherins, the olfactants 1-carvone and cineole produce only a minor local response in the VNO (FIG. 185B). This was true for both men and women. As expected, these olfactants produced a strong response in both men and women ($p<0.01$) when locally applied to the OE (FIG. 185A). The diluent depolarized olfactory receptors to a lesser extent than cineole or 1-carvone ($p<0.01$), and it did not produce an olfactory sensation.

Reflex Effects of Vomeropherins: Studies were s conducted to determine the central nervous system (CNS) reflex responses to vomeropherin stimulation of the VNO. The sexually dimorphic local responses induced by vomeropherins (FIG. 184A and FIG. 184B) were mirrored in the autonomic response of male & female subjects. In male subjects (FIG. 184C), A and C decreased skin resistance (electrodermal activity=EDA) ($p<0.01$, $n=30$). In female subjects. (FIG. 184B), F and B produced greater decrease in EDA than A or C ($p<0.01$, $n=30$).

Vomeropherins A and C induced a significant increase in skin temperature (ST) (FIG. 184G) in 30 male subjects ($p<0.01$); however D induced significant temperature decrease ($p<0.01$). In 30 female subjects (FIG. 184H) B and F evoked a significant increase in skin temperature (ST) ($p<0.01$) compared to A and C. In female subjects vomeropherins produced changes in EDA and ST with a greater standard deviation than in males.

Cortical activity was recorded from Cz and Tz in male and female subjects during application to the VNO of air pulses (300 ms to 1 sec) containing 200 fmoles of vomeropherin (FIGS. 184G and 184H). In males (FIG. 184E) A, C and D significantly increased alpha cortical activity with a latency of 270–380 ms. D and A evoked the strongest effect ($p<0.01$). Synchronization of the EEG was sustained for 1.5 to 2.7 minutes after application of a single pulse of active substance. In females (FIG. 184F), a single pulse (200 fmoles) of B or F applied to the VNO increased alpha cortical independent of the response of olfactory receptors. We found characteristic specificities in the response of the human VNO and the olfactory epithelium which suggests that they are independent functional systems with separate connections to the CNS (Brookover, C. (1914). The nervus terminalis in adult man. J. Comp. Neurol. 24:131–135.) There is also preliminary evidence that the EVG is not associated with trigeminal nociceptor endings since application of a local anesthetic (2-lidocaine) to the respiratory epithelium of the nasal septum neither blocks nor diminishes the EVG (Monti-Bloch, L. and Grosser, B. 1. (1991) "Effect of putative pheromones on the electrical activity of the human vomeronasal organ and olfactory epithelium," *J. Steroid Biochem. Molec. Biol.* 39:573–582.), also, subjects failed to report sensations of pain as a consequence of any of the stimulation procedures.

Additional tests we conducted using androsta-5,16-diene-3β,19-diol and four other androstanes, identified by their positions on the chart. The results are shown in FIGS. 193 through 200. The EEG, RF and EKG response for androsta-5,16-diene-3β,19-diol is stronger in females compared to males, while the ST, GSR and EVG response is stronger in males. Some females to whom were administered the compound reported feelings of happiness, which is unusual in that such reports are normally accompanied by much higher RF and GSR data than shown in FIGS. 194B and 194C.

VNO receptors are clearly more sensitive to vomeropherins than to any of the olfactants tested; the opposite is true for olfactory receptors. While the OE may have receptor sites for some vomeropherins, the response specificity of the VNO is clearly different.

Sexual differences were noted in the specificities and effects of two groups of vomeropherins, A, C and D; and B and F. This suggests a possible receptor-related sexual dimorphism. The findings suggest the activation of components of the autonomic nervous system in the adult human by vomeropherin stimulation of the VNO.

Furthermore, the results suggest that stimulation of the VNO with vomeropherins produces synchronization of the EEG (FIGS. 184G and 184H). Thus, the evidence herein indicates that the vomeronasal system responds to a variety of chemosensory stimuli, and that some are able to induce reflex autonomic activity.

Example 142

Electrophysiological Studies

The electrophysiological studies were performed as described in Example 141 in clinically normal human volunteers of both sexes whose ages ranged from 20 to 45 years. No anesthetics were used, and female subjects were excluded if pregnant.

Electro-vomeronasogram (EVG): The integrated EVG is shown in FIGS. 1 and 2 for compounds A1-P1, A2-P1, A4-P1, A3-P1, A1-P4, A2-$P_4$ (referring to Chart I). Artifacts produced by respiratory movements are deleted by training the subjects to practice mouth breathing with velopharyngeal closure. Samples of vomeropherins in concentration of 25–800 fmoles are delivered in the continuous air stream for durations from 300 milliseconds to 1 second.

Example 143

Electrophysiological studies were performed on the compounds of Examples 133, 134 and 134A in clinically normal adult females. The following chart summarizes the results. The data for the EVG and α-CA are shown in FIGS. 219 and 220, respectively.

Summary of effects of estrene vomeropherins on the human female VNO, autonomic activity, electromyogram, and alpha brain waves.

| | EVG | RF | CF | EDA | BT | EMG | α-CA |
|---|---|---|---|---|---|---|---|
| Example 133 | +++ | 0 | 0 | 0 | 0 | 0 | +++ |
| Example 134 | +++ | 0 | 0 | 0 | 0 | 0 | + |
| Example 134A | ++++ | 0 | 0 | 0 | 0 | 0 | 0 |

Example 133: 16α, 17α-Epoxyestra-1, 3, 5 (10)-trien-3-ol
Example 134: Estra-4, 16-dien-10β-ol-3-one
Example 134A: 16α, 17α-Epoxyestr-4-en-10β-ol-3-one
EVG = Electrovomeronasogram
RF = Respiratory Frequency
CF = Cardiac Frequency
EDA = Electrodermal Activity
BT = Body Temperature
EMG = Electromyogram
α-CA = Alpha Brain Waves
0 Compound showed an effect not significantly different from control
+ Arbitrary scale of effects
++ better than the control, correlated
+++ to the significance of differences between
++++ the data (p-value)

| | EVG | EDA | RF | CF | EMG | BT | α-CA | βCA | PERFORMANCE | SCORE |
|---|---|---|---|---|---|---|---|---|---|---|
| Methyl Ether of E2/P8 | +25 | +100 | −5 | −5 | 0 | −2.5 | −10 | −35 | EDA+,RF−,CF−,β− | 5 |
| E9/P2 | +5 | −10 | −2.5 | +10 | +5 | −2.5 | +5 | −35 | CF+,α+,β− | 3 |
| E4/P2 | +2.5 | −10 | −2 | +5 | −5 | 0 | +2.5 | −2.5 | EDA−,EMG− | 3 |
| E7/P1 | +30 | +70 | −5 | −5 | 0 | 0 | −5 | −2 | EDA+RF−CF− | 4 |
| Acetate of E2/P8 | +50 | +130 | 0 | 0 | 0 | +6 | 0 | −1.5 | EDA+,BT+,β− | 4 |
| E3/P1 | +20 | +70 | −2.5 | −2.5 | 0 | +3 | −10 | −30 | EDA+ | 2 |
| E10/P2 | +3 | −10 | 0 | +10 | −5 | 0 | +10 | +10 | EDA−,CF+EMG−,α+ | 5 |
| E2/P7 | +25 | +50 | +5 | −5 | 0 | +10 | −15 | −30 | EDA+,BT+ | 3 |
| E2/P5 | +25 | +30 | 0 | 0 | 0 | 0 | −10 | −40 | 0 | 0 |
| E2/P6 | +20 | +50 | 0 | −5 | 0 | 0 | −15 | −30 | EDA+,CF− | 3 |
| E1/P1 | +45 | +110 | +5 | 0 | 0 | 0 | −5 | −10 | 0 | 0 |
| E2/P1 | +40 | +95 | +3 | +5 | 0 | 0 | 0 | −15 | EDA+,RF+,CF+ | 4 |
| Methyl Ether of E2/P1 | +20 | +85 | −2.5 | −5 | 0 | 0 | −6 | −20 | EDA+,CF− | 3 |
| E13/P1 | +1 | −10 | 0 | 0 | −5 | 0 | 0 | −40 | EDA−,EMG−,β− | 4 |
| E11/P1 | +20 | −10 | 0 | +5 | −2.5 | −1 | 0 | −25 | 0 | 0 |
| E5/P1 | 0 | −10 | 0 | 0 | 0 | 0 | 0 | −40 | 0 | 0 |
| Acetate of E6/P8 | +2.5 | −10 | −2.5 | +2.5 | −5 | −3 | +10 | −20 | EMG−,BT−,α+,β− | 5 |
| E2/P8 | +25 | +110 | 0 | 0 | 0 | +10 | +7 | −20 | EDA+,BT+,α+,β+ | 5 |
| E2/P2 | +20 | +20 | −2.5 | −5 | 0 | −2.5 | +7 | −25 | CF−,BT−,α+,β− | 5 |
| E2/P4 | +50 | +110 | +2.5 | 0 | 0 | 0 | +30 | −10 | EDA+,α+,β− | 4 |
| E12/P8 | +35 | +100 | 0 | −5 | 0 | −3 | −10 | −25 | EDA+,CF−,BT− | 4 |
| E8/P1 | +35 | +105 | +2.5 | 0 | 0 | −1 | −10 | −40 | 0 | 0 |
| Methyl Ether of E2/P8 | +12 | +95 | 0 | −5 | −2.5 | −2.5 | +2.5 | −10 | EDA+,CF− | 3(+) |
| E9/P2 | +20 | −20 | 0 | +2.5 | −2.5 | −5 | −7 | −40 | BT− | 2 |
| E4/P2 | +15 | −20 | 0 | +2.5 | 0 | −2.5 | −2.5 | −20 | 0 | 0 |
| E7/P1 | +18 | +70 | 0 | 0 | 0 | +7 | −2.5 | −30 | EDA+,BT+β− | 4 |
| Acetate of E2/P8 | +40 | −80 | 0 | 0 | 0 | +2.5 | −10 | −20 | EDA+ | 2 |
| E3/P1 | +15 | +50 | 0 | +2.5 | 0 | −5 | −10 | −30 | EDA+,BT−β− | 4 |
| E10/P2 | +20 | −20 | 0 | +2.5 | −2.5 | −1 | 0 | +40 | 0 | 0 |
| E2/P7 | +30 | +120 | 0 | +2.5 | 0 | 0 | −10 | −20 | 0 | 0 |
| E2/P5 | +10 | +90 | 0 | 0 | 0 | +10 | −5 | −30 | EDA+,BT−β− | 4 |
| E2/P6 | +12 | +100 | 0 | 0 | 0 | −2.5 | 0 | −20 | EDA+ | 2 |
| E1/P1 | +35 | +120 | −2.5 | 0 | 0 | +2.5 | −2.5 | −20 | EDA+ | 2 |
| E2/P1 | +30 | +120 | 0 | 0 | 0 | −7 | −10 | −20 | EDA+,BT−,(EEG+) | 4 |
| Methyl Ether of E2/P1 | +15 | +110 | −5 | 0 | 0 | 0 | 0 | −20 | EDA+,RF− | 3 |
| E13/P1 | +20 | −20 | 0 | 0 | −2.5 | 0 | −5 | −15 | 0 | 0 |
| E11/P1 | +18 | −20 | +2.5 | 0 | 0 | −2.5 | −5 | −15 | 0 | 0 |
| E5/P1 | +100 | −20 | 0 | −2.5 | −2.5 | 0 | −5 | −10 | 0 | 0 |
| Acetate of E2/P8 | +2.5 | −20 | 0 | −2.5 | −2.5 | −2.5 | −5 | −15 | 0 | 0 |
| E2/P8 | +30 | +100 | 0 | 0 | 0 | 0 | −10 | −20 | 0 | 0 |
| E2/P2 | +15 | +30 | 0 | 0 | 0 | +2.5 | −5 | −25 | 0 | 0 |
| E2/P4 | +30 | +30 | −2.5 | 0 | 0 | −5 | −10 | −20 | EDA+,BT−,(EEG+) | 4 |
| E12/P8 | +25 | +120 | 0 | 0 | 0 | +2.5 | −10 | −25 | EDA+ | 2 |
| E8/P1 | +30 | +130 | 0 | 0 | 0 | +2.5 | −5 | −20 | EDA+ | 2 |

SUMMARY OF EFFECTS OF 19-NOR PREGNANE VOMEROPHERINS ON EEG AND AUTONOMIC ACTIVITY IN WOMEN, n = 6

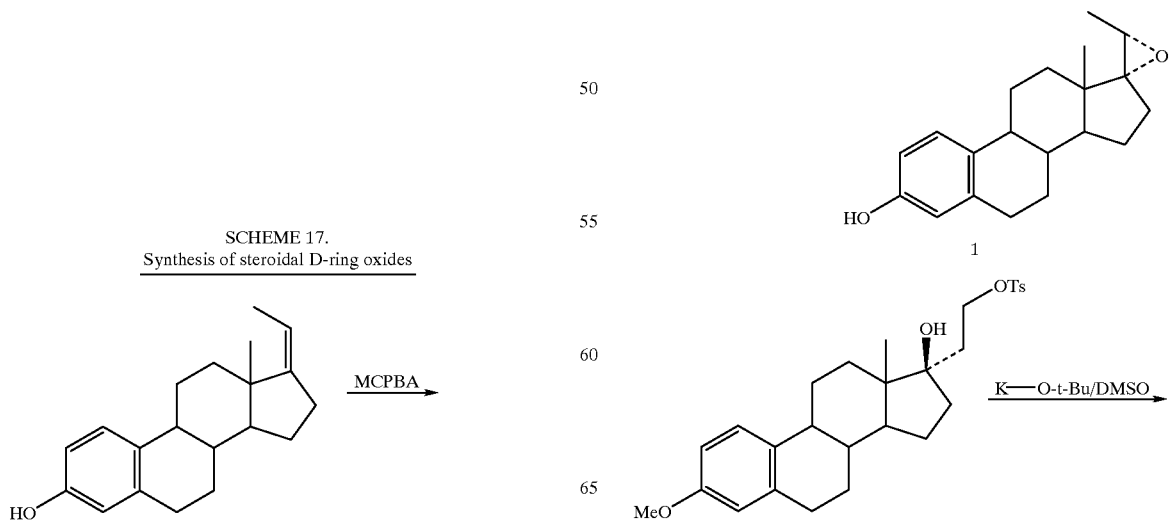

SCHEME 17.
Synthesis of steroidal D-ring oxides

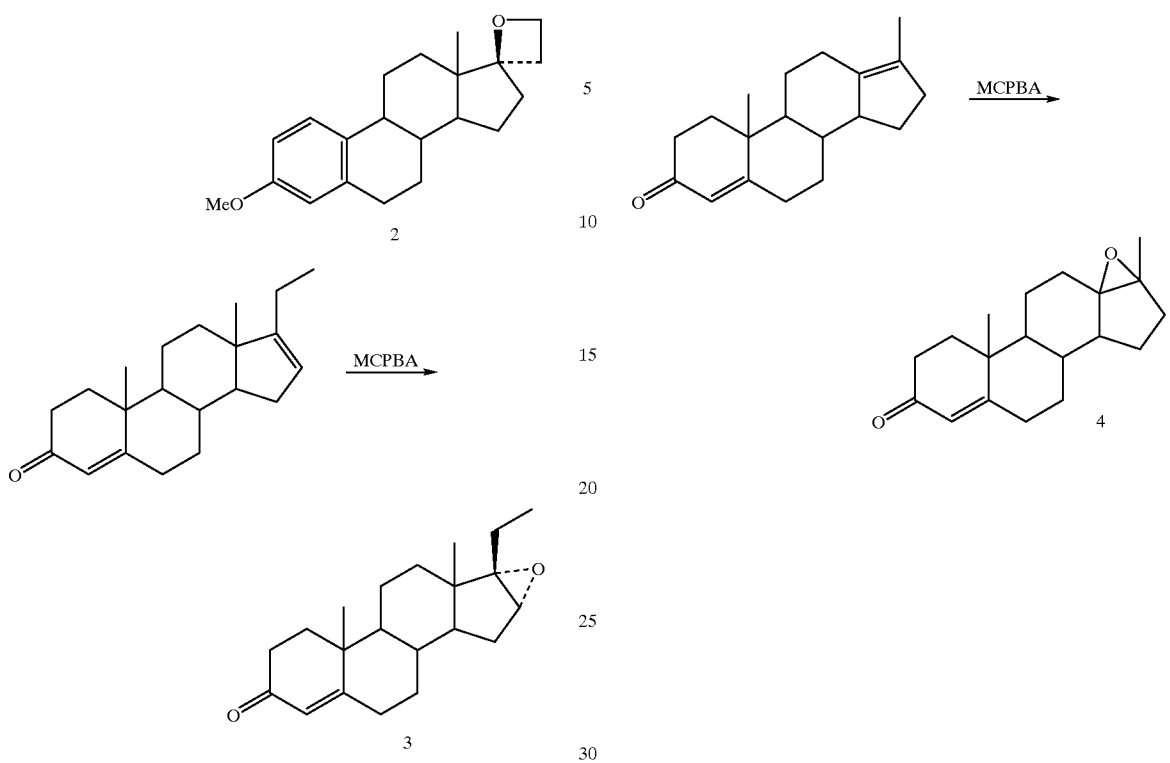
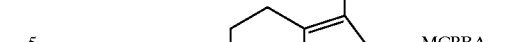
SCHEME 18.
Synthesis of additional steroidal D-ring oxides
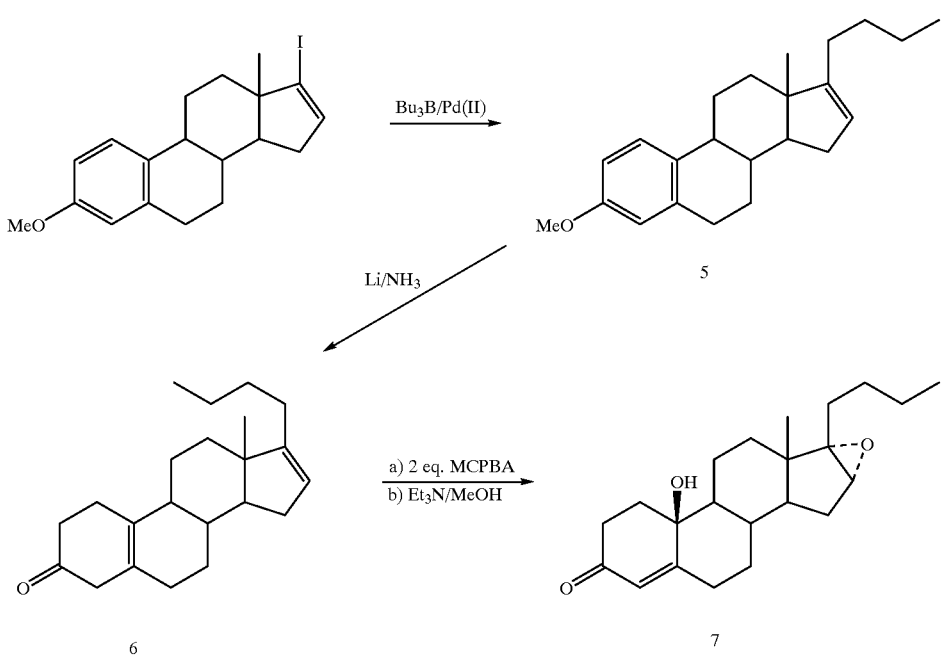

-continued

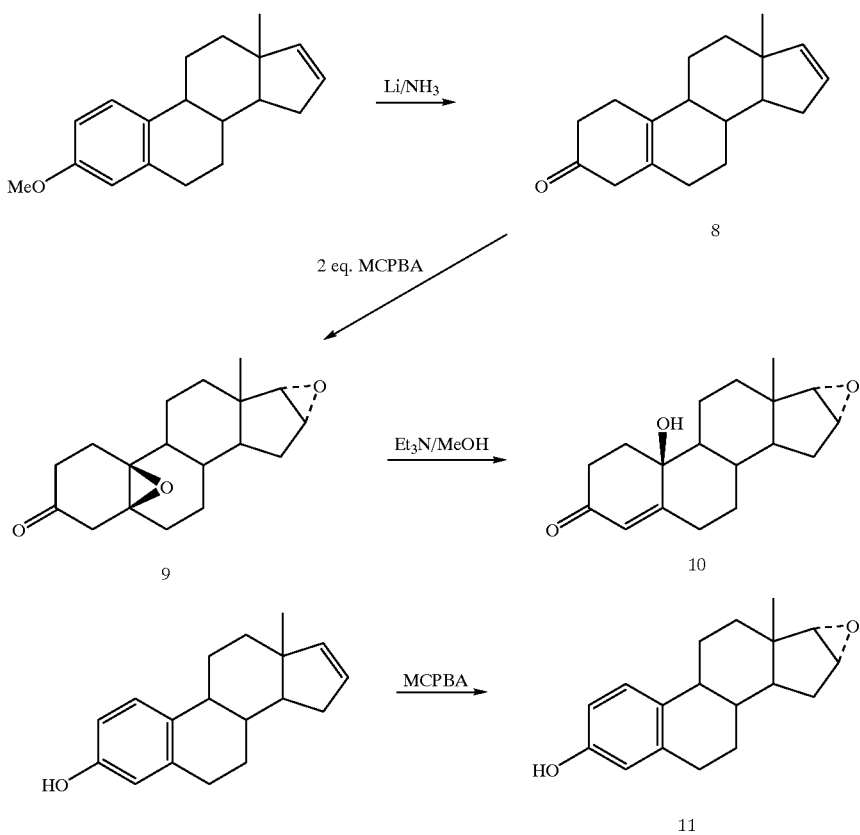

Example 144
17α,2α-Epoxy-19-norpregna-1,3,5(10)-trien-3-ol, 1:

To a solution of 19-norpregna 1,3,5(10),17Z-tetraen-3-ol (282.4 mg, 0.9999 mmol) in 6 mL of 1,2-dimethoxyethane (DME) was added 3-chloroperoxybenzoic acid (92.2%, 207.1 mg, 1.200 mmol) in 6 mL of DME and the reaction was stirred 5 h. The mixture was poured into 50 g of 5% (w/w) sodium thiosulfate pentahydrate and extracted into three 20 mL portions of ethyl acetate. The combined organic extracts were washed with 20 mL of saturated sodium bicarbonate+20 mL of brine, dried over magnesium sulfate, and filtered through Celite 503. The residue was washed with 5 mL of ethyl acetate and the combined filtrates were concentrated under reduced pressure. Two-fold crystallization of the resulting white solid, first from methyl t-butyl ether (MTBE)/hexanes and then from aqueous ethanol, gave fine, lustrous, off-white platelets (160.0 ma, 0.5362 mmol, 54o), m.p. 154–159° C., homogeneous to TLC (25% ethyl acetate/hexanes on silica gel, product $R_f$ 0.42, starting material $R_f$ 0.57, 0.42 (trace))

Example 145
3-Methoxyspiro[estra-1,3,5(10)-17,2'-oxetane], 2:

To 3-methoxy-19-norpregna 1,3,5(10)-trien-17β-ol-21-tosylate (168.1 ma, 0.3469 mmol) and potassium t-butoxide (168.1 ma, 1.498 mmol) under argon was added 8 mL of anhydrous dimethylsulfoxide (DMSO) and the reaction was stirred in a heated (77–99° C.) oil bath for 3½ h. MTBE (20 mL) was added to the upon cooling and the mixture was washed with three 5 mL portions of water+5 mL of brine, dried over magnesium sulfate, and filtered through Celite 503. The residue was washed with 5 mL of MTBE and the combined filtrates were concentrated under reduced pressure. Preparative TLC (10% ethyl acetate/hexanes on silica gel GF. 1000μ) produced off-white crystals (72.2 mg, 0.231 mmol, 67%). TLC (10% ethyl acetate/hexanes on silica gel; estra-1,3,5 (10),16-tetraen-3-yl methyl ether $R_f$ 0.70) showed product ($R_f$ 0. 33) with a trace contaminant ($R_f$ 0.42).

Example 146
16α,17α-Epoxypregn-4-en-3-one, 3:

To a solution of pregna-4,16-dien-3-one (31.0 ma, 0.104 mmol) in 0.6 mL of DME was added 3-chloroperoxybenzoic acid (92%, 21.5 ma, 0.125 mmol) in 0.6 mL of DME and the reaction was stirred 5 h. The mixture was subjected directly to preparative TLC (30% ethyl acetate/hexanes on silica gel GF, 1000μ) to give a white crystalline solid (13.1 mg,41.7 μmol, 40%). TLC (30% ethyl acetate/hexanes on silica gel; starting material $R_f$ 0.53, 0.00 (trace)) showed product (Rf 0.33) with a trace contaminant ($R_f$ 0.38).

Example 147
13,17-Epoxy-10,17-dimethylgona-4-en-3-one, 4:

To a solution of 10,17-dimethylgona-4,13(17)-dien-3-one (342.1 ma, 1.265 mmol) in 7.6 mL of DME was added 3-chloroperoxybenzoic acid (92%, 262.0 ma, 1.518 mmol) in 7.6 mL of DME. After stirring 5 h, the reaction mixture was poured into 60 g of 5% (w/w) sodium thiosulfate pentahydrate and then extracted three times with 30 mL portions of ethyl acetate. The combined organic extracts were washed with 30 mL of saturated sodium bicarbonate+ 30 mL of brine, dried over magnesium sulfate, and filtered through Celite 503. The residue was washed with 10 mL of ethyl acetate and combined filtrates were concentrated under reduced pressure. Flash chromatography (30% ethyl acetate/hexanes on silica gel) of the resulting yellow resin, followed by preparative TLC (30% ethyl acetate/hexanes on silica gel GF, 1000μ) gave a light yellow solid (87.2 ma, 0.304 mmol, 24%) showing 3 spots ($R_f$ 0.23, 0.29, and 0.32) on TLC (30% ethyl acetate/hexanes on silica gel; pregna-4,16-dien-3-one $R_f$ 0.54).

Example 148
19,21-Bisnorchola-1,3,5(10),16-tetraen-3-yl methyl ether, 5:

To 17-iodoestra 1,3,5(10),16-tetraen-3-yl methyl ether (788.6 ma, 2.000 mmol), 15% (w/w) NaOH (2.0 mL), and [1,1'-bis(diphenylphosphino)ferrocene]palladium(II) chloride methylene chloride complex (1:1) (40.8 ma, 50.0 Camel) under argon were added anh. THF (8.0 mL) and tributylborane (1.0 M in THF, 2.2 mL, 2.2 mmol). After refluxing 24, benzene (20 mL) was added to the cooled reaction. The mixture was washed with 10 mL of brine, dried over magnesium sulfate, and filtered through Celite 503. The residue was washed with 5 mL of benzene and the combined filtrates were concentrated under reduced pressure. Flash chromatography (1% ethyl acetate/hexanes on silica gel) of the residual dark syrup, followed by crystallization from 95% ethanol with intermediate charcoal treatment gave white platelets (425.4 ma, 1.311 mmol, 66%), m.p. 50–52° C., homogeneous to TLC (5% ethyl acetate/hexanes on silica gel; $R_f$ 0.48; estra-1,3,5(10),16-tetraen-3-yl methyl ether $R_f$ 0.45).

Example 149
19,21-Bisnorchola-5(10),16-dien-3-one, 6:

Approximately 30 mL of anh. $NH_3$ was distilled through KOH into a flame-dried 3-neck flask fitted with an inlet adapter, magnetic stirring bar, dry ice/acetone condenser, and glass stopper. 19,21-Bisnorchola-1,3,5(10),16-tetraen-3-yl methyl ether(5, 300.0 ma, 0.9245 mmol) in 8 mL of anh. THF and 3.09 g (41.7 mmol) of t-butyl alcohol was added, after which lithium wire (high sodium, 0.13 g,19 mg-atom) cut in small pieces was added. The reaction mixture was stirred 6 h and then quenched with 1.0 mL of methanol. After allowing NH3 to boil off overnight, water (25 mL) was added and the reaction mixture was extracted 3 times with 25 mL aliquots of MTBE. The combined organic extracts were washed 3 times with 25 mL portions of brine, dried over magnesium sulfate, and filtered through Celite 503. The residue was washed with 10 mL of MTBE and the combined filtrates were concentrated under reduced pressure. The resulting syrup was taken up in 25 mL of acetone, oxalic acid dihydrate (0.37 g) in 5 mL of water was added, and the suspension was stirred 4 h. The hydrolysis mixture was poured into 10 mL of saturated sodium bicarbonate and extracted three times with 10 mL aliquots of MTBE. The combined organic extracts were washed 3 times with 10 mL portions of brine, dried over magnesium sulfate, and filtered through Celite 503. The residue was washed with 5 mL of MTBE and the combined filtrates were concentrated under reduced pressure. The residual syrup was taken up in 5 mL of hexanes, dried over magnesium sulfate, and filtered through Celite 503. The residue was washed with 2 mL of hexanes and the combined filtrates were boiled down to about 2 mL. The resulting solution was applied to a preparative TLC plate (silica gel GF, 1000μ) and developed with 10% ethyl acetate/hexanes. Extraction and concentration of the appropriate band gave a colorless syrup (226.4 ma, 0.7245 mmol, 78%). TLC (10% ethyl acetate/hexanes on silica gel) showed product ($R_f$ 0.34) with a trace contaminant ($R_f$ 0.14).

Example 150
16α,17α-Epoxy-19,21-bisnorchol-4-en-10β-ol-3-one, 7:

To a cooled (dry ice/acetone) solution of 19,21-bisnorchola-5(10),16-dien-3-one (6, 270.2 ma, 0.8647 mmol) in 1.6 mL methylene chloride was added 3-chloroperoxybenzoic acid (97.4%, 328.3 mg, 1.902 mmol) in 6.3 mL of methylene chloride over 3 min. Remaining peracid was rinsed into the vessel with 1.8 mL of methylene chloride and the reaction was stirred 5 h. The cooling bath was removed and the reaction was stirred a further 1 h. The reaction was then filtered through Celite 503 and the residue was washed with 1 mL of methylene chloride. The combined filtrates were washed with 5 g of 5% (w/w) sodium thiosulfate pentahydrate+5 mL of saturated sodium bicarbonate+5 mL of brine, dried over magnesium sulfate, and filtered through Celite 503. The residue was washed with 1 mL of methylene chloride and the combined filtrates were concentrated under reduced pressure. The resulting light yellow solid was taken up in 22 mL of methanol with warming, 3.6 mL of triethylamine were added, and the reaction was stirred 2 h. The mixture was then concentrated under reduced pressure to give an amber syrup. This was purified by preparative TLC (50% ethyl acetate/hexanes on silica gel GF, 1000μ) to produce a white crystalline solid (133.0 ma, 0.3861 mmol, 45%). TLC (50% ethyl acetate/hexanes on silica gel; 16α,17α-epoxyestr-en-10β-ol-3-one $R_f$ 0.26) showed product ($R_f$ 0.38) with a trace contaminant ($R_f$ 0.30).

Example 151
Estra-5(10),16-dien-3-one, 8:

Approximately 2.4 L of anhydrous ammonia were distilled through KOH into a flame-dried 4-neck round bottom flask fitted with two acetone/dry ice condensers, a mechanical stirrer, and a glass stopper. Estra-1,3,5(10),16-tetraen-3-yl methyl ether (27.45 g, 0.1023 mol) in 260 mL of anh. THF+133.24 g (1.798 mol) of t-butyl alcohol was added, followed by four 3.12 g (12.49 g total, 1.79 g g-atom) portions of lithium wire cut in small pieces, one portion every ½ h. At times mechanical stirring was interrupted to prevent boiling over. After stirring an additional 3 h, methanol (100 mL) was added and the reaction was stirred overnight while allowing ammonia to boil off. Water (600 mL) was added and the mixture was three times with 300 mL portions of MTBE. The combined organic extracts were washed with 300 mL of brine, dried over magnesium sulfate, and filtered through Celite 503. The residue was washed with 50 mL of MTBE and the combined organic extracts were concentrated under reduced pressure. The resulting light yellow oil was taken up in 500 mL of acetone and oxalic acid dihydrate (7.19 g) in 95 mL of water was added. After stirring 8 h, the hydrolysis mixture was poured into 250 mL of saturated sodium bicarbonate and extracted three times with 250 mL portions of MTBE. The combined organic extracts were washed three times with 250 portions of brine, dried over magnesium sulfate, and filtered through Celite 503. The residue was washed with 50 mL of MTBE and the combined filtrates were concentrated under reduced pressure. Two fold recrystallization from hexanes (intermediate drying over magnesium sulfate necessary to remove residual water) gave two crops of white crystals. The total yield was 12.18 g (47.51 mmol, 46%). First crop m.p. 117.5–119.5° C., second crop m.p. 115–119° C.

Example 152
5β,10β,16α,17α-Bisepoxyestran-3-one, 9:

To a solution of estra-5(10),16-dien-3-one (8, 12.02 g, 46.88 mmol) in 70 mL of methylene chloride cooled to 0° C.

was added 3-chloroperoxybenzoic acid (97.4%, 17.80 g, 0.1031 mol) suspended in 340 mL of methylene chloride over 58 min., so that the reaction temperature was maintained within 2 degrees of 0° C. Further methylene chloride (100 mL) was added to rinse adhering peracid into the reaction vessel and the mixture was stirred 5 h. The resulting suspension was filtered through Celite 503 and the residue was washed with 50 mL of methylene chloride. The combined filtrates were washed with 250 g of 5% (w/w) sodium thiosulfate pentahydrate+250 mL of saturated sodium bicarbonate+250 mL of brine, dried over magnesium sulfate, and filtered through Celite 503. The residue was washed with 50 mL of methylene chloride and the combined filtrates were concentrated under reduced pressure. Recrystallization of the resulting light yellow solid from 95% ethanol with intermediate treatment with charcoal gave shiny, white platelets (11.38 g, 39.46 mmol, 84%), m.p. 168–173° C.

Example 153

16α,17α-Epoxyestr-4-en-10β-ol-3-one, 10:

5β,10β,16α,17α-Bisepoxyestran-3-one (9, 11.30 g, 39.18 mmol) was dissolved in 1 L of methanol with warming and triethylamine (166 mL, 1.19 mmol) was added. After stirring 6 h, the solution was concentrated under reduced pressure and the resulting yellow-tinged solid was taken up in 250 mL of hot 95% ethanol. Charcoal (Darco G-60, 0.58 g) was added and the mixture was heated to boiling. The hot suspension was filtered through Celite 503 and the residue was washed with 50 mL of hot ethanol. The combined filtrates were boiled down to approx. 150 mL and then cooled in tap water with swirling. The solution was seeded with crystals of "byproduct" and was then refrigerated overnight following onset of crystallization. The "byproduct" was filtered off and washed with 10 mL of cold ethanol (after drying the residue weighed 3.2762 g and had m.p. 262–269° C.). The combined filtrates were boiled down to approx. 50 mL and then cooled in tap water with swirling. The solution was seeded with authentic product and then refrigerated overnight following onset of crystallization. The suspension was filtered and the residue dried over P2O5 in vacuo to give flat, white crystals (4.6827 g, 16.283 mmol, 41%), m.p. 193–195° C., homogeneous to TLC (50% ethyl acetate/hexanes on silica gel; product Rf 0.47; authentic sample $R_f$ 0 47)

Example 154

16α,17α-Epoxyestra-1,3,5(10)-trien-3-ol, 11:

To a solution of 1,3,5(10),16-estratetraen-3-ol (CAS No. 11150-90-91, 636.0 ma, 2.500 mmol) in 15 mL of DME was added mchloroperbenzoic acid (862.9 ma, 5.000 mmol) in 25 mL of DME over 3 min., and the reaction was stirred for 6 h. The mixture was poured into 140 g of 5% (w/w) sodium thiosulfate pentahydrate and extracted three times with 100 mL portions of ethyl acetate. The combined organic extracts were washed with 100 mL of saturated sodium bicarbonate+ three 100 mL aliquots of saturated sodium chloride, dried over magnesium sulfate, and filtered through Celite 503. The residue was washed with 50 mL of ethyl acetate and the combined filtrates were concentrated under reduced pressure. Flash chromatography (20% ethyl acetate/hexanes on silica gel) of the resulting residue, followed by recrystallization from ethyl acetate gave lustrous white platelets (349.9 ma, 1.294 mmol, 52%), m.p. 217–219° C. (lit. [Prelog, V., Ruzicka, L., and Wieland, P. (1945): Steroide und Sexualhormone. (111. Mitteilung). Über ein neues Stereoisomeres des Oestriols. Helv. Chim. Acta 28, 250–256.1 m.p. 215° C.), homogeneous to TLC (20% ethyl acetate/hexanes on silica gel; $R_f$ 0.32; starting material $R_f$ 0.50).

Example 155

Electrophysical studies were performed on the compounds of Examples 144, 146, 147, 150, 153 and 154, as well as two other gint-D epoxy steroids in clinically normal adult men and women. The results are summarized in FIGS. 221A and 221B.

The preparation of 17,20-EPOXYPREGN-4-EN-3-ONE is described by J. Hader and E. Blanke in British Patent 1,049,988 (1966).

The preparation of 16B,20B-EPOXYPREGN-4-EN-3B-OL is described by M. Matsui and D. Fukushima, *J. Org. Chem.* 35(3), 561 (1970).

The preparation of 18,20-EPOXYPREGN-4-EN-3-ONE is described by G. Cainelli, B. Kamber, J. Keller, M. Lj. Michailovic, D. Arigoni and 0. Jeger, *Helv. Chim. Acta,* 62, 518 (1961).

16a,17a-EPOXYANDROST-4-EN-3-ONE (ANDROSTEINOXIDE) was prepared according to the literature procedure: F. Sondheimer, 0. Mancera, M. Urquiza and G. Rosenkranz, *J. Chem. Soc.* 77, 4145 (1955).

17B,21-EPOXY-3-METHOXY-19-NOR-17a-PREGNA-1,3,5,(10)-TRIENE was prepared according to the literature procedure: B. Singh and R. G. Christiansen, *J. Pharm. Sci.* 60, 491 (1971).

SCHEME 19.
Synthesis of 17-Iodoestra-1,3,5(10),16-tetraen-3-yl methyl ether

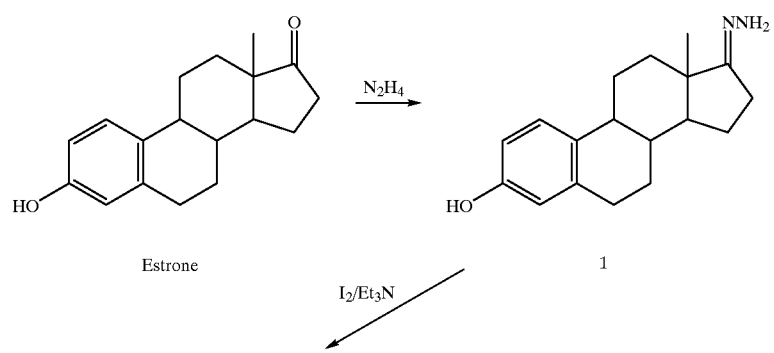

-continued
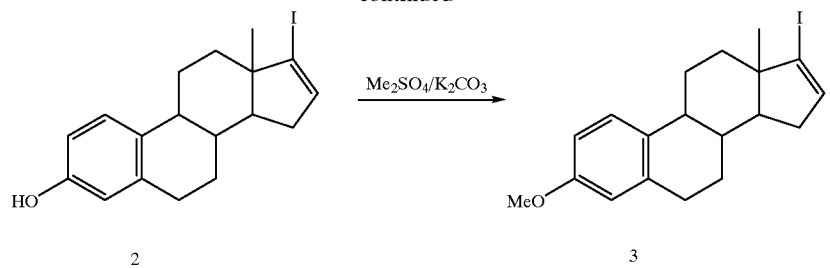
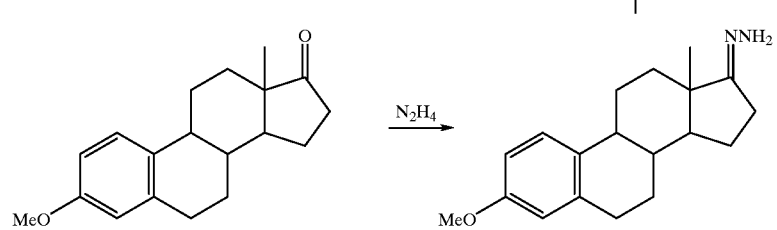
SCHEME 20.
Synthesis of additional steroidal D-ring oxides
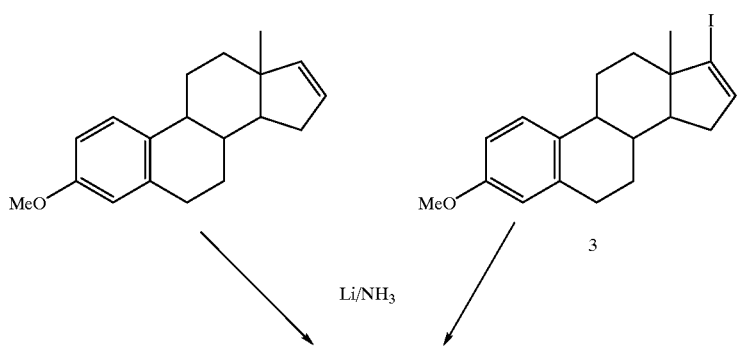

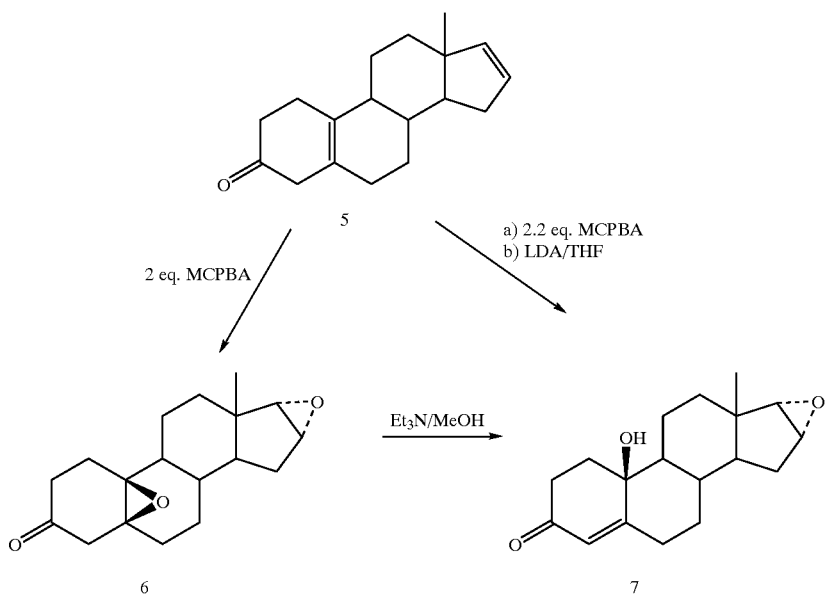

Exampel 156

Estrone hydrazone, 1:

A suspension of estrone (20.00 g, 73.97 mmol) in 150 mL of abs. EtOH, 34 mL (0.24 mol) of triethylamine, and 64 mL (2.0 mol) of hydrazine was refluxed 1½ h with exclusion of moisture. The reaction mixture was added to 580 mL of water with stirring and agitation, and then refrigerated overnight. The crude hydrazone was filtered, washed with 100 mL of water, and dried over $P_2O_5$ in vacuo to give an off-white solid (22.57 g, >100%).

Example 157

17-Iodoestra-1,3,5(10),16-tetraen-3-ol, 2:

To a cooled (ice water bath) mixture of crude estrone hydrazone (1, 22.45 g) with 200 mL of anh. tetrahydrofuran (THF) and 50 mL (0.36 mol) of triethylamine under argon was added iodine (44.31 g, 0.1746 mol) in 150 mL of anh. THF over 33 min. until gas evolution ceased (remaining solution: 8 mL). After stirring a further 20 min., the reaction mixture was poured into 300 mL of 1 N HCI and extracted three times into 100 mL aliquots of ether. The combined organic extracts were washed with three 100 g portions of 5% (w/w) sodium thiosulfate pentahydrate+100 mL of saturated sodium bicarbonate+100 mL of brine, dried over sodium sulfate, and filtered through a coarse glass frit. The residue was washed twice with 50 mL portions of ether and the combined filtrates were concentrated under reduced pressure. The resulting red foam was crystallized twice from aqueous methanol with intermediate treatment with charcoal both times to give fine, off-white platelets (18.70 g, 49.18 mmol, 66% overall from estrone), m.p. 134135° C.

Example 158

17-Iodoestra-1,3,5(10),16-tetraen-3-yl methyl ether, 3, from 17-Iodoestra-1,3,5(10),16-tetraen-3-ol:

A suspension of 17-Iodoestra-1,3,5(10),16-tetraen-3-ol (2, 17,11 g, 44.99 mmol) and potassium carbonate (9.33 g, 67.5 mmol) in 600 mL of acetone was heated to reflux with exclusion of moisture, and dimethyl sulfate (11 mL, 0.12 mol) was added. After 24 h stirring, the cooled reaction mixture was poured into 500 g of 5% (w/w) sodium hydroxide and extracted three times into 250 my aliquots of methyl t-butyl ether (MTBE). The combined organic extracts were washed with 25.0 mL of brine, dried over sodium sulfate, and filtered through Celite 503. The residue was washed with 50 mL of MTBE and the combined filtrates were concentrated tinder reduced pressure. Crystallization of the resulting tan solid gave pink to purple needles (14.85 g, 37.66 mmol, 84%), m.p. 14–147° C.

Example 159

Estra-1,3,5(10)-triene-17-hydrazone-3-yl methyl ether, 4:

A suspension of estrone 3-methyl ether (1.0000 g, 3.5162 mmol) in 7 mL abs. EtOH, triethylamine (1.6 mL, 11 mmol), and hydrazine (3.1 mL, 99 mmol) was refluxed with exclusion of moisture for 90 min., during which time the reaction became homogeneous. Water (28 mL) was added with swirling, and the mixture was refrigerated overnight. Filtration and drying of the residue over $P_2O_5$ in vacua gave fine, shiny white platelets (1.0437 g, 3.4973 mmol, 99%), m.p. 166 169° C.

Example 160

17-Iodoestra-1,3,5(10),16-tetraen-3-yl methyl ether, 3, from estra-1,3.5(10)-triene-17-hydrazone-3-yl methyl ether:

To a mixture of estra-1,3,5(10)-triene-17-hydrazone-3-yl methyl ether (4, 1.0000 g, 3.3509 mmol) in 18 mL of anh. THF and under argon was added iodine (2.01 g, 7.92 mmol) in 10 mL of anh. THF over 30 min. until the yellow color persisted (solution remaining: 3 mL). After stirring a further 15 min., the reaction mixture was poured into 35 mL of 1 N HCI and extracted three times into 15 mL aliquots of ether. The combined organic extracts were washed with 15 g of 5% (w/w) sodium thiosulfate pentahydrate+15 mL of saturated sodium bicarbonate, dried over sodium sulfate, and filtered through a coarse glass frit. The residue was washed with 10 mL of ether and the combined filtrates were concentrated under reduced pressure. The resulting yellow-orange solid was crystallized from abs. EtOH with intermediate treatment with charcoal to give a light yellow crystalline solid (764.5 ma, 1.939 mmol, 58%), m.p. 145–146° C.

Example 161
Estra-5(10),16-dien-3-one, 5, from estra-1,3,5(10),16-tetraen-3-yl methyl ether:

Approximately 2.4 L of anhydrous ammonia were distilled through KOH into a flame-dried 4-neck round bottom flask fitted with two acetone/dry ice condensers, a mechanical stirrer, and a glass stopper. Estra-1,3,5(10),16-tetraen-3-yl methyl ether (27.45 g, 0.1023 mol) in 260 mL of anh. THF+133.24 g (1.798 mol) of t-butyl alcohol was added, followed by four 3.12 g (12.49 g total, 1.799 g-atom) portions of lithium wire cut in small pieces, one portion every ½ h. At times, mechanical stirring was interrupted to prevent foaming over. After stirring an additional 3 h, methanol (100 mL) was added and the reaction was stirred overnight while allowing ammonia to boil off. Water (600 mL) was added and the mixture was extracted three times with 300 mL portions of MTBE. The combined organic extracts were washed with 300 mL of brine, dried over magnesium sulfate, and filtered through Celite 503. The residue was washed with 50 mL of MTBE and the combined organic extracts were concentrated under reduced pressure. The resulting light yellow oil was taken up in 500 mL of acetone, and oxalic acid dihydrate (7.19 g) in 95 mL of water was added. After stirring 8 h, the hydrolysis mixture was poured into 250 mL of saturated sodium bicarbonate and extracted three times with 250 mL portions of MTBE. The combined organic extracts were washed three times with 250 portions of brine, dried over magnesium sulfate, and filtered through Celite 503. The residue was washed with 50 mL of MTBE and the combined filtrates were concentrated under reduced pressure. Two-fold recrystallization from hexanes (intermediate drying over magnesium sulfate necessary to remove residual water) gave two crops of white crystals. The total yield was 12.18 g (47.51 mmol, 46%). First crop m.p. 117.5–119.5° C., second crop m.p. 115–119° C.

Example 162
Estra-5(10),16-dien-3-one, 5, from 17-iodoestra-1,3,5(10),16-tetraen-3-yl methyl ether:

Approx. 1.2 L of anh. NH3 was distilled through KOH into a 3 L 3-neck round bottom flask fitted with two acetone/dry ice condensers and a mechanical stirrer, and containing 17-iodoestra-1,3,5(10),16-tetraen-3-yl methyl ether (14.71 g, 37.31 mmol) in 200 mL of anh. THF. Lithium wire (high sodium, 5.18 g, 0.7469 g-atom) cut in small pieces was added portionwise to control foaming, and the reaction was stirred 1 h. Methanol (40 mL) was added over 3 h, during which the reaction decolorized, and the mixture was stirred overnight while $NH_3$ was allowed to boil off. Water (400 mL) was added and the mixture was extracted three times with 200 mL aliquots of MTBE. The combined organic extracts were washed with 200 mL of brine, dried over magnesium sulfate, and filtered through Celite 503. The residue was washed with 5() mL of MTBE and the combined filtrates were concentrated under reduced pressure. The resulting pale yellow syrup was taken up in 175 mL of acetone, oxalic acid dihydrate (2.51 g) in 33 mL of water was added, and the hydrolysis mixture was stirred 6 h. The mixture was poured into 65 mL of saturated sodium bicarbonate and extracted three times with 65 mL aliquots of MTBE. The combined organic extracts were washed three times with 65 mL portions of brine, dried over magnesium sulfate, and filtered through Celite 503. The residue was washed with 25 mL of MTBE and the combined filtrates were concentrated under reduced pressure. Two- to three -fold recrystallization from hexanes (intermediate drying over magnesium sulfate necessary to remove residual water) gave two crops of light yellow to yellow crystals. The total yield was 4.7217 g (18.416 mmol, Limo). First crop m.p. 116–118° C. second crop m.p. 117–118° C.

Example 163
Purification and titration of 3-chloroperoxybenzeic acid:

Commercially available 3-chloroperoxybenzoic acid (MCPBA, 57–86%, 50.00 g) was added to 1 L of aqueous sodium phosphate buffer (0.5 M monobasic, 0.5 M dibasic) and the suspension was stirred mechanically for 5 min. The mixture was filtered through a coarse glass frit and the residue was washed with 200 mL of water. The residue was dried in vacua over $P_2O_5$ to give a white solid (33.50 g, 67% recovery of mass). Approx. 0.25 g samples of purified peracid were titrated in triplicate as follows: Sodium iodide (1.50 g) was dissolved in water, acetic acid (5.0 mL) and chloroform (5.0 mL) were added, followed by sample peracid. The mixture was stirred rapidly while titrating against standard 0.1 N sodium thiosulfate (available from Aldrich) to a colorless endpoint. The following equations were used to calculate the percentages of MCPBA in the samples:

Apparent molecular weight=2(mass of sample, g)/[(vol. thiosulfate,L)(conc. of standard thiosulfate)]

Percentage MCPBA=172.57/Apparent molecular weight

The triplicate readings were averaged to give a percentage of MCPBA of 92.2%.

Example 164
5β,10β,16α,17α-Bisepexyestran-3-one, 6:

To a solution of estra-5(10),16-dien-3-one (5, 12.02 g, 46.88 mmol) in 70 mL of methylene chloride cooled to 0° C. was added 3-chloroperoxybenzoic acid (97.4%, 17.80 g, 0.1031 mol) suspended in 340 mL of methylene chloride over 58 min., so that the reaction temperature was maintained within 2 degrees of 0° C. Further methylene chloride (100 mL) was added to rinse adhering peracid into the reaction vessel, the cooling bath was removed, and the mixture was stirred 5 h. The resulting suspension was filtered through Celite 503 and the residue was washed with 50 mL of methylene chloride. The combined filtrates were washed with 250 g of 5% (w/w) sodium thiosulfate pentahydrate+250 mL of saturated sodium bicarbonate+250 mL of brine, dried over magnesium sulfate, and filtered through Celite 503. The residue was washed with 50 mL of methylene chloride and the combined filtrates were concentrated under reduced pressure. Recrystallization of the resulting light yellow solid from 95% ethanol with intermediate treatment with charcoal gave shiny, white platelets (1 1.38 g, 39.46 mmol, 84%), m.p. 168–173° C.

Example 165
16α,17α-Epoxyestr-4-3n-10β-ol-3-one, 7, from estra-5(10),16-dien-3-one:

To a solution of estra-5(10),16-dien-3-one (5, 331.8 ma, 1.294 mmol) in 6 mL of 1,2-dimethoxyethane (DME) was added 3-chloroperoxybenzoic acid (95.6%, 491.3 ma, 2.847 mmol) in 16 mL of DME. After stirring 24 h, the reaction mixture was poured into 15 g of 5% (w/w) sodium thiosulfate pentahydrate and extracted three times into 30 mL aliquots of ethyl acetate. The combined organic extracts were washed with 30 mL of saturated sodium bicarbonate+ three 30 mL portions of brine, dried over magnesium sulfate, and filtered through Celite 503. The residue was washed with 15 mL of ethyl acetate and the combined filtrates were concentrated under reduced pressure. The resulting white solid was taken up in 20 mL of anh. THF under argon and cooled in an acetone/dry ice bath. Lithium diisopropylamide (LDA, 1.5 M in cyclohexane, 0.86 mL, 1.3 mmol) was added over 2 rain, and the reaction mixture was stirred a further 25 min. Saturated ammonium chloride (0.5 mL) and ether (30 mL) were added, and the mixture was washed three times with 10 mL portions of brine, dried over magnesium sulfate, and filtered through Celite 503. The residue was washed with 5 mL of ether and the combined filtrates were concentrated under reduced pressure. Flash chromatography (50% ethyl acetate/hexanes on silica gel 150) of the resulting moist yellow solid, followed by preparative TLC (50% ethyl acetate/hexanes on silica gel OF, 1000μ) and recrystallization from methylene chloride/hexanes gave white crystals (47.0 ma, 0.163 mmol, 13%), m.p. 192–194° C., homogeneous to TLC (50% ethyl acetate/hexanes on silica gel; product Rf 0.32; estrone $R_f$ 0.59). UV: λmass 236 nm, E=13,000. IR: 3508 cm$^{-1}$ (OH str.), 1661 cm$^{-1}$ (unsat'd. C=0 str.), 1620 cm$^{-1}$ (C=C str.). $^1$H-NMR (in d$_6$acetone): 5.$_6$δ (1H, s, H-4), 4.1 δ (1H, s, 10β-OH), 3.1–3.3 (2H, AB q, 160-H & 17,0-H), 0.82 δ (3H, s, 18-H). Anal.: Calculated for $C_1H_{24}O_3$: 74.96%, H 8.33%. Found: C 74.94±0.06%, H 8.33+0.07%. HR-EIMS: Calculated for $C_{18}H_{24}O_3$: 288.172544. Found: 288.1726. 180).

Example 166

16α,17α-Epoxyestran-4-en-10β-ol-3-one, 7:

5β,10β,16α,17α-Bisepoxyestr-3-one (6, 11.30 g, 39.18 mmol) was dissolved in 1 L of methanol with warming, and triethylamine (166 mL, 1.19 mmol) was added. After stirring 6 h, the solution was concentrated under reduced pressure and the resulting yellow-tinged solid was taken up in 250 mL of hot 95% ethanol. Charcoal (Darco G-60, 0.58 g) was added and the mixture was heated to boiling. The hot suspension was filtered through Celite 503 and the residue was washed with 50 mL of hot ethanol. The combined filtrates were boiled down to approx. 150 mL and then cooled in tap water with swirling. The solution was seeded with crystals of byproduct and was then refrigerated overnight following onset of crystallization. The byproduct was filtered off and washed with 10 mL of cold ethanol (after drying, the byproduct residue weighed 3.2762 g and had m.p. 262–269° C.). The combined filtrates were boiled down to approx. 50 mL and then cooled in tap water with swirling. The solution was seeded with authentic product and then refrigerated overnight following onset of crystallization. The suspension was filtered and the residue dried over $P_2O_5$ in vacuo to give flat, white crystals (4.6827 g, 16.283 mmol, 41%), m.p. 193–195° C., homogeneous to TLC (50% ethyl acetate/hexanes on silica gel; product $R_f$ 0.47; authentic sample $R_f$ 0.47).

What is claimed:

1. A method of treating paroxistic tachycardia in an individual, said method comprising:
   providing a steroid which binds to receptors on the surface of nasal neuroepithelial cells of said individual wherein said cells are part of tissue other than olfactory epithelia; and,
   administering said effective amount of said steroid within a nasal passage of said individual such that said steroid binds specifically to said receptors and results in alleviation of symptoms of said disorder in said individual.

2. The method of claim 1 wherein said neuroepithelial cell is located within a vomeronasal organ of said individual.

3. The method of claim 2 wherein said steroid comprises a pregnane of the formula:

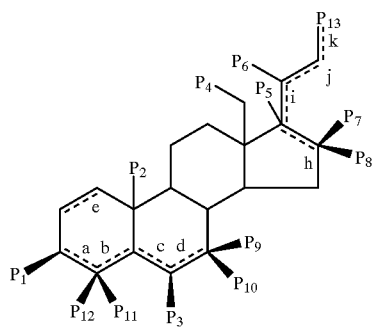

wherein $P_1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, oxo, halo, hydroxy, alkoxy, and acyloxy; $P_4$ through $P_{12}$ may each be, independently, hydrogen, halo, methyl, or halo-, dihalo- or perhalomethyl; $P_{13}$ is hydrogen, methyl, methylene, halo-substituted methyl or halo-substituted methylene, ethyl, ethylenyl, acetylenyl, methyl-methylenyl or methyl-methinyl; and "a", "b", "c", "d", "e", "h", "i", "j" and "k" are alternative sites for optional double bonds and "j" or "k" may also be triple bonds; and when $P_2$ is methyl and $P_3$ is β-hydroxy, $P_2$ and $P_3$ may be joined to form a cyclic ether.

4. A method according to claim 3 wherein "b" is a double bond.

5. A method according to claim 4 wherein "e" or "d" is a double bond.

6. A method according to claims 3 wherein "a" and "c" are double bonds.

7. A method according to claim 3 wherein "h" is an optional double bond, and "i" and "j" are absent.

8. A method according to claim 3 wherein is a double "j" is a double bond.

9. A method according to claim 3 wherein "j" is a triple bond.

10. The method of claim 2 wherein said steroid comprises a 19-nor-pregnane of the formula:

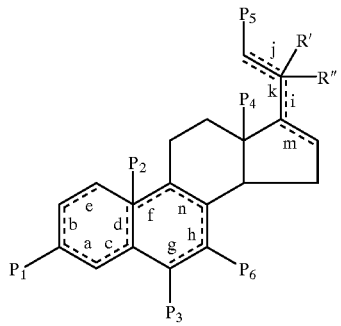

wherein $P_1$ is oxo, α- or A-hydroxy, α- or β-acetoxy, α- or β-propionoxy, α- or β-lower alkoxy, α- or β-lower acyloxy or α- or β-benzyloxy;

"a", "b", "c", "d", "e", "f", "g", "h", "i", "j", "m", and "n" are alternative sites for optional double bonds, and "k" may be absent or present with "j" to form a triple bond;

$P_2$ is a hydroxy, hydrogen, lower alkoxy of 1 to 6 carbon atoms, or $P_2$ is absent;

P₃ is oxo, hydrogen, hydroxy, lower alkoxy of 1–6 carbon atoms or halo;

P₄ is methyl or ethyl;

P₅ is hydrogen, methyl or halo;

P₆ is hydrogen or methyl;

R' and R" are independently, hydrogen or halo, or are absent.

11. A method according to claim 10 wherein "a", "e" and "d" are double bonds.

12. A method according to claim 11 wherein "h" is a double bond.

13. A method according to claim 11 wherein "g" is a double bond.

14. A method according to claim 13 wherein "n" is a double bond.

15. A method according to claim 10 wherein "d" is a double bond.

16. A method according to claim 15 wherein "b" is a double bond.

17. A method according to claim 15 wherein "c" is a double bond.

18. A method according to claim 17 wherein "f" is a double bond.

19. The method of claim 2 wherein said steroid is an estrene which has the formula:

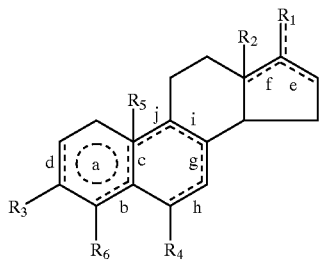

wherein R₁ is selected from the group consisting essentially of one or two hydrogen atoms, methyl, methylene, and one or, two halo atoms; R₂ is absent or is selected from the group consisting essentially of hydrogen and methyl; R₃ is selected from the group consisting essentially of oxo, hydroxy, lower alkoxy, lower acyloxy, benzoyl, cypionyl, glucuronide and sulfonyl; R₄ is selected from the group consisting essentially of hydrogen, hydroxy, lower alkoxy, lower acyloxy and halo; R₅ is absent or is selected from the group consisting essentially of hydrogen, hydroxy, lower alkoxy and lower acyloxy; R₆ is a hydrogen or a halo; and "a" represents optional aromatic unsaturation of ring A of said steroid, or "b", "c", and "d" are each optional double bonds; "e", "f", "g", "h", "i" and "j" are each optional double bonds; and "e" may also form an epoxy ring with C₁₆ and C₁₇.

20. A method according to claim 19 wherein "a" is present and "g", "h" or "i" are optional double bonds.

21. A method according to claim 20 wherein "h" and "i" are both double bonds.

22. A method according to claim 19 wherein "b" is a double bond.

23. A method according to claim 19 wherein "j" is a double bond.

24. A method according to claim 19 wherein "c" is a double bond.

25. A method according to claim 19 wherein "c" and "d" are double bonds.

26. A method according to claim 19 wherein R₂ is methyl and "e" is a double bond.

27. A method according to claim 19 wherein said steroid is selected from the group consisting of Estra-4,16-dien-3-one; Estra-1,3,5(10),16-tetraene-3-ol; 10 Estra-4,16-dien-3α-ol; Estra-4,9(10),16-triene-3-one; Estra-1,3,5(10),16-tetraen-3-ol-6-one; 3-Methoxyl-estra-2,5(10),16-triene; Estra-5(10),16-dien-3α-ol; and Estra-1,3,5(10),16-tetraen-3,6α-diol.

28. A method according to claim 19 wherein R₅ is methyl.

29. A method according to claim 28 wherein said steroid is selected from the group consisting essentially of Estra-1,3,5(10)-trien-3-ol; Estra-1,3,5(10),6-tetraen-3-ol; and Estra-1,3,5(10),7-tetraen 3-ol.

30. A method according to claim 19 wherein R₁ is methylene.

31. A method according to claim 30 wherein said steroid is 17-Methylene-estra-1,3,5(10),6,8(9)hexaen-3-ol.

32. A method according to claim 19 wherein R₁ is methylene or a single hydrogen and R₂ is methyl.

33. A method according to claim 19 wherein "f" is a double bond and R₂ is methyl.

34. The method of claim 33 wherein at least one Estrene steroid is selected from the group consisting of 1,3,5(10),16-Estratetraen-3-methyl ether, ol,1,3,S(10),16-Estratetraen-3-ol 1,3,5(10),16-Estratetraen-3-yl acetate, and 1,3,5 (10), 16-Estratetraen-3-yl propionate.

35. The method of claim 33 wherein the Estrene steroid is 1,3,5(10), 16-Estratetraen-3-ol.

36. A method of claim 19 wherein the estrene is estra-4,16-dien-10β-ol-3-one.

37. A method according to claim 19 wherein "e" forms an epoxy ring with C₁₆ and C₁₇.

38. A method according to claim 37 wherein said estrene is 16α,17α-epoxy-estra-1,3,5(10)-trien-3-ol.

39. A method according to claim 37 wherein said estrene is 16α,17α-epoxyestr-4-en-10β-ol-3-one.

40. The method of claim 2 wherein said steroid is an androstane of the formula:

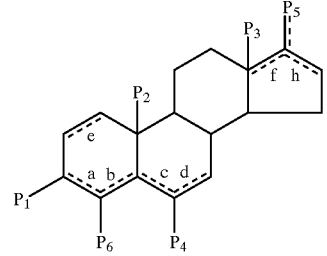

wherein P₁ is selected from the group consisting of oxo, α-(β-) hydroxy, α-(β-) acetoxy, α-(β-) propionoxy, α-(β--); methoxy, α-(β-) lower acyloxy, α-(β-) lower alkyloxy, and α-(β-) benzoyloxy; P₂ is selected from the group consisting of methyl, hydroxymethyl, acyloxymethyl, alkoxymethyl, lower alkyl, hydroxyalkyl, acyloxyalkyl, and alkoxylalkyl; P₃ is absent or is selected from the group consisting of methyl, hydroxymethyl, acyloxymethyl, alkoxymethyl, lower alkyl, hydroxyalkyl, acyloxyalkyl, and alkoxylalkyl; P₄ is selected from the group consisting of hydrogen, oxo, halo, hydroxy, alkoxy, and acyloxy; P₅ represents one or 2 substituents, wherein P₅ comprises one or two hydrogen atoms, methyl, methylene, or one or two halo atoms; P₆ is hydrogen or halo; and "a", "b", "c", "d", "e", "f" and "h" are alternative sites for optional double bonds.

41. A method according to claim 40 wherein "b" is a double bond.

42. A method according to claim 41 wherein "e" or "d" is a double bond.

43. A method according to claim 40 wherein "a" and "c" are double bonds.

44. A method according to claim 40 wherein $P_3$ is methyl, "h" is an optional double bond, and $P_5$ is methylene or one or two hydrogen atoms.

45. A method according to claim 40 wherein $P_3$ is methyl and "h" is a double bond.

46. A method according to claim 45 wherein said steroid is selected from the group consisting of Androsta-5,16-dien-3α-ol, Androsta-4,6,16-triene-3-one; Androsta-4,16-dien-3,6-dione; 19-Hydroxy-androsta-4,16-dien-3-one; 3-Methoxy-androsta-3,5,16-triene: and 6~-Hydroxy-androsta-4-16-dien-3-one.

47. A method according to claim 40 wherein $P_3$ is methyl.

48. A method according to claim 47 wherein said steroid is Androst-4-en-3-one.

49. A method according to claim 40 wherein $P_5$ is methylene.

50. A method according to claim 49 wherein said steroid is selected from the group consisting of 20-Homo-androsta-4,17-dien-3~-ol; 20-Homo androsta-4,17-dien-3β-ol; and 20-Homo androsta-4,17-dien-3,6-dione.

51. A method according to claim 40 wherein $P_5$ is methyl and "f" is a double bond.

52. The method of claim 40 wherein "a" or "b" is a double bond.

53. she method of claim 40 wherein at least one Androstane steroid is selected from the group consisting of Androsta-4, 516-dien-3-one, Androsta-4,16-dien-3α-ol and Androsta-4,16-dien-3β-ol.

54. The method of claim 53 wherein said steroid is Androsta-4,16-dien-3-one.

55. A method according to claim 53 wherein said steroid is Androsta-4,16-dien-3β-ol.

56. A method of claim 2 wherein said steroid is a 19-norcholane of the formula:

wherein $P_1$ is oxo, α- or β-hydroxy, α- or β-acetoxy, or β-propionoxy, α- or β-lower alkoxy, α- or β-lower acyloxy or α- or β-benzyloxy;

"a", "b", "c", "d", "e", "f", "g", "h", "i", "j", "m", "s" and "n" are alternative sites for optional double bonds, and may be absent or present with "j" to form a triple bond;

$P_2$ is hydroxy, hydrogen, lower alkoxy of 1 to 6 carbon atoms, or $P_2$ is absent;

$P_3$ is oxo, hydrogen, hydroxy, lower alkoxy of 1–6 carbon atoms or halo;

$P_4$ is methyl or ethyl;

each $P_5$ and $P_7$ is independently is hydrogen, methyl or halo;

$P_6$ is hydrogen or methyl;

R' and R" are independently, hydrogen halo, or are absent, or together form $=CH_2$;

and q is an integer from 0 to 2;

on the surface of nasal neuroepithelial cell of said individual wherein said cell is a part of tissue other than olfactory epithelia; and administering said 19-nor-cholane derivative within a nasal passage of said individual such that said 19-nor-cholane derivative binds specifically to said receptor and results in an alteration of hypothalamic function of said individual.

57. A method according to claim 56 wherein "a", "e" and "d" are double bonds.

58. A method according to claim 57 wherein "h" is a double bond.

59. A method according to claim 57 wherein "g" is a double bond.

60. A method according to claim 59 wherein "n" is a double bond.

61. A method according to claim 56 wherein "d" is a double bond.

62. A method according to claim 61 wherein "b" is a double bond.

63. A method according to claim 56 wherein "c" is a double bond.

64. A method according to claim 56 wherein "s" is a double bond.

65. The method of claim 1 wherein the amount of said steroid that is administered is at least about 100 picograms, but no more than about 100 micrograms.

66. The method of claim 65 wherein the amount of said steroid that is administered is at least about 1 nanogram, but no more than about 10 micrograms.

67. The method of claim 66 wherein the amount of said steroid that is administered is at least about 10 nanograms, but no more than about 1 microgram.

68. The method of claim 65 wherein said steroid is administered in an ointment.

69. The method of claim 65 wherein said steroid is administered in a liquid.

70. The method of claim 65 wherein said steroid is administered by aerosol.

* * * * *